(12) United States Patent
Stull et al.

(10) Patent No.: US 9,775,916 B1
(45) Date of Patent: *Oct. 3, 2017

(54) ANTI-DLL3 ANTIBODY DRUG CONJUGATES FOR TREATING CANCER

(71) Applicant: ABBVIE STEMCENTRX LLC, North Chicago, IL (US)

(72) Inventors: Robert A. Stull, Alameda, CA (US); Laura Saunders, San Francisco, CA (US); Scott J. Dylla, Emerald Hills, CA (US); Orit Foord, Foster City, CA (US); David Liu, San Francisco, CA (US); Michael Torgov, Los Angeles, CA (US); Hui Shao, Foster City, CA (US)

(73) Assignee: AbbVie Stemcentrx LLC, North Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/608,996

(22) Filed: May 30, 2017

Related U.S. Application Data

(63) Continuation of application No. 15/266,894, filed on Sep. 15, 2016, which is a continuation of application No. 15/135,517, filed on Apr. 21, 2016, now Pat. No. 9,486,537, which is a continuation of application No. 14/859,242, filed on Sep. 18, 2015, now Pat. No. 9,353,182, which is a continuation of application No. 14/807,789, filed on Jul. 23, 2015, now Pat. No. 9,173,959, which is a continuation of application No. 14/466,951, filed on Aug. 22, 2014, now Pat. No. 9,089,617, which is a continuation of application No. 14/466,842, filed on Aug. 22, 2014, now Pat. No. 9,089,615, which is a continuation of application No. PCT/US2013/027391, filed on Feb. 22, 2013.

(60) Provisional application No. 61/719,803, filed on Oct. 29, 2012, provisional application No. 61/603,173, filed on Feb. 24, 2012.

(51) Int. Cl.
| | |
|---|---|
| *A61K 39/395* | (2006.01) |
| *C07K 16/18* | (2006.01) |
| *C12P 21/08* | (2006.01) |
| *A61K 47/48* | (2006.01) |
| *C07K 16/30* | (2006.01) |
| *A61K 31/5517* | (2006.01) |
| *G01N 33/574* | (2006.01) |
| *C07K 16/28* | (2006.01) |
| *A61K 51/10* | (2006.01) |
| *A61K 31/551* | (2006.01) |
| *A61K 45/06* | (2006.01) |
| *A61K 39/00* | (2006.01) |

(52) U.S. Cl.
CPC ...... *A61K 47/48569* (2013.01); *A61K 31/551* (2013.01); *A61K 31/5517* (2013.01); *A61K 39/3955* (2013.01); *A61K 45/06* (2013.01); *A61K 47/48384* (2013.01); *A61K 47/48407* (2013.01); *A61K 47/48469* (2013.01); *A61K 47/48538* (2013.01); *A61K 47/48561* (2013.01); *A61K 47/48592* (2013.01); *A61K 47/48638* (2013.01); *A61K 47/48715* (2013.01); *A61K 47/48723* (2013.01); *A61K 51/1096* (2013.01); *C07K 16/18* (2013.01); *C07K 16/28* (2013.01); *C07K 16/2809* (2013.01); *C07K 16/30* (2013.01); *C07K 16/3023* (2013.01); *C07K 16/3069* (2013.01); *G01N 33/57423* (2013.01); *G01N 33/57492* (2013.01); *A61K 2039/505* (2013.01); *A61K 2039/572* (2013.01); *C07K 2317/20* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/35* (2013.01); *C07K 2317/53* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/626* (2013.01); *C07K 2317/70* (2013.01); *C07K 2317/73* (2013.01); *C07K 2317/732* (2013.01); *C07K 2317/76* (2013.01); *C07K 2317/77* (2013.01); *C07K 2317/92* (2013.01); *C07K 2319/30* (2013.01); *G01N 2333/70596* (2013.01)

(58) Field of Classification Search
None
See application file for complete search history.

(56) References Cited

U.S. PATENT DOCUMENTS

| | | | |
|---|---|---|---|
| 4,676,980 | A | 6/1987 | Segal et al. |
| 4,816,567 | A | 3/1989 | Cabilly et al. |
| 5,112,946 | A | 5/1992 | Maione |

(Continued)

FOREIGN PATENT DOCUMENTS

| | | |
|---|---|---|
| EP | 0307434 | 3/1989 |
| EP | 0367166 | 5/1990 |

(Continued)

OTHER PUBLICATIONS

Accession No. NM_016941; "*Homo sapiens* delta-like 3 (*Drosophila*) (DLL3), transcript variant 1, mRNA".

(Continued)

*Primary Examiner* — Christine J Saoud
*Assistant Examiner* — Jon M Lockard
(74) *Attorney, Agent, or Firm* — Womble Carlyle Sandridge & Rice, LLP

(57) ABSTRACT

Novel modulators, including antibodies and derivatives thereof, and methods of using such modulators to treat proliferative disorders are provided.

30 Claims, 54 Drawing Sheets

(56) References Cited

U.S. PATENT DOCUMENTS

| | | |
|---|---|---|
| 5,122,368 A | 6/1992 | Greenfield et al. |
| 5,223,409 A | 6/1993 | Ladner et al. |
| 5,336,603 A | 8/1994 | Capon et al. |
| 5,349,053 A | 9/1994 | Landolfi |
| 5,359,046 A | 10/1994 | Capon et al. |
| 5,447,851 A | 9/1995 | Beutler et al. |
| 5,545,806 A | 8/1996 | Lonberg et al. |
| 5,545,807 A | 8/1996 | Surani et al. |
| 5,569,825 A | 10/1996 | Lonberg et al. |
| 5,622,929 A | 4/1997 | Willner et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,762 A | 12/1997 | Queen et al. |
| 5,750,373 A | 5/1998 | Garrard et al. |
| 5,824,805 A | 10/1998 | King et al. |
| 6,075,181 A | 6/2000 | Kucherlapati et al. |
| 6,150,584 A | 11/2000 | Kucherlapati et al. |
| 6,180,370 B1 | 1/2001 | Queen et al. |
| 6,214,345 B1 | 4/2001 | Firestone et al. |
| 6,300,064 B1 | 10/2001 | Knappik et al. |
| 6,362,331 B1 | 3/2002 | Kamal et al. |
| 6,982,321 B2 | 1/2006 | Winter |
| 7,049,311 B1 | 5/2006 | Thurston et al. |
| 7,087,409 B2 | 8/2006 | Barbas, III et al. |
| 7,189,710 B2 | 3/2007 | Kamal et al. |
| 7,279,554 B2 | 10/2007 | Chan et al. |
| 7,279,558 B2 | 10/2007 | Ota et al. |
| 7,407,951 B2 | 8/2008 | Thurston et al. |
| 7,422,739 B2 | 9/2008 | Anderson et al. |
| 7,429,658 B2 | 9/2008 | Howard et al. |
| 7,557,099 B2 | 7/2009 | Howard et al. |
| 7,619,068 B2 | 11/2009 | Pikington et al. |
| 7,632,678 B2 | 12/2009 | Hansford et al. |
| 7,700,302 B2 | 4/2010 | Hua et al. |
| 7,741,319 B2 | 6/2010 | Howard et al. |
| 7,825,267 B2 | 11/2010 | Koide et al. |
| 8,029,984 B2 | 10/2011 | Alitalo et al. |
| 8,034,808 B2 | 10/2011 | Delavault et al. |
| 8,133,857 B2 | 3/2012 | Aikawa |
| 8,163,736 B2 | 4/2012 | Gauzy et al. |
| 8,557,965 B2 | 10/2013 | Saunders et al. |
| 8,788,213 B2 | 7/2014 | Bright et al. |
| 9,150,664 B2 | 10/2015 | Kufer et al. |
| 2003/0180784 A1 | 9/2003 | McCarthy et al. |
| 2004/0101920 A1 | 5/2004 | Radziejewski et al. |
| 2005/0008625 A1 | 1/2005 | Balint et al. |
| 2005/0238649 A1 | 10/2005 | Doronina et al. |
| 2007/0141066 A1 | 6/2007 | Phillips et al. |
| 2007/0292414 A1 | 12/2007 | Duntsch |
| 2008/0138313 A1 | 6/2008 | Frankel |
| 2008/0175870 A1 | 7/2008 | Mather et al. |
| 2009/0130105 A1 | 5/2009 | Glaser et al. |
| 2009/0155255 A1 | 6/2009 | Glaser et al. |
| 2010/0162416 A1 | 6/2010 | Krtolica et al. |
| 2010/0184021 A1 | 7/2010 | Sella-Tavor et al. |
| 2010/0273160 A1 | 10/2010 | Donahoe et al. |
| 2010/0275280 A1 | 10/2010 | Clevers et al. |
| 2011/0020221 A1 | 1/2011 | Berman et al. |
| 2011/0256157 A1 | 10/2011 | Howard et al. |
| 2012/0078028 A1 | 3/2012 | Satpayev et al. |
| 2012/0328624 A1 | 12/2012 | Yoshida et al. |
| 2013/0061340 A1 | 3/2013 | Dylla et al. |
| 2013/0061342 A1 | 3/2013 | Dylla et al. |
| 2013/0260385 A1 | 10/2013 | Dylla et al. |
| 2014/0106449 A1 | 4/2014 | June et al. |
| 2014/0363455 A1 | 12/2014 | Stull et al. |
| 2014/0370037 A1 | 12/2014 | Stull et al. |
| 2015/0030636 A1 | 1/2015 | Dylla et al. |

FOREIGN PATENT DOCUMENTS

| | | |
|---|---|---|
| EP | 2530091 A1 | 12/2012 |
| WO | WO 91/00360 | 1/1991 |
| WO | WO 91/06570 | 5/1991 |
| WO | WO 91/17271 | 11/1991 |
| WO | WO 92/00373 | 1/1992 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 94/04690 | 3/1994 |
| WO | WO 96/04388 | 2/1996 |
| WO | WO 96/07754 | 3/1996 |
| WO | WO 96/27011 | 9/1996 |
| WO | WO 97/33899 | 9/1997 |
| WO | WO 97/34911 | 9/1997 |
| WO | WO 98/52976 | 11/1998 |
| WO | WO 99/23105 | 5/1999 |
| WO | WO 00/34317 | 6/2000 |
| WO | WO 01/12664 | 2/2001 |
| WO | WO 02/14358 | 2/2002 |
| WO | WO 03/048731 | 6/2003 |
| WO | WO 03/075957 | 9/2003 |
| WO | WO 2007/080597 A2 | 7/2007 |
| WO | WO 2007/111733 A2 | 10/2007 |
| WO | WO 2008/047925 A1 | 4/2008 |
| WO | WO 2009/124931 A2 | 10/2009 |
| WO | WO 2011/093097 A1 | 8/2011 |
| WO | WO 2011/128650 | 10/2011 |
| WO | WO 2011/130598 | 10/2011 |
| WO | WO 2011/130613 | 10/2011 |
| WO | WO 2011/130616 | 10/2011 |
| WO | WO 2012/031280 | 3/2012 |
| WO | WO 2012/128801 | 9/2012 |
| WO | WO 2013/041606 | 3/2013 |
| WO | WO 2013/119964 | 8/2013 |
| WO | WO 2013/126746 A2 | 8/2013 |
| WO | WO 2015/031693 A1 | 3/2015 |
| WO | WO 2015/031698 | 3/2015 |
| WO | WO 2015/127407 | 8/2015 |
| WO | WO 2016/064749 | 4/2016 |

OTHER PUBLICATIONS

Accession No. NM_203486; "*Homo sapiens* delta-like 3 (*Drosophila*) (DLL3), transcript variant 2, mRNA".
Accession No. NP_982353; "delta-like protein 3 isoform 2 precursor [*Homo sapiens*]".
Accession No. NP_058637; "delta-like protein 3 isoform 1 precursor [*Homo sapiens*]".
Accession No. Q9NYJ7; RecName: Full=Delta-like protein 3; AltName: Full=*Drosophila* Delta homolog 3; Short=Delta3; Flags: Precursor [*Homo sapiens*].
ADC Review: "Rovalpituzumab tesirine / Rova-T / SC16LD6.5 Drug Description", http://adcreview.com Feb. 27, 2016 Retrieved from the Internet: URL:http://adcreview.com/sc161d6-5-drug-description/ [retrieved on Feb. 21, 2017].
Apelqvist, A., et al., "Notch signalling controls pancreatic cell differentiation," *Nature* (1999) 400(6747):877-81.
Ashkenazi et al., "Protection Protection against endotoxic shock by a tumor necrosis factor receptor immunoadhesin," *Proc Natl Acad Sci USA* (1991) 88(23):10535-9.
Ayyanan, A., et al., "Increased Wnt signaling triggers oncogenic conversion of human breast epithelial cells by Notch-dependent mechanism," *Proceedings of theNational Academy of Sciences of USA* (2006) 103(10):3799-3804.
Ball, "Achaete-scute homolog-1 and Notch in lung neuroendocrine development and cancer," *Cancer Letters* (2004) 204(2):159-69.
Barabas et al., "Assembly of combinatorial antibody libraries on phage surfaces: the gene III site," *Proc. Natl. Acad. Sci.* (1991) USA 88:7978-7982.
Bigas, A., and Espinosa, L., "Hematopoietic stem cells: to be or Notch to be," *Blood* (Apr. 5, 2012) 119(14):3226-35.
Boerner et al.,"Production of antigen-specific human monoclonal antibodies from in vitro-primed human splenocytes," *J Immunol.* (Jul. 1, 1991) 147(1):86-95.—Abstract.

(56) References Cited

OTHER PUBLICATIONS

Boswell et al., "An integrated approach to identify normal tissue expression of targets for antibody-drug conjugates: case study of TENB2," *British Journal of Pharmacology* (2013) 168:445-457.
Chapman, G., et al., "Notch inhibition by the ligand DELTA-LIKE 3 defines the mechanism of abnormal vertebral segmentation in spondylocostal dysostosis," *Hum Mol Genet.* (Mar. 1, 2011) 20(5):905-16.
Chen, H., et al., "Conservation of the *Drosophila* lateral inhibition pathway in human lung cancer: a hairy-related protein (HES-1) directly represses achaete-scute homolog-1 expression," *Proc Natl Acad Sci USA* (1997) 94:5355-60. PMID: 9144241.
Chothia et al., "Canonical structures for the hypervariable regions of immunoglobulins," *J Mol Biol.* (1987) 196(4):901-17.
Chothia et al., "Conformations of immunoglobulin hypervariable regions," *Nature* (1989) 342(6252):877-83.
Chothia D et al., "Structural repertoire of the human VH segments," *J Mol Biol.* (Oct. 5, 1992) 227(3):799-817.—Abstract.
Cochran et al., "Domain-level antibody epitope mapping through yeast surface display of epidermal growth factor receptor fragments," *J Immunol Methods.* (Apr. 2004) 287(1-2):147-58.
Cook, G.P., et al., "The human immunoglobulin VH repertoire," *Immunol Today* (May 16, 1995) (5):237-42.—Abstract.
Cook. M., et al., "Notch in the development of thyroid C-cells and the treatment of medullary thyroid cancer," *Am J Transl Res.* (Feb. 10, 2010) 2(1):119-25.
De La Pompa, JL. et al., "Conservation of the Notch signaling pathway in mammalian neurogenesis," *Development* (Mar. 1997) 124(6):1139-48.
Denardo et al., "Comparison of 1,4,7,10-tetraazacyclododecane-N, N,N,N-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts", *Clin Cancer Res.* (Oct. 1998) 4(10):2483-90.
D'Souza Brendan et al., "Canonical and non-canonical Notch ligands," *Curr Top Dev Biol.* (2010) 92:73-129.
Dubowchik et al., "Cathepsin B-labile dipeptide linkers for lysosomal release of doxorubicin from internalizing immunoconjugates: model studies of enzymatic drug release and antigen-specific in vitro anticancer activity," *Bioconjug Chem.* (Jul.-Aug. 2002) 13(4):855-69—Abstract.
Dunwoodie, SL, "The role of Notch in patterning the human vertebral column," *Curr Opin Genet Dev.* (2009) 19(4):329-37.
Dunwoodie et al., "Mouse Dll3: a novel divergent Delta gene which may complement the function of other Delta homologues during early pattern formation in the mouse embryo," *Development* (Aug. 1997) 124(16):3065-76.
Dutta, S. et al., "Notch signaling regulates endocrine cell specification in the zebrafish anterior pituitary," *Dev Biol.* (Jul. 15, 2008) 319(2):248-57.
Dylla et al., "Colorectal cancer stem cells are enriched in xenogeneic tumors following chemotherapy," *PLoS One* (Jun. 18, 2008) 3(6):e2428.
Fre, S., et al., "Notch signals control the fate of immature progenitor cells in the intestine," *Nature.* (Jun. 16, 2005) 435(7044):964-8.
Fre, S., et al., "Notch and Wnt signals cooperatively control cell proliferation and tumorigenesis in the intestine," *Proc Natl Acad Sci U S A.* (Apr. 14, 2009) 106(15):6309-14.
Fuhrmann, S., et al.,"Abstract 5625: In vitro and in vivo pharmacology of MEDI-565 (MT111), a novel CEA/CD3-bispecific single-chain BiTE antibody in development for the treatment of gastrointestinal adenocarcinomas," *Cancer Research* (Apr. 15, 2010) 70:8(1).
Galluzzo, P., and Bocchetta, M., "Notch signaling in lung cancer," *Expert Rev Anticancer Ther.* (Apr. 2011) 11(4):533-40.
Garnett, MC, "Targeted drug conjugates: principles and progress," *Adv Drug Deliv Rev.* (Dec. 17, 2001) 53(2):171-216.

Geffers I et al., "Divergent functions and distinct localization of the Notch ligands DLL1 and DLL3 in vivo," *J Cell Biol.* (Jul. 30, 2007) 178(3):465-76.
Glittenberg M, et al., "Role of conserved intracellular motifs in Serrate signalling, cis-inhibition and endocytosis," *EMBO J.* (Oct. 18, 2006) 25(20):4697-706. Epub Sep. 28, 2006.
Goldbeter, A., and Pourquié, O., "Modeling the segmentation clock as a network of coupled oscillations in the Notch, Wnt and FGF signaling pathways," *J Theor Biol.* (Jun. 7, 2008) 252(3):574-85.
Gregson et al., "Design, Synthesis, and Evaluation of a Novel Pyrrolobenzodiazepine DNA-Interactive Agent with Highly Efficient Cross-Linking Ability and Potent Cytotoxicity," *J Med Chem.* (Mar. 1, 2001) 44(5):737-48.
Habener, JF, et al., "Minireview: transcriptional regulation in pancreatic development," *Endocrinology.* (2005) 146(3):1025-34. Epub Dec. 16, 2004.
Harris, PJ, et al., "Targeting embryonic signaling pathways in cancer therapy," *Expert Opin Ther Targets.* (2012) 16(1):131-45.
Henke, RM, et al., "Ascl1 and Neurog2 form novel complexes and regulate Delta-like3 (DLL3) expression in the neural tube," *Dev Biol.* (2009) 328(2):529-40.
Hochleitner et al., "Characterization of a discontinuous epitope of the human immunodeficiency virus (HIV) core protein p24 by epitope excision and differential chemical modification followed by mass spectrometric peptide mapping analysis," *Protein Sci.* (Mar. 2000) 9(3):487-96.
Hoey et al., "DLL4 blockade inhibits tumor growth and reduces tumor-initiating cell frequency," *Cell Stem Cell.* (2009) 5(2):168-77.
Hoyne GF, et al., "A cell autonomous role for the Notch ligand Delta-like 3 in αβ T-cell development," *Immunol Cell Biol.* (2011) 89(6):696-705.
Huber, K., et al., "Development of chromaffin cells depends on MASH1 function," *Development* (2002) 129(20):4729-38.
Huff, Carol Ann, et al., "Strategies to eliminate cancer stem cells: Clinical implications," *European Journal of Cancer* (2006) 42:1293-1297.
Ito, T., et al., "Basic helix-loop-helix transcription factors regulate the neuroendocrine differentiation of fetal mouse pulmonary epithelium," *Development* (Sep. 2000) 127(18):3913-21.
Jensen, J., et al., "Control of endodermal endocrine development by Hes-1," *Nat Genet.* (2000) 24(1):36-44.
Jones et al., "Replacing the complementarity-determining regions in a human antibody with those from a mouse," *Nature* (1986) 4; 321(6069):522-5—Abstract.
Junutula et al., "Site-specific conjugation of a cytotoxic drug to an antibody improves the therapeutic index," *Nat Biotechnol.* (Aug. 2008) 26(8):925-32. doi: 10.1038/nbt.1480. Epub (Jul. 20, 2008).
Kageyama R, et al., "Oscillator mechanism of Notch pathway in the segmentation clock," *Dev Dyn.* (2007) 236(6):1403-9.
Kameda Y et al., "Mash1 regulates the development of C cells in mouse thyroid glands," *Dev Dyn.* (Jan. 2007) 236(1):262-70.
Klein T, et al., "An intrinsic dominant negative activity of serrate that is modulated during wing development in *Drosophila,*" *Dev Biol.* (Sep. 1, 1997) 189(1):123-34.
Klimstra DS, et al., "The pathologic classification of neuroendocrine tumors: a review of nomenclature, grading, and staging systems," *Pancreas.* (Aug. 2010) 39(6):707-12.
Klöppel, G., "Classification and pathology of gastroenteropancreatic neuroendocrine neoplasms. Endocr Relat Cancer," *Endocr. Relat Cancer.* (2011) 18 Suppl 1:S1-16.
Koch, U., and Radtke, F., "Notch signaling in solid tumors," *Curr Top Dev Biol.* (2010) 92:411-55.
Kroesen, BJ, et al., "Approaches to lung cancer treatment using the CD3 x EGP-2-directed bispecific monoclonal antibody BIS-1," *Cancer Immunol Immunother.* (1997) 45(3-4):203-6.
Kusumi K et al., "The mouse pudgy mutation disrupts Delta homologue DLL3 and initiation of early somite boundaries," *Nat Genet.* (1988) 19(3):274-8.
Ladi E et al., "The divergent DSL ligand D113 does not activate Notch signaling but cell autonomously attenuates signaling induced by other DSL ligands," *J Cell Biol.* (2005) 170(6):983-92.

(56) References Cited

OTHER PUBLICATIONS

Liu J et al., "Notch signaling in the regulation of stem cell self-renewal and differentiation," *Curr Top Dev Biol.* (2010) 92:367-409.
Lonberg et al., "Human antibodies from transgenic mice," *Int Rev Immunol.* (1995) 13(1):65-93—Abstract.
MacCallum et al., "Antibody-antigen interactions: contact analysis and binding site topography," J *Mol Biol.* (1966) 262(5):732-45.
Maemura, Kentaro, et al., "Delta-like 3 is silenced by methylation and induces apoptosisin human hepatocellular carcinoma," *Int J Oncol.* (2013) 42(3):817-822.
Marks et al., "By-passing immunization: building high affinity human antibodies by chain shuffling," *Biotechnology* (NY) (1992) 10(7):779-783—Abstract.
Millipore "Anti-Delta3, clone 1E7.2," (Jul. 15, 2008) pp. 1-3 (XP002697359).
Milstein et al., "Hybridomas and their use in immunohistochemistry," *Nature* (1983) 305:537-539—Abstract.
Morrison et al., "Chimeric human antibody molecules: mouse antigen-binding domains with human constant region domains," *Proc Natl Acad Sci U S A.* (1984) 81(21):6851-5.
Nagase, H., et al., "γ-Secretase-regulated signaling pathways, such as notch signaling, mediate the differentiation of hematopoietic stem cells, development of the immune system, and peripheral immune responses," *Curr Stem Cell Res Ther.* (2011) 6(2):131-41.
Peterson et al., "Enzymatic cleavage of peptide-linked radiolabels from immunoconjugates," *Bioconjug Chem.* (1999) 10(4):553-7.
"Phase I/II Open Label Dose Escalation Study of the Safety, Pharmacokinetics, and Preliminary Efficacy of SC16LD6.5 as a Single Agent in Patients With Recurrent Small Cell Lung Cancer," Clinical Trials.gov archive, URL:https://clinicaltrials.gov/archive/NCT01901653/2013_08_20 (Aug. 20, 2013).
R&D Systems: "Human DLL3 Antibody Monoclonal Mouse IgG2B Clone #378703, Catalog No. MA4315" (May 5, 2010) pp. 1-1, (XP002697358).
Raetzman LT et al., "Developmental regulation of Notch signaling genes in the embryonic pituitary: Prop1 deficiency affects Notch2 expression," *Dev Biol.* (2004) 265(2):329-40.
Rebay I, et al., "Specific EGF repeats of Notch mediate interactions with Delta and Serrate: implications for Notch as a multifunctional receptor," *Cell.* (Nov. 15, 1991) 67(4):687-99.
Reineke, U., "Antibody epitope mapping using arrays of synthetic peptides," *Methods Mol Biol.* (2004) 248:443-63.
Retter et al., "VBASE2, an integrative V gene database," *Nucleic Acids Res.* (Jan. 1, 2005) 33 (Database issue):D671-4.
Robine, S., et al., "Notch signals control the fate of immature progenitor cells in the intestine," *Med Sci* (Paris). (Aug.-Sep. 2005) 21(8-9):780-2.
Roitt, I., et al., *Immunology*, Moscow, Mir (2000) Chap. 6, pp. 110-111.
Sakamoto K et al., "Intracellular cell-autonomous association of Notch and its ligands: a novel mechanism of Notch signal modification," *Dev Biol.* (Jan. 15, 2002) 241(2):313-26. PMID: 11784114.
Saunders et al., "A DLL3-targeted antibody-drug conjugate eradicates high-grade pulmonary neuroendocrine tumor-initiating cells in vivo," *Sci Transl Med.* (Aug. 26, 2015) 7(302):302ra136. doi: 10.1126/scitranslmed.aac9459.
Schalper et al., "Programmed death-1/programmed death-1 ligand axis as a therapeutic target in oncology: current insights," Journal of Receptor, Ligand and Channel Research ePub (Dec. 23, 2014) 8: 1-7.
Schildbach, J.F., et al., "Modulation of antibody affinity by a non-contact residue," *Protein Sci* (1993) 2:206-214.
Schonhoff, S.E., et al., "Minireview: Development and differentiation of gut endocrine cells," *Endocrinology.* (Jun. 2004) 145(6):2639-44.
Schulenburg et al., "Neoplastic stem cells: current concepts and clinical perspectives," *Crit Rev Oncol Hematol.* (Nov. 2010) 76(2):79-98.
Sebastian, Martin, et al., "Treatment of non-small cell lung cancer patients with the trifunctional monoclonal antibody catumaxomab (anti-EpCAM x anti-CD3): a phase I study," *Cancer Immunol Immunother.* (2007) 56(10):1637-44. Epub Apr. 5, 2007.
Sheets et al., "Efficient construction of a large nonimmune phage antibody library: the production of high-affinity human single-chain antibodies to protein antigens," *Proc Natl Acad Sci U S A.* (1998) 95(11):6157-62.
Shimizu, K., et al., "Mouse jagged1 physically interacts with notch2 and other notch receptors. Assessment by quantitative methods," *J Biol Chem.* (Nov. 12, 1999) 274(46):32961-9.
Shinkai Y et al., "New mutant mouse with skeletal deformities caused by mutation in delta like 3 (DLL3) gene," *Exp Anim.* (Apr. 2004) 53(2):129-36.
Spigel et al., "Rationale for chemotherapy, immunotherapy, and checkpoint blockade in SCLC: beyond traditional treatment approaches," *J Thorac Oncol.* (May 2013) 8(5):587-98. doi: 10.1097/JTO.0b013e318286cf88.
Sprinzak D et al., "Cis-interactions between Notch and Delta generate mutually exclusive signalling states," *Nature.* (May 6, 2010) 465(7294):86-90.
Sriuranpong, V., et al., "Notch signaling induces rapid degradation of achaete-scute homolog 1," *Mol Cell Biol.* (2002) 22(9):3129-39.
Sternberg, P.W., "Lateral inhibition during vulval induction in Caenorhabditis elegans," *Nature* (1988) 335(6190):551-4.
Takahashi et al., "Human Fas ligand: gene structure, chromosomal location and species specificity," *International Immunology*, (1994) vol. 6, No. 10, pp. 1567-1574; PMID 7826947.
Tomlinson et al., "The repertoire of human germline VH sequences reveals about fifty groups of VH segments with different hypervariable loops," *Mol Biol.* (Oct. 5, 1992) 227(3):776-98—Abstract.
Tomlinson et al., "The structural repertoire of the human V kappa domain," *EMBO J.* (Sep. 15, 1995) 14(18):4628-38.
Turnpenny, P.D., et al., "A gene for autosomal recessive spondylocostal dysostosis maps to 19q13.1-q13.3," *Am J Hum Genet.* (Jul. 1999) 65(1):175-82.
Vaughan et al., "Human antibodies with sub-nanomolar affinities isolated from a large non-immunized phage display library," *Nature Biotechnol.* (Mar. 1996) 14(3):309-14—Abstract.
Vié et al., "Human fusion proteins between interleukin 2 and IgM heavy chain are cytotoxic for cells expressing the interleukin 2 receptor," *Proc Natl Acad Sci U S A.* (Dec. 1, 1992) 89(23):11337-41.
Visvader et al., "Cancer stem cells in solid tumours: accumulating evidence and unresolved questions," *Nat Rev Cancer.* (Oct. 2008) 8(10):755-68.
Wharton KA, et al., "Nucleotide sequence from the neurogenic locus notch implies a gene product that shares homology with proteins containing EGF-like repeats," *Cell.* (Dec. 1985) 43(3 Pt 2):567-81.
Yao JC et al., "One hundred years after "carcinoid": epidemiology of and prognostic factors for neuroendocrine tumors in 35,825 cases in the United States," *J Clin Oncol.* (Jun. 20, 2008) 26:3063-72.
Zarebczan B, Chen H., "Signaling mechanisms in neuroendocrine tumors as targets for therapy," *Endocrinol Metab Clin North Am.* (2010) 39(4):801-10.
Zheng et al., "Administration of noncytolytic IL-10/Fc in murine models of lipopolysaccharide-induced septic shock and allogeneic islet transplantation," *J Immunol.* (1995) 154(10):5590-600.
Zhou, Bin-Bing S., et al., "Tumour-initiating cells: challenges and opportunities for anticancer drug discovery," *Nat Rev Drug Disco.* (Oct. 2009) 8(10):806-23.
Zimmerman et al., "A triglycine linker improves tumor uptake and biodistributions of 67-Cu-labeled anti-neuroblastoma MAb chCE7 F(ab')2 fragments," *Nucl Med Biol.* (1999) 26(8):943-50.
DLL3 Aptamer Presentation "Aptamer Technology for Cell-Specific Cancer Therapy," (Jul. 7, 2010) Academia Sinica.
Extended European Search Report issued in European patent application (No. 16164567.6).
Extended European Search Report issued in European patent application (No. 16164549.4).
Extended European Search Report issued in European patent application (No. 16164551.0).

(56) References Cited

OTHER PUBLICATIONS

International Search Report dated Apr. 4, 2014, issued in PCT/GB2014/050407.
International Search Report and Written Opinon of the International Searching Authority issued in PCT/US2013/027391 on Jan. 31, 2014.
Official action dated Jan. 16, 2015, issued in Australian patent application (No. 2013203459).
Official action dated May 15, 2015, issued in New Zealand patent application (No. 628804).
Official action dated Nov. 13, 2015, issued in European patent application (No. 13707525.5).
Official action dated Mar. 22, 2016, issued in European patent application (No. 13707525.5).
Official action dated Mar. 24, 2016, issued in Japanese patent application (No. 2014-558882).
Official action dated Mar. 24, 2016, issued in Japanese patent application (No. 2016-30269).
Official action dated Jun. 28, 2016, issued in Colombia patent application (No. 14-184.798).
Official action dated Aug. 1, 2016, issued in Chinese patent application (No. 201380010475.2).
Official action dated Oct. 10, 2016, issued in Australian patent application (No. 2013203459).
Official action dated Aug. 18, 2016, issued in Japanese patent application (No. 2014-558882).
Official acton dated Oct. 25, 2016, issued in Colombian patent application (No. NC2016/0002218).
Official action dated Mar. 26, 2017, issued in Israeli patent application (No. 234155).
Official action dated Feb. 28, 2017, issued in Japanese patent application (No. 2016-30270).
Official action dated Jan. 30, 2017, issued in New Zealand patent application (No. 628804).
Official action dated Jan. 30, 2017, issued in New Zealand patent application (No. 726045).
Official action dated Feb. 17, 2017, issued in New Zealand patent application (No. 628804).
Official action dated Jan. 26, 2017, issued in Russian patent application (No. 2014138474).

Homo sapiens delta-like 3 (DLL3), transcript variant 1, mRNA
>gi|189163470|ref|NM_016941.3|

SEQ ID NO:1

AGATATAAGGCTTGAAGCCAGCAGCTGCGACTCCCGAGACCCCCCACCAGAAGGCCATGGTGTCCCCACGGATGT
CCGGGCTCCTCTCCAGACTGTGATCCTAGCGCTCATTTCCTCCCCAGGTCCCCCCGCCCCGGTCTTCGAGCTG
CAGATCCACCTCTTTTCGGGCCGGGTCTGCGAAGCCTGGCTCTCCAGAGAGGAGGCCGCCCGGCCGGCCTGCTGCCCCTGA
CTTCTTCAGAGTCTGCCTGAACCGGTCTACACCGAGACAGCCGGCACCTTCTCTTTCATCATGAAACCTGGAGAGGAGTTAGGAGACCAGAT
GTGCGCGGACGCCGGTCTACACCGAGACAGCCGGCACCTTCTCTTTCATCATGAAACCTGGAGAGGAGTTAGGAGACCAGAT
GTGCCCTTCCGGACGCCTGGCCTGGCCTGCTGCGGCGGTGACCACCGGCAGGCGGGCGCCCTGCGCGTGCTGGGACCCGG
TGGAGGGCCCGCCTGGCCAGGCAGGCGCCCCTGGGAGCGCTGGGCGCCGCCCCTGGACACTGCGCCGTGCTGGGACCGCG
ACATTCAGCGCGCAGGACCCTGCGCCGTCGCGAGCGCCCCTCGGCGGTGCGTCCGAGCTGCCCCTGCGCACCGCTCGAGGA
TGCACGCGCCTCTGCCCTCCGCGAGCCGCTGCGGCTGTGCCGGACCCCCCTCGCAGCATCCTCCAGCCCGCCGAGGA
CGAATGCTGAGGGCCGCTGGGCTGGTCAGTGAGAAGAACCGGCCTGGGTCCAGCACCAGCCCGTGAATGCC
GATGCCTAGAGGCCTACGACACCCTCTGCAGGCGCCTGGGCCTGCGCGGAGCCTCGGAGACCCCGGACGATGCCTGG
TCCTCTGCTACCACGCCGATGCTCTTTGAATGACACCTGCGGCCTGCGTGCCAATGAGGCAGCTG
TAGTGAGACACAGCCAGGTCCTTTGAATGACCTGCGGGTCTACGGCGTGACCGGCAGCCGGGACCCTGGGTGA
CATGTGCAGATGCAGATCCCGGTTTCCAAGCGCTCCAAGTGTGAGAAGAAGCAATGTGAGGACCGGGTGACAGCGGTGGACCGGTCAGCCTGGAGCCATGCCGCAATGGCGG
ACTCTGCCTGGACCTGGGCCACGCCTGGGCCCTGGCGCTAACGGGGCGGCGGCGGCACGTGTGTGCCGCCGCTGCACCGCTGCTCCTGC
TGGACGACTGCCCGGGCTCGCGGGCCGCCGCGGCGCTCGGCGTCTGCGCGCGAGCTCTCGCGGGCTACAATGGGAGCGGTGTGAGTTCCCAGTGC
GCGCTGGGCTTCGCGGGCGGCCGACTGCTCTCGGCGCGCCGGGGCGGGGGCCTGCGCGCGCCTGCCAGCGCTCCCGGGACCCTCCCAGCGCTGAACTGGAGCCGCGGTACCCTGAGTGTCCCAGTGCC
CTGCTACCGCGGCGCAAGCGCCCTTCCAGGCCGCCGACGGCCTTGCCCGCCGCCGGGCCTTGGCGCTGCGCCGCGCCCCGGAGGACCCTCTGCTCAGTCACGTGGCGCCGCCGTGGCCA
CCGGGCTCTGGGACTGCTCGTCGGGTCTCGCTGCTGCAGCCCCGAGCTCGCTGCAGTCCGTCCTGTCCAGCTCCCGATGCACTCCCGATCACTCAACA
CTCCCAGGAGCACGTCTGGGTGAGGTTCCGGAGCTGCCCATGCTGGGACCCCGAGCTCGTCCGAGGAGCCGTGATTGGAATCGCCCCTGAAGATCTAGACCCT
CAAGGGATTTATGTCATATCTGTCTGGGCAGGAGCAGCCCATTTTCCCTACCGCTCCGATTCTGTCCGTGAAATGAATTGGGTAGA
TGGGCGCTGGGACAGGAGGCGCACATTTTTAAGCCACCATTTTGGAATCTGTCCGATTCTGTCCGTGAAATGAATTGGGTAGA
GTCTCTGGAAGGTTTTAAGCCACCATTTTCAGTCAACTCAGTTCAGTTCATCCTATTTGCAATCCCTCTTATCGTTTTGAG
CTACCTGCCATCTCTCTTTGAAAAACCTATGGCTTGAGGAGGTCACGATGCCGACTCCGCCAGAGCTTTTCCACT
GATTGTACTCAGCGGGGAGGCAGGGGAGGCAGGGCCAGCCGTTGATTTTCCTCTCTAAATGCTTCCTACTCATTTTGTTTCTAGGCC
TGACGCGTCTCCTCCATCCGACACCTTGAAGGGCGTCTCTGGGGGAACACCCTATAAAGGCTATTATTGTGATCAGTTTGAATAATGGTTATTA
CAGAAGGCTTTGAGTTCAATCTTGAAGGGCGTCTCTGGGGGAACACCCTATAAAGGCTATTATTGTGATCAGTTTGATCAGTTTGACTAACAAAA
TATCCTATTTTTTCTCACCCCATCCTCTAGAAACACCTATAAAGGCTATTATTGTGATCAGTTTGACTAACAAAA

FIG. 1A

Homo sapiens delta-like 3 (DLL3), transcript variant 2, mRNA
>gi|189163469|ref|NM_203486.2|

SEQ ID NO. 2

AGATATAAGGCTTGGAAGCCAGCAGCTGCGACTCCCGAGACCCCCACCAGAAGGCCATGGTCTCCCACGATGTC
CGGGCTCCTCTCCCAGACTGTGATCCTAGCGCTCTAGCCTCATTTCCTCCCAGACACGGCCCGCTGGCGTCTTCGAGCTGCA
GATCCACTCTTTCGGGCCGGGTCCAGGCCCTGAGCCCTGGGGCCCGGTCCGAGTCCCCGGTGCCCCGGCGGCGCCCGCCTCTT
CTTCAGAGTCTCCCTGAAGCCTGGCCTCTCAGAGGAGGCGGCCCCGAGCCCGGCCCTGATCTCCCACTGCCGGCGCCTTGCAGGTGCC
GCGGGACCGGTCTACACCGAGCAGCCTGGCACCTTTCTCTTTGCAATCATGGAGAGAGGAGTTAGGAGACCAGAGTTGGAGG
CTTCCGGGACGCGCCTGGCCTGCTGGGCCGCGTGGCCGCGTCTGGCCAGCGGCCCGTGGCCCGGACATTCA
GCCCGCCTGGAGCGCCTGCTGGGAGCGCCTGGAGCTGCTGGTACCGGGGGTCCGGGACGCGCCTGCACGCG
CCCTCGCCGTCCGCAGCGCCCCCCTCGCGGACTGCGGGGACTGCTTCTGTGAACAGCCGGTGAATGCCAGGAATGA
GGCTGGTGTGCCGAGCAGCTGCCAGGCCCCTCTGCAGGTTCCCACCAGCAGCTGCCTCAGCAGCCCCGTCCTCTGCTAC
GGCTGGACTGGACCCCCTCTGCAGGTTCCCTGGGCCTGTGGGCTTCTACGCGTGCCAGGGCTGCAATGAGGCCGCTGTAGTGCAGACACC
CAGGTCCTTTGAATGCCACTGCTTCAACCGGCTTGTGTGTTGTGAGAGAGAGGGTGCAGACCCTGACTCTGCCTTACACATCTGCCACTGCCTGCACCGT
ACCCTGCTTCAACGCTCCAACTGTGAGAGAGAGGGGTGACCGGCAGCCGTGCAGCGCCATGGCGAATGGCGGACACCTGCGGCTGCGCGGG
CCAAGGCTCCAACTGTGAGAGAGAGGGGTGCCGCGGCCTGCGCACGTGTGTGGAGGCGGCACGTGGGCGCGCGGG
GGCCACGCCCCTGCGCGCTGCCTGCCCGCGCTAACGGGGCGCGCGCCACGTGTGTCCGGGAGCACGACCTGCGCGTTGGGCTTCGGCGG
CCGCGCGCTGCGCGCGCCCTGAGGGGCGCGGCTGCGCGCTGCGCCTGTGCTCATGGGAGAGCCCCTGCAGTCCTGGGACCCGGGGCTACCGCTCTC
CGGACTGCCGCAGCGTGGCCCGCCCTCCCGGCCTCAGGCCCGGGCTCCCCTGGGCCCTACATGCGGGTGGCTACACATGCCCGGCGTCCACCCGACGCGC
CTTGCCCCGCGGGGCCGGGTGCCCGGGCCTCGGCCTCGGCCCGGGCTGGGCCTGGTCAGTCAGCGACCTCAGCGCACTCCCGCGCGCCACTCCCGGCTCTTGGGGTCTCGT
GGCGGGCGGCCCGGTGGCCGCGGCCTGCCGCTGCCGTCAGCTCCCACGTCCCGGATGCACTCAACAACCTAAGGACGCAGGAGGGTTC
CTTGCTGGCTGGGACCCCGAGCTCGTCCGTAGATTGGAATCGCCCTGAAGATGTAGACCCCACCTGGAGTCAGACGTCAGAGCGTGGATTTTTGTATTTG
CGGGGATGGTCCGGTCCGAGCTCGTCCGTAGATTGGAATCGCCCTGAAGATGTAGACCCCACCTGGAGTCAGACGTCAGAGCGTGGATTTTTGTATTTG
TCCTTCCATCTACGCTCGGAGGCCTGACGCGTCTGAGGGCTTTCGGAGCTTAATCTTCACCCCCATCTCTCTAGAAACACCTATAAAGGCTATTATTG
AAGTTGTAAATAATGGTTATTTTATATCCTATTTTCTCACCCCATCTCTCTAGAAACACCTATAAAGGCTATTATTG
TGATCAGTTTTGACTAACAAAAAA

FIG. 1B

Homo sapiens delta-like protein 3 (DLL3) isoform 1 precursor
>gi|8393264|ref|NP_058637.1|

SEQ ID NO. 3

MVSPRMSGLLSQTVILALIFLPQTRPAGVFELQIHSFGPGPGPGAPRSPCSARLPCRLFFRVCLKPGLSE
EAAESPCALGAALSARGPVYTEQPGAPAPDLPLPDGLLQVPFRDAWPGTFSFIIETWREELGDQIGGPAW
SLLARVAGRRRLAAGGPWARDIQRAGAMELRFSYRARCEPPAVGTACTRLCRPRSAPSRCGPLRPCAPL
EDECEAPLVCRAGCSPEHGFCEQPGECRCLEGWTGPLCTVPVSTSSCLSPRGPSSATTGCLVPGPGPCDG
NPCANGGSCSETPRSFECTCPRGFYGLRCEVSGVTCADGPCFNGGLCVGGADPDSAYICHCPPGFQGSNC
EKRVDRCSLQPCRNGGLCLDLGHALRCRCRAGEAGPRCEHDLDDCAGRACANGTCVEGGAHRCSCALG
FGGRDCRERADPCAAHPCAHGGRCYAHFSGLVCACAPGYMGARCEFPVHPDGASALPAAPPGLRPGDPQR
YLLPPALGLIVAAGVAGAALLLVHVRRRGHSQDAGSRLLAGTPEPSVHALPDALNNLRTQEGSGDGPSSS
VDWNRPEDVDPQGIYVISAPSIYAREVATPLFPPLHTGRAGQRQHLLFPYPSSILSVK

FIG. 1C

Homo sapiens delta-like protein 3 (DLL3) isoform 2 precursor
>gi|45243561|ref|NP_982353.1|
SEQ ID NO. 4

MVSPRMSGLLSQTVILALIFLPQTRPAGVFELQIHSFGPGPGPGAPRSPCSARLPCRLFFRVCLKPGLSE
EAAESPCALGAALSARGPVYTEQPGAPAPDLPLPDGLLQVPFRDAWPGTFSFIETWREELGDQIGGPAW
SLLARVAGRRRLAAGGPWARDIQRAGAWELRFSYRARCEPPAVGTACTRLCRPRSAPSRCGPGLRPCAPL
EDECEAPLVCRAGCSPEHGFCEQPGECRCLEGWTGPLCTVPVSTSSCLSPRGPSSATTGCLVPGPGPCDG
NPCANGGSCSETPRSFECTCPRGFYGLRCEVSGVTCADGPCFNGGLCVGGADPDSAYICHCPPGFQGSNC
EKRVDRCSLQPCRNGGLCLDLGHALRCRCRAGFAGPRCEHDLDDCAGRACANGGTCVEGGAHRCSCALG
FGGRDCRERADPCAARPCAHGGRCYAHFSGLVCACAPGYMGARCEFPVHPDGASALPAAPPGLRPGDPQR
YLLPPALGLLVAAGVAGAALLLVHVRRRGHSQDAGSRLLAGTPEPSVHALPDALNNLRTQEGSGDGPSSS
VDWNRPEDVDPQGIYVISAPSIYAREA

FIG. 1D

Alignment of two human DLL3 isoforms (NP_058637 = var 1; NP_928353 = var 2)

```
                    1                                                                               80
NP_058637    (1)    MVSPRMSGLLSQTVTLALIFLPQTRPAGVTFLQIHSFGPGPGPGAPRSPCSARLPCRLPFRVCLKPGLSEEAAESPCALG
NP_982353    (1)    MVSPRMSGLLSQTVTLALIFLPQTRPAGVTFLQIHSFGPGPGPGAPRSPCSARLPCRLPFRVCLKPGLSEEAAESPCALG 81                                                                              160
NP_058637    (81)   AALSARGPVYTEQPGAPAPDLPLPDGLLQVPFRDAWPGTFSFIIETWREELGDQIGGPAWSLLARVAGRRRLAAGGPWAR
NP_982353    (81)   AALSARGPVYTEQPGAPAPDLPLPDGLLQVPFRDAWPGTFSFIIETWREELGDQIGGPAWSLLARVAGRRRLAAGGPWAR 161                                                                             240
NP_058637    (161)  DIQRAGAWELRFSYRARCEPPAVGTACTRLCRPRSAPSRCGPGLRPCAPLEDECEAPLVCRAGCSPEHGFCEQPGECRCL
NP_982353    (161)  DIQRAGAWELRFSYRARCEPPAVGTACTRLCRPRSAPSRCGPGLRPCAPLEDECEAPLVCRAGCSPEHGFCEQPGECRCL 241                                                                             320
NP_058637    (241)  EGWTGPLCTVPVSTSSCLSPRGPSSATTGCLVPGPGPCDGNPCANGGSCSETPRSFECTCPRGFYGLRCEVSGVTCADGP
NP_982353    (241)  EGWTGPLCTVPVSTSSCLSPRGPSSATTGCLVPGPGPCDGNPCANGGSCSETPRSFECTCPRGFYGLRCEVSGVTCADGP 321                                                                             400
NP_058637    (321)  CFNGGLCVGGADPDSAYICHCPPGFQGSNCEKRVDRCSLQPCRNGGLCLDLGHALRCRCRAGFAGPRCEHDLDDCAGRAC
NP_982353    (321)  CFNGGLCVGGADPDSAYICHCPPGFQGSNCEKRVDRCSLQPCRNGGLCLDLGHALRCRCRAGFAGPRCEHDLDDCAGRAC 401                                                                             480
NP_058637    (401)  ANGGTCVEGGGAHRCSCALGFGGRDCRERADPCAARPCAHGGRCYAHFSGLVCACAPGYMGARCEFPVHPDGASALPAAP
NP_982353    (401)  ANGGTCVEGGGAHRCSCALGFGGRDCRERADPCAARPCAHGGRCYAHFSGLVCACAPGYMGARCEFPVHPDGASALPAAP 481                                                                             560
NP_058637    (481)  PGLRPGDPQRYLLPPALGLLVAAGVAGAALLLVHVRRGHSQDAGSRLLAGTPEPSVHALPDALNNLRTQEGSGDGPSSS
NP_982353    (481)  PGLRPGDPQRYLLPPALGLLVAAGVAGAALLLVHVRRGHSQDAGSRLLAGTPEPSVHALPDALNNLRTQEGSGDGPSSS 561                                618
NP_058637    (561)  VDWNRPEDVDPQGIYVISAPSIYAREVATPLFPPLHTGRAGQRHLLFPYPSSILSVK                          SEQ ID NO. 3
NP_982353    (561)  VDWNRPEDVDPQGIYVISAPSIYAREA-----                                                   SEQ ID NO. 4
```

FIG. 1E

Percent Identity Between Homo sapiens DLL Family Member Proteins

Complete protein

| DLL Family Homo sapiens | DLL1 (NP_005609) | DLL3v1 (NP_058637) | DLL3v2 (NP_982353) |
|---|---|---|---|
| DLL3v1 (NP_058637) | 28.8% | | |
| DLL3v2 (NP_982353) | 28.0% | 94.8% | |
| DLL4 (NP_061947) | 48.1% | 28.0% | 28.8% |

ECD

| DLL Family Homo sapiens | DLL1 (NP_005609) | DLL3v1 (NP_058637) | DLL3v2 (NP_982353) |
|---|---|---|---|
| DLL3v1 (NP_058637) | 33.8% | | |
| DLL3v2 (NP_982353) | 33.8% | 100.0% | |
| DLL4 (NP_061947) | 52.0% | 32.6% | 32.6% |

FIG. 2A

Percent Identity Between DLL3 Proteins From Various Species

| DLL3 | rhesus (XP_001088937) | mouse (NP_031892) | rat (NP_446118) |
|---|---|---|---|
| human | 95.7% (v1) | 82.6% (v2) | 81.5% (v2) |
| mouse (NP_031892) | | | 93.9% |

FIG. 2B

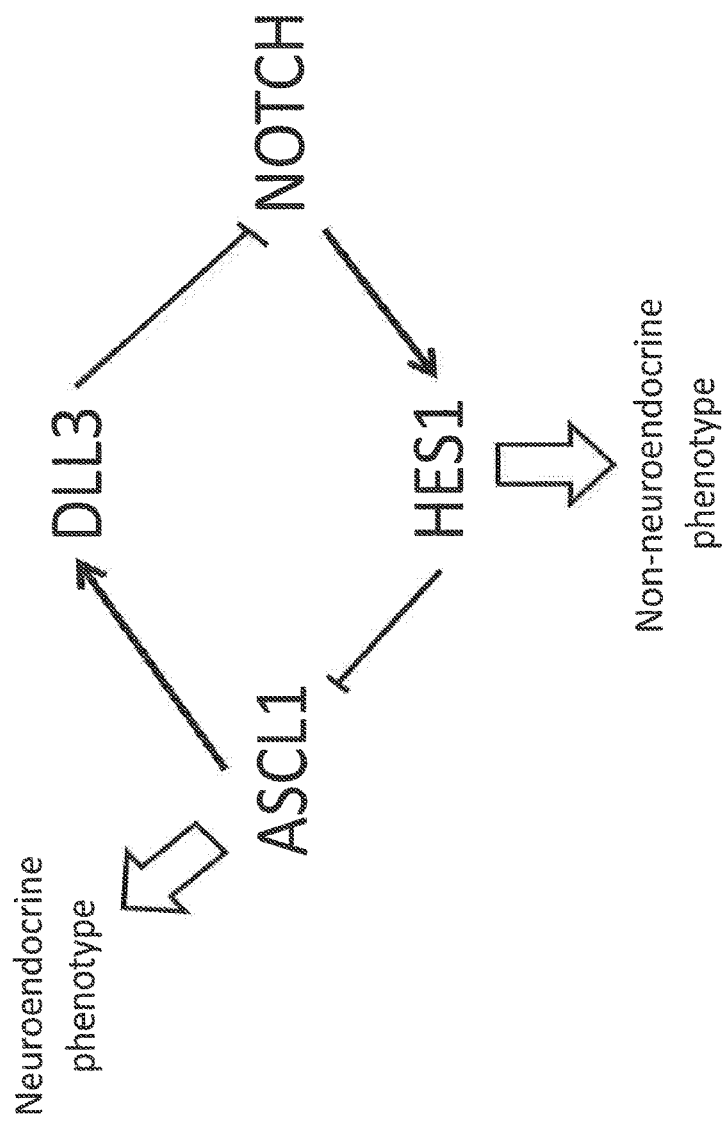

Relative Expression Values for Selected mRNA Transcripts in Various Samples as Determined by Whole Transcriptome Sequencing

| | DLL1 | DLL3 | DLL4 | NOTCH1 | NOTCH2 | NOTCH3 | NOTCH4 | ASCL1 | NCAM1 | CHGA | HES1 | HES6 | HEY1 |
|---|---|---|---|---|---|---|---|---|---|---|---|---|---|
| LU37p3-LCNEC | 86.1 | 93.7 | 4.5 | 0.1 | 14.4 | 7.8 | 0.7 | 269.9 | 72.0 | 94.0 | 2.7 | 55.1 | 5.6 |
| LU54p2-SCLC | 10.9 | 34.3 | 10.8 | 8.2 | 0.2 | 0.7 | 5.7 | 418.4 | 57.8 | 295.3 | 6.3 | 305.2 | 2.0 |
| LU73p1-SCLC | 109.8 | 227.8 | 16.6 | 4.2 | 0.0 | 33.0 | 195.6 | 269.6 | 77.5 | 55.0 | 34.5 | 271.0 | 33.9 |
| LU86p3-SCLC | 4.7 | 11.9 | 12.2 | 18.7 | 176.8 | 14.5 | 0.5 | 0.4 | 269.2 | 17.7 | 13.9 | 285.2 | 9.9 |
| LU95p2-SCLC | 2.4 | 16.0 | 1.5 | 2.1 | 0.4 | 8.5 | 12.2 | 273.2 | 125.5 | 18.2 | 2.8 | 72.6 | 9.3 |
| LU137p0-LU_Ad | 1.8 | 0.0 | 4.3 | 10.6 | 387.7 | 27.5 | 0.4 | 0.0 | 0.0 | 0.0 | 54.6 | 1.5 | 1.7 |
| LU146p0-LU_Ad | 0.0 | 0.0 | 0.3 | 5.6 | 56.8 | 37.9 | 3.9 | 0.0 | 0.8 | 0.0 | 40.9 | 0.8 | 0.3 |
| LU153p0-LU_Ad | 0.8 | 0.0 | 5.7 | 8.1 | 195.1 | 8.0 | 6.5 | 0.2 | 4.4 | 0.0 | 4.8 | 0.2 | 1.4 |
| LU49p4-LU_SCC | 2.6 | 0.7 | 0.0 | 7.6 | 104.2 | 0.0 | 1.3 | 0.0 | 0.0 | 0.3 | 92.1 | 4.3 | 0.0 |
| LU70p4-LU_SCC | 4.7 | 0.0 | 0.6 | 12.6 | 123.2 | 1.8 | 0.1 | 0.0 | 0.8 | 0.3 | 42.3 | 2.1 | 0.0 |
| LU75p5-LU_SCC | 0.8 | 0.0 | 4.8 | 20.0 | 32.5 | 0.1 | 0.0 | 3.4 | 0.3 | 0.3 | 23.0 | 0.8 | 0.0 |
| OV26p3-OV | 34.2 | 65.4 | 15.7 | 0.0 | 101.0 | 17.4 | 0.6 | 253.7 | 138.8 | 23.1 | 4.3 | 35.1 | 7.1 |
| OV108p0-OV | 0.0 | 0.5 | 0.4 | 3.6 | 154.3 | 16.3 | 0.5 | 0.0 | 2.0 | 0.0 | 0.0 | 0.0 | 17.3 |
| OV45p3-OV | 1.7 | 1.9 | 0.1 | 14.9 | 53.2 | 84.5 | 2.7 | 0.0 | 60.4 | 0.1 | 14.6 | 2.4 | 6.7 |
| OV55p5-OV | 0.3 | 0.2 | 0.0 | 31.0 | 139.8 | 71.7 | 1.4 | 0.0 | 11.4 | 0.0 | 19.4 | 1.9 | 2.0 |
| OV72METp0-OV | 0.0 | 0.1 | 0.2 | 1.6 | 207.1 | 46.8 | 0.2 | 0.3 | 34.5 | 0.1 | 17.1 | 1.9 | 1.0 |
| OV91METp0-OV | 0.3 | 1.6 | 0.1 | 10.5 | 360.2 | 306.7 | 2.3 | 0.0 | 3.9 | 0.0 | 31.7 | 1.2 | 11.4 |
| Normal Lung 1 | 1.7 | 0.0 | 5.7 | 8.2 | 85.9 | 33.1 | 11.4 | 0.4 | 3.4 | 0.0 | 13.8 | 0.1 | 6.5 |
| Normal Lung 2 | 17.0 | 0.1 | 8.8 | 24.0 | 81.5 | 54.0 | 92.3 | 5.3 | 4.5 | 0.4 | 23.2 | 2.4 | 40.5 |
| Normal Lung 3 | 26.9 | 0.2 | 36.6 | 160.6 | 25.6 | 238.5 | 91.3 | 0.8 | 1.8 | 1.3 | 11.9 | 8.1 | 14.1 |
| Normal Lung 4 | 0.2 | 0.0 | 6.0 | 11.8 | 81.5 | 40.4 | 15.8 | 0.0 | 1.2 | 0.0 | 11.4 | 0.3 | 0.8 |
| Normal Ovary | 0.3 | 0.0 | 5.1 | 7.8 | 250.6 | 44.1 | 5.1 | 0.6 | 125.5 | 0.2 | 8.5 | 0.7 | 0.4 |

FIG. 4A

Average Normalized Intensity Values for Common Markers of Neuroendocrine Phenotype

| | Gene Symbol | Median (48 samples) | Cluster C | | | | | | | Cluster D | | | Cluster G | |
|---|---|---|---|---|---|---|---|---|---|---|---|---|---|---|
| | | | KD66 | LU50 (LCNEC) | OV26 | LU102 (SCLC) | LU37 (LCNEC) | LU86 (SCLC) | LU64 (SCLC) | LU95 (SCLC) | LU49 (SCC) | LU85 (SCC) |
| Achaete-scute complex homolog 1 | ASCL1 | 9 | 6589 | 8238 | 9352 | 12169 | 9664 | 11 | 3396 | 10298 | 8 | 5 |
| Calcitonin | CALCA | 73 | 16138 | 8352 | 11035 | 14633 | 4547 | 70 | 24 | 247 | 52 | 39 |
| CGRP | CALCB | 143 | 2534 | 1147 | 1547 | 2584 | 2757 | 6189 | 483 | 126 | 65 | 81 |
| CD117, Kit receptor | KIT | 343 | 5978 | 4907 | 3561 | 6416 | 6254 | 12760 | 11215 | 15387 | 34 | 301 |
| Chromogranin A | CHGA | 53 | 6167 | 8302 | 12846 | 8206 | 7408 | 7850 | 10866 | 9571 | 249 | 236 |
| Chromogranin B | CHGB | 22 | 1615 | 2252 | 1516 | 1456 | 1242 | 2365 | 1362 | 4151 | 32 | 24 |
| Dopa decarboxylase | DDC | 2441 | 21606 | 4512 | 23555 | 21824 | 25701 | 1498 | 4234 | 9297 | 134 | 286 |
| Gamma (Neural) Enolase | ENO2 | 1910 | 2054 | 1881 | 1911 | 1573 | 1262 | 4043 | 4737 | 11020 | 2472 | 2241 |
| GFRA1 | GFRA1 | 9 | 263 | 29 | 37 | 146 | 133 | 90 | 4 | 6 | 9 | 4 |
| CD56 | NCAM1 | 82 | 551 | 875 | 801 | 999 | 777 | 2618 | 2519 | 3296 | 425 | 106 |
| PGP9.5 | UCHL1 | 415 | 16445 | 5168 | 12862 | 7412 | 4957 | 4414 | 9745 | 15738 | 122 | 825 |
| Proopiomelanocortin | POMC | 94 | 751 | 407 | 530 | 750 | 657 | 66 | 560 | 5204 | 213 | 160 |
| Somatostatin | SST | 67 | 27000 | 1316 | 18913 | 5869 | 2189 | 35 | 9 | 62 | 90 | 28 |
| Somatostatin Receptor 5 | SSTR5 | 613 | 733 | 906 | 875 | 636 | 633 | 907 | 344 | 622 | 918 | 401 |
| Synaptophysin | SYP | 19 | 15 | 15 | 9 | 17 | 15 | 27 | 53 | 91 | 11 | 19 |
| Thyroid Transcription Factor 1 | NKX2-1 | 18 | 3137 | 3508 | 2754 | 5180 | 3315 | 1258 | 3585 | 2229 | 85 | 8 |

FIG. 6B

Average Normalized Intensity Values for Selected Genes in the Notch Pathway and ASCL1

| | Median (48 samples) | Cluster C | | | | | Cluster D | | | Cluster G | |
|---|---|---|---|---|---|---|---|---|---|---|---|
| | | KD66 | LU50(LCNEC) | OV26 | LU102(SCLC) | LU37(LCNEC) | LU86(SCLC) | LU64(SCLC) | LU95(SCLC) | LU49(SCC) | LU85(SCC) |
| ASCL1 | 9 | 6589 | 8238 | 8982 | 11169 | 9664 | 11 | 3390 | 10298 | 8 | 5 |
| DLL1 | 51 | 348 | 565 | 406 | 497 | 179 | 218 | 98 | 514 | 29 | 120 |
| DLL3 | 350 | 4584 | 3985 | 6232 | 5884 | 5233 | 1686 | 3137 | 5814 | 601 | 492 |
| DLL4 | 614 | 601 | 445 | 592 | 301 | 280 | 763 | 198 | 673 | 357 | 469 |
| HES1 | 670 | 128 | 129 | 160 | 92 | 82 | 551 | 137 | 335 | 2665 | 2024 |
| HES6 | 117 | 196 | 361 | 481 | 416 | 279 | 5456 | 2716 | 3535 | 28 | 33 |
| HEY1 | 89 | 86 | 101 | 116 | 103 | 77 | 1660 | 680 | 2502 | 3776 | 231 |
| HEYL | 87 | 157 | 132 | 128 | 148 | 132 | 2645 | 102 | 267 | 333 | 80 |
| JAG1 | 630 | 159 | 114 | 110 | 95 | 111 | 743 | 524 | 311 | 9131 | 678 |
| JAG2 | 125 | 335 | 529 | 398 | 420 | 247 | 324 | 513 | 611 | 159 | 153 |
| NOTCH1 | 666 | 34 | 23 | 41 | 17 | 14 | 1039 | 381 | 202 | 4720 | 438 |
| NOTCH2 | 26 | 6 | 11 | 12 | 16 | 12 | 105 | 11 | 1 | 37 | 5 |
| NOTCH3 | 101 | 13 | 27 | 91 | 81 | 72 | 302 | 37 | 136 | 1474 | 322 |
| NOTCH4 | 14 | 6 | 7 | 13 | 9 | 5 | 14 | 15 | 69 | 14 | 7 |
| RBPJ | 1289 | 1891 | 2255 | 1933 | 2717 | 2278 | 4502 | 2678 | 5107 | 1226 | 1029 |

FIG. 6C

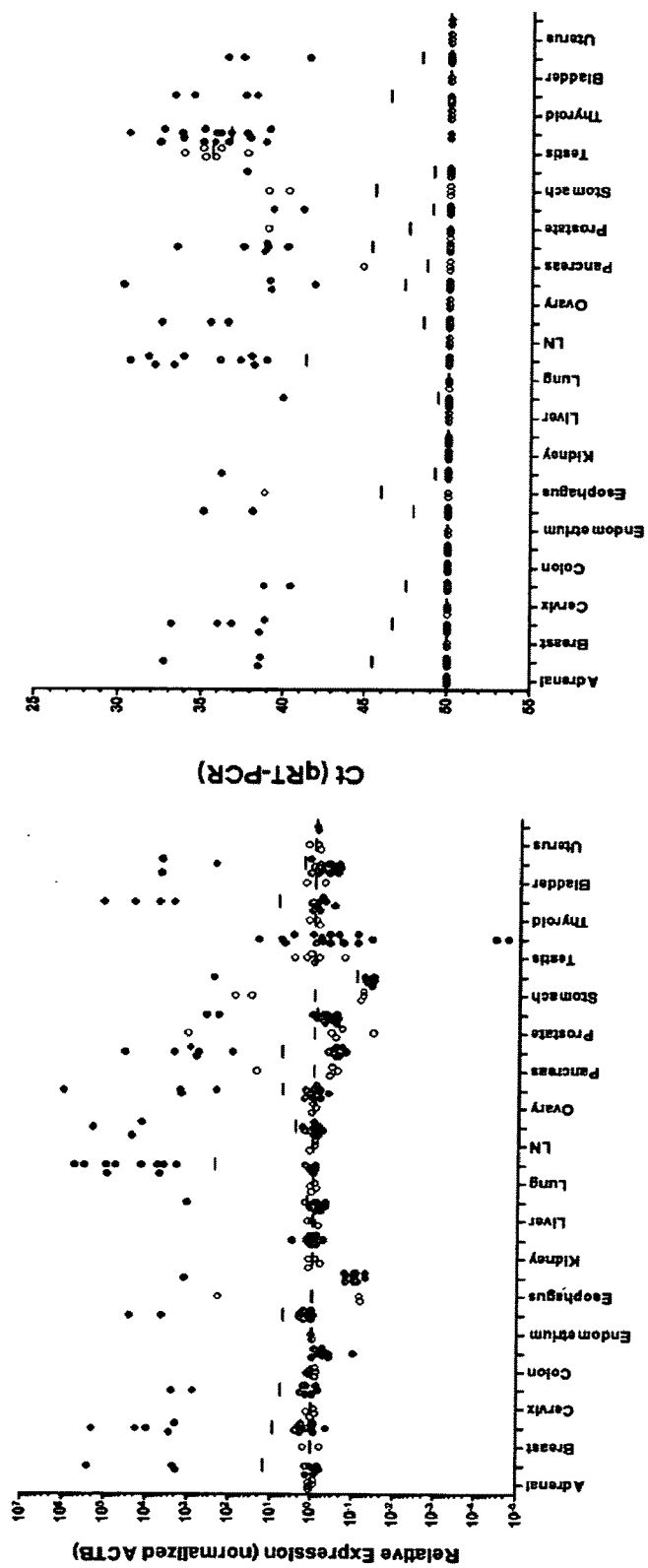

>mature murine DLL3 DNA in lentiviral vector

SEQ ID NO. 5

GCTGGTGTCTTCGAGCTACAAATTCATTCTTTCGGGCCAGGCCCAGGCCCTCGGGACCCCACGCT
CCCCCTGCAACGCCCGAGGCCCTTGCCGCGCCTCTTCTTCAGGGTCTGCCTGAAGCCCGGAGTCTC
CCAGGAGGCCACCGAGTCCCCTGTGCGCGCAGCAGCACTGAGCACGAGCGTCCCGGTCTAT
ACGGAGCACCCCGGAGAGTCAGCGGCTGCCCTGCCCTGCCCTGATGCCTCGTACGTGTGCCCT
TCCCGATGCTTGGCCGGGCACCTTCTCCCTGTCATTGAAAACCTGGAGAGAGCAGCTGGGAGA
GCATGCTGGAGGGCCCGCCTGGAACCTGCTAGCACGTGGTCGGCCGTAGACGCCTGGCGGCT
GGGGGCCCCGTGGGCCCCGATGTGCAGCGCACAGGCACATGGGAGTTGCACTTCTCCTACCCG
CGCGGTGCGAGCGCGCCCGTCGGGCGCCTGTGCCGCCTGTGCCGCTCACGCAGTGCCC
CTCGCGGTGTGGCCGGGACTGCAGCCCGACCACGGCCTACTGCTCCTGAAGACGCTGAAGTCCCGTTGCC
GTGTGTCGACCAGGCTGCAGCCCCCTCTGCAGCACCGGTCCCTGTCTCCACCAGTAGCTGCCTGAACTCCAG
TGGAGGGCTGGACTGGACCCGTCCGCCAGCACTGGATGCCTTTGAAAACCTCTGGCCTTCCTGTCCTGTCCCCGGGAT
GGTTCCTGGTCCTGCCAGCACTGTAGTGAAGATCCTGACTCCTTTGAAAACCTCTGGCCTTCCTGTCCTGTCCCCGGGAT
TGTGCCAATGGGGCAGTCTTGAGGGTGCAGGTGGAGCTCCCGCAGATGACCCTGCTTCAATGGCGG
TCTACGGGCTTCGATGTGAGGGTGGGTCACGTGCCCGCAGATGACCCTGCTTCAATGGCGG
CTTGTGTGTTGCGGTGAAGATGTGACTCTGCCTATGTCTGTCATTGCCACCTGGTTTCCAA
GGCTCTAACTGTGAAGAGAGGGTTGCGCACGGTGGCCCATGTCCAGCCATGTCAGAATGGCGGCTCT
GCACGACCTGGCCACGGCGTTGCGCCGGCCGTGCGCGCCTCGCCAACGGCGGCACGTGCGTGGAGGGCGGC
GGCTCGCGCCGCTGACGACTGCGCCTCCTGTCGCCGCCTGGGCTTGCGGCCGACTGCCGAGAACGCGCCGACC
CCTGCGCCCCCCGCGGCTACATGGGCCTGAGGCGTGAGATGCGAGGCGTGAGATCCGAGTTCGCTGTGCGCCGACGGCGGAC
GCGGTGCCCGCGCGCCGCGCCCCCGGGGCCGCCGGATCCACAGCAGGCGATCCACAGCTCTTGCTTCTTCTGCCTCCG
CCTTGGGGCTGCTGGTGGTGGCCGCCGGTTTGGCTGCTGGCGGACCTGCCTGCTTTCTGGACCCGCTTGCCGCCACGTTCGCCG
CCGAGGTCCTGGCCAGGATACCGGGACTCGCCTGCTTTCTGGACCCGGAGCCTTGGTCCAC
ACGCTCCCCGATGCACTCAACAACCTGAAGTTACAAGACGGTGCTGGGGATGCTGGGGGATGGCCCCAGTTCGT
CGGCTGACTGGAATCATCCTGAAGATGGAGACTCTAGATCCATTTATGTCATACCAGCCCCTTC
CATTTATGCACGAGAGGCCTGA

FIG. 10A

>translation of mature murine DLL3 in lentiviral vector

SEQ ID NO. 6

AGVFELQIHSFGPGPGLGTPRSPCNARGPCRLFFFRVCLKPGVSQEATESLCALGAALSTS
VPVYTEHPGESAAALPLPDGLVRVPFRDAWPGTFSLVIETWREQLGEHAGGPAWNLLARV
VGRRRLAAGGPWARDVQRTGTWELHFSYRARCEPPAVGAACARLCRSRSAPSRCGPGLRP
CTPFPDECEAPSVCRPGCSPEHGYCEEPDECRCLEGWTGPLCTVPVSTSSCLNSRVPGPA
STGCLLPGPGPCDGNPCANGGSCSETSGSFECACPRGFYGLRCEVSGVTCADGPCFNGGL
CVGGEDPDSAYVCHCPPGFQGSNCEKRVDRCSLQPCQNGGLCLDLGHALRCRCRAGFAGP
RCEHDLDDCAGRACANGGTCVEGGSRRCSCALGFGGRDCRERADPCASRPCAHGGRCYA
HFSGLVCACAPGYMGVRCEFAVRPDGADAVPAAPRGLRQADPQRFLLPPALGLLVAAGLLA
GAALLVIHVRRRGPGQDTGTRLLSGTREPSVHTLPDALNNLRLQDGAGDGPSSSADWNHP
EDGDSRSIYVIPAPSIYAREA

FIG. 10B

>Deduced mature cynomolgus DLL3 DNA                                    SEQ ID NO. 7

FIG. 10C

>translation of mature cynomolgus DLL3          SEQ ID NO. 8

PQARPAGVFELQIHSFGPGPGPGAPRSPCSARGPCRLFFRVCLKPGLSEEAAESPCALGA
ALSARGPVYTEQPEAPAPDLPLPNGLLQVPFRDAWPGTFSLIIETWREELGDQIGGPAWS
LLARVTRRRLAAGGPWARDIQRAGAWELRFSYRARCELPAVGTACTRLCRPRSAPSRCG
PGLRPCAPLEDECEAPPVCRAGCSLEHGFCEQPGECRCLEGWTGPLCMVPVSTSSCLGLR
GPSSATTGCLVPGPGPCDGNPCANGGSCSETPGSFECTCPRGFYGLRCEVSGVTCADGPC
FNGGLCVGGADPDSAYICHCPPGFQGSNCEKRVDRCSLQFCRNGGLCLDLGHALRCRCRA
GFAGPRCEHDLDDCAGRACANGGTCVEGGGAHRCSCALGFGGRDCRERADPCAARPCAHG
GRCYAHFSGLVCACAPGYMGARCEFPVHPDGVSALPAAPPGLRPGDPQRYLLPPALGLLV
AAGVAGAALLLGHVRRRGHAQDAGSRLLAGTPEPSVHALPDALNNLRTQEGPGDVPSSSV
DWNRPEDVDSRGIYVISAPSIYAREVAMPLFPPLHTGRAGQRQNLLFPYPSSILSVK

FIG. 10D

Protein Sequences of Exemplary DLL3 Modulator Light Chain Variable Regions

| mAb | FR1 | CDR1 | FR2 | CDR2 | FR3 | CDR3 | SEQ ID NO. |
|---|---|---|---|---|---|---|---|
| SC16.3 | QIVLTQSPAIMSVSLGERVTMTC | TASSSVSSSY | LHWYQQKPGSSPKLWIY | STSNLAS | GVPARFSGSGSGTSYFFTISSMEAEDAATYYC | HQYHRSPFTFGAGTKLEIR | 20 |
| SC16.4 | DIQMTQTTSSLSASLGDRVTISC | RASQDISNY | LNWYQQKPDGTVKLLIY | YTSRLHS | GVPSRFSGSGSGTDYSLTISNLELEDIATYFC | QQGDMLPWTFGGGTKLEIK | 22 |
| SC16.5 | QIVLTQSPAIMSASPGEKVTMTC | SASSSVSY | MHWYQQKSGTSPKRWIY | DTSKLAS | GVPARFSGSGSGTSYSLTISSMEAEDAATYYC | QQWTRNPLTFGAGTKLEIK | 24 |
| SC16.7 | NIMMMTQSPSSLAVSAGEKVTMSC | KSSQSVLVSSNQKNY | LAWYQQKPGQSPKLLIY | WASTRES | GVPDRFTGSGSGTDFTLTISTVQEDLAVYYC | HQYLSSWTFGGGTKLEIK | 26 |
| SC16.8 | EIQMTQSPSSMSASLGDRITITC | QATQERVKN | LNWYQQKPGKPSFLIY | YAIELAE | GVPSRFSGSGSGTDYSLTISNLESEDFADYYC | LQFEPPFTFGAGTKLELK | 28 |
| SC16.10 | QIVLTQSPAIMSASLGERVTMTC | TASSSVSSSY | LHWYQQKPGSSPKLWIY | STSNLAS | GVPTRFSGSGSGTSYSLTISSMEAEDAATYYC | HQYHRSPFTFGSGTKLEIK | 30 |
| SC16.11 | DVEMTQTPLTLSVTIGQPASISC | KSSQSLSDSDGKTY | LNWMFQRPGRSPKRLIY | LVSKLDS | GVPDRFTGSGSGTDFLKISRVEAEDLGVYYC | WQGKHFPWTFGSGGTKLEIK | 32 |
| SC16.13 | QIVLTQSPALVSASPGEKVTMTC | SASSSVSY | MFWYQQKPESSPKPWIY | LTSNLAS | GVPARFSGSGSGTSYSLTISSMEAEDAATYYC | QQWRSNPFTFGSGTKLEIK | 34 |
| SC16.15 | DKQMTQSPASLAASVGETVAITC | RASENIYYN | LAWYQQKQGKSPQLLIY | TANSLED | GVPSRFSGSGSGTQYSLKINSMQPEDSATYFC | KQAYDVPPTFGGGTKLEIK | 36 |
| SC16.18 | DIQMTQTTSSLSASLGDRVTISC | RASQDWIHY | LNWYQQKPDGTVKLLIY | YTSRLHS | GVPSRFSGSGSGTDYSLTISNLEPEDIATYYC | QQYSERPYTFGGGTKLEIKR | 38 |
| SC16.19 | DIQMTQSPSSLSASLGGKVTFTC | KASQBIHKY | VAWYQHKPGKGPRLLIH | YTSTLQP | GISSRFSGSGSGRDYSFSISNLEPEDIATYYC | LQYNNLYTFGGGTKLEIKR | 40 |
| SC16.20 | EIQMTQSPSSMSASLGDRITITC | QATQDIVKN | LNWYQQKPGKPPSFLIY | YATELAE | GVPSRFSGSGSGTDYSLTIRNLESEDFADHYC | LQFEPPFTFGAGTKLELK | 42 |
| SC16.21 | DNVMTQSPSSLAMSVGQKVTMSC | KSSQSLLNSSNQKNV | LAWYQQKPGQSPKLLVS | FASTRES | GVPDRFTGSGSGTDFTLTISGVQAEDLAVYYC | QQHYSIPLTFGAGTKLELK | 44 |
| SC16.22 | DIQMTQSPSSLSASLGDRVTISC | RASQDIKNY | LNWYQQKPDGTVKPLIY | YTSRVHS | GVPSRFSGSGSGTDYSLTISNLEQEDIATYFC | QQGYTLPTFGSGYKLE | 46 |
| SC16.23 | QIVLTQSPAIMSASPGEKVTLTC | SASSSVSSRY | LYWYQQKPGSSSPKLWIY | STSNLAS | GVPARFSGSGSGTSYSLTISSMEAEDAA5YFC | HQWSNYPLTFGAGTKLELK | 48 |
| SC16.25 | QIVLTQSPAIMSASPGEKVTMTC | SASSSVSY | MHWYQQKSGTSPKRWHY | DSSKLAS | GVPARFSGSGSGTSYSLTISSMEAEDAATYYC | QQWSSNLTFGAGTKLELK | 50 |
| SC16.26 | DVEMTQTPLTLSVTIGQPASISC | KSSQSLSDSDGKTY | LNWMFQRPGRSPKRLIY | LVSKLDS | GVPDRFTGSGSGTDFLKISRVEAEDLGVYYC | WQGKHFPWTFGGGTKLEIK | 52 |
| SC16.29 | QIVLTQSPAIMSASPGEKVTITC | SASSSVSY | MHWFQQKPGTSPKLWIY | TTSNLAS | GVPARFSGSGSGTSYSLTVSRMEAEDAATYYC | QQHSLYPTFGGGTKVEIK | 54 |
| SC16.30 | QIVLTQSPTIMSASLGERVTMTC | TASSSVTSSY | LHWYLQQRPESSPKLWIY | STSNLAS | GVPARFSGSGSGTSYSLTISSMEAEDAATYYC | HQSHRSPFTFGSGTKLEIK | 56 |
| SC16.31 | DIVLTQSPSLSLPVNIGDQASISC | KSTKSLLNSDGFFY | LDWYLQRPGQSPQEFLIY | LVSNRFS | GVPDRFSGSGSGTDFLKISRVEAEDLGVYYC | FQSNYLPLTFGAGTKLELR | 58 |
| SC16.34 | SIVIMTQTPKFLLVSAGDRVTITC | KASQSVSND | VAWYQQKPGQSPKLLIY | YASNRYS | GVPDRFTGSGVGTDFTFTISTVQAEDLAVYFC | QQDYSSPWTFGGGTKLEIK | 60 |
| SC16.35 | DIQMTQTTSSLSASLGDRVTISC | RASQDISNY | LNWYQQKPDGTVKLLIY | YTSRLHS | GVPSRFSGSGSGTDYSLTISNLEQEDIATYYC | QQGNTLPYTFGGGTKLEIK | 62 |
| SC16.36 | ETTVTQSPASLSVTTGEKVTIRC | ITTPDIDDD | MNWYQQKPGEPPNLLIS | EGMSLRP | GVPSRFSSSGYGTNFVFTIENTLSEDVADYYC | LQSDNMPFTFGSGTKLEIK | 64 |

FIG. 11A

Protein Sequences of Exemplary DLL3 Modulator Light Chain Variable Regions

| mAb | FR1 | CDR1 | FR2 | CDR2 | FR3 | CDR3 | SEQ ID NO. |
|---|---|---|---|---|---|---|---|
| SC16.38 | QIVLTQSPAIMSASPGEKVTMTC | SASSSIHV | MHWYQQKPGTSPKRWIY | DTSKLAS | GVPARFSGSGSGTSYSLTISSMEAEDAATYYC | HQRSTWTFGGGTKLEIK | 66 |
| SC16.41 | DIQMTQTTSSLSASLGDRVTISC | RASQDVHNY | LNWYQQKPDGTVKLLIY | YTSRLHS | GVPSRFSGSGSGRTDYSLTISNLEPEDIATYYC | QQYSERPYTFGGGTKLEIKR | 68 |
| SC16.42 | DVLMTQSPLSLSVSLGDQASISC | RSSQNIVHSDRYTY | LEWYLQKPGQSPKLLIY | GVSNRFS | GVPDRFSGSGSGTDFTLKISRVEAEDMGVYYC | FQGTHVPYTFGGGTKLEIK | 70 |
| SC16.45 | EIQMTQSPSSMSASLGDRIITIC | QATQDIVKN | LNWYQQKPGKPPSFLIY | YATELAE | GVPSRFSGSGSGTDYTISNLESEDFADYHC | LQFVEPPTFGAGTKLELA | 72 |
| SC16.47 | DIVLTQSPLSLPVNIGDQASISC | KSTKSLLNSDGFFY | LDWYLQRPGQSPQFLIY | LVSNRFS | GVPDRFSGSGSGSGTDFTLKISRVEAEDLGVYYC | FQSNYLPLTFGAGTKLELR | 74 |
| SC16.49 | DIKMTQSPSSMYASLGERVTITC | KASQDINSYL | SWFQQKPGKPKTLIY | RANRLVD | GVPSRFSGSGSGGQDYSLTITSSLEYEDMGIYYC | LQYDEFPLTFGAGTKLEIK | 76 |
| SC16.50 | DIQMTQTTSSLSASLGDRVTISC | RASQDISNY | LNWYQQKPDGTVKLLIY | YTSRLHS | GVPSRFSGSGSGTDYSLTISNLEQEDIATYFC | QQGNTLRTFGGGTKLEIK | 78 |
| SC16.52 | DIQMQSPSSMFASLGDRVSLSC | RASQGIRGT | LDWYQQKPGNGTIKLLIY | STSNLNS | GVPSRFSGSGSGDYSLTISSLESEDFADYC | LQRNAYPLTFGGGTKLEIK | 80 |
| SC16.55 | DIKMTQSPSSMAYASLGERVTITC | KASQDINSY | LNWFQQKPGKSPKTLIY | RANRLVD | GVPSRFSGSGSGQDYSLTISSLEYEDMGIYYC | LQYDEFPYTFGGGTKLEIKR | 82 |
| SC16.56 | SIVMTQTPKFLLVSAGDRVFITC | KASQSVSND | VVWYQKPGQSPKLLIY | YASNRYT | GVPDRFAGSGYGTDFSFTISVQAEDLAVYYC | QQDYTSPWTFGGGTKLEIR | 84 |
| SC16.57 | DIVMTQSHKFMSISVGDRVSITC | KASQDVSIF | VAWYQEQKPGQSPKLLIY | SASYRYT | GVPDRFTGSGSGTDFFTISSVQAEDLAVYYC | QQHYGTPTFGSGTKLKIR | 86 |
| SC16.58 | DIQMTQSPASLSSSVGETVTITC | RASENIYSY | LAWYQQKQGHGSPQLLVY | NAKTLAE | GVPSRFSGSGSGTQFSLKINSLQPEDFGTYYC | QHHYDSPLTFGAGTKLELR | 88 |
| SC16.61 | DIVMTQSTSSLAMSVGQKVTMSC | KSSQELNSSNQKRY | LAWYQQKPGQSPKLLVS | FASTRES | GVPDRFTGSGSGTDFTLTISGVQAEDLAVYYC | QQHYSIPLTFGAGTKLEIK | 90 |
| SC16.62 | DIKMTQSPSSMYASLGERVTITC | KASQDINSF | LSWFQQRKPGKSPKTLIY | RANRLVD | GVPSRFTGSGSGCQEFSLTISSLEYEDLGIYYC | LQYDEFPYTFGSGTKLEIKR | 92 |
| SC16.63 | QIVLTQSPAIMSASPGEKVTMTC | SVTSVSY | MYWYQQKPGSGTSPKRWIY | DTSKLAS | GVPARFSGSGSGTSYSLTISSVEAEDAATYYC | QQWSSNPYTFGGGTKVEIK | 94 |
| SC16.65 | QVLTQSPAILMSASPGEKVTMTC | RSSTGAVTTSNY | MYWYQQKPRSSPKPWIY | LTSNLAS | GVPARFSGSGSGIGDRAALTITGAQTEDEAIYFC | QQWRNNPFTFGGGTKVEIK | 96 |
| SC16.67 | QAVVTQESALTTSPGETVTLTC | ITSTDIDED | ANWIQEKPDHLFTGLIG | GTMNRAP | GVPARFSGSGSGIGDRAALTITGAQTEDEAIYFC | QQVVRNNPFTFGGGTKVEIK | 98 |
| SC16.68 | ETTVFTQSPAFLSVATGEKVTIRC | RSSTDIDED | MNWYQQKPGEPPWVLIS | EGNTLRP | GVPSRFSGSGSGTDVFTIENMLSEDVADYYC | GLWYSAHLVFGGGTKLTVL | 100 |
| SC16.72 | ENVLTQSPAIMSASLGEKVTMSC | RASSSVNY | MSWYQQKSDASPKLWIY | YTSNLAP | GVPARFSGSGSGMSYSLTISSMEGEDAATYYC | LQSDNMAPLTFGAGTKLEIK | 102 |
| SC16.73 | DIQMTQSPSSLSLSASLGERVSLTC | RASQDHGVS | LNWLQEPDGTKRLIY | ATSSLDS | GVPSRFSGSGSGTDYSLTISLSESEDFVDYYC | QQFTSSPYTFGGGTKLEIKR | 104 |
| SC16.78 | DIKMTQSPSSMYVASLGERVTITC | KASQDINSY | LSWFQQKPGRSPKTLIY | RAMRLVD | GVPSRFSGSGSGSQDYSLTISSLDYEDMGIYYC | LQYASSPWTFGSGTKLEIK | 106 |
| SC16.79 | DVMSQSPSSLAVSAGEKVTMSC | KSQSLLNSRTRKRY | LAWYQQKPGQSPKLLIY | WASTRES | GVPDRFTGSGSGTDFTLTISVQAEDLAVVYC | LQYDEFPFTFGSGTKLKKR | 108 |
| SC16.80 | ETTVFQSPASLSMAIGEKVTIRC | ITSTDIDDD | MHWYQQKPGEPPKLLIS | EGNTLRP | GVPSRFSSSGVGTDVFTIENMLSEDVADYYC | KQSYNRLYTFGGGTKLKKA | 110 |
| SC16.81 | QIVLTQSPASLSMAIGEKVTIRC | TASSSVSSY | MHWYQQKPGSSPKMLWIY | STSMLAS | GVPTRFSGSGSGTSYSLRISSMEAEDAATYYC | LKREDLPYTFGGGTQVEMKR | 112 |
| SC16.84 | DIQMTQSPSSLSASLGGRVTITC | KASQDIKKY | IAWYQHKPGKGPRLLIH | YTSTLEP | GIPSRFSGSGSGRDYSFSISNLEPEDIATYYC | HQYNRSPLTFGAGTKLEIK | 114 |
| SC16.88 | ENVLTQSPAIMAASLGQKVTMTC | SASSVSSSY | LHWYQQKSGASPKPLIH | RTSNLAS | GVPARFSGSGSGGTSYSLTISSVEAEDDATYYC | LQYDILWTFGGGTKLEIK | 116 |
| | | | | | | RQWSGVPWTFGGGTKLEIK | 116 |

FIG. 11A (Cont.)

Protein Sequences of Exemplary DLL3 Modulator Light Chain Variable Regions

| mAb | FR1 | CDR1 | FR2 | CDR2 | FR3 | CDR3 | SEQ ID NO. |
|---|---|---|---|---|---|---|---|
| SC16.101 | QIVLTQSPAIMSASLGERVTMTC | TASSSVSSSY | LHWYQQKPGSSPKLWIY | STSNLAS | GVPARFSGSESGTSYSLTISMEAEDAATYYC | HQYHRSPFTFGSGTKLEIK | 118 |
| SC16.103 | DIVLTQSPASLAVSLGQRATISC | RASKSVSTSGYSY | MHWYQQKPGQPPKLLIY | LASNLES | GVPARFSGSGSGTDFTLNIHPVEEEDAATYYC | QHSRELPLTFGAGTKLELK | 120 |
| SC16.104 | QIVLSQSPAILSASPGEKVTMTC | RASSSVSY | IHHWYRQKPGSSPKPWIY | ATSNLAS | GVPARFSGSGSGTSYSLTISRVEAEDAATYYC | QQWSSNPPTFGAGTKLELK | 122 |
| SC16.105 | DIVMTQSHKFMSTSVGDRVSIT | KASQDVGTA | VAWYQQKPGQSPKLLIY | WASIRHT | GVPSRFSGSGSGTDFTLTISNVQSEDLADYFC | QQYSSYPLTFGAGTKLELK | 124 |
| SC16.106 | DIKMTQSPSSMYASLGERVTITC | KASQDINSY | LSWFQQKPGKSPKTLIY | RANRLVD | GVPSRFSGSGSGQDYSLTISSLEYEDMGIYYC | LQYDEPPTFGSSGTKLEIK | 126 |
| SC16.107 | DIWMTQSHKFMSTSVGDRVSITC | KASQDVNTA | VGWYQQKPGQSPKLLIY | SASYRYT | GVPDRFTGSGSGTDFTFTISSVQAEDLAVYYC | QQHYSSPYTFGGGTKLEIKR | 128 |
| SC16.108 | DIQMTQSPASLSASVGFTVTC | RASENIYSY | LAWYQQKQKSPQLLVY | NAKTLAE | GVPSRFSGSRSGSQFSLKINSLQEDPGSSYC | QHHYGTPYTFGDGTKLEIK | 130 |
| SC16.109 | QIVLTQSPAIMSASPGERVTMTC | SASSSVSY | MYWYQQKPGSSPRLLIY | DTSNLAS | GVPARFSGSGSGTSFLTISRMEAEDTATYYC | QEWSGNPLTFGDGTKLELK | 132 |
| SC16.110 | NIVMTQTPKFLLVSAGDRVTITC | KASQSVSND | VAWYQQKQKGSPKQLIY | YASMRYT | GVPDRFTGSGYGTDFTFTISTVQAEDLAVYFC | QQDYSSPPTFGGGTKLEIK | 134 |
| SC16.111 | DIQMTQSPASLAASVGETVTTC | RASENIYYS | LAWYQQKQKGSPKQLLIY | NANSLED | GVPSRFSGSGSGSGTQYSMKNSMAQPEDTATYFC | KQTYDVPLTFGAGTKLEIK | 136 |
| SC16.113 | DIVMTQTPLTLSVTIGQPASISC | KSSQSLLDSDGTTY | LNWFLLQRPGQSPKRLIY | LVSKLDS | GVPDRFTGSGSGTDFTLKISRVEAEDLGVYYC | WQGTHFPLTFGAGTKLEIK | 138 |
| SC16.114 | QIVLSQSPAILSASPGEKVTMTC | RASSSVSY | MHWYQQKPGSSPKPWIY | ATSNLAS | GVPARFSGSGSGTSYSLTISRVEAEDAATYYC | QQWSSNPVTFGGGTKLEIKR | 140 |
| SC16.115 | DIVMTQTPLTLSVTIGQPASISC | KSSQSLLDSDGTTY | LNWLLQRPGQSPKRLIY | LVSKLDS | GVPDRFTGSGSGTDFTLTISSLQAEDLAVYYC | WQGTHFPLTFGAGTKLEIK | 142 |
| SC16.116 | DIVMTQSPSSLTVTAGEKVTMSC | TSSQSLLTSGMQKNY | LTWYQQKPGQPPKLIIQ | WASTRES | GVPDRFTGSGSGTDFTLTISSLQAEDLAVYYC | QNDYSLTFGAGTKLEIK | 144 |
| SC16.117 | DIQMNQSPSSLSASLGDTITIC | HVSQHINVW | LSWYQQKPGNIPKLLQ | KASNLHT | GIPARFSGSGSGTDFTLNIHPVEEEDAATYYC | QQGGSYPFFGGGTKLEIKR | 146 |
| SC16.118 | DIVLTQSPASLAVSLGQRATISC | KASQSVDYDGDSY | LTWYQQKPGQPPKLLIY | AASNLES | GVPDRFTGSGSGTDFTLTISSVKAEDLAVYYC | QQSNEDPYTFGGGTKLEIKR | 148 |
| SC16.120 | DIVMSQSPSSLAVSVGEKVTMSC | KSSQSLLYSSTQKNY | LAWYQQKPGQSPKLLIY | WASTRES | GVPDRFTGSGSGTSYSLTISRMEAEDLAVYYC | QQRSSYPYTFGGGTKLEIKR | 150 |
| SC16.121 | QIVLTQSPAIMSASPGEKVTITC | SASSSVSY | MHWYQQKPGTSPKLWIY | STSNLAS | GVPARFSGSGSGTDFTLTISMVQSEDLAEFFC | QQRSSYPPTFGGGTKLEIKR | 152 |
| SC16.122 | DIVMTQSQKFMSTSVGDRVSVTC | KASQNVGTN | VAWYQQKPGQSPKVLIY | SASYRYS | GVPDRFTGSGSGTDFTLLTSSMFTEDAATYYC | QQYMSYPLTFGGGTKLEIK | 154 |
| SC16.123 | QIVLTQSPAIMSASLGERVTMTC | TASSSVSSSY | LHWYQQKPGSSPKLWIY | STSNLAS | GVPARFSGSGSGTSYSLTISTSSMETEDAATYYC | HQYHRSPFTFGSGTKLEIK | 156 |
| SC16.124 | DIQMTQSPASQSASGSLSEVITC | LASQTHGTW | LAWYQQKPGKSPQLLIS | AATSLAD | GVPSRFSGSGSGTKFSKFKISSLQAEDFVSYYC | QQLYSTPWTFGGGTKLEIK | 158 |
| SC16.125 | DIQMNQSPSLSASLGDTITITC | HASQHINVW | LSWYQQKPGNIPKLLIY | KASILHT | GVPSRFSGSGSGTGTGTLTISSLQPEDIATYSC | QQGGSYPYTFGGGTKLEIK | 160 |

FIG. 11A (Cont.)

Protein Sequences of Exemplary DLL3 Modulator Light Chain Variable Regions

| mAb | FR1 | CDR1 | FR2 | CDR2 | FR3 | CDR3 | SEQ ID NO. |
|---|---|---|---|---|---|---|---|
| SC16.126 | DIQMNQSPSSLSASLGDTITITC | HASQNINVW | LSWYQQKPGNIPKLLIY | KASNLHT | GVPSRFSGSGSGTGFTLTISSLQPEDIATYYC | QQGQSYPFTGSGTKLEIK | 162 |
| SC16.129 | DIQMTQSPASQSASLGESVTITC | LASQTIGTW | LAWYQQKPGKSPQLLIY | AATSLAD | GVPSRFSGSGSGSGTKFSFKISSLQAEDFVSYYC | QQLYSTPYTFGGGTKLEIK | 164 |
| SC16.130 | DIQLTQSPASLSASVGETVTITC | RASGSHNY | LAWYQQKQGKSPQLLVY | NAKTLVD | GVPSRFSGSGSGTQYSLKINSLQPEDFGYYYC | QHFWTTPWTFGGGTKLEIK | 166 |
| SC16.131 | DIQMNQSPSSLSASLGDTITITC | HVSQNINVW | LSWYQQKPGNIPKLLIQ | KASNLHT | GVPSRFSGSGSGTGFTLTISSLQPEDIATYYC | QQGQSYPFTGSGTKLEIK | 168 |
| SC16.132 | DIQMTQSPASQSASLGESVTITC | LASQTIGTW | LAWYQQKPGKSPQLLIY | AATSLAD | GVPSRFSGSGSGTKFSFKISSLQAEDFVSYYC | QQLYSTPWTFGGGTKLEIK | 170 |
| SC16.133 | SIVMTQTPKFLLVSAGDRVTITC | KASQSVSND | VAWYQQKPGQSPKLLIY | CASNRYT | GVPDRFTGSGYGTDFTFTISTVQAEDLAVYYC | QQDYSSPLITFGAGTKLEIK | 172 |
| SC16.134 | DIVLTQSPASLAVSLGQRATISC | KASQSVDHAGDSY | MNWYQQKPEQPPKLLIY | AASNLES | GIPARFSGSGSGTDFTLNIHPVEEEDAATYYC | QQSNEDPYTFGGGTKLEIKR | 174 |
| SC16.135 | DIKMTQSHKFMSTSVGDRVSITC | KASQDINRY | LSWFCQKPGKSPKTLIY | RANRLVD | GVPSRFSGSGSGQDYSLTISSLEYEDMGHYYC | LQYDEFPFTFGSGTKLEIK | 176 |
| SC16.136 | DIQMTQSPASLSASVGETVTITC | RASGMIHNY | LAWYQQKPGKSPHLLVY | NAKTLAD | GVPSRFSGSGSGTQYSLKINSLQPEDFGSYYC | QHFWSTPWTFGGGTKLEIK | 178 |
| SC16.137 | QIVLTQSPAIMSASLGEEITLTC | SASSVSY | MHWYQQKSGTSPKLLIY | STSNLAS | GVPSRFSGSGSGTFYSLTISSVEAEDAADYYC | HQWSSYHTFGGGTKLEIK | 180 |
| SC16.138 | DIQMTQSPASQSASLGESVTITC | LASQTIGTW | LAWYQQKPGKSPQLLIY | SATSLAD | GVPSRFSGSGSGTKFSFKISSLQAEDFVSYYC | QQLYSTPWTFGGGTKLEIK | 182 |
| SC16.139 | DIKMTQSHKFMSTSVGDRVSITC | KASQDVNTA | VGWYQQKPGQSPKLLIY | SASYRYT | GVPDRFTGSGSGTDFTFTISYVQAEDLAVYYC | QQHYSTPYTFGGGTKLEIK | 184 |
| SC16.140 | DIVLTQSLASLAVSLGQRATISC | RASKSVSTSGYSY | MHWYQQKPGQPPKLLIY | LASMLES | GVPARFSGSGSGTDFTLMIHPVEDEDAATYYC | QHSRELPFTFGGGTKLEIKR | 186 |
| SC16.141 | DIKMTQSPSSMYASLGERVTITC | KASQDINSY | LSWFCQKPGKSPKTLIY | RANRLVD | GVPSRFSGSGSGCQDYSLTISSLEYEDMGHYVC | LCQYDEFPFTFGGGTKLEIK | 188 |
| SC16.142 | DIKMTQSPSSMYASLGERVTITC | KASQDINNY | LSWFCQKPGKSPKTLIY | RANRLVD | GVPSRFSGSGSGCQDYSLTISSLEYEDMGIYYC | LQYDEFPYTFGGGTKLEIK | 190 |
| SC16.143 | DVLMTQTPLSLPVSLGQQASHSC | RSSCSIVMSNGNTY | LEWYLQKPGQSPKLLIY | KVSNRFS | GVPDRFTGSGYGTDFTLKISRVEAEDLGVYYC | FCGSHVPLTFGAGTKLEIK | 192 |
| SC16.144 | SIVMTQTPKFLLVSAGDRVTITC | KASQSVSND | VGWYQQKPGQSPKLLIY | YASNRYM | GVPDRFTGSGVGTDFTFTISTVQAEDLAVYFC | QQDYSSPWTFGGGTKLEIK | 194 |
| SC16.147 | DIQMTQTASSLSASLGDRVTISC | RASQDINNY | LNWYQQKPDGTVKLLIY | YTSRLHS | GVPSRFSGSGSGTQYSLTISILEQEDATYFC | QQGDTLPWTFGGGTKLEIK | 196 |
| SC16.148 | QIVLTQSPAIMSASPGEKVTMTC | SASSSVSY | MYWYQQKPGSSPRLLIY | DTSNLAS | GVPVRFSGSGSGTSYSLTISRMEAEDTATYYC | QEWSNNPLTFGDGGTKLEIK | 198 |
| SC16.149 | DIQMNQSPSSLSASLGDTITITC | HASQNINVW | LSWYQQKPGNIPKLLIY | KASHLHT | GVPSRLSGSGSGTGFTLTISSLQPEDIATYYC | QQGQSYPFTFGSGTTLEIK | 200 |
| SC16.150 | DIVMSQSPSSLTVSVGEKVTMSC | MSSCQSLLYSSTQKNY | LAWYLQKPGQSPKLLIN | WASTRES | GVPDRFTGSGSGTDFTLTISSVKAEDLAVYYC | QQYSYPYTFGGGTKLEIKR | 202 |

FIG. 11A (Cont.)

Protein Sequences of Exemplary Humanized DLL3 Modulator Light Chain Variable Regions

| hmAb | FR1 | CDR1 | FR2 | CDR2 | FR3 | CDR3 | SEQ ID NO. |
|---|---|---|---|---|---|---|---|
| hSC16.13 | DIQMTQSPSSLSASVGDRVTITC | SASSSVSY | MYWYQQKPGKAPKLLIY | LTSNLAS | GVPSRFSGSGSGTDFTLTISSLQPEDFATYYC | QQWSNPFTFGQGTKLEIKR | 204 |
| hSC16.15 | AIQLTQSPSSLSASVGDRVTITC | RASENIYYN | LAWYQQKPGKAPKLLIY | TANSLED | GVPSRFSGSGSGTDFTLTISSLQPEDFATYFC | KQAYDVPPTFGGGTKLEIK | 206 |
| hSC16.25 | EIVLTQSPDFQSVTPKEKVTITC | SASSSVSY | MHWYQQKPDQSPKLLIK | DSSKLAS | GVPSRFSGSGSGTDFTLTINSLEAEDAATYYC | QQWSSNPLTFGQGTKLEIK | 208 |
| hSC16.34 | DIQMTQSPSSLSASVGDRVTITC | KASQSVSND | VAWYQQKPGKVPKLLIY | YASNRYS | GVPSRFSGSGSGTDFTLTISSLQPEDVATYFC | QQDYSSPWTFGGGTKVEIK | 210 |
| hSC16.56 | EIVMTQSPATLSVSPGERATLSC | KASQSVSND | VVWYQQKPGQAPRLLIY | YASNRYT | GIPARFSGSGSGTEFTLTISSLQSEDFAVYYC | QQDYTSPWTFGQGTKLEIKR | 212 |

FIG. 11A (Cont.)

Protein Sequences of Exemplary DLL3 Modulator Heavy Chain Variable Regions

| mAb | FR1 | CDR1 | FR2 | CDR2 | FR3 | CDR3 | SEQ ID NO. |
|---|---|---|---|---|---|---|---|
| SC16.3 | QVTLKESGPGILQPSQTLSLTCSFS | GFSLSTSGMG | VGWIRQPSGKGLEWLAH | IWWDDVK | RYNPALKSRLTISKDTSSSQVFLKIASVDTAEFTATYYC | ARIADYGGDYAMDYWGQGTSVTVSS | 21 |
| SC16.4 | QIQLVQSGPELKKPGETVKISCKAS | GYTFTDYS | MHWVKQAPGKGLKWMGW | INTETGEP | GYADDFKGRFAFSLETSASTAYLQINNLNEDTATYFC | ARVDGYAMDYWGQGTSVTVSS | 23 |
| SC16.5 | QVTLKESGPGILQPSQTLSLTCSFS | GFSLSTSGMG | VGWIRQPSGEGLEWLAD | IWWDDRNK | YYNPSLKSRLTISKDTSSNQVFLKITSVDTADTIATYYC | ARRVNYVDPYYAMDYWGQGTSVTVSS | 25 |
| SC16.7 | EVQLQQSGPELVKPGASVKISCKAS | GYSFTGYK | MHWVKQSHVKSLEWIGR | IMPYNGAT | SYNQNPKDKATLTVDKSSSTAYMDLHSLTSEDSAVYFC | ARGDYRYCWYFAYWGQGTLVTVSA | 27 |
| SC16.8 | QAQLQQSGAELVRPGTSVKVSCKAS | GYAFTNYL | IEWVKQRPGQGLEWIGV | INPGTGGT | NYNENFKGKATLTADKSSSTAYMQLSSLTSDDSAVYFC | ARSPYDYHEGAMDYWGQGTSVTVSS | 29 |
| SC16.10 | QVTLKESGPGILQSSQTLSITCSFS | GFSLSTSGMG | VGWIRQPSGKGLEWLAH | IWWDDVK | RYNPVLKSRLTISKDTSSSQVFLKIASVDTAGTATYYC | ARLVDDLYFDYWGQGTTLTVSS | 31 |
| SC16.11 | QIQLVQSGPELKKPGETVKISCKAS | GYTFTDYS | MHWVKQAPGKGLKWMGW | INTETVEP | TYADDFMGHFAFSLETSASTAFLQINNLENEDTATYFC | ARFGSYAMDYWGQGTSVTVSS | 33 |
| SC16.13 | QVTLKESGPGILQPSQTLSLTCSFS | GFSLSTSGMG | VGWIRQPSGKGLEWLAH | IWWDDVK | RYNPALKSRLTISKDTSSSQVFLKIASVDTAEFTATYYC | ARIVSFDNDVVSAMDYWGQGTSVTVSS | 35 |
| SC16.15 | QVQLQQSGAELAKPGASVKMSCKA | SGYTFTRYW | IHWMKQRPGQGLEWIGY | INPTTVYT | EFNQNFKDKFKQKATLTADKSSTASMQLSSLTSEDSAVYYC | ARCGSNFFDYWGQGTGTLVTVSS | 37 |
| SC16.18 | EVKLEESGGGLVQPGESMRLSCAAS | GFTESDAW | MDWVRQSPEKGLEWVAE | IRNKANMHAT | YYAESVKGRFTISRDDSKSRVYLQMMNLRAADTGIYYC | TAYSRFAYWGQGTLVTVST | 39 |
| SC16.19 | EVQLQQSGAELVRPGTSVRVSCKA | GFNIKDSL | LHWVKQRPEKGLEWIGY | IEPEDGET | KYAPNFQDKATITITDSSSNTAYLQLSLTSVDTAIYYC | AYGNVVRHFDYWGQGTLLTVSS | 41 |
| SC16.20 | QVQLQSGTELVRPGTSVRVSCKA | SGYAFGNHL | IEWVKQRPGQGLEWIGV | INPGTGGT | HYNEKFKDKARLTADKSSNTAYMHLRSLTSDDSAVYFC | ARSPYEDYHEGAMDYWGQGTSVTVSS | 43 |
| SC16.21 | QVQLQQSGPELVKPGASVKISCKAS | GYAFSSSW | MHWVKQRPGKGLEWIGR | IYPGDGDT | NYNGKFKGKATLTVDKSSTAYMQLSSLTSEDSAVYFC | AMGYWNFDGSRYYSMDYWGQGTSVTVSS | 45 |
| SC16.22 | QVQLCQSGPGAELVKPGASVKLSCKAS | GYTFTTYW | MHWVKQRPGQGLEWIGE | IDPSDSYT | YYNQKFKGKATLTVDKSSSTAYMQLSSLTSEDSAVYYC | ARGDYGNPYAMDYWGQGSSVTVSS | 47 |
| SC16.23 | QVTLKESGPGILQPSQTLSLTCSFS | GFSLSTSNTG | IGWIRQPSGTGLEWLAH | IWWNEDK | YYNPSLKSRLTISKETSNMQVFLKITNVDTADTASYFC | VQJIGRDYSNYAWYFDVWGAGTTVTVSS | 49 |
| SC16.25 | QVFLKESGPGILQPSQTLSLTCSFS | GFSLSTSGMG | VGWIRQPSGEGLEWLTD | IWWDDRNK | YYNPSLKSRLTISKDTSSNQVFLNITSVDTADTIATYYC | ARRVNYYYDPYYAMDYWGQGTSVTVSS | 51 |
| SC16.26 | QIQLVQSGPELKKPGETVKISCKAS | GYSFTDYS | MHWVKQAPGKGLKWMGW | INTETVEPT | YADDFMGHFAFSLETSASTAFLQINNLENEDTATYFC | ARFGSYAMDYWGQGTS | 53 |
| SC16.29 | QIQLVQSGAELARPGASVKLSCKAS | GYTFTDQY | INWVKQRTGQGLEWIGE | IYPGRGNT | YYNEKFKGRATLTADKSSSTAYMQLSSLTSEDSAVYFC | AREDGGYVDDAWFAYWGQGTLVTVSA | 55 |
| SC16.30 | QVFLKESGPGILQPSQTLSLTCSFS | GFSLSTSGMG | VGWIRQPSGKGLEWLAH | IWWGDVK | RYKPALKSRLTVSKDTSSSMQVFLKIATVDAAADTGTYYC | ARIVDGHPPFAYWGQGTLVTVSA | 57 |
| SC16.31 | EVQLQQSGPELVKPGASVKISCKAS | GYSFSRFY | MHWVKQSPEINSLEWGE | IMPSTGGT | ISYNQKFKGKATLTVDKSSSTAYMQLKSLTSEESAVYYC | TRGYGSNWYFDVWGAGTTVTVST | 59 |
| SC16.34 | QIQLVQSGPELKRPGETVKISCKAS | GYTFTNYG | MHWVKQAPGKGLKWMGW | INTYYGDP | TYADDFKGRFAFSLETSASTAYLQINNLKNEDTATYFC | ARIGGNSPSDYWGQGTSLTVSS | 61 |
| SC16.35 | SDVQLQESGPGLVKPSQSLSLTCTVT | GYSFSDYA | WNWIRQFPGNKLEWMGY | ISYSGST | SYNPSLKSRISITRDTSKNQJFFLQLNSVTTEDTATYFC | ARFYGSSSYAMEYWGQGTSVTVSS | 63 |
| SC16.36 | TVQLQQSGAELAKPGASVKMSCKAS | GYTFTTYW | MHWVKQRPGQGLEWIGY | INPSSGYT | EYNQKFKDKATLTADKSSSTAYMQLSSLTSEDSSVYYC | ARKGSNRGFAYWGQGTLVTVS | 65 |
| SC16.38 | EVQLQQSGAELVKPGASVKLSCTVS | GFNIKDTY | IHWVKQRPEQGLEWIGR | IDPANGNT | KVDPKFQGKATITADTSSNTAYLQLSSLTSEDTAVYYC | ARPTGYFEYWGQGTLLTVSS | 67 |

FIG. 11B

Protein Sequences of Exemplary DLL3 Modulator Heavy Chain Variable Regions

| mAb | FR1 | CDR1 | FR2 | CDR2 | FR3 | CDR3 | SEQ ID NO. |
|---|---|---|---|---|---|---|---|
| SC16.41 | EVKLEESGGGLVQPGGSMKLSCAAS | GFTFSDAW | MDWVRQSPEKGLEWVAE | IRNKANNHAT | YYPESVKGRFTISRDDSKRVYLQMNNLRAEDTGIYYC | TGYSSFAYWGQGTLVTVSA | 69 |
| SC16.42 | QIQLVQSGPELKKPGETVKISCKAS | GYTFTTAG | MQWVQKAMPSKGFKMHGW | INTHSGEP | KYADDFKGRFAFSLETSASTAYLQISNLKDEDTATFFC | APLWSDSSFAYWGQGTLVTVSA | 71 |
| SC16.45 | QVQLQQSGADLVRPGTSVKVSCKAS | GYSFTNYL | IEWVKQRPGQGLEWIGV | INPGSGGT | HYNEKFKDKAVLTADKSSTAHMQLSSLTSDSAVYYC | ARSPYDYNDGAMDYWGQGTSVTVSS | 73 |
| SC16.47 | EVQLQQSGPELVKPGASVKISCKAS | GVSFSRFY | MHWVKQSPENSLEWIGE | INPSTGGT | SYNQKFKGKATLTADKSSTAYMQLSSLTSEESAVYYC | TRGYGSNCYFDVWNGAGTTVTVST | 75 |
| SC16.49 | QVQLQQSGPELVKPGTLVKISCKAS | GYTFTSYD | INWVKQRPGQGLEWIGW | IYPGDGNT | KYSEKFKGKATLTADKSSSTAYMQLTSLTSENSAVYFC | ARDYDPFAYWGQGTLVTVSS | 77 |
| SC16.50 | EVQLVECGGGLVKPGGYLKLSCAAS | GFTFSSYA | MSWVRQSPEKRLEWVAE | ISIGGSYT | YYPDTVTGRFTISRDNAKNTLYLEMSSLRSEDTAMYYC | AREGYDYDVRAMDYWGQGTSVTVSS | 79 |
| SC16.52 | QVQLVESGGGLVQPGGSLSITCAVS | GFSLTSFA | IHWFRKPPGKGLEWLGV | IWTGGTT | MYNSALMSRLSISKDNSKSQVFLKMNSLQTEDTAMYYC | AREDYDNNYAAMDYWGQGTSVTVSS | 81 |
| SC16.55 | EVQLVESGGGLVQPGGSLKLSCAVS | AFTFTTYA | MNWVRQAPGKGLEWVAR | IRNKSNNYAT | YYADSVKDRFTISRDCSQSMLYLQMNNLKIEDTAMYYC | VFYDYVYWGQGTLVTVSA | 83 |
| SC16.56 | QIQLVQSGPELKKPGETVKISCKAS | GYTFTNYG | MNWVKQAPGKGLAWMAAW | INTYTGEP | TYADDFKGRFAFSLETSASTASLQBNLKREDTATYFC | ARIGDSSPSDYAWGQGTLTVSS | 85 |
| SC16.57 | EVKLVESGGDLVKPGGSLKLSCAAS | GFAFSSYD | MSWVRQTPEKRLEWVAT | ISSGGSYT | YYPDSVKGRFTISRDNVRDTLYLCQMSSLRSEDTALYYC | ARQAIGTYFDYWGQGTLTVSS | 87 |
| SC16.58 | DVQLVESGGGLVQPGGSRKLSCAAS | GFTFSSFG | MHWVRQAPEKGLEWVAY | ISSGSSMI | YYADTVKGRFTISRDNPKNTLFLQMTSLSEDTAMYYC | ARGYYGNYDAMDYWGQGTSVTVSS | 89 |
| SC16.61 | EVLLQRSGPDLVKPAGASVTIPCKAS | GYTFTDYN | MDWSHGKSLEWIGN | INTYNGGT | IYNQKFKGKATLTVDKPSSTAYMELRSLTSEDTAVYYC | ARRLRVGGHYFDYWGQGTALTVSS | 91 |
| SC16.62 | EVMLVESGGDLVKPGGASVKISCAAS | GFTFSSYA | MSWVRQTPEKRLEWVAY | ISGGGDHH | YYPDSVRGRFTISRDNAKDTLYLQMSSLRSEDTALYDC | ARVRDWYFDVWGAGTTVTVSS | 93 |
| SC16.63 | QVQLQQSGTELLRPGASVKSCKAT | GYTFSSYW | MEWVKQRPGHGLEWIGE | ILPGSGTT | QYNEKFKGKATPLTADTSSNTAYMHLSSLTSEDSAVYYC | ARGTNSLWGQGTLVTVSA | 95 |
| SC16.65 | QVFLKESGPGILQPSQTLSLTCSFS | GFSLSTSGMG | VGWIRQPSSKGLEWLALI | WWDDVYK | RYNPALKSRLTISKDASSSAQVFLKIASVDFTADTATYYC | ARIASYDYDVVVAAMDYWGQGTSVSVSS | 97 |
| SC16.67 | EVQLVETGGGLVQPKGSLKLSCAVS | AFTFTTYA | MNWVRQAPGKGLEWVAR | IRNKSNNYAT | YYADSVKDRFTISRDCSMLYLQMNNLKIEDTAMYYC | VFYDYVYWGQGTLVTVSA | 99 |
| SC16.68 | QVQLQQSGAELVKPGASVKMSCKAS | GYTFTNYN | MHWVKQTPGQGLEWIGHA | IPPGNGGT | SYNQKFKGKATLTADKSSTAYMQLITSLTSGDSAVYYC | ARWCYGSSGLYAMDYWGQGTSVTVSS | 101 |
| SC16.72 | EVQLQQSGPELVKPGASVKMSCKAS | GYTFTSYV | MHWVKQKPGQGLEWIGY | INPYNDGT | KYMEKFKGKATLTSRDSSTAYMELLSSLTSEDSAVYYC | ARLRSRAMDYWGQGTSVTVSS | 103 |
| SC16.73 | QVQLQQSGAELMKPGASVMKISCKAN | GYTFSSYW | IEWVKLQRPGHGLEWIGE | ILPGSDMS | NYNEKFKGKATPLTADTSSNTAYMQLSSLTSEESAVYYC | TRGLRRDGSYYYYMAEHWGQGTSVTVSS | 105 |
| SC16.78 | EVKLVESGGGLVKPGGSLKLSCAAS | GFTFGRYV | MSWVRQTPEKKLEWVAS | ITSGGTT | YYPDSVKGRFTISRDNARWILYLQMSSLRSEDTAMYYC | ARVYHYDEDFAYWGQGTLVTVSA | 107 |
| SC16.79 | EVQLQQSGPELVKPGASVKISCKTS | GYTFTEYT | MHWVKQSHGKSLEWIGG | INPNNGGT | SYNQKFKGKATLTVDKSSSTAYMELRSLTSEDSAVYYC | ARGPAWFAYWGQGTLVTVSA | 109 |
| SC16.80 | EVQLQQSGPELVKPGGSKKISCKAS | GYSFTGYS | MNWVKQSHGKNLEWIGL | INPYSGGT | IYNQKFKGKATLTVDKSSTAYMELLSSLTSEDSAVYYC | ARRSDYPLYYWGQGTLVTVSA | 111 |
| SC16.81 | QVQLKESGPVLVAPSQSLSITCTVS | GFSLTSYG | VHWVRQPPGKGLEWLGV | IWAGGST | MYNESALMSRLSISKDNSKSQVFLKMNSLQTEDTAMYYC | AKQGNFYAMDYWGQGTSVTVSS | 113 |
| SC16.84 | EVQLQQSGPELVKPGASMKKLSCKAS | GYSFTGYT | MNWVKQSHGKNLEWIGL | INPYNGGT | TYNQKFKGKATLTVDKSSSTAYMELLSLTSEDSAVYYC | ALGYYGNYRRYFDVWGQGTLVTVSS | 115 |
| SC16.88 | QVQLQQSGAELARPGASVKLSCKAS | GYTCTSYW | MQWVKQRPGQGLEWIGA | IYPGDGDT | RYTQKFKGKATLTADKSSTAYMQLSSLASEDSAVYYC | ARGRRTEAWFAYWGQGTLVTVSA | 117 |

FIG. 11B (Cont.)

Protein Sequences of Exemplary DLL3 Modulator Heavy Chain Variable Regions

| mAb | FR1 | CDR1 | FR2 | CDR2 | FR3 | CDR3 | FR4 | SEQ ID NO. |
|---|---|---|---|---|---|---|---|---|
| SC16.101 | QVTLKESGPGILQPSQTLSLTCSFS | GFSLSTSGMG | VGWIRQPSGKGLEWLAH | IWWDDVK | RYNPALKSRLTISKDASSSQVFLKIASVDTAETATYYC | AHILDRAYYFDYWGQGTTLTVTS | | 119 |
| SC16.103 | QVTLKESGPGILKPSQTLSLTCSFS | GFSLSTSGM | IGWIRQPSGKGLEWLAH | IWWDDDK | YYNPSLKSQLTISKDSSRNQVFLKITSVDTADTATYYC | ABRGTAYYFDYWGQGTTLTVSS | | 121 |
| SC16.104 | QVQLKESGPGDLVQPSQTLSLTCTVS | GFSLTPYG | VHWVRQPSGKGLEWVGT | MGWDDKK | YYNSALKRLSISRDTSKNQVFLKLSSLQTEDTAMYYC | TRGGTGFDYWGQGTLTVSS | | 123 |
| SC16.105 | QVQLQQPGAELVKPGASVKLSCKAS | GYTFTSYW | MHWVKQRPGQGLEWIGR | INPSNGRT | NYNEKFKGKATLTVDKSSSTAYMQLSSLTSEDSAVYYC | ARRRELGTLYAMDYWGQGTSVTVSS | | 125 |
| SC16.106 | QVQLKQSGPGLVAPSQSLSIFTCTVS | GFSLTSYE | INWVRQPPGKGLEWLGV | IWTGGST | NVNSALISRLSISKDNSKSLVFLKQMNSLQTDDTAFYYC | VRGVYAMDYWGQGTSVTVSS | | 127 |
| SC16.107 | EVQLQQSGPELVKPGASVKMSCKAS | GYTFTNYV | MHWVKKQKPGQGLEWIGY | INPYNDGT | KYNEKFKGKATLTSDKSSTTAYMAISLTSEDSAVYYC | AVAYYSNWGFAYWGQGTLVTVSA | | 129 |
| SC16.108 | QVQLEESGAELARPGASVKLSCKAS | GYSYW | MQWIKQRPGQGLEWIGA | NPGNGDT | RYTQKFKGKATLTADKSSSTAYMQLSSLASEDSAVYYC | ARSPAYYRYGEGYFDYWGQGTTLTVSS | | 131 |
| SC16.109 | QLQLVQSGPELKKKPGETVKISCKAS | GYTFTNYG | MNWVKQAPGKGLKWMGW | INTYTGEP | AYADDFKGRAFASLETSASAAYLQHMLKWEDTATHFC | AMHKRPTRGFAYWGQGTLGTVSA | | 133 |
| SC16.110 | EVQLQQSGPGLVRTGASVKISCKAS | GYSFTGYY | MHWVKQSHGKSLEWIGY | ISCYNGAT | TYNQMFKGKATFIVDTSSSTAYMQFNSLTSEDSAVYYC | ARSDGGHAMDYWGQGTSVTVSS | | 135 |
| SC16.111 | EVQLQQSGPELKPGASVMSCKAS | GYSFTGYN | MNWVKQSNGKSLEWIGN | IDPYYGGS | SYKQKFEGKATLTVDKSSSTAYMQLKSLTSEDSAVYYC | ARGGSNFHDYWGQGTTLTVSS | | 137 |
| SC16.113 | DVKLVESGGGLVKPGGSLKLSCAAS | GFTFSSYT | MSWVRQTPEKRLEWVAT | ISSGGSYP | YYPDSVKGRFTISRDNAKNTLYLQMSSLKSEDTAMYYC | TRDVYDGYSYWGQGTTLTVSS | | 139 |
| SC16.114 | EVQLQQSGAELVKPGASVKLSCTAS | GFNIKDTY | IHWVKQRPEQGLEWIGR | IDPANGNT | KYDPKFQGKATTIPDTSSNTAYLQLSSLTSEDTAVYYC | ARSWRNVGSSPWYFDYVWGAGTTVTVSS | | 141 |
| SC16.115 | DVKLVESGGGLVKPGGSLKLSCAAS | GFTFSSYT | MSWVRQTPEKRLEWVAT | ISSGGSYP | YYPDSVKGRFTISRDNAKNTLYLQMSSLKSEDTAMYYC | TRDVYDGYSYWGRGTTLTVSS | | 143 |
| SC16.116 | QVQLKQSGPGRVQPSQSLSITCTVS | GFSLTSNGV | VHWVRQSPGKGLEWLGV | LWSGGST | DYNAAFISRLSISKDNYKSQVFFKMNSLQANDTAYYC | ARMNNRYGAMDYWGQGTSVTVSS | | 145 |
| SC16.117 | QVQLKESGPGLVAPSQSLSIPCTVS | GFSLTNYG | VHWVRQCPPGKGLEWLGV | IWAGGIT | NYNSALMSRLSISEDNSKSCQVFLKMNSLQTDDTAMYYC | ARMLGPYAMDYWGQGTSVTVSS | | 147 |
| SC16.118 | EVQLQQSGPDLVKPGASVKSCKAS | GYSFTGYY | MHWVKQSHGKSLEWIGR | VNPNNGGT | SYNQKFKGKAHLTADIKSSSTAYMELRSLTSEDSAVYYC | ARGSYDYAEGWGQGTLVTVSA | | 149 |
| SC16.120 | EIQLQQSGPELVKPGASVKJSCKAS | GYAFFSYN | MYWVMQSHGKSLEWIGY | VDPYNGGT | SYNQKFKGKATLTVDKSSSTAYMHLNSLTSEDSAVYYC | ARENVRYFDYWGQGTTLTVSS | | 151 |
| SC16.121 | EVQLVESGGGLVQPKGSLKLSCAAS | GFTFNTYA | MNWVRQAPGKGLEWVARR | IKSNNYAT | YYADSVKDRFTISRDESQNMMLYLQMNNNLKTEDTAVYYC | VRQGYSYDWGPWFAYWGQGTLTVSA | | 153 |
| SC16.122 | EVQLVESGGGLVKPGGSLKLSCAAS | GFTFSDYY | MFWVRQTPEKRLEWVAT | ISDGGSY | TYFPDSVKGRFTISRDNAQNMLYLQMSSLKSEDTAMYYC | ARAGTLYAMDYWGQGTSVTVSS | | 155 |
| SC16.123 | QVALKESGPGILQPSQTLSLTCSFS | GFSLSTSGMG | VGWIRQPSGKGLEWLAH | IWWDDVK | RYNPALKSRLTISKDTSSSQVFLKIASVDTADTATYYC | ARMEEDYGSSSYFDFWGHGTTLTVSS | | 157 |
| SC16.124 | EVQLQQSGPELVKPGASVKMSCKAS | GYTFTSYV | MHWVKKQKPGQGLEWIGY | INPYNDGT | KYNEKFKGKATLTSDKSSSTAYMELSSLTSEDSAVYYC | ARGALYYGNVLGYFDVWGAGTTVTVSS | | 159 |
| SC16.125 | SDVQLQESGPDLVKPSQSLSLTCTVT | GYSITSGYS | VHWIRQFPGNKLEWMGY | IHYSGST | NYNPSLKSRISITRDTSKNQFFLQFKSVTTEDSATYYC | ALEGWYDGFAYWGQGTLVTVS | | 161 |

FIG. 11B (Cont.)

Protein Sequences of Exemplary DLL3 Modulator Heavy Chain Variable Regions

| mAb | FR1 | CDR1 | FR2 | CDR2 | FR3 | CDR3 | SEQ ID NO. |
|---|---|---|---|---|---|---|---|
| SC16.126 | QVQMKESGPGLVAPSQSLSITCTVS | GSSLITNYG | VHWVRQPPGKGLEWLGV | IWAGGST | NYNSALMSRLSISKDNSKSQVFLKMNSLQTDDTAMYYC | ARDWEGWFAYWGQGTLVTVSA | 163 |
| SC16.129 | QVQLKESGPGLVAPSQSLSITCTVS | SGFSLTDYG | VSWIRQPPGKGLEWLGV | IWGGGST | YYNSALKSRLSISKDNSKSQVFLELNSLQTDDTAIYYC | AKHYGHYAAYWGQGTLVTVSS | 165 |
| SC16.130 | EVQLQQSGPELVKPGASVKMSCKAS | GYTFTSYV | MHWVKQKPGQGLEWIGY | INPYNDGT | EYNEKFKGKATLTSDKSSSTAYMELSSLTSEDSAVYYC | ARGVYDGYSYFDYWGQGTLVTVSS | 167 |
| SC16.131 | EVQLKESGPGLVAPSQSLSITCTVS | GFSLTRNYGV | VHWVRQPPGKGLEWLGV | IWAGGIT | NYNSALMSRLSISEDKSKSQVFLKMNSLQTDDTAMYYC | ARNLGPYAMDYWGQGTSVTVSS | 169 |
| SC16.132 | QVQLKESGPGLVAPSQSLSITCTVS | GFSLTDYG | VSWIRQPPGKGLEWLGV | VWGSGST | YYNSALKSRLSITKDNSKSQVFLKMNSLQTDDTAMYYC | AKQRGQYGAYWGQGTLVTVSA | 171 |
| SC16.133 | QVQLKESGPGLVAPSQSLSITCTVS | GFSLTNYA | VHWVRQPSHGKRLEWIGR | IWSDGST | DYNAAFISRLSISEKDNSKSQVFFKMNSLQAEDTAMYYC | ARKKGGWFPWFAYWGQGTLVTVSA | 173 |
| SC16.134 | EVQLVQSGPDLVKPGASVKISKAS | GYSFTGYY | MHWVKQSHGKRLEWIGR | VNPNNGGT | RYNQKFKGKAHLTVDKSSSTAYMELRSLTSADSAVYFC | ARGSYDNAEGWGQGTLVTVSA | 175 |
| SC16.135 | QVQLQQSGAELVRPGTSVKMSCKAS | GYAFTNYL | IEWVKQRPGQGGLEWIGV | INPGSGGT | MSMEKFKAKATLTADKSSSTAYMQLSSLTSADSAVYFC | APSDYDAFYAMDYWGQGTLVTVSS | 177 |
| SC16.136 | EFQLQQSGPELVRPGASVKMSCKAS | GYTFTSYN | MHWVKQRPGQGLEWIGY | INPYNDGT | KYNEKFKGKATLTSDKSSSTAYMELSSLTSEDSAVYYC | ARDRSGYEDYYGMDYWGQGTSVTVSS | 179 |
| SC16.137 | EVQLVESGGDLVKPGGSLKLSCAAS | GFTFSSYG | MSWVRQTPDKRLEWVAT | ISSGGSYT | YYPDSVKGRFTISRDNAKNTLYLQMSLKSEDTAMYYC | ARRRADAMDYWGQGTLVTVSS | 181 |
| SC16.138 | QVQLKESGPGLVAPSQSLSITCTVS | GFSLTDYG | VSWIRQPPGKGLEWLGV | VWGGGST | YYNSALKGRLSISKDNSKSQVFLKMNSLQTDDTAMYYC | AKQRGQYVGAYWGQGTLVTVSA | 183 |
| SC16.139 | EVQLQQSGPELVKPGASVKMSCKAS | GYTFTNYV | MHWVKQKPGQGLEWIGY | INPYNDGT | KYNEKFKGKATLTSDKSSSTAYMALSSLTSEDSAVYY | AVAYYSNWGFAYWGQGTLVTVSA | 185 |
| SC16.140 | QVQLQQSGPELVRPGASVKMSCKAS | GYTFTSYW | MHWVKQRPGQGLEWIGM | IDPSNSET | RLNQKFKDKATLNVDKSSNTAYMQLSSLTSEDSAVYYC | AVMDYFDYWGQGTLVTVSS | 187 |
| SC16.141 | QVQLKQSGPGLVAPSQSLFITCTVS | GFSLTSYE | INWVRQPPGKGLEWLGM | IWTGGST | NYNSALISRLSEKDNSKSLVFLKMNSLQTDDTAIYYC | VRGYYAMDYWGQGTSVTVSS | 189 |
| SC16.142 | EVQLQQSGPELVKPGASVKISCKAS | GYTFTDYN | MHWVKQHSHGKSLEWIGF | FYPYNGNT | VYSQKFKSKATLTVDNSSSTAYMELRSLTSEDSAVYYC | ARLNWEGYWGQGTTLTVSS | 191 |
| SC16.143 | QVQLQQSGPELVKPGASVRESCKAS | GYTFTSYY | IHWVKQRPGQGLEWIGW | IYPGMGNT | KYNEKFKGKATLTADKSSSTAYMQISSLTSEDSAVYFC | ARERWLLIWFAYWGQGTLVTVSA | 193 |
| SC16.144 | QVQLVQSGPELKKPGETVKISCKAS | GYTFTNYG | MNWVKQAPGKSLKWVGW | INTYTGEP | TYAADDFKGRFAFSLETSASTAYLQIBNLKNEDTATYFC | ARVGDYVGFDYWGQGTSVTVSS | 195 |
| SC16.147 | QVQLVQSGPELITKPGETVKISCKAS | GYTFTDYS | LHWVKQALCKGLKWMGW | INTETGEP | AYAEDFKGRFAFSLETSASTAYLQIHDLKNEDTTTYFC | GIYDGYAMDYWGQGTSVTVSS | 197 |
| SC16.148 | QIQLVQSGPELKKPGETVKISCKAS | GYTFTNYG | MNWVKQAPGKSLKWMGW | INTYTGEP | TYAADDFKGRFAFSLETSARIVYLQINNLKNEDTATYFC | AKYEAHEGRVYWGQGTLVTVSS | 199 |
| SC16.149 | QVQLKESGPGLVAPSQSLSITCAVS | GFSLTSFG | VHWVRQPPGKGLEWLGV | IWAGGSTN | YYSALMSRLSISIDRNSKSQVFLKMNSLQTDDTAMYYC | ARDWEGWFAYWGQGTLVTVSA | 201 |
| SC16.150 | EIQLQQSGPELVKPGASVKMSCKAS | GVAFTSYN | MYWVSCQSHGKSLEWIGY | IDPYNGET | SYNQKFRGKATLVDKSSSTAYMHLNSLTSEDSAVYYC | ARENVRYFDFWGQGTLLTVSG | 203 |

FIG. 11B (Cont.)

Protein Sequences of Exemplary Humanized
DLL3 Modulator Heavy Chain Variable Regions

| hmAb | FR1 | CDR1 | FR2 | CDR2 | FR3 | CDR3 | SEQ ID NO. |
|---|---|---|---|---|---|---|---|
| hSC16.13 | QIFLKESGPTLVKPTQTLTLTCTFS | GFSLSTSGMG | VGWIRQPPGKALEWLAH | IWWNDDVK | RVSPSLKSRLTITKDTSKNQVVLTMTNMDPVDTATYYC | ARIVSFDNDVVSAMDYWGQGTLVTVSS | 205 |
| hSC16.15 | QVQLVQSGAEVKKPGASVKVSCKAS | GYTFTRYW | IHWIRQAPGQGLEWMGY | INPTTVYT | EFMQNFKDRVTMTRDTSTSTVYMELSSLRSEDTAVYYC | ARGGSMFFDYWGQGTTVTVSS | 207 |
| hSC16.25 | QIFLKESGPTLVKPTQTLTLTCTFS | GFSLSTSGMG | VGWIRQPPGKALEWLTD | IWWDDNK | YYNPSLKSRLTITKDTSKNQVVLTMTNMDPVDTATYYC | ARRVNYYYDPYYAMDYWGQGTTLVTVSS | 209 |
| hSC16.34 | QVQLVQSGAEVKKPGASVKVSCKAS | GYTFTNYG | MNWVRQAPGCRLEWMGW | INTYTGDP | TYAEDFKGRVTITRDTSASTAYMELSSLRSEDTAVYYC | ARIGGINSPSDYWGQGTVTVSS | 211 |
| hSC16.56 | QVQLVQSGAEVKKPGASVKVSCKAS | GYTFTNYG | MNWVRQAPGQGLEWMGW | INTYTGEP | TYADDFKGRVTMTTDTSTSTAYMELRSEDTAVYYC | ARIGDSSPSDYWGQGTLVTVSS | 213 |

FIG. 11B (Cont.)

Biochemical Characteristics of Selected DLL3 Modulators

| Clone | Bin | Domain | Affinity (nM) | % Live Cells (in vitro) | Cyno XR | Mouse & Rat XR |
|---|---|---|---|---|---|---|
| SC16.4 | F | EGF4 | 0.5[F] | 49 | N.D. | Yes |
| SC16.8 | A | EGF5 | 0.5[F] | 82 | N.D. | Yes |
| SC16.10 | E | EGF2 | 4.0[F] | 18 | N.D. | No |
| SC16.13 | B | EGF2 | 2.0[B] | 31 | No[Y] | No |
| SC16.15 | G | N-terminal | 0.5[B] | 24 | Yes[B] | Yes |
| SC16.25 | C | N-terminal | 0.2[B] | 28 | Yes[B] | No |
| SC16.34 | D | DSL | 0.2[B] | 12 | Yes[B] | Yes |
| SC16.39 | I | EGF6 | 1.0[F] | 98 | N.D. | Yes |
| SC16.46 | A | EGF1 | 0.5[F] | 19 | No[Y] | Yes |
| SC16.51 | H | N-terminal | 2.0[F] | 56 | Yes[B] | Yes |
| SC16.56 | D | DSL | 1.0[B] | 16 | Yes[B] | Yes |
| SC16.65 | B | EGF2 | 0.9[B] | 13 | No[B] | No |
| SC16.67 | D | EGF3 | 0.5[F] | 37 | Yes[Y] | No |

[B] Biacore; [F] ForteBio; [Y] Yeast Display

FIG. 12

Binding Characteristics of Exemplary DLL3 Modulators
Biacore curves – SC16.15
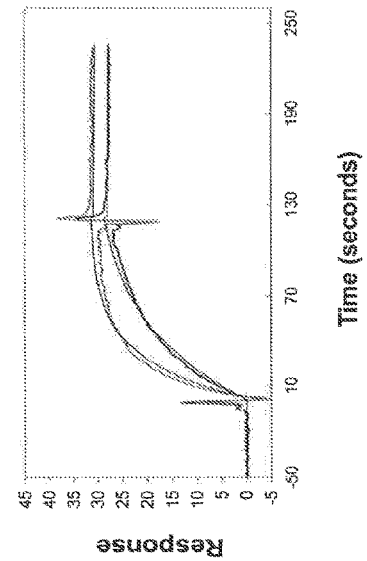
FIG. 13A
Biacore curves – hSC16.15
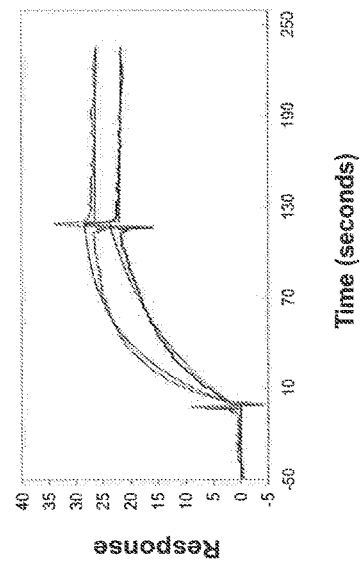
FIG. 13B
| hClone | Bin | Mouse Ag Binding | Hu Ag Affinity (Murine mAb) | Hu Ag Affinity (Human mAb) |
|--------|-----|------------------|------------------------------|------------------------------|
| SC16.13 | B | No | 0.3nM | 0.5nM |
| SC16.15 | G | Yes | 0.2nM | 0.2nM |
| SC16.25 | C | No | <0.2nM | <0.2nM |
| SC16.34 | D | Yes | 0.6nM | 0.9nM |
| SC16.56 | D | Yes | 0.5nM | 0.5nM |
FIG. 13C

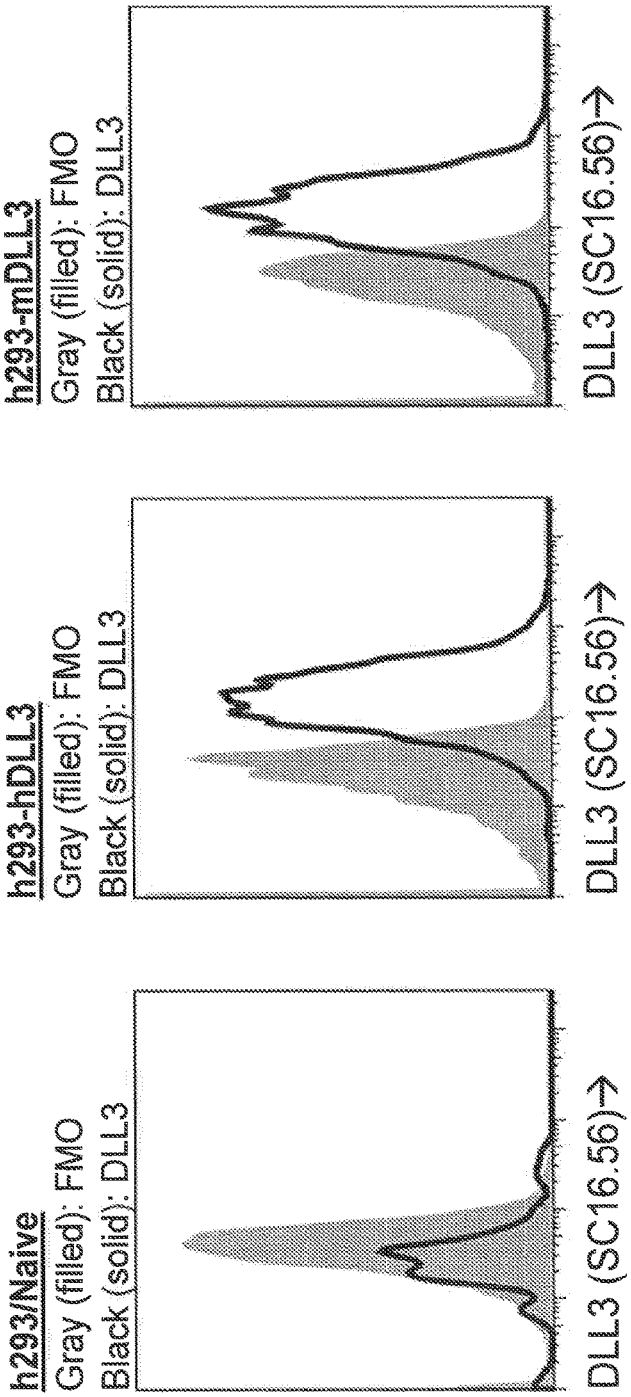

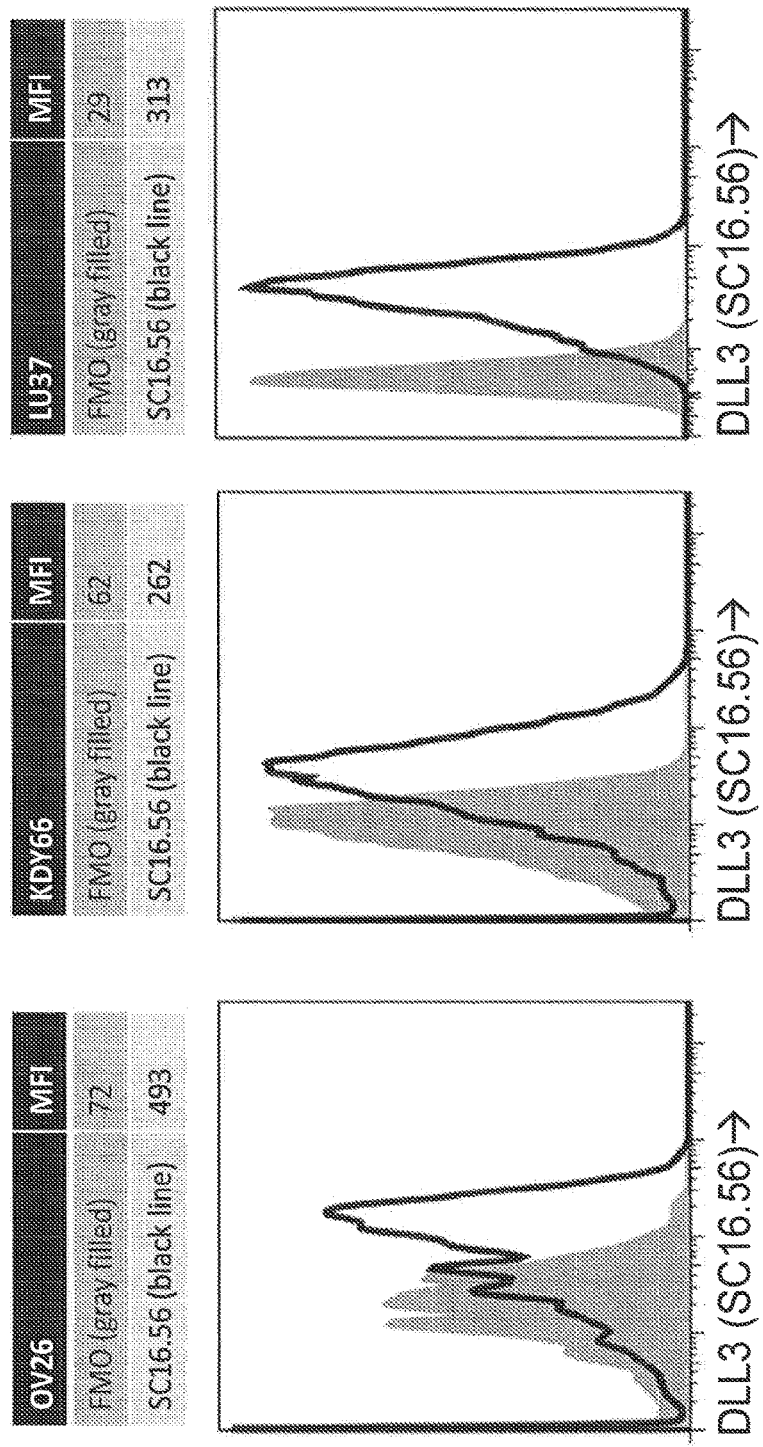

Immunohistochemistry Staining of DLL3 in NTX Tumors and Normal Human Tissues

| NTX Tumor | SC16.65 |
|---|---|
| KDY27p3 | - |
| KDY66p4 | +++, 80% |
| KDY67p2 | +++, 70% |
| LU100p1 | - |
| LU102p1 | +++, 70% |
| LU109p2 | +++, 70% |
| LU111p1 | -/+, 10% |
| LU117p2 | -/+, 70% |
| LU124p1 | -/+, 10% |
| LU126p2 | - |
| LU135p3 | +++, 70% |
| LU37p5 | - |
| LU50p1 | - |
| LU64p1 | +, 60% |
| LU73p2 | -/+, 20% |
| LU80p3 | - |
| LU86p1 | +, 70% |
| LU95p1 | +, 30% |
| LU49p2 | - |
| OV26p2 | - |
| SK11p4 | - |
| SK13p3 | - |
| SK19p3 | +, 70% |
| SK23p1 | - |
| SK29p2 | - |
| SK6p4 | - |

FIG. 16D

| Organ | SC16.65 |
|---|---|
| Skin | - |
| Skin | - |
| Subcutis | - |
| Subcutis | - |
| Breast | - |
| Breast | - |
| Spleen | - |
| Spleen | - |
| Lymphnode | - |
| Lymphnode | - |
| Skeletal muscle | - |
| Skeletal muscle | - |
| Lung | - |
| Lung | - |
| Heart | - |
| Heart | - |
| Aorta | - |
| Aorta | - |
| Salivary gland | - |
| Salivary gland | - |
| Liver | - |
| Liver | - |
| Gallbladder | - |
| Gallbladder | - |
| Pancreas | - |
| Pancreas | - |
| Tonsil | - |
| Tonsil | - |
| Esophagus | - |
| Esophagus | - |

| Organ | SC16.65 |
|---|---|
| Stomach | - |
| Stomach | - |
| Small intestine | - |
| Small intestine | - |
| Colon | - |
| Colon | - |
| Kidney, cortex | - |
| Kidney, cortex | - |
| Kidney, medulla | - |
| Kidney, medulla | - |
| Uterus | - |
| Uterus | - |
| Prostate | - |
| Prostate | - |
| Placenta | - |
| Placenta | - |
| Umbilical cord | - |
| Umbilical cord | - |
| Adrenal | - |
| Adrenal | - |
| Thyroid | - |
| Thyroid | - |
| Thymus | - |
| Thymus | - |
| Gray matter, cerebrum | - |
| Gray matter, cerebrum | - |
| White matter, cerebrum | - |
| White matter, cerebrum | - |
| Cerebellum | - |
| Cerebellum | - |

FIG. 16E

Immunohistochemistry Staining of DLL3 in Human Tumors

| Core | Tissues/Diagnosis | stage | SC16.65 | CHGA |
|---|---|---|---|---|
| A1 | Small cell carcinoma | I | -/+, 20% | + |
| A2 | Small cell carcinoma | I | -/+, 10% | + |
| A3 | Small cell carcinoma | I | - | - |
| A4 | Small cell carcinoma | I | +, 40% | + |
| A5 | Small cell carcinoma | I | ++, 90% | + |
| A6 | Small cell carcinoma | II | - | - |
| A7 | Small cell carcinoma | I | -/+, 20% | + |
| A8 | Small cell carcinoma | I | +/++, 70% | + |
| A9 | Small cell carcinoma | I | ++, 80% | + |
| B1 | Small cell carcinoma | I | - | - |
| B2 | Small cell carcinoma | I | - | - |
| B3 | Small cell carcinoma | I | +, 70% | + |
| B4 | Small cell carcinoma | III | +, 10% | + |
| B5 | Small cell carcinoma | III | ++, 70% | - |
| B6 | Small cell carcinoma | III | ++/+++, 90% | + |
| B7 | Small cell carcinoma | III | +++, 90% | + |
| B8 | Small cell carcinoma | III | ++, 80% | + |
| B9 | Small cell carcinoma | III | ++, 70% | + |
| C1 | Small cell carcinoma | III | - | - |
| C2 | Small cell carcinoma | III | +, 40% | + |
| C3 | Small cell carcinoma | III | +, 10% | + |
| C4 | Small cell carcinoma | III | +, 50% | + |
| C5 | Small cell carcinoma | III | - | - |
| C6 | Small cell carcinoma | III | ++/+++, 90% | + |
| C7 | Small cell carcinoma | III | +++, 90% | + |
| C8 | Small cell carcinoma | III | +, 50% | + |
| C9 | Small cell carcinoma | I | ++/+++, 80% | + |

| Core | Tissues/Diagnosis | stage | SC16.65 | CHGA |
|---|---|---|---|---|
| D1 | Small cell carcinoma | II | - | - |
| D2 | Small cell carcinoma | II | +, 20% | + |
| D3 | Small cell carcinoma | II | +, 30% | + |
| D4 | Small cell carcinoma | IIIa | +, 10% | + |
| D5 | Small cell carcinoma | IIIa | - | - |
| D6 | Small cell carcinoma | II | ++/+++, 90% | + |
| D7 | Small cell carcinoma | II | +, 70% | + |
| D8 | Small cell carcinoma | II | +++, 90% | + |
| D9 | Small cell carcinoma | IIIa | +, 70% | - |
| E1 | Small cell carcinoma | IIIa | +, 20% | + |
| E2 | Small cell carcinoma | IIIa | +, 10% | + |
| E3 | Small cell carcinoma | IIIb | +, 20% | + |
| E4 | Small cell carcinoma | IIIa | +, 70% | + |
| E5 | Empty core | | | |
| E6 | Small cell carcinoma | IIIb | +, 70% | + |
| E7 | Small cell carcinoma | IIIa | ++, 70% | - |
| E8 | Small cell carcinoma | IIIb | ++, 80% | + |
| E9 | Small cell carcinoma | IIIb | ++, 90% | + |

FIG. 16F

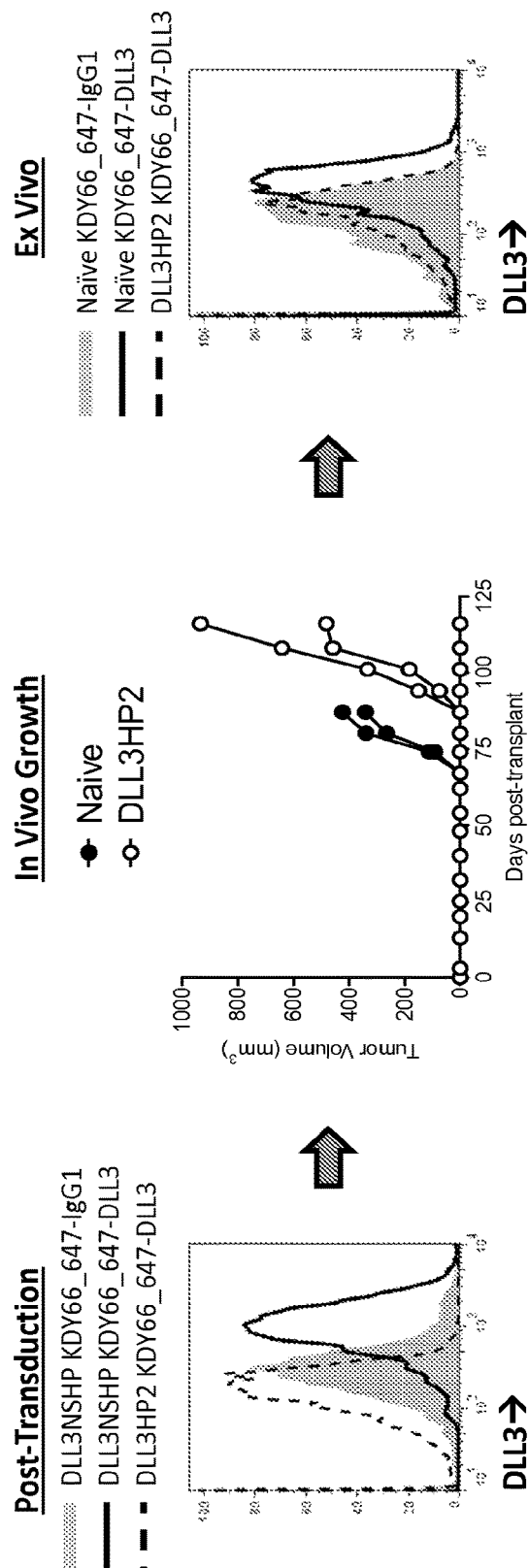

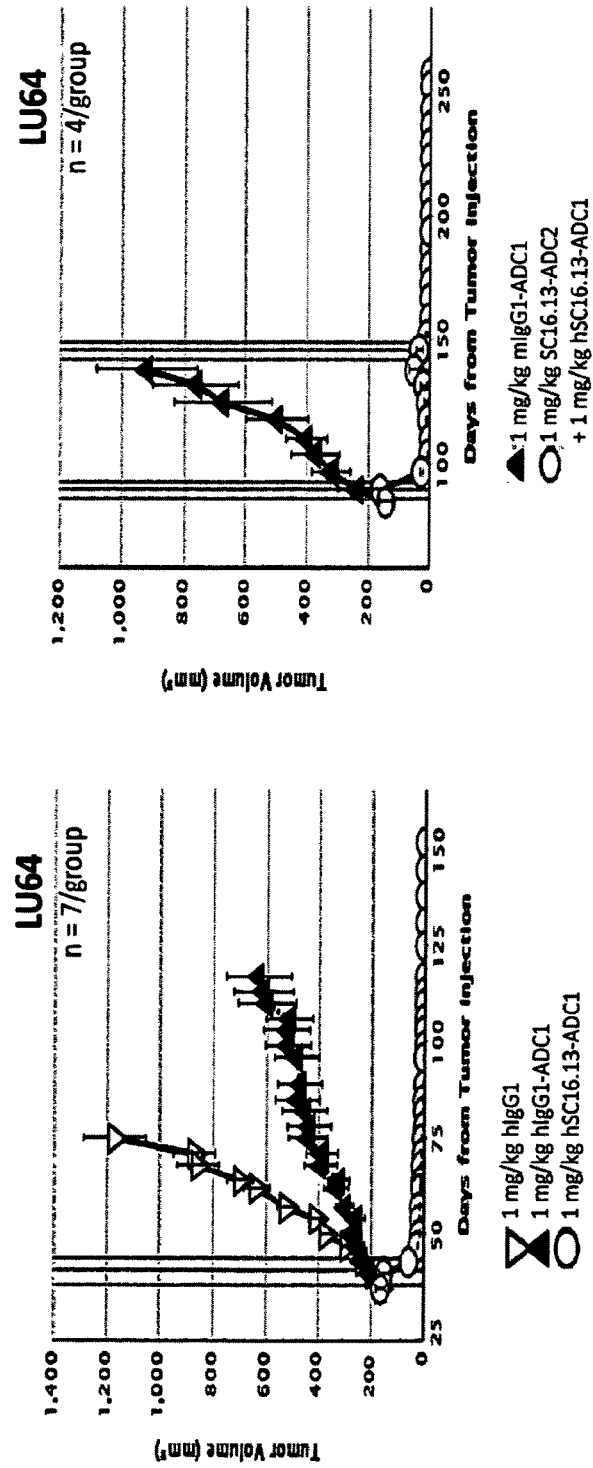

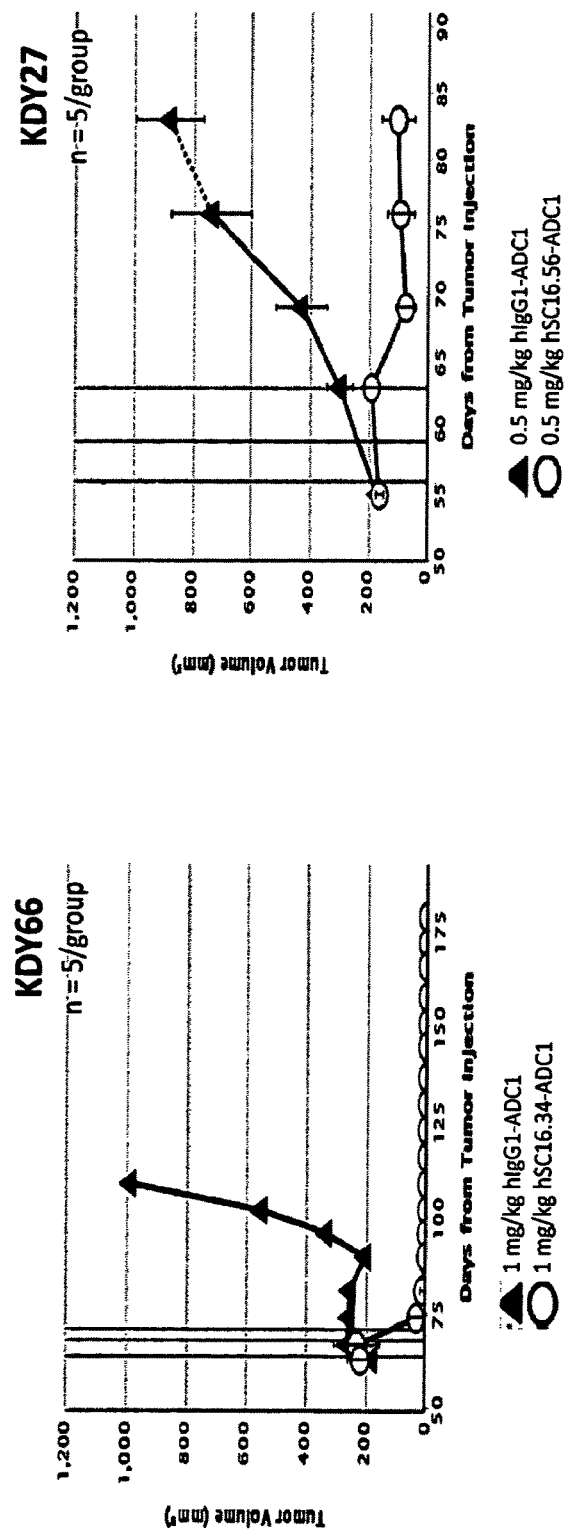

SEQUENCE LISTING

<160> NUMBER OF SEQ ID NOS: 413

<210> SEQ ID NO 1
<211> LENGTH: 2387
<212> TYPE: DNA
<213> ORGANISM: Homo sapiens

<400> SEQUENCE: 1

| | | | | | | |
|---|---|---|---|---|---|---|
| agatataagg | cttggaagcc | agcagctgcg | actcccgaga | cccccccacc | agaaggccat | 60 |
| ggtctcccca | cggatgtccg | ggctcctctc | ccagactgtg | atcctagcgc | tcattttcct | 120 |
| cccccagaca | cggcccgctg | gcgtcttcga | gctgcagatc | cactctttcg | ggccgggtcc | 180 |
| aggccctggg | gccccgcggt | ccccctgcag | cgcccggctc | cctgccgcc | tcttcttcag | 240 |
| agtctgcctg | aagcctgggc | tctcagagga | ggccgccgag | tccccgtgcg | ccctgggcgc | 300 |
| ggcgctgagt | gcgcgcggac | cggtctacac | cgagcagccc | ggagcgcccg | cgcctgatct | 360 |
| cccactgccc | gacggcctct | tgcaggtgcc | cttccgggac | gcctggcctg | gcaccttctc | 420 |
| tttcatcatc | gaaacctgga | gagggagtt | aggagaccag | attggagggc | ccgcctggag | 480 |
| cctgctggcg | cgcgtggctg | gcaggcggcg | cttggcagcc | ggaggcccgt | gggcccggga | 540 |
| cattcagcgc | gcaggcgcct | gggagctgcg | cttctcgtac | cgcgcgcgct | gcgagccgcc | 600 |
| tgccgtcggg | accgcgtgca | cgcgcctctg | ccgtccgcgc | agcgccccct | cgcggtgcgg | 660 |
| tccgggactg | cgcccctgcg | caccgctcga | ggacgaatgt | gaggcgccgc | tggtgtgccg | 720 |
| agcaggctgc | agccctgagc | atggcttctg | tgaacagccc | ggtgaatgcc | gatgcctaga | 780 |
| gggctggact | ggaccctct | gcacggtccc | tgtctccacc | agcagctgcc | tcagccccag | 840 |
| gggcccgtcc | tctgctacca | ccggatgcct | tgtccctggg | cctgggccct | gtgacgggaa | 900 |
| cccgtgtgcc | aatggaggca | gctgtagtga | gacacccagg | tcctttgaat | gcacctgccc | 960 |
| gcgtgggttc | tacgggctgc | ggtgtgaggt | gagcggggtg | acatgtgcag | atggaccctg | 1020 |
| cttcaacggc | ggcttgtgtg | tcgggggtgc | agaccctgac | tctgcctaca | tctgccactg | 1080 |
| cccacccggt | ttccaaggct | ccaactgtga | agagggtg | gaccggtgca | gcctgcagcc | 1140 |
| atgccgcaat | ggcggactct | gcctggacct | gggccacgcc | ctgcgctgcc | gctgccgcgc | 1200 |
| cggcttcgcg | gtcctcgct | gcgagcacga | cctggacgac | tgcgcgggcc | gcgcctgcgc | 1260 |
| taacggcggc | acgtgtgtgg | agggcggcgg | cgcgcaccgc | tgctcctgcg | cgctgggctt | 1320 |
| cggcggccgc | gactgccgcg | agcgcgcgga | cccgtgcgcc | gcgcgcccct | gtgctcacgg | 1380 |
| cggccgctgc | tacgcccact | tctccggcct | cgtctgcgct | tgcgctcccg | gctacatggg | 1440 |
| agcgcggtgt | gagttcccag | tgcaccccga | cggcgcaagc | gccttgcccg | cggcccgcc | 1500 |
| gggcctcagg | cccggggacc | ctcagcgcta | ccttttgcct | ccggctctgg | gactgctcgt | 1560 |
| ggccgcgggc | gtggccggcg | ctgcgctctt | gctggtccac | gtgcgccgcc | gtggccactc | 1620 |
| ccaggatgct | gggtctcgct | tgctggctgg | gaccccggag | ccgtcagtcc | acgcactccc | 1680 |
| ggatgcactc | aacaacctaa | ggacgcagga | gggttccggg | gatggtccga | gctcgtccgt | 1740 |
| agattggaat | cgccctgaag | atgtagaccc | tcaagggatt | tatgtcatat | ctgctccttc | 1800 |
| catctacgct | cggaggtag | cgacgcccct | tttcccccg | ctacacactg | ggcgcgctgg | 1860 |
| gcagaggcag | cacctgcttt | ttccctaccc | ttcctcgatt | ctgtccgtga | aatgaattgg | 1920 |
| gtagagtctc | tggaaggttt | taagcccatt | ttcagttcta | acttactttc | atcctatttt | 1980 |
| gcatccctct | tatcgttttg | agctacctgc | catcttctct | ttgaaaaacc | tatgggcttg | 2040 |
| aggaggtcac | gatgccgact | ccgccagagc | ttttccactg | attgtactca | gcggggaggc | 2100 |

-continued

| | |
|---|---|
| aggggaggca gaggggcagc ctctctaatg cttcctactc attttgtttc taggcctgac | 2160 |
| gcgtctcctc catccgcacc tggagtcaga gcgtggattt ttgtatttgc tcggtggtgc | 2220 |
| ccagtctctg ccccagaggc tttggagttc aatcttgaag gggtgtctgg gggaacttta | 2280 |
| ctgttgcaag ttgtaaataa tggttattta tatcctattt tttctcaccc catctctcta | 2340 |
| gaaacaccta taaaggctat tattgtgatc agttttgact aacaaaa | 2387 |

<210> SEQ ID NO 2
<211> LENGTH: 2052
<212> TYPE: DNA
<213> ORGANISM: Homo sapiens

<400> SEQUENCE: 2

| | |
|---|---|
| agatataagg cttggaagcc agcagctgcg actcccgaga ccccccacc agaaggccat | 60 |
| ggtctcccca cggatgtccg ggctcctctc ccagactgtg atcctagcgc tcatttcct | 120 |
| cccccagaca cggcccgctg gcgtcttcga gctgcagatc cactctttcg ggccgggtcc | 180 |
| aggccctggg gccccgcggt ccccctgcag cgcccggctc ccctgccgcc tcttcttcag | 240 |
| agtctgcctg aagcctgggc tctcagagga ggccgccgag tccccgtgcg ccctgggcgc | 300 |
| ggcgctgagt gcgcgcggac cggtctacac cgagcagccc ggagcgcccg cgcctgatct | 360 |
| cccactgccc gacggcctct tgcaggtgcc cttccgggac gcctggcctg gcaccttctc | 420 |
| tttcatcatc gaaacctgga gagaggagtt aggagaccag attggagggc ccgcctggag | 480 |
| cctgctggcg cgcgtggctg gcaggcggcg cttggcagcc ggaggcccgt gggcccggga | 540 |
| cattcagcgc gcaggcgcct gggagctgcg cttctcgtac cgcgcgcgct gcgagccgcc | 600 |
| tgccgtcggg accgcgtgca cgcgcctctg ccgtccgcgc agcgccccct cgcggtgcgg | 660 |
| tccgggactg cgcccctgcg caccgctcga ggacgaatgt gaggcgccgc tggtgtgccg | 720 |
| agcaggctgc agccctgagc atggcttctg tgaacagccc ggtgaatgcc gatgcctaga | 780 |
| gggctggact ggacccctct gcacggtccc tgtctccacc agcagctgcc tcagcccag | 840 |
| gggcccgtcc tctgctacca ccggatgcct tgtccctggg cctgggccct gtgacgggaa | 900 |
| cccgtgtgcc aatggaggca gctgtagtga gacacccagg tcctttgaat gcacctgccc | 960 |
| gcgtggggttc tacgggctgc ggtgtgaggt gagcggggtg acatgtgcag atggaccctg | 1020 |
| cttcaacggc ggcttgtgtg tcgggggtgc agaccctgac tctgcctaca tctgccactg | 1080 |
| cccacccggt ttccaaggct ccaactgtga gaagagggtg gaccggtgca gcctgcagcc | 1140 |
| atgccgcaat ggcggactct gcctggacct gggccacgcc ctgcgctgcc gctgcgcgc | 1200 |
| cggcttcgcg ggtcctcgct gcgagcacga cctggacgac tgcgcgggcc gcgcctgcgc | 1260 |
| taacggcggc acgtgtgtgg agggcggcgg cgcgcaccgc tgctcctgcg cgctgggctt | 1320 |
| cggcggccgc gactgccgcg agcgcgcgga cccgtgcgcc gcgcgcccct gtgctcacgg | 1380 |
| cggccgctgc tacgcccact ctctccggcct cgtctgcgct tgcgctcccg gctacatggg | 1440 |
| agcgcggtgt gagttcccag tgcaccccga cggcgcaagc gccttgcccg cggccccgcc | 1500 |
| gggcctcagg cccggggacc ctcagcgcta ccttttgcct ccggctctgg gactgctcgt | 1560 |
| ggccgcgggc gtggccggcg ctgcgctctt gctggtccac gtgcgccgcc gtggccactc | 1620 |
| ccaggatgct gggtctcgct tgctggctgg gaccccggag ccgtcagtcc acgcactccc | 1680 |
| ggatgcactc aacaacctaa ggacgcagga gggttccggg gatggtccga gctcgtccgt | 1740 |
| agattggaat cgccctgaag atgtagaccc tcaagggatt tatgtcatat ctgctccttc | 1800 |

-continued

```
catctacgct cgggaggcct gacgcgtctc ctccatccgc acctggagtc agagcgtgga   1860
tttttgtatt tgctcggtgg tgcccagtct ctgccccaga ggctttggag ttcaatcttg   1920 aagggtgtc tggggaact tactgttgc aagttgtaaa taatggttat ttatatccta     1980 tttttctca ccccatctct ctagaaacac ctataaaggc tattattgtg atcagttttg   2040
actaacaaaa aa                                                       2052
```

<210> SEQ ID NO 3
<211> LENGTH: 618
<212> TYPE: PRT
<213> ORGANISM: Homo sapiens

<400> SEQUENCE: 3

```
Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Ala Pro Arg Ser
        35                  40                  45

Pro Cys Ser Ala Arg Leu Pro Cys Arg Leu Phe Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Gly Ala Asp Pro Asp Ser Ala
```

```
                    325                 330                 335
Tyr Ile Cys His Cys Pro Pro Gly Phe Gln Gly Ser Asn Cys Glu Lys
                340                 345                 350

Arg Val Asp Arg Cys Ser Leu Gln Pro Cys Arg Asn Gly Gly Leu Cys
            355                 360                 365

Leu Asp Leu Gly His Ala Leu Arg Cys Arg Cys Arg Ala Gly Phe Ala
        370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Ala His Arg Cys Ser
                405                 410                 415

Cys Ala Leu Gly Phe Gly Gly Arg Asp Cys Arg Glu Arg Ala Asp Pro
                420                 425                 430

Cys Ala Ala Arg Pro Cys Ala His Gly Gly Arg Cys Tyr Ala His Phe
                435                 440                 445

Ser Gly Leu Val Cys Ala Cys Ala Pro Gly Tyr Met Gly Ala Arg Cys
        450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
                485                 490                 495

Leu Gly Leu Leu Val Ala Ala Gly Val Ala Gly Ala Ala Leu Leu Leu
                500                 505                 510

Val His Val Arg Arg Arg Gly His Ser Gln Asp Ala Gly Ser Arg Leu
        515                 520                 525

Leu Ala Gly Thr Pro Glu Pro Ser Val His Ala Leu Pro Asp Ala Leu
    530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Val Ala Thr Pro Leu Phe
            580                 585                 590

Pro Pro Leu His Thr Gly Arg Ala Gly Gln Arg Gln His Leu Leu Phe
                595                 600                 605

Pro Tyr Pro Ser Ser Ile Leu Ser Val Lys
            610                 615

<210> SEQ ID NO 4
<211> LENGTH: 587
<212> TYPE: PRT
<213> ORGANISM: Homo sapiens

<400> SEQUENCE: 4

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
                20                  25                  30

Gln Ile His Ser Phe Gly Pro Gly Pro Gly Pro Gly Ala Pro Arg Ser
            35                  40                  45

Pro Cys Ser Ala Arg Leu Pro Cys Arg Leu Phe Phe Arg Val Cys Leu
        50                  55                  60

Lys Pro Gly Leu Ser Glu Glu Ala Ala Glu Ser Pro Cys Ala Leu Gly
65                  70                  75                  80
```

```
Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
        355                 360                 365

Leu Asp Leu Gly His Ala Leu Arg Cys Arg Cys Arg Ala Gly Phe Ala
    370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Gly Ala His Arg Cys Ser
                405                 410                 415

Cys Ala Leu Gly Phe Gly Gly Arg Asp Cys Arg Glu Arg Ala Asp Pro
            420                 425                 430

Cys Ala Ala Arg Pro Cys Ala His Gly Gly Arg Cys Tyr Ala His Phe
        435                 440                 445

Ser Gly Leu Val Cys Ala Cys Ala Pro Gly Tyr Met Gly Ala Arg Cys
    450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Leu Pro Pro Ala
                485                 490                 495

Leu Gly Leu Leu Val Ala Ala Gly Val Ala Gly Ala Ala Leu Leu Leu
```

|  |  |  |  | 500 |  |  |  | 505 |  |  |  | 510 |  |
|---|---|---|---|---|---|---|---|---|---|---|---|---|---|
Val | His | Val | Arg | Arg | Gly | His | Ser | Gln | Asp | Ala | Gly | Ser | Arg | Leu
 |  |  |  | 515 |  |  |  | 520 |  |  |  | 525 |  |

Leu Ala Gly Thr Pro Glu Pro Ser Val His Ala Leu Pro Asp Ala Leu
530                535                540

Asn Asn Leu Arg Thr Gln Glu Gly Ser Gly Asp Gly Pro Ser Ser Ser
545                 550                555                 560

Val Asp Trp Asn Arg Pro Glu Asp Val Asp Pro Gln Gly Ile Tyr Val
                565                570                575

Ile Ser Ala Pro Ser Ile Tyr Ala Arg Glu Ala
            580                585

<210> SEQ ID NO 5
<211> LENGTH: 1686
<212> TYPE: DNA
<213> ORGANISM: Mus sp.

<400> SEQUENCE: 5

```
gctggtgtct tcgagctaca aattcattct ttcgggccag gcccaggcct cgggacccca    60
cgctccccct gcaacgcccg aggcccttgc cgcctcttct tcagggtctg cctgaagccc   120
ggagtctccc aggaggccac cgagtccctg tgcgccctgg gcgcagcact gagcacgagc   180
gtcccggtct atacggagca ccccggagag tcagcggctg ccctgccgct gcctgatggc   240
ctcgtacgtg tgcccttccg cgatgcttgg ccgggcacct tctccctcgt cattgaaacc   300
tggagagagc agctgggaga gcatgctgga ggggcccgcct ggaacctgct agcacgtgtg   360
gtcggccgta gacgcctggc ggctggggc cgtgggccc gcgatgtgca gcgcacaggc   420
acatgggagt tgcacttctc ctaccgcgcg cggtgcgagc cgcccgccgt cggggccgcc   480
tgcgcgcgcc tgtgccgctc acgcagtgcc ccctcgcggt gtggcccggg actgcgaccc   540
tgcacgccat tcccagacga gtgcgaagcc cgtctgtgt gtcgaccagg ctgcagcccc   600
gagcacggct actgtgaaga gcctgatgaa tgccgttgcc tggagggctg gactggaccc   660
ctctgcacgg tccctgtctc caccagtagc tgcctgaact ccagggttcc tggtcctgcc   720
agcactggat gccttttacc tgggcctgga ccttgtgatg gaacccatg tgccaatggg   780
ggcagctgta gtgaaacctc tggctccttt gaatgtgcct gtcccgggg attctacggg   840
cttcgatgtg aggtgagcgg ggtcacgtgc gcagatggac cctgcttcaa tggcggcttg   900
tgtgttggcg gtgaagatcc tgactctgcc tatgtctgtc attgccacc tggtttccaa   960
ggctctaact gtgagaagag ggtggaccgc tgtagcctgc agccatgtca gaatggcggc  1020
ctctgcctgg acctgggcca cgcgttgcgc tgccgctgtc gcgcgggatt cgccgggccg  1080
cgctgcgagc acgacctgga cgactgcgcc ggccgcgcct gtgccaacgg cggcacgtgc  1140
gtggagggcg gcggctcgcg ccgctgctcc tgtgcgctgg gcttcggcgg gcgcgactgc  1200
cgagaacgcg ccgaccctg cgcctcccgc cctgcgcgc atggaggccg ttgctacgcc  1260
cacttctctg gcctggtctg cgcctgcgcg cccggctaca tgggcgtgag atgcgagttc  1320
gctgtgcgcc cggacggcgc ggacgcggtg cccgccgccc cgcggggcct gaggcaggcg  1380
gatccacagc gctttcttct gcctcccgcc ttggggctgc tggtgccgc cggtttggct  1440
ggcgccgcac tcttggtcat ccacgttcgc cgccgaggtc ctggccagga taccgggact  1500
cgcctgcttt ctgggacccg ggagccttcg gtccacacgc tccgggatgc actcaacaac  1560
ctgaggttac aagacggtgc tggggatggc cccagttcgt cggctgactg gaatcatcct  1620
```

-continued

```
gaagatggag actctagatc catttatgtc ataccagccc cttccattta tgcacgagag    1680
gcctga                                                                1686
```

<210> SEQ ID NO 6
<211> LENGTH: 561
<212> TYPE: PRT
<213> ORGANISM: Mus sp.

<400> SEQUENCE: 6

```
Ala Gly Val Phe Glu Leu Gln Ile His Ser Phe Gly Pro Gly Pro Gly
 1               5                  10                  15

Leu Gly Thr Pro Arg Ser Pro Cys Asn Ala Arg Gly Pro Cys Arg Leu
            20                  25                  30

Phe Phe Arg Val Cys Leu Lys Pro Gly Val Ser Gln Glu Ala Thr Glu
        35                  40                  45

Ser Leu Cys Ala Leu Gly Ala Ala Leu Ser Thr Ser Val Pro Val Tyr
    50                  55                  60

Thr Glu His Pro Gly Glu Ser Ala Ala Ala Leu Pro Leu Pro Asp Gly
65                  70                  75                  80

Leu Val Arg Val Pro Phe Arg Asp Ala Trp Pro Gly Thr Phe Ser Leu
                85                  90                  95

Val Ile Glu Thr Trp Arg Glu Gln Leu Gly Glu His Ala Gly Gly Pro
            100                 105                 110

Ala Trp Asn Leu Leu Ala Arg Val Val Gly Arg Arg Leu Ala Ala
        115                 120                 125

Gly Gly Pro Trp Ala Arg Asp Val Gln Arg Thr Gly Thr Trp Glu Leu
    130                 135                 140

His Phe Ser Tyr Arg Ala Arg Cys Glu Pro Pro Ala Val Gly Ala Ala
145                 150                 155                 160

Cys Ala Arg Leu Cys Arg Ser Arg Ser Ala Pro Ser Arg Cys Gly Pro
                165                 170                 175

Gly Leu Arg Pro Cys Thr Pro Phe Pro Asp Glu Cys Glu Ala Pro Ser
            180                 185                 190

Val Cys Arg Pro Gly Cys Ser Pro Glu His Gly Tyr Cys Glu Glu Pro
        195                 200                 205

Asp Glu Cys Arg Cys Leu Glu Gly Trp Thr Gly Pro Leu Cys Thr Val
    210                 215                 220

Pro Val Ser Thr Ser Ser Cys Leu Asn Ser Arg Val Pro Gly Pro Ala
225                 230                 235                 240

Ser Thr Gly Cys Leu Leu Pro Gly Pro Gly Pro Cys Asp Gly Asn Pro
                245                 250                 255

Cys Ala Asn Gly Gly Ser Cys Ser Glu Thr Ser Gly Ser Phe Glu Cys
            260                 265                 270

Ala Cys Pro Arg Gly Phe Tyr Gly Leu Arg Cys Glu Val Ser Gly Val
        275                 280                 285

Thr Cys Ala Asp Gly Pro Cys Phe Asn Gly Gly Leu Cys Val Gly Gly
    290                 295                 300

Glu Asp Pro Asp Ser Ala Tyr Val Cys His Cys Pro Pro Gly Phe Gln
305                 310                 315                 320

Gly Ser Asn Cys Glu Lys Arg Val Asp Arg Cys Ser Leu Gln Pro Cys
                325                 330                 335

Gln Asn Gly Gly Leu Cys Leu Asp Leu Gly His Ala Leu Arg Cys Arg
            340                 345                 350

Cys Arg Ala Gly Phe Ala Gly Pro Arg Cys Glu His Asp Leu Asp Asp
```

```
                355                 360                 365
Cys Ala Gly Arg Ala Cys Ala Asn Gly Gly Thr Cys Val Glu Gly Gly
            370                 375                 380
Gly Ser Arg Arg Cys Ser Cys Ala Leu Gly Phe Gly Gly Arg Asp Cys
385                 390                 395                 400
Arg Glu Arg Ala Asp Pro Cys Ala Ser Arg Pro Cys Ala His Gly Gly
                405                 410                 415
Arg Cys Tyr Ala His Phe Ser Gly Leu Val Cys Ala Cys Ala Pro Gly
            420                 425                 430
Tyr Met Gly Val Arg Cys Glu Phe Ala Val Arg Pro Asp Gly Ala Asp
                435                 440                 445
Ala Val Pro Ala Ala Pro Arg Gly Leu Arg Gln Ala Asp Pro Gln Arg
        450                 455                 460
Phe Leu Leu Pro Pro Ala Leu Gly Leu Leu Val Ala Ala Gly Leu Ala
465                 470                 475                 480
Gly Ala Ala Leu Leu Val Ile His Val Arg Arg Arg Gly Pro Gly Gln
                485                 490                 495
Asp Thr Gly Thr Arg Leu Leu Ser Gly Thr Arg Glu Pro Ser Val His
            500                 505                 510
Thr Leu Pro Asp Ala Leu Asn Asn Leu Arg Leu Gln Asp Gly Ala Gly
        515                 520                 525
Asp Gly Pro Ser Ser Ala Asp Trp Asn His Pro Glu Asp Gly Asp
530                 535                 540
Ser Arg Ser Ile Tyr Val Ile Pro Ala Pro Ser Ile Tyr Ala Arg Glu
545                 550                 555                 560
Ala

<210> SEQ ID NO 7
<211> LENGTH: 1794
<212> TYPE: DNA
<213> ORGANISM: Macaca fascicularis

<400> SEQUENCE: 7
ccccaagcca ggcccgctgg cgtgttcgaa ctgcagatcc atagcttcgg ccctggccct        60
ggacccggag cccctagaag cccttgttcc gctagaggcc cctgcagact gttcttcaga       120
gtctgcctga agcctggcct gagcgaggag gctgctgaga gcccttgtgc tctgggagct       180
gccctcagcg ctaggggccc tgtctacacc gagcaacctg aggctcccgc tcccgatctg       240
cctctcccta acggcctgct gcaggtgccc ttcagggatg cttggcccgg aaccttcagc       300
ctcatcatcg agacctggag ggaggaactc ggagaccaga ttggaggacc cgcctggtcc       360
ctgctcgcta gagtgacaag aagaagaagg ctggctgctg gcggaccttg gctagagat        420
atccagagag ctggcgcctg ggagctcagg ttcagctaca gggccagatg tgagctccct       480
gccgtgggca ccgcttgtac caggctgtgt aggcccagat ccgccccttc agatgtggc        540
cccggactca gaccttgcgc tcctctcgag gacgagtgtg aagctcctcc cgtctgtagg       600
gccggatgca gcctcgagca cggcttctgt gagcagcctg gcgaatgtag gtgcctcgaa       660
ggctggaccg gccctctctg tatggtgcct gtctccacct cctcctgtct cggactgagg       720
ggcccttcct ccgctacaac cggatgtctg gtccctggac ctggaccttg cgacggaaac       780
ccttgtgcca acggaggctc ctgtagcgag accccggaa gctttgaatg tacctgcccc       840
aggggctttt acggctcag atgcgaggtc agcggagtca catgcgccga cggaccctgc       900
tttaatggag gactctgcgt gggaggagcc gaccctgata gcgcttacat ctgtcactgt       960
```

-continued

```
cccccggct tcagggctc caactgcgag aagagggtcg acaggtgctc cctgcaaccc    1020
tgtagaaatg gcggcctctg cctggatctg gacatgctc tcaggtgcag atgtagagct    1080
ggattcgccg acccaggtg cgagcatgat ctcgacgatt gtgctggcag ggcctgcgct    1140 aatgaggaa catgtgtgga aggaggcgga gcccacagat gcagctgcgc tctcggcttc    1200
ggcggaagag actgcagaga gagggctgac ccttgtgccg ccaggccttg tgctcatggc    1260
ggaaggtgct acgcccattt ctccggactc gtgtgcgcct gcgcccctgg atatatgggc    1320
gctaggtgcg agtttcccgt ccaccctgat ggagtcagcg ctctccctgc cgctcctcct    1380
ggactgagac ctggagatcc tcagagatac ctgctccctc ctgccctcgg actcctggtc    1440
gctgctggag tcgctggagc cgctctcctc ctgggacacg tcaggagaag aggccacgcc    1500
caggatgctg gaagcagact gctggccgga cacccgagc cttccgtcca tgccctgcct    1560
gacgccctca acaacctgag gacccaggag ggccctggag atgtgcctag cagctccgtc    1620
gactggaaca gacctgagga tgtggactcc aggggcatct acgtgatcag cgcccccctcc    1680 atctatgcca gggaggtcgc catgccctc tttcctcctc tgcatacagg cagagccggc    1740
cagagacaga acctgctctt cccctacccc agcagcatcc tgtccgtgaa gtga          1794
```

<210> SEQ ID NO 8
<211> LENGTH: 597
<212> TYPE: PRT
<213> ORGANISM: Macaca fascicularis

<400> SEQUENCE: 8

```
Pro Gln Ala Arg Pro Ala Gly Val Phe Glu Leu Gln Ile His Ser Phe
1               5                   10                  15

Gly Pro Gly Pro Gly Pro Gly Ala Pro Arg Ser Pro Cys Ser Ala Arg
            20                  25                  30

Gly Pro Cys Arg Leu Phe Phe Arg Val Cys Leu Lys Pro Gly Leu Ser
        35                  40                  45

Glu Glu Ala Ala Glu Ser Pro Cys Ala Leu Gly Ala Ala Leu Ser Ala
    50                  55                  60

Arg Gly Pro Val Tyr Thr Glu Gln Pro Glu Ala Pro Ala Pro Asp Leu
65                  70                  75                  80

Pro Leu Pro Asn Gly Leu Leu Gln Val Pro Phe Arg Asp Ala Trp Pro
                85                  90                  95

Gly Thr Phe Ser Leu Ile Ile Glu Thr Trp Arg Glu Glu Leu Gly Asp
            100                 105                 110

Gln Ile Gly Gly Pro Ala Trp Ser Leu Leu Ala Arg Val Thr Arg Arg
        115                 120                 125

Arg Arg Leu Ala Ala Gly Gly Pro Trp Ala Arg Asp Ile Gln Arg Ala
    130                 135                 140

Gly Ala Trp Glu Leu Arg Phe Ser Tyr Arg Ala Arg Cys Glu Leu Pro
145                 150                 155                 160

Ala Val Gly Thr Ala Cys Thr Arg Leu Cys Arg Pro Arg Ser Ala Pro
                165                 170                 175

Ser Arg Cys Gly Pro Gly Leu Arg Pro Cys Ala Pro Leu Glu Asp Glu
            180                 185                 190

Cys Glu Ala Pro Pro Val Cys Arg Ala Gly Cys Ser Leu Glu His Gly
        195                 200                 205

Phe Cys Glu Gln Pro Gly Glu Cys Arg Cys Leu Glu Gly Trp Thr Gly
    210                 215                 220
```

```
Pro Leu Cys Met Val Pro Val Ser Thr Ser Ser Cys Leu Gly Leu Arg
225                 230                 235                 240

Gly Pro Ser Ser Ala Thr Thr Gly Cys Leu Val Pro Gly Pro Gly Pro
            245                 250                 255

Cys Asp Gly Asn Pro Cys Ala Asn Gly Gly Ser Cys Ser Glu Thr Pro
        260                 265                 270

Gly Ser Phe Glu Cys Thr Cys Pro Arg Gly Phe Tyr Gly Leu Arg Cys
    275                 280                 285

Glu Val Ser Gly Val Thr Cys Ala Asp Gly Pro Cys Phe Asn Gly Gly
290                 295                 300

Leu Cys Val Gly Gly Ala Asp Pro Asp Ser Ala Tyr Ile Cys His Cys
305                 310                 315                 320

Pro Pro Gly Phe Gln Gly Ser Asn Cys Glu Lys Arg Val Asp Arg Cys
            325                 330                 335

Ser Leu Gln Pro Cys Arg Asn Gly Gly Leu Cys Leu Asp Leu Gly His
        340                 345                 350

Ala Leu Arg Cys Arg Cys Arg Ala Gly Phe Ala Gly Pro Arg Cys Glu
    355                 360                 365

His Asp Leu Asp Asp Cys Ala Gly Arg Ala Cys Ala Asn Gly Gly Thr
370                 375                 380

Cys Val Glu Gly Gly Gly Ala His Arg Cys Ser Cys Ala Leu Gly Phe
385                 390                 395                 400

Gly Gly Arg Asp Cys Arg Glu Arg Ala Asp Pro Cys Ala Ala Arg Pro
            405                 410                 415

Cys Ala His Gly Gly Arg Cys Tyr Ala His Phe Ser Gly Leu Val Cys
        420                 425                 430

Ala Cys Ala Pro Gly Tyr Met Gly Ala Arg Cys Glu Phe Pro Val His
    435                 440                 445

Pro Asp Gly Val Ser Ala Leu Pro Ala Ala Pro Pro Gly Leu Arg Pro
450                 455                 460

Gly Asp Pro Gln Arg Tyr Leu Leu Pro Ala Leu Gly Leu Leu Val
465                 470                 475                 480

Ala Ala Gly Val Ala Gly Ala Ala Leu Leu Leu Gly His Val Arg Arg
            485                 490                 495

Arg Gly His Ala Gln Asp Ala Gly Ser Arg Leu Leu Ala Gly Thr Pro
        500                 505                 510

Glu Pro Ser Val His Ala Leu Pro Asp Ala Leu Asn Asn Leu Arg Thr
    515                 520                 525

Gln Glu Gly Pro Gly Asp Val Pro Ser Ser Val Asp Trp Asn Arg
530                 535                 540

Pro Glu Asp Val Asp Ser Arg Gly Ile Tyr Val Ile Ser Ala Pro Ser
545                 550                 555                 560

Ile Tyr Ala Arg Glu Val Ala Met Pro Leu Phe Pro Pro Leu His Thr
            565                 570                 575

Gly Arg Ala Gly Gln Arg Gln Asn Leu Leu Phe Pro Tyr Pro Ser Ser
        580                 585                 590

Ile Leu Ser Val Lys
        595

<210> SEQ ID NO 9
<211> LENGTH: 5
<212> TYPE: PRT
<213> ORGANISM: Homo sapiens

<400> SEQUENCE: 9
```

-continued

```
Gln Pro Gly Ala Pro
1               5

<210> SEQ ID NO 10
<211> LENGTH: 4
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Any amino acid

<400> SEQUENCE: 10

Gly Xaa Arg Pro
1

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19
```

-continued

000

<210> SEQ ID NO 20
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

```
Gln Ile Val Leu Thr Gln Ser Pro Ala Ile Met Ser Val Ser Leu Gly
1               5                  10                  15

Glu Arg Val Thr Met Thr Cys Thr Ala Ser Ser Ser Val Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Phe Phe Thr Ile Ser Ser Met Glu
65                  70                  75                  80

Ala Glu Asp Ala Ala Thr Tyr Tyr Cys His Gln Tyr His Arg Ser Pro
                85                  90                  95

Phe Thr Phe Gly Ala Gly Thr Lys Leu Lys Ile Arg
            100                 105
```

<210> SEQ ID NO 21
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

```
Gln Val Thr Leu Lys Glu Ser Gly Pro Gly Ile Leu Gln Pro Ser Gln
1               5                  10                  15

Thr Leu Ser Leu Thr Cys Ser Phe Ser Gly Phe Ser Leu Ser Thr Ser
                20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Val Lys Arg Tyr Asn Pro Ala
        50                  55                  60

Leu Lys Ser Arg Leu Thr Ile Ser Lys Asp Thr Ser Ser Ser Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ala Asp Tyr Gly Gly Asp Tyr Tyr Ala Met Asp Tyr
            100                 105                 110

Trp Gly Gln Gly Thr Ser Val Thr Val Ser Ser
        115                 120
```

<210> SEQ ID NO 22
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 22

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Leu
65                  70                  75                  80

Glu Asp Ile Ala Thr Tyr Phe Cys Gln Gln Gly Asp Met Leu Pro Trp
                85                  90                  95

Thr Phe Gly Gly Gly Thr Lys Leu Glu Ile Lys
            100                 105

<210> SEQ ID NO 23
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Gly Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Tyr Asp Gly Tyr Ala Met Asp Tyr Trp Gly Gln Gly Thr Ser
            100                 105                 110

Val Thr Val Ser Ser
        115

<210> SEQ ID NO 24
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

```
His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Thr Arg Asn Pro Leu Thr
                85                  90                  95

Phe Gly Ala Gly Thr Lys Leu Glu Leu Lys
            100                 105

<210> SEQ ID NO 25
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Glu Gly Leu Glu
        35                  40                  45

Trp Leu Ala Asp Ile Trp Trp Asp Asp Asn Lys Tyr Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Val Asn Tyr Val Tyr Asp Pro Tyr Tyr Ala Met Asp
            100                 105                 110

Tyr Trp Gly Gln Gly Thr Ser Val Thr Val Ser Ser
        115                 120

<210> SEQ ID NO 26
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80
```

```
Ile Ser Thr Val Gln Val Glu Asp Leu Ala Val Tyr Tyr Cys His Gln
                85                  90                  95

Tyr Leu Ser Ser Trp Thr Phe Gly Gly Gly Thr Lys Leu Glu Ile Lys
            100                 105                 110
```

<210> SEQ ID NO 27
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Lys Met His Trp Val Lys Gln Ser His Val Lys Ser Leu Glu Trp Ile
            35                  40                  45

Gly Arg Ile Asn Pro Tyr Asn Gly Ala Thr Ser Tyr Asn Gln Asn Phe
    50                  55                  60

Lys Asp Lys Ala Thr Leu Thr Val Asp Lys Ser Ser Thr Ala Tyr
65                  70                  75                  80

Met Asp Leu His Ser Leu Thr Ser Glu Asp Ser Ala Val Tyr Phe Cys
                85                  90                  95

Ala Arg Gly Asp Tyr Arg Tyr Asp Trp Phe Ala Tyr Trp Gly Gln Gly
            100                 105                 110

Thr Leu Val Thr Val Ser Ala
        115
```

<210> SEQ ID NO 28
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

```
Glu Ile Gln Met Thr Gln Ser Pro Ser Ser Met Ser Ala Ser Leu Gly
1               5                   10                  15

Asp Arg Ile Thr Ile Thr Cys Gln Ala Thr Gln Asp Ile Val Lys Asn
                20                  25                  30

Leu Asn Trp Tyr Gln Gln Lys Pro Gly Lys Pro Pro Ser Phe Leu Ile
            35                  40                  45

Tyr Tyr Ala Ile Glu Leu Ala Glu Gly Val Pro Ser Arg Phe Ser Gly
    50                  55                  60

Ser Gly Ser Gly Ser Asp Tyr Ser Leu Thr Ile Ser Asn Leu Glu Ser
65                  70                  75                  80

Glu Asp Phe Ala Asp Tyr Tyr Cys Leu Gln Phe Tyr Glu Phe Pro Phe
                85                  90                  95

Thr Phe Gly Ala Gly Thr Lys Leu Glu Leu Lys
            100                 105
```

<210> SEQ ID NO 29
<211> LENGTH: 121
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29
```

Gln Ala Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Thr Gly Gly Thr Asn Tyr Asn Glu Asn Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Ser Pro Tyr Asp Tyr His Glu Gly Ala Met Asp Tyr Trp Gly
            100                 105                 110

Gln Gly Thr Ser Val Thr Val Ser Ser
            115                 120

```
<210> SEQ ID NO 30
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30
```

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Thr Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Phe Thr Phe Gly Ser Gly Thr Lys Leu Glu Ile Lys
            100                 105

```
<210> SEQ ID NO 31
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31
```

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
            35                  40                  45

Trp Leu Ala His Ile Trp Asp Asp Val Lys Arg Tyr Asn Pro Val
 50                  55                  60

Leu Lys Ser Arg Leu Thr Ile Ser Lys Asp Thr Ser Ser Ser Gln Val
 65                  70                  75                  80

Phe Leu Lys Ile Ala Ser Val Asp Thr Ala Asp Thr Ala Thr Tyr Tyr
                 85                  90                  95

Cys Ala Arg Leu Val Asp Asp Leu Tyr Tyr Phe Asp Tyr Trp Gly Gln
                100                 105                 110

Gly Thr Thr Leu Thr Val Ser Ser
            115                 120

<210> SEQ ID NO 32
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Asp Val Glu Met Thr Gln Thr Pro Leu Thr Leu Ser Val Thr Ile Gly
 1               5                  10                  15

Gln Pro Ala Ser Ile Ser Cys Lys Ser Ser Gln Ser Leu Ser Asp Ser
            20                  25                  30

Asp Gly Lys Thr Tyr Leu Asn Trp Met Phe Gln Arg Pro Gly Arg Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Lys His Phe Pro Trp Thr Phe Gly Gly Gly Thr Lys Leu Glu Ile Lys
                100                 105                 110

<210> SEQ ID NO 33
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
            35                  40                  45

Gly Trp Ile Asn Thr Glu Thr Val Glu Pro Thr Tyr Ala Asp Asp Phe
 50                  55                  60

-continued

```
Met Gly Arg Phe Ala Phe Ser Leu Glu Thr Ser Ala Ser Thr Ala Phe
 65                  70                  75                  80

Leu Gln Ile Asn Asn Leu Glu Asn Glu Asp Thr Ala Thr Tyr Phe Cys
                 85                  90                  95

Ala Arg Phe Gly Ser Tyr Ala Met Asp Tyr Trp Gly Gln Gly Thr Ser
            100                 105                 110

Val Thr Val Ser Ser
            115

<210> SEQ ID NO 34
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Gln Ile Val Leu Thr Gln Ser Pro Ala Leu Val Ser Ala Ser Pro Gly
  1               5                  10                  15

Glu Lys Val Thr Met Thr Cys Ser Ala Ser Ser Ser Val Ser Tyr Met
                 20                  25                  30

Tyr Trp Tyr Gln Gln Lys Pro Arg Ser Ser Pro Lys Pro Trp Ile Tyr
             35                  40                  45

Leu Thr Ser Asn Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Arg Ser Asn Pro Phe Thr
                 85                  90                  95

Phe Gly Ser Gly Thr Lys Leu Glu Ile Lys
            100                 105

<210> SEQ ID NO 35
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Val Thr Leu Lys Glu Ser Gly Pro Gly Ile Leu Gln Pro Ser Gln
  1               5                  10                  15

Thr Leu Ser Leu Thr Cys Ser Phe Ser Gly Phe Ser Leu Ser Thr Ser
                 20                  25                  30

Gly Met Gly Val Gly Trp Ile Arg Gln Pro Ser Gly Lys Gly Leu Glu
             35                  40                  45

Trp Leu Ala His Ile Trp Trp Asp Asp Val Lys Arg Tyr Asn Pro Ala
 50                  55                  60

Leu Lys Ser Arg Leu Thr Ile Ser Lys Asp Thr Ser Ser Ser Gln Val
 65                  70                  75                  80

Phe Leu Lys Ile Ala Ser Val Asp Thr Ala Asp Thr Ala Thr Tyr Tyr
                 85                  90                  95

Cys Ala Arg Ile Val Ser Phe Asp Asn Asp Val Val Ser Ala Met Asp
            100                 105                 110

Tyr Trp Gly Gln Gly Thr Ser Val Thr Val Ser Ser
```

```
                115                 120

<210> SEQ ID NO 36
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Ile Gln Met Thr Gln Ser Pro Ala Ser Leu Ala Ala Ser Val Gly
1               5                   10                  15

Glu Thr Val Ala Ile Thr Cys Arg Ala Ser Glu Asn Ile Tyr Tyr Asn
            20                  25                  30

Leu Ala Trp Tyr Gln Gln Lys Gln Gly Lys Ser Pro Gln Leu Leu Ile
        35                  40                  45

Tyr Thr Ala Asn Ser Leu Glu Asp Gly Val Pro Ser Arg Phe Ser Gly
    50                  55                  60

Ser Gly Ser Gly Thr Gln Tyr Ser Leu Lys Ile Asn Ser Met Gln Pro
65                  70                  75                  80

Glu Asp Ser Ala Thr Tyr Phe Cys Lys Gln Ala Tyr Asp Val Pro Pro
                85                  90                  95

Thr Phe Gly Gly Gly Thr Lys Leu Glu Ile Lys
            100                 105

<210> SEQ ID NO 37
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Tyr
            20                  25                  30

Trp Ile His Trp Ile Lys Gln Arg Pro Gly Gln Gly Leu Glu Trp Ile
        35                  40                  45

Gly Tyr Ile Asn Pro Thr Thr Val Tyr Thr Glu Phe Asn Gln Asn Phe
    50                  55                  60

Lys Asp Lys Ala Thr Leu Thr Ala Asp Lys Ser Ser Thr Thr Ala Ser
65                  70                  75                  80

Met Gln Leu Ser Ser Leu Thr Ser Glu Asp Ser Ala Val Tyr Tyr Cys
                85                  90                  95

Ala Arg Gly Gly Ser Asn Phe Phe Asp Tyr Trp Gly Gln Gly Thr Thr
            100                 105                 110

Leu Thr Val Ser Ser
        115

<210> SEQ ID NO 38
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 38

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asn Ile Ile Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Glu Arg Pro Tyr
                85                  90                  95

Thr Phe Gly Gly Gly Thr Lys Leu Glu Ile Lys Arg
            100                 105

<210> SEQ ID NO 39
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Glu Val Lys Leu Glu Glu Ser Gly Gly Gly Leu Val Gln Pro Gly Glu
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Asn Asn His Ala Thr Tyr Tyr Ala Glu
50                  55                  60

Ser Val Lys Gly Lys Phe Thr Ile Ser Arg Asp Asp Ser Lys Ser Arg
65                  70                  75                  80

Val Tyr Leu Gln Met Asn Asn Leu Arg Ala Ala Asp Thr Gly Ile Tyr
                85                  90                  95

Tyr Cys Thr Ala Tyr Ser Asn Phe Ala Tyr Trp Gly Gln Gly Thr Leu
            100                 105                 110

Val Thr Val Ser Thr
        115

<210> SEQ ID NO 40
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Asp Ile Gln Met Thr Gln Ser Pro Ser Ser Leu Ser Ala Ser Leu Gly
1               5                   10                  15

Gly Lys Val Thr Phe Thr Cys Lys Ala Ser Gln Asp Ile His Lys Tyr
            20                  25                  30

```
Val Ala Trp Tyr Gln His Lys Pro Gly Lys Gly Pro Arg Leu Leu Ile
         35                  40                  45

His Tyr Thr Ser Thr Leu Gln Pro Gly Ile Ser Arg Phe Ser Gly
 50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asn Asn Leu Tyr Thr
                 85                  90                  95

Phe Gly Gly Gly Thr Lys Leu Glu Ile Lys Arg
             100                 105
```

<210> SEQ ID NO 41
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

```
Glu Val Gln Leu Gln Gln Ser Gly Ala Glu Leu Val Arg Pro Gly Ala
 1               5                  10                  15

Ser Val Lys Leu Ser Cys Thr Ala Ser Gly Phe Asn Ile Lys Asp Ser
                 20                  25                  30

Leu Leu His Trp Val Lys Gln Arg Pro Glu Lys Gly Leu Glu Trp Ile
             35                  40                  45

Gly Trp Ile Asp Pro Glu Asp Gly Glu Thr Lys Tyr Ala Pro Asn Phe
 50                  55                  60

Gln Asp Lys Ala Thr Ile Thr Thr Asp Ser Ser Ser Asn Thr Ala Tyr
 65                  70                  75                  80

Leu Gln Leu Ile Ser Leu Thr Ser Val Asp Thr Ala Ile Tyr Tyr Cys
                 85                  90                  95

Ala Tyr Gly Asn Tyr Val Arg His Phe Asp Tyr Trp Gly Gln Gly Thr
             100                 105                 110

Thr Leu Thr Val Ser Ser
         115
```

<210> SEQ ID NO 42
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

```
Glu Ile Gln Met Thr Gln Ser Pro Ser Ser Met Ser Ala Ser Leu Gly
 1               5                  10                  15

Asp Arg Ile Thr Ile Thr Cys Gln Ala Thr Gln Asp Ile Val Lys Asn
                 20                  25                  30

Leu Asn Trp Tyr Gln Gln Lys Pro Gly Lys Pro Pro Ser Phe Leu Ile
             35                  40                  45

Tyr Tyr Ala Thr Glu Leu Ala Glu Gly Val Pro Ser Arg Phe Ser Gly
             50                  55                  60

Ser Gly Ser Gly Ser Asp Tyr Ser Leu Thr Ile Arg Asn Leu Glu Ser
 65                  70                  75                  80

Glu Asp Phe Ala Asp His Tyr Cys Leu Gln Phe Tyr Glu Phe Pro Phe
```

```
                        85                  90                  95
Thr Phe Gly Ala Gly Thr Lys Leu Glu Leu Lys
                100                 105

<210> SEQ ID NO 43
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Val Gln Leu Gln Gln Ser Gly Thr Glu Leu Val Arg Pro Gly Thr
1               5                   10                  15

Ser Val Arg Val Ser Cys Lys Ala Ser Gly Tyr Ala Phe Gly Asn His
                20                  25                  30

Leu Ile Glu Trp Val Lys Gln Arg Pro Gly Gln Gly Leu Glu Trp Ile
            35                  40                  45

Gly Val Ile Asn Pro Gly Thr Gly Gly Thr His Tyr Asn Glu Lys Phe
        50                  55                  60

Lys Asp Lys Ala Arg Leu Thr Ala Asp Lys Ser Ser Asn Thr Ala Tyr
65                  70                  75                  80

Met His Leu Asn Ser Leu Thr Ser Asp Asp Ser Ala Val Tyr Phe Cys
                85                  90                  95

Ala Arg Ser Pro Tyr Asp Tyr His Glu Gly Ala Met Asp Tyr Trp Gly
                100                 105                 110

Gln Gly Thr Ser Val Thr Val Ser Ser
            115                 120

<210> SEQ ID NO 44
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
                20                  25                  30

Ser Asn Gln Lys Asn Tyr Leu Ala Trp Tyr Gln Gln Glu Pro Gly Gln
            35                  40                  45

Ser Pro Lys Leu Leu Val Ser Phe Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Gly Val Gln Ala Glu Asp Leu Ala Val Tyr Tyr Cys Gln Gln
                85                  90                  95

His Tyr Ser Ile Pro Leu Thr Phe Gly Ala Gly Thr Lys Leu Glu Leu
                100                 105                 110

Lys

<210> SEQ ID NO 45
<211> LENGTH: 124
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Met Gly Ile Tyr Asn Tyr Asp Gly Ser Arg Tyr Tyr Ser Met Asp
            100                 105                 110

Tyr Trp Gly Gln Gly Thr Ser Val Thr Val Ser Ser
        115                 120

<210> SEQ ID NO 46
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Lys Asn Tyr
            20                  25                  30

Leu Asn Trp Tyr Gln Gln Lys Pro Asp Gly Thr Val Lys Pro Leu Ile
        35                  40                  45

Tyr Tyr Thr Ser Arg Val His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Pro Phe
                85                  90                  95

Thr Phe Gly Ser Gly Thr Lys Leu Glu
            100                 105

<210> SEQ ID NO 47
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Val Gln Leu Gln Gln Pro Gly Ala Glu Leu Val Lys Pro Gly Ala
```

-continued

```
                1               5                  10                 15
Ser Val Lys Leu Ser Cys Lys Ala Ser Gly Tyr Thr Phe Thr Thr Tyr
              20                  25                 30

Trp Met His Trp Val Lys Gln Arg Pro Gly Gln Gly Leu Glu Trp Ile
              35                  40                 45

Gly Glu Ile Asp Pro Ser Asp Ser Tyr Thr Tyr Tyr Asn Gln Lys Phe
    50                  55                 60

Lys Gly Lys Ala Thr Leu Thr Val Asp Lys Ser Ser Ser Thr Ala Tyr
65                  70                  75                 80

Met Gln Leu Ser Ser Leu Thr Ser Glu Asp Ser Ala Val Tyr Tyr Cys
              85                  90                 95

Ala Arg Gly Asp Tyr Gly Asn Pro Tyr Ala Met Asp Tyr Trp Gly Gln
              100                 105                110

Gly Ser Ser Val Thr Val Ser Ser
              115                 120
```

<210> SEQ ID NO 48
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Gln Ile Val Leu Thr Gln Ser Pro Ala Ile Met Ser Ala Ser Pro Gly
1               5                  10                 15

Glu Lys Val Thr Leu Thr Cys Ser Ala Ser Ser Ser Val Ser Ser Arg
              20                  25                 30

Tyr Leu Tyr Trp Tyr Gln Gln Lys Pro Gly Ser Ser Pro Lys Leu Trp
              35                  40                 45

Ile Tyr Ser Thr Ser Asn Leu Ala Ser Gly Val Pro Ala Arg Phe Ser
    50                  55                 60

Gly Ser Gly Ser Gly Thr Ser Tyr Ser Leu Ile Ile Ser Ser Met Glu
65                  70                  75                 80

Ala Glu Asp Ala Ala Ser Tyr Phe Cys His Gln Trp Ser Asn Tyr Pro
              85                  90                 95

Leu Thr Phe Gly Ala Gly Thr Lys Leu Glu Leu Lys
              100                 105
```

<210> SEQ ID NO 49
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

```
Gln Val Thr Leu Lys Glu Ser Gly Pro Gly Ile Leu Gln Pro Ser Gln
1               5                  10                 15

Thr Leu Ser Leu Thr Cys Ser Phe Ser Gly Phe Ser Leu Ser Thr Ser
              20                  25                 30

Asn Thr Gly Ile Gly Trp Ile Arg Gln Pro Ser Gly Thr Gly Leu Glu
              35                  40                 45

Trp Leu Ala His Ile Trp Trp Asn Asp Asp Lys Tyr Tyr Asn Pro Ser
    50                  55                 60
```

```
Leu Lys Ser Arg Leu Thr Ile Ser Lys Glu Thr Ser Asn Asn Gln Val
 65                  70                  75                  80

Phe Leu Lys Ile Thr Asn Val Asp Thr Ala Asp Thr Ala Ser Tyr Phe
                 85                  90                  95

Cys Val Gln Ile Gly Arg Asp Tyr Ser Asn Tyr Ala Trp Tyr Phe Asp
                100                 105                 110

Val Trp Gly Ala Gly Thr Thr Val Thr Val Ser Ser
            115                 120
```

<210> SEQ ID NO 50
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

```
Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Val Ser Tyr Met
                 20                  25                  30

His Trp Tyr Gln Gln Lys Ser Gly Thr Ser Pro Lys Arg Trp Ile Tyr
             35                  40                  45

Asp Ser Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys
                100                 105
```

<210> SEQ ID NO 51
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

```
Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
                 20                  25                  30

Gly Met Gly Val Gly Trp Ile Arg Gln Pro Ser Gly Glu Gly Leu Glu
             35                  40                  45

Trp Leu Thr Asp Ile Trp Trp Asp Asp Lys Tyr Tyr Asn Pro Ser
 50                  55                  60

Leu Lys Ser Arg Leu Thr Ile Ser Lys Asp Thr Ser Ser Asn Gln Val
 65                  70                  75                  80

Phe Leu Asn Ile Thr Ser Val Asp Thr Ala Asp Thr Ala Thr Tyr Tyr
                 85                  90                  95

Cys Ala Arg Arg Val Asn Tyr Tyr Asp Pro Tyr Tyr Ala Met Asp
                100                 105                 110
```

-continued

```
Tyr Trp Gly Gln Gly Thr Ser Val Thr Val Ser Ser
            115                 120
```

<210> SEQ ID NO 52
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

```
Asp Val Glu Met Thr Gln Thr Pro Leu Thr Leu Ser Val Thr Ile Gly
1               5                   10                  15

Gln Pro Ala Ser Ile Ser Cys Lys Ser Ser Gln Ser Leu Ser Asp Ser
            20                  25                  30

Asp Gly Lys Thr Tyr Leu Asn Trp Met Phe Gln Arg Pro Gly Arg Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Lys His Phe Pro Trp Thr Phe Gly Gly Gly Thr Lys Leu Glu Ile Lys
            100                 105                 110
```

<210> SEQ ID NO 53
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Val Glu Pro Thr Tyr Ala Asp Asp Phe
    50                  55                  60

Met Gly Arg Phe Ala Phe Ser Leu Glu Thr Ser Ala Ser Thr Ala Phe
65                  70                  75                  80

Leu Gln Ile Asn Asn Leu Glu Asn Glu Asp Thr Ala Thr Tyr Phe Cys
                85                  90                  95

Ala Arg Phe Gly Ser Tyr Ala Met Asp Tyr Trp Gly Gln Gly Thr Ser
            100                 105                 110
```

<210> SEQ ID NO 54
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

```
<400> SEQUENCE: 54

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Ile Tyr
            35                  40                  45

Thr Thr Ser Asn Leu Ala Ser Gly Val Pro Ala Arg Phe Ser Gly Ser
        50                  55                  60

Gly Ser Gly Thr Ser Tyr Ser Leu Thr Val Ser Arg Met Glu Ala Glu
65                  70                  75                  80

Asp Ala Ala Thr Tyr Tyr Cys Gln Gln Arg Ser Leu Tyr Pro Tyr Thr
                85                  90                  95

Phe Gly Gly Gly Thr Lys Val Glu Ile Lys
            100                 105

<210> SEQ ID NO 55
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Gln
                20                  25                  30

Tyr Ile Asn Trp Val Lys Gln Arg Thr Gly Gln Gly Leu Glu Trp Ile
            35                  40                  45

Gly Glu Ile Tyr Pro Gly Arg Gly Asn Thr Tyr Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Asp Gly Gly Tyr Asp Asp Ala Trp Phe Ala Tyr Trp Gly
            100                 105                 110

Gln Gly Thr Leu Val Thr Val Ser Ala
        115                 120

<210> SEQ ID NO 56
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Gln Ile Val Leu Thr Gln Ser Pro Thr Ile Met Ser Ala Ser Leu Gly
1               5                   10                  15

Glu Arg Val Thr Met Thr Cys Thr Ala Ser Ser Ser Val Thr Ser Ser
                20                  25                  30

Tyr Leu His Trp Tyr Gln Gln Lys Pro Gly Ser Ser Pro Lys Leu Trp
            35                  40                  45
```

```
Ile Tyr Ser Thr Ser Asn Leu Ala Ser Gly Val Pro Ala Arg Phe Ser
         50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Phe His Arg Ser Pro
                 85                  90                  95

Phe Thr Phe Gly Ser Gly Thr Lys Leu Glu Ile Lys
                100                 105

<210> SEQ ID NO 57
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
             20                  25                  30

Gly Met Gly Val Gly Trp Ile Arg Gln Pro Ser Gly Lys Gly Leu Glu
         35                  40                  45

Trp Leu Ala His Ile Trp Trp Asp Val Lys Arg Tyr Lys Pro Ala
 50                  55                  60

Leu Lys Ser Arg Leu Thr Val Ser Lys Asp Thr Ser Ser Asn Gln Val
 65                  70                  75                  80

Phe Leu Lys Ile Ala Thr Val Asp Ala Ala Asp Thr Gly Thr Tyr Tyr
                 85                  90                  95

Cys Ala Arg Ile Val Asp Gly His Pro Pro Phe Ala Tyr Trp Gly Gln
                100                 105                 110

Gly Thr Leu Val Thr Val Ser Ala
        115                 120

<210> SEQ ID NO 58
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Asp Ile Val Leu Thr Gln Ser Pro Leu Ser Leu Pro Val Asn Ile Gly
 1               5                  10                  15

Asp Gln Ala Ser Ile Ser Cys Lys Ser Thr Lys Ser Leu Leu Asn Ser
             20                  25                  30

Asp Gly Phe Thr Tyr Leu Asp Trp Tyr Leu Gln Arg Pro Gly Gln Ser
         35                  40                  45

Pro Gln Phe Leu Ile Tyr Leu Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Ser
                 85                  90                  95
```

```
Asn Tyr Leu Pro Leu Thr Phe Gly Ala Gly Thr Lys Leu Glu Leu Arg
            100                 105                 110
```

<210> SEQ ID NO 59
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Arg Phe
            20                  25                  30

Tyr Met His Trp Val Lys Gln Ser Pro Glu Asn Ser Leu Glu Trp Gly
        35                  40                  45

Glu Ile Asn Pro Ser Thr Gly Gly Thr Ile Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Gly Tyr Gly Ser Asn Trp Tyr Phe Asp Val Trp Gly Ala Gly
            100                 105                 110

Thr Thr Val Thr Val Ser Thr
        115
```

<210> SEQ ID NO 60
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Ser Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105
```

<210> SEQ ID NO 61
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 61

Gln Ile Gln Leu Val Gln Ser Gly Pro Glu Leu Lys Arg Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Asp Pro Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ile Gly Gly Asn Ser Pro Ser Asp Tyr Trp Gly Gln Gly Thr
            100                 105                 110

Ser Leu Thr Val Ser Ser
        115

<210> SEQ ID NO 62
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 62

Asp Ile Gln Met Thr Gln Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 63
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 63

Ser Asp Val Gln Leu Gln Glu Ser Gly Pro Gly Leu Val Lys Pro Ser
1               5                   10                  15

Gln Ser Leu Ser Leu Thr Cys Thr Val Thr Gly Tyr Ser Ile Thr Ser
                20                  25                  30

-continued

```
Asp Tyr Ala Trp Asn Trp Ile Arg Gln Phe Pro Gly Asn Lys Leu Glu
            35                  40                  45

Trp Met Gly Tyr Ile Ser Tyr Ser Gly Ser Thr Ser Tyr Asn Pro Ser
 50                  55                  60

Leu Lys Ser Arg Ile Ser Ile Thr Arg Asp Thr Ser Lys Asn Gln Phe
 65                  70                  75                  80

Phe Leu Gln Leu Asn Ser Val Thr Thr Glu Asp Thr Ala Thr Tyr Tyr
                 85                  90                  95

Cys Ala Arg Phe Tyr Tyr Gly Ser Ser Tyr Ala Met Asp Tyr Trp Gly
                100                 105                 110

Gln Gly Thr Ser Val Thr Val Ser Ser
            115                 120

<210> SEQ ID NO 64
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Glu Thr Thr Val Thr Gln Ser Pro Ala Ser Leu Ser Val Thr Thr Gly
 1               5                  10                  15

Glu Lys Val Thr Ile Arg Cys Ile Thr Thr Pro Asp Ile Asp Asp Asp
                20                  25                  30

Met Asn Trp Tyr Gln Gln Lys Pro Gly Glu Pro Pro Asn Leu Leu Ile
            35                  40                  45

Ser Glu Gly Asn Ser Leu Arg Pro Gly Val Pro Ser Arg Phe Ser Ser
 50                  55                  60

Ser Gly Tyr Gly Thr Asn Phe Val Phe Thr Ile Glu Asn Thr Leu Ser
 65                  70                  75                  80

Glu Asp Val Ala Asp Tyr Tyr Cys Leu Gln Ser Asp Asn Met Pro Phe
                 85                  90                  95

Thr Phe Gly Ser Gly Thr Lys Leu Glu Ile Lys
                100                 105

<210> SEQ ID NO 65
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Gln Val Gln Leu Gln Gln Ser Gly Ala Glu Leu Ala Lys Pro Gly Ala
 1               5                  10                  15

Ser Val Lys Met Ser Cys Lys Ala Ser Gly Tyr Thr Phe Thr Thr Tyr
                20                  25                  30

Trp Met His Trp Val Lys Gln Arg Pro Gly Gln Gly Leu Glu Trp Ile
            35                  40                  45

Gly Tyr Ile Asn Pro Ser Ser Gly Tyr Thr Glu Tyr Asn Gln Lys Phe
 50                  55                  60

Lys Asp Lys Ala Thr Leu Thr Ala Asp Lys Ser Ser Ser Thr Ala Tyr
 65                  70                  75                  80
```

```
Met Gln Leu Ser Ser Leu Thr Ser Glu Asp Ser Val Tyr Tyr Cys
                85                  90                  95

Ala Arg Lys Gly Ser Asn Arg Gly Phe Ala Tyr Trp Gly Gln Gly Thr
            100                 105                 110

Leu Val Thr Val Ser
            115

<210> SEQ ID NO 66
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Asn Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Thr Trp Thr Phe Gly
                85                  90                  95

Gly Gly Thr Lys Leu Glu Ile Lys
            100

<210> SEQ ID NO 67
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Glu Val Gln Leu Gln Gln Ser Gly Ala Glu Leu Val Lys Pro Gly Ala
1               5                   10                  15

Ser Val Lys Leu Ser Cys Thr Val Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Pro Thr Gly Tyr Phe Glu Tyr Trp Gly Gln Gly Thr Thr Leu
            100                 105                 110

Thr Val Ser Ser
            115
```

<210> SEQ ID NO 68
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Val Ile Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Arg Thr Asp Tyr Ser Leu Thr Ile Ser Asn Leu Glu Pro
65                  70                  75                  80

Glu Asp Ile Ala Thr Tyr Tyr Cys Gln Gln Tyr Ser Glu Arg Pro Tyr
                85                  90                  95

Thr Phe Gly Gly Gly Thr Lys Leu Glu Ile Lys Arg
            100                 105

<210> SEQ ID NO 69
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Val Lys Leu Glu Glu Ser Gly Gly Gly Leu Val Gln Phe Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Asn Asn His Ala Thr Tyr Tyr Pro Glu
    50                  55                  60

Ser Val Lys Gly Arg Phe Thr Ile Ser Arg Asp Asp Ser Lys Ser Arg
65                  70                  75                  80

Val Tyr Leu Gln Met Asn Asn Leu Arg Ala Glu Asp Thr Gly Ile Tyr
                85                  90                  95

Tyr Cys Thr Gly Tyr Ser Ser Phe Ala Tyr Trp Gly Gln Gly Thr Leu
            100                 105                 110

Val Thr Val Ser Ala
        115

<210> SEQ ID NO 70
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

-continued

```
Asp Val Leu Met Thr Gln Ser Pro Leu Ser Leu Ser Val Ser Leu Gly
1               5                   10                  15

Asp Gln Ala Ser Ile Ser Cys Arg Ser Ser Gln Asn Ile Val His Ser
            20                  25                  30

Asp Arg Tyr Thr Tyr Leu Glu Trp Tyr Leu Gln Lys Pro Gly Gln Ser
        35                  40                  45

Pro Lys Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Met Gly Val Tyr Tyr Cys Phe Gln Gly
                85                  90                  95

Thr His Val Pro Tyr Thr Phe Gly Gly Gly Thr Lys Leu Glu Ile Lys
            100                 105                 110
```

<210> SEQ ID NO 71
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Ala
            20                  25                  30

Gly Met Gln Trp Val Gln Lys Met Pro Gly Lys Gly Phe Lys Trp Ile
        35                  40                  45

Gly Trp Ile Asn Thr His Ser Gly Glu Pro Lys Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asp Glu Asp Thr Ala Thr Phe Phe Cys
                85                  90                  95

Ala Pro Leu Trp Ser Asp Ser Ser Phe Ala Tyr Trp Gly Gln Gly Thr
            100                 105                 110

Leu Val Thr Val Ser Ala
        115
```

<210> SEQ ID NO 72
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 72

```
Glu Ile Gln Met Thr Gln Ser Pro Ser Ser Met Ser Ala Ser Leu Gly
1               5                   10                  15

Asp Arg Ile Thr Ile Thr Cys Gln Ala Thr Gln Asp Ile Val Lys Asn
            20                  25                  30

Leu Asn Trp Tyr Gln Gln Lys Pro Gly Lys Pro Pro Ser Phe Leu Ile
        35                  40                  45
```

```
Tyr Tyr Ala Thr Glu Leu Ala Glu Gly Val Pro Ala Arg Phe Ser Gly
        50                  55                  60

Ser Gly Ser Gly Ser Asp Tyr Ser Leu Thr Ile Ser Asn Leu Glu Ser
 65                  70                  75                  80

Glu Asp Phe Ala Asp Tyr His Cys Leu Gln Phe Tyr Glu Phe Pro Phe
                 85                  90                  95

Thr Phe Gly Ala Gly Thr Lys Leu Glu Leu Lys
                100                 105
```

<210> SEQ ID NO 73
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

```
Gln Val Gln Leu Gln Gln Ser Gly Ala Asp Leu Val Arg Pro Gly Thr
 1               5                  10                  15

Ser Val Lys Val Ser Cys Lys Ala Ser Gly Tyr Ser Phe Thr Asn Tyr
                20                  25                  30

Leu Ile Glu Trp Val Lys Gln Arg Pro Gly Gln Gly Leu Glu Trp Ile
            35                  40                  45

Gly Val Ile Asn Pro Gly Ser Gly Gly Thr His Tyr Asn Glu Lys Phe
        50                  55                  60

Lys Asp Lys Ala Val Leu Thr Ala Asp Lys Ser Ser Thr Thr Ala His
 65                  70                  75                  80

Met Gln Leu Ser Ser Leu Thr Ser Asp Ser Ala Val Tyr Phe Cys
                 85                  90                  95

Ala Arg Ser Pro Tyr Asp Tyr Asn Asp Gly Ala Met Asp Tyr Trp Gly
                100                 105                 110

Gln Gly Thr Ser Val Thr Val Ser Ser
            115                 120
```

<210> SEQ ID NO 74
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

```
Asp Val Val Leu Thr Gln Ser Pro Leu Ser Leu Pro Val Asn Ile Gly
 1               5                  10                  15

Asp Gln Ala Ser Ile Ser Cys Lys Ser Thr Lys Ser Leu Leu Asn Ser
                20                  25                  30

Asp Gly Phe Thr Tyr Leu Asp Trp Tyr Leu Gln Arg Pro Gly Gln Ser
            35                  40                  45

Pro Gln Phe Leu Ile Tyr Leu Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Ser
                 85                  90                  95

Asn Tyr Leu Pro Leu Thr Phe Gly Ala Gly Thr Lys Leu Glu Leu Arg
```

<210> SEQ ID NO 75
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 75

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Arg Phe
            20                  25                  30

Tyr Met His Trp Val Lys Gln Ser Pro Glu Asn Ser Leu Glu Trp Ile
        35                  40                  45

Gly Glu Ile Asn Pro Ser Thr Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Gly Tyr Gly Ser Asn Cys Tyr Phe Asp Val Trp Gly Ala Gly
            100                 105                 110

Thr Thr Val Thr Val Ser Thr
        115

<210> SEQ ID NO 76
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Thr Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys
            100                 105

<210> SEQ ID NO 77
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 77

Gln Val Gln Leu Gln Gln Ser Gly Pro Glu Leu Val Lys Pro Gly Thr
1               5                   10                  15

Leu Val Lys Ile Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Asn Thr Lys Tyr Ser Glu Lys Phe
    50                  55                  60

Lys Gly Lys Ala Thr Leu Thr Ala Asp Lys Ser Ser Ser Thr Ala Tyr
65                  70                  75                  80

Met Gln Leu Thr Ser Leu Thr Ser Glu Asn Ser Ala Val Tyr Phe Cys
                85                  90                  95

Ala Arg Asp Tyr Asp Tyr Pro Phe Ala Tyr Trp Gly Gln Gly Thr Leu
            100                 105                 110

Val Thr Val Ser Ala
        115

<210> SEQ ID NO 78
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Arg Thr
                85                  90                  95

Phe Gly Gly Gly Thr Lys Leu Glu Ile Lys
            100                 105

<210> SEQ ID NO 79
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Glu Val Gln Leu Val Glu Cys Gly Gly Cys Leu Val Lys Pro Gly Gly
1               5                   10                  15

Tyr Leu Lys Leu Ser Cys Ala Ala Ser Gly Phe Thr Phe Ser Ser Tyr
            20                  25                  30

```
Ala Met Ser Trp Val Arg Gln Ser Pro Glu Lys Arg Leu Glu Trp Val
            35                  40                  45

Ala Glu Ile Ser Ile Gly Gly Ser Tyr Thr Tyr Tyr Pro Asp Thr Val
 50                  55                  60

Thr Gly Arg Phe Thr Ile Ser Arg Asp Asn Ala Lys Asn Thr Leu Tyr
 65                  70                  75                  80

Leu Glu Met Ser Ser Leu Arg Ser Glu Asp Thr Ala Met Tyr Tyr Cys
                85                  90                  95

Ala Arg Glu Gly Tyr Asp Tyr Asp Val Arg Ala Met Asp Tyr Trp Gly
                100                 105                 110

Gln Gly Thr Ser Val Thr Val Ser Ser
            115                 120
```

<210> SEQ ID NO 80
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

```
Asp Ile Gln Met Ile Gln Ser Pro Ser Ser Met Phe Ala Ser Leu Gly
 1               5                  10                  15

Asp Arg Val Ser Leu Ser Cys Arg Ala Ser Gln Gly Ile Arg Gly Thr
                20                  25                  30

Leu Asp Trp Tyr Gln Gln Lys Pro Asn Gly Thr Ile Lys Leu Leu Ile
            35                  40                  45

Tyr Ser Thr Ser Asn Leu Asn Ser Gly Val Pro Ser Arg Phe Ser Gly
 50                  55                  60

Ser Gly Ser Gly Ser Asp Tyr Ser Leu Thr Ile Ser Ser Leu Glu Ser
 65                  70                  75                  80

Glu Asp Phe Ala Asp Tyr Tyr Cys Leu Gln Arg Asn Ala Tyr Pro Leu
                85                  90                  95

Thr Phe Gly Ala Gly Thr Lys Leu Glu Leu Lys
                100                 105
```

<210> SEQ ID NO 81
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

```
Gln Val Gln Leu Lys Glu Ser Gly Pro Gly Leu Val Ala Pro Ser Gln
 1               5                  10                  15

Ser Leu Ser Ile Thr Cys Ala Val Ser Gly Phe Ser Leu Thr Ser Phe
                20                  25                  30

Ala Ile His Trp Phe Arg Lys Pro Pro Gly Lys Gly Leu Glu Trp Leu
            35                  40                  45

Gly Val Ile Trp Thr Gly Gly Thr Thr Asn Tyr Asn Ser Ala Leu Met
 50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Met Tyr Tyr Cys Ala
```

-continued

```
                85                  90                  95

Arg Asp Asp Tyr Asp Asn Asn Tyr Ala Met Asp Tyr Trp Gly Gln Gly
            100                 105                 110

Thr Ser Val Thr Val Ser Ser
        115

<210> SEQ ID NO 82
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Asn Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg
            100                 105

<210> SEQ ID NO 83
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Glu Val Gln Leu Val Glu Ser Gly Gly Gly Leu Val Gln Pro Lys Gly
1               5                   10                  15

Ser Leu Lys Leu Ser Cys Ala Val Ser Ala Phe Thr Phe Thr Thr Tyr
            20                  25                  30

Ala Met Asn Trp Val Arg Gln Ala Pro Gly Lys Gly Leu Glu Trp Val
        35                  40                  45

Ala Arg Ile Arg Asn Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Ile Glu Asp Thr Ala Met Tyr
                85                  90                  95

Tyr Cys Val Phe Tyr Tyr Asp Val Tyr Trp Gly Gln Gly Thr Leu
            100                 105                 110

Val Thr Val Ser Ala
        115

<210> SEQ ID NO 84
```

```
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84
```

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Val Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ala Gly
50                  55                  60

Ser Gly Tyr Gly Thr Asp Phe Ser Phe Thr Ile Ser Thr Val Gln Ala
65                  70                  75                  80

Glu Asp Leu Ala Val Tyr Phe Cys Gln Gln Asp Tyr Thr Ser Pro Trp
                85                  90                  95

Thr Phe Gly Gly Gly Thr Lys Leu Glu Ile Arg
            100                 105

```
<210> SEQ ID NO 85
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85
```

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Ala Trp Ile Asn Thr Tyr Thr Gly Glu Pro Thr Tyr Ala Asp Asp Phe
50                  55                  60

Lys Gly Arg Phe Ala Phe Ser Leu Glu Thr Ser Ala Ser Thr Ala Ser
65                  70                  75                  80

Leu Gln Ile Ile Asn Leu Lys Asn Glu Asp Thr Ala Thr Tyr Phe Cys
                85                  90                  95

Ala Arg Ile Gly Asp Ser Ser Pro Ser Asp Tyr Trp Gly Gln Gly Thr
            100                 105                 110

Thr Leu Thr Val Ser Ser
        115

```
<210> SEQ ID NO 86
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86
```

```
Asp Ile Val Met Thr Gln Ser His Lys Phe Met Ser Ile Ser Val Gly
 1               5                  10                  15

Asp Arg Val Ser Ile Thr Cys Lys Ala Ser Gln Asp Val Ser Ile Phe
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
 50                  55                  60

Ser Gly Ser Gly Thr Asp Phe Ile Phe Thr Ile Ser Ser Val Gln Ala
 65                  70                  75                  80

Glu Asp Leu Ala Val Tyr Tyr Cys Gln Gln His Tyr Gly Thr Pro Phe
                85                  90                  95

Thr Phe Gly Ser Gly Thr Lys Leu Lys Ile Arg
            100                 105
```

<210> SEQ ID NO 87
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

```
Glu Val Lys Leu Val Glu Ser Gly Gly Asp Leu Val Lys Pro Gly Gly
 1               5                  10                  15

Ser Leu Lys Leu Ser Cys Ala Ala Ser Gly Phe Ala Phe Ser Ser Tyr
                20                  25                  30

Asp Met Ser Trp Val Arg Gln Thr Pro Glu Lys Arg Leu Glu Trp Val
            35                  40                  45

Ala Thr Ile Ser Ser Gly Gly Ser Tyr Thr Tyr Tyr Pro Asp Ser Val
 50                  55                  60

Lys Gly Arg Phe Thr Ile Ser Arg Asp Asn Val Arg Asp Thr Leu Tyr
 65                  70                  75                  80

Leu Gln Met Ser Ser Leu Arg Ser Glu Asp Thr Ala Leu Tyr Tyr Cys
                85                  90                  95

Ala Arg Gln Ala Ile Gly Thr Tyr Phe Asp Tyr Trp Gly Gln Gly Thr
            100                 105                 110

Thr Leu Thr Val Ser Ser
            115
```

<210> SEQ ID NO 88
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

```
Asp Ile Gln Met Thr Gln Ser Pro Ala Ser Leu Ser Ser Ser Val Gly
 1               5                  10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
```

```
                    50                  55                  60
Ser Gly Ser Gly Thr Gln Phe Ser Leu Lys Ile Asn Ser Leu Gln Pro
 65                  70                  75                  80

Glu Asp Phe Gly Thr Tyr Tyr Cys Gln His His Tyr Asp Ser Pro Leu
                 85                  90                  95

Thr Phe Gly Ala Gly Thr Lys Leu Glu Leu Arg
            100                 105

<210> SEQ ID NO 89
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Asp Val Gln Leu Val Glu Ser Gly Gly Gly Leu Val Gln Pro Gly Gly
 1               5                  10                  15

Ser Arg Lys Leu Ser Cys Ala Ala Ser Gly Phe Thr Phe Ser Ser Phe
             20                  25                  30

Gly Met His Trp Val Arg Gln Ala Pro Glu Lys Gly Leu Glu Trp Val
         35                  40                  45

Ala Tyr Ile Ser Ser Gly Ser Ser Asn Ile Tyr Tyr Ala Asp Thr Val
     50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Gly Tyr Tyr Gly Asn Tyr Asp Ala Met Asp Tyr Trp Gly Gln
            100                 105                 110

Gly Thr Ser Val Thr Val Ser Ser
        115                 120

<210> SEQ ID NO 90
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Asp Ile Val Met Thr Gln Ser Thr Ser Ser Leu Ala Met Ser Val Gly
 1               5                  10                  15

Gln Lys Val Thr Met Ser Cys Lys Ser Ser Gln Ser Leu Leu Asn Ser
             20                  25                  30

Ser Asn Gln Lys Asn Tyr Leu Ala Trp Tyr Gln Gln Glu Pro Gly Gln
         35                  40                  45

Ser Pro Lys Leu Leu Val Ser Phe Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Gly Val Gln Ala Glu Asp Leu Ala Val Tyr Tyr Cys Gln Gln
                 85                  90                  95

His Tyr Ser Ile Pro Leu Thr Phe Gly Ala Gly Thr Lys Leu Glu Leu
            100                 105                 110
```

Lys

<210> SEQ ID NO 91
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Glu Val Leu Leu Gln Arg Ser Gly Pro Asp Leu Val Lys Pro Gly Ala
1               5                   10                  15

Ser Val Thr Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asn Ile Asn Thr Tyr Asn Gly Gly Thr Ile Tyr Asn Gln Lys Phe
    50                  55                  60

Lys Gly Lys Ala Thr Leu Thr Val Asp Lys Pro Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Arg Leu Arg Tyr Gly Gly His Tyr Phe Asp Tyr Trp Gly Gln
            100                 105                 110

Gly Thr Ala Leu Thr Val Ser Ser
        115                 120

<210> SEQ ID NO 92
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Phe
            20                  25                  30

Leu Ser Trp Phe Gln Arg Lys Pro Gly Lys Ser Pro Lys Thr Leu Ile
        35                  40                  45

Tyr Arg Ala Asn Arg Leu Val Asp Gly Val Pro Ser Arg Phe Thr Gly
    50                  55                  60

Ser Gly Ser Gly Gln Glu Phe Ser Leu Thr Ile Ser Ser Leu Glu Tyr
65                  70                  75                  80

Glu Asp Leu Gly Ile Tyr Tyr Cys Leu Gln Tyr Asp Glu Phe Pro Tyr
                85                  90                  95

Thr Phe Gly Gly Gly Thr Lys Leu Glu Ile Lys Arg
            100                 105

<210> SEQ ID NO 93
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 93

Glu Val Met Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Tyr Ile Ser Gly Gly Gly Asp His Ile Tyr Tyr Pro Asp Ser Val
    50                  55                  60

Arg Gly Arg Phe Thr Ile Ser Arg Asp Asn Ala Lys Asp Thr Leu Tyr
65                  70                  75                  80

Leu Gln Met Ser Ser Leu Arg Ser Glu Asp Thr Ala Leu Tyr Asp Cys
                85                  90                  95

Ala Arg Val Arg Asp Trp Tyr Phe Asp Val Trp Gly Ala Gly Thr Thr
            100                 105                 110

Val Thr Val Ser Ser
            115

<210> SEQ ID NO 94
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 94

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Ile Lys
            100                 105

<210> SEQ ID NO 95
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 95

Gln Val Gln Leu Gln Gln Ser Gly Thr Glu Leu Leu Arg Pro Gly Ala
1               5                   10                  15

Ser Val Lys Ile Ser Cys Lys Ala Thr Gly Tyr Thr Phe Ser Ser Tyr
            20                  25                  30

Trp Met Glu Trp Val Lys Gln Arg Pro Gly His Gly Leu Glu Trp Ile
            35                  40                  45

Gly Glu Ile Leu Pro Gly Ser Gly Thr Thr Gln Tyr Asn Glu Lys Phe
    50                  55                  60

Lys Gly Lys Ala Thr Phe Thr Ala Asp Thr Ser Ser Asn Thr Ala Tyr
65                  70                  75                  80

Met His Leu Ser Ser Leu Thr Ser Glu Asp Ser Ala Val Tyr Tyr Cys
                85                  90                  95

Ala Arg Gly Thr Asn Ser Leu Trp Gly Gln Gly Thr Leu Val Thr Val
            100                 105                 110

Ser Ala

<210> SEQ ID NO 96
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Gln Ile Val Leu Thr Gln Ser Pro Ala Leu Met Ser Ala Ser Pro Gly
1               5                   10                  15

Glu Lys Val Thr Met Thr Cys Ser Val Thr Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Trp Arg Asn Asn Pro Phe Thr
                85                  90                  95

Phe Gly Ser Gly Thr Lys Val Glu Ile Lys
            100                 105

<210> SEQ ID NO 97
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala Leu Ile Trp Trp Asp Asp Val Lys Arg Tyr Asn Pro Ala
    50                  55                  60

Leu Lys Ser Arg Leu Thr Ile Ser Lys Asp Ala Ser Ser Ser Gln Val
65                  70                  75                  80

Phe Leu Lys Ile Ala Ser Val Asp Thr Ala Asp Thr Ala Thr Tyr Tyr 85                  90                  95

Cys Ala Arg Ile Ala Ser Tyr Asp Tyr Asp Val Val Tyr Ala Met Asp
                100                 105                 110

Tyr Trp Gly Gln Gly Thr Ser Val Ser Val Ser Ser
            115                 120

<210> SEQ ID NO 98
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Ile Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Gly Leu Trp Tyr Ser Asn
                85                  90                  95

His Leu Val Phe Gly Gly Gly Thr Lys Leu Thr Val Leu
            100                 105

<210> SEQ ID NO 99
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Glu Val Gln Leu Val Glu Thr Gly Gly Gly Leu Val Gln Pro Lys Gly
1               5                   10                  15

Ser Leu Lys Leu Ser Cys Ala Val Ser Ala Phe Thr Phe Thr Thr Tyr
            20                  25                  30

Ala Met Asn Trp Val Arg Gln Ala Pro Gly Lys Gly Leu Glu Trp Val
        35                  40                  45

Ala Arg Ile Arg Asn Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Ile Glu Asp Thr Ala Met Tyr
                85                  90                  95

Tyr Cys Val Phe Tyr Tyr Asp Tyr Val Tyr Trp Gly Gln Gly Thr Leu
            100                 105                 110

Val Thr Val Ser Ala
        115

<210> SEQ ID NO 100

-continued

<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Glu Thr Thr Val Thr Gln Ser Pro Ala Phe Leu Ser Val Ala Thr Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Asn Val Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Thr Leu Ser
65                  70                  75                  80

Glu Asp Val Ala Asp Tyr Tyr Cys Leu Gln Ser Asp Asn Met Pro Leu
                85                  90                  95

Thr Phe Gly Ala Gly Thr Lys Leu Glu Leu Lys
            100                 105

<210> SEQ ID NO 101
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Asn Met His Trp Val Lys Gln Thr Pro Gly Gln Gly Leu Glu Trp Ile
        35                  40                  45

Gly Ala Ile Phe Pro Gly Asn Gly Gly Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Thr Ser Leu Thr Ser Gly Asp Ser Ala Val Tyr Tyr Cys
                85                  90                  95

Ala Arg Trp Gly Tyr Gly Ser Gly Leu Tyr Ala Met Asp Tyr Trp Gly
            100                 105                 110

Gln Gly Thr Ser Val Thr Val Ser Ser
        115                 120

<210> SEQ ID NO 102
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Val Asn Tyr Met
            20                  25                  30

Ser Trp Tyr Gln Gln Lys Ser Asp Ala Ser Pro Lys Leu Trp Ile Tyr
            35                  40                  45

Tyr Thr Ser Asn Leu Ala Pro Gly Val Pro Ala Arg Phe Ser Gly Ser
            50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Ile Lys Arg
            100                 105

<210> SEQ ID NO 103
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
            50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Leu Arg Ser Arg Ala Met Asp Tyr Trp Gly Gln Gly Thr Ser
            100                 105                 110

Val Thr Val Ser Ser
            115

<210> SEQ ID NO 104
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Tyr Ser
            20                  25                  30

Leu Asn Trp Leu Gln Gln Glu Pro Asp Gly Thr Ile Lys Arg Leu Ile
            35                  40                  45

Tyr Ala Thr Ser Ser Leu Asp Ser Gly Val Pro Lys Arg Phe Ser Gly

```
                        50                  55                  60
Ser Arg Ser Gly Ser Asp Tyr Ser Leu Thr Ile Ser Ser Leu Glu Ser
 65                  70                  75                  80

Glu Asp Phe Val Asp Tyr Tyr Cys Leu Gln Tyr Ala Ser Ser Pro Trp
                 85                  90                  95

Thr Phe Gly Gly Gly Thr Lys Leu Glu Ile Lys
            100                 105
```

<210> SEQ ID NO 105
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

```
Gln Val Gln Leu Gln Gln Ser Gly Ala Glu Leu Met Lys Pro Gly Ala
 1               5                  10                  15

Ser Val Lys Ile Ser Cys Lys Ala Asn Gly Tyr Thr Phe Ser Ser Tyr
                20                  25                  30

Trp Ile Glu Trp Leu Arg Gln Arg Pro Gly His Gly Leu Glu Trp Ile
            35                  40                  45

Gly Glu Ile Leu Pro Gly Ser Asp Asn Ser Asn Tyr Asn Glu Lys Phe
        50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Ser Glu Glu Ser Ala Val Tyr Tyr Cys
                 85                  90                  95

Thr Arg Gly Leu Arg Arg Asp Gly Ser Tyr Tyr Tyr Val Met Glu His
            100                 105                 110

Trp Gly Gln Gly Thr Ser Val Thr Val Ser Ser
        115                 120
```

<210> SEQ ID NO 106
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

```
Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Arg Ser Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Asp Tyr
 65                  70                  75                  80

Glu Asp Met Gly Ile Tyr Tyr Cys Leu Gln Tyr Asp Glu Phe Pro Phe
                 85                  90                  95

Thr Phe Gly Ser Gly Thr Lys Leu Glu Ile Lys
            100                 105
```

<210> SEQ ID NO 107
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 107

Glu Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Gly Arg Tyr
            20                  25                  30

Val Met Ser Trp Val Arg Gln Thr Pro Glu Lys Lys Leu Glu Trp Val
        35                  40                  45

Ala Ser Ile Thr Ser Gly Gly Thr Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Val Tyr Tyr His Tyr Asp Asp Ile Phe Ala Tyr Trp Gly Gln Gly
            100                 105                 110

Thr Leu Val Thr Val Ser Ala
        115

<210> SEQ ID NO 108
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 108

Asp Ile Val Met Ser Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Lys Ile Lys
            100                 105                 110

Arg

<210> SEQ ID NO 109
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 109

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Pro Ala Trp Phe Ala Tyr Trp Gly Gln Gly Thr Leu Val
            100                 105                 110

Thr Val Ser Ala
        115

<210> SEQ ID NO 110
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 110

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30

Met Ile Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Lys Arg Asp Asp Leu Pro Tyr
                85                  90                  95

Thr Phe Gly Gly Gly Thr Gln Val Glu Ile Lys Arg
            100                 105

<210> SEQ ID NO 111
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 111

Glu Val Gln Leu Gln Gln Ser Gly Pro Glu Leu Val Lys Pro Gly Gly
1               5                   10                  15

Ser Lys Lys Ile Ser Cys Lys Ala Ser Gly Tyr Ser Phe Thr Gly Tyr
            20                  25                  30

```
Ser Met Asn Trp Val Lys Gln Ser His Gly Lys Asn Leu Glu Trp Ile
        35                  40                  45

Gly Leu Ile Asn Pro Tyr Ser Gly Gly Thr Ile Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Arg Ser Asp Tyr Pro Leu Val Tyr Trp Gly Gln Gly Thr Leu
            100                 105                 110

Val Thr Val Ser Ala
        115
```

<210> SEQ ID NO 112
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

```
Gln Ile Val Leu Thr Gln Ser Pro Ala Ile Met Ser Ala Ser Leu Gly
1               5                   10                  15

Glu Arg Val Thr Leu Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Thr Arg Phe Ser
    50                  55                  60

Gly Ser Gly Ser Gly Thr Ser Tyr Ser Leu Arg Ile Ser Ser Met Glu
65                  70                  75                  80

Ala Glu Asp Ala Ala Thr Tyr Tyr Cys His Gln Tyr Asn Arg Ser Pro
                85                  90                  95

Leu Thr Phe Gly Ala Gly Thr Lys Leu Glu Leu Lys
            100                 105
```

<210> SEQ ID NO 113
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

```
Gln Val Gln Leu Lys Glu Ser Gly Pro Val Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80
```

```
Lys Met Asn Ser Leu Gln Thr Asp Asp Thr Ala Met Tyr Tyr Cys Ala
            85                  90                  95

Lys Gln Gly Asn Phe Tyr Ala Met Asp Tyr Trp Gly Gln Gly Thr Ser
            100                 105                 110

Val Thr Val Ser Ser
            115

<210> SEQ ID NO 114
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Lys Lys Tyr
            20                  25                  30

Ile Ala Trp Tyr Gln His Lys Pro Gly Lys Gly Pro Arg Leu Leu Ile
            35                  40                  45

His Tyr Thr Ser Thr Leu Glu Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Ile Leu Trp Thr
                85                  90                  95

Phe Gly Gly Gly Thr Lys Leu Glu Ile Lys
            100                 105

<210> SEQ ID NO 115
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Thr Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Leu Gly Tyr Tyr Gly Asn Tyr Arg Arg Tyr Phe Asp Val Trp Gly
            100                 105                 110

Ala Gly Thr Thr Val Thr Val Ser Ser
            115                 120
```

```
<210> SEQ ID NO 116
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Glu Asn Val Leu Thr Gln Ser Pro Ala Ile Met Ala Ala Ser Leu Gly
1               5                   10                  15

Gln Lys Val Thr Met Thr Cys Ser Ala Ser Ser Ser Val Ser Ser
                20                  25                  30

Tyr Leu His Trp Tyr Gln Gln Lys Ser Gly Ala Ser Pro Lys Pro Leu
            35                  40                  45

Ile His Arg Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys Arg Gln Trp Ser Gly Tyr Pro
                85                  90                  95

Trp Thr Phe Gly Gly Gly Thr Lys Leu Glu Ile Lys
                100                 105

<210> SEQ ID NO 117
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Cys Thr Ser Tyr
                20                  25                  30

Trp Met Gln Trp Val Lys Gln Arg Pro Gly Gln Gly Leu Glu Trp Ile
            35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Gly Arg Arg Thr Glu Ala Trp Phe Ala Tyr Trp Gly Gln Gly
                100                 105                 110

Thr Leu Val Thr Val Ser Ala
        115

<210> SEQ ID NO 118
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118
```

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
50                  55                  60

Gly Ser Glu Ser Gly Thr Ser Tyr Ser Leu Thr Ile Ser Asn Met Glu
65                  70                  75                  80

Ala Glu Asp Ala Ala Thr Tyr Tyr Cys His Gln Tyr His Arg Ser Pro
                85                  90                  95

Phe Thr Phe Gly Ser Gly Thr Lys Leu Glu Ile Lys
            100                 105

<210> SEQ ID NO 119
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Val Lys Arg Tyr Asn Pro Ala
50                  55                  60

Leu Lys Ser Arg Leu Thr Ile Ser Lys Asp Ala Ser Ser Ser Gln Val
65                  70                  75                  80

Phe Leu Lys Ile Ala Ser Val Asp Thr Ala Glu Thr Ala Thr Tyr Tyr
                85                  90                  95

Cys Ala His Ile Leu Asp Arg Ala Tyr Tyr Phe Asp Tyr Trp Gly Gln
            100                 105                 110

Gly Thr Thr Leu Thr Val Thr Ser
        115                 120

<210> SEQ ID NO 120
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

```
Lys Leu Leu Ile Tyr Leu Ala Ser Asn Leu Glu Ser Gly Val Pro Ala
         50                  55                  60

Arg Phe Ser Gly Ser Gly Ser Gly Thr Asp Phe Thr Leu Asn Ile His
 65                  70                  75                  80

Pro Val Glu Glu Asp Ala Ala Thr Tyr Tyr Cys Gln His Ser Arg
                 85                  90                  95

Glu Leu Pro Leu Thr Phe Gly Ala Gly Thr Lys Leu Glu Leu Lys
             100                 105                 110
```

<210> SEQ ID NO 121
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

```
Gln Val Thr Leu Lys Glu Ser Gly Pro Gly Ile Leu Lys Pro Ser Gln
 1               5                  10                  15

Thr Leu Ser Leu Thr Cys Ser Phe Ser Gly Phe Ser Leu Ser Thr Ser
             20                  25                  30

Gly Met Ile Gly Trp Ile Arg Gln Pro Ser Gly Lys Gly Leu Glu Trp
         35                  40                  45

Leu Ala His Ile Trp Trp Asp Asp Lys Tyr Tyr Asn Pro Ser Leu
         50                  55                  60

Lys Ser Gln Leu Thr Ile Ser Lys Asp Ser Arg Asn Gln Val Phe
 65                  70                  75                  80

Leu Lys Ile Thr Ser Val Asp Thr Ala Asp Thr Ala Thr Tyr Tyr Cys
                 85                  90                  95

Ala Arg Arg Gly Thr Ala Tyr Tyr Phe Asp Tyr Trp Gly Gln Gly Thr
             100                 105                 110

Thr Leu Thr Val Ser Ser
         115
```

<210> SEQ ID NO 122
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

```
Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
             20                  25                  30

His Trp Tyr Arg Gln Lys Pro Gly Ser Ser Pro Lys Pro Trp Ile Tyr
         35                  40                  45

Ala Thr Ser Asn Leu Ala Ser Gly Val Pro Ala Arg Phe Ser Gly Ser
         50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Ser Asn Pro Pro Thr
                 85                  90                  95

Phe Gly Ala Gly Thr Lys Leu Glu Leu Lys
```

<210> SEQ ID NO 123
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 123

Gln Val Gln Leu Lys Glu Ser Gly Pro Asp Leu Val Gln Pro Ser Gln
1               5                   10                  15

Thr Leu Ser Leu Thr Cys Thr Val Ser Gly Phe Ser Leu Thr Phe Tyr
            20                  25                  30

Gly Val His Trp Val Arg Gln Pro Pro Gly Lys Gly Leu Glu Trp Val
        35                  40                  45

Gly Thr Met Gly Trp Asp Asp Lys Lys Tyr Tyr Asn Ser Ala Leu Lys
    50                  55                  60

Ser Arg Leu Ser Ile Ser Arg Asp Thr Ser Lys Asn Gln Val Phe Leu
65                  70                  75                  80

Lys Leu Ser Ser Leu Gln Thr Glu Asp Thr Ala Met Tyr Tyr Cys Thr
                85                  90                  95

Arg Gly Gly Thr Gly Phe Asp Tyr Trp Gly Gln Gly Thr Thr Leu Thr
            100                 105                 110

Val Ser Ser
        115

<210> SEQ ID NO 124
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 124

Asp Ile Val Met Thr Gln Ser His Lys Phe Met Ser Thr Ser Val Gly
1               5                   10                  15

Asp Arg Val Ser Ile Thr Lys Ala Ser Gln Asp Val Gly Thr Ala Val
            20                  25                  30

Ala Trp Tyr Gln Gln Lys Pro Gly Gln Ser Pro Lys Leu Leu Ile Tyr
        35                  40                  45

Trp Ala Ser Ile Arg His Thr Gly Val Pro Asp Arg Phe Thr Gly Ser
    50                  55                  60

Gly Ser Gly Thr Asp Phe Thr Leu Thr Ile Ser Asn Val Gln Ser Glu
65                  70                  75                  80

Asp Leu Ala Asp Tyr Phe Cys Gln Gln Tyr Ser Ser Tyr Pro Leu Thr
                85                  90                  95

Phe Gly Ala Gly Thr Lys Leu Glu Leu Lys
            100                 105

<210> SEQ ID NO 125
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 125

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asn Pro Ser Asn Gly Arg Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Arg Glu Leu Gly Thr Leu Tyr Ala Met Asp Tyr Trp Gly
            100                 105                 110

Gln Gly Thr Ser Val Thr Val Ser Ser
        115                 120

<210> SEQ ID NO 126
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Phe
                85                  90                  95

Thr Phe Gly Ser Gly Thr Lys Leu Glu Ile Lys
            100                 105

<210> SEQ ID NO 127
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Gln Val Gln Leu Lys Gln Ser Gly Pro Gly Leu Val Ala Pro Ser Gln
1               5                   10                  15

Ser Leu Phe Ile Thr Cys Thr Val Ser Gly Phe Ser Leu Thr Ser Tyr
            20                  25                  30

```
Glu Ile Asn Trp Val Arg Gln Pro Pro Gly Lys Gly Leu Glu Trp Leu
             35                  40                  45

Gly Val Ile Trp Thr Gly Gly Ser Thr Asn Tyr Asn Ser Ala Leu Ile
 50                      55                  60

Ser Arg Leu Ser Ile Ser Lys Asp Asn Ser Lys Ser Leu Val Phe Leu
 65                  70                  75                  80

Lys Met Asn Ser Leu Gln Thr Asp Asp Thr Ala Ile Tyr Tyr Cys Val
                 85                  90                  95

Arg Gly Val Tyr Ala Met Asp Tyr Trp Gly Gln Gly Thr Ser Val Thr
                100                 105                 110

Val Ser Ser
        115

<210> SEQ ID NO 128
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Asn Thr Ala
                 20                  25                  30

Val Gly Trp Tyr Gln Gln Lys Pro Gly Gln Ser Pro Lys Leu Leu Ile
             35                  40                  45

Tyr Ser Ala Ser Tyr Arg Tyr Thr Gly Val Pro Asp Arg Phe Thr Gly
 50                      55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Ser Pro Tyr
                 85                  90                  95

Thr Phe Gly Gly Gly Thr Lys Leu Glu Ile Lys Arg
                100                 105

<210> SEQ ID NO 129
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Asn Tyr
                 20                  25                  30

Val Met His Trp Val Lys Gln Lys Pro Gly Gln Gly Leu Glu Trp Ile
             35                  40                  45

Gly Tyr Ile Asn Pro Tyr Asn Asp Gly Thr Lys Tyr Asn Glu Lys Phe
 50                      55                  60

Lys Gly Lys Ala Thr Leu Thr Ser Asp Lys Ser Ser Thr Thr Ala Tyr
 65                  70                  75                  80

Met Ala Leu Ser Ser Leu Thr Ser Glu Asp Ser Ala Val Tyr Tyr Cys
```

```
                    85                  90                  95
Ala Val Ala Tyr Tyr Ser Asn Trp Gly Phe Ala Tyr Trp Gly Gln Gly
                100                 105                 110

Thr Leu Val Thr Val Ser Ala
        115
```

```
<210> SEQ ID NO 130
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
    50                  55                  60

Ser Arg Ser Gly Ser Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Tyr
                85                  90                  95

Thr Phe Gly Gly Gly Thr Lys Leu Glu Ile Lys Arg
                100                 105
```

```
<210> SEQ ID NO 131
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Gln Val Gln Leu Glu Glu Ser Gly Ala Glu Leu Ala Arg Pro Gly Ala
1               5                   10                  15

Ser Val Lys Leu Ser Cys Lys Ala Ser Gly Tyr Ser Tyr Trp Met Gln
                20                  25                  30

Trp Ile Lys Gln Arg Pro Gly Gln Gly Leu Glu Trp Ile Gly Ala Ile
            35                  40                  45

Tyr Pro Gly Asn Gly Asp Thr Arg Tyr Thr Gln Lys Phe Lys Gly Lys
    50                  55                  60

Ala Thr Leu Thr Ala Asp Lys Ser Ser Ser Thr Ala Tyr Met Gln Leu
65                  70                  75                  80

Ser Ser Leu Ala Ser Glu Asp Ser Ala Val Tyr Tyr Cys Ala Arg Ser
                85                  90                  95

Pro Ala Tyr Tyr Arg Tyr Gly Gly Tyr Phe Asp Tyr Trp Gly Gln
                100                 105                 110

Gly Thr Thr Leu Thr Val Ser Ser
        115                 120
```

```
<210> SEQ ID NO 132
```

```
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Phe Ser Leu Thr Ile Ser Arg Met Glu Ala Glu
65                  70                  75                  80

Asp Thr Ala Thr Tyr Tyr Cys Gln Glu Trp Ser Gly Asn Pro Leu Thr
                85                  90                  95

Phe Gly Asp Gly Thr Lys Leu Glu Leu Lys
            100                 105

<210> SEQ ID NO 133
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Ala Tyr Ala Asp Asp Phe
    50                  55                  60

Lys Gly Arg Phe Ala Phe Ser Leu Glu Thr Ser Ala Ser Ala Ala Tyr
65                  70                  75                  80

Leu Gln Ile Asn Asn Leu Lys Asn Glu Asp Thr Ala Thr Phe Phe Cys
                85                  90                  95

Ala Asn Met Arg Pro Thr Arg Gly Phe Ala Tyr Trp Gly Gln Gly Thr
            100                 105                 110

Leu Gly Thr Val Ser Ala
        115

<210> SEQ ID NO 134
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134
```

Asn Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Pro
                85                  90                  95

Thr Phe Gly Gly Gly Thr Lys Leu Glu Ile Lys
                100                 105

<210> SEQ ID NO 135
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Glu Val Gln Leu Gln Gln Ser Gly Pro Gly Leu Val Arg Thr Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
            35                  40                  45

Gly Tyr Ile Ser Cys Tyr Asn Gly Ala Thr Thr Tyr Asn Gln Asn Phe
50                  55                  60

Lys Gly Lys Ala Thr Phe Ile Val Asp Thr Ser Ser Thr Ala Tyr
65                  70                  75                  80

Met Gln Phe Asn Ser Leu Thr Ser Glu Asp Ser Ala Val Tyr Tyr Cys
                85                  90                  95

Ala Arg Ser Asp Gly Gly His Ala Met Asp Tyr Trp Gly Gln Gly Thr
                100                 105                 110

Ser Val Thr Val Ser Ser
        115

<210> SEQ ID NO 136
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu Asn Ile Tyr Tyr Ser
            20                  25                  30

Leu Ala Trp Tyr Gln Gln Lys Gln Gly Lys Ser Pro Gln Leu Leu Ile
            35                  40                  45

Tyr Asn Ala Asn Ser Leu Glu Asp Gly Val Pro Ser Arg Phe Ser Gly

```
                50                  55                  60
Ser Gly Ser Gly Thr Gln Tyr Ser Met Lys Ile Asn Ser Met Gln Pro
 65                  70                  75                  80

Glu Asp Thr Ala Thr Tyr Phe Cys Lys Gln Thr Tyr Asp Val Pro Leu
                 85                  90                  95

Thr Phe Gly Ala Gly Thr Lys Leu Glu Leu Lys
                100                 105
```

<210> SEQ ID NO 137
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

```
Glu Val Gln Leu Gln Gln Ser Gly Pro Glu Leu Glu Lys Pro Gly Ala
 1               5                  10                  15

Ser Val Lys Ile Ser Cys Lys Ala Ser Gly Tyr Ser Phe Thr Gly Tyr
                20                  25                  30

Asn Met Asn Trp Val Lys Gln Ser Asn Gly Lys Ser Leu Glu Trp Ile
            35                  40                  45

Gly Asn Ile Asp Pro Tyr Tyr Gly Gly Ser Ser Tyr Lys Gln Lys Phe
 50                  55                  60

Glu Gly Lys Ala Thr Leu Thr Val Asp Lys Ser Ser Ser Thr Ala Tyr
 65                  70                  75                  80

Met Gln Leu Lys Ser Leu Thr Ser Glu Asp Ser Ala Val Tyr Tyr Cys
                 85                  90                  95

Ala Arg Gly Gly Ser Asn Phe Phe Asp Tyr Trp Gly Gln Gly Thr Thr
                100                 105                 110

Leu Thr Val Ser Ser
            115
```

<210> SEQ ID NO 138
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

```
Asp Val Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
                20                  25                  30

Asp Gly Thr Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Leu Thr Phe Gly Ala Gly Thr Lys Leu Glu Leu Lys
                100                 105                 110
```

<210> SEQ ID NO 139
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Ser Tyr Pro Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Val Tyr Asp Gly Tyr Ser Tyr Trp Gly Gln Gly Thr Thr
            100                 105                 110

Leu Thr Val Ser Ser
        115

<210> SEQ ID NO 140
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Ile Lys Arg
            100                 105

<210> SEQ ID NO 141
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
50                  55                  60

Gln Gly Lys Ala Thr Ile Thr Pro Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Ser Trp Arg Asn Tyr Gly Ser Ser Phe Trp Tyr Phe Asp Val
            100                 105                 110

Trp Gly Ala Gly Thr Thr Val Thr Val Ser Ser
        115                 120

<210> SEQ ID NO 142
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 142

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Thr Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Leu Lys
            100                 105                 110

<210> SEQ ID NO 143
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 143

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val

```
                35                  40                  45
Ala Thr Ile Ser Ser Gly Gly Ser Tyr Pro Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Thr Arg Asp Val Tyr Asp Gly Tyr Ser Tyr Trp Gly Gln Gly Thr Thr
                100                 105                 110

Leu Thr Val Ser Ser
            115

<210> SEQ ID NO 144
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Asp Ile Val Met Thr Gln Ser Pro Ser Ser Leu Thr Val Thr Ala Gly
  1               5                  10                  15

Glu Lys Val Thr Met Ser Cys Thr Ser Ser Gln Ser Leu Leu Thr Ser
                 20                  25                  30

Gly Asn Gln Lys Asn Tyr Leu Thr Trp Tyr Gln Gln Lys Pro Gly Gln
                 35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Leu Gln Ala Glu Asp Leu Ala Val Tyr Tyr Cys Gln Asn
                 85                  90                  95

Asp Tyr Ser Leu Thr Phe Gly Ala Gly Thr Lys Leu Glu Leu Lys
                100                 105                 110

<210> SEQ ID NO 145
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Gln Val Gln Leu Lys Gln Ser Gly Pro Gly Arg Val Gln Pro Ser Gln
  1               5                  10                  15

Ser Leu Ser Ile Thr Cys Thr Val Ser Gly Phe Ser Leu Thr Ser Asn
                 20                  25                  30

Gly Val Val His Trp Val Arg Gln Ser Pro Gly Lys Gly Leu Glu Trp
                 35                  40                  45

Leu Gly Val Leu Trp Ser Gly Gly Ser Thr Asp Tyr Asn Ala Ala Phe
 50                  55                  60

Ile Ser Arg Leu Ser Ile Ser Lys Asp Asn Tyr Lys Ser Gln Val Phe
 65                  70                  75                  80

Phe Lys Met Asn Ser Leu Gln Ala Asn Asp Thr Ala Ile Tyr Tyr Cys
                 85                  90                  95
```

Ala Arg Asn Asn Asn Arg Tyr Gly Ala Met Asp Tyr Trp Gly Gln Gly
            100                 105                 110

Thr Ser Val Thr Val Ser Ser
        115

<210> SEQ ID NO 146
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Asp Ile Gln Met Asn Gln Ser Pro Ser Ser Leu Ser Ala Ser Leu Gly
1               5                   10                  15

Asp Thr Ile Thr Ile Thr Cys His Val Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Gln Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Phe
                85                  90                  95

Thr Phe Gly Ser Gly Thr Lys Leu Glu Ile Lys
            100                 105

<210> SEQ ID NO 147
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Gln Val Gln Leu Lys Glu Ser Gly Pro Gly Leu Val Ala Pro Ser Gln
1               5                   10                  15

Ser Leu Ser Ile Pro Cys Thr Val Ser Gly Phe Ser Leu Thr Asn Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ile Thr Asn Tyr Asn Ser Ala Leu Met
    50                  55                  60

Ser Arg Leu Ser Ile Ser Glu Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asn Leu Gly Pro Tyr Ala Met Asp Tyr Trp Gly Gln Gly Thr Ser
            100                 105                 110

Val Thr Val Ser Ser
        115

<210> SEQ ID NO 148
<211> LENGTH: 112

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Thr Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys Arg
            100                 105                 110

<210> SEQ ID NO 149
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Val Asn Pro Asn Asn Gly Gly Thr Ser Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Ser Tyr Asp Tyr Ala Glu Gly Trp Gly Gln Gly Thr Leu
            100                 105                 110

Val Thr Val Ser Ala
        115

<210> SEQ ID NO 150
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 150

Asp Ile Val Met Ser Gln Ser Pro Ser Ser Leu Ala Val Ser Val Gly
```

```
  1               5                  10                 15
Glu Lys Val Thr Met Ser Cys Lys Ser Ser Gln Ser Leu Leu Tyr Ser
                20                 25                 30

Ser Thr Gln Lys Asn Tyr Leu Ala Trp Tyr Gln Gln Lys Pro Gly Gln
                35                 40                 45

Ser Pro Lys Leu Leu Ile Tyr Trp Ala Ser Thr Arg Glu Ser Gly Val
       50                 55                 60

Pro Asp Arg Phe Thr Gly Ser Gly Ser Gly Thr Asp Phe Thr Leu Thr
 65                 70                 75                 80

Ile Ser Ser Val Lys Ala Glu Asp Leu Ala Val Tyr Tyr Cys Gln Gln
                85                 90                 95

Tyr Tyr Ser Tyr Pro Tyr Thr Phe Gly Gly Gly Thr Lys Leu Glu Ile
               100                105                110

Lys Arg
```

<210> SEQ ID NO 151
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 151

```
Glu Ile Gln Leu Gln Gln Ser Gly Pro Glu Leu Val Lys Pro Gly Ala
 1               5                  10                 15

Ser Val Lys Val Ser Cys Lys Ala Ser Gly Tyr Ala Phe Thr Ser Tyr
                20                 25                 30

Asn Met Tyr Trp Val Met Gln Ser His Gly Lys Ser Leu Glu Trp Ile
                35                 40                 45

Gly Tyr Val Asp Pro Tyr Asn Gly Gly Thr Ser Tyr Asn Gln Lys Phe
       50                 55                 60

Lys Gly Lys Ala Thr Leu Thr Val Asp Lys Ser Ser Ser Thr Ala Tyr
 65                 70                 75                 80

Met His Leu Asn Ser Leu Thr Ser Glu Asp Ser Ala Val Tyr Tyr Cys
                85                 90                 95

Ala Arg Glu Asn Tyr Arg Tyr Phe Asp Tyr Trp Gly Gln Gly Thr Thr
               100                105                110

Leu Thr Val Ser Ser
       115
```

<210> SEQ ID NO 152
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

```
Gln Ile Val Leu Thr Gln Ser Pro Ala Ile Met Ser Ala Ser Pro Gly
 1               5                  10                 15

Glu Lys Val Thr Ile Thr Cys Ser Ala Ser Ser Ser Val Ser Tyr Met
                20                 25                 30

His Trp Phe Gln Gln Lys Pro Gly Thr Ser Pro Lys Leu Trp Ile Tyr
                35                 40                 45
```

```
Ser Thr Ser Asn Leu Ala Ser Gly Val Pro Ala Arg Phe Ser Gly Ser
    50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Arg Ser Ser Tyr Pro Pro Thr
                85                  90                  95
Phe Gly Gly Gly Thr Lys Leu Glu Ile Lys Arg
            100                 105
```

<210> SEQ ID NO 153
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

```
Glu Val Gln Leu Val Glu Ser Gly Gly Gly Leu Val Gln Pro Lys Gly
1               5                   10                  15
Ser Leu Lys Leu Ser Cys Ala Ala Ser Gly Phe Thr Phe Asn Thr Tyr
            20                  25                  30
Ala Met Asn Trp Val Arg Gln Ala Pro Gly Lys Gly Leu Glu Trp Val
        35                  40                  45
Ala Arg Ile Arg Ile Lys Ser Asn Asn Tyr Ala Thr Tyr Tyr Ala Asp
    50                  55                  60
Ser Val Lys Asp Arg Phe Thr Ile Ser Arg Asp Asp Ser Gln Asn Met
65                  70                  75                  80
Leu Tyr Leu Gln Met Asn Asn Leu Lys Thr Glu Asp Thr Ala Val Tyr
                85                  90                  95
Tyr Cys Val Arg Gln Gly Tyr Ser Tyr Asp Trp Gly Pro Trp Phe Ala
            100                 105                 110
Tyr Trp Gly Gln Gly Thr Leu Val Thr Val Ser Ala
        115                 120
```

<210> SEQ ID NO 154
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

```
Asp Ile Val Met Thr Gln Ser Gln Lys Phe Met Ser Thr Ser Val Gly
1               5                   10                  15
Asp Arg Val Ser Val Thr Cys Lys Ala Ser Gln Asn Val Gly Thr Asn
            20                  25                  30
Val Ala Trp Tyr Gln Gln Lys Pro Gly Gln Ser Pro Lys Val Leu Ile
        35                  40                  45
Tyr Ser Ala Ser Tyr Arg Tyr Ser Gly Val Pro Asp Arg Phe Thr Gly
    50                  55                  60
Ser Gly Ser Gly Thr Asp Phe Thr Leu Thr Ile Ser Asn Val Gln Ser
65                  70                  75                  80
Glu Asp Leu Ala Glu Phe Phe Cys Gln Gln Tyr Asn Ser Tyr Pro Leu
                85                  90                  95
Thr Phe Gly Gly Gly Thr Lys Leu Glu Ile Lys
```

<210> SEQ ID NO 155
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 155

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Phe Trp Val Arg Gln Thr Pro Glu Lys Arg Leu Glu Trp Val
        35                  40                  45

Ala Thr Ile Ser Asp Gly Gly Ser Tyr Thr Tyr Phe Pro Asp Ser Val
    50                  55                  60

Lys Gly Arg Phe Thr Ile Ser Arg Asp Asn Ala Gln Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Ala Gly Thr Leu Tyr Ala Met Asp Tyr Trp Gly Gln Gly Thr
            100                 105                 110

Ser Val Thr Val Ser Ser
        115

<210> SEQ ID NO 156
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 156

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Thr Glu Asp Ala Ala Thr Tyr Tyr Cys His Gln Tyr His Arg Ser Pro
                85                  90                  95

Phe Thr Phe Gly Ser Gly Thr Lys Leu Glu Ile Lys
            100                 105

<210> SEQ ID NO 157
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 157

Gln Val Ala Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Ser Ser Gln Val
65                  70                  75                  80

Phe Leu Lys Ile Ala Ser Val Asp Thr Ala Asp Thr Ala Thr Tyr Tyr
                85                  90                  95

Cys Ala Arg Met Glu Asp Tyr Gly Ser Ser Ser Tyr Phe Asp Phe Trp
            100                 105                 110

Gly His Gly Thr Thr Leu Thr Val Ser Ser
        115                 120

<210> SEQ ID NO 158
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 158

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Ser Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Trp
                85                  90                  95

Thr Phe Gly Gly Gly Thr Lys Leu Glu Ile Lys
            100                 105

<210> SEQ ID NO 159
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
 50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ala Leu Tyr Tyr Gly Asn Tyr Leu Gly Tyr Phe Asp Val
            100                 105                 110

Trp Gly Ala Gly Thr Thr Val Thr Val Ser Ser
            115                 120

<210> SEQ ID NO 160
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
            35                  40                  45

Tyr Lys Ala Ser Ile Leu His Thr Gly Val Pro Ser Arg Phe Ser Gly
 50                 55                  60

Ser Gly Ser Gly Thr Gly Phe Thr Leu Thr Ile Ser Ser Leu Gln Pro
65                  70                  75                  80

Glu Asp Ile Ala Thr Tyr Ser Cys Gln Gln Gly Gln Ser Tyr Pro Tyr
                85                  90                  95

Thr Phe Gly Gly Gly Thr Lys Leu Glu Ile Lys
            100                 105

<210> SEQ ID NO 161
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 161

Ser Asp Val Gln Leu Gln Glu Ser Gly Pro Asp Leu Val Lys Pro Ser
1               5                   10                  15

Gln Ser Leu Ser Leu Thr Cys Thr Val Thr Gly Tyr Ser Ile Thr Ser
            20                  25                  30

Gly Tyr Ser Trp His Trp Ile Arg Gln Phe Pro Gly Asn Lys Leu Glu
            35                  40                  45

Trp Met Gly Tyr Ile His Tyr Ser Gly Ser Thr Asn Tyr Asn Pro Ser
 50                 55                  60

Leu Lys Ser Arg Ile Ser Ile Thr Arg Asp Thr Ser Lys Asn Gln Phe
65                  70                  75                  80

Phe Leu Gln Phe Lys Ser Val Thr Thr Glu Asp Ser Ala Thr Tyr Tyr 85                  90                  95

Cys Ala Leu Glu Gly Asn Tyr Asp Gly Phe Ala Tyr Trp Gly Gln Gly
            100                 105                 110

Thr Leu Val Thr Val Ser
        115

<210> SEQ ID NO 162
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Phe
                85                  90                  95

Thr Phe Gly Ser Gly Thr Lys Leu Glu Ile Lys
            100                 105

<210> SEQ ID NO 163
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163

Gln Val Gln Met Lys Glu Ser Gly Pro Gly Leu Val Ala Pro Ser Gln
1               5                   10                  15

Ser Leu Ser Ile Thr Cys Thr Val Ser Gly Ser Ser Leu Thr Asn Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asp Trp Glu Gly Trp Phe Ala Tyr Trp Gly Gln Gly Thr Leu Val
            100                 105                 110

Thr Val Ser Ala
        115

<210> SEQ ID NO 164

```
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164
```

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Tyr
                85                  90                  95

Thr Phe Gly Gly Gly Thr Lys Leu Glu Ile Lys Arg
            100                 105

```
<210> SEQ ID NO 165
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165
```

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp
            20                  25                  30

Tyr Gly Val Ser Trp Ile Arg Gln Pro Pro Gly Lys Gly Leu Glu Trp
        35                  40                  45

Leu Gly Val Ile Trp Gly Gly Ser Thr Tyr Tyr Asn Ser Ala Leu
    50                  55                  60

Lys Ser Arg Leu Ser Ile Ser Lys Asp Asn Ser Lys Ser Gln Val Phe
65                  70                  75                  80

Leu Glu Leu Asn Ser Leu Gln Thr Asp Asp Thr Ala Ile Tyr Tyr Cys
                85                  90                  95

Ala Lys His Tyr Gly His Tyr Ala Ala Tyr Trp Gly Gln Gly Thr Leu
            100                 105                 110

Val Thr Val Ser Ala
        115

```
<210> SEQ ID NO 166
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 166
```

```
Asp Ile Gln Leu Thr Gln Ser Pro Ala Ser Leu Ser Ala Ser Val Gly
1               5                   10                  15

Glu Thr Val Thr Ile Thr Cys Arg Ala Ser Gly Ser Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Val Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Tyr Tyr Tyr Cys Gln His Phe Trp Thr Thr Pro Trp
                85                  90                  95

Thr Phe Gly Gly Gly Thr Lys Leu Glu Ile Lys
            100                 105
```

<210> SEQ ID NO 167
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Glu Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Val Tyr Asp Gly Tyr Ser Tyr Phe Asp Tyr Trp Gly Gln
                100                 105                 110

Gly Thr Thr Leu Thr Val Ser Ser
            115                 120
```

<210> SEQ ID NO 168
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

```
Asp Ile Gln Met Asn Gln Ser Pro Ser Ser Leu Ser Ala Ser Leu Gly
1               5                   10                  15

Asp Thr Ile Thr Ile Thr Cys His Val Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Gln Lys Ala Ser Asn Leu His Thr Gly Val Pro Ser Arg Phe Ser Gly
```

```
                    50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Tyr Pro Phe
                     85                  90                  95

Thr Phe Gly Ser Gly Thr Lys Leu Glu Ile Lys
                100                 105

<210> SEQ ID NO 169
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

Gln Val Gln Leu Lys Glu Ser Gly Pro Gly Leu Val Ala Pro Ser Gln
 1               5                   10                  15

Ser Leu Ser Ile Thr Cys Thr Val Ser Gly Phe Ser Leu Thr Asn Tyr
                20                  25                  30

Gly Val His Trp Val Arg Gln Pro Pro Gly Lys Gly Leu Glu Trp
             35                  40                  45

Leu Gly Val Ile Trp Ala Gly Gly Ile Thr Asn Tyr Asn Ser Ala Leu
 50                  55                  60

Met Ser Arg Leu Ser Ile Ser Glu Asp Asn Ser Lys Ser Gln Val Phe
 65                  70                  75                  80

Leu Lys Met Asn Ser Leu Gln Thr Asp Thr Ala Met Tyr Tyr Cys
                 85                  90                  95

Ala Arg Asn Leu Gly Pro Tyr Ala Met Asp Tyr Trp Gly Gln Gly Thr
                100                 105                 110

Ser Val Thr Val Ser Ser
        115

<210> SEQ ID NO 170
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 170

Asp Ile Gln Met Thr Gln Ser Pro Ala Ser Gln Ser Ala Ser Leu Gly
 1               5                   10                  15

Glu Ser Val Thr Ile Thr Cys Leu Ala Ser Gln Thr Ile Gly Thr Trp
                20                  25                  30

Leu Ala Trp Tyr Gln Gln Lys Pro Gly Lys Ser Pro Gln Leu Leu Ile
             35                  40                  45

Tyr Ala Ala Thr Ser Leu Ala Asp Gly Val Pro Ser Arg Phe Ser Gly
 50                  55                  60

Ser Gly Ser Gly Thr Lys Phe Ser Phe Lys Ile Ser Ser Leu Gln Ala
 65                  70                  75                  80

Glu Asp Phe Val Ser Tyr Tyr Cys Gln Gln Leu Tyr Ser Thr Pro Trp
                 85                  90                  95

Thr Phe Gly Gly Gly Thr Lys Leu Glu Ile Lys
                100                 105
```

<210> SEQ ID NO 171
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Ser Trp Ile Arg Gln Pro Pro Gly Lys Gly Leu Glu Trp Leu
        35                  40                  45

Gly Val Val Trp Gly Gly Gly Ser Thr Tyr Tyr Asn Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys Gln Arg Gly Gln Tyr Gly Ala Tyr Trp Gly Gln Gly Thr Leu Val
            100                 105                 110

Thr Val Ser Ala
        115

<210> SEQ ID NO 172
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Cys Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Leu
                85                  90                  95

Thr Phe Gly Ala Gly Thr Lys Leu Glu Leu Lys
            100                 105

<210> SEQ ID NO 173
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Val His Trp Val Arg Gln Ser Pro Gly Lys Gly Leu Glu Trp Leu
        35                  40                  45

Gly Val Ile Trp Ser Asp Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Met Tyr Tyr Cys Ala
                85                  90                  95

Arg Lys Lys Gly Gly Trp Phe Pro Trp Phe Ala Tyr Trp Gly Gln Gly
            100                 105                 110

Thr Leu Val Thr Val Ser Ala
        115

<210> SEQ ID NO 174
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 174

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp His Ala
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys Arg
            100                 105                 110

<210> SEQ ID NO 175
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 175

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Arg Leu Glu Trp Ile

```
                    35                  40                  45
Gly Arg Val Asn Pro Asn Asn Gly Gly Thr Asn Tyr Asn Gln Lys Phe
    50                  55                  60
Lys Gly Lys Ala Ile Leu Thr Val Asp Lys Ser Ser Thr Ala Tyr
 65                  70                  75                  80
Met Glu Leu Arg Ser Leu Thr Ser Glu Asp Ser Ala Val Tyr Tyr Cys
                85                  90                  95
Ala Arg Gly Ser Tyr Asp Asn Ala Glu Gly Trp Gly Gln Gly Thr Leu
                100                 105                 110
Val Thr Val Ser Ala
            115

<210> SEQ ID NO 176
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Asp Ile Lys Met Thr Gln Ser Pro Ser Ser Met Tyr Ala Ser Leu Gly
 1               5                  10                  15
Glu Arg Val Thr Ile Thr Cys Lys Ala Ser Gln Asp Ile Asn Arg Tyr
                20                  25                  30
Leu Ser Trp Phe Gln Gln Lys Pro Gly Lys Ser Pro Lys Thr Leu Ile
            35                  40                  45
Tyr Arg Ala Asn Arg Leu Val Asp Gly Val Pro Ser Arg Phe Ser Gly
    50                  55                  60
Ser Gly Ser Gly Gln Asp Tyr Ser Leu Thr Ile Ser Ser Leu Glu Tyr
 65                  70                  75                  80
Glu Asp Met Gly Ile Tyr Tyr Cys Leu Gln Tyr Asp Glu Phe Pro Phe
                85                  90                  95
Thr Phe Gly Ser Gly Thr Lys Leu Glu Ile Lys
                100                 105

<210> SEQ ID NO 177
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 177

Gln Val Gln Leu Gln Gln Ser Gly Ala Glu Leu Val Arg Pro Gly Thr
 1               5                  10                  15
Ser Val Lys Val Ser Cys Lys Ala Ser Gly Tyr Ala Phe Thr Asn Tyr
                20                  25                  30
Leu Ile Glu Trp Val Lys Gln Arg Pro Gly Gln Gly Leu Glu Trp Ile
            35                  40                  45
Gly Val Ile Asn Pro Gly Ser Gly Gly Thr Asn Ser Asn Glu Lys Phe
    50                  55                  60
Lys Ala Lys Ala Thr Leu Thr Ala Asp Lys Ser Ser Thr Ala Tyr
 65                  70                  75                  80
Met Gln Leu Ser Ser Leu Thr Ser Ala Asp Ser Ala Val Tyr Phe Cys
                85                  90                  95
```

Ala Arg Ser Asp Tyr Asp Tyr Ala Phe Tyr Ala Met Asp Tyr Trp Gly
            100                 105                 110

Gln Gly Thr Ser Val Thr Val Ser Ser
        115                 120

<210> SEQ ID NO 178
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro His Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys
            100                 105

<210> SEQ ID NO 179
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Glu Phe Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Asp Arg Ser Gly Tyr Glu Asp Tyr Tyr Gly Met Asp Tyr Trp
            100                 105                 110

Gly Gln Gly Thr Ser Val Thr Val Ser Ser
        115                 120

<210> SEQ ID NO 180
<211> LENGTH: 106

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180

Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Val Ser Tyr Met
            20                  25                  30

His Trp Tyr Gln Gln Lys Ser Gly Thr Ser Pro Lys Leu Leu Ile Tyr
            35                  40                  45

Ser Thr Ser Asn Leu Ala Ser Gly Val Pro Ser Arg Phe Ser Gly Ser
50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Tyr His Thr Phe
                85                  90                  95

Gly Gly Gly Thr Lys Leu Glu Ile Lys Arg
            100                 105

<210> SEQ ID NO 181
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Arg Ala Asp Ala Met Asp Tyr Trp Gly Gln Gly Thr Ser
            100                 105                 110

Val Thr Val Ser Ser
        115

<210> SEQ ID NO 182
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Asp Ile Gln Met Thr Gln Ser Pro Ala Ser Gln Ser Ala Ser Leu Gly

```
            1               5                   10                  15
        Glu Ser Val Thr Ile Thr Cys Leu Ala Ser Gln Thr Ile Gly Thr Trp
                            20                  25                  30

Leu Ala Trp Tyr Gln Gln Lys Pro Gly Lys Ser Pro Gln Leu Leu Ile
                    35                  40                  45

Tyr Ser Ala Thr Ser Leu Ala Asp Gly Val Pro Ser Arg Phe Ser Gly
                50                  55                  60

Ser Gly Ser Gly Thr Lys Phe Ser Phe Lys Ile Ser Ser Leu Gln Ala
        65                  70                  75                  80

Glu Asp Phe Val Ser Tyr Tyr Cys Gln Gln Leu Tyr Ser Thr Pro Trp
                        85                  90                  95

Thr Phe Gly Gly Gly Thr Lys Leu Glu Ile Lys
                        100                 105
```

<210> SEQ ID NO 183
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

```
        Gln Val Gln Leu Lys Glu Ser Gly Pro Gly Leu Val Ala Pro Ser Gln
        1               5                   10                  15

Ser Leu Ser Ile Thr Cys Thr Val Ser Gly Phe Ser Leu Thr Asp Tyr
                        20                  25                  30

Gly Val Ser Trp Ile Arg Gln Pro Pro Gly Lys Gly Leu Glu Trp Leu
                    35                  40                  45

Gly Val Val Trp Gly Gly Gly Ser Thr Tyr Tyr Asn Ser Ala Leu Lys
                50                  55                  60

Ser Arg Leu Ser Ile Ser Lys Asp Asn Ser Lys Ser Gln Val Phe Leu
        65                  70                  75                  80

Lys Met Asn Ser Leu Gln Thr Asp Asp Thr Ala Met Tyr Tyr Cys Ala
                        85                  90                  95

Lys Gln Arg Gly Gln Tyr Gly Ala Tyr Trp Gly Gln Gly Thr Leu Val
                    100                 105                 110

Thr Val Ser Ala
                    115
```

<210> SEQ ID NO 184
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 184

```
        Asp Ile Val Met Thr Gln Ser His Lys Phe Met Ser Thr Ser Val Gly
        1               5                   10                  15

Asp Arg Val Ser Ile Thr Cys Lys Ala Ser Gln Asp Val Asn Thr Ala
                        20                  25                  30

Val Gly Trp Tyr Gln Gln Lys Pro Gly Gln Ser Pro Lys Leu Leu Ile
                    35                  40                  45

Tyr Ser Ala Ser Tyr Arg Tyr Thr Gly Val Pro Asp Arg Phe Thr Gly
                50                  55                  60
```

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ser Pro Tyr
                85                  90                  95

Thr Phe Gly Gly Gly Thr Lys Leu Glu Ile Lys
            100                 105

<210> SEQ ID NO 185
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Thr Ala Tyr
65                  70                  75                  80

Met Ala Leu Ser Ser Leu Thr Ser Glu Asp Ser Ala Val Tyr Tyr Ala
                85                  90                  95

Val Ala Tyr Tyr Ser Asn Trp Gly Phe Ala Tyr Trp Gly Gln Gly Thr
            100                 105                 110

Leu Val Thr Val Ser Ala
        115

<210> SEQ ID NO 186
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186

Asp Ile Val Leu Thr Gln Ser Leu Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Glu Asp Ala Ala Thr Tyr Tyr Cys Gln His Ser Arg
                85                  90                  95

Glu Leu Pro Phe Thr Phe Gly Gly Gly Thr Lys Leu Glu Ile Lys Arg
            100                 105                 110

<210> SEQ ID NO 187
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 187

Gln Val Gln Leu Gln Gln Ser Gly Pro Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Trp Met His Val Lys Gln Arg Pro Gly Gln Gly Leu Glu Trp Ile
        35                  40                  45

Gly Met Ile Asp Pro Ser Asn Ser Glu Thr Arg Leu Asn Gln Lys Phe
    50                  55                  60

Lys Asp Lys Ala Thr Leu Asn Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Val Met Asp Tyr Tyr Phe Asp Tyr Trp Gly Gln Gly Thr Thr Leu
                100                 105                 110

Thr Val Ser Ser
            115

<210> SEQ ID NO 188
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 188

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Phe
                85                  90                  95

Thr Phe Gly Ser Gly Thr Lys Leu Glu Ile Lys
                100                 105

<210> SEQ ID NO 189
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 189

Gln Val Gln Leu Lys Gln Ser Gly Pro Gly Leu Val Ala Pro Ser Gln
1               5                   10                  15

Ser Leu Phe Ile Thr Cys Thr Val Ser Gly Phe Ser Leu Thr Ser Tyr
            20                  25                  30

Glu Ile Asn Trp Val Arg Gln Pro Pro Gly Lys Gly Leu Glu Trp Leu
        35                  40                  45

Gly Val Ile Trp Thr Gly Gly Ser Thr Asn Tyr Asn Ser Ala Leu Ile
50                  55                  60

Ser Arg Leu Ser Ile Ser Lys Asp Asn Ser Lys Ser Leu Val Phe Leu
65                  70                  75                  80

Lys Met Asn Ser Leu Gln Thr Asp Asp Thr Ala Ile Tyr Tyr Cys Val
                85                  90                  95

Arg Gly Val Tyr Ala Met Asp Tyr Trp Gly Gln Gly Thr Ser Val Thr
            100                 105                 110

Val Ser Ser
        115

<210> SEQ ID NO 190
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 190

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Asn Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg
            100                 105

<210> SEQ ID NO 191
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 191

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

```
Gly Phe Phe Tyr Pro Tyr Asn Gly Asn Thr Val Tyr Ser Gln Lys Phe
        50                  55                  60

Lys Ser Lys Ala Thr Leu Thr Val Asp Asn Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Leu Asn Trp Glu Gly Tyr Trp Gly Gln Gly Thr Thr Leu Thr
            100                 105                 110

Val Ser Ser
        115
```

<210> SEQ ID NO 192
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 192

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Leu Lys
            100                 105                 110
```

<210> SEQ ID NO 193
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 193

```
Gln Val Gln Leu Gln Gln Ser Gly Pro Glu Leu Val Lys Pro Gly Ala
 1               5                  10                  15

Ser Val Arg Ile Ser Cys Lys Ala Ser Gly Tyr Thr Phe Thr Ser Tyr
             20                  25                  30

Tyr Ile His Trp Val Lys Gln Arg Pro Gly Gln Gly Leu Glu Trp Ile
         35                  40                  45

Gly Trp Ile Tyr Pro Gly Asn Gly Asn Thr Lys Tyr Asn Glu Lys Phe
     50                  55                  60

Lys Gly Lys Ala Thr Leu Thr Ala Asp Lys Ser Ser Ser Thr Ala Tyr
 65                  70                  75                  80

Met Gln Ile Ser Ser Leu Thr Ser Glu Asp Ser Ala Val Tyr Phe Cys
                 85                  90                  95
```

Ala Arg Glu Arg Trp Leu Leu Leu Trp Phe Ala Tyr Trp Gly Gln Gly
            100                 105                 110

Thr Leu Val Thr Val Ser Ala
        115

<210> SEQ ID NO 194
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Gly Trp Tyr Gln Gln Lys Pro Gly Gln Ser Pro Lys Leu Leu Ile
        35                  40                  45

Tyr Tyr Ala Ser Asn Arg Tyr Asn Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 195
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Val
        35                  40                  45

Gly Trp Ile Asn Thr Tyr Thr Gly Glu Pro Thr Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asp Asn Leu Lys Asn Glu Asp Thr Ala Thr Tyr Phe Cys
                85                  90                  95

Ala Arg Val Gly Asp Tyr Val Gly Phe Asp Tyr Trp Gly Gln Gly Thr
            100                 105                 110

Thr Leu Thr Val Ser Ser
        115

<210> SEQ ID NO 196
<211> LENGTH: 107
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 196

Asp Ile Gln Met Thr Gln Thr Ala Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Leu Glu Gln
65                  70                  75                  80

Glu Asp Ile Ala Thr Tyr Phe Cys Gln Gln Gly Asp Thr Leu Pro Trp
                85                  90                  95

Thr Phe Gly Gly Gly Thr Lys Leu Glu Ile Lys
            100                 105

<210> SEQ ID NO 197
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 197

Gln Ile Gln Leu Val Gln Ser Gly Pro Glu Leu Thr Lys Pro Gly Glu
1               5                   10                  15

Thr Val Lys Ile Ser Cys Lys Ala Ser Gly Tyr Thr Phe Thr Asp Tyr
            20                  25                  30

Ser Leu His Trp Val Lys Gln Ala Leu Gly Lys Gly Leu Lys Trp Met
        35                  40                  45

Gly Trp Ile Asn Thr Glu Thr Gly Glu Pro Ala Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asp Leu Lys Asn Glu Asp Thr Thr Thr Tyr Phe Cys
                85                  90                  95

Gly Ile Tyr Asp Gly Tyr Ala Met Asp Tyr Trp Gly Gln Gly Thr Ser
            100                 105                 110

Val Thr Val Ser Ser
        115

<210> SEQ ID NO 198
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 198

Gln Ile Val Leu Thr Gln Ser Pro Ala Ile Met Ser Ala Ser Pro Gly
1               5                   10                  15

```
Glu Lys Val Thr Met Thr Cys Ser Ala Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
50                  55                  60

Gly Ser Gly Thr Ser Tyr Ser Leu Thr Ile Ser Arg Met Glu Ala Glu
65                  70                  75                  80

Asp Thr Ala Thr Tyr Tyr Cys Gln Gln Trp Ser Asn Asn Pro Leu Thr
                85                  90                  95

Phe Gly Asp Gly Thr Lys Leu Glu Leu Lys
            100                 105

<210> SEQ ID NO 199
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Leu Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
50                  55                  60

Lys Gly Arg Phe Ala Phe Ser Leu Glu Thr Ser Ala Arg Ile Val Tyr
65                  70                  75                  80

Leu Gln Ile Asn Asn Leu Lys Asn Glu Asp Thr Ala Thr Tyr Phe Cys
                85                  90                  95

Ala Lys Tyr Glu Ala His Glu Gly Phe Val Tyr Trp Gly Gln Gly Thr
            100                 105                 110

Leu Val Thr Val Ser Ala
        115

<210> SEQ ID NO 200
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 200

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser His Leu His Thr Gly Val Pro Ser Arg Leu Ser Gly
50                  55                  60
```

```
Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Tyr Pro Phe
                 85                  90                  95

Thr Phe Gly Ser Gly Thr Leu Glu Ile Lys
            100                 105

<210> SEQ ID NO 201
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 201

Gln Val Gln Leu Lys Glu Ser Gly Pro Gly Leu Val Ala Pro Ser Gln
 1               5                  10                  15

Ser Leu Ser Ile Thr Cys Ala Val Ser Gly Phe Ser Leu Thr Ser Phe
                 20                  25                  30

Gly Val His Trp Val Arg Gln Pro Pro Gly Lys Gly Leu Glu Trp Leu
             35                  40                  45

Gly Val Ile Trp Ala Gly Gly Ser Thr Asn Tyr Tyr Ser Ala Leu Met
         50                  55                  60

Ser Arg Leu Ser Ile Ser Ile Asp Asn Ser Lys Ser Gln Val Phe Leu
 65                  70                  75                  80

Lys Met Asn Ser Leu Gln Thr Asp Asp Thr Ala Met Tyr Tyr Cys Ala
                 85                  90                  95

Arg Asp Trp Glu Gly Trp Phe Ala Tyr Trp Gly Gln Gly Thr Leu Val
            100                 105                 110

Thr Val Ser Ala
        115

<210> SEQ ID NO 202
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Asp Ile Val Met Ser Gln Ser Pro Ser Ser Leu Thr Val Ser Val Gly
 1               5                  10                  15

Glu Lys Val Thr Met Ser Cys Met Ser Ser Gln Ser Leu Leu Tyr Ser
                 20                  25                  30

Ser Thr Gln Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Tyr Thr Phe Gly Gly Gly Thr Lys Leu Glu Ile
            100                 105                 110

Lys Arg
```

<210> SEQ ID NO 203
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 203

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Ser Gln Ser His Gly Lys Ser Leu Glu Trp Ile
        35                  40                  45

Gly Tyr Ile Asp Pro Tyr Asn Gly Gly Thr Ser Tyr Asn Gln Lys Phe
    50                  55                  60

Arg Gly Lys Ala Thr Leu Thr Val Asp Lys Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Glu Asn Tyr Arg Tyr Phe Asp Phe Trp Gly Gln Gly Thr Thr
            100                 105                 110

Leu Thr Val Ser Ser
        115

<210> SEQ ID NO 204
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 204

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Leu Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Arg Ser Asn Pro Phe Thr
                85                  90                  95

Phe Gly Gln Gly Thr Lys Leu Glu Ile Lys Arg
            100                 105

<210> SEQ ID NO 205
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 205

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Val Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Ile Val Ser Phe Asp Asn Asp Val Val Ser Ala Met Asp
            100                 105                 110

Tyr Trp Gly Gln Gly Thr Leu Val Thr Val Ser Ser
        115                 120

<210> SEQ ID NO 206
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 206

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Asn Ile Tyr Tyr Asn
            20                  25                  30

Leu Ala Trp Tyr Gln Gln Lys Pro Gly Lys Ala Pro Lys Leu Leu Ile
        35                  40                  45

Tyr Thr Ala Asn Ser Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Lys Gln Ala Tyr Asp Val Pro Pro
            85                  90                  95

Thr Phe Gly Gly Gly Thr Lys Leu Glu Ile Lys
            100                 105

<210> SEQ ID NO 207
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 207

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Trp Ile His Trp Ile Arg Gln Ala Pro Gly Gln Gly Leu Glu Trp Met

-continued

```
                 35                  40                  45

Gly Tyr Ile Asn Pro Thr Thr Val Tyr Thr Glu Phe Asn Gln Asn Phe
             50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ser Asn Phe Phe Asp Tyr Trp Gly Gln Gly Thr Thr
            100                 105                 110

Val Thr Val Ser Ser
            115

<210> SEQ ID NO 208
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 208

Glu Ile Val Leu Thr Gln Ser Pro Asp Phe Gln Ser Val Thr Pro Lys
  1               5                  10                  15

Glu Lys Val Thr Ile Thr Cys Ser Ala Ser Ser Val Ser Tyr Met
             20                  25                  30

His Trp Tyr Gln Gln Lys Pro Asp Gln Ser Pro Lys Leu Leu Ile Lys
             35                  40                  45

Asp Ser Ser Lys Leu Ala Ser Gly Val Pro Ser Arg Phe Ser Gly Ser
 50                  55                  60

Gly Ser Gly Thr Asp Phe Thr Leu Thr Ile Asn Ser Leu Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Gln Gly Thr Lys Leu Glu Ile Lys
            100                 105

<210> SEQ ID NO 209
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Gln Ile Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Gly Val Gly Trp Ile Arg Gln Pro Pro Gly Lys Ala Leu Glu
             35                  40                  45

Trp Leu Thr Asp Ile Trp Trp Asp Asp Lys Tyr Tyr Asn Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95
```

Cys Ala Arg Arg Val Asn Tyr Tyr Asp Pro Tyr Tyr Ala Met Asp
            100                 105                 110

Tyr Trp Gly Gln Gly Thr Thr Leu Val Thr Val Ser Ser
            115                 120                 125

<210> SEQ ID NO 210
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Val Pro Lys Leu Leu Ile
        35                  40                  45

Tyr Tyr Ala Ser Asn Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Asp Tyr Ser Ser Pro Trp
                85                  90                  95

Thr Phe Gly Gly Gly Thr Lys Val Glu Ile Lys
            100                 105

<210> SEQ ID NO 211
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 211

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Arg Leu Glu Trp Met
        35                  40                  45

Gly Trp Ile Asn Thr Tyr Thr Gly Asp Pro Thr Tyr Ala Asp Asp Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Gly Gly Asn Ser Pro Ser Asp Tyr Trp Gly Gln Gly Thr
            100                 105                 110

Thr Val Thr Val Ser Ser
            115

<210> SEQ ID NO 212
<211> LENGTH: 108

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212
```

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Val Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Thr Ser Pro Trp
                85                  90                  95

Thr Phe Gly Gln Gly Thr Lys Leu Glu Ile Lys Arg
            100                 105

```
<210> SEQ ID NO 213
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 213
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ile Gly Asp Ser Ser Pro Ser Asp Tyr Trp Gly Gln Gly Thr
            100                 105                 110

Leu Val Thr Val Ser Ser
        115

```
<210> SEQ ID NO 214

<400> SEQUENCE: 214

000

<210> SEQ ID NO 215

<400> SEQUENCE: 215

000
```

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 220

```
caaattgttc tcacccagtc tccagcaatc atgtctgtat ctctagggga cgggtcacc     60 atgacctgca ctgccagctc aagtgtaagt tccagttact tgcactggta ccaacaaaag    120
ccaggatcct cccccaaact ctggatttat agcacatcca acctggcttc tggagtccca    180
gctcgcttca gtggcagtgg gtctgggacc tcttattttt tcacaatcag cagcatggag    240
gctgaagatg ctgccactta ttactgccac cagtatcatc gttccccatt cacgttcggc    300
gcggggacaa agttgaaaat aagac                                          325
```

<210> SEQ ID NO 221
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 221

```
caggttactc tgaaagagtc tggccctggg atattgcagc cctcccagac cctcagtctg     60
acttgttctt tctctggggtt ttcactgagc acttctggta tgggtgtagg ctggattcgt   120
cagccatcag ggaagggtct ggagtggctg gcacacattt ggtgggatga tgtcaagcgc   180
tataacccag ccctgaagag ccgactaact atctccaagg atacctccag cagccaggta   240
ttcctcaaga tcgccagtgt ggacactgca gatactgcca catactactg tgctcgaata   300
gctgactatg gcggagatta ctatgctatg gactactggg gtcaaggaac ctcagtcacc   360
gtctcctca                                                           369
```

<210> SEQ ID NO 222
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 222

```
gatatccaga tgacacagac tacatcttcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg cgtcccatca     180
aggttcagtg gcagtgggtc tggaacagat tattctctca ccattagcaa cctggagcta     240
gaagatattg ccacttactt ttgccaacag ggtgatatgc ttccgtggac gttcggtgga     300
ggcaccaagc tggaaatcaa ac                                              322
```

<210> SEQ ID NO 223
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 223

```
cagatccagt tggtgcagtc tggacctgag ctgaagaagc ctggagagac agtcaagatc      60
tcctgcaagg cttctggtta taccttcaca gactattcaa tgcactgggt gaagcaggct     120
ccaggaaagg gtttaaagtg gatgggctgg ataaacactg agactggtga gccaggatat     180
gcagatgact tcaagggacg gtttgccttc tctttggaaa cctctgccag cactgcctat     240
ttgcagatca acaacctcaa aaatgaggac acggctacat atttctgtgc tcggtacgac     300
gggtatgcta tggactattg gggtcaagga acctcagtca ccgtctcctc a              351
```

<210> SEQ ID NO 224
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 224

```
caaattgttc tcacccagtc tccagcaatc atgtctgcat ctccagggga gaaggtcacc      60
atgacctgca gtgccagctc aagtgtaagt tacatgcact ggtaccagca gaagtcaggc     120
acctccccca aaagatggat ttatgacaca tccaaactgg cttctggagt ccctgctcgc     180
ttcagtggca gtgggtctgg gacctcttac tctctcacaa tcagcagcat ggaggctgaa     240
gatgctgcca cttattactg ccagcagtgg actagaaacc cgctcacgtt cggggctgga     300
accaagctgg agctgaaac                                                  319
```

<210> SEQ ID NO 225
<211> LENGTH: 372
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic polynucleotide"

<400> SEQUENCE: 225
caggttactc tgaaagagtc tggccctggg atattgcagc cctcccagac cctcagtctg      60
acttgttctt tctctgggtt ttcactgagc acttctggta tgggtgtagg ctggattcgt     120
cagccttcag gagagggtct agagtggctg gcagacattt ggtgggatga caataagtac     180
tataacccat ccctgaagag ccggctcaca atctccaagg atacctccag caaccaggta     240
ttcctcaaga tcaccagtgt ggacactgca gatactgcca cttactactg tgctcgaaga     300
gttaactatg tttacgaccc gtactatgct atggactact ggggtcaagg aacctcagtc     360
accgtctcct ca                                                         372

<210> SEQ ID NO 226
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 226
aacattatga tgacacagtc gccatcatct ctggctgtgt ctgcaggaga aaaggtcact      60
atgagctgta agtccagtca aagtgtttta tacagttcaa atcagaagaa ctacttggcc     120
tggtaccaac agaaaccagg gcagtctcct aaactgctga tctactgggc atccactagg     180
gaatctggtg tccctgatcg cttcacaggc agtggatctg ggacagattt tactcttacc     240
atcagcactg tacaagttga agacctggca gtttattact gtcatcaata cctctcctcg     300
tggacgttcg gtggaggcac caagctggaa atcaaac                              337

<210> SEQ ID NO 227
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 227
gaggtccagc tgcaacagtc tggacctgag ctggtgaagc ctggggcttc agtgaagatt      60
tcctgcaagg cttctggtta ctcattcact ggctataaaa tgcactgggt gaagcaaagc     120
catgtaaaga gccttgagtg gattggacgt attaatcctt acaatggtgc tactagctac     180
aaccagaatt tcaaggacaa ggccaccttg actgtagata gtcctccag cacagcctac     240 atggacctcc acagcctgac atctgaggac tctgcagtct atttctgtgc aagaggggac     300
tataggtacg actggttttgc ttactggggc caagggactc tggtcactgt ctctgca      357

<210> SEQ ID NO 228
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 228
```

```
gaaatccaga tgacccagtc tccatcctct atgtctgcat ctctgggaga cagaataacc      60
atcacttgcc aggcaactca agacattgtt aagaatttaa actggtatca gcagaaacca     120
gggaaacccc cttcattcct gatctattat gcaattgaac tggcagaagg ggtcccatca     180
aggttcagtg gcagtgggtc tgggtcagac tattctctga caatcagcaa cctggagtct     240
gaagattttg cagactatta ctgtctacag ttttatgagt ttccgttcac gttcggtgct     300
gggaccaagc tggagctgaa ac                                              322
```

```
<210> SEQ ID NO 229
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 229
caggcccagc tgcagcagtc tggagctgag ctggtaaggc ctgggacttc agtgaaggtg      60
tcctgcaagg cttctggata cgccttcact aattacttga tagagtgggt aaagcagagg     120
cctggacagg gccttgagtg gattggagtg attaatcctg aactggtgg tactaactac      180 aatgagaact tcaagggcaa ggcaactctg actgcagaca atcctccag tactgcctac       240 atgcagctca gcagcctgac atctgatgac tctgcggtct atttctgtgc aagatccccc     300
tatgattacc acgagggtgc tatggactac tggggtcaag aacctcagt caccgtctcc      360 tca                                                                    363
```

```
<210> SEQ ID NO 230
<211> LENGTH: 410
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 230
caaattgttc tcacccagtc tccagcaatc atgtctgcat ctctagggga acgggtcacc      60
atgacctgca ctgccagctc aagtgtaagt tccagttact tgcactggta ccagcagaag     120
ccaggatcat cccccaaact ctggatttat agcacttcca acctggcttc tggagtccca     180
actcgcttca gtggcagtgg gtctgggacc tcttactctc tcacaatcag cagcatggag     240
gctgaagatg ctgccactta ttactgccac cagtatcatc gttccccatt cacgttcggc     300
tcggggacaa agttggaaat aaaaccagca tggaggctga agatgctgcc acttattact     360
gccaccagta tcatcgttcc ccattcacgt tcggctcggg acaaagttg                 410
```

```
<210> SEQ ID NO 231
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 231
caggttactc tgaaagagtc tggccctggg atattgcagt cctcccagac cctcagtctg      60
acttgttctt tctctgggtt ttcactgagc acttctggta tgggtgtagg ctggattcgt     120
```

```
cagccatcag ggaagggtct ggagtggctg gcacacattt ggtgggatga tgtcaagcgc    180
tataacccag tcctgaagag ccgactgact atctccaagg atacctccag cagccaggta    240
ttcctcaaga tcgccagtgt ggacactgca gatactgcca catactattg tgctcgatta    300
gttgatgatc tgtactactt tgactactgg ggccaaggca ccactctcac agtctcctca    360
```

<210> SEQ ID NO 232
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 232

```
gatgttgaga tgacccagac tccactcact ttgtcggtta ccattggaca accagcctcc     60
atctcttgca gtcaagtca gagcctctca gacagtgatg aaagacata tttgaattgg    120 atgtttcaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tactattgct ggcaaggtaa acattttccg    300
tggacgttcg gtggaggcac caagctggaa atcaaac                             337
```

<210> SEQ ID NO 233
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 233

```
cagatccagt tggtgcagtc tggacctgag ctgaagaagc ctggagagac agtcaagatc     60
tcctgcaagg cttctggtta taccttcaca gactattcaa tgcactgggt gaagcaggct    120
ccaggaaagg gtttaaagtg gatgggctgg ataaacactg agactgttga gccaacatat    180
gcagatgact tcatgggacg gtttgccttc tctttggaaa cctctgccag cactgccttt    240
ttgcagatca caaacctcga aaatgaggac acggctacat atttctgtgc tagatttggt    300
tcctatgcta tggactactg gggtcaagga acctcagtca ccgtctcctc a              351
```

<210> SEQ ID NO 234
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 234

```
caaattgttc tcacccagtc tccagcactc gtgtctgcat ctccagggga gaaggtcacc     60
atgacctgca gtgccagctc aagtgtaagt tacatgtact ggtaccagca gaaaccaaga    120
tcctccccca aaccctggat ttatctcaca tccaacctgg cttctggagt ccctgctcgc    180
ttcagtggca gtgggtctgg gacctcttac tctctcacaa tcagcagcat ggaggctgaa    240
gatgctgcca cttattactg ccagcagtgg cgtagtaacc cattcacgtt cggctcgggg    300
```
acaaagttgg aaataaaac                                                319

<210> SEQ ID NO 235
<211> LENGTH: 371
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 235
caggttactc tgaaagagtc tggccctggg atattgcagc cctcccagac cctcagtctg    60
acttgttctt tctctggggtt ttcactgagc acttctggta tgggtgtagg ctggattcgg   120
cagccatcag ggaagggtct ggagtggctg gcacacattt ggtgggatga tgtcaagcgc   180
tataacccag ccctgaagag ccgactgact atctccaagg atacctccag cagccaggta   240
ttcctcaaga tcgccagtgt ggacactgca gatactgcca catactactg tgctcgcata   300
gtttcctttg ataacgacgt tgtctctgct atggactact ggggtcaagg aacctcagtc   360
accgtctcct c                                                        371

<210> SEQ ID NO 236
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 236
gacatccaga tgactcagtc tccagcctcc ctggctgcat ctgtgggaga aactgtcgcc    60
atcacatgtc gagcaagtga aaacatttac acaatttag catggtatca gcagaaacaa   120
gggaaatctc ctcagctcct gatctatact gcaaacagtt tggaagatgg tgtcccatcg   180
aggttcagtg gcagtggatc tgggacacag tattctttga agatcaacag catgcagcct   240
gaagattccg caacttattt ctgtaaacag gcttatgacg ttcctccgac gttcggtgga   300
ggcaccaagc tggaaatcaa ac                                            322

<210> SEQ ID NO 237
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 237
caggtccagc ttcagcagtc tggggctgaa ctggcaaaac ctggggcctc agtgaagatg    60
tcctgtaagg cttctggcta cacctttact cgctactgga tacactggat aaaacagagg   120
cctggacagg gtctggaatg gattggatac attaatccta caactgttta tactgagttc   180
aatcagaact caaggacaa ggccactttg actgcagaca atcctccac cacagcctcc     240 atgcaactga gcagcctgac atctgaggac tctgcagtct attactgtgc aagaggcggt   300
agtaacttct tgactactg ggggccaaggc accactctca cagtctcctc a            351

<210> SEQ ID NO 238
<211> LENGTH: 323

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 238
gatatccaga tgacacagac tacatcctcc ctgtctgcct ctttgggaga cagagtcacc    60
atcagttgca gggcaagtca gaatattatc aattatttaa actggtatca gcagaagcca   120
gatggaactg ttaaactcct gatctactac acatcaagat tacactcagg agtcccatca   180
aggttcagtg gcagtgggtc tgggacagat tattctctca ccatcagcaa cctggaacct   240
gaagatattg ccacttacta ttgtcaacag tatagtgagc gtccgtacac gttcggggg    300 gggaccaagc tggaaataaa acg                                           323

<210> SEQ ID NO 239
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 239
gaagtgaagc tggaggagtc aggaggaggc ttggtacaac ctggagaatc catgaaactc    60
tcttgtgctg cttctggatt cacttttagt gatgcctgga tggactgggt ccgccagtct   120
ccagagaagg gacttgagtg ggttgctgaa attagaaaca aagctaataa tcatgcaaca   180
tattatgctg agtctgtgaa agggaaattc accatctcaa gagatgattc caaaagtaga   240
gtgtacctgc aaatgaacaa cttaagagct gcagacactg gcatttatta ctgtacggcc   300
tatagtaact tgcttactg gggccaaggg actctggtca ctgtctctac a             351

<210> SEQ ID NO 240
<211> LENGTH: 320
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 240
gacatccaga tgacacagtc tccatcctca ctgtctgcat ctctgggagg caaagtcacc    60
ttcacttgca aggcaagcca agacattcac aagtatgtag cttggtacca acacaagcct   120
ggaaaaggtc ctaggctgct catacattac acatctacat tacagccagg catctcatca   180
aggttcagtg gaagtgggtc tgggagagat tattccttca gcatcagcaa cctggagcct   240
gaagatattg caacttatta ttgtctacag tataataatc tgtacacgtt cggagggggg   300
accaagctgg aaataaaacg                                               320

<210> SEQ ID NO 241
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 241

```
gaggttcagc tgcagcagtc tggggctgag cttgtgaggc caggggcctc agtcaagttg    60
tcctgcacag cttctggctt caacattaaa gacagccttt tgcactgggt gaagcagagg   120
cctgaaaagg gcctggagtg gattgggtgg attgatcctg aggatggtga aactaaatat   180
gccccgaact tccaggacaa ggccactata actacagact catcctccaa cacagcctac   240
ctgcaactca tcagcctgac atctgttgac actgccatct attactgtgc ctatggtaac   300
tacgtgcggc actttgacta ctggggccaa ggcaccactc tcacagtctc ctca         354
```

<210> SEQ ID NO 242
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 242

```
gaaatccaga tgacccagtc tccatcctct atgtctgcat ctctgggaga cagaataacc    60
atcacttgcc aggcaactca agacattgtt aagaatttaa actggtatca gcagaaacca   120
gggaaacccc cttcattcct gatctattat gcaactgaac tggcagaagg ggtcccatca   180
aggttcagtg gcagtgggtc tgggtcagac tattctctga caatcaggaa cctggagtct   240
gaagactttg cagaccatta ctgtctacag ttttatgagt ttccgttcac gttcggtgct   300
gggaccaagc tggagctgaa ac                                            322
```

<210> SEQ ID NO 243
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 243

```
caggtccagt tgcagcagtc tggaactgag ctggtaaggc ctgggacttc agtgagggtg    60
tcctgcaagg cttctggata cgccttcggt aatcacttga ttgagtgggt gaagcagagg   120
cctggacagg gccttgagtg gattggagtg attaatcctg aactggtgg tactcactac   180 aatgagaagt tcaaggacaa ggcaagactg accgcagaca atcctccaa cactgcctac   240 atgcacctca acagcctgac atctgatgac tctgcggtct atttctgtgc aagatccccc   300
tatgattacc acgagggtgc tatggactac tggggtcaag gaacctcagt caccgtctcc   360
tca                                                                363
```

<210> SEQ ID NO 244
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 244

```
gacattgtga tgacacagtc tccatcctcc ctggctatgt cagtaggaca gaaggtcact    60
atgagctgca agtccagtca gagcctttta aatagtagca atcaaaagaa ttatttggcc   120
```

```
tggtatcagc aggaaccagg acagtctcct aaacttctgg tatcctttgc atccactagg    180
gaatctgggg tccctgatcg cttcacaggc agtggatctg ggacagattt cactcttacc    240
atcagcggtg tgcaggctga agacctggca gtttattact gtcagcaaca ttatagcatt    300
ccgctcacgt tcggtgctgg gaccaagctg gagctgaaa                           339
```

```
<210> SEQ ID NO 245
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 245
caggttcagc tacaacagtc tggacctgag ctggtgaagc ctggggcctc agtgaagatt    60
tcctgcaagg cttctggcta tgcattcagt agctcctgga tgaactgggt gaagcagagg    120
cctggaaagg gtcttgagtg gattggacgg atttatcctg agatggaga  tactaactac    180 aatgggaagt tcaagggcaa ggccacactg actgcagaca atcctccag cacagcctac    240 atgcaactca gcagcctgac atctgaggac tctgcggtct acttctgtgc aatgggtatt    300
tataactacg atggtagccg ttactattct atggactact ggggtcaagg aacctcagtc    360
accgtctcct ca                                                        372
```

```
<210> SEQ ID NO 246
<211> LENGTH: 315
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 246
gatatccaga tgacacagac tacatcctcc ctgtctgcct ctctgggaga cagagtcacc    60
atcagttgca gggcaagtca ggacattaag aattatttaa actggtatca gcagaaacca    120
gatggaactg ttaaacccct gatctactac acatcaagag tacactcagg agtcccatca    180
aggttcagtg gcagtgggtc tggaacagat tattctctca ccattagcaa cctggagcaa    240
gaagatattg ccacttactt ttgccagcag ggttatacgc ttccattcac gttcggctcg    300
gggacaaagt tggaa                                                     315
```

```
<210> SEQ ID NO 247
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 247
caggtccagc tgcagcagcc tggggctgaa ctggtgaagc ctggggcttc agtgaagctg    60
tcctgtaagg cttctggata caccttcact acctactgga tgcactgggt gaagcagagg    120
cctggacaag gccttgagtg gatcggagag attgatcctt ctgatagtta tacttactac    180
aatcaaaagt tcaagggcaa ggccacattg actgtagaca atcctccag cacagcctac    240
```
atgcaactca gcagcctgac atctgaggac tctgcggtct attattgtgc aagaggggac    300
tatggtaacc cctatgctat ggactactgg ggtcaaggat cctcagtcac cgtctcctca    360

<210> SEQ ID NO 248
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 248
caaattgttc tcacccagtc tccagcaatc atgtctgcat ctcctgggga aaggtcacc     60 ttgacctgca gtgccagctc aagtgtaagt tccaggtact tgtactggta ccagcagaag   120
ccaggatcct cccccaaact ctggatttat agcacatcca acctggcttc tggagtccct   180
gctcgcttca gtggcagtgg gtctgggacc tcttactctc tcataatcag cagcatggag   240
gctgaagatg ctgcctctta tttctgccat cagtggagta attacccact cacgttcggt   300
gctgggacca agctggagct gaaac                                         325

<210> SEQ ID NO 249
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 249
caggttactc tgaaagagtc tggccctggg atattgcagc cctcccagac cctcagtctg    60
acttgttctt tctctgggtt ttcactgagc acttctaata cgggcatagg ctggattcgt   120
cagccttcag ggacgggtct ggagtggctg gcacacattt ggtggaatga tgataagtac   180
tataatccat ccctgaagag ccggctcaca atctccaagg aaacctccaa caaccaggta   240
ttcctcaaga tcaccaatgt ggacactgca gatactgcct catacttctg tgttcaaatc   300
gggcgcgact acagtaacta cgcctggtat ttcgatgtct ggggcgcagg gaccacggtc   360
accgtctcct ca                                                       372

<210> SEQ ID NO 250
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 250
caaattgttc tcacccagtc tccagcaatc atgtctgcat ctccagggga aaggtcacc     60 atgacctgca gtgccagctc aagtgtaagt tacatgcact ggtaccagca gaagtcaggc   120
acctccccca aaagatggat ttatgactca tccaaactgg cttctggagt ccctgctcgc   180
ttcagtggca gtgggtctgg gacctcttac tctctcacaa tcagcagcat ggaggctgaa   240
gatgctgcca cttattactg ccagcagtgg agtagtaacc cgctcacgtt cggtgctggg   300
accaagctgg agctgaaac                                                319

<210> SEQ ID NO 251
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 251
caggttactc tgaaagagtc tggccctggg atattgcagc cctcccagac cctcagtctg     60
acttgttctt tctctgggtt ttcactgagc acttctggta tgggtgtagg ctggattcgt    120
cagccttcag gagagggtct agagtggctg acagacattt ggtgggatga caataagtac    180
tataacccat ccctgaagag ccggctcaca atctccaagg atacctccag caaccaggta    240
ttcctcaata tcaccagtgt ggacactgca gatactgcca cttactactg tgctcgaaga    300
gttaactatt attcgacccc gtactatgct atggactact ggggtcaagg aacctcagtc    360
accgtctcct ca                                                        372

<210> SEQ ID NO 252
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 252
gatgttgaga tgacccagac tccactcact ttgtcggtta ccattggaca accagcctcc     60
atctcttgca agtcaagtca gagcctctca gacagtgatg gaaagacata tttgaattgg    120
atgtttcaga ggccaggccg gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tactattgct ggcaaggtaa acatttccg     300 tggacgttcg gtggaggcac caagctggaa atcaaac                             337

<210> SEQ ID NO 253
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 253
cagatccagt tggtgcagtc tggacctgag ctgaagaagc ctggagagac agtcaagatc     60
tcctgcaagg cttctggtta ttccttcaca gactattcaa tgcactgggt gaagcaggct    120
ccaggaaagg gtttaaagtg gatgggctgg ataaacactg agactgttga gccaacatat    180
gcagatgact tcatgggacg gtttgccttc tctttggaaa cctctgccag cactgccttt    240
ttgcagatca acaacctcga aaatgaggac acggctacat atttctgtgc tagatttggt    300
tcctatgcta tggactactg gggtcaagga acctcag                             337

<210> SEQ ID NO 254
<211> LENGTH: 320
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 254
caaattgttc tcacccagtc tccagcaatc atgtctgcat ctccagggga gaaggtcacc    60
ataacctgca gtgccagctc aagtgtaagt tacatgcact ggttccagca gaagccaggc   120
acttctccca aactctggat ttataccaca tccaacctgg cttctggagt ccctgctcgc   180
ttcagtggca gtggatctgg gacctcttac tctctcacag tcagccgaat ggaggctgaa   240
gatgctgcca cttattactg ccagcaaagg agtctttatc cgtacacgtt cggagggggg   300
accaaggtgg aaataaaacg                                                320

<210> SEQ ID NO 255
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 255
caggttcagc tacagcagtc tggagctgag ctggcgaggc ccggggcttc agtgaagctg    60
tcctgcaagg cttcaggcta caccttcact gaccagtata taaactgggt gaagcagagg   120
actggacagg gccttgagtg gattggagag atttatcccg aaggggtaa  tacttactac   180 aatgagaagt tcaagggcaa ggccacactg actgcagaca aatcctccag cacagcctac   240
atgcaactca gcagcctgac atctgaggac tctgcagtct atttctgtgc aagagaggat   300
ggtggttacg acgatgcctg gtttgcttac tggggccaag gactctggt  cactgtctct   360 gca                                                                  363

<210> SEQ ID NO 256
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 256
caaattgttc tgacccagtc tccaacaatc atgtctgcat ctctagggga acgggtcacc    60
atgacctgca ctgccagctc aagtgtaact tccagttact tgcactggta ccagcagaag   120
ccaggatcct cccccaaact ctggatttat agcacatcca acctggcttc tggagtccca   180
gctcgcttca gtggcagtgg gtctgggacc tcttactctc tcacaatcag cagcatggag   240
gctgaagatg ctgccactta ttactgccac cagtttcatc gttccccatt cacgttcggc   300
tcggggacaa agttggaaat aaaac                                          325

<210> SEQ ID NO 257
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 257
```

```
caggttactc tgaaagagtc tggccctggg atattgcagc cctcccagac cctcagtctg    60
acttgttctt tctctgggtt ttcactgagc acttctggta tgggtgtagg ctggattcgt   120
cagccatcag ggaagggtct ggagtggctg gcacacattt ggtgggatga tgtcaagcgc   180
tataaaccag ccctgaagag ccgactgact gtctccaagg atacctccag caaccaggtt   240
ttcctcaaga tcgccactgt ggacgctgca gatactggca catactactg tgctcgaatc   300
gttgatggtc accccccgtt tgcttactgg ggccaaggga ctctggtcac tgtctctgca   360
```

<210> SEQ ID NO 258
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 258

```
gacattgtgc tgacccagtc tccactctct ctgcctgtca atattggaga tcaagcctct    60
atctcttgca gtctactaa gagtcttctg aatagtgatg gattcactta tttggactgg   120
tatttgcaga ggccaggcca gtctccacaa ttcctaatat atttggtttc taatcgattt   180
tctggagttc cagacaggtt cagtggcagt gggtcaggaa cagatttcac actcaagatc   240
agcagagtgg aggctgagga tttgggagta tattattgct tccagagtaa ctatcttccg   300
ctcacgttcg gtgctgggac caagctggag ctgagac                            337
```

<210> SEQ ID NO 259
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 259

```
gaggtccaac tgcagcagtc tggacctgag ctggtgaagc ctggggcttc agtgaagata    60
tcctgcaagg cttctggtta ctcattcagt cgtttctata tgcactgggt gaagcaaagt   120
cctgaaaata gtcttgagtg gattggagag attaatccta gcactggggg tacaagctac   180
aaccagaagt tcaagggcaa ggccacatta actgtagata atcctccag cacagcctac   240 atgcagctca gagcctgac atctgaagag tctgcagtct attactgtac tagggggttac   300 gggagcaact ggtacttcga tgtctggggc gcagggacca cggtcaccgt ctccaca     357
```

<210> SEQ ID NO 260
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 260

```
agtattgtga tgacccagac tcccaaattc ctgcttgtat cagcaggaga cagggttacc    60
ataacctgca aggccagtca gagtgtgagt aatgatgtag cttggtacca acagaagcca   120
gggcagtctc ctaaactgct gatatactat gcatccaatc gctacagtgg agtccctgat   180
```

```
cgcttcactg gcagtggata tgggacggat tcactttca ccatcagcac tgtgcaggct    240
gaagacctgg cagtttattt ctgtcagcag gattatagct ctccgtggac gttcggtgga    300
ggcaccaagc tggaaatcaa ac                                             322
```

<210> SEQ ID NO 261
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 261

```
cagatccagt tggtgcagtc tggacctgag ctgaagaggc ctggagagac agtcaagatc     60
tcctgcaagg cttctggata taccttcaca aactatggaa tgaactgggt gaagcaggct    120
ccaggaaagg gtttaaagtg gatgggctgg ataaacacgt acactggaga cccaacatat    180
gctgatgact caagggacg gtttgccttc tctttggaaa cctctgccag cactgcctat    240
ttgcagatca caacctcaa aaatgaggac acggctacat atttctgtgc aagaattggc    300
ggtaatagtc cctctgatta ctggggccaa ggcacctctc tcacagtctc ctca          354
```

<210> SEQ ID NO 262
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 262

```
gatatccaga tgacacagac tacatcctcc ctgtctgcct ctctgggaga cagagtcacc     60
atcagttgca gggcaagtca ggacattagc aattatttaa actggtatca gcagaaacca    120
gatggaactg ttaaactcct gatctactac acatcaagat tacactcagg agtcccatca    180
aggttcagtg gcagtgggtc tggaacagat tattctctca ccattagcaa cctggagcaa    240
gaagatattg ccacttactt ttgccaacag ggtaatacgc ttccgtacac gttcggaggg    300
gggaccaagc tggaaataaa acg                                             323
```

<210> SEQ ID NO 263
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 263

```
tctgatgtgc agcttcagga gtcgggacct ggcctggtga aaccttctca gtctctgtcc     60
ctcacctgca ctgtcactgg ctactcaatc accagtgatt atgcctggaa ctggatccgg    120
cagtttccag gaaacaaact ggagtggatg ggctacataa gctacagtgg tagcactagc    180
tacaacccat ctctcaaaag tcgaatctct atcactcgag acacatccaa gaaccagttc    240
ttcctgcagt tgaattctgt gactactgag gacacagcca catattactg tgcaagattt    300
tactacggta gtagctatgc tatggactac tggggtcaag gaacctcagt caccgtctcc    360
tca                                                                   363
```

<210> SEQ ID NO 264
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 264

```
gaaacaactg tgacccagtc tccagcatcc ctgtccgtga ctacaggaga aaaagtcact    60
atcagatgca taaccacccc tgatattgat gatgatatga actggtacca gcagaagcca   120
ggggaacctc ctaacctcct tatttcagaa ggcaatagtc ttcgtcctgg agtcccatcc   180
cgattctcca gcagtggcta tgcacaaaat tttgttttta caattgaaaa cacgctctca   240
gaagatgttg cagattacta ctgtttgcaa agtgataaca tgccattcac gttcggctcg   300
gggacaaagt tggaaata                                                 318
```

<210> SEQ ID NO 265
<211> LENGTH: 352
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 265

```
caggtccagc tgcagcagtc tggggctgaa ctggcaaaac ctggggcctc agtgaagatg    60
tcctgcaagg cttctggcta caccttact acctactgga tgcactgggt aaaacagagg   120
cctggacagg gtctggaatg gattggatac attaatccta gcagtggtta tactgagtac   180
aatcagaagt tcaaggacaa ggccacattg actgcagaca atcctccag cacagcctac   240
atgcaactaa gcagcctgac atctgaggac tcttcagtct attactgtgc aagaaagggt   300
agtaacaggg ggtttgctta ctggggccaa gggactctgg tcactgtctc tg           352
```

<210> SEQ ID NO 266
<211> LENGTH: 313
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 266

```
caaattgttc tcacccagtc tccagcaatc atgtctgcat ctccagggga gaaggtcacc    60
atgacctgca gtgccagctc aagtataaat tacatgcact ggtaccagca gaagccaggc   120
acctccccca aaagatggat ttatgacaca tccaaactgg cttctggagt ccctgctcgc   180
ttcagtggca gtgggtctgg gacctcttat tctctcacaa tcagcagcat ggaggctgaa   240
gatgctgcca cttattactg ccatcagcgg agtacgtgga cgttcggtgg aggcaccaag   300
ctggaaatca aac                                                     313
```

<210> SEQ ID NO 267
<211> LENGTH: 348
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 267
gaggttcagc tgcagcagtc tggggcagag cttgtgaagc caggggcctc agtcaagttg      60
tcctgcacag tttctggctt caacattaaa gacacctata tacactgggt gaagcagagg     120
cctgaacagg gcctggagtg gattggaagg attgatcctg cgaatggtaa tactaaatat     180
gacccgaagt tccagggcaa ggccactata acagcagaca catcctccaa cacagcctac     240
ctgcagctca gcagcctgac atctgaggac actgccgtct attactgtgc tagaccgacg     300
gggtactttg aatactgggg ccaaggcacc actctcacag tctcctca                  348

<210> SEQ ID NO 268
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 268
gatatccaga tgacacagac tacatcctcc ctgtctgcct ctttgggaga cagagtcacc      60
atcagttgca gggcaagtca ggatgttatc aattatttaa actggtatca gcagaaacca     120
gatggaactg ttaaactcct gatctactac acatcaaggt tacactcagg agtcccatca     180
aggttcagtg gcagtgggtc taggacagat tattctctca ccatcagcaa cctggaacct     240
gaagatattg ccacttacta ttgtcagcag tatagtgagc gtccgtacac gttcggaggg     300
gggaccaagc tggaaataaa acg                                              323

<210> SEQ ID NO 269
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 269
gaagtgaagc ttgaggagtc tggaggaggc ttggtgcaat ttggaggatc catgaaactc      60
tcttgtgctg cttctggatt cacttttagt gatgcctgga tggactgggt ccgccagtct     120
ccagagaagg ggcttgagtg ggttgctgaa attagaaaca aagctaataa tcatgcaaca     180
tattatcctg agtctgtgaa agggaggttc accatctcaa gagatgattc caaaagtaga     240
gtgtacctgc aaatgaacaa cttaagagct gaagacactg gcatttatta ctgtacgggt     300
tactcctcgt ttgcttactg gggccaaggg actctggtca ctgtctctgc a              351

<210> SEQ ID NO 270
<211> LENGTH: 338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 270
gatgttttga tgacacagtc tccactctcc ctgtctgtca gtcttggaga tcaagcctcc      60
```

```
atctcttgta gatctagtca gaacattgta cacagtgata gatacaccta tttagaatgg    120
tacctgcaga aaccaggcca gtcgccaaaa ctcctgatat atggggtttc caaccgattt    180
tctggggtcc cagacaggtt cagtggcagt ggatcaggga cagatttcac actcaagatc    240
agcagagtgg aggctgagga tatgggagtt tattactgct ttcaaggtac acatgttccg    300
tacacgttcg gaggggggac caagctggaa ataaaacg                           338
```

```
<210> SEQ ID NO 271
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 271
cagatccagt tggtgcagtc tggacctgaa ctgaagaagc ctggagagac agtcaagatc     60
tcctgcaagg cttctgggta taccttcaca actgctggaa tgcagtgggt gcaaaagatg    120
ccaggaaagg gttttaagtg gattggctgg ataaacaccc actctggaga gccaaaatat    180
gcagatgact tcaagggacg gtttgccttc tctttggaaa cctctgccag cactgcctat    240
ttacagataa gcaacctcaa agacgaggac acggctacgt ttttctgtgc gcccctatgg    300
tccgatagta gttttgctta ctggggccaa ggaactctgg tcactgtctc tgca          354
```

```
<210> SEQ ID NO 272
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 272
gaaatccaga tgacccagtc tccatcctct atgtctgcat ctctgggaga cagaataacc     60
atcacttgcc aggcaactca agacattgtt aagaatttaa actggtatca gcagaaacca    120
gggaaacccc cttcattcct gatctattat gcaactgaac tggcagaagg ggtcccagca    180
aggttcagtg gcagtgggtc tgggtcagac tattctctga caatcagcaa cctgagtct     240 gaagattttg cagactatca ctgtctacag ttttatgagt ttccgttcac gttcggtgct    300
gggaccaagc tggagctgaa ac                                             322
```

```
<210> SEQ ID NO 273
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 273
caggtccagc tgcagcagtc tggagctgac ctggtaaggc ctggggcttc agtgaaggtg     60
tcctgcaagg cttctggata ctccttcact aattacctga tagagtgggt aaagcagagg    120
ccaggacagg gccttgagtg gattggagtg attaatcctg gaagtggtgg aactcactac    180
aatgagaaat tcaaggacaa ggcagttctg actgcagaca aatcctccac tactgcccac    240
```

```
atgcagctca gcagcctgac atctgatgac tctgcggtct atttctgtgc aagatccccc      300
tatgattata acgatggtgc tatggactac tggggtcaag aacctcagt caccgtctct      360 tca                                                                    363
```

<210> SEQ ID NO 274
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 274

```
gatgttgttc tgacccagtc tccactctct ctgcctgtca atattggaga tcaagcctct       60
atctcttgca agtctactaa gagtcttctg aatagtgatg gattcactta tttggactgg      120
tatttgcaga ggccaggcca gtctccacaa ttcctaatat atttggtttc taatcgattt      180
tctggagttc cagacaggtt cagtggcagt gggtcaggaa cagatttcac actcaagatc      240
agcagagtgg aggctgagga tttgggagta tattattgct tccagagtaa ctatcttccg      300
ctcacgttcg gtgctgggac caagctggag ctgagac                              337
```

<210> SEQ ID NO 275
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 275

```
gaggtccaac tgcagcagtc tggacctgag ctggtgaagc ctggggcttc agtgaagata       60
tcctgcaagg cttctggtta ctcattcagt cgtttctata tgcactgggt gaagcaaagt      120
cctgaaaata gtcttgagtg gattggagag attaatccta gcactggggg tacaagctac      180
aaccagaagt tcaagggcaa ggccacatta actgtagata atcctccag cacagcctac      240 atgcagctca agagcctgac atctgaagag tctgcagtct attactgtac tagggggttac      300 gggagcaact gttacttcga tgtctggggc cagggacca cggtcaccgt ctccaca         357
```

<210> SEQ ID NO 276
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 276

```
gacatcaaga tgacccagtc tccatcttcc atgtatgcat ctctaggaga gagagtcact       60
atcacttgca aggcgagtca ggacattaat agttatttaa gctggttcca gcagaaacca      120
gggaaatctc ctaagaccct gatctatcga gcaaacagat ggtagatgg ggtcccatca      180 aggttcagtg gcagtggatc tgggcaagat tattctctca ccatcaccag cctggagtat      240
gaagatatgg gaatttatta ttgtctacag tatgatgaat ttccgctcac gttcggtgct      300
gggaccaagc tggagctgaa ac                                              322
```

<210> SEQ ID NO 277
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 277

```
caggttcaac tgcagcagtc tggacctgag ctggtgaagc ctgggacttt agtgaagata    60
tcctgcaagg cttctggtta caccttcaca agctacgata taaactgggt gaagcagagg   120
cctggacagg gacttgaatg gattggatgg atttatcctg gagatggtaa tactaagtac   180
agtgagaaat tcaagggcaa ggccacactg actgcagaca atcctccag cacagcctac    240 atgcagctca ccagcctgac ttctgagaac tctgcagtct atttctgtgc aagagactat   300
gattaccctt ttgcttactg gggccaaggg actctggtca ctgtctctgc a            351
```

<210> SEQ ID NO 278
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 278

```
gatatccaga tgacacagac tacatcctcc ctgtctgcct ctctgggaga cagagtcacc    60
atcagttgca gggcaagtca ggacattagc aattatttaa actggtatca gcagaaacca   120
gatggaactg ttaaactcct gatctactac acatcaagat tacactcagg agtcccatca   180
aggttcagtg gcagtgggtc tggtacagat tattctctca ccattagcaa cctggagcaa   240
gaagatattg ccacttactt ttgccaacag ggtaatacgc ttcggacgtt cggtggaggc   300
accaagctgg aaatcaaac                                                319
```

<210> SEQ ID NO 279
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 279

```
gaagtgcagc tggtggagtg tgggggatgc ttagtgaagc ctggagggta cctgaaactc    60
tcctgtgcag cctctggatt cactttcagt agctatgcca tgtcttgggt tcgccagtct   120
ccagagaaga ggctggagtg ggtcgcagaa atcagtattg gtggtagcta cacctactat   180
ccagacactg tgacgggccg attcaccatc tccagagaca tgccaagaa caccctgtac    240 ctggaaatga gcagtctgag gtctgaggac acggccatgt attactgtgc aagggagggc   300
tatgattacg acgtgagagc tatggactac tggggtcaag gaacctcagt caccgtctcc   360
tca                                                                 363
```

<210> SEQ ID NO 280
<211> LENGTH: 322
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 280

```
gacatccaga tgattcagtc tccatcgtcc atgtttgcct ctctgggaga cagagtcagt    60
ctctcttgtc gggctagtca gggcattaga gggactttag actggtatca acagaaacca   120
aatggaacta ttaaactcct gatctactcc acatccaatt taaattctgg tgtcccatca   180
aggttcagtg gcagtgggtc tgggtcagat tattctctca ccatcagcag cctagagtct   240
gaagattttg cagactatta ctgtctacag cgtaatgcgt atcctctcac gttcggtgct   300
gggaccaagc tggagctgaa ac                                            322
```

<210> SEQ ID NO 281
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 281

```
caggtgcagc tgaaggagtc aggacctggc ctggtggcgc cctcacagag cctgtccatc    60
acgtgcgctg tctctggatt ttcattaacc agctttgcaa tacactggtt tcgcaagcct   120
ccaggaaagg gtctggagtg gctgggagta atatggactg gtggaaccac aaattataat   180
tcggctctca tgtccagact gagcatcagc aaagacaact ccaagagcca gttttctta    240 aaaatgaaca gtctgcaaac tgatgacaca gccatgtact actgtgccag agacgattac   300
gacaataatt atgctatgga ctactgggt caaggaacct cagtcaccgt ctcctca      357
```

<210> SEQ ID NO 282
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 282

```
gacatcaaga tgacccagtc tccatcttcc atgtatgcat ctctaggaga gagagtcact    60
atcacttgca aggcgagtca ggacattaat agctatttaa actggttcca gcagaaacca   120
gggaaatctc ctaagaccct gatctatcgt gcaaacagat tggtagatgg ggtcccatca   180
aggttcagtg gcagtggatc tgggcaagat tattctctca ccatcagcag cctggagtat   240
gaagatatgg gaatttatta ttgtctacag tatgatgagt ttccgtacac gttcggaggg   300
gggaccaagc tggaaataaa acg                                           323
```

<210> SEQ ID NO 283
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 283

```
gaggtgcagc ttgttgagtc tggtggagga ttggtgcagc ctaaagggtc attgaaactc    60
```

```
tcatgtgcag tctctgcatt caccttcact acctacgcca tgaactgggt ccgccaggct    120
ccaggaaagg gtttggagtg ggttgctcgc ataagaaata aaagtaataa ttatgcaaca    180
tattatgccg attcagtgaa agacaggttc accatctcca gagatgattc acaaagcatg    240
ctctatctgc aaatgaacaa cttgaaaatt gaggacacag ccatgtatta ctgtgtgttc    300
tactatgatt acgtctactg gggccaaggg actctggtca ctgtctctgc a            351
```

<210> SEQ ID NO 284
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 284

```
agtattgtga tgacccagac tcccaaattc ctgcttgtat cagcaggaga cagggttacc    60
ataacctgca aggccagtca gagtgtgagt aatgatgtag tatggtacca acagaagcca    120
gggcagtctc ctaaactgct gatatactat gcatccaatc gctacactgg agtccctgat    180
cgcttcgctg gcagtggata tgggacggat ttctcttttca ccatcagcac tgtgcaggct    240
gaagacctgg cagtttattt ctgtcagcag gattatacct ctccgtggac gttcggtgga    300
ggcaccaagc tggaaatcag ac                                             322
```

<210> SEQ ID NO 285
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 285

```
cagatccagt tggtgcagtc tggacctgaa ctgaagaagc ctggagagac agtcaagatc    60
tcctgcaagg cttctgggta taccttcaca aactatggaa tgaactgggt gaagcaggct    120
ccaggaaagg gtttaaagtg gatggcctgg ataaacacct acactggaga gccaacatat    180
gctgatgact caagggacg gtttgccttc tctttggaaa cctctgccag cactgcctct    240
ttgcagatca tcaacctcaa aaatgaggac acggctacat atttctgtgc aaggatcggc    300
gatagtagtc cctctgacta ctgggggcag ggcaccactc tcacagtctc ctca         354
```

<210> SEQ ID NO 286
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 286

```
gacattgtga tgacccagtc tcacaaattc atgtccatat cagtaggaga cagggtcagc    60
atcacctgca aggccagtca ggatgtgagt atttttgtag cctggtatca acagaaacca    120
ggacaatctc ctaaactact gatttactcg gcatcctacc ggtacactgg agtccctgat    180
cgcttcactg gcagtggatc tgggacggat ttcattttca ccatcagcag tgtgcaggct    240
```

```
gaagacctgg cagtttacta ctgtcagcaa cattatggta ctccattcac gttcggctcg    300
gggacaaagt tgaaaataag ac                                              322
```

<210> SEQ ID NO 287
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 287

```
gaagtgaaac tggtggagtc tgggggagac ttagtgaagc ctggagggtc cctaaaactc     60
tcctgtgcag cctctggatt cgctttcagt agttatgaca tgtcttgggt tcgccagact    120
ccggagaaga gactggagtg ggtcgcaacc attagcagtg gtggtagtta cacctattat    180
ccagacagtg tgaagggccg attcaccatc tccagagaca atgtcaggga cacccctgtac   240 ctgcaaatga gcagtttgag gtctgaggac acggccttgt attactgtgc aagacaggca   300
attgggacgt actttgacta ctggggccaa ggcaccactc tcacagtctc ctca          354
```

<210> SEQ ID NO 288
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 288

```
gacatccaga tgactcagtc tccagcctcc ctatcttcat ctgtgggaga aactgtcacc     60
atcacatgtc gagcaagtga gaatatttac agttatttag catggtatca gcagaaacag    120
ggaaaatctc ctcagctcct ggtctataat gcaaaaactt tagcagaagg tgtgccatca    180
aggttcagtg gcagtggatc aggcacacag ttttctctga agatcaacag cctgcagcct   240
gaagattttg ggacttatta ctgtcaacat cattatgatt ctccgctcac gttcggtgct    300
gggaccaagc tggagctgag ac                                              322
```

<210> SEQ ID NO 289
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 289

```
gatgtgcagc tggtggagtc tgggggaggc ttagtgcagc ctggagggtc ccggaaactc     60
tcctgtgcag cctctggatt cactttcagt agctttggaa tgcactgggt tcgtcaggct    120
ccagagaagg ggctggagtg ggtcgcatac attagtagtg gcagtagtaa catctactat    180
gcagacacag tgaagggccg attcaccatc tccagagaca atcccaagaa caccctgttc    240
ctgcaaatga ccagtctaag gtctgaggac acggccatgt attactgtgc aagaggctac   300
tatggtaact acgatgctat ggactactgg ggtcaaggaa cctcagtcac cgtctcctca   360
```

<210> SEQ ID NO 290
<211> LENGTH: 340

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 290
gatattgtga tgacacagtc tacatcctcc ctggctatgt cagtaggaca gaaggtcact     60
atgagctgca agtccagtca gagccttttta aatagtagca atcaaaagaa ttatttggcc    120
tggtaccagc aggaaccagg acagtctcct aaacttctgg tatcctttgc atccactagg    180
gaatctgggg tccctgatcg cttcacaggc agtggatctg ggacagattt cactcttacc    240
atcagcggtg tgcaggctga agacctggca gtttattact gtcagcaaca ttatagcatt    300
ccgctcacgt tcggtgctgg aaccaagctg gagctgaaac                          340

<210> SEQ ID NO 291
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 291
gaggtcctgc tccaacggtc tggacctgac ctggtgaagc ctggggcttc agtgacgata     60
ccctgcaagg cttctggata cacattcact gactacaaca tggactgggt gaagcagagc    120
catggaaaga gccttgagtg gattggaaat attaatactt acaatggtgg tactatctac    180
aaccagaagt tcaagggcaa ggccacattg actgtagaca gccctccag cacagcctac     240 atggagctcc gcagcctgac atctgaggac actgcagtct attactgtgc aagacgtcta    300
cggtatgggg gacactactt tgactactgg ggccaaggca ccgctctcac agtctcctca    360

<210> SEQ ID NO 292
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 292
gacatcaaga tgacccagtc tccatcttcc atgtatgcat ctctaggaga gagagtcact     60
atcacttgca aggcgagtca ggacattaat agcttttttaa gctggttcca gcggaaacca    120
gggaaatctc cgaagaccct gatctatcgt gcaaacagat tagtagatgg agtcccatca    180
aggttcactg gcagtggatc tgggcaagaa ttttctctca ccatcagcag cctggagtat    240
gaagatttgg gaatttatta ttgtcttcag tatgatgagt ttccgtacac gttcggaggg    300
gggaccaagc tggaaataaa acg                                            323

<210> SEQ ID NO 293
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 293

```
gaagtgatgc tggtagagtc tgggggagac ttagtgaagc ctggagggtc cctgaaactc    60
tcctgtgcag cctctggatt cactttcagt agctatgcca tgtcttgggt tcgccagact   120
ccggagaaga ggctggagtg ggtcgcatac attagcggtg gtggtgatca catctattat   180
ccagacagtg tgaggggccg attcaccatc tccagagaca atgccaagga cacctgtac    240
ctgcaaatga gcagtctgag gtctgaggac acggccttgt atgactgtgc aagagtgaga   300
gactggtact cgatgtctg gggcgcaggg accacggtca ccgtctcctc a             351
```

<210> SEQ ID NO 294
<211> LENGTH: 316
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 294

```
caaattgttc tcacccagtc tccagcaatc atgtctgcat ctccagggga gaaggtcacc    60
atgacctgca gtgccagctc aagtgtcagt tacatgtact ggtaccagca gaagtcaggc   120
acctccccca aaagatggat ttatgacaca tccaaactgg cttctggagt ccctgctcgc   180
ttcagtggca gtgggtctgg gacctcttac tctctcacaa tcagcagcat ggaggctgaa   240
gatgctgcca cttattactg ccagcagtgg agtagtaacc cgtacacgtt cggagggggg   300
accaagctgg aaataa                                                    316
```

<210> SEQ ID NO 295
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 295

```
caggttcagc tgcagcagtc tggaactgag ctgctgaggc ctggggcctc agtgaagata    60
tcctgcaagg ctactggcta cacattcagt agctactgga tggagtgggt aaagcagagg   120
cctggacatg gccttgagtg gattggagag attttacctg gaagtggtac tactcagtac   180
aatgagaagt tcaagggcaa ggccaccttc actgcagata catcctccaa cacagcctac   240
atgcatctca gcagcctgac atctgaggac tctgccgtct attactgtgc aagagggact   300
aactctctct ggggccaagg gactctggtc actgtctctg ca                      342
```

<210> SEQ ID NO 296
<211> LENGTH: 304
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 296

```
caaattgttc tcacccagtc tccagcactc atgtctgcat ctccagggga gaaggtcacc    60
atgacctgca gtgtcacctc aagtgtaagt tacatgtact ggtaccagca gaagcctaga   120
tcctccccca aaccctggat ttatctcaca tccaacctgg cttctggagt ccctgctcgc   180
```

```
ttcagtggca gtgggtctgg gacctcttac tctctcacaa tcagcagcgt ggaggctgaa      240
gatgctgcca cttattactg ccagcagtgg aggaataacc cattcacgtt cggctcgggg      300
acaa                                                                  304
```

<210> SEQ ID NO 297
<211> LENGTH: 387
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 297

```
caggttactc tgaaagagtc tggccctggg atattgcagc cctcccagac cctcagtctg       60
acttgttctt tctctgggtt ttcactgagc acttctggta tgggtgtagg ctggattcgt      120
cagccatcag ggaagggtct ggagtggctg gcactcattt ggtgggatga tgtcaagcgc      180
tataatccag ccctgaagag tcgactgact atctccaagg atgcctccag cagccaggtc      240
ttcctcaaga tcgccagtgt ggacactgca gatactgcca catactactg tgctcgaata      300
gcttcctatg attacgacgt agtctatgct atggactact ggggtcaagg aacctcagtc      360
agcgtctcct caaggtggaa ataaaac                                          387
```

<210> SEQ ID NO 298
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 298

```
caggctgttg tgactcagga atctgcactc accacatcac ctggtgaaac agtcacactc       60
acttgtcgct caagtactgg ggctgttaca actagtaact atgccaactg gatccaagaa      120
aaaccagatc atttattcac tggtctaata ggtggtacca caaccgagc tccaggtgtt      180 cctgccagat tctcaggctc cctgattgga gacaaggctg ccctcaccat cacaggggca      240
cagactgagg atgaggcaat atatttctgt ggtctatggt acagcaacca tttggtgttc      300
ggtggaggaa ccaaactgac tgtcctag                                         328
```

<210> SEQ ID NO 299
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 299

```
gaggtgcagc ttgttgagac tggtggagga ttggtgcagc ctaaagggtc attgaaactc       60
tcatgtgcag tctctgcatt caccttcact acctacgcca tgaactgggt ccgccaggct      120
ccaggaaagg gtttggagtg ggttgctcgc ataagaaata aagtaataa ttatgcaaca      180 tattatgccg attcagtgaa agacaggttc accatctcca gagatgattc acaaagcatg      240
ctctatctgc aaatgaacaa cttgaaaatt gaggacacag ccatgtatta ctgtgtgttc      300
```

```
tactatgatt acgtctactg gggccaaggg actctggtca ctgtctctgc a            351
```

<210> SEQ ID NO 300
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 300

```
gaaacaactg tgacccagtc tccagcattc ctgtccgtgg ctacaggaga aaaagtcact    60
atcagatgca taaccagcac tgatattgat gatgatatga actggtacca gcagaagcca   120
ggggaacctc ctaatgtcct tatttcagaa ggcaatactc ttcgtcctgg agtcccatcc   180
cgattctcca gcagtggcta tggcacagat tttgttttta caattgaaaa cacgctctca   240
gaagatgttg cagattacta ctgtttgcaa agtgataaca tgcctctcac gttcggtgct   300
gggaccaagc tggagctgaa ac                                            322
```

<210> SEQ ID NO 301
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 301

```
caggtgcaac tgcagcagcc tggggctgag ctggtgaagc ctggggcctc agtgaagatg    60
tcctgcaagg cttctggcta cacatttacc aattacaata tgcactgggt aaagcagaca   120
cctggacagg gcctggaatg gattggggct attttttccag gaaatggtgg tacttcctac   180
aatcagaagt tcaaaggcaa ggccacattg actgcagaca atcctccag cacagcctac   240 atgcagctca ccagtttgac atctggggac tctgcagtct attactgtgc aagatggggc   300
tacggtagtg gcctttatgc tatggactac tggggtcaag gaacctcagt caccgtctcc   360
tca                                                                 363
```

<210> SEQ ID NO 302
<211> LENGTH: 320
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 302

```
gaaaatgtac tcacccagtc tccagcaatc atgtctgcat ctctagggga aaggtcacc     60 atgagctgca gggccagctc aagtgtaaat tacatgtcct ggtaccagca gaagtcagat   120
gcctccccca aactatggat ttattacaca tccaacctgg ctcctggagt cccagctcgc   180
ttcagtggca gtgggtctgg gaactcttat tctctcacaa tcagcagcat ggaggtgaa    240 gatgctgcca cttattactg ccagcagttt actagttccc cgtacacgtt cggagggggg   300
accaagctgg aaataaaacg                                               320
```

<210> SEQ ID NO 303
<211> LENGTH: 351

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 303
gaggtccagc tgcagcagtc tggacctgag ctggtaaagc ctggggcttc agtgaagatg      60
tcctgcaagg cttctggata cacattcact agctatgtta tgcactgggt gaagcagaag     120
cctgggcagg gccttgagtg gattggatat attaatcctt acaatgatgg tactaagtac     180
aatgagaagt tcaaaggcaa ggccacactg acttcagaca aatcctccag cacagcctac     240
atggagctca gcagcctgac ctctgaggac tctgcggtct attactgtgc aagattgagg     300
tcgagggcta tggactactg gggtcaagga acctcagtca ccgtctcctc a             351

<210> SEQ ID NO 304
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 304
gacatccaga tgacccagtc tccatcctcc ttatctgcct ctctgggaga gagagtcagt      60
ctcacttgtc gggcaagtca ggacattggt tatagcttaa actggcttca gcaggaacca    120
gatggaacta ttaaacgcct gatctacgcc acatccagtt tagattctgg tgtccccaaa    180
aggttcagtg gcagtaggtc tgggtcagat tattctctca ccatcagcag ccttgagtct    240
gaagattttg tagactatta ctgtctacaa tatgctagtt ctccgtggac gttcggtgga    300
ggcaccaagc tggaaatcaa ac                                             322

<210> SEQ ID NO 305
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 305
caggtgcagc tgcagcagtc tggagctgag ctgatgaagc ctggggcctc agtgaagata      60
tcctgcaagg ctaatggcta cacattcagt agctactgga tagagtggtt aaggcagagg    120
cctggacatg gccttgagtg gattggagag atttttacctg gaagtgataa tagtaattat    180
aatgagaagt tcaagggcaa ggccacattc actgcagata catcctccaa cacagcctac    240
atgcaactca gcagcctgac atctgaggaa tctgccgtct attactgtac aaggggatta    300
cgacgagacg gctcatatta ctatgttatg gaacattggg gtcaaggaac ctcagtcacc    360
gtctcctca                                                            369

<210> SEQ ID NO 306
<211> LENGTH: 312
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 306

```
gacatcaaga tgacccagtc tccatcttcc atgtatgcat ctctaggaga gagagtcact    60
atcacttgca aggcgagtca ggacattaat agctatttaa gctggttcca gcagaagcca   120
gggagatctc ctaagaccct gatctatcgt gcaaacagat tggtagatgg ggtcccatca   180
aggttcagtg gcagtggatc tgggcaagat tattctctca ccatcagcag cctggactat   240
gaagatatgg gaatttatta ttgtctacag tatgatgaat ttccattcac gttcggctcg   300
gggacaaagt tg                                                       312
```

<210> SEQ ID NO 307
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 307

```
gaagtgaagc tggtggagtc tgggggaggc ttagtgaagc ctggagggtc cctgaaactc    60
tcctgtgcag cctctggatt cactttcggt cgctatgtca tgtcttgggt tcgccagact   120
ccagaaaaga aactggagtg ggtcgcatcc attactagtg gtggtactac ctactatcca   180
gacagtgtga agggccgatt caccatctcc agagataatg ccaggaacat cctgtaccta   240
caaatgagca gtctgaggtc tgaggacacg gccatgtatt actgtgcaag agtctactat   300
cattacgacg acatctttgc ttactggggc caagggactc tggtcactgt ctctgca      357
```

<210> SEQ ID NO 308
<211> LENGTH: 338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 308

```
gacattgtga tgtcacagtc tccatcctcc ctggctgtgt cagcaggaga gaaggtcact    60
atgagctgca aatccagtca gagtctgctc aacagtagaa cccgaaagaa ctacttggct   120
tggtaccagc agaaaccagg gcagtctcct aaactgctga tctactgggc atccactagg   180
gaatctgggg tccctgatcg cttcacaggc agtggatctg gacagattt cactctcacc    240
atcagcagtg tgcaggctga agacctggca gtttattact gcaagcaatc ttataatctt   300
tacacgttcg ggggggggac caagctgaaa ataaaacg                           338
```

<210> SEQ ID NO 309
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 309

```
gaggtccagc tgcaacagtc tggacctgag ctggtgaagc ctggggcttc agtgaagata    60
tcctgcaaga cttctggata cacattcact gaatacacca tgcactgggt gaagcagagc   120
```

```
catggaaaga gccttgagtg gattggaggt attaatccta acaatggtgg tactagctac    180
aaccagaagt tcaagggcaa ggccacattg actgtagaca agtcctccag cacagcctac    240
atggagctcc gcagcctgac atctgaggat tctgcagtct attactgtgc aagggtccc     300 gcctggtttg cttactgggg ccaagggact ctggtcactg tctctgca                 348
```

<210> SEQ ID NO 310
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 310

```
gaaacaactg tgacccagtc tccagcatcc ctgtccatgg ctataggaga aaaagtcacc    60
atcagatgca taaccagcac tgatattgat gatgatatga tctggtacca gcagaagcca   120
ggggaacctc ctaagctcct tatttcagaa ggcaatactc ttcgtcctgg agtcccatcc   180
cgattctcca gcagtggcta tggtacagat tttgttttta caattgaaaa catgctctca   240
gaagatgttg ccgattacta ctgtttgaaa agggatgact gccttacac gttcggcggg    300 gggacacagg tggaaattaa acg                                           323
```

<210> SEQ ID NO 311
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 311

```
gaggtccagc tgcaacagtc tggacctgag ctggtgaagc ctggaggttc aaagaagata    60
tcctgcaagg cttctggtta ctcattcact ggctacagta tgaactgggt gaagcagagc   120
catggaaaga accttgagtg gattggactt attaatcctt acagtggtgg tactatctac    180
aaccagaaat tcaagggcaa ggccacatta actgtagaca agtcatccag cacagcctac   240
atggagctcc tcagtctgac atctgaggac tctgcagtct attactgtgc aagaaggagt   300
gattacccgt tagtttactg gggccaaggg actctggtca ctgtctctgc a             351
```

<210> SEQ ID NO 312
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 312

```
caaattgttc tcacccagtc tccagcaatc atgtctgcat ctctagggga acgggtcacc    60
ctgacctgca ctgccagctc aagtgtaagt tccagttact gcactggta ccagcagaag    120 ccaggatcct cccccaaact ctggatttat agcacatcca acctggcttc tggagtccca   180
actcgcttca gtggcagtgg gtctgggacc tcttactctc tcagaatcag cagcatggag   240
gctgaagatg ctgccactta ttactgccac cagtataatc gttccccgct cacgttcggt   300
```

```
gctgggacca agctggagct gaaac                                        325
```

<210> SEQ ID NO 313
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 313

```
caggtgcagc tgaaggagtc aggacctgtc ctggtggcgc cctcacagag cctgtccatc   60
acttgcactg tctctgggtt ttcattaacc agctatggtg tacactgggt tcgccagcct  120
ccaggaaagg gtctggagtg gctgggagta atttgggctg gtggaagtac aaattataat  180
tcagctctca tgtccagact gagcatcagc aaagacaact ccaagagcca gttttctta   240 aaaatgaaca gtctgcaaac tgatgacaca gccatgtact actgtgccaa cagggcaac   300 ttctatgcta tggactactg gggtcaagga acctcagtca ccgtctcctc a           351
```

<210> SEQ ID NO 314
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 314

```
gacatccaga tgacacagtc tccatcctca ctgtctgcat ctctgggagg caaagtcacc   60
atcacttgca aggcaagcca agacattaag agtatatag cttggtacca acacaagcct  120
ggaaaaggtc ctaggctact catacattac acatctacat tagagccagg catcccatca  180
aggttcagtg gaagtgggtc tgggagagat tattccttca gcatcagcaa cctggagcct  240
gaagatattg caacttatta ttgtctacaa tatgatattc tgtggacgtt cggtggaggc  300
accaagctgg aaatcaaac                                                319
```

<210> SEQ ID NO 315
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 315

```
gaggtccagc tgcaacagtc tggacctgag ctggtgaagc ctggagcttc aatgaagata   60
tcctgcaagg cttctggtta ctcattcact ggctacacca tgaactgggt gaagcagagc  120
catggaaaga accttgagtg gattggactt attaatcctt acaatggtgg tactacctac  180
aaccagaagt tcaagggcaa ggccacatta actgtagaca gtcatccag cacagcctac  240 atggagctcc tcagtctgac atctgaggac tctgcagtct attactgtgc attaggttac  300
tatggtaact acaggaggta cttcgatgtc tggggcgcag ggaccacggt caccgtctcc  360
tca                                                                 363
```

<210> SEQ ID NO 316
<211> LENGTH: 325

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 316
gaaaatgtgc tcacccagtc tccagcaata atggctgcct ctctggggca gaaggtcacc      60
atgacctgca gtgccagctc aagtgtaagt tccagttact tgcactggta ccagcagaag     120
tcaggcgctt cccccaaacc cttgattcat aggacatcca acctggcttc tggagtccca     180
gctcgcttca gtggcagtgg gtctgggacc tcttactctc tcacaatcag cagcgtggag     240
gctgaagatg atgcaactta ttactgccgg cagtggagtg gttacccgtg gacgttcggt     300
ggaggcacca agctggaaat caaac                                           325

<210> SEQ ID NO 317
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 317
caggttcagc tgcagcagtc tggggctgag ctggcaagac ctggggcttc agtgaagttg      60
tcctgcaagg cttctggcta cacctgtact agctactgga tgcagtgggt aaaacagagg     120
cctggacagg gtctggaatg gattgggget atttatcctg agatggtga tactaggtac      180 actcagaagt tcaagggcaa ggccacattg actgcagata atcctccag cacagcctac     240 atgcaactca gcagcttggc atctgaggac tctgcggtct attactgtgc aaggggagg     300 cggacggagg cctggtttgc ttactggggc caagggactc tggtcactgt ctctgca       357

<210> SEQ ID NO 318
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 318
caaattgttc tcacccagtc tccagcaatc atgtctgcat ctctagggga acgggtcacc      60
atgacctgca ctgccagctc aagtgtaagt tccagttact tgcactggta ccagcagaag     120
ccaggatcct cccccaaact ctggatttat agcacatcca acctggcttc tggagtccca     180
gctcgcttca gtggcagtga gtctgggacc tcttactctc tcacaatcag caacatggag     240
gctgaggatg ctgccactta ttactgccac cagtatcatc gttccccatt cacgttcggc     300
tcggggacaa agttggaaat aaaac                                           325

<210> SEQ ID NO 319
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

```
<400> SEQUENCE: 319
caggttactc tgaaagagtc tggccctggg atattgcagc cctcccagac cctcagtctg    60
acttgttctt tctctggatt ttcactgagc acttctggta tgggcgtagg ctggattcgt   120
cagccatcag ggaagggtct ggagtggctg gcacacattt ggtgggatga tgtcaagcgc   180
tataacccag cccttaagag ccgactgact atctccaagg atgcctccag cagccaggta   240
ttcctcaaga tcgccagtgt ggacactgca gaaactgcca catactactg tgcccacatc   300
ctcgaccggg cttactactt tgactactgg ggccaaggca ccactctcac agtcacctca   360

<210> SEQ ID NO 320
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 320
gacattgtgc tgacacagtc tcctgcttcc ttagctgtat ctctggggca gagggccacc    60
atctcatgca gggccagcaa aagtgtcagt acatctggct atagttatat gcactggtac   120
caacagaaac caggacagcc acccaaactc ctcatctatc ttgcatccaa cctagaatct   180
ggggtccctg ccaggttcag tggcagtggg tctgggacag acttcaccct caacatccat   240
cctgtggagg aggaggatgc tgcaacctat tactgtcagc acagtaggga gcttcctctc   300
acgttcggtg ctgggaccaa gctggagctg aaac                               334

<210> SEQ ID NO 321
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 321
caagttactc taaaagagtc tggccctggg atattgaagc cctcacagac cctcagtctg    60
acttgttctt tctctgggtt ttcactgagc acttctggta tgggtatagg ctggattcgt   120
cagccttcag ggaagggtct ggagtggctg gcacacattt ggtgggatga tgataagtac   180
tataacccat ccctgaagag ccagctcaca atctccaagg attcctccag aaaccaggtt   240
ttcctcaaga tcaccagtgt ggacactgca gatactgcca cttactactg tgctcgaaga   300
gggactgcgt actactttga ctactggggc caaggcacca ctctcacagt ctcctca     357

<210> SEQ ID NO 322
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 322
caaattgttc tctcccagtc tccagcaatc ctgtctgcat ctccagggga gaaggtcaca    60
atgacttgca gggccagttc aagtgtaagt tacattcact ggtaccggca gaagccagga   120
tcctccccca aaccctggat ttatgccaca tccaacctgg cttctggagt ccctgctcgc   180
```

```
ttcagtggca gtgggtctgg gacctcttac tctctcacaa tcagcagagt ggaggctgaa    240
gatgctgcca cttattactg ccagcagtgg agcagtaatc cacccacgtt cggtgctggg    300
accaagctgg agctgaaac                                                 319
```

<210> SEQ ID NO 323
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 323

```
caggtgcagc tgaaggagtc aggacctgac cttgtgcagc cctcacagac cctgtctctc     60
acctgcactg tctctgggtt ctcattaacc ttctatggtg ttcactgggt tcgccagcct    120
ccaggaaagg gactggagtg ggtgggaaca atgggctggg atgacaaaaa atattataat    180
tcagctctaa aatctcgact gagcatcagc agggatacct ccaagaacca ggttttctta    240
aaactgagca gtctgcaaac tgaagacaca gccatgtact actgtactag aggtgggacg    300
gggtttgact actggggcca aggcaccact ctcacagtct cctca                    345
```

<210> SEQ ID NO 324
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 324

```
gacattgtga tgacccagtc gcacaaattc atgtccacat cagtaggaga cagggtcagc     60
atcacctgca aggccagtca ggatgtgggt actgctgtag cctggtatca acagaaacca    120
gggcaatctc ctaaactact gatttactgg gcatccatcc ggcacactgg agtccctgat    180
cgcttcacag gcagtggatc tgggacagat ttcactctca ccattagcaa tgtgcagtct    240
gaagacttgg cagattattt ctgtcagcaa tatagcagct atccgctcac gttcggtgct    300
gggaccaagc tggagctgaa ac                                             322
```

<210> SEQ ID NO 325
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 325

```
caggtccaac tgcagcagcc tggggctgag cttgtgaagc ctggggcttc agtgaagctg     60
tcctgcaagg cttctggcta caccttcacc agctactgga tgcactgggt gaagcagagg    120
cctggacaag gccttgagtg gattggagtg attaatccta gcaacggtcg tactaactac    180
aatgagaagt tcaagagcaa ggccacactg actgtagaca atcctccag cacagcctac    240 atgcaactca gcagcctgac atctgaggac tctgcggtct attactgtgc aagaagaagg    300
gaactgggaa ccctctatgc tatggactac tggggtcaag aacctcagt caccgtctcc     360
```

```
tca                                                                 363

<210> SEQ ID NO 326
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 326
gacatcaaga tgacccagtc tccatcttcc atgtatgcat ctctaggaga gagagtcact    60
atcacttgca aggcgagtca ggacattaat agctatttaa gctggttcca gcagaaacca   120
gggaaatctc ctaagaccct gatctatcgt gcaaacagat tggtagatgg ggtcccatca   180
aggttcagtg gcagtggatc tgggcaagat tattctctca ccatcagcag cctggagtat   240
gaagatatgg gaatttatta ttgtctacag tatgatgagt ttccattcac gttcggctcg   300
gggacaaagt tggaaataaa ac                                            322

<210> SEQ ID NO 327
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 327
caggtgcaac tgaagcagtc aggacctggc ctggtggcgc cctcacagag cctgttcatc    60
acatgcaccg tctcagggtt ctcattaacc agctatgaaa taaactgggt tcgccagcct   120
ccaggaaagg gtctggagtg gctgggagtg atatggactg gtggaagcac aaattataat   180
tcagctctca tatccagact gagcatcagc aaagacaact ccaagagcct agttttctta   240
aaaatgaaca gtctgcaaac tgatgacaca gccatatatt actgtgtaag aggtgtttat   300
gctatggact actggggtca aggaacctca gtcaccgtct cctca                  345

<210> SEQ ID NO 328
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 328
gacattgtga tgacccagtc tcacaaattc atgtccacat cagtaggaga cagggtcagc    60
atcacctgca aggccagtca ggatgtgaat actgctgtag ctggtatcaa acagaaacca   120
ggacaatctc ctaaactact gatttactcg gcatcctacc ggtacactgg agtccctgat   180
cgcttcactg gcagtggatc tgggacggat ttcactttca ccatcagcag tgtgcaggct   240
gaagacctgg cagtttatta ctgtcagcaa cattatagta gtccgtacac gttcggaggg   300
gggaccaagg tggaaataaa acg                                          323

<210> SEQ ID NO 329
<211> LENGTH: 357
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 329
gaggtccagc tgcagcagtc tggacctgag ctggtaaagc ctggggcttc agtgaagatg      60
tcctgcaagg cttctggata cacattcact aactatgtta tgcactgggt gaagcagaag     120
cctgggcagg gccttgagtg gattggatat attaatcctt acaatgatgg tactaaatac     180
aatgagaagt tcaaaggcaa ggccacactg acttcagaca atcctccac cacagcctac      240 atggcgctca gcagcctgac ctctgaggac tctgcggtct attactgtgc agtagcctac     300
tatagtaact gggggtttgc ttactggggc caagggactc tggtcactgt ctctgca        357

<210> SEQ ID NO 330
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 330
gacatccaga tgactcagtc tccagcctcc ctatctgcat ctgtgggaga aactgtcacc      60
atcacatgtc gagcaagtga gaatatttac agttatttag catggtatca gcagaaacag     120
ggaaaatctc ctcagctcct ggtctataat gcaaaaacct tagcagaagg tgtgccatca     180
aggttcagtg gcagtagatc aggctcacag ttttctctga agatcaacag cctgcagcct     240
gaagattttg ggagttatta ctgtcaacat cattatggta ctccgtacac gttcggaggg     300
gggaccaagc tggaaataaa acg                                             323

<210> SEQ ID NO 331
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 331
caggttcagc tggaggagtc aggggctgag ctggcaagac ctggggcttc agtgaagttg      60
tcctgcaagg cttctggcta tagctactgg atgcagtgga taaaacagag gcctggacag     120
ggtctggaat ggattggggc tatttatcct ggaaatggtg atactaggta cactcagaag     180
ttcaagggca aggccacatt gactgcagat aaatcctcca gcacagccta catgcaactc     240
agcagcttgg catctgagga ctctgcggtc tattactgtg caagatctcc ggcctactat     300
aggtacggcg agggctactt tgactactgg ggccaaggca ccactctcac agtctcctca     360

<210> SEQ ID NO 332
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 332
```

```
caaattgttc tcacccagtc tccagcaatc atgtctgcat ctccagggga gaaggtcacc    60
atgacctgca gtgccagctc aagtgtaagt tacatgtact ggtaccagca gaagccagga   120
tcctccccca gactcctgat ttatgacaca tccaacctgg cttctggagt ccctgttcgc   180
ttcagtggca gtgggtctgg gacctctttc tctctcacaa tcagccgaat ggaggctgaa   240
gatactgcca cttattactg ccaggagtgg agtggtaatc cgctcacgtt cggtgatggg   300
accaagctgg agctgaaac                                                319
```

```
<210> SEQ ID NO 333
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 333
cagatccagt tggtgcagtc tggacctgag ctgaagaagc ctggagagac agtcaagatc    60
tcctgcaagg cttctgggta taccttcaca aactatggaa tgaactgggt gaagcaggct   120
ccaggaaagg gtttaaagtg gatgggctgg ataaacacct acactggaga gccagcatat   180
gctgatgact tcaagggacg gtttgccttc tctttggaaa cctctgccag cgctgcctat   240
ttgcagatca caacctcaa aaatgaggac acggctactt ttttctgtgc aaatatgagg   300
cccacgaggg ggtttgctta ctgggggcaa gggactctgg cactgtctc tgca          354
```

```
<210> SEQ ID NO 334
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 334
aatattgtga tgacccagac tcccaaattc ctgcttgtat cagcaggaga cagggttacc    60
ataacctgca aggccagtca gagtgtgagt aatgatgtag cttggtacca acagaagcca   120
gggcagtctc ctaaactgct gatatactat gcatccaatc gctacactgg agtccctgat   180
cgcttcactg gcagtggata tgggacggat ttcactttca ccatcagcac tgtgcaggct   240
gaagacctgg cagtttattt ctgtcagcag gattatagct ctcctccgac gttcggtgga   300
ggcaccaagc tggaaatcaa ac                                            322
```

```
<210> SEQ ID NO 335
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 335
gaggtccagc tgcagcagtc tggacctggg ctagtgagga ctggggcttc agtgaagata    60
tcctgcaagg cttctggtta ctcattcact ggttactaca tgcactgggt caagcagagc   120
catggaaaga gccttgagtg gattggatat attagttgtt acaatggtgc tactacctac   180
aaccagaact tcaagggcaa ggccacattt attgtagaca tcctccag cacagcctac   240
```
atgcagttca acagcctgac atctgaggac tctgcggtct attactgtgc aagatccgac    300 gggggggcatg ctatggacta ctggggtcaa ggaacctcag tcaccgtctc ctca         354

<210> SEQ ID NO 336
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 336
gacatccaga tgactcagtc tccagcctcc ctggctgcat ctgtgggaga aactgtcacc    60
atcacatgtc gagcaagtga gaacatttac tacagtttag catggtatca gcagaagcaa    120
gggaaatctc ctcagctcct gatctataat gcaaacagct tggaagatgg tgtcccatcg    180
aggttcagtg gcagtggatc tgggacacag tattctatga agatcaacag catgcagcct    240
gaagataccg caacttattt ctgtaagcag acttatgacg ttccgctcac gttcggtgct    300
gggaccaagc tggagctgaa ac                                             322

<210> SEQ ID NO 337
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 337
gaggttcagc tgcagcagtc tggacctgag ctggagaagc ctggcgcttc agtgaagata    60
tcctgcaagg cttctggtta ctcattcact ggctacaaca tgaactgggt gaagcagagc    120
aatggaaaga gccttgagtg gattggaaat attgatcctt attatggtgg ttctagctac    180
aaacagaagt tcgagggcaa ggccacattg actgtagaca atcctccag cacagcctac    240 atgcagctca agagcctgac atctgaggac tctgcagtct attactgtgc aagaggtggt    300
agtaacttct ttgactactg gggccaaggc accactctca cagtctcctc a             351

<210> SEQ ID NO 338
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 338
gatgttgtga tgacccagac tccactcact ttgtcggtta ccattggaca accagcctcc    60
atctcttgca gtcaagtca gagcctctta gatagtgatg gaacgacata tttgaattgg    120
ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acatttccg     300 ctcacgttcg gtgctgggac caagctggag ctgaaac                             337

<210> SEQ ID NO 339

```
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 339
gacgtgaagc tggtggagtc tgggggaggc ttagtgaagc ctggagggtc cctgaaactc      60
tcctgtgcag cctctggatt cactttcagt agctatacca tgtcttgggt tcgccagact     120
ccggagaaga ggctggagtg ggtcgcaacc attagtagtg gtggtagtta cccctactat     180
ccagacagtg tgaagggccg attcaccatc tccagagaca atgccaagaa caccctgtac     240
ctgcaaatga gcagtctgaa gtctgaggac acagccatgt attactgtac aagagatgtc     300
tatgatggtt actcctactg gggccaaggc accactctca cagtctcctc a              351

<210> SEQ ID NO 340
<211> LENGTH: 320
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 340
caaattgttc tctcccagtc tccagcaatc ctgtctgcat ctccagggga aaggtcaca       60 atgacttgca gggccagctc aagtgtaagt tacatgcact ggtaccagca gaagccagga    120
tcctccccca aaccctggat ttatgccaca tccaacctgg cttctggagt ccctgctcgc    180
ttcagtggca gtgggtctgg gacctcttac tctctcacaa tcagcagagt ggaggctgaa    240
gatgctgcca cttattactg ccagcagtgg agtagtaacc catacacgtt cggagggggg    300
accaagctgg aaataaaacg                                                320

<210> SEQ ID NO 341
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 341
gaggttcagc tgcagcagtc tggggcagaa cttgtgaagc caggggcctc agtcaaattg      60
tcctgcacag cttctggctt caacattaaa gacacctata tacactgggt gaaacagagg    120
cctgaacagg gcctggagtg gattggaagg attgatcctg cgaatggtaa tactaaatat    180
gacccgaagt tccagggcaa ggccactata acaccagaca catcctccaa cacagcctac    240
ctgcagctca gcagcctgac atctgaggac actgccgtct attactgtgc tagaagctgg    300
cgaaactacg gtagtagttt ctggtacttc gatgtctggg gcgcagggac cacggtcacc    360
gtctcctca                                                            369

<210> SEQ ID NO 342
<211> LENGTH: 337
<212> TYPE: DNA
<213> ORGANISM: Artificial Sequence
<220> FEATURE:
<221> NAME/KEY: source
```

<223> OTHER INFORMATION: /note="Description of Artificial Sequence:
Synthetic polynucleotide"

<400> SEQUENCE: 342

```
gatgttgtga tgacccagac tccactcact ttgtcggtta ccattggaca accagcctcc      60
atctcttgca agtcaagtca gagcctctta gatagtgatg aacgacata tttgaattgg     120
ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttccg    300
ctcacgttcg gtgctgggac caagctggag ctgaaac                              337
```

<210> SEQ ID NO 343
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 343

```
gacgtgaagc tggtggagtc tgggggaggc ttagtgaagc ctggagggtc cctgaaactc     60
tcctgtgcag cctctggatt cactttcagt agctatacca tgtcttgggt tcgccagact    120
ccggagaaga ggctggagtg ggtcgcaacc attagtagtg gtggtagtta cccctactat    180
ccagacagtg tgaagggccg attcaccatc tccagagaca atgccaagaa caccctgtac    240
ctgcaaatga gcagtctgaa gtctgaggac acagccatgt attactgtac aagagatgtc    300
tatgatggtt actcctactg gggccaaggc accactctca cagtctcctc a              351
```

<210> SEQ ID NO 344
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 344

```
gacattgtga tgacacagtc tccatcctcc ctgactgtga cagcaggaga gaaggtcact     60
atgagctgca cgtccagtca gagtctgtta accagtggaa atcaaaagaa ctacttgacc    120
tggtaccagc agaaaccagg gcagcctcct aaactgttga tctactgggc atccactagg    180
gaatctgggg tccctgatcg cttcacaggc agtggatctg gaacagattt cactctcacc    240
atcagcagtt tgcaggctga agacctggca gtttattact gtcagaatga ttatagtctc    300
acgttcggtg ctgggaccaa gctggagctg aaac                                 334
```

<210> SEQ ID NO 345
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 345

```
caggtgcagc tgaagcagtc aggacctggc cgagtgcagc cctcacagag cctgtccatc      60
```

```
acctgcacag tctctggttt ttcattaact agcaatggtg tacactgggt tcgccagtct    120
ccaggaaagg gtctggagtg gctgggagtg ctatggagtg gtggaagcac agactataat    180
gcagctttca tatccagact gagcatcagc aaggacaatt acaagagcca agttttcttt    240
aaaatgaaca gtctgcaagc taatgacaca gccatatatt actgtgccag aaataataat    300
aggtacggag ctatggacta ctggggtcaa ggaacctcag tcaccgtctc ctca           354

<210> SEQ ID NO 346
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 346
gacatccaga tgaaccagtc tccatccagt ctgtctgcat cccttggaga cacaattacc    60
atcacttgcc atgtcagtca gaacattaat gtttggttaa gctggtacca gcagaaacca    120
ggaaatattc ctaaactatt gatccaaaag gcttccaact tgcacacagg cgtcccctca    180
aggtttagtg gcagtggatc tggaacaggt ttcacattaa ccatcagcag cctgcagcct    240
gaagacattg ccacttacta ctgtcaacag ggtcaaagtt atccattcac gttcggctcg    300
gggacaaagt tggaaataaa ac                                              322

<210> SEQ ID NO 347
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 347
caggtgcagc tgaaggagtc aggacctggc ctggtggcgc cctcacagag cctgtccatc    60
acttgcactg tctctgggtt ttcattaacc aactatggtg tacactgggt tcgccagcct    120
ccaggaaagg gtctggagtg gctgggagta atatgggctg gtggaatcac aaattataat    180
tcggctctca tgtccagact gagcatcagc gaagacaact ccaagagcca agttttctta    240
aaaatgaaca gtctgcaaac tgatgacaca gccatgtact actgtgccag aaatttaggt    300
ccctatgcta tggactactg gggtcaagga acctcagtca ccgtctcctc a              351

<210> SEQ ID NO 348
<211> LENGTH: 335
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 348
gacattgtgc tgacccaatc tccagcttct ttggctgtgt ctctagggca gagggccacc    60
atctcctgca aggccagcca agtgttgat tatgatggtg atagttattt gacctggtac    120
caacagaaac caggacagcc acccaaactc ctcatctatg ctgcatccaa tctagaatct    180
gggatcccag ccaggtttag tggcagtggg tctgggacag acttcaccct caacatccat    240
cctgtggagg aggaggacgc tgcaacctat tactgtcagc aaagtaatga ggatccgtac    300
```

```
acgttcggag gggggaccaa gctggaaata aaacg                          335
```

<210> SEQ ID NO 349
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 349

```
gaggtccagc tgcagcagtc tggacctgac ctggtgaagc ctggggcttc agtgaagata    60
tcctgcaagg cttctggtta ctcattcact ggctactaca tgcactgggt gaagcagagc   120
catggaaaga gccttgagtg gattggacgt gttaatccta acaatggtgg tactagctac   180
aaccagaagt tcaagggcaa ggccatatta actgcagaca agtcatccag cacagcctac   240
atggagctcc gcagcctgac atctgaggac tctgcggtct attactgtgc aagagggagt   300
tatgattacg ccgagggctg gggccaaggg actctggtca ctgtctctgc a            351
```

<210> SEQ ID NO 350
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 350

```
gacattgtga tgtcacagtc tccatcctcc ctagctgtgt cagttggaga gaaggttact    60
atgagctgca gtccagtca gagccttta tatagtagca ctcaaaagaa ctacttggcc    120
tggtaccagc agaaaccagg gcagtctcct aaactgctga tttactgggc atccactagg   180
gaatctgggg tccctgatcg cttcacaggc agtggatctg gacagatttt cactctcacc   240
atcagcagtg tgaaggctga agacctggca gtttattact gtcagcaata ttatagctat   300
ccgtacacgt tcggagggg gaccaagctg gaaataaaac g                        341
```

<210> SEQ ID NO 351
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 351

```
gagatccagc tgcagcagtc tggacctgag ctggtgaagc ctggggcttc agtgaaggta    60
tcctgcaagg cttctggtta tgcattcact agctacaaca tgtactgggt gatgcagagc   120
catggaaaga gccttgagtg gattggatat gttgatcctt acaatggtgg tactagctac   180
aaccagaagt tcaagggcaa ggccacattg actgttgaca gtcctccag cacagcctac    240 atgcatctca acagcctgac atctgaggac tctgcagtct attactgtgc aagagaaaac   300
tataggtact ttgactactg gggccaaggc accactctca cagtctcctc a            351
```

<210> SEQ ID NO 352
<211> LENGTH: 316
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 352

| | |
|---|---|
| caaattgttc tcacccagtc tccagcaatc atgtctgcat ctccagggga gaaggtcacc | 60 |
| ataacctgca gtgccagctc aagtgtaagt tacatgcact ggttccagca gaagccaggc | 120 |
| acttctccca aactctggat ttatagcaca tccaacctgg cttctggagt ccctgctcgc | 180 |
| ttcagtggca gtggatctgg gacctcttac tctctcacaa tcagccgaat ggaggctgaa | 240 |
| gatgctgcca cttattactg ccagcaaagg agtagttacc cacccacgtt cggagggggg | 300 |
| accaagctgg aaataa | 316 |

<210> SEQ ID NO 353
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 353

| | |
|---|---|
| gaggtgcagc ttgttgagtc tggtggagga ttggtgcagc ctaaagggtc attgaaactc | 60 |
| tcatgtgcag cctctggatt caccttcaat acctacgcca tgaactgggt ccgccaggct | 120 |
| ccaggaaagg gtttggaatg ggttgctcgc ataagaatta aaagtaataa ttatgcaaca | 180 |
| tattatgccg attcagtaaa agacaggttc accatctcca gagatgattc acaaaacatg | 240 |
| ctctatctgc aaatgaacaa cttgaaaact gaggacacag ccgtgtatta ctgtgtgaga | 300 |
| caaggctata gttacgactg ggggaccctgg tttgcttact ggggccaagg gactctggtc | 360 |
| actgtctctg ca | 372 |

<210> SEQ ID NO 354
<211> LENGTH: 320
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 354

| | |
|---|---|
| caaattgttc tcacccagtc tccagcaatc atgtctgcat ctccagggga gaaggtcacc | 60 |
| ataacctgca gtgccagctc aagtgtaagt tacatgcact ggttccagca gaagccaggc | 120 |
| acttctccca aactctggat ttatagcaca tccaacctgg cttctggagt ccctgctcgc | 180 |
| ttcagtggca gtggatctgg gacctcttac tctctcacaa tcagccgaat ggaggctgaa | 240 |
| gatgctgcca cttattactg ccagcaaagg agtagttacc cacccacgtt cggagggggg | 300 |
| accaagctgg aaataaaacg | 320 |

<210> SEQ ID NO 355
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 355

| | | | | | |
|---|---|---|---|---|---|
| gaagtgcagc | tggtggagtc | tgggggaggc | ttagtgaagc | ctggagggtc | cctgaaactc | 60 |
| tcctgtgcag | cctctggatt | cactttcagt | gactattaca | tgttttgggt | tcgccagact | 120 |
| ccggaaaaga | ggctggagtg | ggtcgcaacc | attagtgatg | gtggtagtta | cacctacttt | 180 |
| ccagacagtg | tgaaggggcg | attcaccatc | tccagagaca | atgcccagaa | caacctgtac | 240 |
| ctgcaaatga | gcagtctgaa | gtctgaggac | acagccatgt | attactgtgc | aagagccggg | 300 |
| accctctatg | ctatggacta | ctggggtcaa | ggaacctcag | tcaccgtctc | ctca | 354 |

<210> SEQ ID NO 356
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 356

| | | | | | |
|---|---|---|---|---|---|
| caaattgttc | tcacccagtc | tccagcaatc | atgtctgcat | ctctagggga | acgggtcacc | 60 |
| atgacctgca | ctgccagctc | aagtgtaagt | tccagttact | tgcactggta | ccagcagaag | 120 |
| ccaggatcct | cccccaaact | ctggatttat | agcacatcca | acctggcttc | tggagtccca | 180 |
| gctcgcttca | gtggcagtgg | gtctgggacc | tcttactctc | tcacaatcag | cagcatggag | 240 |
| actgaagatg | ctgccactta | ttactgccac | cagtatcatc | gttccccctt | cacgttcggc | 300 |
| tcggggacaa | agttggaaat | aaaac | | | | 325 |

<210> SEQ ID NO 357
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 357

| | | | | | |
|---|---|---|---|---|---|
| caggttgctc | tgaaagagtc | tggccctggg | atattgcagc | cctcccagac | cctcagtctg | 60 |
| acttgttctt | tctctgggtt | ttcactgagc | acttctggta | tgggtgtagg | ctggattcgt | 120 |
| cagccatcag | ggaagggtct | ggagtggctg | gcacacattt | ggtgggatga | tgtcaagcgc | 180 |
| tataacccag | ccctgaagag | ccgactgact | atctccaagg | ataccTccag | cagccaggta | 240 |
| ttcctcaaga | tcgccagtgt | ggacactgca | gatactgcca | catactactg | tgctcgaatg | 300 |
| gaggactacg | gtagtagctc | ctactttgac | ttctggggcc | acggcaccac | tctcacagtc | 360 |
| tcctca | | | | | | 366 |

<210> SEQ ID NO 358
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 358

| | | | | | |
|---|---|---|---|---|---|
| gacattcaga | tgacccagtc | tcctgcctcc | cagtctgcat | ctctgggaga | aagtgtcacc | 60 |

```
atcacatgcc tggcaagtca gaccattggt acatggttag catggtatca gcagaaacca    120
gggaaatctc ctcagctcct gattctgct gcaaccagct tggcagatgg ggtcccatca     180
aggttcagtg gtagtggatc tggcacaaaa ttttctttca agatcagcag cctacaggct    240
gaagattttg taagttatta ctgtcaacaa ctttacagta ctccgtggac gttcggtgga    300
ggcaccaagc tggaaatcaa ac                                             322
```

<210> SEQ ID NO 359
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 359

```
gaggtccagc tgcagcagtc tggacctgag ctggtaaagc ctggggcttc agtgaagatg     60
tcctgcaagg cttctggata cacattcact agctatgtta tgcactgggt gaagcagaag    120
cctgggcagg gccttgagtg gattggatat attaatcctt acaatgatgg tactaagtac    180
aatgagaagt tcaaaggcaa ggccacactg acttcagaca atcctccag cacagcctac     240 atggagctca gcagcctgac ctctgaggac tctgcggtct attactgtgc aagaggggct    300
ctctactatg gtaactacct cgggtacttc gatgtctggg gcgcagggac cacggtcacc    360
gtctcctca                                                            369
```

<210> SEQ ID NO 360
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 360

```
gacatccaga tgaaccagtc tccatccagt ctgtctgcat cccttggaga cacaattacc     60
atcacttgcc atgccagtca gaacattaat gtttggttaa gctggtacca gcagaaacca    120
ggaaatattc ctaaactatt gatctataag gcttccatct tacacacagg cgtcccatca    180
aggtttagtg gcagtggatc tggaacaggt ttcacattaa ccatcagcag cctgcagcct    240
gaagacattg ccacttactc ctgtcaacag ggtcaaagtt atccgtacac gttcggaggg    300
gggaccaagc tggaaataaa a                                              321
```

<210> SEQ ID NO 361
<211> LENGTH: 355
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 361

```
tctgatgtgc agcttcagga gtcaggacct gacctggtga aaccttctca gtcactttca     60
ctcacctgca ctgtcactgg ctactccatc accagtggtt atagctggca ctggatccgg    120
cagtttccag gaaacaaact ggaatggatg ggctacatac actacagtgg tagcactaac    180
tacaacccat ctctcaaaag tcgaatctct atcactcgag acacatccaa gaaccagttc    240
```

```
ttcctgcagt tcaaatctgt gactactgaa gactcagcca catattactg tgccctagag    300
gggaattacg acgggtttgc ttactggggc caagggactc tggtcactgt ctctg         355
```

<210> SEQ ID NO 362
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 362

```
gacatccaga tgaaccagtc tccatccagt ctgtctgcat cccttggaga cacaattacc    60
atcacttgcc atgccagtca gaacataaat gtttggttaa gctggtacca gcagaaacca   120
ggaaatattc ctaaactatt gatctataag gcttccaact tgcacacagg cgtcccatca   180
aggtttagtg gcagtggatc tggaacaggt ttcacattaa ccatcagcag cctgcagcct   240
gaagacattg ccacttacta ctgtcaacag ggtcaaagtt atccattcac gttcggctcg   300
gggacaaagt tggaaataaa ac                                            322
```

<210> SEQ ID NO 363
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 363

```
caggtgcaga tgaaggagtc aggacctggc ctggtggcgc cctcacagag cctgtccatc    60
acttgcactg tctctgggtc ttcattaacc aactatggtg tacactgggt tcgccagcct   120
ccaggaaagg gtctagagtg gctgggagta atatgggctg tggaagcac aaattataat    180 tcggctctca tgtccagact gagtatcagc aaagacaact ccaagagcca agttttctta   240
aaaatgaaca gtctgcaaac tgatgacaca gccatgtact actgtgccag agactgggag   300
ggctggtttg cttactgggg ccaagggact ctggtcactg tctctgca                348
```

<210> SEQ ID NO 364
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 364

```
gacattcaga tgacccagtc tcctgcctcc cagtctgcat ctctgggaga aagtgtcacc    60
atcacatgcc tggcaagtca gaccattggt acatggttag catggtatca gcagaaacca   120
gggaaatctc ctcagctcct gatttatgct gcaaccagct ggcagatgg ggtcccatca    180 aggttcagtg gtagtggatc tggcacaaaa ttttctttca agatcagcag cctacaggct   240
gaagattttg taagttatta ctgtcaacaa ctttacagta ctccgtacac gttcggaggg   300
gggaccaagc tggaaataaa acg                                           323
```

<210> SEQ ID NO 365

```
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 365
caggtgcagc taaaggagtc aggacctggc ctggtggcgc cctcacagag cctgtccatc    60
acatgcactg tctcagggtt ctcattaacc gactatggtg taagctggat tcgccagcct   120
ccaggaaagg gtctggagtg gctgggagta atatggggtg gtggaagcac atactataat   180
tcagctctca aatccagact gagcatcagc aaggacaact ccaagagcca gttttctta    240 gaactgaaca gtctgcaaac tgatgacaca gccatttact actgtgccaa acattatggt   300
cactacgctg cttactgggg ccaagggact ctggtcactg tctctgca                348

<210> SEQ ID NO 366
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 366
gacatccagt tgactcagtc tccagcctcc ctatctgcat ctgtgggaga aactgtcacc    60
atcacatgtc gagcaagtgg gagtattcac aattatttag catggtatca gcagaaacag   120
ggaaagtctc ctcagctcct ggtctataat gcaaaaacct tagtagatgg tgtgccatca   180
aggttcagtg gcagtggatc aggaacacaa tattctctca agatcaacag cctgcagcct   240
gaagattttg ggtattatta ctgtcaacat ttttggacta ctccgtggac attcggtgga   300
ggcaccaagc tggaaatcaa ac                                            322

<210> SEQ ID NO 367
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 367
gaggtccagc tgcagcagtc tggacctgag ctggtaaagc ctggggcttc agtgaagatg    60
tcctgcaagg cttctggata cacattcact agctatgtta tgcactgggt gaagcagaag   120
cctgggcagg gccttgagtg gattggatat attaatcctt acaatgatgg tactgagtac   180
aatgagaagt tcaaaggcaa ggccacactg acttcagaca atcctccag cacagcctac    240 atggagctca gcagcctgac ctctgaggac tctgcggtct attactgtgc aagagggtc    300 tatgatggtt actcttactt tgactactgg ggccaaggca ccactctcac agtctcctca   360

<210> SEQ ID NO 368
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 368

```
gacatccaga tgaaccagtc tccatccagt ctgtctgcat cccttggaga cacaattacc    60
atcacttgcc atgtcagtca gaacattaat gtttggttaa gctggtacca gcagaaacca   120
ggaaatattc ctaaactatt gatccaaaag gcttccaact tgcacacagg cgtcccctca   180
aggtttagtg gcagtggatc tggaacaggt ttcacattaa ccatcagcag cctgcagcct   240
gaagacattg ccacttacta ctgtcaacag ggtcaaagtt atccattcac gttcggctcg   300
gggacaaagt tggaaataaa ac                                            322
```

<210> SEQ ID NO 369
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 369

```
caggtgcagc tgaaggagtc aggacctggc ctggtggcgc cctcacagag cctgtccatc    60
acttgcactg tctctgggtt ttcattaacc aactatggtg tacactgggt tcgccagcct   120
ccaggaaagg gtctggagtg gctgggagta atatgggctg gtggaatcac aaattataat   180
tcggctctca tgtccagact gagcatcagc gaagacaact ccaagagcca gttttcttta   240
aaaatgaaca gtctgcaaac tgatgacaca gccatgtact actgtgccag aaatttaggt   300
ccctatgcta tggactactg gggtcaagga acctcagtca ccgtctcctc a            351
```

<210> SEQ ID NO 370
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 370

```
gacattcaga tgacccagtc tcctgcctcc cagtctgcat ctctgggaga aagtgtcacc    60
atcacatgcc tggcaagtca gaccattggt acatggttag catggtatca gcagaaacca   120
gggaaatctc ctcagctcct gatttatgct gcaaccagct ggcagatggg gtcccatca    180 aggttcagtg gtagtggatc tggcacaaaa ttttctttca agatcagcag cctacaggct   240
gaagattttg taagttatta ctgtcaacaa ctttacagta ctccgtggac gttcggtgga   300
ggcaccaagc tggagatcaa ac                                            322
```

<210> SEQ ID NO 371
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 371

```
caggtgcagc tgaaggagtc aggacctggc ctggtggcgc cctcacagag cctgtccatc    60
acatgcactg tctcagggtt ctcattaacc gactatggtg taagctggat tcgccagcct   120
```

```
ccaggaaagg gtctggagtg gctgggagta gtatggggtg gtggaagcac atactataat    180
tccgctctca aatccagact gagcatcacc aaggacaact ccaagagcca agttttctta    240
aaaatgaaca gtctgcaaac tgatgacaca gccatgtact actgtgccaa acagagggt     300 cagtacgggg cttactgggg ccaagggact ctggtcactg tctctgca                 348
```

<210> SEQ ID NO 372
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 372

```
agtattgtga tgacccagac tcccaaattc ctgcttgttt cagcaggaga cagggttacc     60
ataacctgca aggccagtca gagtgtgagt aatgatgtag cttggtacca acagaagcca    120
gggcagtctc ctaaactgct gatatactgt gcatccaatc gctacactgg agtccctgat    180
cgcttcactg gcagtggata tgggacggat ttcactttca ccatcagcac tgtgcaggct    240
gaagacctgg cagtttattt ctgtcagcag gattatagct ctccgctcac gttcggtgct    300
gggaccaagc tggagctgaa ac                                             322
```

<210> SEQ ID NO 373
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 373

```
caggtgcagc tgaaggagtc aggacctggc ctggtggcgc cctcacagag cctgtccatc     60
acctgcacag tctctggttt ctcattaacc aactatgctg tacactgggt tcgccagtct    120
ccaggaaagg gtctggagtg gctgggagtg atatggagtg atggaagcac agactataat    180
gcagctttca tatctagact gagcatcagc aaggacaact ccaagagcca agttttcttt    240
aagatgaaca gtctgcaagc tgatgacaca gccatgtact actgtgcccg aaagaaagga    300
ggatggtttc cctggtttgc ttactggggc caagggactc tggtcactgt ctctgca       357
```

<210> SEQ ID NO 374
<211> LENGTH: 335
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 374

```
gacattgtgc tgacccaatc tccagcttct ttggctgtgt ctctagggca gagggccacc     60
atctcctgca aggccagcca aagtgttgat catgctggtg atagttatat gaactggtac    120
caacagaaac caggacagcc acccaaactc ctcatctatg ctgcatccaa tctagaatct    180
gggatcccag ccaggtttag tggcagtggg tctgggacag acttcaccct caacatccat    240
cctgtggagg aggaggatgc tgcaacctat tactgtcagc aaagtaatga ggatccgtac    300
acgttcggag gggggaccaa gctggaaatc aaacg                               335
```

<210> SEQ ID NO 375
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 375

```
gaggtccagc tgcagcagtc tggacctgac ctggtgaagc ctggggcttc agtgaagata      60
tcctgcaagg cttctggtta ctcattcact ggctactaca tgcactgggt gaagcagagc     120
catggaaaga ggcttgagtg gattggacgt gttaatccta acaatggtgg tactaactac     180
aaccagaaat tcaagggcaa ggccatatta actgtagaca agtcatccag cacagcctac     240
atggagctcc gcagcctgac atctgaggac tctgcggtct attactgtgc aagagggagt     300
tatgataacg ccgagggctg gggccaaggg actctggtca ctgtctctgc a              351
```

<210> SEQ ID NO 376
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 376

```
gacatcaaga tgacccagtc tccatcttcc atgtatgcat ctctaggaga gagagtcact      60
atcacttgca aggcgagtca ggacattaat aggtatttaa gctggttcca gcagaaacca     120
gggaaatctc ctaagaccct gatctatcgt gcaaacagat tggtagatgg ggtcccatca     180
aggttcagtg gcagtggatc tgggcaagat tattctctca ccatcagcag cctggagtat     240
gaagatatgg gaatttatta ttgtctacag tatgatgagt ttccattcac gttcggctcg     300
gggacaaagt tggaaataaa ac                                              322
```

<210> SEQ ID NO 377
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 377

```
caggtccagt tgcagcagtc tggagctgag ctggtaaggc ctggggcttc agtgaaggtg      60
tcctgcaagg cttctggata cgccttcact aattacttga tagagtgggt aaagcagagg     120
cctggacagg gccttgagtg gattggggtg attaatcctg aagtggtgg tactaactcc     180
aatgagaagt tcaaggccaa ggcaacactg actgcagaca atcctccag cactgcctac     240
atgcagctca gcagcctgac atctgctgac tctgcggtct atttctgtgc aagatcggac     300
tatgattacg ccttctatgc tatggactac tggggtcaag gaacctcagt caccgtctcc     360
tca                                                                   363
```

<210> SEQ ID NO 378
<211> LENGTH: 322
<212> TYPE: DNA

-continued

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 378
gacatccaga tgactcagtc tccagcctcc ctatctgcat ctgtgggaga aactgtcacc    60
atcacatgtc gagcaagtgg gaatattcac aattatttag catggtatca gcagaaacag   120
ggaaaatctc ctcacctcct ggtctataat gcaaaaacct tagcagatgg tgtgccatca   180
aggttcagtg gcagtggatc aggaacacaa tattctctca agatcaacag cctgcagcct   240
gaagattttg ggagttatta ctgtcaacat ttttggagta ctccgtggac gttcggtgga   300
ggcaccaagc tggaaatcaa ac                                            322

<210> SEQ ID NO 379
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 379
gagttccagc tgcagcagtc tggacctgag ctggtaaagc ctggggcttc agtgaagatg    60
tcctgcaagg cttctggata cacattcact agctatgtta tgcactgggt gaagcagaag   120
cctgggcagg gccttgagtg gattggatat attaatcctt acaatgatgg tactaagtac   180
aatgagaagt tcaaaggcaa ggccacactg acttcagaca atcctccag cacagcctac   240 atggagctca gcagcctgac ctctgaggac tctgcggtct attactgtgc aagagacagg   300
tcgggctacg aagattacta tggtatggac tactggggtc aaggaacctc agtcaccgtc   360
tcctca                                                              366

<210> SEQ ID NO 380
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 380
caaattgttc tcacccagtc tccagcaatc atgtctgcat ctctagggga ggagatcacc    60
ctaacctgca gtgccagctc gagtgtaagt tacatgcact ggtaccagca gaagtcaggc   120
acttctccca aactcttgat ttatagcaca tccaacctgg cttctggagt cccttctcgc   180
ttcagtggca gtgggtctgg gacctttat tctctcacaa tcagcagtgt ggaggctgaa   240
gatgctgccg attattactg ccatcagtgg agtagttatc cacgttcgg agggggggacc   300 aagctggaaa taaaacgg                                                 318

<210> SEQ ID NO 381
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 381
gaggtgcagc tggtggagtc tgggggagac ttagtgaagc ctggagggtc cctgaaactc     60
tcctgtgcag cctctggatt cactttcagt agctatggca tgtcttgggt tcgccagact    120
ccagacaaga ggctggagtg ggtcgcaacc attagtagtg gtggtagtta cacctactat    180
ccagacagtg tgaaggggcg attcaccatc tccagagaca atgccaagaa caccctgtac    240
ctgcaaatga gcagtctgaa gtctgaggac acagccatgt attactgtgc aagacgaaga    300
gccgatgcta tggactactg gggtcaagga acctcagtca ccgtctcctc a            351

<210> SEQ ID NO 382
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 382
gacattcaga tgacccagtc tcctgcctcc cagtctgcat ctctgggaga aagtgtcacc     60
atcacatgcc tggcaagtca gaccattggt acatggttag catggtatca gcagaaacca    120
gggaaatctc ctcagctcct gatttattct gcaaccagct ggcagatgg ggtcccatca    180 aggttcagtg gtagtggatc tggcacaaaa ttttcttca agatcagcag cctacaggct    240
gaagattttg taagttatta ctgtcaacaa ctttacagta ctccgtggac gttcggtgga    300
ggcaccaagc tggaaatcaa ac                                             322

<210> SEQ ID NO 383
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 383
caggtgcagc tgaaggagtc aggacctggc ctggtggcgc cctcacagag cctgtccatc     60
acatgcactg tctcagggtt ctcattaacc gactatggta taagctggat tcgccagcct    120
ccaggaaagg gtctggagtg gctgggagta gtatgggtg gtggaagcac atactataat    180
tccgctctca aatccagact gagcatcagc aaggacaact ccaagagcca gttttctta    240 aaaatgaaca gtctgcaaac tgatgacaca gccatgtact actgtgccaa acagagggt    300 cagtacgggg cttactgggg ccaagggact ctggtcactg tctctgca                348

<210> SEQ ID NO 384
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 384
gacattgtga tgacccagtc tcacaaattc atgtccacat cagtaggaga cagggtcagc     60
atcacctgca aggccagtca ggatgtgaat actgctgtag gctggtatca acagaaacca    120

```
ggacaatctc ctaaactact gatttactcg gcatcctacc ggtacactgg agtccctgat    180
cgcttcactg gcagtggatc tgggacggat ttcactttca ccatcagcag tgtgcaggct    240
gaagacctgg cagtttatta ctgtcagcaa cattatagta gtccgtacac gttcggaggg    300
gggaccaagc tggaaattaa a                                              321
```

<210> SEQ ID NO 385  
<211> LENGTH: 357  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 385

```
gaggtccagc tgcagcagtc tggacctgag ctggtaaagc ctggggcttc agtgaagatg     60
tcctgcaagg cttctggata cacattcact aactatgtta tgcactgggt gaagcagaag    120
cctgggcagg gccttgagtg gattggatat attaatcctt acaatgatgg tactaaatac    180
aatgagaagt tcaaaggcaa ggccacactg acttcagaca atcctccac cacagcctac     240 atggcgctca gcagcctgac ctctgaggac tctgcggtct attactgtgc agtagcctac    300
tatagtaact gggggtttgc ttactggggc caagggactc tggtcactgt ctctgca       357
```

<210> SEQ ID NO 386  
<211> LENGTH: 335  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 386

```
gacattgtgc tgacacagtc tcttgcttcc ttagctgtat ctctggggca gagggccacc     60
atctcatgca gggccagcaa agtgtcagt acatctggct atagttatat gcactggtac    120
caacagaaac caggacagcc acccaaactc ctcatttatc ttgcatcctc ggaggggga    180 ccaagctgga ataaagcga acctagaatc tggggtccct gccaggttca gtggcagtgg    240
gtctgggaca gacttcaccc tcaacatcca tcctgtggaa gacgaagatg ctgcaaccta    300
ttactgtcag cacagtaggg agcttccgtt cacgt                               335
```

<210> SEQ ID NO 387  
<211> LENGTH: 348  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 387

```
caggtccaac tgcagcagtc tgggcctgag ctggtgaggc ctggggcttc agtgaagatg     60
tcctgcaagg cttcaggcta taccttcacc agctactgga tgcactgggt gaaacagagg    120
cctggacaag gccttgagtg gattggcatg attgatcctt ccaatagtga aactaggtta    180
aatcagaagt tcaaggacaa ggccacattg aatgtagaca atcctccaa cacagcctac    240 atgcagctca gcagcctgac atctgaggac tctgcagtct attactgtgc agtaatggac    300
tactactttg actactgggg ccaaggcacc actctcacag tctcctca                 348
```

<210> SEQ ID NO 388
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 388

```
gacatcaaga tgacccagtc tccatcttcc atgtatgcat ctctaggaga gagagtcact    60
atcacttgca aggcgagtca ggacattaat agctatttaa gctggttcca gcagaaacca   120
gggaaatctc ctaagaccct gatctatcgt gcaaacagat tggtagatgg ggtcccatca   180
aggttcagtg gcagtggatc tgggcaagat tattctctca ccatcagcag cctggagtat   240
gaagatatgg gaatttatta ttgtctacag tatgatgagt ttccattcac gttcggctcg   300
gggacaaagt tggaaataaa ac                                            322
```

<210> SEQ ID NO 389
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 389

```
caggtgcaac tgaagcagtc aggacctggc ctggtggcgc cctcacagag cctgttcatc    60
acatgcaccg tctcagggtt ctcattaacc agctatgaaa taaactgggt tcgccagcct   120
ccaggaaagg gtctggagtg gctggagtg atatggactg gtggaagcac aaattataat    180
tcagctctca tatccagact gagcatcagc aagacaact ccaagagcct agttttctta   240
aaaatgaaca gtctgcaaac tgatgacaca gccatatatt actgtgtaag aggtgtttat   300
gctatggact actggggtca aggaacctca gtcaccgtct cctca                   345
```

<210> SEQ ID NO 390
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 390

```
gacatcaaga tgacccagtc tccatcttcc atgtatgcat ctctaggaga gagagtcact    60
atcacttgca aggcgagtca ggacattaat aattatttaa gctggttcca gcagaaacca   120
gggaaatctc ctaagaccct gatctatcgt gcaaacagat tggtagatgg ggtcccatca   180
aggttcagtg gcagtggatc tgggcaagat tattctctca ccatcagcag cctggagtat   240
gaagatatgg gaatttatta ttgtctacag tatgatgagt ttccgtacac gttcggaggg   300
gggaccaagc tggaaataaa acg                                           323
```

<210> SEQ ID NO 391
<211> LENGTH: 333
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 391
gaggtccagc ttcagcagtc aggacctgag ctggtgaaac ctggggcctc agtgaagata      60
tcctgcaagg cttctggata cacattcact gactacaaca tgcactgggt gaagcagagc     120
catggaaaga gccttgagtg gattggattc ttttatcctt acaacggtaa tactgtctac     180
agccagaagt tcaagagcaa ggccacattg actgtagaca attcctccag cacagcctac     240
atggagctcc gcagcctgac atctgaggac tctgcagtct attactgtgc aagacttaac     300
tgggagggct actggggcca aggcaccacc ctc                                   333

<210> SEQ ID NO 392
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 392
gatgttttga tgacccaaac tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
ctcacgttcg gtgctgggac caagctggag ctgaaac                              337

<210> SEQ ID NO 393
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 393
caggtccagc tgcagcagtc tggacctgag ctggtgaagc ctggggcttc agtgaggata      60
tcctgcaagg cttctggcta cacctcaca agctactata tacactgggt gaagcagagg     120
cctggacagg gacttgagtg gattggatgg atttatcctg gaaatggtaa tactaagtac     180
aatgagaagt tcaagggcaa ggccacactg actgcagaca atcctccag cacagcctac     240 atgcagatca gcagcctgac ctctgaggac tctgcggtct atttctgtgc aagagagaga     300
tggttactac tatggtttgc ttactggggc caagggactc tggtcactgt ctctgca        357

<210> SEQ ID NO 394
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 394
agtattgtga tgacccagac tcccaaattc ctgcttgtat cagcaggaga cagggttacc      60
```

```
ataacctgca aggccagtca gagtgtgagt aatgatgtag gttggtacca acagaagcca      120
gggcagtctc ctaaactgct gatatactat gcatccaatc gctacaatgg agtccctgat      180
cgcttcactg gcagtggata tgggacggat ttcactttca ccatcagcac tgtgcaggct      240
gaagacctgg cagtttattt ctgtcagcag gattatagct ctccgtggac gttcggtgga      300
ggcaccaagc tggaaatcaa ac                                               322
```

<210> SEQ ID NO 395
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 395

```
cagatccagt tggtgcagtc tggacctgag ctgaagaagc ctggagagac agtcaagatc       60
tcctgcaagg cttctgggta taccttcaca aactatggaa tgaactgggt gaagcaggct      120
ccaggaaagg gtttaaagtg ggtgggctgg ataaacacct acactggaga gccaacatat      180
gctgatgact caagggacg gtttgccttc tctttggaaa cctctgccag cactgcctat       240
ttgcagatcg acaacctcaa aaatgaggac acggctacat atttctgtgc aagagtgggg      300
gattacgtcg gctttgacta ctggggccaa ggcaccactc tcacagtctc ctca            354
```

<210> SEQ ID NO 396
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 396

```
gatatccaga tgacacagac tgcatcctcc ctgtctgcct ctctgggaga cagagtcacc       60
atcagttgca gggcaagtca ggacattaac aattatttaa actggtatca gcagaaacca      120
gatggaactg ttaaactcct gatctactac acatcaagat tacactcagg agtcccatca      180
aggttcagtg gcagtgggtc tggaacagat tattctctca ccattagcat cctggaacaa      240
gaagatattg ccacttactt ttgccaacag ggtgatacgc ttccgtggac gttcggtgga      300
ggcaccaagc tggaaatcaa ac                                               322
```

<210> SEQ ID NO 397
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 397

```
cagatccagt tggtgcagtc tggacctgag ctgacgaagc ctggagagac agtcaagatc       60
tcctgcaagg cctctggata taccttcaca gactattcat tgcactgggt gaagcaggct      120
ctaggaaagg gtttaaagtg gatgggctgg ataaacactg agactggtga gccagcatat      180
gcagatgact caagggacg gtttgccttc tctttggaaa cctctgccag cactgcctat       240
```

```
ttgcagatca acgacctcaa aaatgaggac acgactacat atttctgtgg tatttacgac    300
gggtatgcta tggactactg gggtcaagga acctcagtca ccgtctcctc a             351
```

<210> SEQ ID NO 398
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 398

```
caaattgttc tcacccagtc tccagcaatc atgtctgcat ctccagggga agggtcacc    60 atgacctgca gtgccagctc aagtgtaagt tacatgtact ggtaccagca gaagccagga   120
tcctccccca gactcctgat ttatgacaca tccaacctgg cttctggagt ccctgttcgc   180
ttcagtggca gtgggtctgg gacctcttac tctctcacaa tcagccgaat ggaggctgaa   240
gatactgcca cttattattg ccaggagtgg agtaataatc cgctcacgtt cggtgatggg   300
accaagctgg agctgaaac                                                319
```

<210> SEQ ID NO 399
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 399

```
cagatccagt tggtgcagtc tggacctgag ctgaagaagc ctggagagac agtcaagatc    60
tcctgcaagg cttctgggta taccctcaca aactatggaa tgaactgggt gaagcaggct   120
ccaggaaagg gtttaaagtg gatgggctgg ataaacacct acactggaga gccaacatat   180
gctgatgact tcaagggacg gtttgccttc tctttggaaa cctctgccag gattgtctat   240
ttgcagatca acaacctcaa aaatgaggac acggctacat atttctgtgc aaaatatgag   300
gcccacgagg ggtttgttta ttggggccaa gggactctgg tcactgtctc tgca          354
```

<210> SEQ ID NO 400
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 400

```
gacatccaga tgaaccagtc tccatccagt ctgtctgcat cccttggaga cacaattacc    60
atcacttgcc atgccagtca gaacattaat gtttggttaa ctggtacca gcagaaacca   120 ggaaatattc caaaactatt gatctataag gcttcccact tgcacacagg cgtcccatca   180
aggttgagtg gcagtggatc tggaacaggt ttcacattaa ccatcagcag cctgcagcct   240
gaagacattg ccacttacta ctgtcaacag ggtcaaagtt atccattcac gttcggctcg   300
gggacaacgt tggaaataaa ac                                            322
```

<210> SEQ ID NO 401
<211> LENGTH: 348

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 401
caggtgcagc tgaaggagtc aggacctggc ctggtggcgc cctcacagag cctgtccatc    60
acttgcgctg tctctggggtt ttcattaacc agctttggtg tacactgggt tcgccagcct  120
ccaggaaagg gtctggagtg gctgggagtt atatgggctg gtggaagcac aaattattat   180
tcggctctca gtccagact gagcatcagc atagacaact ccaagagcca agttttctta    240
aagatgaaca gtctgcaaac tgatgacaca gccatgtact actgtgccag agactgggag   300
ggctggtttg cttactgggg ccaagggact ctggtcactg tctctgca                348

<210> SEQ ID NO 402
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 402
gacattgtga tgtcacagtc tccatcctcc ctaactgtgt cagttggaga gaaggttact    60
atgagctgca gtccagtca gagccttta tatagtagca ctcaaaagaa ctacttggcc     120
tggtaccagc agaaaccagg gcagtctcct aaactgctga tttactgggc atccactagg   180
gaatctgggg tccctgatcg cttcacaggc agtggatctg ggacagattt cactctcacc   240
atcagcagtg tgaaggctga agacctggca gtttattact gtcagcaata ttatagctat   300
ccgtacacgt tcggagggggg gaccaagctg gaaataaaac g                      341

<210> SEQ ID NO 403
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 403
gagatccagc tgcagcagtc tggacctgag ctggtgaagc ctggggcttc agtgaaggta    60
tcctgcaagg cttctggtta tgcattcact agctacaaca tgtactgggt gagtcagagc   120
catggaaaga gccttgagtg gattggatat attgatcctt acaatggtgg cactagctac   180
aaccagaagt tcaggggcaa ggccacattg actgttgaca gtcctcaag cacagcctac    240 atgcatctca acagcctgac atctgaggac tcggcagtct attattgtgc aagagagaac   300
tataggtact ttgacttctg ggggccaaggc accactctca cagtctcctc a            351

<210> SEQ ID NO 404
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 404

```
gacatccaga tgacccagtc tccatcctcc ctgtctgcat ctgtaggaga cagagtcacc    60
atcacttgca gtgcaagtag cagcgttagc tatatgtatt ggtatcagca gaaaccaggg   120
aaagccccta agctcctgat ctacctcact agtaacttgg caagtggggt cccatcaagg   180
ttcagtggca gtggatctgg gacagatttc actctcacca tcagcagtct gcaacctgaa   240
gattttgcaa cttactactg tcaacagtgg cgtagtaacc cattcacgtt cggccagggg   300
acaaagttgg aaataaaac                                                319
```

<210> SEQ ID NO 405
<211> LENGTH: 373
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 405

```
cagatcacct tgaaggagtc tggtcctacg ctggtgaaac ccacacagac cctcacgctg    60
acctgcacct tctctgggtt ctcactcagc actagtggaa tgggtgtggg ctggatccgt   120
cagcccccag gaaaggccct ggagtggctt gcacacattt ggtgggatga tgttaagcgc   180
tacagcccat ctctgaagag caggctcacc atcaccaagg acacctccaa aaaccaggtg   240
gtccttacaa tgaccaacat ggaccctgtg gacacagcca catattactg tgcacgcata   300
gtttcctttg ataacgacgt tgtctctgct atggactact ggggtcaagg aaccctagtc   360
accgtctcct ccg                                                      373
```

<210> SEQ ID NO 406
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 406

```
gccatccagt tgacccagtc tccatcctcc ctgtctgcat ctgtaggaga cagagtcacc    60
atcacttgcc gggcaagtga gaacatttat taaatttag cctggtatca gcagaaacca   120
gggaaagctc ctaagctcct gatctatact gccaatagtt tggaagatgg ggtcccatca   180
aggttcagcg gcagtggatc tgggacagat ttcactctca ccatcagcag cctgcagcct   240
gaagattttg caacttattt ttgtaaacag gcttatgacg ttcctccgac gttcggtgga   300
ggcaccaagc tggaaatcaa ac                                            322
```

<210> SEQ ID NO 407
<211> LENGTH: 352
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 407

```
caggtgcagc tggtgcagtc tggggctgag gtgaagaagc ctggggcctc agtgaaggtt    60
tcctgcaagg catctggata caccttcacc aggtactgga tacactggat acgacaggcc   120
```

```
cctggacaag ggcttgagtg gatgggatac atcaaccta caactgttta tactgagttc    180
aatcagaact tcaaggacag agtcaccatg accagggaca cgtccacgag cacagtctac    240
atggagctga gcagcctgag atctgaggac acggccgtgt attactgtgc gagaggcggt    300
agtaacttct ttgactactg gggccaaggc accactgtca cagtctcctc ag           352
```

<210> SEQ ID NO 408
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 408

```
gaaattgtgc tgactcagtc tccagacttt cagtctgtga ctccaaagga gaaagtcacc     60
atcacctgca gtgccagtag cagtgtgagc tacatgcact ggtaccagca gaaaccagat    120
cagtctccaa agctcctcat caaggatagt tccaaactcg cctcagggt ccccctcgagg    180 ttcagtggca gtggatctgg gacagatttc accctcacca tcaatagcct ggaagctgaa    240
gatgctgcaa cgtattactg tcagcagtgg agtagtaacc cgctcacgtt cggtcagggg    300
accaagctgg agatcaaac                                                 319
```

<210> SEQ ID NO 409
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 409

```
cagatcaccct tgaaggagtc tggtcctacg ctggtgaaac ccacacagac cctcacgctg     60 acctgcaccct tctctgggtt ctcactcagc actagtggaa tgggtgtggg ctggatccgt    120
cagcccccag gaaaggccct ggagtggctt acagacattt ggtgggatga taataagtac    180
tacaacccat ctctgaagag caggctcacc atcaccaagg acacctccaa aaaccaggtg    240
gtccttacaa tgaccaacat ggaccctgtg gacacagcca tatactgtg cacgaaga      300 gttaactatt attacgaccc gtactatgct atggactact ggggtcaagg aacc           354
```

<210> SEQ ID NO 410
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 410

```
gacatccaga tgacccagtc tccatcctcc ctgtctgcat ctgtaggaga cagagtcacc     60
atcacttgca aggcgagtca gagcgttagc aatgatgtag cctggtatca gcagaaacca    120
gggaaagttc ctaagctcct gatctattat gcatccaata ggtactcagg ggtcccatct    180
cggttcagtg gcagtggatc tgggacagat ttcactctca ccatcagcag cctgcagcct    240
gaagatgttg caacttattt ctgtcagcag gattatagct ctccgtggac gttcggtgga    300
```

```
ggcaccaagg tggaaatcaa ac                                              322
```

<210> SEQ ID NO 411
<211> LENGTH: 355
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 411

```
caggtccagc ttgtgcagtc tggggctgag gtgaagaagc ctggggcctc agtgaaggtt       60
tcctgcaagg cttctggata caccttcact aactatggta tgaattgggt gcgccaggcc      120
cccggacaaa ggcttgagtg gatgggatgg atcaacactt acactggtga cccaacatat      180
gcagatgatt tcaagggcag agtcaccatt accagggaca catccgcgag cacagcctac      240
atggagctga gcagcctgag atctgaagac acggctgtgt attactgtgc gagaattggc      300
ggtaatagtc cctctgatta ctggggccaa ggcaccactg tcacagtctc ctcag           355
```

<210> SEQ ID NO 412
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 412

```
gagatcgtga tgacccagtc ccctgccaca ctgtccgtgt cccctggaga gagggccacc       60
ctgtcctgca aggcctccca gtccgtgtcc aacgacgtgg tgtggtacca gcagaagccc      120
ggacaggctc ccaggctgct gatctactac gcctccaaca ggtacaccgg catccctgcc      180
aggttctccg gatccggatc cggcaccgag ttcaccctga ccatctcctc cctgcagtcc      240
gaggacttcg ccgtgtacta ctgccagcag gactacacct cccctggac ctttggccag       300 ggcaccaagc tggagatcaa gagg                                             324
```

<210> SEQ ID NO 413
<211> LENGTH: 353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 413

```
caggtgcagc tggtgcagtc cggcgccgaa gtgaagaaac ccggcgcctc cgtgaaggtg       60
tcctgcaagg cctccggcta caccttcacc aactacggca tgaactgggt gaggcaggct      120
cctggacagg gactggagtg gatgggctgg atcaacacct acaccggcga acccacctac      180
gccgacgact tcaagggcag ggtgaccatg accaccgaca cctccacctc caccgcctac      240
atggagctga gtccctgag gtccgacgac accgccgtgt actactgcgc taggattggc       300
gactcctccc cctccgatta ctggggacag ggcaccctcg tgaccgtctc ctc             353
```

ANTI-DLL3 ANTIBODY DRUG CONJUGATES FOR TREATING CANCER

CROSS REFERENCED APPLICATIONS

This application claims priority from U.S. Provisional Application No. 61/603,173 filed on Feb. 24, 2012, and U.S. Provisional Application No. 61/719,803 filed on Oct. 29, 2012 each of which is incorporated herein by reference in its entirety.

SEQUENCE LISTING

The instant application contains a sequence listing which has been submitted in ASCII format via EFS-Web and is hereby incorporated by reference in its entirety. Said ASCII copy, created on Feb. 19, 2013, is named 11200.0013-00304_SL.txt and is 381,637 bytes in size.

FIELD OF THE INVENTION

This application generally relates to novel compounds, compositions and methods of their use in diagnosing, preventing, treating or ameliorating proliferative disorders and any expansion, recurrence, relapse or metastasis thereof. In a broad aspect, the present invention relates to the use of delta-like ligand 3 (DLL3) modulators, including anti-DLL3 antibodies and fusion constructs, for the treatment, diagnosis or prophylaxis of neoplastic disorders. Selected embodiments of the present invention provide for the use of such DLL3 modulators, including antibody drug conjugates, for the immunotherapeutic treatment of malignancies preferably comprising a reduction in tumor initiating cell frequency.

BACKGROUND OF THE INVENTION

Stem and progenitor cell differentiation and cell proliferation are normal ongoing processes that act in concert to support tissue growth during organogenesis and cell replacement and repair of most tissues during the lifetime of all living organisms. In the normal course of events cellular differentiation and proliferation is controlled by numerous factors and signals that are generally balanced to maintain cell fate decisions and tissue architecture. Thus, to a large extent it is this controlled microenvironment that regulates cell division and tissue maturation where signals are properly generated based on the needs of the organism. In this regard cell proliferation and differentiation normally occurs only as necessary for the replacement of damaged or dying cells or for growth. Unfortunately, disruption of cell proliferation and/or differentiation can result from a myriad of factors including, for example, the under- or overabundance of various signaling chemicals, the presence of altered microenvironments, genetic mutations or some combination thereof. When normal cellular proliferation and/or differentiation is disturbed or somehow disrupted it can lead to various diseases or disorders including proliferative disorders such as cancer.

Conventional treatments for cancer include chemotherapy, radiotherapy, surgery, immunotherapy (e.g., biological response modifiers, vaccines or targeted therapeutics) or combinations thereof. Unfortunately, certain cancers are non-responsive or minimally responsive to such treatments. For example, in some patients tumors exhibit gene mutations that render them non-responsive despite the general effectiveness of selected therapies. Moreover, depending on the type of cancer and what form it takes some available treatments, such as surgery, may not be viable alternatives. Limitations inherent in current standard of care therapeutics are particularly evident when attempting to treat patients who have undergone previous treatments and have subsequently relapsed. In such cases the failed therapeutic regimens and resulting patient deterioration may contribute to refractory tumors which often manifest themselves as a relatively aggressive disease that ultimately proves to be incurable. Although there have been great improvements in the diagnosis and treatment of cancer over the years, overall survival rates for many solid tumors have remained largely unchanged due to the failure of existing therapies to prevent relapse, tumor recurrence and metastases. Thus, it remains a challenge to develop more targeted and potent therapies for proliferative disorders.

SUMMARY OF THE INVENTION

These and other objectives are provided for by the present invention which, in a broad sense, is directed to methods, compounds, compositions and articles of manufacture that may be used in the treatment of DLL3 associated disorders (e.g., proliferative disorders or neoplastic disorders). To that end, the present invention provides novel Delta-like ligand 3 (or DLL3) modulators that effectively target tumor cells and/or cancer stem cells and may be used to treat patients suffering from a wide variety of malignancies. As will be discussed in more detail herein, there are at least two naturally occurring DLL3 isoforms or variants and the disclosed modulators may comprise or associate selectively with one isoform or the other or with both. Moreover, in certain embodiments the disclosed DLL3 modulators may further react with one or more DLL family members (e.g., DLL1 or DLL4) or, in other embodiments, may be generated and selected for so as to exclusively associate or react with one or more DLL3 isoforms. In any event the modulators may comprise any compound that recognizes, competes, agonizes, antagonizes, interacts, binds or associates with a DLL3 genotypic or phenotypic determinant (or fragment thereof) and modulates, adjusts, alters, regulates, changes or modifies the impact of the DLL3 protein on one or more physiological pathways and/or eliminates DLL3 associated cells. Thus, in a broad sense the present invention is generally directed to isolated DLL3 modulators and uses thereof. In preferred embodiments the invention is more particularly directed to isolated DLL3 modulators comprising antibodies (i.e., antibodies that immunopreferentially bind, react with or associate with at least one isoform of DLL3) that, in particularly preferred embodiments, are associated or conjugated to one or more cytotoxic agents. Moreover, as discussed extensively below, such modulators may be used to provide pharmaceutical compositions useful for the prophylaxis, diagnosis or treatment of proliferative disorders including cancer.

In selected embodiments of the invention, DLL3 modulators may comprise a DLL3 polypeptide or fragments thereof, either in an isolated form or fused or associated with other moieties (e.g., Fc-DLL3, PEG-DLL3 or DLL3 associated with a targeting moiety). In other selected embodiments DLL3 modulators may comprise DLL3 antagonists which, for the purposes of the instant application, shall be held to mean any construct or compound that recognizes, competes, interacts, binds or associates with DLL3 and neutralizes, eliminates, reduces, sensitizes, reprograms, inhibits or controls the growth of neoplastic cells including tumor initiating cells. In preferred embodiments the DLL3 modulators of the instant invention comprise anti-DLL3 antibodies, or fragments or derivatives thereof, that have unexpectedly been found to silence, neutralize, reduce, decrease, deplete, moderate, diminish, reprogram, eliminate, or otherwise inhibit the ability of tumor initiating cells to propagate, maintain, expand, proliferate or otherwise facilitate the survival, recurrence, regeneration and/or metastasis of neoplastic cells. In particularly preferred embodiments the antibodies or immunoreactive fragments may be associated with, or conjugated to, one or more anti-cancer agents (e.g., a cytotoxic agent).

With regard to such modulators it will be appreciated that compatible antibodies may take on any one of a number of forms including, for example, polyclonal and monoclonal antibodies, chimeric, CDR grafted, humanized and human antibodies and immunoreactive fragments and/or variants of each of the foregoing. Preferred embodiments will comprise antibodies that are relatively non-immunogenic such as humanized or fully human constructs. Of course, in view of the instant disclosure those skilled in the art could readily identify one or more complementarity determining regions (CDRs) associated with heavy and light chain variable regions of DLL3 antibody modulators and use those CDRs to engineer or fabricate chimeric, humanized or CDR grafted antibodies without undue experimentation. Accordingly, in certain preferred embodiments the DLL3 modulator comprises an antibody that incorporates one or more complementarity determining regions (CDRs) as defined in FIGS. 11A and 11B and derived from the light (FIG. 11A) or heavy (FIG. 11B) contiguous chain murine variable regions (SEQ ID NOS: 20-203) set forth therein. Such CDR grafted variable regions are also shown in FIG. 11 comprising SEQ ID NOS: 204-213. In preferred embodiments such antibodies will comprise monoclonal antibodies and, in even more preferred embodiments, will comprise chimeric, CDR grafted or humanized antibodies.

Exemplary nucleic acid sequences encoding each of the amino acid sequences set forth in FIGS. 11A and 11B are appended hereto in the sequence listing and comprise SEQ ID NOS: 220 to 413. In this respect it will be appreciated that the invention further comprises nucleic acid molecules (and associated constructs, vectors and host cells) encoding disclosed antibody variable region amino acid sequences including those set forth in the attached sequence listing. More particularly in selected embodiments compatible DLL3 modulators may comprise an antibody having a light chain variable region and a heavy chain variable region wherein said light chain variable region comprises an amino acid sequence having at least 60% identity to an amino acid sequence selected from the group consisting of amino acid sequences as set forth in SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162 SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 198, SEQ ID NO: 200 and SEQ ID NO: 202 and wherein said heavy chain variable region comprises an amino acid sequence having at least 60% identity to an amino acid sequence selected from the group consisting of amino acid sequences as set forth in SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201 and SEQ ID NO: 203. In other preferred embodiments the selected modulators will comprise heavy and light chain variable regions that comprise 65, 70, 75 or 80% identity to the aforementioned murine sequences. In still other embodiments the modulators will comprise heavy and light chain variable regions that comprise 85, 90 or even 95% identity to the disclosed murine sequences.

In other preferred embodiments the selected modulators will comprise one or more CDRs obtained from any of the foregoing light and heavy chain variable region amino acid sequences. Accordingly, selected embodiments of the invention include a DLL3 modulator comprising one or more CDRs from any one of SEQ ID NOS; 20 to 203. In still other embodiments the modulators of the instant invention will comprise any antibody or immunoreactive fragment thereof that competes for binding with any of the foregoing modulators.

Another aspect of the invention comprises modulators obtained or derived from SC16.3, SC16.4, SC16.5, SC16.7, SC16.8, SC16.10, SC16.11, SC16.13, SC16.15, SC16.18, SC16.19, SC16.20, SC16.21, SC16.22, SC16.23, SC16.25, SC16.26, SC16.29, SC16.30, SC16.31, SC16.34, SC16.35, SC16.36, SC16.38, SC16.39, SC16.41, SC16.42, SC16.45, SC16.47, SC16.49, SC16.50, SC16.52, SC16.55, SC16.56, SC16.57, SC16.58, SC16.61, SC16.62, SC16.63, SC16.65, SC16.67, SC16.68, SC16.72, SC16.73, SC16.78, SC16.79, SC16.80, SC16.81, SC16.84, SC16.88, SC16.101, SC16.103, SC16.104, SC16.105, SC16.106, SC16.107, SC16.108, SC16.109, SC16.110, SC16.111, SC16.113, SC16.114, SC16.115, SC16.116, SC16.117, SC16.118, SC16.120, SC16.121, SC16.122, SC16.123, SC16.124, SC16.125, SC16.126, SC16.129, SC16.130, SC16.131, SC16.132, SC16.133, SC16.134, SC16.135, SC16.136, SC16.137, SC16.138, SC16.139, SC16.140, SC16.141, SC16.142, SC16.143, SC16.144, SC16.147, SC16.148, SC16.149 and SC16.150. In other embodiments the invention will comprise a DLL3 modulator having one or more CDRs from any of the aforementioned modulators.

In yet other compatible embodiments the instant invention will comprise the CDR grafted or humanized DLL3 modulators hSC16.13, hSC16.15, hSC16.25, hSC16.34 and hSC16.56. Still other embodiments are directed to a DLL3 modulator comprising a humanized antibody wherein said humanized antibody comprises a light chain variable region and a heavy chain variable region wherein said light chain variable region comprises an amino acid sequence having at least 60% identity to an amino acid sequence selected from the group consisting of amino acid sequences as set forth in SEQ ID NO: 204, SEQ ID NO: 206, SEQ ID NO: 208, SEQ ID NO: 210 and SEQ ID NO: 212 and wherein said heavy chain variable region comprises an amino acid sequence having at least 60% identity to an amino acid sequence selected from the group consisting of amino acid sequences as set forth in SEQ ID NO: 205, SEQ ID NO: 207, SEQ ID NO: 209, SEQ ID NO: 211 and SEQ ID NO: 213. Moreover, as described immediately above nucleic acid sequences encoding the humanized heavy and light chain variable regions are set forth in the attached sequence listing as SEQ ID NOS: 404-413.

Besides the aforementioned aspects, other preferred embodiments of the instant invention will comprise DLL3 modulators associated or conjugated to one or more drugs to provide modulator conjugates that may be particularly effective in treating proliferative disorders (alone or in combination with other pharmaceutically active agents). More generally, once the modulators of the invention have been fabricated and selected they may be linked with, fused to, conjugated to (e.g., covalently or non-covalently) or otherwise associated with pharmaceutically active or diagnostic moieties or biocompatible modifiers. As used herein the term "conjugate" or "modulator conjugate" or "antibody conjugate" will be used broadly and held to mean any biologically active or detectable molecule or drug associated with the disclosed modulators regardless of the method of association. In this respect it will be understood that such conjugates may, in addition to the disclosed modulators, comprise peptides, polypeptides, proteins, prodrugs which are metabolized to an active agent in vivo, polymers, nucleic acid molecules, small molecules, binding agents, mimetic agents, synthetic drugs, inorganic molecules, organic molecules and radioisotopes. Moreover, as indicated above the selected conjugate may be covalently or non-covalently associated with, or linked to, the modulator and exhibit various stoichiometric molar ratios depending, at least in part, on the method used to effect the conjugation.

Particularly preferred aspects of the instant invention will comprise antibody modulator conjugates or antibody-drug conjugates that may be used for the diagnosis and/or treatment of proliferative disorders. Such conjugates may be represented by the formula M-[L-D]n where M stands for a disclosed modulator or target binding moiety, L is an optional linker or linker unit, D is a compatible drug or prodrug and n is an integer from about 1 to about 20. It will be appreciated that, unless otherwise dictated by context, the terms "antibody-drug conjugate" or "ADC" or the formula M-[L-D]n shall be held to encompass conjugates comprising both therapeutic and diagnostic moieties. In such embodiments antibody-drug conjugate compounds will typically comprise anti-DLL3 as the modulator unit (M), a therapeutic or diagnostic moiety (D), and optionally a linker (L) that joins the drug and the antigen binding agent. In a preferred embodiment, the antibody is a DLL3 mAb comprising at least one CDR from the heavy and light chain variable regions as described above.

As previously indicated one aspect of the invention may comprise the unexpected therapeutic association of DLL3 polypeptides with cancer stem cells. Thus, in certain other embodiments the invention will comprise a DLL3 modulator that reduces the frequency of tumor initiating cells upon administration to a subject. Preferably the reduction in frequency will be determined using in vitro or in vive limiting dilution analysis. In particularly preferred embodiments such analysis may be conducted using in vive limiting dilution analysis comprising transplant of live human tumor cells into immunocompromised mice (e.g., see Example 17 below). Alternatively, the limiting dilution analysis may be conducted using in vitro limiting dilution analysis comprising limiting dilution deposition of live human tumor cells into in vitro colony supporting conditions. In either case, the analysis, calculation or quantification of the reduction in frequency will preferably comprise the use of Poisson distribution statistics to provide an accurate accounting. It will be appreciated that, while such quantification methods are preferred, other, less labor intensive methodologies such as flow cytometry or immunohistochemistry may also be used to provide the desired values and, accordingly, are expressly contemplated as being within the scope of the instant invention. In such cases the reduction in frequency may be determined using flow cytometric analysis or immunohistochemical detection of tumor cell surface markers known to enrich for tumor initiating cells.

As such, another preferred embodiment of the instant invention comprises a method of treating a DLL3 associated disorder comprising administering a therapeutically effective amount of a DLL3 modulator to a subject in need thereof whereby the frequency of tumor initiating cells is reduced. Preferably the DLL3 associated disorder comprises a neoplastic disorder. Again, the reduction in the tumor initiating cell frequency will preferably be determined using in vitro or in vivo limiting dilution analysis.

In this regard it will be appreciated that the present invention is based, at least in part, upon the discovery that DLL3 immunogens are therapeutically associated with tumor perpetuating cells (i.e., cancer stem cells) that are involved in the etiology of various proliferative disorders including neoplasia. More specifically, the instant application unexpectedly demonstrates that the administration of various exemplary DLL3 modulators can mediate, reduce, deplete, inhibit or eliminate tumorigenic signaling by tumor initiating cells (i.e., reduce the frequency of tumor initiating cells). This reduced signaling, whether by depletion, neutralization, reduction, elimination, reprogramming or silencing of the tumor initiating cells or by modifying tumor cell morphology (e.g., induced differentiation, niche disruption), in turn allows for the more effective treatment of DLL3 associated disorders by inhibiting tumorigenesis, tumor maintenance, expansion and/or metastasis and recurrence.

Besides the aforementioned association with cancer stem cells, there is evidence that DLL3 isoforms may be implicated in the growth, recurrence or metastatic potential of tumors comprising or exhibiting neuroendocrine features or determinants (genotypic or phenotypic). For the purposes of the instant invention such tumors will comprise neuroendocrine tumors and pseudo neuroendocrine tumors. Intervention in the proliferation of such tumorigenic cells using the novel DLL3 modulators described herein, may thereby ameliorate or treat a disorder by more than one mechanism (e.g., tumor initiating cell reduction and disruption of oncogenic pathway signaling) to provide additive or synergistic effects. Still other preferred embodiments may take advantage of the cellular internalization of cell surface DLL3 protein to deliver a modulator mediated anti-cancer agent. In this regard it will be appreciated that the present invention is not limited by any particular mechanism of action but rather encompasses the broad use of the disclosed modulators to treat DLL3 associated disorders (including various neoplasia).

Thus, in other embodiments the present invention will comprise the use of the disclosed modulators to treat tumors comprising neuroendocrine features in a subject in need thereof. Of course the same modulators may be used for the prophylaxis, prognosis, diagnosis, theragnosis, inhibition or maintenance therapy of these same tumors.

Other facets of the instant invention exploit the ability of the disclosed modulators to potentially disrupt oncogenic pathways (e.g., Notch) while simultaneously silencing tumor initiating cells. Such multi-active DLL3 modulators (e.g., DLL3 antagonists) may prove to be particularly effective when used in combination with standard of care anticancer agents or debulking agents. Accordingly preferred embodiments of the instant invention comprise using the disclosed modulators as anti-metastatic agents for maintenance therapy following initial treatments. In addition, two or more DLL3 antagonists (e.g. antibodies that specifically bind to two discrete epitopes on DLL3) may be used in combination in accordance with the present teachings. Moreover, as discussed in some detail below, the DLL3 modulators of the present invention may be used in a conjugated or unconjugated state and, optionally, as a sensitizing agent in combination with a variety of chemical or biological anti-cancer agents.

Accordingly another preferred embodiment of the instant invention comprises a method of sensitizing a tumor in a subject for treatment with an anti-cancer agent comprising the step of administering a DLL3 modulator to said subject. Other embodiments comprise a method of reducing metastasis or tumor recurrence following treatment comprising administering a DLL3 modulator to a subject in need thereof. In a particularly preferred aspect of the invention the DLL3 modulator will specifically result in a reduction of tumor initiating cell frequency is as determined using in vitro or in vivo limiting dilution analysis.

More generally preferred embodiments of the invention comprise a method of treating a DLL3 associated disorder in a subject in need thereof comprising the step of administering a DLL3 modulator to the subject. In particularly preferred embodiments the DLL3 modulator will be associated (e.g., conjugated) with an anti-cancer agent. In yet other embodiments the DLL3 modulator will internalize following association or binding with DLL3 on or near the surface of the cell. Moreover the beneficial aspects of the instant invention, including any disruption of signaling pathways and collateral benefits, may be achieved whether the subject tumor tissue exhibits elevated levels of DLL3 or reduced or depressed levels of DLL3 as compared with normal adjacent tissue. Particularly preferred embodiments will comprise the treatment of disorders exhibiting elevated levels of DLL3 on tumorigenic cells as compared to normal tissue or non-tumorigenic cells.

In yet another aspect the present invention will comprise a method of treating a subject suffering from neoplastic disorder comprising the step of administering a therapeutically effective amount of at least one internalizing DLL3 modulator. Preferred embodiments will comprise the administration of internalizing antibody modulators wherein the modulators are conjugated or associated with a cytotoxic agent.

Other embodiments are directed to a method of treating a subject suffering from a DLL3 associated disorder comprising the step of administering a therapeutically effective amount of at least one depleting DLL3 modulator.

In yet another embodiment the present invention provides methods of maintenance therapy wherein the disclosed effectors or modulators are administered over a period of time following an initial procedure (e.g., chemotherapeutic, radiation or surgery) designed to remove at least a portion of the tumor mass. Such therapeutic maintenance regimens may be administered over a period of weeks, a period of months or even a period of years wherein the DLL3 modulators may act prophylactically to inhibit metastasis and/or tumor recurrence. In yet other embodiments the disclosed modulators may be administrated in concert with known debulking regimens to prevent or retard metastasis, tumor maintenance or recurrence.

As previously alluded to the DLL3 modulators of the instant invention may be fabricated and/or selected to react with both isoform(s) of DLL3 or a single isoform of the protein or, conversely, may comprise a pan-DLL modulator that reacts or associates with at least one additional DLL family member in addition to DLL3. More specifically, preferred modulators such as antibodies may be generated and selected so that they react with domains (or epitopes therein) that are exhibited by DLL3 only or with domains that are at least somewhat conserved across multiple or all DLL family members.

In yet other preferred embodiments the modulators will associate or bind to a specific epitope, portion, motif or domain of DLL3. As will be discussed in some detail below, both DLL3 isoforms incorporate an identical extracellular region (see FIG. 1F) comprising at least an N-terminal domain, a DSL (Delta/Serrate/lag-2) domain and six EGF-like domains (i.e., EGF1-EGF6). Accordingly, in certain embodiments the modulators will bind or associate with the N-terminal domain of DLL3 (i.e. amino acids 27-175 in the mature protein) while in other selected embodiments the modulators will associate with the DSL domain (i.e. amino acids 176-215) or epitope therein. Other aspects of the instant invention comprise modulators that associate or bind to a specific epitope located in a particular EGF-like domain of DLL3. In this regard the particular modulator may associate or bind to an epitope located in EGF1 (amino acids 216-249), EGF2 (amino acids 274-310), EGF3 (amino acids 312-351), EGF4 (amino acids 353-389), EGF5 (amino acids 391-427) or EGF6 (amino acids 429-465). Of course it will be appreciated that each of the aforementioned domains may comprise more than one epitope and/or more than one bin. In particularly preferred embodiments the invention will comprise a modulator that binds, reacts or associates with the DSL domain or an epitope therein. In other preferred embodiments the invention will comprise modulators that bind, react or associate with a particular EGF-like domain or an epitope therein. In yet other embodiments the modulators will bind, react or associate with the N-terminal domain or an epitope therein.

With regard to modulator or antibody "bins" it will be appreciated that the DLL3 antigen may be analyzed or mapped through competitive antibody binding using art-recognized techniques to define specific bins located on or along the protein. While discussed in more detail herein and shown in Examples 9 and 10 below, two antibodies (one of which may be termed a "reference antibody," "bin delineating antibody" or "delineating antibody") may be considered to be in the same bin if they compete with each other for binding to the target antigen. In such cases the subject antibody epitopes may be identical, substantially identical or close enough (either in a linear sense where they are separated by a few amino acids or conformationally) so that both antibodies are sterically or electrostatically inhibited or precluded from binding to the antigen. Such defined bins may be generally associated with certain DLL3 domains (e.g. the reference antibody will bind with an epitope contained in a specific domain) though the correlation is not always precise (e.g., there may be more than one bin in a domain or the bin may be defined conformationally and comprise more than one domain). It will be appreciated that those skilled in the art can readily determine the relationship between the DLL3 domains and empirically determined bins.

With regard to the present invention competitive binding analysis using art-recognized techniques (e.g., ELISA, surface plasmon resonance or bio-layer interferometry) defined at least nine distinct bins, each of which was found to contain a number of antibody modulators. For the purposes of the instant disclosure the nine bins were termed bin A to bin I. Thus, in selected embodiments the present invention will comprise a modulator residing in a bin selected from the group consisting of bin A, bin B, bin C, bin D, bin E, bin F, bin G, bin H and bin I. In other embodiments the present invention comprise a modulator residing in a bin defined by a reference antibody selected from the group consisting of SC16.3, SC16.4, SC16.5, SC16.7, SC16.8, SC16.10, SC16.11, SC16.13, SC16.15, SC16.18, SC16.19, SC16.20, SC16.21, SC16.22, SC16.23, SC16.25, SC16.26, SC16.29, SC16.30, SC16.31, SC16.34, SC16.35, SC16.36, SC16.38, SC16.39, SC16.41, SC16.42, SC16.45, SC16.47, SC16.49, SC16.50, SC16.52, SC16.55, SC16.56, SC16.57, SC16.58, SC16.61, SC16.62, SC16.63, SC16.65, SC16.67, SC16.68, SC16.72, SC16.73, SC16.78, SC16.79, SC16.80, SC16.81, SC16.84, SC16.88, SC16.101, SC16.103, SC16.104, SC16.105, SC16.106, SC16.107, SC16.108, SC16.109, SC16.110, SC16.111, SC16.113, SC16.114, SC16.115, SC16.116, SC16.117, SC16.118, SC16.120, SC16.121, SC16.122, SC16.123, SC16.124, SC16.125, SC16.126, SC16.129, SC16.130, SC16.131, SC16.132, SC16.133, SC16.134, SC16.135, SC16.136, SC16.137, SC16.138, SC16.139, SC16.140, SC16.141, SC16.142, SC16.143, SC16.144, SC16.147, SC16.148, SC16.149 and SC16.150. In still other embodiments the invention will comprise modulators from bin A, modulators from bin B, modulators from bin C, modulators from bin D, modulators from bin E, modulators from bin F, modulators from bin G, modulators from bin H or modulators from bin I. Yet other preferred embodiments will comprise a reference antibody modulator and any antibody that competes with the reference antibody.

The term "compete" or "competing antibody" when used in the context of the disclosed modulators means binding competition between antibodies as determined by an assay in which a reference antibody or immunologically functional fragment substantially prevents or inhibits (e.g., greater than 40%, 45%, 50%, 55%, 60%, 65%, 70%, 75%, 80%, 85% or 90%.) specific binding of a test antibody to a common antigen. Compatible methods for determining such competition comprise art known techniques such as, for example, bio-layer interferometry, surface plasmon resonance, flow cytometry, competitive ELISA, etc.

Besides the aforementioned modulators, in selected embodiments the invention comprises a pan-DLL modulator that associates with DLL3 and at least one other DLL family member. In other selected embodiments the invention comprises a DLL3 modulator that immunospecifically associates with one or more isoform of DLL3 but does not immunospecifically associate with any other DLL family member. In yet other embodiments the present invention comprises a method of treating a subject in need thereof comprising administering a therapeutically effective amount of a pan-DLL modulator. Still other embodiments comprise a method of treating a subject in need thereof comprising administering a therapeutically effective amount of a DLL3 modulator that immunospecifically associates with one or more isoforms of DLL3 but does not immunospecifically associate with any other DLL family member.

Beyond the therapeutic uses discussed above it will also be appreciated that the modulators of the instant invention may be used to detect, diagnose or classify DLL3 related disorders and, in particular, proliferative disorders. They may also be used in the prognosis and/or theragnosis of such disorders. In some embodiments the modulator may be administered to the subject and detected or monitored in vivo. Those of skill in the art will appreciate that such modulators may be labeled or associated with effectors, markers or reporters as disclosed below and detected using any one of a number of standard techniques (e.g., MRI, CAT scan, PET scan, etc.).

Thus, in some embodiments the invention will comprise a method of diagnosing, detecting or monitoring a DLL3 associated disorder in vivo in a subject in need thereof comprising the step of administering a DLL3 modulator.

In other instances the modulators may be used in an in vitro diagnostic setting using art-recognized procedures (e.g., immunohistochemistry or IHC). As such, a preferred embodiment comprises a method of diagnosing a hyperproliferative disorder in a subject in need thereof comprising the steps of:
 a. obtaining a tissue sample from said subject;
 b. contacting the tissue sample with at least one DLL3 modulator; and
 c. detecting or quantifying the DLL3 modulator associated with the sample.

Such methods may be easily discerned in conjunction with the instant application and may be readily performed using generally available commercial technology such as automatic plate readers, dedicated reporter systems, etc. In selected embodiments the DLL3 modulator will be associated with tumor perpetuating cells (i.e., cancer stem cells) present in the sample. In other preferred embodiments the detecting or quantifying step will comprise a reduction of tumor initiating cell frequency which may be monitored as described herein.

In a similar vein the present invention also provides kits or devices and associated methods that are useful in the diagnosis and monitoring of DLL3 associated disorders such as cancer. To this end the present invention preferably provides an article of manufacture useful for detecting, diagnosing or treating DLL3 associated disorders comprising a receptacle containing a DLL3 modulator and instructional materials for using said DLL3 modulator to treat, monitor or diagnose the DLL3 associated disorder. In selected embodiments the devices and associated methods will comprise the step of contacting at least one circulating tumor cell.

Other preferred embodiments of the invention also exploit the properties of the disclosed modulators as an instrument useful for identifying, characterizing, isolating, sectioning or enriching populations or subpopulations of tumor initiating cells through methods such as immunohistochemistry, flow cytometric analysis including fluorescence activated cell sorting (FACS) or laser mediated sectioning.

As such, another preferred embodiment of the instant invention is directed to a method of identifying, isolating, sectioning or enriching a population of tumor initiating cells comprising the step of contacting said tumor initiating cells with a DLL3 modulator.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIGS. 1A-1F are various representations of DLL3 including nucleic acid or amino acid sequences wherein full length mRNAs containing the ORFs (underlined) encoding DLL3 isoforms are depicted in FIGS. 1A and 1B (SEQ ID NOS: 1 and 2), FIGS. 1C and 1D provide the translation of the ORFs denoted in FIGS. 1A and 1B (SEQ ID NOS: 3 and 4), respectively, with underlined residues indicating the predicted transmembrane spanning domain for each protein isoform, FIG. 1E depicts the alignment of the two protein isoforms to illustrate the sequence differences in the cytoplasmic termini of each isoform, again with the underlined residues indicating the predicted transmembrane spanning domain and FIG. 1F provides a schematic representation of the extracellular region of DLL3 protein illustrating the positions of the various domains;

FIGS. 2A and 2B are tabular representations of the percent identity at the protein level between DLL3 and other Delta-like family members in the human genome (FIG. 2A), or the closest human isoform of DLL3 and rhesus monkey, mouse and rat DLL3 proteins (FIG. 2B);

FIG. 3 schematically illustrates genetic interactions between several "master" genes relevant to cell fate choices leading to either neuroendocrine or non-neuroendocrine phenotypes (arrows indicating promotion of gene expression and barred arrows indicating inhibition of gene expression), in which the expression of the transcription factor ASCL1 both initiates a gene cascade (open arrow) leading to a neuroendocrine phenotype while simultaneously activating DLL3, which in turn suppresses NOTCH1 and its effector HES1, both of which are normally responsible for the suppression of ASCL1 and the activation of gene cascades leading to a non-neuroendocrine phenotype;

FIGS. 4A and 4B are tabular (FIG. 4A) and graphical (FIG. 4B) depictions of gene expression levels of DLL3 and, in FIG. 4A, other Notch pathway genes or genes associated with a neuroendocrine phenotype as measured using whole transcriptome (SOLiD) sequencing of RNA derived from tumor cell subpopulations or normal tissues;

FIGS. 6A-6D show gene expression data and clustering of tumors exhibiting neuroendocrine features wherein FIG. 6A depicts unsupervised clustering of microarray profiles for 46 tumor lines and 2 normal tissues comprising selected tumors and normal control tissues, FIGS. 6B and 6C are tabular representations of normalized intensity values corresponding to relative expression levels of selected genes related to neuroendocrine phenotypes (FIG. 6B) or the Notch signaling pathway (FIG. 6C) wherein unshaded cells and relatively low numbers indicate little to no expression and darker cells and relatively higher numbers indicate higher expression levels and FIG. 6D is a graphical representation showing relative expression levels of HES6 mRNA in various tumors and normal tissues as measured using qRT-PCR;

FIGS. 8A-8C are graphical representations showing the relative (FIG. 8A) or absolute (FIG. 8B) gene expression levels of human DLL3 as measured by qRT-PCR in whole tumor specimens (grey dot) or matched normal adjacent tissue (NAT; white dot) from patients with one of eighteen different solid tumor types while FIG. 8C shows the relative protein expression of human DLL3 as measured using an electrochemiluminescent sandwich ELISA assay;

FIGS. 10A-10D provide, respectively, the cDNA sequence (FIG. 10A; SEQ ID NO: 5) and the amino acid sequence (FIG. 10B; SEQ ID NO: 6) encoding mature murine DLL3 protein cloned into a lentiviral expression vector and the cDNA sequence (FIG. 10C; SEQ ID NO:7) and the amino acid sequence (FIG. 10D; SEQ ID NO: 8) encoding mature cynomolgus DLL3 protein cloned into a lentiviral expression vector where the vectors are used to generate cells overexpressing murine and cynomolgus DLL3;

FIGS. 11A and 11B provide, in a tabular form, contiguous amino acid sequences (SEQ ID NOS: 20-213) of light and heavy chain variable regions of a number of murine and humanized exemplary DLL3 modulators isolated, cloned and engineered as described in the Examples herein;

FIG. 12 sets forth biochemical and immunological properties of exemplary DLL3 modulators as well as their ability to kill KDY66 NTX cell in vitro as represented in a tabular format;

FIGS. 13A-13C illustrate binding characteristics of selected modulators wherein FIGS. 13A and 13B show comparative binding characteristics of a selected murine modulator and its humanized counterpart using surface plasmon resonance while FIG. 13C provides certain properties of humanized constructs in a tabular form;

FIGS. 15A-15C are flow cytometry histograms showing DLL3 expression using the exemplary anti-DLL3 modulator SC16.56 on naive 293 cells (FIG. 15A), 293 cells engineered to over-express human DLL3 proteins (h293-hDLL3; FIG. 15B) or 293 cells engineered to over-express murine DLL3 protein (h293-mDLL3; FIG. 15C);

FIGS. 16A-16F comprise flow cytometry histograms (FIGS. 16A-16C) and immunohistochemistry results in a tabular form (FIGS. 16D-16F) illustrating, respectively, relatively high surface expression of DLL3 using the exemplary anti-DLL3 modulator SC16.56 on live human cells from ovary (OV26; FIG. 16A), kidney (KDY66; FIG. 16B) and a lung large cell neuroendocrine carcinoma (LU37; FIG. 16C) NTX tumors and the expression of DLL3 protein in various NTX tumors (FIG. 16D) and primary small cell carcinoma (FIG. 16F) tumor cells while demonstrating that normal tissue lack DLL3 expression (FIG. 16E);

FIGS. 18A-18E illustrate various properties of the disclosed modulators wherein FIGS. 18A and 18C demonstrate by flow cytometry that DLL3 NSHP KDY66 and naïve KDY66 have expression of DLL3 while expression of DLL3 was efficiently knocked down in DLL3HP2 KDY66 cells, FIG. 18B shows that growth of DLL3HP2 tumor cells lags behind naïve KDY66 cells and FIGS. 18D and 18E demonstrate that conjugated embodiments of the instant invention immunospecifically target and kill KDY66 expressing DLL3 tumor cells but not KDY66 with DLL3 knocked down;

FIGS. 20A-20F depict the ability of conjugated modulators of the instant invention to substantially eradicate tumors and prevent tumor recurrence in vivo—achieving durable remissions in immunodeficient mice engrafted with exemplary ovarian (FIG. 20A), lung (FIGS. 20B-20D) and kidney tumors (FIGS. 20E and 20F); FIGS. 21A and 21D show the effect of the conjugates on tumor growth, FIGS. 21B and 21E show the results of the LDA and FIGS. 21C and 21F graphically present the reduction in cancer stem cell frequency brought about by treatment with the selected anti-DLL3 antibody conjugate.

DETAILED DESCRIPTION OF THE INVENTION

I. Introduction

Figure 1F:
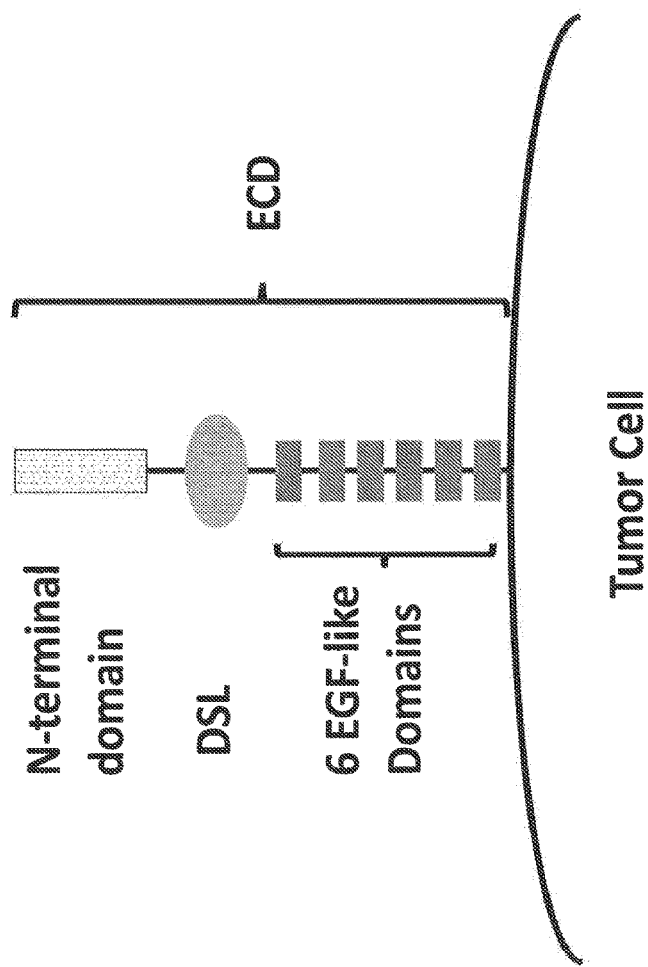

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes only and are not to be construed as limiting the subject matter described. Finally, for the purposes of the instant disclosure all identifying sequence Accession numbers may be found in the NCBI Reference Sequence (RefSeq) database and/or the NCBI GenBank® archival sequence database unless otherwise noted.

As discussed above it has surprisingly been found that DLL3 genotypic and/or phenotypic determinants are associated with various proliferative disorders, including neoplasia exhibiting neuroendocrine features, and that DLL3 and variants or isoforms thereof provide useful tumor markers which may be exploited in the treatment of related diseases. Moreover, as shown in the instant application it has unexpectedly been found that DLL3 markers or determinants such as cell surface DLL3 protein are therapeutically associated with cancer stem cells (also known as tumor perpetuating cells) and may be effectively exploited to eliminate or silence the same. The ability to selectively reduce or eliminate cancer stem cells (e.g., through the use of conjugated DLL3 modulators) is particularly surprising in that such cells are known to generally be resistant to many conventional treatments. That is, the effectiveness of traditional, as well as more recent targeted treatment methods, is often limited by the existence and/or emergence of resistant cancer stem cells that are capable of perpetuating tumor growth even in face of these diverse treatment methods. Further, determinants associated with cancer stem cells often make poor therapeutic targets due to low or inconsistent expression, failure to remain associated with the tumorigenic cell or failure to present at the cell surface. In sharp contrast to the teachings of the prior art, the instantly disclosed compounds and methods effectively overcome this inherent resistance and to specifically eliminate, deplete, silence or promote the differentiation of such cancer stem cells thereby negating their ability to sustain or re-induce the underlying tumor growth. Moreover, as expression of DLL3 protein has largely been associated with intracellular locations such as the Golgi, it was uncertain that phenotypic determinants could be successfully exploited as a therapeutic target as taught herein.

Thus, it is particularly remarkable that DLL3 modulators such as those disclosed herein may advantageously be used in the prognosis, diagnosis, theragnosis, treatment and/or prevention of selected proliferative (e.g., neoplastic) disorders in subjects in need thereof. It will be appreciated that, while preferred embodiments of the invention will be discussed extensively below, particularly in terms of particular domains, regions or epitopes or in the context of cancer stem cells or tumors comprising neuroendocrine features and their interactions with the disclosed modulators, those skilled in the art will appreciate that the scope of the instant invention is not limited by such exemplary embodiments. Rather, the most expansive embodiments of the present invention and the appended claims are broadly and expressly directed to DLL3 modulators (including conjugated modulators) and their use in the prognosis, diagnosis, theragnosis, treatment and/or prevention of a variety of DLL3 associated or mediated disorders, including neoplastic or cell proliferative disorders, regardless of any particular mechanism of action or specifically targeted tumor, cellular or molecular component.

To that end, and as demonstrated in the instant application, it has unexpectedly been found that the disclosed DLL3 modulators can effectively be used to target and eliminate or otherwise incapacitate proliferative or tumorigenic cells and treat DLL3 associated disorders (e.g., neoplasia). As used herein a "DLL3 associated disorder" shall be held to mean any disorder or disease (including proliferative disorders) that is marked, diagnosed, detected or identified by a phenotypic or genotypic aberration of DLL3 genetic components or expression ("DLL3 determinant") during the course or etiology of the disease or disorder. In this regard a DLL3 phenotypic aberration or determinant may, for example, comprise elevated or depressed levels of DLL3 protein expression, abnormal DLL3 protein expression on certain definable cell populations or abnormal DLL3 protein expression at an inappropriate phase or stage of a cell lifecycle. Of course, it will be appreciated that similar expression patterns of genotypic determinants (e.g., mRNA transcription levels) of DLL3 may also be used to classify, detect or treat DLL3 disorders.

As used herein the term "determinant" or "DLL3 determinant" shall mean any detectable trait, property, marker or factor that is identifiably associated with, or specifically found in or on a particular cell, cell population or tissue including those identified in or on a tissue, cell or cell population affected by a DLL3 associated disease or disorder. In selected preferred embodiments the DLL3 modulators may associate, bind or react directly with the DLL3 determinant (e.g., cell surface DLL3 protein or DLL3 mRNA) and thereby ameliorate the disorder. More generally determinants may be morphological, functional or biochemical in nature and may be genotypic or phenotypic. In other preferred embodiments the determinant is a cell surface antigen or genetic component that is differentially or preferentially expressed (or is not) by specific cell types (e.g., cancer stem cells) or by cells under certain conditions (e.g., during specific points of the cell cycle or cells in a particular niche). In still other preferred embodiments the determinant may comprise a gene or genetic entity that is differently regulated (up or down) in a specific cell or discrete cell population, a gene that is differentially modified with regard to its physical structure and chemical composition or a protein or collection of proteins physically associated with a gene that show differential chemical modifications. Determinants contemplated herein are specifically held to be positive or negative and may denote a cell, cell subpopulation or tissue (e.g., tumors) by its presence (positive) or absence (negative).

In a similar vein "DLL3 modulators" of the invention broadly comprise any compound that recognizes, reacts, competes, antagonizes, interacts, binds, agonizes, or associates with a DLL3 variant or isoform (or specific domains, regions or epitopes thereof) or its genetic component. By these interactions, the DLL3 modulators may advantageously eliminate, reduce or moderate the frequency, activity, recurrence, metastasis or mobility of tumorigenic cells (e.g., tumor perpetuating cells or cancer stem cells). Exemplary modulators disclosed herein comprise nucleotides, oligonucleotides, polynucleotides, peptides or polypeptides. In certain preferred embodiments the selected modulators will comprise antibodies to a DLL3 protein isoform or immunoreactive fragments or derivatives thereof. Such antibodies may be antagonistic or agonistic in nature and may optionally be conjugated or associated with a therapeutic or diagnostic agent. Moreover, such antibodies or antibody fragments may comprise depleting, neutralizing or internalizing antibodies. In other embodiments, modulators within the instant invention will constitute a DLL3 construct comprising a DLL3 isoform or a reactive fragment thereof. It will be appreciated that such constructs may comprise fusion proteins and can include reactive domains from other polypeptides such as immunoglobulins or biological response modifiers. In still other aspects, the DLL3 modulator will comprise a nucleic acid moiety (e.g. miRNA, siRNA, shRNA, antisense constructs, etc.) that exerts the desired effects at a genomic level. Still other modulators compatible with the instant teachings will be discussed in detail below.

More generally DLL3 modulators of the present invention broadly comprise any compound that recognizes, reacts, competes, antagonizes, interacts, binds, agonizes, or associates with a DLL3 determinant (genotypic or phenotypic) including cell surface DLL3 protein. Whichever form of modulator is ultimately selected it will preferably be in an isolated and purified state prior to introduction into a subject. In this regard the term "isolated DLL3 modulator" or "isolated DLL3 antibody" shall be construed in a broad sense and in accordance with standard pharmaceutical practice to mean any preparation or composition comprising the modulator in a state substantially free of unwanted contaminants (biological or otherwise). Moreover these preparations may be purified and formulated as desired using various art-recognized techniques. Of course, it will be appreciated that such "isolated" preparations may be intentionally formulated or combined with inert or active ingredients as desired to improve the commercial, manufacturing or therapeutic aspects of the finished product and provide pharmaceutical compositions. In a broader sense the same general considerations may be applied to an "isolated" DLL3 isoform or variant or an "isolated" nucleic acid encoding the same.

Further, it has surprisingly been found that modulators interacting, associating or binding to particular DLL3 domains, motifs or epitopes are especially effective in eliminating tumorigenic cells and/or silencing or attenuating cancer stem cell influences on tumor growth or propagation. That is, while modulators that react or associate with domains that are proximal to the cell surface (e.g., one of the EGF-like domains) are effective in depleting or neutralizing tumorigenic cells it has unexpectedly been discovered that modulators associating or binding to domains, motifs or regions that are relatively more distal to the cell surface are also effective in eliminating, neutralizing, depleting or silencing tumorigenic cells. In particular, and as shown in the appended Examples, it has been discovered that modulators that react, associate or bind to the DSL or N-terminal regions of the DLL3 protein are surprisingly effective at eliminating or neutralizing tumorigenic cells including those exhibiting neuroendocrine features and/or cancer stem cells. This is especially true of conjugated modulators such as, for example, anti-DLL3 antibody drug conjugates comprising a cytotoxic agent. As such, it will be appreciated that certain preferred embodiments of the instant invention are directed to compounds, compositions and methods that comprise DLL3 modulators which associate, bind or react with a relatively distal portion of DLL3 including the DSL domain and the N-terminal region.

While the present invention expressly contemplates the use of any DLL3 modulator in the treatment of any DLL3 disorder, including any type of neoplasia, in particularly preferred embodiments the disclosed modulators may be used to prevent, treat or diagnose tumors comprising neuroendocrine features (genotypic or phenotypic) including neuroendocrine tumors. True or "canonical neuroendocrine tumors" (NETs) arise from the dispersed endocrine system and are typically highly aggressive. Neuroendocrine tumors occur in the kidney, genitourinary tract (bladder, prostate, ovary, cervix, and endometrium), gastrointestinal tract (stomach, colon), thyroid (medullary thyroid cancer), and lung (small cell lung carcinoma and large cell neuroendocrine carcinoma). Moreover, the disclosed modulators may advantageously be used to treat, prevent or diagnose pseudo neuroendocrine tumors (pNETs) that genotypically or phenotypically mimic, comprise, resemble or exhibit common traits with canonical neuroendocrine tumors. "Pseudo neuroendocrine tumors" are tumors that arise from cells of the diffuse neuroendocrine system or from cells in which a neuroendocrine differentiation cascade has been aberrantly reactivated during the oncogenic process. Such pNETs commonly share certain genotypic, phenotypic or biochemical characteristics with traditionally defined neuroendocrine tumors, including the ability to produce subsets of biologically active amines, neurotransmitters, and peptide hormones. Accordingly, for the purposes of the instant invention the phrases "tumors comprising neuroendocrine features" or "tumors exhibiting neuroendocrine features" shall be held to comprise both neuroendocrine tumors and pseudo neuroendocrine tumors unless otherwise dictated by context.

Besides the association with tumors generally discussed above, there are also indications of phenotypic or genotypic association between selected tumor initiating cells (TIC) and DLL3 determinants. In this regard selected TICs (e.g., cancer stem cells) may express elevated levels of DLL3 protein when compared to normal tissue and non-tumorigenic cells (NTG), which together typically comprise much of a solid tumor. Thus, DLL3 determinants may comprise a tumor associated marker (or antigen or immunogen) and the disclosed modulators may provide effective agents for the detection and suppression of TIC and associated neoplasia due to altered levels of the proteins on cell surfaces or in the tumor microenvironment. Accordingly, DLL3 modulators, including immunoreactive antagonists and antibodies that associate, bind or react with the proteins, may effectively reduce the frequency of tumor initiating cells and could be useful in eliminating, depleting, incapacitating, reducing, promoting the differentiation of, or otherwise precluding or limiting the ability of these tumor-initiating cells to lie dormant and/or continue to fuel tumor growth, metastasis or recurrence in a patient. In this regard those skilled in the art will appreciate that the present invention further provides DLL3 modulators and their use in reducing the frequency of tumor initiating cells.

II. DLL3 Physiology

The Notch signaling pathway, first identified in *C. elegans* and *Drosophila* and subsequently shown to be evolutionarily conserved from invertebrates to vertebrates, participates in a series of fundamental biological processes including normal embryonic development, adult tissue homeostasis, and stem cell maintenance (D'Souza et al., 2010; Liu et al., 2010). Notch signaling is critical for a variety of cell types during specification, patterning and morphogenesis. Frequently, this occurs through the mechanism of lateral inhibition, in which cells expressing Notch ligand(s) adopt a default cell fate, yet suppress this fate in adjacent cells via stimulation of Notch signaling (Sternberg, 1988, Cabrera 1990). This binary cell fate choice mediated by Notch signaling is found to play a role in numerous tissues, including the developing nervous system (de la Pompa et al., 1997), the hematopoietic and immune systems (Bigas and Espinosoa, 2012; Hoyne et al, 2011; Nagase et al., 2011), the gut (Fre et al., 2005; Fre et al., 2009), the endocrine pancreas (Apelqvist et al., 1999; Jensen et al., 2000), the pituitary (Raetzman et al., 2004), and the diffuse neuroendocrine system (Ito et al., 2000; Schonhoff et al, 2004). A generalized mechanism for implementing this binary switch appears conserved despite the wide range of developmental systems in which Notch plays a role—in cells where the default cell fate choice is determined by transcriptional regulators known as basic helix-loop-helix (bHLH) proteins, Notch signaling leads to activation of a class of Notch responsive genes, which in turn suppress the activity of the bHLH proteins (Ball, 2004). These binary decisions take place in the wider context of developmental and signaling cues that permit Notch signaling to effect proliferation or inhibit it, and to trigger self-renewal or inhibit it.

In *Drosophila*, Notch signaling is mediated primarily by one Notch receptor gene and two ligand genes, known as Serrate and Delta (Wharton et al, 1985; Rebay et al., 1991). In humans, there are four known Notch receptors and five DSL (Delta-Serrate LAG2) ligands—two homologs of Serrate, known as Jagged1 and Jagged 2, and three homologs of Delta, termed delta-like ligands or DLL1, DLL3 and DLL4. In general, Notch receptors on the surface of the signal-receiving cell are activated by interactions with ligands expressed on the surface of an opposing, signal-sending cell (termed a trans-interaction). These trans-interactions lead to a sequence of protease mediated cleavages of the Notch receptor. In consequence, the Notch receptor intracellular domain is free to translocate from the membrane to the nucleus, where it partners with the CSL family of transcription factors (RBPJ in humans) and converts them from transcriptional repressors into activators of Notch responsive genes.

Of the human Notch ligands, DLL3 is different in that it seems incapable of activating the Notch receptor via trans-interactions (Ladi et al., 2005). Notch ligands may also interact with Notch receptors in cis (on the same cell) leading to inhibition of the Notch signal, although the exact mechanisms of cis-inhibition remain unclear and may vary depending upon the ligand (for instance, see Klein et al., 1997; Ladi et al., 2005; Glittenberg et al., 2006). Two hypothesized modes of inhibition include modulating Notch signaling at the cell surface by preventing trans-interactions, or by reducing the amount of Notch receptor on the surface of the cell by perturbing the processing of the receptor or by physically causing retention of the receptor in the endoplasmic reticulum or Golgi (Sakamoto et al., 2002; Dunwoodie, 2009). It is clear, however, that stochastic differences in expression of Notch receptors and ligands on neighboring cells can be amplified through both transcriptional and non-transcriptional processes, and subtle balances of cis- and trans-interactions can result in a fine tuning of the Notch mediated delineation of divergent cell fates in neighboring tissues (Sprinzak et al., 2010).

Figure 5:
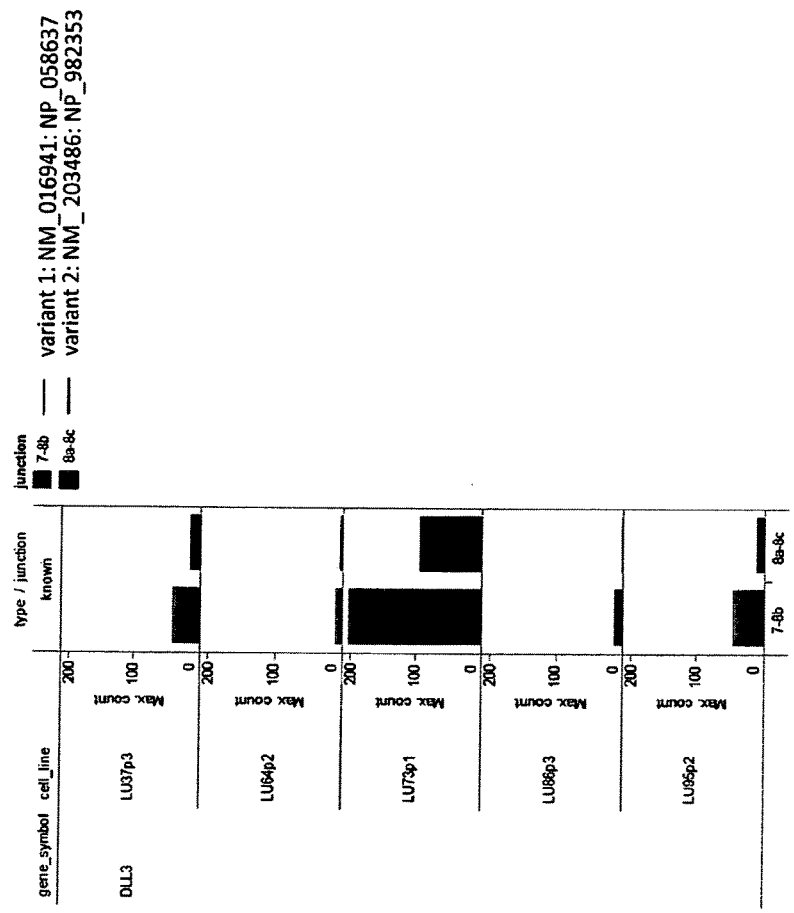
FIG. 5 is a graphical depiction of the relative expression levels of DLL3 mRNA transcript variants 1 and 2 as determined by whole transcriptome (SOLiD) sequencing in selected non-traditional xenograft (NTX) tumors derived from lung cancers.

DLL3 (also known as Delta-like 3 or SCDO1) is a member of the Delta-like family of Notch DSL ligands. Representative DLL3 protein orthologs include, but are not limited to, human (Accession Nos. NP_058637 and NP_982353), chimpanzee (Accession No. XP_003316395), mouse (Accession No. NP_031892), and rat (Accession No. NP_446118). In humans, the DLL3 gene consists of 8 exons spanning 9.5 kBp located on chromosome 19q13. Alternate splicing within the last exon gives rise to two processed transcripts, one of 2389 bases (Accession No. NM_016941; FIG. 1A, SEQ ID NO: 1) and one of 2052 bases (Accession No. NM_203486; FIG. 1B, SEQ ID NO: 2). The former transcript encodes a 618 amino acid protein (Accession No. NP_058637; FIG. 1C, SEQ ID NO: 3), whereas the latter encodes a 587 amino acid protein (Accession No. NP_982353; FIG. 1D, SEQ ID NO: 4). These two protein isoforms of DLL3 share overall 100% identity across their extracellular domains and their transmembrane domains, differing only in that the longer isoform contains an extended cytoplasmic tail containing 32 additional residues at the carboxy terminus of the protein (FIG. 1E). The biological relevance of the isoforms is unclear, although both isoforms can be detected in tumor cells (FIG. 5). Percent identities for each of the members of the delta-like family of proteins in humans are shown in FIG. 2A, as well as cross species identities in FIG. 2B.

In general, DSL ligands are composed of a series of structural domains: a unique N-terminal domain, followed by a conserved DSL domain, multiple tandem epidermal growth factor (EGF)-like repeats, a transmembrane domain, and a cytoplasmic domain not highly conserved across ligands but one which contains multiple lysine residues that are potential sites for ubiquitination by unique E3 ubiquitin ligases. The DSL domain is a degenerate EGF-domain that is necessary but not sufficient for interactions with Notch receptors (Shimizu et al., 1999). Additionally, the first two EGF-like repeats of most DSL ligands contain a smaller protein sequence motif known as a DOS domain that co-operatively interacts with the DSL domain when activating Notch signaling.

FIG. 1F provides a schematic diagram of the extracellular region of the DLL3 protein, illustrating the general juxtaposition of the six EGF-like domains, the single DSL domain and the N-terminal domain. Generally, the EGF domains are recognized as occurring at about amino acid residues 216-249 (domain 1), 274-310 (domain 2), 312-351 (domain 3), 353-389 (domain 4), 391-427 (domain 5) and 429-465 (domain 6), with the DSL domain at about amino acid residues 176-215 and the N-terminal domain at about amino acid residues 27-175 of hDLL3 (SEQ ID NOS: 3 and 4). As discussed in more detail herein and shown in Example 10 below, each of the EGF-like domains, the DSL domain and the N-terminal domain comprise part of the DLL3 protein as defined by a distinct amino acid sequence. Note that, for the purposes of the instant disclosure the respective EGF-like domains may be termed EGF1 to EGF6 with EGF1 being closest to the N-terminal portion of the protein. In regard to the structural composition of the protein one significant aspect of the instant invention is that the disclosed DLL3 modulators may be generated, fabricated, engineered or selected so as to react with a selected domain, motif or epitope. In certain cases such site specific modulators may provide enhanced reactivity and/or efficacy depending on their primary mode of action.

Note that, as used herein the terms "mature protein" or "mature polypeptide" as used herein refers to the form(s) of the protein produced by expression in a mammalian cell. It is generally hypothesized that once export of a growing protein chain across the rough endoplasmic reticulum has been initiated, proteins secreted by mammalian cells have a signal peptide (SP) sequence which is cleaved from the complete polypeptide to produce a "mature" form of the protein. In both isoforms of DLL3 the mature protein comprises a signal peptide of 26 amino acids that may be clipped prior to cell surface expression. Thus, in mature proteins the N-terminal domain will extend from position 27 in the protein until the beginning of the DSL domain. Of course, if the protein is not processed in this manner the N-terminal domain would be held to extend to position one of SEQ ID NOS: 3 & 4.

Of the various Delta-like ligands, DLL3 is the most divergent from the others in the family, since it contains a degenerate DSL domain, no DOS motifs, and an intracellular domain which lacks lysine residues. The degenerate DSL and lack of DOS motifs are consistent with the inability of DLL3 to trigger Notch signaling in trans (between cells), suggesting that DLL3, unlike DLL1 or DLL4, acts only as an inhibitor of Notch signaling (Ladi et al., 2005). Studies have shown that DLL3 may be resident primarily in the cis-Golgi (Geffers et al., 2007), which would be consistent with a hypothesized ability to retain Notch receptor intracellularly, or to interfere with processing of Notch receptors, preventing export to the cell surface and instead retargeting it to the lysosome (Chapman et al., 2011). Some DLL3 protein may appear at the cell surface, however, when the protein is artificially overexpressed in model systems (Ladi et al., 2005), but it is not obvious that this would be the case in normal biological contexts nor in tumors in which the DLL3 mRNA transcript is elevated; somewhat surprisingly, the protein levels detected in tumor types disclosed herein indicate significant DLL3 protein is escaping to the cell surface of various tumors.

Defects in the DLL3 gene have been linked to spondylocostal dysostosis in humans, a severe congenital birth defect resulting in abnormal vertebrae formation and rib abnormalities (Dunwoodie, 2009). This is linked to alterations in Notch signaling, known to play a crucial role in determining the polarity and patterning of somites, the embryonic precursors to the vertebrae that require a finely regulated oscillating interplay between Notch, Wnt, and FGF signaling pathways for proper development (Kageyama et al., 2007; Goldbeter and Pourquie, 2008). Although DLL1 and DLL3 are typically expressed in similar locations within the developing mouse embryo, experiments with transgenic mice have demonstrated that DLL3 does not compensate for DLL1 (Geffers et al., 2007). DLL1 knock-out mice are embryonic lethal, but DLL3 mutant mice do survive yet show a phenotype similar to that found in humans with spondylocostal dysostosis (Kusumi et al., 1998; Shinkai et al., 2004). These results data are consistent with a subtle interplay of Notch trans- and cis-interactions crucial for normal development.

Further, as discussed above Notch signaling plays a role in the development and maintenance of neuroendocrine cells and tumors exhibiting neuroendocrine features. In this regard Notch signaling is involved in a wide range of cell fate decisions in normal endocrine organs and in the diffuse neuroendocrine system. For instance, in the pancreas, Notch signaling is required to suppress the development of a default endocrine phenotype mediated by the bHLH transcription factor NGN3 (Habener et al, 2005). Similar Notch mediated suppression of endocrine cell fates occurs in enteroendocrine cells (Schonhoff et al., 2004), thyroid parafollicular cells (Cook et al., 2010), in specifying the relative ratios of neuroendocrine cell types in the pituitary (Dutta et al., 2011), and is likely involved in decisions of cells within the lungs to adopt a neuroendocrine or non-neuroendocrine phenotype (Chen et al., 1997; Ito et al., 2000; Sriuranpong et al., 2002). Hence it is clear that in many tissues, suppression of Notch signaling is linked to neuroendocrine phenotypes.

Inappropriate reactivation of developmental signaling pathways or disregulation of normal signaling pathways are commonly observed in tumors, and in the case of Notch signaling, have been associated with numerous tumor types (Koch and Radtke, 2010; Harris et al., 2012). The Notch pathway has been studied as an oncogene in lymphomas, colorectal, pancreatic, and some types of non-small cell lung cancer (see Zarenczan and Chen, 2010 and references therein). In contrast, Notch is reported to act as a tumor suppressor in tumors with neuroendocrine features (see Zarenczan and Chen, 2010 supra). Tumors with neuroendocrine features arise infrequently in a wide range of primary sites, and while their exhaustive classification remains problematic (Yao et al., 2008; Klimstra et al., 2010; Klöppel, 2011), they may be classified into four major types: low grade benign carcinoids, low-grade well-differentiated neuroendocrine tumors with malignant behavior, tumors with mixed neuroendocrine and epithelial features, and high-grade poorly differentiated neuroendocrine carcinomas. Of these classifications, the poorly differentiated neuroendocrine carcinomas, which include small cell lung cancer (SCLC) and subsets of non-small cell lung cancer (NSCLC), are cancer types with dismal prognoses. It has been postulated that SCLC is bronchogenic in origin, arising in part from pulmonary neuroendocrine cells (Galluzzo and Bocchetta, 2011). Whatever the specific cellular source of origin for each of these tumors possessing a neuroendocrine phenotype, it may be expected that suppression of Notch signaling, either by direct lesions in the Notch pathway genes themselves, or by activation of other genes that suppress Notch signaling, may lead to the acquisition of the neuroendocrine phenotype of these tumors. By extension, the genes that lead to the perturbation of the Notch pathway may afford therapeutic targets for the treatment of tumors with neuroendocrine phenotypes, particularly for indications that currently have poor clinical outcomes.

ASCL1 is one such gene that appears to interact with Notch signaling pathway via DLL3. It is clear that many neuroendocrine tumors show a poorly differentiated (i.e. partially complete) endocrine phenotype; for instance, marked elevation or expression of various endocrine proteins and polypeptides (e.g. chromogranin A, CHGA; calcitonin, CALCA; propiomelanocorin, POMC; somatostatin, SST), proteins associated with secretory vesicles (e.g., synaptophysin, SYP), and genes involved in the biochemical pathways responsible for the synthesis of bioactive amines (e.g., dopa decarboxylase, DDC). Perhaps not surprisingly, these tumors frequently over-express ASCL1 (also known as mASH1 in mice, or hASH1 in humans), a transcription factor known to play a role in orchestrating gene cascades leading to neural and neuroendocrine phenotypes. Although the specific molecular details of the cascade remain ill-defined, it is increasingly clear that for certain cell types, particularly thyroid parafollicular cells (Kameda et al., 2007), chromaffin cells of the adrenal medulla (Huber et al., 2002) and cells found in the diffuse neuroendocrine system of the lung (Chen et al., 1997; Ito et al., 2000; Sriuranpong et al., 2002), ASCL1 is part of a finely tuned developmental regulatory loop in which cell fate choices are mediated by the balance of ASCL1-mediated and Notch-mediated gene expression cascades (FIG. 3). For instance, ASCL1 was found in to be expressed in normal mouse pulmonary neuroendocrine cells, while the Notch signaling effector HES1, was expressed in pulmonary non-neuroendocrine cells (Ito et al., 2000). That these two cascades are in a fine balance with potential cross-regulation is increasingly appreciated. The Notch effector HES1 has been shown to downregulate ASCL1 expression (Chen et al., 1997; Sriuranpong et al., 2002). These results clearly demonstrate that Notch signaling can suppress neuroendocrine differentiation. However, demonstration that ASCL1 binding to the DLL3 promoter activates DLL3 expression (Henke et al., 2009) and the observation that DLL3 attenuates Notch signaling (Ladi et al., 2005) closes the genetic circuit for cell fate choices between neuroendocrine and non-neuroendocrine phenotypes.

Given that Notch signaling appears to have evolved to amplify subtle differences between neighboring cells to permit sharply bounded tissue domains with divergent differentiation paths (e.g., "lateral inhibition," as described above), these data together suggest that a finely tuned developmental regulatory loop (FIG. 3) has become reactivated and disregulated in cancers with neuroendocrine phenotypes. While it is not obvious that DLL3 would provide a suitable cell surface target for the development of antibody therapeutics given its normal residence within interior membranous compartments of the cell (Geffers et al., 2007) and its presumed interactions with Notch therein, it is possible that the resultant elevation of DLL3 expression in neuroendocrine tumors may offer a unique therapeutic target for tumors with the neuroendocrine phenotype (e.g., NETs and pNETs). It is commonly observed that vast overexpression of proteins in laboratory systems may cause mislocalization of the overexpressed protein within the cell. Therefore it is a reasonable hypothesis, yet not obvious without experimental verification, that overexpression of DLL3 in tumors may lead to some cell surface expression of the protein, and thereby present a target for the development of antibody therapeutics.

III. Cancer Stem Cells

As alluded to above it has surprisingly been discovered that aberrant DLL3 expression (genotypic and/or phenotypic) is associated with various tumorigenic cell subpopulations. In this respect the present invention provides DLL3 modulators that may be particularly useful for targeting such cells, and especially tumor perpetuating cells, thereby facilitating the treatment, management or prevention of neoplastic disorders. Thus, in preferred embodiments modulators of DLL3 determinants (phenotypic or genotypic) may be advantageously be used to reduce tumor initiating cell frequency in accordance with the present teachings and thereby facilitate the treatment or management of proliferative disorders.

For the purposes of the instant application the term "tumor initiating cell" (TIC) encompasses both "tumor perpetuating cells" (TPC; i.e., cancer stem cells or CSC) and highly proliferative "tumor progenitor cells" (termed TProg), which together generally comprise a unique subpopulation (i.e. 0.1-40%) of a bulk tumor or mass. For the purposes of the instant disclosure the terms "tumor perpetuating cells" and "cancer stem cells" or "neoplastic stem cells" are equivalent and may be used interchangeably herein. TPC differ from TProg in that TPC can completely recapitulate the composition of tumor cells existing within a tumor and have unlimited self-renewal capacity as demonstrated by serial transplantation (two or more passages through mice) of low numbers of isolated cells, whereas TProg will not display unlimited self-renewal capacity.

Those skilled in the art will appreciate that fluorescence-activated cell sorting (FACS) using appropriate cell surface markers is a reliable method to isolate highly enriched cancer stem cell subpopulations (e.g., >99.5% purity) due, at least in part, to its ability to discriminate between single cells and clumps of cells (i.e. doublets, etc.). Using such techniques it has been shown that when low cell numbers of highly purified TProg cells are transplanted into immunocompromised mice they can fuel tumor growth in a primary transplant. However, unlike purified TPC subpopulations the TProg generated tumors do not completely reflect the parental tumor in phenotypic cell heterogeneity and are demonstrably inefficient at reinitiating serial tumorigenesis in subsequent transplants. In contrast, TPC subpopulations completely reconstitute the cellular heterogeneity of parental tumors and can efficiently initiate tumors when serially isolated and transplanted. Thus, those skilled in the art will recognize that a definitive difference between TPC and TProg, though both may be tumor generating in primary transplants, is the unique ability of TPC to perpetually fuel heterogeneous tumor growth upon serial transplantation at low cell numbers. Other common approaches to characterize TPC involve morphology and examination of cell surface markers, transcriptional profile, and drug response although marker expression may change with culture conditions and with cell line passage in vitro.

Accordingly, for the purposes of the instant invention tumor perpetuating cells, like normal stem cells that support cellular hierarchies in normal tissue, are preferably defined by their ability to self-renew indefinitely while maintaining the capacity for multilineage differentiation. Tumor perpetuating cells are thus capable of generating both tumorigenic progeny (i.e., tumor initiating cells: TPC and TProg) and non-tumorigenic (NTG) progeny. As used herein a "non-tumorigenic cell" (NTG) refers to a tumor cell that arises from tumor initiating cells, but does not itself have the capacity to self-renew or generate the heterogeneous lineages of tumor cells that comprise a tumor. Experimentally, NTG cells are incapable of reproducibly forming tumors in mice, even when transplanted in excess cell numbers.

As indicated, TProg are also categorized as tumor initiating cells (or TIC) due to their limited ability to generate tumors in mice. TProg are progeny of TPC and are typically capable of a finite number of non-self-renewing cell divisions. Moreover, TProg cells may further be divided into early tumor progenitor cells (ETP) and late tumor progenitor cells (LTP), each of which may be distinguished by phenotype (e.g., cell surface markers) and different capacities to recapitulate tumor cell architecture. In spite of such technical differences, both ETP and LTP differ functionally from TPC in that they are generally less capable of serially reconstituting tumors when transplanted at low cell numbers and typically do not reflect the heterogeneity of the parental tumor. Notwithstanding the foregoing distinctions, it has also been shown that various TProg populations can, on rare occasion, gain self-renewal capabilities normally attributed to stem cells and themselves become TPC (or CSC). In any event both types of tumor-initiating cells are likely represented in the typical tumor mass of a single patient and are subject to treatment with the modulators as disclosed herein. That is, the disclosed compositions are generally effective in reducing the frequency or altering the chemosensitivity of such DLL3 positive tumor initiating cells regardless of the particular embodiment or mix represented in a tumor.

In the context of the instant invention, TPC are more tumorigenic, relatively more quiescent and often more chemoresistant than the TProg (both ETP and LTP), NTG cells and the tumor-infiltrating non-TPC derived cells (e.g., fibroblasts/stroma, endothelial & hematopoietic cells) that comprise the bulk of a tumor. Given that conventional therapies and regimens have, in large part, been designed to both debulk tumors and attack rapidly proliferating cells, TPC are likely to be more resistant to conventional therapies and regimens than the faster proliferating TProg and other bulk tumor cell populations. Further, TPC often express other characteristics that make them relatively chemoresistant to conventional therapies, such as increased expression of multi-drug resistance transporters, enhanced DNA repair mechanisms and anti-apoptotic proteins. These properties, each of which contribute to drug tolerance by TPC, constitute a key reason for the failure of standard oncology treatment regimens to ensure long-term benefit for most patients with advanced stage neoplasia; i.e. the failure to adequately target and eradicate those cells that fuel continued tumor growth and recurrence (i.e. TPC or CSC).

Unlike many prior art treatments, the novel compositions of the present invention preferably reduce the frequency of tumor initiating cells upon administration to a subject regardless of the form or specific target (e.g., genetic material, DLL3 antibody or ligand fusion construct) of the selected modulator. As noted above, the reduction in tumor initiating cell frequency may occur as a result of a) elimination, depletion, sensitization, silencing or inhibition of tumor initiating cells; b) controlling the growth, expansion or recurrence of tumor initiating cells; c) interrupting the initiation, propagation, maintenance, or proliferation of tumor initiating cells; or d) by otherwise hindering the survival, regeneration and/or metastasis of the tumorigenic cells. In some embodiments, the reduction in the frequency of tumor initiating cells occurs as a result of a change in one or more physiological pathways. The change in the pathway, whether by reduction or elimination of the tumor initiating cells or by modifying their potential (e.g., induced differentiation, niche disruption) or otherwise interfering with their ability to influence the tumor environment or other cells, in turn allows for the more effective treatment of DLL3 associated disorders by inhibiting tumorigenesis, tumor maintenance and/or metastasis and recurrence.

Among art-recognized methods that can be used to assess such a reduction in the frequency of tumor initiating cells is limiting dilution analysis either in vitro or in vivo, preferably followed by enumeration using Poisson distribution statistics or assessing the frequency of predefined definitive events such as the ability to generate tumors in vivo or not. While such limiting dilution analysis comprise preferred methods of calculating reduction of tumor initiating cell frequency other, less demanding methods, may also be used to effectively determine the desired values, albeit slightly less accurately, and are entirely compatible with the teachings herein. Thus, as will be appreciated by those skilled in the art, it is also possible to determine reduction of frequency values through well-known flow cytometric or immunohistochemical means. As to all the aforementioned methods see, for example, Dylla et al. 2008, PMID: 18560594 & Hoey et al. 2009, PMID: 19664991; each of which is incorporated herein by reference in its entirety and, in particular, for the disclosed methods.

With respect to limiting dilution analysis, in vitro enumeration of tumor initiating cell frequency may be accomplished by depositing either fractionated or unfractionated human tumor cells (e.g. from treated and untreated tumors, respectively) into in vitro growth conditions that foster colony formation. In this manner, colony forming cells might be enumerated by simple counting and characterization of colonies, or by analysis consisting of, for example, the deposition of human tumor cells into plates in serial dilutions and scoring each well as either positive or negative for colony formation at least 10 days after plating. In vivo limiting dilution experiments or analyses, which are generally more accurate in their ability to determine tumor initiating cell frequency encompass the transplantation of human tumor cells, from either untreated control or treated populations, for example, into immunocompromised mice in serial dilutions and subsequently scoring each mouse as either positive or negative for tumor formation at least 60 days after transplant. The derivation of cell frequency values by limiting dilution analysis in vitro or in vivo is preferably done by applying Poisson distribution statistics to the known frequency of positive and negative events, thereby providing a frequency for events fulfilling the definition of a positive event; in this case, colony or tumor formation, respectively.

As to other methods compatible with the instant invention that may be used to calculate tumor initiating cell frequency, the most common comprise quantifiable flow cytometric techniques and immunohistochemical staining procedures. Though not as precise as the limiting dilution analysis techniques described immediately above, these procedures are much less labor intensive and provide reasonable values in a relatively short time frame. Thus, it will be appreciated that a skilled artisan may use flow cytometric cell surface marker profile determination employing one or more antibodies or reagents that bind art-recognized cell surface proteins known to enrich for tumor initiating cells (e.g., potentially compatible markers as are set forth in PCT application 2012/031280 which is incorporated herein in its entirety) and thereby measure TIC levels from various samples. In still another compatible method one skilled in the art might enumerate TIC frequency in situ (e.g., in a tissue section) by immunohistochemistry using one or more antibodies or reagents that are able to bind cell surface proteins thought to demarcate these cells.

Those skilled in the art will recognize that numerous markers (or their absence) have been associated with various populations of cancer stem cells and used to isolate or characterize tumor cell subpopulations. In this respect exemplary cancer stem cell markers comprise OCT4, Nanog, STAT3, EPCAM, CD24, CD34, NB84, TrkA, GD2, CD133, CD20, CD56, CD29, B7H3, CD46, transferrin receptor, JAM3, carboxypeptidase M, ADAM9, oncostatin M, Lgr5, Lgr6, CD324, CD325, nestin, Sox1, Bmi-1, eed, easyh1, easyh2, mf2, yy1, smarcA3, smarckA5, smarcD3, smarcE1, mllt3, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4) SLC7A8, IL1RAP, TEM8, TMPRSS4, MUC16, GPRC5B, SLC6A14, SLC4A11, PPAP2C, CAV1, CAV2, PTPN3, EPHA1, EPHA2, SLC1A1, CX3CL1, ADORA2A, MPZL1, FLJ10052, C4.4A, EDG3, RARRES1, TMEPAI, PTS, CEACAM6, NID2, STEAP, ABCA3, CRIM1, IL1R1, OPN3, DAF, MUC1, MCP, CPD, NMA, ADAM9, GJA1, SLC19A2, ABCA1, PCDH7, ADCY9, SLC39A1, NPC1, ENPP1, N33, GPNMB, LY6E, CELSR1, LRP3, C20orf52, TMIEPAI, FLVCR, PCDHA10, GPR54, TGFBR3, SEMA4B, PCDHB2, ABCG2, CD166, AFP, BMP-4, β-catenin, CD2, CD3, CD9, CD14, CD31, CD38, CD44, CD45, CD74, CD90, CXCR4, decorin, EGFR, CD105, CD64, CD16, CD16a, CD16b, GLI1, GLI2, CD49b, and CD49f. See, for example, Schulenburg et al., 2010, PMID: 20185329, U.S. Pat. No. 7,632,678 and U.S.P.Ns. 2007/0292414, 2008/0175870, 2010/0275280, 2010/0162416 and 2011/0020221 each of which is incorporated herein by reference. It will further be appreciated that each of the aforementioned markers may also be used as a secondary target antigen in the context of the bispecific or multispecific antibodies of the instant invention.

Similarly, non-limiting examples of cell surface phenotypes associated with cancer stem cells of certain tumor types include $CD44^{hi}CD24^{low}$, $ALDH^+$, $CD133^+$, $CD123^+$, $CD34^+CD38^-$, $CD44^+CD24^-$, $CD46^{hi}CD324^+CD66c^-$, $CD133^+$ $CD34^+CD10^-CD19^-$, $CD138^-CD34^-CD19^+$, $CD133^+RC2^+$, $CD44^+\alpha_2\beta_1^{hi}CD133^+$, $CD44^+CD24^+ESA^+$, $CD271^+$, $ABCB5^+$ as well as other cancer stem cell surface phenotypes that are known in the art. See, for example, Schulenburg et al., 2010, supra, Visvader et al., 2008, PMID: 18784658 and U.S.P.N. 2008/0138313, each of which is incorporated herein in its entirety by reference. Those skilled in the art will appreciate that marker phenotypes such as those exemplified immediately above may be used in conjunction with standard flow cytometric analysis and cell sorting techniques to characterize, isolate, purify or enrich TIC and/or TPC cells or cell populations for further analysis. Of interest with regard to the instant invention CD46, CD324 and, optionally, CD66c are either highly or heterogeneously expressed on the surface of many human colorectal ("CR"), breast ("BR"), non-small cell lung (NSCLC), small cell lung (SCLC), pancreatic ("PA"), melanoma ("Mel"), ovarian ("OV"), and head and neck cancer ("HN") tumor cells, regardless of whether the tumor specimens being analyzed were primary patient tumor specimens or patient-derived NTX tumors.

Using any of the above-referenced methods and selected markers as known in the art (and shown in Example 17 below) it is then possible to quantify the reduction in frequency of TIC (or the TPC therein) provided by the disclosed DLL3 modulators (including those conjugated to cytotoxic agents) in accordance with the teachings herein. In some instances, the compounds of the instant invention may reduce the frequency of TIC or TPC (by a variety of mechanisms noted above, including elimination, induced differentiation, niche disruption, silencing, etc.) by 10%, 15%, 20%, 25%, 30% or even by 35%. In other embodiments, the reduction in frequency of TIC or TPC may be on the order of 40%, 45%, 50%, 55%, 60% or 65%. In certain embodiments, the disclosed compounds my reduce the frequency of TIC or TPC by 70%, 75%, 80%, 85%, 90% or even 95%. Of course it will be appreciated that any reduction of the frequency of the TIC or TPC likely results in a corresponding reduction in the tumorigenicity, persistence, recurrence and aggressiveness of the neoplasia.

IV. DLL3 Modulators

In any event, the present invention is directed to the use of DLL3 modulators, including DLL3 antagonists, for the diagnosis, theragnosis, treatment and/or prophylaxis of various disorders including any one of a number of DLL3 associated malignancies. The disclosed modulators may be used alone or in conjunction with a wide variety of anti-cancer compounds such as chemotherapeutic or immunotherapeutic agents (e.g., therapeutic antibodies) or biological response modifiers. In other selected embodiments, two or more discrete DLL3 modulators may be used in combination to provide enhanced anti-neoplastic effects or may be used to fabricate multispecific constructs.

In certain embodiments, the DLL3 modulators of the present invention will comprise nucleotides, oligonucleotides, polynucleotides, peptides or polypeptides. More particularly, exemplary modulators of the invention may comprise antibodies and antigen-binding fragments or derivatives thereof, proteins, peptides, glycoproteins, glycopeptides, glycolipids, polysaccharides, oligosaccharides, nucleic acids, antisense constructs, siRNA, miRNA, bioorganic molecules, peptidomimetics, pharmacological agents and their metabolites, transcriptional and translation control sequences, and the like. In certain embodiments the modulators will comprise soluble DLL3 (sDLL3) or a form, variant, derivative or fragment thereof including, for example, DLL3 fusion constructs (e.g., DLL3-Fc, DLL3-targeting moiety, etc.) or DLL3-conjugates (e.g., DLL3-PEG, DLL3-cytotoxic agent, DLL3-brm, etc.). In other preferred embodiments the DLL3 modulators comprise antibodies or immunoreactive fragments or derivatives thereof. In particularly preferred embodiments the modulators of the instant invention will comprise neutralizing, depleting or internalizing antibodies or derivatives or fragments thereof. Moreover, as with the aforementioned fusion constructs, such antibody modulators may be conjugated, linked or otherwise associated with selected cytotoxic agents, polymers, biological response modifiers (BRMs) or the like to provide directed immunotherapies with various (and optionally multiple) mechanisms of action. As alluded to above such antibodies may be pan-DLL antibodies and associate with two or more DLL family members or, in the alternative, comprise antigen binding molecules that selectively react with one or both isoforms of DLL3. In yet other preferred embodiments the modulators may operate on the genetic level and may comprise compounds as antisense constructs, siRNA, miRNA and the like that interact or associate with the genotypic component of a DLL3 determinant.

It will further be appreciated that the disclosed DLL3 modulators may deplete, silence, neutralize, eliminate or inhibit growth, propagation or survival of tumor cells, including TPC, and/or associated neoplasia through a variety of mechanisms, including agonizing or antagonizing selected pathways or eliminating specific cells depending, for example, on the form of DLL3 modulator, any associated payload or dosing and method of delivery. Thus, while preferred embodiments disclosed herein are directed to the depletion, inhibition or silencing of specific tumor cell subpopulations such as tumor perpetuating cells or to modulators that interact with a specific epitope or domain, it must be emphasized that such embodiments are merely illustrative and not limiting in any sense. Rather, as set forth in the appended claims, the present invention is broadly directed to DLL3 modulators and their use in the treatment, management or prophylaxis of various DLL3 associated disorders irrespective of any particular mechanism, binding region or target tumor cell population.

Regardless of the form of the modulator selected it will be appreciated that the chosen compound may be antagonistic in nature. As used herein an "antagonist" refers to a molecule capable of neutralizing, blocking, inhibiting, abrogating, reducing or interfering with the activities of a particular or specified target (e.g., DLL3), including the binding of receptors to ligands or the interactions of enzymes with substrates. In this respect it will be appreciated that DLL3 antagonists of the instant invention may comprise any ligand, polypeptide, peptide, fusion protein, antibody or immunologically active fragment or derivative thereof that recognizes, reacts, binds, combines, competes, associates or otherwise interacts with the DLL3 protein or fragment thereof and eliminates, silences, reduces, inhibits, hinders, restrains or controls the growth of tumor initiating cells or other neoplastic cells including bulk tumor or NTG cells. Compatible antagonists may further include small molecule inhibitors, aptamers, antisense constructs, siRNA, miRNA and the like, receptor or ligand molecules and derivatives thereof which recognize or associate with a DLL3 genotypic or phenotypic determinant thereby altering expression patterns or sequestering its binding or interaction with a substrate, receptor or ligand.

As used herein and applied to two or more molecules or compounds, the terms "recognizes" or "associates" shall be held to mean the reaction, binding, specific binding, combination, interaction, connection, linkage, uniting, coalescence, merger or joining, covalently or non-covalently, of the molecules whereby one molecule exerts an effect on the other molecule.

Moreover, as demonstrated in the examples herein (e.g., see FIG. 2B), some modulators of human DLL3 may, in certain cases, cross-react with DLL3 from a species other than human (e.g., murine). In other cases exemplary modulators may be specific for one or more isoforms of human DLL3 and will not exhibit cross-reactivity with DLL3 orthologs from other species. Of course, in conjunction with the teachings herein such embodiments may comprise pan-DLL antibodies that associate with two or more DLL family members from a single species or antibodies that exclusively associate with DLL3.

In any event, and as will be discussed in more detail below, those skilled in the art will appreciate that the disclosed modulators may be used in a conjugated or unconjugated form. That is, the modulator may be associated with or conjugated to (e.g. covalently or non-covalently) pharmaceutically active compounds, biological response modifiers, anti-cancer agents, cytotoxic or cytostatic agents, diagnostic moieties or biocompatible modifiers. In this respect it will be understood that such conjugates may comprise peptides, polypeptides, proteins, fusion proteins, nucleic acid molecules, small molecules, mimetic agents, synthetic drugs, inorganic molecules, organic molecules and radioisotopes. Moreover, as indicated herein the selected conjugate may be covalently or non-covalently linked to the DLL3 modulator in various molar ratios depending, at least in part, on the method used to effect the conjugation.

V. Modulator Fabrication and Supply

A. Antibody Modulators

1. Overview

As previously alluded to particularly preferred embodiments of the instant invention comprise DLL3 modulators in the form of antibodies that preferentially associate with one or more domains of an isoform of DLL3 protein and, optionally, other DLL family members. Those of ordinary skill in the art will appreciate the well developed knowledge base on antibodies such as set forth, for example, in Abbas et al., Cellular and Molecular Immunology, 6$^{th}$ ed., W.B. Saunders Company (2010) or Murphey et al., Janeway's Immunobiology, 8$^{th}$ ed., Garland Science (2011), each of which is incorporated herein by reference in its entirety.

The term "antibody" is intended to cover polyclonal antibodies, multiclonal antibodies, monoclonal antibodies, chimeric antibodies, humanized and primatized antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof; antibody fragments such as Fab fragments, F(ab') fragments, single-chain FvFcs, single-chain Fvs; and derivatives thereof including Fc fusions and other modifications, and any other immunologically active molecule so long as they exhibit the desired biological activity (i.e., antigen association or binding). Moreover, the term further comprises all classes of antibodies (i.e. IgA, IgD, IgE, IgG, and IgM) and all isotypes (i.e., IgG1, IgG2, IgG3, IgG4, IgA1, and IgA2), as well as variations thereof unless otherwise dictated by context. Heavy-chain constant domains that correspond to the different classes of antibodies are denoted by the corresponding lower case Greek letter α, δ, ε, γ, and μ, respectively. Light chains of the antibodies from any vertebrate species can be assigned to one of two clearly distinct types, called kappa (κ) and lambda (λ), based on the amino acid sequences of their constant domains.

While all such antibodies are within the scope of the present invention, preferred embodiments comprising the IgG class of immunoglobulin will be discussed in some detail herein solely for the purposes of illustration. It will be understood that such disclosure is, however, merely demonstrative of exemplary compositions and methods of practicing the present invention and not in any way limiting of the scope of the invention or the claims appended hereto.

As is well known, the variable domains of both the light ($V_L$) and heavy ($V_H$) chain portions determine antigen recognition and specificity and the constant domains of the light chain ($C_L$) and the heavy chain ($C_H1$, $C_H2$ or $C_H3$) confer and regulate important biological properties such as secretion, transplacental mobility, circulation half-life, complement binding, and the like.

The "variable" region includes hypervariable sites that manifest themselves in three segments commonly termed complementarity determining regions (CDRs), in both the light-chain and the heavy-chain variable domains. The more highly conserved portions of variable domains flanking the CDRs are termed framework regions (FRs). For example, in naturally occurring monomeric immunoglobulin G (IgG) antibodies, the six CDRs present on each arm of the "Y" are short, non-contiguous sequences of amino acids that are specifically positioned to form the antigen binding site as the antibody assumes its three dimensional configuration in an aqueous environment. Thus, each naturally occurring IgG antibody comprises two identical binding sites proximal to the amino-terminus of each arm of the Y.

It will be appreciated that the position of CDRs can be readily identified by one of ordinary skill in the art using standard techniques. Also familiar to those in the art is the numbering system described in Kabat et al. (1991, NIH Publication 91-3242, National Technical Information Service, Springfield, Va.). In this regard Kabat et al. defined a numbering system for variable domain sequences that is applicable to any antibody. One of ordinary skill in the art can unambiguously assign this system of "Kabat numbering" to any variable domain sequence, without reliance on any experimental data beyond the sequence itself. Unless otherwise specified, references to the numbering of specific amino acid residue positions in an antibody are according to the Kabat numbering system.

Thus, according to Kabat, in the $V_H$, residues 31-35 comprise CDR1, residues 50-65 make up CDR2, and 95-102 comprise CDR3, while in the $V_L$, residues 24-34 are CDR1, 50-56 comprise CDR2, and 89-97 make up CDR3. For context, in a $V_H$, FR1 corresponds to the domain of the variable region encompassing amino acids 1-30; FR2 corresponds to the domain of the variable region encompassing amino acids 36-49; FR3 corresponds to the domain of the variable region encompassing amino acids 66-94, and FR4 corresponds to the domain of the variable region from amino acids 103 to the end of the variable region. The FRs for the light chain are similarly separated by each of the light chain variable region CDRs.

Note that CDRs vary considerably from antibody to antibody (and by definition will not exhibit homology with the Kabat consensus sequences). In addition, the identity of certain individual residues at any given Kabat site number may vary from antibody chain to antibody chain due to interspecies or allelic divergence. Alternative numbering is set forth in Chothia et al., J. Mol. Biol. 196:901-917 (1987) and MacCallum et al., J. Mol. Biol. 262:732-745 (1996), although as in Kabat, the FR boundaries are separated by the respective CDR termini as described above. See also Chothia et al., Nature 342, pp. 877-883 (1989) and S. Dubel, ed., Handbook of Therapeutic Antibodies, 3$^{rd}$ ed., WILEY-VCH Verlag GmbH and Co. (2007), where the definitions include overlapping or subsets of amino acid residues when compared against each other. Each of the aforementioned references is incorporated herein by reference in its entirety and the amino acid residues which comprise binding regions or CDRs as defined by each of the above cited references and are set forth for comparison below.

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 50-58 | 47-58 |
| $V_H$ CDR3 | 95-102 | 95-102 | 93-101 |
| $V_L$ CDR1 | 24-34 | 23-34 | 30-36 |
| $V_L$ CDR2 | 50-56 | 50-56 | 46-55 |
| $V_L$ CDR3 | 89-97 | 89-97 | 89-96 |

[1]Residue numbering follows the nomenclature of Kabat et at, supra
[2]Residue numbering follows the nomenclature of Chothia et at, supra
[3]Residue numbering follows the nomenclature of MacCallum et al., supra In the context of the instant invention it will be appreciated that any of the disclosed light and heavy chain CDRs derived from the murine variable region amino acid sequences set forth in FIG. 11A or FIG. 11B may be combined or rearranged to provide optimized anti-DLL3 (e.g. humanized or chimeric anti-hDLL3) antibodies in accordance with the instant teachings. That is, one or more of the CDRs derived from the contiguous light chain variable region amino acid sequences set forth in FIG. 11A (SEQ ID NOS: 20-202, even numbers) or the contiguous heavy chain variable region amino acid sequences set forth in FIG. 11B (SEQ ID NOS: 21-203, odd numbers) may be incorporated in a DLL3 modulator and, in particularly preferred embodiments, in a CDR grafted or humanized antibody that immunospecifically associates with one or more DLL3 isoforms. Examples of light (SEQ ID NOS: 204-212, even numbers) and heavy (SEQ ID NOS: 205-213, odd numbers) chain variable region amino acid sequences of such humanized modulators are also set forth in FIGS. 11A and 11B. Taken together these novel amino acid sequences depict ninety-two murine and five humanized exemplary modulators in accordance with the instant invention. Moreover, corresponding nucleic acid sequences of each of the ninety-two exemplary murine modulators and five humanized modulators set forth in FIGS. 11A and 11B are included in the sequence listing appended to the instant application (SEQ ID NOS: 220-413).

In FIGS. 11A and 11B the annotated CDRs are defined using Chothia numbering. However, as discussed herein and demonstrated in Example 8 below, one skilled in the art could readily define, identify, derive and/or enumerate the CDRs as defined by Kabat et al., Chothia et al. or MacCallum et al. for each respective heavy and light chain sequence set forth in FIG. 11A or FIG. 11B. Accordingly, each of the subject CDRs and antibodies comprising CDRs defined by all such nomenclature are expressly included within the scope of the instant invention. More broadly, the terms "variable region CDR amino acid residue" or more simply "CDR" includes amino acids in a CDR as identified using any sequence or structure based method as set forth above.

2. Antibody Modulator Generation a. Polyclonal Antibodies

The production of polyclonal antibodies in various host animals, including rabbits, mice, rats, etc. is well known in the art. In some embodiments, polyclonal anti-DLL3 antibody-containing serum is obtained by bleeding or sacrificing the animal. The serum may be used for research purposes in the form obtained from the animal or, in the alternative, the anti-DLL3 antibodies may be partially or fully purified to provide immunoglobulin fractions or homogeneous antibody preparations.

Briefly the selected animal is immunized with a DLL3 immunogen (e.g., soluble DLL3 or sDLL3) which may, for example, comprise selected isoforms, domains and/or peptides, or live cells or cell preparations expressing DLL3 or immunoreactive fragments thereof. Art known adjuvants that may be used to increase the immunological response, depending on the inoculated species include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants may protect the antigen from rapid dispersal by sequestering it in a local deposit, or they may contain substances that stimulate the host to secrete factors that are chemotactic for macrophages and other components of the immune system. Preferably the immunization schedule will involve two or more administrations of the selected immunogen spread out over a predetermined period of time.

The amino acid sequence of a DLL3 protein as shown in FIG. 1C or 1D can be analyzed to select specific regions of the DLL3 protein for generating antibodies. For example, hydrophobicity and hydrophilicity analyses of a DLL3 amino acid sequence are used to identify hydrophilic regions in the DLL3 structure. Regions of a DLL3 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each DLL3 region, domain or motif identified by any of these programs or methods is within the scope of the present invention and may be isolated or engineered to provide immunogens giving rise to modulators comprising desired properties. Preferred methods for the generation of DLL3 antibodies are further illustrated by way of the Examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents are effective. Administration of a DLL3 immunogen is often conducted by injection over a suitable time period and with use of a suitable adjuvant, as is understood in the art. During the immunization schedule, titers of antibodies can be taken as described in the Examples below to determine adequacy of antibody formation.

b. Monoclonal Antibodies

In addition, the invention contemplates use of monoclonal antibodies. As known in the art, the term "monoclonal antibody" (or mAb) refers to an antibody obtained from a population of substantially homogeneous antibodies, i.e., the individual antibodies comprising the population are identical except for possible mutations (e.g., naturally occurring mutations), that may be present in minor amounts. In certain embodiments, such a monoclonal antibody includes an antibody comprising a polypeptide sequence that binds or associates with an antigen wherein the antigen-binding polypeptide sequence was obtained by a process that includes the selection of a single target binding polypeptide sequence from a plurality of polypeptide sequences.

More generally, and as exemplified in Example 6 herein, monoclonal antibodies can be prepared using a wide variety of techniques known in the art including hybridoma, recombinant techniques, phage display technologies, transgenic animals (e.g., a XenoMouse®) or some combination thereof. For example, monoclonal antibodies can be produced using hybridoma and art-recognized biochemical and genetic engineering techniques such as described in more detail in An, Zhigiang (ed.) *Therapeutic Monoclonal Antibodies: From Bench to Clinic*, John Wiley and Sons, $1^{st}$ ed. 2009; Shire et. al. (eds.) *Current Trends in Monoclonal Antibody Development and Manufacturing*, Springer Science+Business Media LLC, $1^{st}$ ed. 2010; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N.Y., 1981) each of which is incorporated herein in its entirety by reference. It should be understood that a selected binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also an antibody of this invention.

c. Chimeric Antibodies

In another embodiment, the antibody of the invention may comprise chimeric antibodies derived from covalently joined protein segments from at least two different species or types of antibodies. As known in the art, the term "chimeric" antibodies is directed to constructs in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)).

In one embodiment, a chimeric antibody in accordance with the teachings herein may comprise murine $V_H$ and $V_L$ amino acid sequences and constant regions derived from human sources. In other compatible embodiments a chimeric antibody of the present invention may comprise a humanized antibody as described below. In another embodiment, the so-called "CDR-grafted" antibody, the antibody comprises one or more CDRs from a particular species or belonging to a particular antibody class or subclass, while the remainder of the antibody chain(s) is/are identical with or homologous to a corresponding sequence in antibodies derived from another species or belonging to another antibody class or subclass. For use in humans, selected rodent CDRs may be grafted into a human antibody, replacing one or more of the naturally occurring variable regions or CDRs of the human antibody. These constructs generally have the advantages of providing full strength modulator functions (e.g., CDC (complement dependent cytotoxicity), ADCC (antibody-dependent cell-mediated cytotoxicity), etc.) while reducing unwanted immune responses to the antibody by the subject.

d. Humanized Antibodies

Similar to the CDR-grafted antibody is a "humanized" antibody. As used herein, "humanized" forms of non-human (e.g., murine) antibodies are chimeric antibodies that contain a minimal sequence derived from one or more non-human immunoglobulins. In one embodiment, a humanized antibody is a human immunoglobulin (recipient or acceptor antibody) in which residues from a CDR of the recipient are replaced by residues from a CDR of a non-human species (donor antibody) such as mouse, rat, rabbit, or nonhuman primate having the desired specificity, affinity, and/or capacity. In certain preferred embodiments, residues in one or more FRs in the variable domain of the human immunoglobulin are replaced by corresponding non-human residues from the donor antibody to help maintain the appropriate three-dimensional configuration of the grafted CDR(s) and thereby improve affinity. Furthermore, humanized antibodies may comprise residues that are not found in the recipient antibody or in the donor antibody to, for example, further refine antibody performance.

CDR grafting and humanized antibodies are described, for example, in U.S. Pat. Nos. 6,180,370 and 5,693,762. The humanized antibody optionally may also comprise at least a portion of an immunoglobulin Fc, typically that of a human immunoglobulin. For further details, see, e.g., Jones et al., *Nature* 321:522-525 (1986); and U.S. Pat. Nos. 6,982,321 and 7,087,409. Still another method is termed "humaneering" which is described, for example, in U.S.P.N. 2005/0008625. Additionally, a non-human antibody may also be modified by specific deletion of human T-cell epitopes or "deimmunization" by the methods disclosed in WO 98/52976 and WO 00/34317. Each of the aforementioned references are incorporated herein in their entirety.

Humanized antibodies may also be bioengineered using common molecular biology techniques, such as isolating, manipulating, and expressing nucleic acid sequences that encode all or part of immunoglobulin variable regions from at least one of a heavy or light chain. In addition to the sources of such nucleic acid noted above, human germline sequences are available as disclosed, for example, in Tomlinson, I. A. et al. (1992) *J. Mol. Biol.* 227:776-798; Cook, G. P. et al. (1995) *Immunol. Today* 16: 237-242; Chothia, D. et al. (1992) *J. Mol. Biol.* 227:799-817; and Tomlinson et al. (1995) *EMBO J* 14:4628-4638. The V-BASE directory (VBASE2—Retter et al., *Nucleic Acid Res.* 33; 671-674, 2005) provides a comprehensive directory of human immunoglobulin variable region sequences (compiled by Tomlinson, I. A. et al. MRC Centre for Protein Engineering, Cambridge, UK). Consensus human FRs can also be used, e.g., as described in U.S. Pat. No. 6,300,064.

In selected embodiments, and as detailed in Example 8 below, at least 60%, 65%, 70%, 75%, or 80% of the humanized or CDR grafted antibody heavy or light chain variable region amino acid residues will correspond to those of the recipient human FR and CDR sequences. In other embodiments at least 85% or 90% of the humanized antibody variable region residues will correspond to those of the recipient FR and CDR sequences. In a further preferred embodiment, greater than 95% of the humanized antibody variable region residues will correspond to those of the recipient FR and CDR sequences.

e. Human Antibodies

In another embodiment, the antibodies may comprise fully human antibodies. The term "human antibody" refers to an antibody which possesses an amino acid sequence that corresponds to that of an antibody produced by a human and/or has been made using any of the techniques for making human antibodies.

Human antibodies can be produced using various techniques known in the art. One technique is phage display in which a library of (preferably human) antibodies is synthesized on phages, the library is screened with the antigen of interest or an antibody-binding portion thereof; and the phage that binds the antigen is isolated, from which one may obtain the immunoreactive fragments. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; and Barbas et al., *Proc. Natl. Acad. Sci. USA* 88:7978-7982 (1991)).

In one embodiment, recombinant human antibodies may be isolated by screening a recombinant combinatorial antibody library prepared as above. In one embodiment, the library is a scFv phage display library, generated using human $V_L$ and $V_H$ cDNAs prepared from mRNA isolated from B-cells.

The antibodies produced by naive libraries (either natural or synthetic) can be of moderate affinity ($K_a$ of about $10^6$ to $10^7$ $M^{-1}$), but affinity maturation can also be mimicked in vitro by constructing and reselecting from secondary libraries as described in the art. For example, mutation can be introduced at random in vitro by using error-prone polymerase (reported in Leung et al., *Technique*, 1: 11-15 (1989)). Additionally, affinity maturation can be performed by randomly mutating one or more CDRs, e.g. using PCR with primers carrying random sequence spanning the CDR of interest, in selected individual Fv clones and screening for higher-affinity clones. WO 9607754 described a method for inducing mutagenesis in a CDR of an immunoglobulin light chain to create a library of light chain genes. Another effective approach is to recombine the $V_H$ or $V_L$ domains selected by phage display with repertoires of naturally occurring V domain variants obtained from unimmunized donors and to screen for higher affinity in several rounds of chain reshuffling as described in Marks at al., *Biotechnol.*, 10: 779-783 (1992). This technique allows the production of antibodies and antibody fragments with a dissociation constant $K_D(k_{off}/k_{on})$ of about $10^{-9}$ M or less.

In other embodiments, similar procedures may be employed using libraries comprising eukaryotic cells (e.g., yeast) that express binding pairs on their surface. See, for example, U.S. Pat. No. 7,700,302 and U.S. Ser. No. 12/404, 059. In one embodiment, the human antibody is selected from a phage library, where that phage library expresses human antibodies (Vaughan et al. *Nature Biotechnology* 14:309-314 (1996): Sheets et al. *Proc. Natl. Acad. Sci. USA* 95:6157-6162 (1998). In other embodiments, human binding pairs may be isolated from combinatorial antibody libraries generated in eukaryotic cells such as yeast. See e.g., U.S. Pat. No. 7,700,302. Such techniques advantageously allow for the screening of large numbers of candidate modulators and provide for relatively easy manipulation of candidate sequences (e.g., by affinity maturation or recombinant shuffling).

Human antibodies can also be made by introducing human immunoglobulin loci into transgenic animals, e.g., mice in which the endogenous immunoglobulin genes have been partially or completely inactivated and human immunoglobulin genes have been introduced. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and U.S. Pat. Nos. 6,075,181 and 6,150,584 regarding XenoMousea technology; and Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies and Cancer Therapy*, Alan R. Liss, p. 77 (1985); Boerner et al., *J. Immunol,* 147 (1):86-95 (1991); and U.S. Pat. No. 5,750,373.

3. Further Processing

No matter how obtained, modulator-producing cells (e.g., hybridomas, yeast colonies, etc.) may be selected, cloned and further screened for desirable characteristics including, for example, robust growth, high antibody production and, as discussed in more detail below, desirable antibody characteristics. Hybridomas can be expanded in vivo in syngeneic animals, in animals that lack an immune system, e.g., nude mice, or in cell culture in vitro. Methods of selecting, cloning and expanding hybridomas and/or colonies, each of which produces a discrete antibody species, are well known to those of ordinary skill in the art.

B. Recombinant Modulator Production

1. Overview

Once the source is perfected DNA encoding the desired DLL3 modulators may be readily isolated and sequenced using conventional procedures (e.g., by using oligonucleotide probes that are capable of binding specifically to genes encoding antibody heavy and light chains). Isolated and subcloned hybridoma cells (or phage or yeast derived colonies) may serve as a preferred source of such DNA if the modulator is an antibody. If desired, the nucleic acid can further be manipulated as described herein to create agents including fusion proteins, or chimeric, humanized or fully human antibodies. More particularly, isolated DNA (which may be modified) can be used to clone constant and variable region sequences for the manufacture antibodies.

Accordingly, in exemplary embodiments antibodies may be produced recombinantly, using conventional procedures (such as those set forth in Al-Rubeai; An, and Shire et. al. all supra, and Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002)) in which the isolated and subcloned hybridoma cells (or phage or yeast derived colonies) serve as a preferred source of nucleic acid molecules.

The term "nucleic acid molecule", as used herein, is intended to include DNA molecules and RNA molecules and artificial variants thereof (e.g., peptide nucleic acids), whether single-stranded or double-stranded. The nucleic acids may encode one or both chains of an antibody of the invention, or a fragment or derivative thereof. The nucleic acid molecules of the invention also include polynucleotides sufficient for use as hybridization probes, PCR primers or sequencing primers for identifying, analyzing, mutating or amplifying a polynucleotide encoding a polypeptide; antisense nucleic acids for inhibiting expression of a polynucleotide, and as well as complementary sequences. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. It will be appreciated that such nucleic acid sequences can further be manipulated to create modulators including chimeric, humanized or fully human antibodies. More particularly, isolated nucleic acid molecules (which may be modified) can be used to clone constant and variable region sequences for the manufacture antibodies as described in U.S. Pat. No. 7,709,611.

The term "isolated nucleic acid" means a that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid that is available for manipulation by recombinant DNA techniques.

Whether the source of the nucleic acid encoding the desired immunoreactive portion of the antibody is obtained or derived from phage display technology, yeast libraries, hybridoma-based technology or synthetically, it is to be understood that the present invention encompasses the nucleic acid molecules and sequences encoding the antibodies or antigen-binding fragments or derivatives thereof. Further, the instant invention is directed to vectors and host cells comprising such nucleic acid molecules.

2. Hybridization and Sequence Identity

As indicated, the invention further provides nucleic acids that hybridize to other nucleic acids under particular hybridization conditions. More specifically the invention encompasses nucleic acids molecules that hybridize under moderate or high stringency hybridization conditions (e.g., as defined below), to the nucleic acid molecules of the invention. Methods for hybridizing nucleic acids are well-known in the art. As is well known, a moderately stringent hybridization conditions comprise a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. By way of comparison hybridization under highly stringent hybridization conditions comprise washing with 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65%, 70%, 75%, 80%, 85%, 90%, 95%, 98% or 99% identical to each other typically remain hybridized to each other.

The invention also includes nucleic acid molecules that are "substantially identical" to the described nucleic acid molecules. In one embodiment, the term substantially identical with regard to a nucleic acid sequence means may be construed as a sequence of nucleic acid molecules exhibiting at least about 65%, 70%, 75%, 80%, 85%, or 90% sequence identity. In other embodiments, the nucleic acid molecules exhibit 95% or 98% sequence identity to the reference nucleic acid sequence.

The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 1; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the nucleic acid.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, the sequence analysis tool GCG (Accelrys Software Inc.) contains programs such as "GAP" and "BEST-FIT" which can be used with default parameters to determine sequence homology or sequence identity between closely related polypeptides, such as homologous polypeptides from different species of organisms or between a wild type protein and a mutein thereof. (See, e.g., GCG Version 6.1 or Durbin et. Al., *Biological Sequence Analysis: Probabilistic models of proteins and nucleic acids.*, Cambridge Press (1998)).

Polypeptide sequences can also be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially blastp or tblastn, using default parameters. See, e.g., Altschul et al. (1990) J. Mol. Biol. 215: 403 410 and Altschul et al. (1997) Nucleic Acids Res. 25:3389 402, each of which is herein incorporated by reference.

In this regard the invention also includes nucleic acid molecules that encode polypeptides that are "substantially identical" with respect to an antibody variable region polypeptide sequence (e.g., either the donor light or heavy chain variable region or the acceptor light or heavy chain variable region). As applied to such polypeptides, the term "substantial identity" or "substantially identical" means that two peptide sequences, when optimally aligned, such as by the programs GAP or BEST-FIT using default gap weights, share at least 60% or 65% sequence identity, preferably at least 70%, 75%, 80%, 85%, or 90% sequence identity, even more preferably at least 93%, 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution.

3. Expression

The varied processes of recombinant expression, i.e., the production of RNA or of RNA and protein/peptide, are well known as set forth, for example, in Berger and Kimmel, Guide to Molecular Cloning Techniques, *Methods in Enzymology* volume 152 Academic Press, Inc., San Diego, Calif.; Sambrook et al., *Molecular Cloning—A Laboratory Manual* (3rd Ed.), Vol. 1-3, Cold Spring Harbor Laboratory, Cold Spring Harbor, N.Y., (2000); and *Current Protocols in Molecular Biology*, F. M. Ausubel et al., eds., Current Protocols, a joint venture between Greene Publishing Associates, Inc. and John Wiley & Sons, Inc., (supplemented through 2006).

Certain terms of interest include "expression control sequence" which comprises promoters, ribosome binding sites, enhancers and other control elements which regulate transcription of a gene or translation of mRNA. As is well known, a "promoter" or "promoter region" relates to a nucleic acid sequence which generally is located upstream (5') to the nucleic acid sequence being expressed and controls expression of the sequence by providing a recognition and binding site for RNA-polymerase.

Exemplary promoters which are compatible according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

In certain embodiments, the nucleic acid molecule may be present in a vector, where appropriate with a promoter, which controls expression of the nucleic acid. The well known term "vector" comprises any intermediary vehicle for a nucleic acid which enables said nucleic acid, for example, to be introduced into prokaryotic and/or eukaryotic cells and, where appropriate, to be integrated into a genome. Methods of transforming mammalian cells are well known in the art. See, for example, U.S. Pat. Nos. 4,399,216, 4,912,040, 4,740,461, and 4,959,455. The vectors may include a nucleotide sequence encoding an antibody of the invention (e.g., a whole antibody, a heavy or light chain of an antibody, a $V_H$ or $V_L$ of an antibody, or a portion thereof, or a heavy- or light-chain CDR, a single chain Fv, or fragments or variants thereof), operably linked to a promoter (see, e.g., PCT Publication WO 86/05807; PCT Publication WO 89/01036; and U.S. Pat. No. 5,122,464).

A variety of host-expression vector systems are commercially available, and many are compatible with the teachings herein and may be used to express the modulators of the invention. Such systems include, but are not limited to, microorganisms such as bacteria (e.g., *E. coli, B. subtilis, streptomyces*) transformed with recombinant bacteriophage DNA, plasmid DNA or cosmid DNA expression vectors containing modulator coding sequences; yeast (e.g., *Saccharomyces, Pichia*) transfected with recombinant yeast expression vectors containing modulator coding sequences; insect cell systems infected with recombinant virus expression vectors (e.g., baculovirus) containing modulator coding sequences; plant cell systems (e.g., *Nicotiana, Arabidopsis*, duckweed, corn, wheat, potato, etc.) infected with recombinant viral expression vectors (e.g., cauliflower mosaic virus; tobacco mosaic virus) or transfected with recombinant plasmid expression vectors (e.g., Ti plasmid) containing modulator coding sequences; or mammalian cell systems (e.g., COS, CHO, BHK, 293, 3T3 cells, etc.) harboring recombinant expression constructs containing promoters derived from the genome of mammalian cells (e.g., metallothionein promoter) or from mammalian viruses (e.g., the adenovirus late promoter; the vaccinia virus 7.5K promoter).

As used herein, the term "host cell" covers any kind of cellular system which can be engineered to generate the polypeptides and antigen-binding molecules of the present invention. In one embodiment, the host cell is engineered to allow the production of an antigen binding molecule with modified glycoforms. In a preferred embodiment, the antigen binding molecule, or variant antigen binding molecule, is an antibody, antibody fragment, or fusion protein. In certain embodiments, the host cells have been further manipulated to express increased levels of one or more polypeptides having N-acetylglucosaminyltransferase III (GnTI11) activity. Compatible host cells include cultured cells, e.g., mammalian cultured cells, such as CHO cells, BHK cells, NSO cells, SP2/0 cells, YO myeloma cells, P3x63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

For long-term, high-yield production of recombinant proteins stable expression is preferred. Accordingly, cell lines that stably express the selected modulator may be engineered using standard art-recognized techniques. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Any of the selection systems well known in the art may be used, including the glutamine synthetase gene expression system (the GS system) which provides an efficient approach for enhancing expression under certain conditions. The GS system is discussed in whole or part in connection with EP patents 0 216 846, 0 256 055, 0 323 997 and 0 338 841 and U.S. Pat. Nos. 5,591,639 and 5,879,936 each of which is incorporated herein by reference. Another preferred expression system, the Freedom™ CHO-S Kit is commercially provided by Life Technologies (Catalog Number A13696-01) also allows for the development of stable cell lines that may be used for modulator production.

Such host-expression systems represent vehicles by which the coding sequences of interest may be produced and subsequently purified, but also represent cells which may, when transformed or transfected with the appropriate nucleotide coding sequences, express a molecule of the invention in situ. The host cell may be co-transfected with two expression vectors of the invention, for example, the first vector encoding a heavy chain derived polypeptide and the second vector encoding a light chain derived polypeptide.

Thus, in certain embodiments, the present invention provides recombinant host cells allowing for the expression of antibodies or portions thereof. Antibodies produced by expression in such recombinant host cells are referred to herein as recombinant antibodies. The present invention also provides progeny cells of such host cells, and antibodies produced by the same.

C. Chemical Synthesis

In addition, the modulators may be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105-111). Furthermore, if desired, nonclassical amino acids or chemical amino acid analogs (such as D-isomers of the common amino acids, 2,4-diaminobutyric acid, a-amino isobutyric acid, 4-aminobutyric acid, and the like) can be introduced as a substitution or addition into a polypeptide sequence.

D. Transgenic Systems

In other embodiments modulators may be produced transgenically through the generation of a mammal or plant that is transgenic for recombinant molecules such as the immunoglobulin heavy and light chain sequences and that produces the desired compounds in a recoverable form. This includes, for example, the production of protein modulators (e.g., antibodies) in, and recovery from, the milk of goats, cows, or other mammals. See, e.g., U.S. Pat. Nos. 5,827,690, 5,756,687, 5,750,172, and 5,741,957. In some embodiments, non-human transgenic animals that comprise human immunoglobulin loci are immunized to produce antibodies.

Other transgenic techniques are set forth in Hogan et al., Manipulating the Mouse Embryo: A Laboratory Manual 2nd ed., Cold Spring Harbor Press (1999); Jackson et al., Mouse Genetics and Transgenics: A Practical Approach, Oxford University Press (2000); and Pinkert. Transgenic Animal Technology: A Laboratory Handbook, Academic Press (1999) and U.S. Pat. No. 6,417,429. In some embodiments, the non-human animals are mice, rats, sheep, pigs, goats, cattle or horses, and the desired product is produced in blood, milk, urine, saliva, tears, mucus and other bodily fluids from which it is readily obtainable using art-recognized purification techniques.

Other compatible production systems include methods for making antibodies in plants such as described, for example, in U.S. Pat. Nos. 6,046,037 and 5,959,177 which are incorporated herein with respect to such techniques.

E. Isolation/Purification

Once a modulator of the invention has been produced by recombinant expression or any other of the disclosed techniques, it may be purified by any method known in the art for purification of immunoglobulins or proteins. In this respect the modulator may be "isolated" which means that it has been identified and separated and/or recovered from a component of its natural environment. Contaminant components of its natural environment are materials that would interfere with diagnostic or therapeutic uses for the polypeptide and may include enzymes, hormones, and other proteinaceous or nonproteinaceous solutes. Isolated modulators include a modulator in situ within recombinant cells because at least one component of the polypeptide's natural environment will not be present.

If the desired molecule is produced intracellularly, as a first step, the particulate debris, either host cells or lysed fragments, may be removed, for example, by centrifugation or ultrafiltration. Where the modulator is secreted into the medium, supernatants from such expression systems are generally first concentrated using a commercially available protein concentration filter, for example, an Amicon or Pellicon ultrafiltration unit (Millipore Corp.). Once the insoluble contaminants are removed the modulator preparation may be further purified using standard techniques such as, for example, hydroxylapatite chromatography, gel electrophoresis, dialysis, and affinity chromatography, with affinity chromatography of particular interest. In this regard protein A can be used to purify antibodies that are based on human IgG1, IgG2 or IgG4 heavy chains (Lindmark, et al., J Immunol Meth 62:1 (1983)) while protein G is recommended for all mouse isotypes and for human IgG3 (Guss, et al., EMBO J 5:1567 (1986)). Other techniques for protein purification such as fractionation on an ion-exchange column, ethanol precipitation, reverse phase HPLC, chromatography on silica, chromatography on heparin, sepharose chromatography on an anion or cation exchange resin (such as a polyaspartic acid column), chromatofocusing, SDS-PAGE and ammonium sulfate precipitation are also available depending on the antibody to be recovered. In particularly preferred embodiments the modulators of the instant invention will be purified, at least in part, using Protein A or Protein G affinity chromatography.

VI. DLL3 Modulator Fragments and Derivatives

Whatever generation and production methodology is selected, modulators of the instant invention will react, bind, combine, complex, connect, attach, join, interact or otherwise associate with a target determinant (e.g., antigen) and thereby provide the desired results. Where the modulator comprises an antibody or fragment, construct or derivative thereof such associations may be through one or more "binding sites" or "binding components" expressed on the antibody, where a binding site comprises a region of a polypeptide that is responsible for selectively binding to a target molecule or antigen of interest. Binding domains comprise at least one binding site (e.g., an intact IgG antibody will have two binding domains and two binding sites). Exemplary binding domains include an antibody variable domain, a receptor-binding domain of a ligand, a ligand-binding domain of a receptor or an enzymatic domain.

A. Antibodies

As noted above, the term "antibody" is intended to cover, at least, polyclonal antibodies, multiclonal antibodies, chimeric antibodies, CDR grafted antibodies, humanized and primatized antibodies, human antibodies, recombinantly produced antibodies, intrabodies, multispecific antibodies, bispecific antibodies, monovalent antibodies, multivalent antibodies, anti-idiotypic antibodies, as well as synthetic antibodies.

B. Fragments

Regardless of which form of the modulator (e.g. chimeric, humanized, etc.) is selected to practice the invention it will be appreciated that immunoreactive fragments of the same may be used in accordance with the teachings herein. An "antibody fragment" comprises at least a portion of an intact antibody. As used herein, the term "fragment" of an antibody molecule includes antigen-binding fragments of antibodies, and the term "antigen-binding fragment" refers to a polypeptide fragment of an immunoglobulin or antibody that immunospecifically binds or reacts with a selected antigen or immunogenic determinant thereof or competes with the intact antibody from which the fragments were derived for specific antigen binding.

Exemplary fragments include: $V_L$, $V_H$, scFv, F(ab')2 fragment, Fab fragment, Fd fragment, Fv fragment, single domain antibody fragments, diabodies, linear antibodies, single-chain antibody molecules and multispecific antibodies formed from antibody fragments. In addition, an active fragment comprises a portion of the antibody that retains its ability to interact with the antigen/substrates or receptors and modify them in a manner similar to that of an intact antibody (though maybe with somewhat less efficiency).

In other embodiments, an antibody fragment is one that comprises the Fc region and that retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment.

As would be well recognized by those skilled in the art, fragments can be obtained via chemical or enzymatic treatment (such as papain or pepsin) of an intact or complete antibody or antibody chain or by recombinant means. See, e.g., Fundamental Immunology, W. E. Paul, ed., Raven Press, N.Y. (1999), for a more detailed description of antibody fragments.

C. Derivatives

The invention further includes immunoreactive modulator derivatives and antigen binding molecules comprising one or more modifications.

1. Multivalent Antibodies

In one embodiment, the modulators of the invention may be monovalent or multivalent (e.g., bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen). See, for example, U.S.P.N. 2009/0130105. In each case at least one of the binding sites will comprise an epitope, motif or domain associated with a DLL3 isoform.

In one embodiment, the modulators are bispecific antibodies in which the two chains have different specificities, as described in Millstein et al., 1983, Nature, 305:537-539. Other embodiments include antibodies with additional specificities such as trispecific antibodies. Other more sophisticated compatible multispecific constructs and methods of their fabrication are set forth in U.S.P.N. 2009/0155255, as well as WO 94/04690; Suresh et al., 1986, Methods in Enzymology, 121:210; and WO96/27011.

As alluded to above, multivalent antibodies may immunospecifically bind to different epitopes of the desired target molecule or may immunospecifically bind to both the target molecule as well as a heterologous epitope, such as a heterologous polypeptide or solid support material. While preferred embodiments of the anti-DLL3 antibodies only bind two antigens (i.e. bispecific antibodies), antibodies with additional specificities such as trispecific antibodies are also encompassed by the instant invention. Bispecific antibodies also include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

In yet other embodiments, antibody variable domains with the desired binding specificities (antibody-antigen combining sites) are fused to immunoglobulin constant domain sequences, such as an immunoglobulin heavy chain constant domain comprising at least part of the hinge, $C_H2$, and/or $C_H3$ regions, using methods well known to those of ordinary skill in the art.

2. Fc Region Modifications

In addition to the various modifications, substitutions, additions or deletions to the variable or binding region of the disclosed modulators (e.g., Fc-DLL3 or anti-DLL3 antibodies) set forth above, those skilled in the art will appreciate that selected embodiments of the present invention may also comprise substitutions or modifications of the constant region (i.e. the Fc region). More particularly, it is contemplated that the DLL3 modulators of the invention may contain inter alia one or more additional amino acid residue substitutions, mutations and/or modifications which result in a compound with preferred characteristics including, but not limited to: altered pharmacokinetics, increased serum half life, increase binding affinity, reduced immunogenicity, increased production, altered Fc ligand binding to an Fc receptor (FcR), enhanced or reduced "ADCC" (antibody-dependent cell mediated cytotoxicity) or "CDC" (complement-dependent cytotoxicity) activity, altered glycosylation and/or disulfide bonds and modified binding specificity. In this regard it will be appreciated that these Fc variants may advantageously be used to enhance the effective anti-neoplastic properties of the disclosed modulators.

To this end certain embodiments of the invention may comprise substitutions or modifications of the Fc region, for example the addition of one or more amino acid residue, substitutions, mutations and/or modifications to produce a compound with enhanced or preferred Fc effector functions. For example, changes in amino acid residues involved in the interaction between the Fc domain and an Fc receptor (e.g., FcγRI, FcγRIIA and B, FcγRIII and FcRn) may lead to increased cytotoxicity and/or altered pharmacokinetics, such as increased serum half-life (see, for example, Ravetch and Kinet, Annu. Rev. Immunol 9:457-92 (1991); Capel et al., Immunomethods 4:25-34 (1994); and de Haas et al., J. Lab. Clin. Med. 126:330-41 (1995) each of which is incorporated herein by reference).

In selected embodiments, antibodies with increased in vive half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311. With regard to such embodiments, Fc variants may provide half-lives in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-life results in a higher serum titer which thus reduces the frequency of the administration of the antibodies and/or reduces the concentration of the antibodies to be administered. Binding to human FcRn in vive and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FeRns. See also, e.g., Shields et al. J. Biol. Chem. 9(2):6591-6604 (2001).

In other embodiments, Fc alterations may lead to enhanced or reduced ADCC or CDC activity. As in known in the art, CDC refers to the lysing of a target cell in the presence of complement, and ADCC refers to a form of cytotoxicity in which secreted Ig bound onto FcRs present on certain cytotoxic cells (e.g., Natural Killer cells, neutrophils, and macrophages) enables these cytotoxic effector cells to bind specifically to an antigen-bearing target cell and subsequently kill the target cell with cytotoxins. In the context of the instant invention antibody variants are provided with "altered" FcR binding affinity, which is either enhanced or diminished binding as compared to a parent or unmodified antibody or to an antibody comprising a native sequence FcR. Such variants which display decreased binding may possess little or no appreciable binding, e.g., 0-20% binding to the FcR compared to a native sequence, e.g. as determined by techniques well known in the art. In other embodiments the variant will exhibit enhanced binding as compared to the native immunoglobulin Fc domain. It will be appreciated that these types of Fc variants may advantageously be used to enhance the effective anti-neoplastic properties of the disclosed antibodies. In yet other embodiments, such alterations lead to increased binding affinity, reduced immunogenicity, increased production, altered glycosylation and/or disulfide bonds (e.g., for conjugation sites), modified binding specificity, increased phagocytosis; and/or down regulation of cell surface receptors (e.g. B cell receptor; BCR), etc.

3. Altered Glycosylation

Still other embodiments comprise one or more engineered glycoforms, i.e., a DLL3 modulator comprising an altered glycosylation pattern or altered carbohydrate composition that is covalently attached to the protein (e.g., in the Fc domain). See, for example, Shields, R. L. et al. (2002) J. Biol. Chem. 277:26733-26740. Engineered glycoforms may be useful for a variety of purposes, including but not limited to enhancing or reducing effector function, increasing the affinity of the modulator for a target or facilitating production of the modulator. In certain embodiments where reduced effector function is desired, the molecule may be engineered to express an aglycosylated form. Substitutions that may result in elimination of one or more variable region framework glycosylation sites to thereby eliminate glycosylation at that site are well known (see e.g. U.S. Pat. Nos. 5,714,350 and 6,350,861). Conversely, enhanced effector functions or improved binding may be imparted to the Fc containing molecule by engineering in one or more additional glycosylation sites.

Other embodiments include an Fc variant that has an altered glycosylation composition, such as a hypofucosylated antibody having reduced amounts of fucosyl residues or an antibody having increased bisecting GlcNAc structures. Such altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTI11)), by expressing a molecule comprising an Fe region in various organisms or cell lines from various organisms or by modifying carbohydrate(s) after the molecule comprising Fc region has been expressed (see, for example, WO 2012/117002).

4. Additional Processing

The modulators may be differentially modified during or after production, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Various post-translational modifications also encompassed by the invention include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. Moreover, the modulators may also be modified with a detectable label, such as an enzymatic, fluorescent, radioisotopic or affinity label to allow for detection and isolation of the modulator.

VII. Modulator Characteristics

No matter how obtained or which of the aforementioned forms the modulator takes, various embodiments of the disclosed modulators may exhibit certain characteristics. In selected embodiments, antibody-producing cells (e.g., hybridomas or yeast colonies) may be selected, cloned and further screened for favorable properties including, for example, robust growth, high modulator production and, as discussed in more detail below, desirable modulator characteristics. In other cases characteristics of the modulator may be imparted or influenced by selecting a particular antigen (e.g., a specific DLL3 isoform) or immunoreactive fragment of the target antigen for inoculation of the animal. In still other embodiments the selected modulators may be engineered as described above to enhance or refine immunochemical characteristics such as affinity or pharmacokinetics.

A. Neutralizing Modulators

In certain embodiments, the modulators will comprise "neutralizing" antibodies or derivatives or fragments thereof. That is, the present invention may comprise antibody molecules that bind specific domains, motifs or epitopes and are capable of blocking, reducing or inhibiting the biological activity of DLL3. More generally the term "neutralizing antibody" refers to an antibody that binds to or interacts with a target molecule or ligand and prevents binding or association of the target molecule to a binding partner such as a receptor or substrate, thereby interrupting a biological response that otherwise would result from the interaction of the molecules.

It will be appreciated that competitive binding assays known in the art may be used to assess the binding and specificity of an antibody or immunologically functional fragment or derivative thereof. With regard to the instant invention an antibody or fragment will be held to inhibit or reduce binding of DLL3 to a binding partner or substrate when an excess of antibody reduces the quantity of binding partner bound to DLL3 by at least about 20%, 30%, 40%, 50%, 60%, 70%, 80%, 85%, 90%, 95%, 97%, 99"%0 or more as measured, for example, by Notch receptor activity or in an in vitro competitive binding assay. In the case of antibodies to DLL3 for example, a neutralizing antibody or antagonist will preferably alter Notch receptor activity by at least about 20%, 30%, 40%, 50%, 60%, 70%, 80%, 85%, 90%, 95%, 97%, 99% or more. It will be appreciated that this modified activity may be measured directly using art-recognized techniques or may be measured by the impact the altered activity has downstream (e.g., oncogenesis, cell survival or activation or suppression of Notch responsive genes). Preferably, the ability of an antibody to neutralize DLL3 activity is assessed by inhibition of DLL3 binding to a Notch receptor or by assessing its ability to relieve DLL3 mediated repression of Notch signaling.

B. Internalizing Modulators

There is evidence that a substantial portion of expressed DLL3 protein remains associated with the tumorigenic cell surface, thereby allowing for localization and internalization of the disclosed modulators. In preferred embodiments such modulators may be associated with, or conjugated to, anti-cancer agents such as cytotoxic moieties that kill the cell upon internalization. In particularly preferred embodiments the modulator will comprise an internalizing antibody drug conjugate.

As used herein, a modulator that "internalizes" is one that is taken up (along with any payload) by the cell upon binding to an associated antigen or receptor. As will be appreciated, the internalizing modulator may, in preferred embodiments, comprise an antibody including antibody fragments and derivatives thereof, as well as antibody conjugates. Internalization may occur in vitro or in vivo. For therapeutic applications, internalization will preferably occur in vive in a subject in need thereof. The number of antibody molecules internalized may be sufficient or adequate to kill an antigen-expressing cell, especially an antigen-expressing cancer stem cell. Depending on the potency of the antibody or antibody conjugate, in some instances, the uptake of a single antibody molecule into the cell is sufficient to kill the target cell to which the antibody binds. For example, certain toxins are so highly potent that the internalization of a few molecules of the toxin conjugated to the antibody is sufficient to kill the tumor cell. Whether an antibody internalizes upon binding to a mammalian cell can be determined by various assays including those described in the Examples below (e.g., Examples 12 and 15-17). Methods of detecting whether an antibody internalizes into a cell are also described in U.S. Pat. No. 7,619,068 which is incorporated herein by reference in its entirety.

C. Depleting Modulators

In other embodiments the antibodies will comprise depleting antibodies or derivatives or fragments thereof. The term "depleting" antibody refers to an antibody that preferably binds to or associates with an antigen on or near the cell surface and induces, promotes or causes the death or elimination of the cell (e.g., by CDC, ADCC or introduction of a cytotoxic agent). In some embodiments, the selected depleting antibodies will be associated or conjugated to a cytotoxic agent.

Preferably a depleting antibody will be able to remove, incapacitate, eliminate or kill at least 20%, 30%, 40%, 50%, 60%, 70%, 80%, 85%, 90%, 95%, 97%, or 99% of DLL3 tumorigenic cells in a defined cell population. In some embodiments the cell population may comprise enriched, sectioned, purified or isolated tumor perpetuating cells. In other embodiments the cell population may comprise whole tumor samples or heterogeneous tumor extracts that comprise tumor perpetuating cells. Those skilled in the art will appreciate that standard biochemical techniques as described in the Examples below (e.g., Examples 13 and 14) may be used to monitor and quantify the depletion of tumorigenic cells or tumor perpetuating cells in accordance with the teachings herein.

D. Binning and Epitope Binding

It will further be appreciated the disclosed anti-DLL3 antibody modulators will associate with, or bind to, discrete epitopes or immunogenic determinants presented by the selected target or fragment thereof. In certain embodiments, epitope or immunogenic determinants include chemically active surface groupings of molecules such as amino acids, sugar side chains, phosphoryl groups, or sulfonyl groups, and, in certain embodiments, may have specific three-dimensional structural characteristics, and/or specific charge characteristics. Thus, as used herein the term "epitope" includes any protein determinant capable of specific binding to an immunoglobulin or T-cell receptor or otherwise interacting with a molecule. In certain embodiments, an antibody is said to specifically bind (or immunospecifically bind or react) an antigen when it preferentially recognizes its target antigen in a complex mixture of proteins and/or macromolecules. In preferred embodiments, an antibody is said to specifically bind an antigen when the equilibrium dissociation constant ($K_D$) is less than or equal to $10^{-6}$M or less than or equal to $10^{-7}$M, more preferably when the equilibrium dissociation constant is less than or equal to $10^{-8}$M, and even more preferably when the dissociation constant is less than or equal to $10^{-9}$M More directly the term "epitope" is used in its common biochemical sense and refers to that portion of the target antigen capable of being recognized and specifically bound by a particular antibody modulator. When the antigen is a polypeptide such as DLL3, epitopes may generally be formed from both contiguous amino acids and noncontiguous amino acids juxtaposed by tertiary folding of a protein ("conformational epitopes"). In such conformational epitopes the points of interaction occur across amino acid residues on the protein that are linearly separated from one another. Epitopes formed from contiguous amino acids (sometimes referred to as "linear" or "continuous" epitopes) are typically retained upon protein denaturing, whereas epitopes formed by tertiary folding are typically lost upon protein denaturing. In any event an antibody epitope typically includes at least 3, and more usually, at least 5 or 8-10 amino acids in a unique spatial conformation.

In this respect it will be appreciated that, in certain embodiments, an epitope may be associated with, or reside in, one or more regions, domains or motifs of the DLL3 protein (e.g., amino acids 1-618 of isoform 1). As discussed in more detail herein the extracellular region of the DLL3 protein comprises a series of generally recognized domains including six EGF-like domains and a DSL domain. For the purposes of the instant disclosure the term "domain" will be used in accordance with its generally accepted meaning and will be held to refer to an identifiable or definable conserved structural entity within a protein that exhibits a distinctive secondary structure content. In many cases, homologous domains with common functions will usually show sequence similarities and be found in a number of disparate proteins (e.g., EGF-like domains are reportedly found in at least 471 different proteins). Similarly, the art-recognized term "motif" will be used in accordance with its common meaning and shall generally refer to a short, conserved region of a protein that is typically ten to twenty contiguous amino acid residues. As discussed throughout, selected embodiments comprise modulators that associate with or bind to an epitope within specific regions, domains or motifs of DLL3.

In any event once a desired epitope on an antigen is determined, it is possible to generate antibodies to that epitope, e.g., by immunizing with a peptide comprising the epitope using techniques described in the present invention. Alternatively, during the discovery process, the generation and characterization of antibodies may elucidate information about desirable epitopes located in specific domains or motifs. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731. Other methods of binning or domain level or epitope mapping comprising modulator competition or antigen fragment expression on yeast is set forth in Examples 9 and 10 below.

As used herein, the term "binning" refers to methods used to group or classify antibodies based on their antigen binding characteristics and competition. While the techniques are useful for defining and categorizing modulators of the instant invention, the bins do not always directly correlate with epitopes and such initial determinations of epitope binding may be further refined and confirmed by other art-recognized methodology as described herein. However, as discussed and shown in the Examples below, empirical assignment of antibody modulators to individual bins provides information that may be indicative of the therapeutic potential of the disclosed modulators.

More specifically, one can determine whether a selected reference antibody (or fragment thereof) binds to the same epitope or cross competes for binding with a second test antibody (i.e., is in the same bin) by using methods known in the art and set forth in the Examples herein. In one embodiment, a reference antibody modulator is associated with DLL3 antigen under saturating conditions and then the ability of a secondary or test antibody modulator to bind to DLL3 is determined using standard immunochemical techniques. If the test antibody is able to substantially bind to DLL3 at the same time as the reference anti-DLL3 antibody, then the secondary or test antibody binds to a different epitope than the primary or reference antibody. However, if the test antibody is not able to substantially bind to DLL3 at the same time, then the test antibody binds to the same epitope, an overlapping epitope, or an epitope that is in close proximity (at least sterically) to the epitope bound by the primary antibody. That is, the test antibody competes for antigen binding and is in the same bin as the reference antibody.

The term "compete" or "competing antibody" when used in the context of the disclosed modulators means competition between antibodies as determined by an assay in which a test antibody or immunologically functional fragment under test prevents or inhibits specific binding of a reference antibody to a common antigen. Typically, such an assay involves the use of purified antigen (e.g., DLL3 or a domain or fragment thereof) bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess and/or allowed to bind first. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the Examples herein. Usually, when a competing antibody is present in excess, it will inhibit specific binding of a reference antibody to a common antigen by at least 30%, 40%, 45%, 50%, 55%, 60%, 65%, 70% or 75%. In some instance, binding is inhibited by at least 80%, 85%, 90%, 95%, or 97% or more.

Conversely, when the reference antibody is bound it will preferably inhibit binding of a subsequently added test antibody (i.e., a DLL3 modulator) by at least 30%, 40%, 45%, 50%, 55%, 60%, 65%, 70% or 75%. In some instance, binding of the test antibody is inhibited by at least 80%, 85%, 90%, 95%, or 97% or more.

With regard to the instant invention, and as set forth in the Examples 9 and 10 below, it has been determined (via surface plasmon resonance or bio-layer interferometry) that the extracellular domain of DLL3 defines at least nine bins by competitive binding termed "bin A" to "bin I" herein. Given the resolution provided by modulator binning techniques, it is believed that these nine bins comprise the majority of the bins that are present in the extracellular region of the DLL3 protein.

In this respect, and as known in the art and detailed in the Examples below, the desired binning or competitive binding data can be obtained using solid phase direct or indirect radioimmunoassay (RIA), solid phase direct or indirect enzyme immunoassay (EIA or ELISA), sandwich competition assay, a Biacore™ 2000 system (i.e., surface plasmon resonance—GE Healthcare), a ForteBio® Analyzer (i.e., bio-layer interferometry—ForteBio, Inc.) or flow cytometric methodology. The term "surface plasmon resonance," as used herein, refers to an optical phenomenon that allows for the analysis of real-time specific interactions by detection of alterations in protein concentrations within a biosensor matrix. The term "bio-layer interferometry" refers to an optical analytical technique that analyzes the interference pattern of white light reflected from two surfaces: a layer of immobilized protein on a biosensor tip, and an internal reference layer. Any change in the number of molecules bound to the biosensor tip causes a shift in the interference pattern that can be measured in real-time. In particularly preferred embodiments the analysis (whether surface plasmon resonance, bio-layer interferometry or flow cytometry) is performed using a Biacore or ForteBio instrument or a flow cytometer (e.g., FACSAria II) as demonstrated in the Examples below.

In order to further characterize the epitopes that the disclosed DLL3 antibody modulators associate with or bind to, domain-level epitope mapping was performed using a modification of the protocol described by Cochran et al. (J Immunol Methods. 287 (1-2): 147-158 (2004) which is incorporated herein by reference). Briefly, individual domains of DLL3 comprising specific amino acid sequences were expressed on the surface of yeast and binding by each DLL3 antibody was determined through flow cytometry. The results are discussed below in Example 10 and shown in FIGS. 14A and 14B.

Other compatible epitope mapping techniques include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety). In other embodiments Modification-Assisted Profiling (MAP), also known as Antigen Structure-based Antibody Profiling (ASAP) provides a method that categorizes large numbers of monoclonal antibodies (mAbs) directed against the same antigen according to the similarities of the binding profile of each antibody to chemically or enzymatically modified antigen surfaces (U.S.P.N. 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. It will be appreciated that MAP may be used to sort the hDLL3 antibody modulators of the invention into groups of antibodies binding different epitopes Agents useful for altering the structure of the immobilized antigen include enzymes such as proteolytic enzymes (e.g., trypsin, endoproteinase Glu-C, endoproteinase Asp-N, chymotrypsin, etc.). Agents useful for altering the structure of the immobilized antigen may also be chemical agents, such as, succinimidyl esters and their derivatives, primary amine-containing compounds, hydrazines and carbohydrazines, free amino acids, etc.

The antigen protein may be immobilized on either biosensor chip surfaces or polystyrene beads. The latter can be processed with, for example, an assay such as multiplex LUMINEX™ detection assay (Luminex Corp.). Because of the capacity of LUMINEX to handle multiplex analysis with up to 100 different types of beads, LUMINEX provides almost unlimited antigen surfaces with various modifications, resulting in improved resolution in antibody epitope profiling over a biosensor assay.

E. Modulator Binding Characteristics

Besides epitope specificity the disclosed antibodies may be characterized using physical characteristics such as, for example, binding affinities. In this regard the present invention further encompasses the use of antibodies that have a high binding affinity for one or more DLL3 isoforms or, in the case of pan-antibodies, more than one member of the DLL family.

The term "$K_D$", as used herein, is intended to refer to the dissociation constant of a particular antibody-antigen interaction. An antibody of the invention is said to immunospecifically bind its target antigen when the dissociation constant $K_D$ ($k_{off}/k_{on}$) is $\leq 10^{-7}$ M. The antibody specifically binds antigen with high affinity when the $K_D$ is $\leq 5\times10^{-9}$M, and with very high affinity when the $K_D$ is $\leq 5\times10^{-10}$M. In one embodiment of the invention, the antibody has a $K_D$ of $\leq 10^{-9}$M and an off-rate of about $1\times10^{-4}$/sec. In one embodiment of the invention, the off-rate is $<1\times10^{-5}$/sec. In other embodiments of the invention, the antibodies will bind to DLL3 with a $K_D$ of between about $10^{-7}$M and $10^{-10}$M, and in yet another embodiment it will bind with a $K_D \leq 2\times10^{-10}$M. Still other selected embodiments of the present invention comprise antibodies that have a disassociation constant or $K_D$ ($k_{off}/k_{on}$) of less than $10^{-2}$M, less than $5\times10^{-2}$M, less than $10^{-3}$M, less than $5\times10^{-3}$M, less than $10^{-4}$M, less than $5\times10^{-4}$M, less than $10^{-5}$M, less than $5\times10^{-5}$M, less than $10^{-6}$M, less than $5\times10^{-6}$M, less than $10^{-7}$M, less than $5\times10^{-7}$M, less than $10^{-8}$M, less than $5\times10^{-8}$M, less than $10^{-9}$M, less than $5\times10^{-9}$M, less than $10^{-10}$M, less than $5\times10^{-10}$M, less than $10^{-11}$M, less than $5\times10^{-11}$M, less than $10^{-12}$M, less than $5\times10^{-12}$M, less than $10^{-13}$M, less than $5\times10^{-13}$M, less than $10^{-14}$M, less than $5\times10^{-14}$M, less than $10^{-15}$M or less than $5\times10^{-15}$M.

In specific embodiments, an antibody of the invention that immunospecifically binds to DLL3 has an association rate constant or $k_{on}$ (or $k_a$) rate (DLL3 (Ab)+antigen $(Ag)_{on}{}^k\leftarrow$Ab-Ag) of at least $10^5M^{-1}$ $s^{-1}$, at least $2\times10^5M^{-1}$ $s^{-1}$, at least $5\times10^5M^{-1}$ $s^{-1}$, at least $10^6M^{-1}s^{-1}$, at least $5\times10^6M^{-1}$ $s^{-1}$, at least $10^7M^{-1}s^{-1}$, at least $5\times10^7M^{-1}s^{-1}$, or at least $10M^{-1}s^{-1}$.

In another embodiment, an antibody of the invention that immunospecifically binds to DLL3 has a disassociation rate constant or $k_{off}$ (or $k_d$) rate (DLL3 (Ab)+antigen $(Ag)_{off}{}^k\leftarrow$Ab-Ag) of less than $10^{-1}s^{-1}$, less than $5\times10^{-1}s^{-1}$, less than $10^{-2}s^{-1}$, less than $5\times10^{-2}$ $s^{-1}$, less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$ less than $10^{-7}$ $s^{-1}$, less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$ or less than $10^{-10}$ $s^{-1}$.

In other selected embodiments of the present invention anti-DLL3 antibodies will have an affinity constant or $K_a$ ($k_{on}/k_{off}$) of at least $10^2M^{-1}$, at least $5\times10^2M^{-1}$, at least $10^3M^{-1}$, at least $5\times10^3M^{-1}$, at least $10^4M^{-1}$, at least $5\times10^4M^{-1}$, at least $10^5M^{-1}$, at least $5\times10^6M^{-1}$, at least $10^6M^{-1}$, at least $5\times10^6M^{-1}$, at least $10^7M^{-1}$, at least $5\times10^7M^{-1}$, at least $10^8M^{-1}$, at least $5\times10^8M^{-1}$, at least $10^9M^{-1}$, at least $5\times10^9M^{-1}$, at least $10^{10}M^{-1}$, at least $5\times10^{10}M^{-1}$, at least $10^{11}M^{-1}$, at least $5\times10^{11}M^{-1}$, at least $10^{12}M^{-1}$, at least $5\times10^{12}M^{-1}$, at least $10^{13}M^{-1}$, at least $5\times10^{13}M^{-1}$, at least $10^{14}M^{-1}$, at least $5\times10^{14}M^{-1}$, at least $10^{15}M^{-1}$ or at least $5\times10^{15}M^{-1}$.

Besides the aforementioned modulator characteristics antibodies of the instant invention may further be characterized using additional physical characteristics including, for example, thermal stability (i.e, melting temperature; Tm), and isoelectric points. (See, e.g., Bjellqvist et al., 1993, Electrophoresis 14:1023; Vermeer et al., 2000, Biophys. J. 78:394-404; Vermeer et al., 2000, Biophys. J. 79: 2150-2154 each of which is incorporated herein by reference).

VIII. Conjugated Modulators

A. Overview

Once the modulators of the invention have been generated and/or fabricated and selected according to the teachings herein they may be linked with, fused to, conjugated to (e.g., covalently or non-covalently) or otherwise associated with pharmaceutically active or diagnostic moieties or biocompatible modifiers. As used herein the term "conjugate" or "modulator conjugate" or "antibody conjugate" will be used broadly and held to mean any biologically active or detectable molecule or drug associated with the disclosed modulators regardless of the method of association. In this respect it will be understood that such conjugates may, in addition to the disclosed modulators, comprise peptides, polypeptides, proteins, prodrugs which are metabolized to an active agent in vivo, polymers, nucleic acid molecules, small molecules, binding agents, mimetic agents, synthetic drugs, inorganic molecules, organic molecules and radioisotopes. Moreover, as indicated above the selected conjugate may be covalently or non-covalently associated with, or linked to, the modulator and exhibit various stoichiometric molar ratios depending, at least in part, on the method used to effect the conjugation.

Particularly preferred aspects of the instant invention will comprise antibody modulator conjugates or antibody-drug conjugates that may be used for the diagnosis and/or treatment of proliferative disorders. It will be appreciated that, unless otherwise dictated by context, the term "antibody-drug conjugate" or "ADC" or the formula M-[L-D]n shall be held to encompass conjugates comprising both therapeutic and diagnostic moieties. In such embodiments antibody-drug conjugate compounds will comprise a DLL3 modulator (typically an anti-DLL3 antibody) as the modulator or cellular binding unit (abbreviated as CBA, M, or Ab herein), a therapeutic (e.g., anti-cancer agent) or diagnostic moiety (D), and optionally a linker (L) that joins the drug and the antigen binding agent. For the purposes of the instant disclosure "n" shall be held to mean an integer from 1 to 20. In a preferred embodiment, the modulator is a DLL3 mAb comprising at least one CDR from the heavy and light chain variable regions as described above.

Those skilled in the art will appreciate that a number of different reactions are available for the attachment or association of therapeutic or diagnostic moieties and/or linkers to binding agents. In selected embodiments this may be accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates and azlactones can also be used as coupling agents for covalently attaching drugs to binding agents.

In other embodiments the disclosed modulators of the invention may be conjugated or associated with proteins, polypeptides or peptides that impart selected characteristics (e.g., biotoxins, biomarkers, purification tags, etc.). In certain preferred embodiments the present invention encompasses the use of modulators or fragments thereof recombinantly fused or chemically conjugated (including both covalent and non-covalent conjugations) to a heterologous protein or peptide wherein the protein or peptide comprises at least 10, at least 20, at least 30, at least 40, at least 50, at least 60, at least 70, at least 80, at least 90 or at least 100 amino acids. The construct does not necessarily need to be directly linked, but may occur through amino acid linker sequences. For example, antibodies may be used to target heterologous polypeptides to particular cell types expressing DLL3, either in vitro or in vivo, by fusing or conjugating the modulators of the present invention to antibodies specific for particular cell surface receptors to provide bispecific constructs. Moreover, modulators fused or conjugated to heterologous polypeptides may also be used in in vitro immunoassays and may be particularly compatible with purification methodology (e.g., his-tags) as is known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452.

B. Linkers

Besides the aforementioned peptide linkers or spacers, it will be appreciated that several other varieties or types of linker may be used to associate the disclosed modulators with pharmaceutically active or diagnostic moieties or biocompatible modifiers. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

The linkers of the ADC are preferably stable extracellularly, prevent aggregation of ADC molecules and keep the ADC freely soluble in aqueous media and in a monomeric state. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS. Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

To this end certain embodiments of the invention comprise the use a linker that is cleavable by a cleaving agent that is present in the intracellular environment (e.g., within a lysosome or endosome or caveolae). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, each of which is known to hydrolyze dipeptide drug derivatives resulting in the release of active drug inside target cells. Exemplary peptidyl linkers that are cleavable by the thiol-dependent protease Cathepsin-B are peptides comprising Phe-Leu since Cathepsin-B has been found to be highly expressed in cancerous tissue. Other examples of such linkers are described, for example, in U.S. Pat. No. 6,214,345 and U.S.P.N. 2012/0078028 each of which incorporated herein by reference in its entirety. In a specific preferred embodiment, the peptidyl linker cleavable by an intracellular protease is a Val-Cit linker, an Ala-Val linker or a Phe-Lys linker such as is described in U.S. Pat. No. 6,214,345. One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, oxime, semicarbazone, thiosemicarbazone, cis-aconitic amide, orthoester, acetal, ketal, or the like) can be used (See, e.g., U.S. Pat. Nos. 5,122,368; 5,824,805; 5,622,929). Such linkers are relatively stable under neutral pH conditions, such as those in the blood, but are unstable at below pH 5.5 or 5.0, the approximate pH of the lysosome.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio) butyrate) and SMPT (N-succinimidyl-oxycarbonyl-alpha-methyl-alpha-(2-pyridyldithio)toluene). In yet other specific embodiments, the linker is a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12). In yet other embodiments, the linker unit is not cleavable and the drug is released by antibody degradation. (See U.S. Publication No. 2005/0238649 incorporated by reference herein in its entirety and for all purposes).

More particularly, in preferred embodiments (set forth in U.S.P.N. 2011/0256157 which is incorporated herein by reference in its entirety) compatible linkers will comprise:

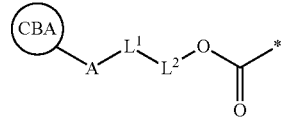

where the asterisk indicates the point of attachment to the cytotoxic agent, CBA is a cell binding agent/modulator, $L^1$ is a linker, A is a connecting group connecting $L^1$ to the cell binding agent, $L^2$ is a covalent bond or together with —OC(=O)— forms a self-immolative linker, and $L^1$ or $L^2$ is a cleavable linker.

$L^1$ is preferably the cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidising conditions may also find use in the present invention.

$L^1$ may comprise a contiguous sequence of amino acids. The amino acid sequence may be the target substrate for enzymatic cleavage, thereby allowing release of $R^{10}$ from the N10 position.

In one embodiment, $L^1$ is cleavable by the action of an enzyme. In one embodiment, the enzyme is an esterase or a peptidase.

In one embodiment, $L^2$ is present and together with —C(=O)O— forms a self-immolative linker. In one embodiment, $L^2$ is a substrate for enzymatic activity, thereby allowing release of $R^{10}$ from the N10 position.

In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from:

—C(=O)NH—, —C(=O)O—, —NHC(=O)—, —OC(=O)—, —OC(=O)O—, —NHC(=O)O—, —OC(=O)NH—, and —NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2H$, $^3H$, $^{14}C$, $^{15}N$), protected forms, and racemic mixtures thereof.

In one embodiment, —C(=O)O— and $L^2$ together form the group:

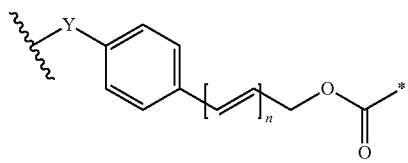

where the asterisk indicates the point of attachment to the drug or cytotoxic agent position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

The self-immolative linker will allow for release of the protected compound when a remote site is activated, proceeding along the lines shown below (for n=0):

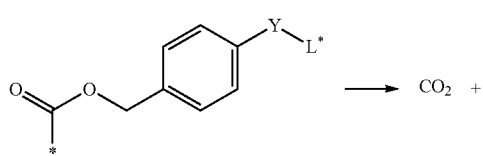

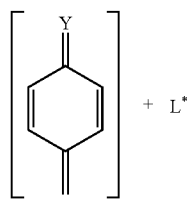

where $L^*$ is the activated form of the remaining portion of the linker. These groups have the advantage of separating the site of activation from the compound being protected. As described above, the phenylene group may be optionally substituted.

In one embodiment described herein, the group $L^*$ is a linker $L^1$ as described herein, which may include a dipeptide group.

In another embodiment, —C(=O)O— and $L^2$ together form a group selected from:

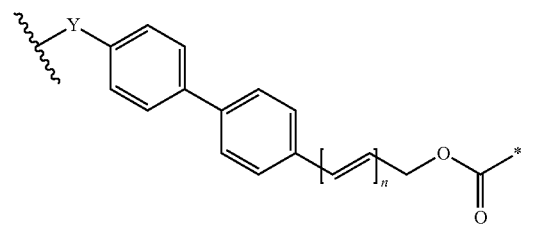

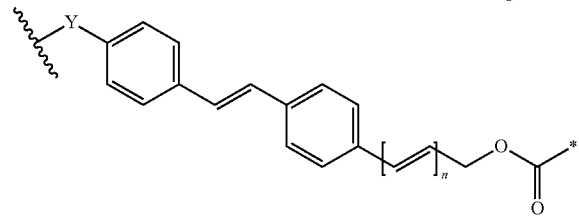

where the asterisk, the wavy line, Y, and n are as defined above. Each phenylene ring is optionally substituted with one, two or three substituents as described herein. In one embodiment, the phenylene ring having the Y substituent is optionally substituted and the phenylene ring not having the Y substituent is unsubstituted. In one embodiment, the phenylene ring having the Y substituent is unsubstituted and the phenylene ring not having the Y substituent is optionally substituted.

In another embodiment, —C(=O)O— and $L^2$ together form a group selected from:

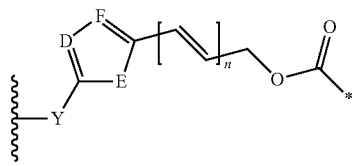

where the asterisk, the wavy line, Y, and n are as defined above, E is O, S or NR, D is N, CH, or CR, and F is N, CH, or CR.

In one embodiment, D is N.
In one embodiment, D is CH.
In one embodiment, E is O or S.
In one embodiment, F is CH.

In a preferred embodiment, the linker is a cathepsin labile linker.

In one embodiment, $L^1$ comprises a dipeptide. The dipeptide may be represented as —NH—$X_1$-$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$-$X_2$— in dipeptide, —NH—$X_1$-$X_2$—CO—, is selected from:

-Phe-Lys-, -Val-Ala-, -Val-Lys-, -Ala-Lys-, -Val-Cit-, -Phe-Cit-, -Leu-Cit-, -Tle-Cit-, -Phe-Arg- and -Trp-Cit- where Cit is citrulline.

Preferably, the group —$X_1$-$X_2$— in dipeptide, —NH— $X_1$-$X_2$—CO—, is selected from:

-Phe-Lys-, -Val-Ala-, -Val-Lys-, -Ala-Lys-, and -Val-Cit-.

Most preferably, the group —$X_1$—$X_2$— in dipeptide, —NH—$X_1$-$X_2$—CO—, is -Phe-Lys- or -Val-Ala-.

Other dipeptide combinations may be used, including those described by Dubowchik et al., *Bioconjugate Chemistry,* 2002, 13,855-869, which is incorporated herein by reference.

In one embodiment, the amino acid side chain is derivatised, where appropriate. For example, an amino group or carboxy group of an amino acid side chain may be derivatised.

In one embodiment, an amino group $NH_2$ of a side chain amino acid, such as lysine, is a derivatised form selected from the group consisting of NHR and NRR'.

In one embodiment, a carboxy group COOH of a side chain amino acid, such as aspartic acid, is a derivatised form selected from the group consisting of COOR, $CONH_2$, CONHR and CONRR'.

In one embodiment, the amino acid side chain is chemically protected, where appropriate. The side chain protecting group may be a group as discussed below in relation to the group $R^L$. Protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:

Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z, Alloc;
Ser: Bzl, TBDMS, TBDPS;
Thr: Bz;
Trp: Boc;
Tyr: Bzl, Z, Z—Br.

In one embodiment, the side chain protection is selected to be orthogonal to a group provided as, or as part of, a capping group, where present. Thus, the removal of the side chain protecting group does not remove the capping group, or any protecting group functionality that is part of the capping group.

In other embodiments of the invention, the amino acids selected are those having no reactive side chain functionality. For example, the amino acids may be selected from: Ala, Gly, Ile, Leu, Met, Phe, Pro, and Val.

In one embodiment, the dipeptide is used in combination with a self-immolative linker. The self-immolative linker may be connected to —$X_2$—.

Where a self-immolative linker is present, —$X_2$— is connected directly to the self-immolative linker. Preferably the group —$X_2$—CO— is connected to Y, where Y is NH, thereby forming the group —$X_2$—CO—NH—.

—NH—$X_1$— is connected directly to A. A may comprise the functionality —CO— thereby to form an amide link with —$X_1$—.

In one embodiment, $L^1$ and $L^2$ together with —OC (=O)— comprise the group NH—$X_1$-$X_2$—CO-PABC-. The PABC group is connected directly to the cytotoxic agent. Preferably, the self-immolative linker and the dipeptide together form the group —NH-Phe-Lys-CO—NH-PABC-, which is illustrated below:

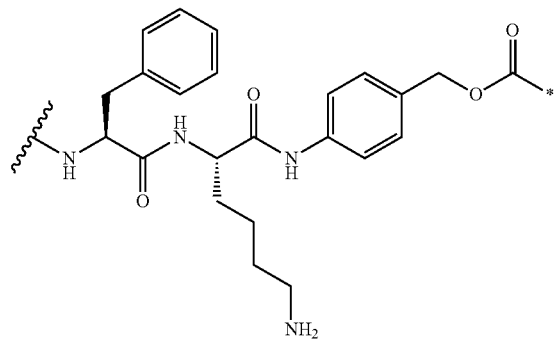 [SMILES: *N[C@@H](Cc1ccccc1)C(=O)N[C@@H](CCCCN)C(=O)Nc1ccc(COC(*)=O)cc1]

where the asterisk indicates the point of attachment to the selected cytotoxic moiety, and the wavy line indicates the point of attachment to the remaining portion of the linker $L^1$ or the point of attachment to A. Preferably, the wavy line indicates the point of attachment to A. The side chain of the Lys amino acid may be protected, for example, with Boc, Fmoc, or Alloc, as described above.

Alternatively, the self-immolative linker and the dipeptide together form the group —NH-Val-Ala-CO—NH-PABC-, which is illustrated below:

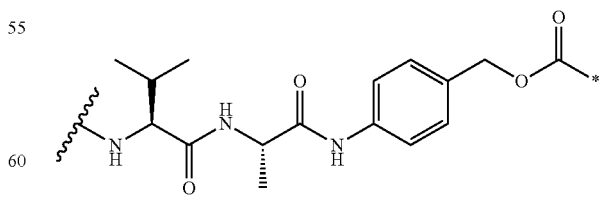

where the asterisk and the wavy line are as defined above.

Alternatively, the self-immolative linker and the dipeptide together form the group —NH-Val-Cit-CO—NH-PABC-, which is illustrated below:

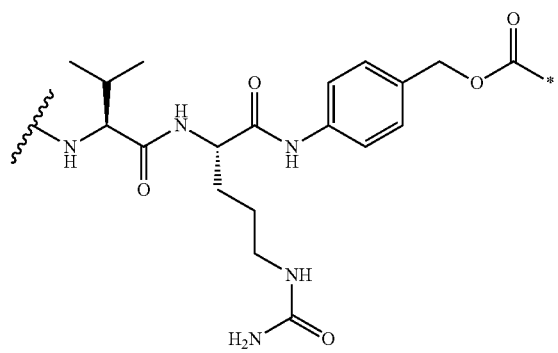 [SMILES: *N[C@H](C(=O)N[C@@H](CCCNC(N)=O)C(=O)Nc1ccc(COC(*)=O)cc1)C(C)C]

where the asterisk and the wavy line are as defined above.

In some embodiments of the present invention, it may be preferred that if the drug moiety contains an unprotected imine bond, e.g. if moiety B is present, then the linker does not contain a free amino (H$_2$N—) group. Thus if the linker has the structure -A-L$^1$-L$^2$- then this would preferably not contain a free amino group. This preference is particularly relevant when the linker contains a dipeptide, for example as L$^1$; in this embodiment, it would be preferred that one of the two amino acids is not selected from lysine.

Without wishing to be bound by theory, the combination of an unprotected imine bond in the drug moiety and a free amino group in the linker can cause dimerisation of the drug-linker moiety which may interfere with the conjugation of such a drug-linker moiety to an antibody. The cross-reaction of these groups may be accelerated in the case the free amino group is present as an ammonium ion (H$_3$N$^+$—), such as when a strong acid (e.g. TFA) has been used to deprotect the free amino group.

In one embodiment, A is a covalent bond. Thus, L$^1$ and the cell binding agent are directly connected. For example, where L$^1$ comprises a contiguous amino acid sequence, the N-terminus of the sequence may connect directly to the cell binding agent.

Thus, where A is a covalent bond, the connection between the cell binding agent and L$^1$ may be selected from:
—C(=O)NH—, —C(=O)O—, —NHC(=O)—, —OC(=O)—, —OC(=O)O—, —NHC(=O)O—, —OC(=O)NH—, —NHC(=O)NH—, —C(=O)NHC(O)—, —S—, —S—S—, —CH$_2$C(=O)—, and =N—NH—.

An amino group of L$^1$ that connects to the DLL3 modulator may be the N-terminus of an amino acid or may be derived from an amino group of an amino acid side chain, for example a lysine amino acid side chain.

A carboxyl group of L$^1$ that connects to the modulator may be the C-terminus of an amino acid or may be derived from a carboxyl group of an amino acid side chain, for example a glutamic acid amino acid side chain.

A hydroxyl group of L$^1$ that connects to the cell binding agent may be derived from a hydroxyl group of an amino acid side chain, for example a serine amino acid side chain.

A thiol group of L$^1$ that connects to a modulator agent may be derived from a thiol group of an amino acid side chain, for example a serine amino acid side chain.

The comments above in relation to the amino, carboxyl, hydroxyl and thiol groups of L$^1$ also apply to the cell binding agent.

In one embodiment, L$^2$ together with —OC(=O)— represents:

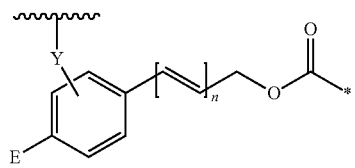

where the asterisk indicates the point of attachment to the N10 position, the wavy line indicates the point of attachment to L$^1$, n is 0 to 3, Y is a covalent bond or a functional group, and E is an activatable group, for example by enzymatic action or light, thereby to generate a self-immolative unit. The phenylene ring is optionally further substituted with one, two or three substituents as described herein. In one embodiment, the phenylene group is optionally further substituted with halo, NO$_2$, R or OR. Preferably n is 0 or 1, most preferably 0.

E is selected such that the group is susceptible to activation, e.g. by light or by the action of an enzyme. E may be —NO$_2$ or glucuronic acid. The former may be susceptible to the action of a nitroreductase, the latter to the action of a β-glucoronidase.

In this embodiment, the self-immolative linker will allow for release of the protected compound when E is activated, proceeding along the lines shown below (for n=0):

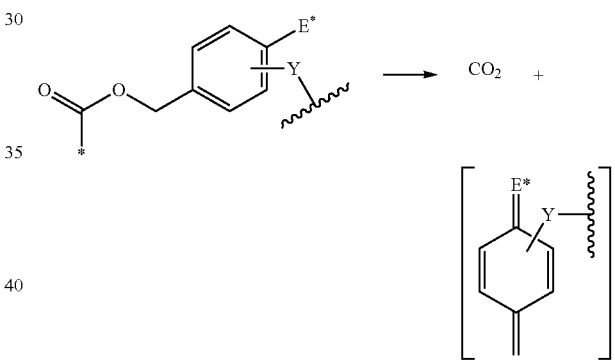

where the asterisk indicates the point of attachment to the N10 position, E. is the activated form of E, and Y is as described above. These groups have the advantage of separating the site of activation from the compound being protected. As described above, the phenylene group may be optionally further substituted.

The group Y may be a covalent bond to L$^1$.

The group Y may be a functional group selected from:
—C(=O)—, —NH—, —O—, —C(=O)NH—, —C(=O)O—, —NHC(=O)—, —OC(=O)—, —OC(=O)O—, —NHC(=O)O—, —OC(=O)NH—, —NHC(=O)NH—, —NHC(=O)NH, —C(=O)NHC(=O)—, and —S—.

Where L$^1$ is a dipeptide, it is preferred that Y is —NH— or —C(=O)—, thereby to form an amide bond between L$^1$ and Y. In this embodiment, the dipeptide sequence need not be a substrate for an enzymatic activity.

In another embodiment, A is a spacer group. Thus, L$^1$ and the cell binding agent are indirectly connected.

L$^1$ and A may be connected by a bond selected from:
—C(=O)NH—, —C(=O)O—, —NHC(=O)—, —OC(=O)—, —OC(=O)O—, —NHC(=O)O—, —OC(=O)NH—, and —NHC(=O)NH—.

Preferably, the linker contains an electrophilic functional group for reaction with a nucleophilic functional group on the modulator. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) aldehydes, ketones, carboxyl, and, some of which are exemplified as follows:

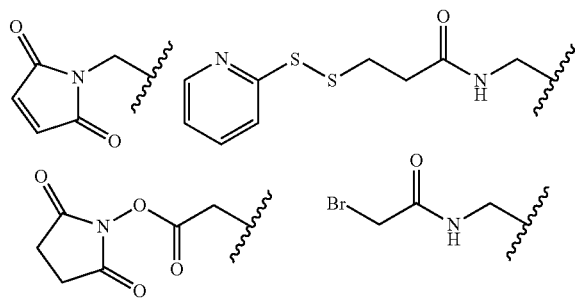

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, a linker has a reactive nucleophilic group which is reactive with an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a linker include, but are not limited to, hydrazide, oxime, amino, hydroxyl, hydrazine, thiosemicarbazone, hydrazine carboxylate, and arylhydrazide. The electrophilic group on an antibody provides a convenient site for attachment to a Linker.

In one embodiment, the group A is:

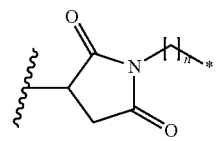

where the asterisk indicates the point of attachment to $L^1$, the wavy line indicates the point of attachment to the cell binding agent, and n is 0 to 6. In one embodiment, n is 5.

In one embodiment, the group A is:

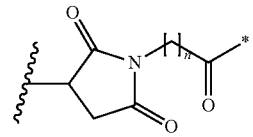

where the asterisk indicates the point of attachment to $L^1$, the wavy line indicates the point of attachment to the cell binding agent, and n is 0 to 6. In one embodiment, n is 5.

In one embodiment, the group A is:

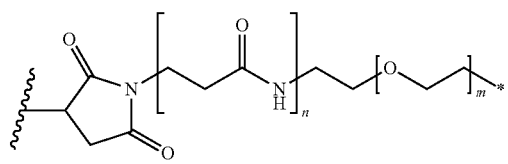

where the asterisk indicates the point of attachment to $L^1$, the wavy line indicates the point of attachment to the cell binding agent, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the group A is:

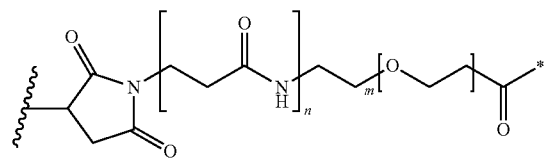

where the asterisk indicates the point of attachment to $L^1$, the wavy line indicates the point of attachment to the cell binding agent, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the connection between the cell binding agent and A is through a thiol residue of the cell binding agent and a maleimide group of A.

In one embodiment, the connection between the cell binding agent and A is:

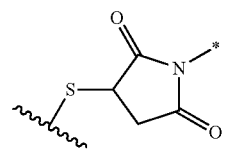

where the asterisk indicates the point of attachment to the remaining portion of A and the wavy line indicates the point of attachment to the remaining portion of the cell binding agent. In this embodiment, the S atom is typically derived from the modulator.

In each of the embodiments above, an alternative functionality may be used in place of the maleimide-derived group shown below:

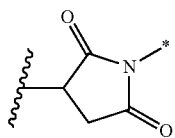

where the wavy line indicates the point of attachment to the cell binding agent as before, and the asterisk indicates the bond to the remaining portion of the A group.

In one embodiment, the maleimide-derived group is replaced with the group:

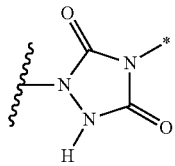

where the wavy line indicates point of attachment to the cell binding agent, and the asterisk indicates the bond to the remaining portion of the A group.

In one embodiment, the maleimide-derived group is replaced with a group, which optionally together with the cell binding agent, is selected from:
—C(=O)NH—, —C(=O)O—, —NHC(=O)—, —OC(=O)—, —OC(=O)O—, —NHC(=O)O—, —OC(=O)NH—, —NHC(=O)NH—, —NHC(=O)NH, —C(=O)NHC(=O)—, —S—, —S—S—, —CH$_2$C(=O)—, —C(=O)CH$_2$—, =N—NH— and —NH—N=.

In one embodiment, the maleimide-derived group is replaced with a group, which optionally together with the cell binding agent, is selected from:

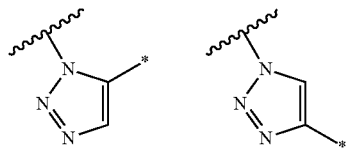

where the wavy line indicates either the point of attachment to the cell binding agent or the bond to the remaining portion of the A group, and the asterisk indicates the other of the point of attachment to the cell binding agent or the bond to the remaining portion of the A group.

Other groups suitable for connecting $L^1$ to the selected modulator are described in WO 2005/082023.

In another preferred embodiment the modulators of the instant invention may be associated with biocompatible polymers comprising drug linker units. In this respect one such type of compatible polymer comprises Fleximer® polymers (Mersana Therapeutics). Such polymers are reportedly biodegradable, well tolerated and have been clinically validated. Moreover, such polymers are compatible with a number of customizable linker technologies and chemistries allowing for control of pharmacokinetics, localization of drug release and improved biodistribution.

The selected modulators can also be directly conjugated radioisotopes or may comprise macrocyclic chelators useful for conjugating radiometal ions (as described herein). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

More generally, techniques for conjugating therapeutic moieties or cytotoxic agents to modulators are well known. As discussed above moieties can be conjugated to modulators by any art-recognized method, including, but not limited to aldehyde/Schiff linkage, sulphydryl linkage, acid-labile linkage, cis-aconityl linkage, hydrazone linkage, enzymatically degradable linkage (see generally Garnett, 2002, Adv Drug Deliv Rev 53:171). Also see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119. In preferred embodiments a DLL3 modulator that is conjugated to a therapeutic moiety or cytotoxic agent may be internalized by a cell upon binding to a DLL3 molecule associated with the cell surface thereby delivering the therapeutic payload.

C. Biocompatible Modifiers

In selected embodiments the modulators of the invention may be conjugated or otherwise associated with biocompatible modifiers that may be used to adjust, alter, improve or moderate modulator characteristics as desired. For example, antibodies or fusion constructs with increased in vive half-lives can be generated by attaching relatively high molecular weight polymer molecules such as commercially available polyethylene glycol (PEG) or similar biocompatible polymers. Those skilled in the art will appreciate that PEG may be obtained in many different molecular weight and molecular configurations that can be selected to impart specific properties to the antibody (e.g. the half-life may be tailored). PEG can be attached to modulators or antibody fragments or derivatives with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed modulators can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. 0 413, 622. Other biocompatible conjugates are evident to those of ordinary skill and may readily be identified in accordance with the teachings herein.

D. Diagnostic or Detection Agents

In other preferred embodiments, modulators of the present invention, or fragments or derivatives thereof, are conjugated to a diagnostic or detectable agent, marker or reporter which may be, for example, a biological molecule (e.g., a peptide or nucleotide), a small molecule, fluorophore, or radioisotope. Labeled modulators can be useful for monitoring the development or progression of a hyperproliferative disorder or as part of a clinical testing procedure to determine the efficacy of a particular therapy including the disclosed modulators (i.e. theragnostics) or to determine a future course of treatment. Such markers or reporters may also be useful in purifying the selected modulator, modulator analytics (e.g., epitope binding or antibody binning), separating or isolating TIC or in preclinical procedures or toxicology studies.

Such diagnosis analysis and/or detection can be accomplished by coupling the modulator to detectable substances including, but not limited to, various enzymes comprising for example horseradish peroxidase, alkaline phosphatase, beta-galactosidase, or acetylcholinesterase; prosthetic groups, such as but not limited to streptavidinlbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{67}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, nonradioactive paramagnetic metal ions, and molecules that are radiolabeled or conjugated to specific radioisotopes. In such embodiments appropriate detection methodology is well known in the art and readily available from numerous commercial sources.

As indicated above, in other embodiments the modulators or fragments thereof can be fused or conjugated to marker sequences or compounds, such as a peptide or fluorophore to facilitate purification or diagnostic or analytic procedures such as immunohistochemistry, bio-layer interferometry, surface plasmon resonance, flow cytometry, competitive ELISA, FACs, etc. In preferred embodiments, the marker comprises a his-tag such as that provided by the pQE vector (Qiagen), among others, many of which are commercially available. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

E. Therapeutic Moities

As previously alluded to the modulators or fragments or derivatives thereof may also be conjugated, linked or fused to or otherwise associated with a"therapeutic moiety" or "drug" such as an anti-proliferative or anti-cancer agent including, but not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents.

Preferred exemplary anti-cancer agents include cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4 (Immunogen, Inc.), dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Additional compatible cytotoxins comprise dolastatins and auristatins, including monomethyl auristatin E (MMAE) and monomethyl auristatin F (MMAF) (Seattle Genetics, Inc.), amanitins such as alpha-amanitin, beta-amanitin, gamma-amanitin or epsilon-amanitin (Heidelberg Pharma AG), DNA minor groove binding agents such as duocarmycin derivatives (Syntarga, B.V.) and modified pyrrolobenzodiazepine dimers (Spirogen, Ltd.), splicing inhibitors such as meayamycin analogs or derivatives (e.g., FR901464 as set forth in U.S. Pat. No. 7,825,267), tubular binding agents such as epothilone analogs and paclitaxel and DNA damaging agents such as calicheamicins and esperamicins. Furthermore, in certain embodiments the DLL3 modulators of the instant invention may be associated with anti-CD3 binding molecules to recruit cytotoxic T-cells and have them target the tumor initiating cells (BiTE technology; see e.g., Fuhrmann, S. et. al. Annual Meeting of AACR Abstract No. 5625 (2010) which is incorporated herein by reference).

Still additional compatible anti-cancer agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa, chlorambucil, melphalan, carmustine (BCNU) and lomustine (CCNU), busulfan, dibromomannitol, streptozotocin, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, and anthramycin (AMC)), and anti-mitotic agents (e.g., vincristine and vinblastine). A more extensive list of therapeutic moieties can be found in PCT publication WO 03/075957 and U.S.P.N. 2009/0155255 each of which is incorporated herein by reference.

As indicated above selected embodiments of the instant invention are directed to conjugated DLL3 modulators such as anti-DLL3 antibody drug conjugates that comprise pyrrolobenzodiazepine (PBD) as a cytotoxic agent. It will be appreciated that PBDs are alkylating agents that exert antitumor activity by covalently binding to DNA in the minor groove and inhibiting nucleic acid synthesis. In this respect PBDs have been shown to have potent antitumor properties while exhibiting minimal bone marrow depression. PBDs compatible with the present invention may be linked to the DLL3 modulator using any one of several types of linker (e.g., a peptidyl linker comprising a maleimido moiety with a free sulfhydryl) and, in certain embodiments are dimeric in form (i.e., PBD dimers). Compatible PBDs (and optional linkers) that may be conjugated to the disclosed modulators are described, for example, in U.S. Pat. Nos. 6,362,331, 7,049,311, 7,189,710, 7,429,658, 7,407,951, 7,741,319, 7,557,099, 8,034,808, 8,163,736 U.S.P.N. 2011/0256157 and PCT filings WO2011/130613, WO2011/128650 and WO2011/130616 each of which is incorporated herein by reference. Accordingly, in particularly preferred embodiments the modulator will comprise an anti DLL3 antibody conjugated or associated with one or more PBD dimers (i.e., a DLL3-PBD ADC).

In particularly preferred embodiments compatible PBDs that may be conjugated to the disclosed modulators are described, in U.S.P.N. 2011/0256157. In this disclosure, PBD dimers, i.e. those comprising two PBD moieties may be preferred. Thus, preferred conjugates of the present invention are those having the formulae (AR) or (AC):

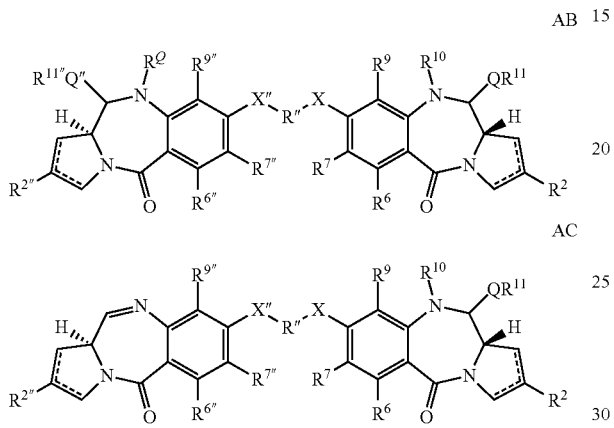

wherein:

the dotted lines indicate the optional presence of a double bond between C1 and C2 or C2 and C3;

$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo;

where $R^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

$R^{10}$ is a linker connected to a modulator or fragment or derivative thereof, as described above;

Q is independently selected from O, S and NH;

$R^{11}$ is either H, or R or, where Q is O, SO$_3$M, where M is a metal cation;

R and R' are each independently selected from optionally substituted $C_{1-12}$ alkyl, $C_{3-20}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring; and wherein $R^{2''}$, $R^{6'''}$, $R^{7'''}$, $R^{9'''}$, $X''$, $Q''$ and $R^{11'''}$ and are as defined according to $R^2$, $R^6$, $R^7$, $R^9$, X, Q and $R^{11}$ respectively, and $R^C$ is a capping group.

Double Bond

In one embodiment, there is no double bond present between C1 and C2, and C2 and C3.

In one embodiment, the dotted lines indicate the optional presence of a double bond between C2 and C3, as shown below:

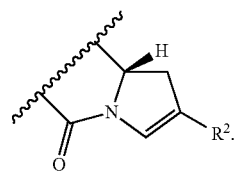

In one embodiment, a double bond is present between C2 and C3 when $R^2$ is $C_{5-20}$ aryl or $C_{1-12}$ alkyl.

In one embodiment, the dotted lines indicate the optional presence of a double bond between C1 and C2, as shown below:

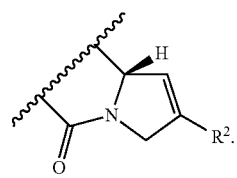

In one embodiment, a double bond is present between C1 and C2 when $R^2$ is $C_{5-20}$ aryl or $C_{1-12}$ alkyl.

$R^2$

In one embodiment, $R^2$ is independently selected from H, OH, =O, =CH$_2$, CN, R, OR, =CH—R$^D$, —C(R$^D$)$_2$, O—SO$_2$—R, CO$_2$R and COR, and optionally further selected from halo or dihalo.

In one embodiment, $R^2$ is independently selected from H, OH, =O, —CH$_2$, CN, R, OR, =CH—R$^D$, =C(R$^D$)$_2$, O—SO$_2$—R, CO$_2$R and COR.

In one embodiment, $R^2$ is independently selected from H, =O, =CH$_2$, R, =CH—R$^D$, and =C(R$^D$)$_2$.

In one embodiment, $R^2$ is independently H.

In one embodiment, $R^2$ is independently =o.

In one embodiment, $R^2$ is independently =CH$_2$.

In one embodiment, $R^2$ is independently =CH—R$^D$. Within the PBD compound, the group —CH—R$^D$ may have either configuration shown below:

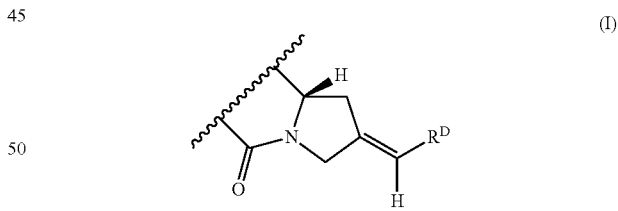

In one embodiment, the configuration is configuration (I).

In one embodiment, $R^2$ is independently =C(R$^D$)$_2$.

In one embodiment, $R^2$ is independently =CF$_2$.

In one embodiment, $R^2$ is independently R.

In one embodiment, $R^2$ is independently optionally substituted $C_{5-20}$ aryl.

In one embodiment, $R^2$ is independently optionally substituted $C_{1-12}$ alkyl.

In one embodiment, $R^2$ is independently optionally substituted $C_{5-20}$ aryl.

In one embodiment. $R^2$ is independently optionally substituted $C_{5-7}$ aryl.

In one embodiment, $R^2$ is independently optionally substituted $C_{8-10}$ aryl.

In one embodiment, $R^2$ is independently optionally substituted phenyl.

In one embodiment, $R^2$ is independently optionally substituted napthyl.

In one embodiment, $R^2$ is independently optionally substituted pyridyl.

In one embodiment, $R^2$ is independently optionally substituted quinolinyl or isoquinolinyl.

In one embodiment, $R^2$ bears one to three substituent groups, with 1 and 2 being more preferred, and singly substituted groups being most preferred. The substituents may be any position.

Where $R^2$ is a $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

In one embodiment, $R^2$ is selected from:

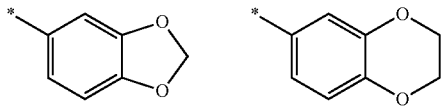 [SMILES: *c1ccc2c(c1)OCO2 ; *c1ccc2c(c1)OCCO2]

where the asterisk indicates the point of attachment.

Where $R^2$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

In one embodiment, where $R^2$ is optionally substituted, the substituents are selected from those substituents given in the substituent section below.

Where R is optionally substituted, the substituents are preferably selected from:

Halo, Hydroxyl, Ether, Formyl, Acyl, Carboxy, Ester, Acyloxy, Amino, Amido, Acylamido, Aminocarbonyloxy, Ureido, Nitro, Cyano and Thioether.

In one embodiment, where R or $R^2$ is optionally substituted, the substituents are selected from the group consisting of R, OR, SR, NRR', $NO_2$, halo, $CO_2R$, COR, $CONH_2$, CONHR, and CONRR'.

Where $R^2$ is $C_{1-12}$ alkyl, the optional substituent may additionally include $C_{3-20}$ heterocyclyl and $C_{5-20}$ aryl groups.

Where $R^2$ is $C_{3-20}$ heterocyclyl, the optional substituent may additionally include $C_{1-12}$ alkyl and $C_{5-20}$ aryl groups.

Where $R^2$ is $C_{5-20}$ aryl groups, the optional substituent may additionally include $C_{3-20}$ heterocyclyl and $C_{1-12}$ alkyl groups.

It is understood that the term "alkyl" encompasses the sub-classes alkenyl and alkynyl as well as cycloalkyl. Thus, where $R^2$ is optionally substituted $C_{1-12}$ alkyl, it is understood that the alkyl group optionally contains one or more carbon-carbon double or triple bonds, which may form part of a conjugated system. In one embodiment, the optionally substituted $C_{1-12}$ alkyl group contains at least one carbon-carbon double or triple bond, and this bond is conjugated with a double bond present between C1 and C2, or C2 and C3. In one embodiment, the $C_{1-12}$ alkyl group is a group selected from saturated $C_{1-12}$ alkyl, $C_{2-12}$ alkenyl, $C_{2-12}$ alkynyl and $C_{3-12}$ cycloalkyl.

If a substituent on $R^2$ is halo, it is preferably F or Cl, more preferably Cl.

If a substituent on $R^2$ is ether, it may in some embodiments be an alkoxy group, for example, a $C_{1-7}$ alkoxy group (e.g. methoxy, ethoxy) or it may in some embodiments be a $C_{5-7}$ aryloxy group (e.g phenoxy, pyridyloxy, furanyloxy).

If a substituent on $R^2$ is $C_{1-7}$ alkyl, it may preferably be a $C_{1-4}$ alkyl group (e.g. methyl, ethyl, propyl, butyl).

If a substituent on $R^2$ is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups.

If a substituent on $R^2$ is bis-oxy-$C_{1-3}$ alkylene, this is preferably bis-oxy-methylene or bis-oxy-ethylene.

Particularly preferred substituents for $R^2$ include methoxy, ethoxy, fluoro, chloro, cyano, bis-oxy-methylene, methyl-piperazinyl, morpholino and methyl-thienyl.

Particularly preferred substituted $R^2$ groups include, but are not limited to, 4-methoxyphenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthienyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl.

In one embodiment, $R^2$ is halo or dihalo. In one embodiment, $R^2$ is —F or —$F_2$, which substituents are illustrated below as (III) and (IV) respectively:

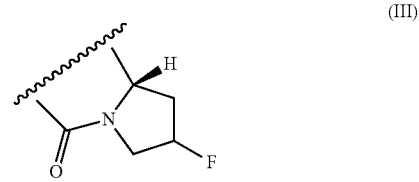

(III)

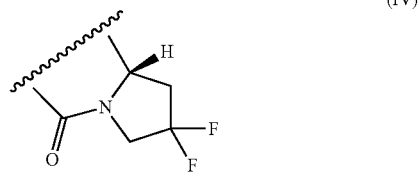

(IV)

$R^D$

In one embodiment, $R^D$ is independently selected from R, $CO_2R$, COR, CHO, $CO_2H$, and halo.

In one embodiment, $R^D$ is independently R.

In one embodiment, $R^D$ is independently halo.

$R^6$

In one embodiment, $R^6$ is independently selected from H, R, OH, OR, SH, SR, $NH_2$, NHR, NRR', $NO_2$, $Me_3Sn$— and Halo.

In one embodiment, $R^6$ is independently selected from H, OH, OR, SH, $NH_2$, $NO_2$ and Halo.

In one embodiment, $R^6$ is independently selected from H and Halo.

In one embodiment, $R^6$ is independently H.

In one embodiment, $R^6$ and $R^7$ together form a group —O—$(CH_2)_p$—O—, where p is 1 or 2.

$R^7$ $R^7$ is independently selected from H, R, OH, OR, SH, SR, $NH_2$, NHR, NRR', $NO_2$, $Me_3Sn$ and halo.

In one embodiment, $R^7$ is independently OR.

In one embodiment, $R^7$ is independently $OR^{7A}$, where $R^{7A}$ is independently optionally substituted $C_{1-6}$ alkyl.

In one embodiment, $R^{7A}$ is independently optionally substituted saturated $C_{1-6}$ alkyl.

In one embodiment, $R^{7A}$ is independently optionally substituted $C_{2-4}$ alkenyl.

In one embodiment, $R^{7A}$ is independently Me.

In one embodiment, $R^{7A}$ is independently $CH_2Ph$.

In one embodiment, $R^{7A}$ is independently allyl.

In one embodiment, the compound is a dimer where the $R^7$ groups of each monomer form together a dimer bridge having the formula X—R"—X linking the monomers.

$R^8$

In one embodiment, the compound is a dimer where the $R^8$ groups of each monomer form together a dimer bridge having the formula X—R"—X linking the monomers.

In one embodiment, $R^8$ is independently $OR^{8A}$, where $R^{8A}$ is independently optionally substituted $C_{1-4}$ alkyl.

In one embodiment, $R^{8A}$ is independently optionally substituted saturated $C_{1-6}$ alkyl or optionally substituted $C_{2-4}$ alkenyl.

In one embodiment, $R^{8A}$ is independently Me.

In one embodiment, $R^{8A}$ is independently $CH_2Ph$.

In one embodiment, $R^{8A}$ is independently allyl.

In one embodiment, $R^8$ and $R^7$ together form a group —O—$(CH_2)_p$—O—, where p is 1 or 2.

In one embodiment, $R^1$ and $R^9$ together form a group —O—$(CH_2)_p$—O—, where p is 1 or 2.

$R^9$

In one embodiment, $R^9$ is independently selected from H, R, OH, OR, SH, SR, $NH_2$, NHR, NRR', $NO_2$, $Me_3Sn$— and Halo.

In one embodiment, $R^9$ is independently H.

In one embodiment, $R^9$ is independently R or OR.

R and R'

In one embodiment, R is independently selected from optionally substituted $C_{1-12}$ alkyl, $C_{3-20}$ heterocyclyl and $C_{5-20}$ aryl groups. These groups are each defined in the substituents section below.

In one embodiment, R is independently optionally substituted $C_{1-12}$ alkyl.

In one embodiment, R is independently optionally substituted $C_{3-20}$ heterocyclyl.

In one embodiment, R is independently optionally substituted $C_{5-20}$ aryl.

In one embodiment, R is independently optionally substituted $C_{1-12}$ alkyl.

Described above in relation to $R^2$ are various embodiments relating to preferred alkyl and aryl groups and the identity and number of optional substituents. The preferences set out for $R^2$ as it applies to R are applicable, where appropriate, to all other groups R, for examples where $R^6$, $R^7$, $R^8$ or $R^9$ is R.

The preferences for R apply also to R'.

In some embodiments of the invention there is provided a compound having a substituent group —NRR'. In one embodiment, R and R' together with the nitrogen atom to which they are attached form an optionally substituted 4-, 5-, 6- or 7-membered heterocyclic ring. The ring may contain a further heteroatom, for example N, O or S.

In one embodiment, the heterocyclic ring is itself substituted with a group R. Where a further N heteroatom is present, the substituent may be on the N heteroatom.

R"

R" is a $C_{3-12}$ alkylene group, which chain may be interrupted by one or more heteroatoms, e.g. O, S, N(H), NMe and/or aromatic rings, e.g. benzene or pyridine, which rings are optionally substituted.

In one embodiment, R" is a $C_{3-12}$ alkylene group, which chain may be interrupted by one or more heteroatoms and/or aromatic rings, e.g. benzene or pyridine.

In one embodiment, the alkylene group is optionally interrupted by one or more heteroatoms selected from O, S, and NMe and/or aromatic rings, which rings are optionally substituted.

In one embodiment, the aromatic ring is a $C_{5-20}$ arylene group, where arylene pertains to a divalent moiety obtained by removing two hydrogen atoms from two aromatic ring atoms of an aromatic compound, which moiety has from 5 to 20 ring atoms.

In one embodiment, R" Is a $C_{3-12}$ alkylene group, which chain may be interrupted by one or more heteroatoms, e.g. O, S, N(H), NMe and/or aromatic rings, e.g. benzene or pyridine, which rings are optionally substituted by $NH_2$.

In one embodiment, R" is a $C_{3-12}$ alkylene group.

In one embodiment, R" is selected from a $C_3$, $C_5$, $C_7$, $C_9$ and a $C_{11}$ alkylene group.

In one embodiment, R" is selected from a $C_3$, $C_5$ and a $C_7$ alkylene group.

In one embodiment, R" is selected from a $C_3$ and a $C_5$ alkylene group.

In one embodiment, R" is a $C_3$ alkylene group.

In one embodiment, R" is a $C_5$ alkylene group.

The alkylene groups listed above may be optionally interrupted by one or more heteroatoms and/or aromatic rings, e.g. benzene or pyridine, which rings are optionally substituted.

The alkylene groups listed above may be optionally interrupted by one or more heteroatoms and/or aromatic rings, e.g. benzene or pyridine.

The alkylene groups listed above may be unsubstituted linear aliphatic alkylene groups.

X

In one embodiment, X is selected from O, S, or N(H).

Preferably, X is O.

$R^{10}$

Preferably compatible linkers such as those described above attach a DLL3 modulator (CBA/Ab/M), to a PBD drug moiety D through covalent bond(s) at the $R^{10}$ position (i.e., N10). The linker is a bifunctional or multifunctional moiety which can be used to link one or more drug moiety (D) and a modulator (preferably an antibody) to form antibody-drug conjugates (ADC). The linker (L) may be stable outside a cell, i.e. extracellular, or it may be cleavable by enzymatic activity, hydrolysis, or other metabolic conditions. Antibody-drug conjugates (ADC) can be conveniently prepared using a linker having reactive functionality for binding to the drug moiety and to the antibody. A cysteine thiol, or an amine, e.g. N-terminus or amino acid side chain such as lysine, of the antibody (Ab) can form a bond with a functional group of a linker or spacer reagent, PBD drug moiety (D) or drug-linker reagent (D-L).

Many functional groups on the linker attached to the N10 position of the PBD moiety may be useful to react with the cell binding agent. For example, ester, thioester, amide, thioamide, carbamate, thiocarbamate, urea, thiourea, ether, thioether, or disulfide linkages may be formed from reaction of the linker-PBD drug intermediates and the cell binding agent.

In another embodiment, the linker may be substituted with groups that modulate aggregation, solubility or reactivity. For example, a sulfonate substituent may increase water solubility of the reagent and facilitate the coupling reaction of the linker reagent with the antibody or the drug moiety, or facilitate the coupling reaction of Ab-L with D, or D-L with Ab, depending on the synthetic route employed to prepare the ADC.

In one preferred embodiment, $R^{10}$ is a group:

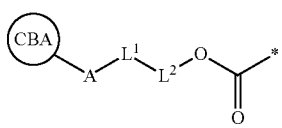

where the asterisk indicates the point of attachment to the N10 position, CBA is a cell binding agent/modulator, $L^1$ is a linker, A is a connecting group connecting $L^1$ to the cell binding agent, $L^2$ is a covalent bond or together with —OC(=O)— forms a self-immolative linker, and $L^1$ or $L^2$ is a cleavable linker.

$L^1$ is preferably the cleavable linker, and may be referred to as a trigger for activation of the linker for cleavage.

As discussed in the linker section above the nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidizing conditions may also find use in the present invention.

$L^1$ may comprise a contiguous sequence of amino acids. The amino acid sequence may be the target substrate for enzymatic cleavage, thereby allowing release of $R^{10}$ from the N10 position.

In one embodiment, $L^1$ is cleavable by the action of an enzyme. In one embodiment, the enzyme is an esterase or a peptidase.

In one embodiment, $L^2$ is present and together with —C(=O)O— forms a self-immolative linker. In one embodiment, $L^2$ is a substrate for enzymatic activity, thereby allowing release of $R^{10}$ from the N10 position.

In one embodiment, where $L^1$ is cleavable by the action of an enzyme and $L^2$ is present, the enzyme cleaves the bond between $L^1$ and $L^2$.

With regard to attaching the chosen linker to a selected PBD the group $R^C$ is removable from the N10 position of certain PBD moieties to leave an N10-C11 imine bond, a carbinolamine, a substituted carbinolamine, where $QR^{11}$ is $OSO_3M$, a bisulfite adduct, a thiocarbinolamine, a substituted thiocarbinolamine, or a substituted carbinalamine.

In one embodiment, $R^C$, may be a protecting group that is removable to leave an N10-C11 imine bond, a carbinolamine, a substituted cabinolamine, or, where $QR^{11}$ is $OSO_3M$, a bisulfite adduct. In one embodiment, $R^C$ is a protecting group that is removable to leave an N10-C11 imine bond.

The group $R^C$ is intended to be removable under the same conditions as those required for the removal of the group $R^{10}$, for example to yield an N10-C11 imine bond, a carbinolamine and so on. The capping group acts as a protecting group for the intended functionality at the N10 position. The capping group is intended not to be reactive towards a cell binding agent. For example, $R^C$ is not the same as $R^L$.

Compounds having a capping group may be used as intermediates in the synthesis of dimers having an imine monomer. Alternatively, compounds having a capping group may be used as conjugates, where the capping group is removed at the target location to yield an imine, a carbinolamine, a substituted cabinolamine and so on. Thus, in this embodiment, the capping group may be referred to as a therapeutically removable nitrogen protecting group, as defined in WO 00/12507.

In one embodiment, the group $R^C$ is removable under the conditions that cleave the linker $R^L$ of the group $R^{10}$. Thus, in one embodiment, the capping group is cleavable by the action of an enzyme.

In an alternative embodiment, the capping group is removable prior to the connection of the linker $R^L$ to the modulator. In this embodiment, the capping group is removable under conditions that do not cleave the linker $R^L$.

Where a compound includes a functional group $G^1$ to form a connection to the cell binding agent, the capping group is removable prior to the addition or unmasking of $G^1$.

The capping group may be used as part of a protecting group strategy to ensure that only one of the monomer units in a dimer is connected to a cell binding agent.

The capping group may be used as a mask for a N10-C11 imine bond. The capping group may be removed at such time as the imine functionality is required in the compound. The capping group is also a mask for a carbinolamine, a substituted cabinolamine, and a bisulfite adduct, as described above.

In one embodiment, $R^C$ is a carbamate protecting group.

In one embodiment, the carbamate protecting group is selected from:

Alloc, Fmoc, Boc, Troc, Teoc, Psec, Cbz and PNZ.

Optionally, the carbamate protecting group is further selected from Moc.

In one embodiment, $R^C$ is a linker group $R^L$ lacking the functional group for connection to the cell binding agent.

This application is particularly concerned with those $R^C$ groups which are carbamates.

In one embodiment, $R^C$ is a group:

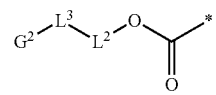

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker.

Where $L^3$ and $L^2$ are both covalent bonds, $G^2$ and OC(=O) together form a carbamate protecting group as defined above.

$L^1$ is as defined above in relation to $R^{10}$.
$L^2$ is as defined above in relation to $R^{10}$.

Various terminating groups are described below, including those based on well known protecting groups.

In one embodiment $L^3$ is a cleavable linker $L^1$, and $L^2$, together with OC(=O), forms a self-immolative linker. In this embodiment, $G^2$ is Ac (acetyl) or Moc, or a carbamate protecting group selected from: Alloc, Fmoc, Boc, Troc, Teoc, Psec, Cbz and PNZ. Optionally, the carbamate protecting group is further selected from Moc.

In another embodiment, $G^2$ is an acyl group —C(=O)$G^3$, where $G^3$ is selected from alkyl (including cycloalkyl, alkenyl and alkynyl), heteroalkyl, heterocyclyl and aryl (including heteroaryl and carboaryl). These groups may be optionally substituted. The acyl group together with an amino group of $L^3$ or $L^2$, where appropriate, may form an amide bond. The acyl group together with a hydroxy group of $L^3$ or $L^2$, where appropriate, may form an ester bond.

In one embodiment, $G^3$ is heteroalkyl. The heteroalkyl group may comprise polyethylene glycol. The heteroalkyl group may have a heteroatom, such as O or N, adjacent to the acyl group, thereby forming a carbamate or carbonate group, where appropriate, with a heteroatom present in the group $L^3$ or $L^2$, where appropriate.

In one embodiment, $G^3$ is selected from $NH_2$, NHR and NRR'. Preferably, $G^3$ is NRR'.

In one embodiment $G^2$ is the group:

where the asterisk indicates the point of attachment to $L^3$, n is 0 to 6 and $G^4$ is selected from OH, OR, SH, SR, COOR, $CONH_2$, CONHR, CONRR', $NH_2$, NHR, NRR', $NO_2$, and halo. The groups OH, SH, $NH_2$ and NHR are protected. In one embodiment, n is 1 to 6, and preferably n is 5. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Most preferably $G^4$ is OMe.

In one embodiment, the group $G^2$ is:

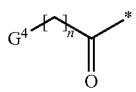

where the asterisk indicates the point of attachment to $L^3$, and n and $G^4$ are as defined above.

In one embodiment, the group $G^2$ is:

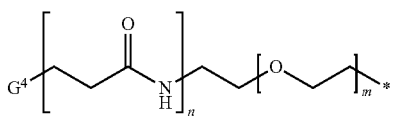

where the asterisk indicates the point of attachment to $L^3$, n is 0 or 1, m is 0 to 50, and $G^4$ is selected from OH, OR, SH, SR, COOR, $CONH_2$, CONHR, CONRR', $NH_2$, NHR, NRR', $NO_2$, and halo. In a preferred embodiment, n is 1 and m is 0 to 10, 1 to 2, preferably 4 to 8, and most preferably 4 or 8. In another embodiment, n is 1 and m is 10 to 50, preferably 20 to 40. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

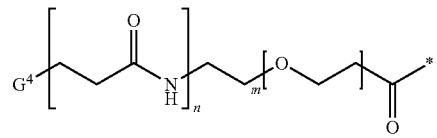

where the asterisk indicates the point of attachment to $L^3$, and n, m and $G^4$ are as defined above.

In one embodiment, the group $G^2$ is:

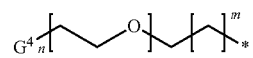

where n is 1-20, m is 0-6, and $G^4$ is selected from OH, OR, SH, SR, COOR, $CONH_2$, CONHR, CONRR', $NH_2$, NHR, NRR', $NO_2$, and halo. In one embodiment, n is 1-10. In another embodiment, n is 10 to 50, preferably 20 to 40. In one embodiment, n is 1. In one embodiment, m is 1. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

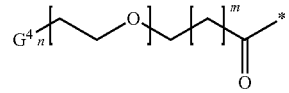

where the asterisk indicates the point of attachment to $L^3$, and n, m and $G^4$ are as defined above.

In each of the embodiments above $G^4$ may be OH, SH, $NH_2$ and NHR. These groups are preferably protected.

In one embodiment, OH is protected with Bzl, TBDMS, or TBDPS.

In one embodiment, SH is protected with Acm, Bzl, Bzl-OMe, Bzl-Me, or Trt.

In one embodiment, $NH_2$ or NHR are protected with Boc, Moc, Z—Cl, Fmoc, Z, or Alloc.

In one embodiment, the group $G^2$ is present in combination with a group $L^3$, which group is a dipeptide.

The capping group is not intended for connection to the modulator. Thus, the other monomer present in the dimer serves as the point of connection to the modulator via a linker. Accordingly, it is preferred that the functionality present in the capping group is not available for reaction with a modulator. Thus, reactive functional groups such as OH, SH, $NH_2$, COOH are preferably avoided. However, such functionality may be present in the capping group if protected, as described above.

Thus, in accordance with the teachings herein one embodiment of the invention comprises a conjugate comprising a compound:

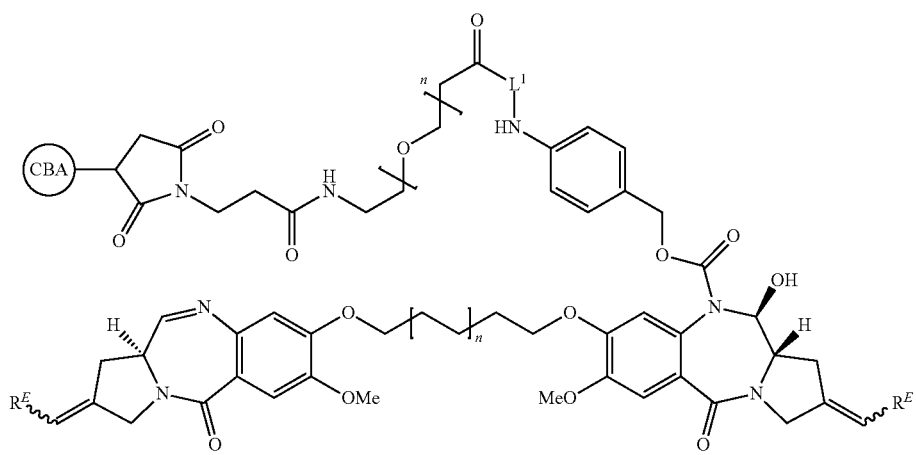

wherein CBA is a cell binding agent/modulator, and n is 0 or 1. $L^1$ is as previously defined, and $R^E$ and $R^{E''}$ are each independently selected from H or $R^D$.

In another embodiment, the conjugate comprises a compound:

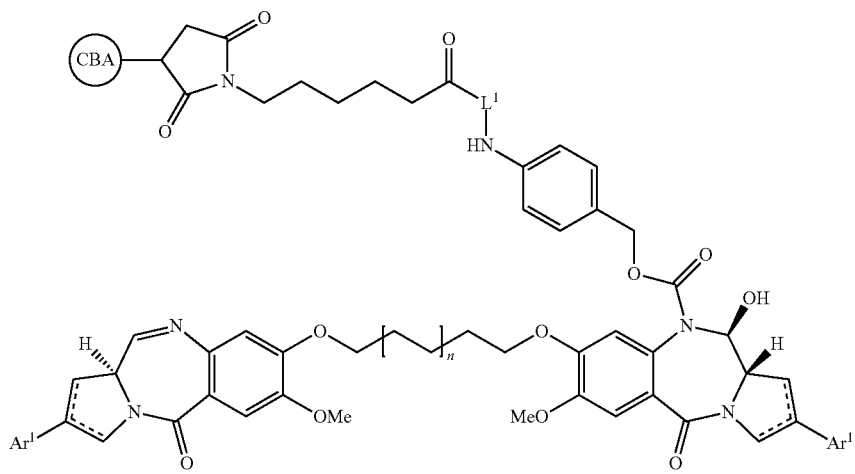

wherein CBA is a cell binding agent/modulator, $L^1$ is as previously defined, $Ar^1$ and $Ar^2$ are each independently optionally substituted $C_{5-20}$ aryl, and n is 0 or 1.

Those of skill in the art will appreciate that other symmetric and asymmetric PBD dimers and linkers are compatible with the instant invention and could be selected without undue experimentation based on the teachings herein and the prior art.

Another aspect of the invention includes ADCs comprising radioisotopes. Exemplary radioisotopes that may be compatible with such embodiments include, but are not limited to, iodine ($^{131}$I, $^{125}$I, $^{123}$I, $^{121}$I), carbon ($^{14}$C), copper ($^{62}$Cu, $^{64}$Cu, $^{67}$Cu), sulfur ($^{35}$S), tritium ($^{3}$H), indium ($^{115}$In, $^{113}$In, $^{112}$In, $^{111}$In), bismuth ($^{212}$Bi, $^{213}$Bi), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{117}$Sn, $^{225}$Ac, $^{76}$Br, and $^{211}$At. Other radionuclides are also available as diagnostic and therapeutic agents, especially those in the energy range of 60 to 4,000 keV. Depending on the condition to be treated and the desired therapeutic profile, those skilled in the art may readily select the appropriate radioisotope for use with the disclosed modulators.

DLL3 modulators of the present invention may also be conjugated to a therapeutic moiety or drug that modifies a given biological response (e.g., biological response modifiers or BRMs). That is, therapeutic agents or moieties compatible with the instant invention are not to be construed as limited to classical chemical therapeutic agents. For example, in particularly preferred embodiments the drug moiety may be a protein or polypeptide or fragment thereof possessing a desired biological activity. Such proteins may include, for example, a toxin such as abrin, ricin A, Onconase (or another cytotoxic RNase), pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")). As set forth above, methods for fusing or conjugating modulators to polypeptide moieties are known in the art. In addition to the previously disclosed subject references see, e.g., U.S. Pat. Nos. 5,336,603; 5,622,929; 5,359,046; 5,349,053; 5,447,851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337 each of which is incorporated herein by reference. Moreover, as set forth above the association of a modulator with such moieties does not necessarily need to be direct, but may occur through linker sequences. As previously alluded to, such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171 each of which is incorporated herein.

IX. Diagnostics and Screening

A. Diagnostics

In yet other embodiments, the invention provides in vitro or in vivo methods for detecting, diagnosing or monitoring proliferative disorders and methods of screening cells from a patient to identify tumorigenic cells including CSCs. Such methods include identifying an individual having cancer for treatment or monitoring progression of a cancer comprising contacting the patient or a sample obtained from a patient (i.e. either in vivo or in vitro) with a modulator as described herein and detecting presence or absence, or level of association, of the modulator to bound or free target molecules in the sample. In particularly preferred embodiments the modulator will comprise a detectable label or reporter molecule as described herein.

In some embodiments, the association of the modulator, such as an antibody, with particular cells in the sample likely denotes that the sample may contain CSCs, thereby indicating that the individual having cancer may be effectively treated with a modulator as described herein. The methods may further comprise a step of comparing the level of binding to a control. Conversely, when the modulator is a Fc-construct, the binding properties may be exploited and monitored (directly or indirectly, in vivo or in vitro) when in contact with the sample to provide the desired information.

Exemplary compatible assay methods include radioimmunoassays, enzyme immunoassays, competitive-binding assays, fluorescent immunoassay, immunoblot assays, Western Blot analysis, flow cytometry assays, and ELISA assays. Compatible in vive theragnostics or diagnostics may comprise art-recognized imaging or monitoring techniques such as magnetic resonance imaging, computerized tomography (e.g. CAT scan), positron tomography (e.g., PET scan) radiography, ultrasound, etc., as would be known by those skilled in the art.

In another embodiment, the invention provides a method of analyzing cancer progression and/or pathogenesis in vivo. In another embodiment, analysis of cancer progression and/or pathogenesis in vivo comprises determining the extent of tumor progression. In another embodiment, analysis comprises the identification of the tumor. In another embodiment, analysis of tumor progression is performed on the primary tumor. In another embodiment, analysis is performed over time depending on the type of cancer as known to one skilled in the art. In another embodiment, further analysis of secondary tumors originating from metastasizing cells of the primary tumor is analyzed in-vivo. In another embodiment, the size and shape of secondary tumors are analyzed. In some embodiments, further ex vivo analysis is performed.

In another embodiment, the invention provides a method of analyzing cancer progression and/or pathogenesis in vive including determining cell metastasis or detecting and quantifying the level of circulating tumor cells. In yet another embodiment, analysis of cell metastasis comprises determination of progressive growth of cells at a site that is discontinuous from the primary tumor. In another embodiment, the site of cell metastasis analysis comprises the route of neoplastic spread. In some embodiment, cells can disperse via blood vasculature, lymphatics, within body cavities or combinations thereof. In another embodiment, cell metastasis analysis is performed in view of cell migration, dissemination, extravasation, proliferation or combinations thereof.

Accordingly, in a particularly preferred embodiment the modulators of the instant invention may be used to detect and quantify DLL3 levels in a patient sample (e.g., plasma or blood) which may, in turn, be used to detect, diagnose or monitor DLL3 associated disorders including proliferative disorders. In related embodiments the modulators of the instant invention may be used to detect, monitor and/or quantify circulating tumor cells either in vivo or in vitro (see, for example, WO 2012/0128801 which is incorporated herein by reference). In still other preferred embodiments the circulating tumor cells may comprise cancer stem cells.

In certain examples, the tumorigenic cells in a subject or a sample from a subject may be assessed or characterized using the disclosed modulators prior to therapy or regimen to establish a baseline. In other examples the sample is derived from a subject that was treated. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the tumorigenic cells are assessed or characterized after a certain number of doses (e.g., after 2, 5, 10, 20, 30 or more doses of a therapy). In other examples, the tumorigenic cells are characterized or assessed after 1 week, 2 weeks, 1 month, 2 months, 1 year, 2 years, 3 years, 4 years or more after receiving one or more therapies.

In another aspect, and as discussed in more detail below, the present invention provides kits for detecting, monitoring or diagnosing a hyperproliferative disorder, identifying individual having such a disorder for possible treatment or monitoring progression (or regression) of the disorder in a patient, wherein the kit comprises a modulator as described herein, and reagents for detecting the impact of the modulator on a sample.

Yet another aspect of the instant invention comprises the use of labeled DLL3 for immunohistochemistry (IHC). In this respect DLL3 IHC may be used as a diagnostic tool to aid in the diagnosis of various proliferative disorders and to monitor the potential response to treatments including DLL3 modulator therapy. Compatible diagnostic assays may be performed on tissues that have been chemically fixed (including but not limited to: formaldehyde, gluteraldehyde, osmium tetroxide, potassium dichromate, acetic acid, alcohols, zinc salts, mercuric chloride, chromium tetroxide and picric acid) and embedded (including but not limited to:

glycol methacrylate, paraffin and resins) or preserved via freezing. As discussed in more detail below such assays could be used to guide treatment decisions and determine dosing regimens and timing.

B. Screening

In certain embodiments, the modulators can also be used to screen for or identify compounds or agents (e.g., drugs) that alter a function or activity of tumorigenic cells or progeny thereof by interacting with an antigen (e.g., genotypic or phenotypic components thereof). Such compounds and agents can be drug candidates that are screened for the treatment of a proliferative disorder, for example. In one embodiment, a system or method includes tumorigenic cells comprising DLL3 and a compound or agent (e.g., drug), wherein the cells and compound or agent are in contact with each other. In such embodiments the subject cells may have been identified, monitored and/or enriched using the disclosed modulators.

In yet another embodiment, a method includes contacting, directly or indirectly, tumorigenic cells or progeny thereof with a test agent or compound and determining if the test agent or compound modulates an activity or function of the antigen-associated tumorigenic cells. One example of a direct interaction is physical interaction, while an indirect interaction includes the action of a composition upon an intermediary molecule that, in turn, acts upon the referenced entity (e.g., cell or cell culture). Exemplary activities or functions that can be modulated include changes in cell morphology or viability, expression of a marker, differentiation or de-differentiation, cell respiration, mitochondrial activity, membrane integrity, maturation, proliferation, viability, apoptosis or cell death.

Methods of screening and identifying agents and compounds include those suitable for high throughput screening, which include arrays of cells (e.g., microarrays) positioned or placed, optionally at pre-determined locations or addresses. For example, cells can be positioned or placed (pre-seeded) on a culture dish, tube, flask, roller bottle or plate (e.g., a single multi-well plate or dish such as an 8, 16, 32, 64, 96, 384 and 1536 multi-well plate or dish). High-throughput robotic or manual handling methods can probe chemical interactions and determine levels of expression of many genes in a short period of time. Techniques have been developed that utilize molecular signals (e.g., via fluorophores) and automated analyses that process information at a very rapid rate (see, e.g., Pinhasov et al., Comb. Chem. High Throughput Screen. 7:133 (2004)). For example, microarray technology has been extensively used to probe the interactions of thousands of genes at once, while providing information for specific genes (see, e.g., Mocellin and Rossi, Adv. Exp. Med. Biol. 593:19 (2007)).

Libraries that can be screened include, for example, small molecule libraries, phage display libraries, fully human antibody yeast display libraries (Adimab, LLC), siRNA libraries, and adenoviral transfection vectors.

X. Pharmaceutical Preparations and Therapeutic Uses

A. Formulations and Routes of Administration

Depending on the form of the modulator along with any optional conjugate, the mode of intended delivery, the disease being treated or monitored and numerous other variables, compositions of the invention may be formulated as desired using art-recognized techniques. In some embodiments, the therapeutic compositions of the invention may be administered neat or with a minimum of additional components while others may optionally be formulated to contain suitable pharmaceutically acceptable carriers comprising excipients and auxiliaries that are well known in the art (see, e.g., Gennaro, Remington: The Science and Practice of Pharmacy with Facts and Comparison: Drugfacts Plus, 20th ed. (2003); Ansel et al., Pharmaceutical Dosage Forms and Drug Delivery Syrtems, 7th ed., Lippencott Williams and Wilkins (2004); Kibbe et al., Handbook of Pharmaceutical Excipients, 3rd ed., Pharmaceutical Press (2000)). Various pharmaceutically acceptable carriers, which include vehicles, adjuvants, and diluents, are readily available from numerous commercial sources. Moreover, an assortment of pharmaceutically acceptable auxiliary substances, such as pH adjusting and buffering agents, tonicity adjusting agents, stabilizers, wetting agents and the like, are also available. Certain non-limiting exemplary carriers include saline, buffered saline, dextrose, water, glycerol, ethanol, and combinations thereof.

More particularly it will be appreciated that, in some embodiments, the therapeutic compositions of the invention may be administered neat or with a minimum of additional components. Conversely the DLL3 modulators of the present invention may optionally be formulated to contain suitable pharmaceutically acceptable carriers comprising excipients and auxiliaries that are well known in the art and are relatively inert substances that facilitate administration of the modulator or which aid processing of the active compounds into preparations that are pharmaceutically optimized for delivery to the site of action. For example, an excipient can give form or consistency or act as a diluent to improve the pharmacokinetics or stability of the modulator. Suitable excipients or additives include, but are not limited to, stabilizing agents, wetting and emulsifying agents, salts for varying osmolarity, encapsulating agents, buffers, and skin penetration enhancers. In certain preferred embodiments the pharmaceutical compositions may be provided in a lyophilized form and reconstituted in, for example, buffered saline prior to administration.

Disclosed modulators for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in Remington, The Science and Practice of Pharmacy 20th Ed. Mack Publishing (2000). Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, hexylsubstituted poly(lactide), sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

Suitable formulations for enteral administration include hard or soft gelatin capsules, pills, tablets, including coated tablets, elixirs, suspensions, syrups or inhalations and controlled release forms thereof.

In general the compounds and compositions of the invention, comprising DLL3 modulators may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

B. Dosages

Similarly, the particular dosage regimen, i.e., dose, timing and repetition, will depend on the particular individual and that individual's medical history, as well as empirical considerations such as pharmacokinetics (e.g., half-life, clearance rate, etc.). Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In other embodiments the dosage administered may be adjusted or attenuated to manage potential side effects and/or toxicity. Alternatively, sustained continuous release formulations of a subject therapeutic composition may be appropriate.

In general, the modulators of the invention may be administered in various ranges. These include about 10 µg/kg body weight to about 100 mg/kg body weight per dose; about 50 µg/kg body weight to about 5 mg/kg body weight per dose; about 100 µg/kg body weight to about 10 mg/kg body weight per dose. Other ranges include about 100 µg/kg body weight to about 20 mg/kg body weight per dose and about 0.5 mg/kg body weight to about 20 mg/kg body weight per dose. In certain embodiments, the dosage is at least about 100 µg/kg body weight, at least about 250 µg/kg body weight, at least about 750 µg/kg body weight, at least about 3 mg/kg body weight, at least about 5 mg/kg body weight, at least about 10 mg/kg body weight.

In selected embodiments the modulators will be administered at approximately 10, 20, 30, 40, 50, 60, 70, 80, 90 or 100 µg/kg body weight per dose. Other embodiments will comprise the administration of modulators at 200, 300, 400, 500, 600, 700, 800 or 900 µg/kg body weight per dose. In other preferred embodiments the disclosed modulators will be administered at 1, 2, 3, 4, 5, 6, 7, 8, 9 or 10 mg/kg. In still other embodiments the modulators may be administered at 12, 14, 16, 18 or 20 mg/kg body weight per dose. In yet other embodiments the modulators may be administered at 25, 30, 35, 40, 45, 50, 55, 60, 65, 70, 75, 80, 90 or 100 mg/kg body weight per dose. In accordance with the teachings herein it will be appreciated that the aforementioned dosages are applicable to both unconjugated modulators and modulators conjugated to a cytotoxic agent. One of skill in the art could readily determine appropriate dosages for various conjugated and unconjugated modulators based on preclinical animal studies, clinical observations and standard medical and biochemical techniques and measurements.

With regard to conjugated modulators particularly preferred embodiments will comprise dosages of between about 50 µg/kg to about 5 mg/kg body weight per dose. In this regard conjugated modulators may be administered at 50, 75 or 100 µg/kg or at 0.2, 0.3, 0.4, 0.5, 0.6, 0.7, 0.8, 0.9 or 1 mg/kg body weight per dose. In other preferred embodiments the conjugated modulators of the instant invention may be administered at 1.25, 1.5, 1.75, 2, 2.25, 2.5, 2.75, 3, 3.25, 3.5, 3.75, 4, 4.25, 4.5, 4.75 or 5 mg/kg body weight per dose. In particularly preferred embodiments such conjugated modulator dosages will be administered intravenously over a period of time. Moreover, such dosages may be administered multiple times over a defined course of treatment.

Other dosing regimens may be predicated on Body Surface Area (BSA) calculations as disclosed in U.S. Pat. No. 7,744,877. As is well known, the BSA is calculated using the patient's height and weight and provides a measure of a subject's size as represented by the surface area of his or her body. In certain embodiments, the modulators may be administered in dosages from 10 mg/m$^2$ to 800 mg/m$^2$, from 50 mg/m$^2$ to 500 mg/m$^2$ and at dosages of 100 mg/m$^2$, 150 mg/m$^2$, 200 mg/m$^2$, 250 mg/m$^2$, 300 mg/m$^2$, 350 mg/m$^2$, 400 mg/m$^2$ or 450 mg/m$^2$.

It will also be appreciated that art recognized and empirical techniques may be used to determine appropriate dosage for conjugated modulators (i.e., ADCs).

In any event, DLL3 modulators (both conjugated and unconjugated) are preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like. Generally, an effective dose of the DLL3 modulator is administered to a subject one or more times. More particularly, an effective dose of the modulator is administered to the subject once a month, more than once a month, or less than once a month. In certain embodiments, the effective dose of the DLL3 modulator may be administered multiple times, including for periods of at least a month, at least six months, at least a year, at least two years or a period of several years. In yet other embodiments, several days (2, 3, 4, 5, 6 or 7), several weeks (1, 2, 3, 4, 5, 6, 7 or 8) or several months (1, 2, 3, 4, 5, 6, 7 or 8) or even a year or several years may lapse between administration of the disclosed modulators.

In certain preferred embodiments the course of treatment involving conjugated modulators will comprise multiple doses of the selected drug product (i.e., an ADC) over a period of weeks or months. More specifically, conjugated modulators of the instant invention may administered once every day, every two days, every four days, every week, every ten days, every two weeks, every three weeks, every month, every six weeks, every two months, every ten weeks or every three months. In this regard it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments the dosage may be gradually increased or reduced or attenuated based respectively on empirically determined or observed side effects or toxicity. To assess efficacy of the selected composition, a marker of the specific disease, disorder or condition can be followed as described previously. In embodiments where the individual has cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or an antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

C. Combination Therapies

Combination therapies may be particularly useful in decreasing or inhibiting unwanted neoplastic cell proliferation, decreasing the occurrence of cancer, decreasing or preventing the recurrence of cancer, or decreasing or preventing the spread or metastasis of cancer. In such cases the modulators of the instant invention may function as sensitizing or chemosensitizing agents by removing the CSCs that would otherwise prop up and perpetuate the tumor mass and thereby allow for more effective use of current standard of care debulking or anti-cancer agents. That is, the disclosed modulators may, in certain embodiments provide an enhanced effect (e.g., additive or synergistic in nature) that potentiates the mode of action of another administered therapeutic agent. In the context of the instant invention "combination therapy" shall be interpreted broadly and merely refers to the administration of a modulator and one or more anti-cancer agents that include, but are not limited to, cytotoxic agents, cytostatic agents, anti-angiogenic agents, debulking agents, chemotherapeutic agents, radiotherapy and radiotherapeutic agents, targeted anti-cancer agents (including both monoclonal antibodies and small molecule entities), BRMs, therapeutic antibodies, cancer vaccines, cytokines, hormone therapies, radiation therapy and anti-metastatic agents and immunotherapeutic agents, including both specific and non-specific approaches.

There is no requirement for the combined results to be additive of the effects observed when each treatment (e.g., antibody and anti-cancer agent) is conducted separately. Although at least additive effects are generally desirable, any increased anti-tumor effect above one of the single therapies is beneficial. Furthermore, the invention does not require the combined treatment to exhibit synergistic effects. However, those skilled in the art will appreciate that with certain selected combinations that comprise preferred embodiments, synergism may be observed.

In practicing combination therapy, the modulator and anti-cancer agent may be administered to the subject simultaneously, either in a single composition, or as two or more distinct compositions using the same or different administration routes. Alternatively, the modulator may precede, or follow, the anti-cancer agent treatment by, e.g., intervals ranging from minutes to weeks. The time period between each delivery is such that the anti-cancer agent and modulator are able to exert a combined effect on the tumor. In at least one embodiment, both the anti-cancer agent and the modulator are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the modulator and the anti-cancer agent.

The combination therapy may be administered once, twice or at least for a period of time until the condition is treated, palliated or cured. In some embodiments, the combination therapy is administered multiple times, for example, from three times daily to once every six months. The administering may be on a schedule such as three times daily, twice daily, once daily, once every two days, once every three days, once weekly, once every two weeks, once every month, once every two months, once every three months, once every six months or may be administered continuously via a minipump. The combination therapy may be administered via any route, as noted previously. The combination therapy may be administered at a site distant from the site of the tumor.

In one embodiment a modulator is administered in combination with one or more anti-cancer agents for a short treatment cycle to a subject in need thereof. The invention also contemplates discontinuous administration or daily doses divided into several partial administrations. The modulator and anti-cancer agent may be administered interchangeably, on alternate days or weeks; or a sequence of antibody treatments may be given, followed by one or more treatments of anti-cancer agent therapy. In any event, as will be understood by those of ordinary skill in the art, the appropriate doses of chemotherapeutic agents will be generally around those already employed in clinical therapies wherein the chemotherapeutics are administered alone or in combination with other chemotherapeutics.

In another preferred embodiment the DLL3 modulators of the instant invention may be used in maintenance therapy to reduce or eliminate the chance of tumor recurrence following the initial presentation of the disease. Preferably the disorder will have been treated and the initial tumor mass eliminated, reduced or otherwise ameliorated so the patient is asymptomatic or in remission. At such time the subject may be administered pharmaceutically effective amounts of the disclosed modulators one or more times even though there is little or no indication of disease using standard diagnostic procedures. In some embodiments, the modulators will be administered on a regular schedule over a period of time, such as weekly, every two weeks, monthly, every six weeks, every two months, every three months every six months or annually. Given the teachings herein, one skilled in the art could readily determine favorable dosages and dosing regimens to reduce the potential of disease recurrence. Moreover such treatments could be continued for a period of weeks, months, years or even indefinitely depending on the patient response and clinical and diagnostic parameters.

In yet another preferred embodiment the modulators of the present invention may be used to prophylactically or as an adjuvant therapy to prevent or reduce the possibility of tumor metastasis following a debulking procedure. As used in the instant disclosure a "debulking procedure" is defined broadly and shall mean any procedure, technique or method that eliminates, reduces, treats or ameliorates a tumor or tumor proliferation. Exemplary debulking procedures include, but are not limited to, surgery, radiation treatments (i.e., beam radiation), chemotherapy, immunotherapy or ablation. At appropriate times readily determined by one skilled in the art in view of the instant disclosure the disclosed modulators may be administered as suggested by clinical, diagnostic or theragnostic procedures to reduce tumor metastasis. The modulators may be administered one or more times at pharmaceutically effective dosages as determined using standard techniques. Preferably the dosing regimen will be accompanied by appropriate diagnostic or monitoring techniques that allow it to be modified.

Yet other embodiments of the invention comprise administering the disclosed modulators to subjects that are asymptomatic but at risk of developing a proliferative disorder. That is, the modulators of the instant invention may be used in a truly preventative sense and given to patients that have been examined or tested and have one or more noted risk factors (e.g., genomic indications, family history, in vive or in vitro test results, etc.) but have not developed neoplasia. In such cases those skilled in the art would be able to determine an effective dosing regimen through empirical observation or through accepted clinical practices.

D. Anti-Cancer Agents

The term "anti-cancer agent" or "anti-proliferative agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in selected embodiments as discussed above, such anti-cancer agents may comprise conjugates and may be associated with modulators prior to administration. In certain embodiments the disclosed anti-cancer agent will be linked to a DLL3 modulator to provide an ADC as set forth herein.

As used herein the term "cytotoxic agent" means a substance that is toxic to the cells and decreases or inhibits the function of cells and/or causes destruction of cells. Typically, the substance is a naturally occurring molecule derived from a living organism. Examples of cytotoxic agents include, but are not limited to, small molecule toxins or enzymatically active toxins of bacteria (e.g., *Diphtheria* toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca* mericana proteins (PAPI, PAPII, and PAP-S), *Momordica charantia* inhibitor, curcin, crotin, *saponaria officinalis* inhibitor, gelonin, mitegellin, restrictocin, phenomycin, neomycin, and the tricothecenes) or animals, (e.g., cytotoxic RNases, such as extracellular pancreatic RNases; DNase I, including fragments and/or variants thereof).

For the purposes of the instant invention a "chemotherapeutic agent" comprises a chemical compound that nonspecifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI. Again, in selected embodiments such chemotherapeutic agents may be conjugated to the disclosed modulators.

Examples of anti-cancer agents that may be used in combination with (or conjugated to) the modulators of the present invention include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, erlotinib, vemurafenib, crizotinib, sorafenib, ibrutinib, enzalutamnide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, Oreg.), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluoromethylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above.

In other embodiments the modulators of the instant invention may be used in combination with any one of a number of antibodies (or immunotherapeutic agents) presently in clinical trials or commercially available. To this end the disclosed modulators may be used in combination with an antibody selected from the group consisting of abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, 3F8 and combinations thereof.

Still other particularly preferred embodiments will comprise the use of antibodies approved for cancer therapy including, but not limited to, rituximab, trastuzumab, gemtuzumab ozogamcin, alemtuzumab, ibritumomab tiuxetan, tositumomab, bevacizumab, cetuximab, panitumumab, ofatumumab, ipilimumab and brentuximab vedotin. Those skilled in the art will be able to readily identify additional anti-cancer agents that are compatible with the teachings herein.

E. Radiotherapy

The present invention also provides for the combination of modulators with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

XI. Indications

It will be appreciated that the modulators of the instant invention may be used to diagnose, treat or inhibit the occurrence or recurrence of any DLL3 associated disorder. Accordingly, whether administered alone or in combination with an anti-cancer agent or radiotherapy, the modulators of the invention are particularly useful for generally treating neoplastic conditions in patients or subjects which may include benign or malignant tumors (e.g., adrenal, liver, kidney, bladder, breast, gastric, ovarian, colorectal, prostate, pancreatic, lung, thyroid, hepatic, cervical, endometrial, esophageal and uterine carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic, immunologic disorders and disorders caused by pathogens. Particularly, key targets for treatment are neoplastic conditions comprising solid tumors, although hematologic malignancies are within the scope of the invention. Preferably the "subject" or "patient" to be treated will be human although, as used herein, the terms are expressly held to comprise any mammalian species.

More specifically, neoplastic conditions subject to treatment in accordance with the instant invention may be selected from the group including, but not limited to, adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In certain preferred embodiments the proliferative disorder will comprise a solid tumor including, but not limited to, adrenal, liver, kidney, bladder, breast, gastric, ovarian, cervical, uterine, esophageal, colorectal, prostate, pancreatic, lung (both small cell and non-small cell), thyroid, carcinomas, sarcomas, glioblastomas and various head and neck tumors. In other preferred embodiments, and as shown in the Examples below, the disclosed modulators are especially effective at treating small cell lung cancer (SCLC) and non-small cell lung cancer (NSCLC) (e.g., squamous cell non-small cell lung cancer or squamous cell small cell lung cancer). In one embodiment, the lung cancer is refractory, relapsed or resistant to a platinum based agent (e.g., carboplatin, cisplatin, oxaliplatin, topotecan) and/or a taxane (e.g., docetaxel, paclitaxel, larotaxel or cabazitaxel). Further, in particularly preferred embodiments the disclosed modulators may be used in a conjugated form to treat small cell lung cancer.

With regard to small cell lung cancer particularly preferred embodiments will comprise the administration of conjugated modulators (ADCs). In selected embodiments the conjugated modulators will be administered to patients exhibiting limited stage disease. In other embodiments the disclosed modulators will be administered to patients exhibiting extensive stage disease. In other preferred embodiments the disclosed conjugated modulators will be administered to refractory patients (i.e., those who recur during or shortly after completing a course of initial therapy). Still other embodiments comprise the administration of the disclosed modulators to sensitive patients (i.e, those whose relapse is longer than 2-3 months after primary therapy. In each case it will be appreciated that compatible modulators may be in a conjugated or unconjugated state depending the selected dosing regimen and the clinical diagnosis.

As discussed above the disclosed modulators may further be used to prevent, treat or diagnose tumors with neuroendocrine features or phenotypes including neuroendocrine tumors. True or canonical neuroendocrine tumors (NETs) arising from the dispersed endocrine system are relatively rare, with an incidence of 2-5 per 100,000 people, but highly aggressive. Neuroendocrine tumors occur in the kidney, genitourinary tract (bladder, prostate, ovary, cervix, and endometrium), gastrointestinal tract (colon, stomach), thyroid (medullary thyroid cancer), and lung (small cell lung carcinoma and large cell neuroendocrine carcinoma). These tumors may secrete several hormones including serotonin and/or chromogranin A that can cause debilitating symptoms known as carcinoid syndrome. Such tumors can be denoted by positive immunohistochemical markers such as neuron-specific enolase (NSE, also known as gamma enolase, gene symbol=ENO2), CD56 (or NCAM1), chromogranin A (CHGA), and synaptophysin (SYP) or by genes known to exhibit elevated expression such as ASCL1. Unfortunately traditional chemotherapies have not been particularly effective in treating NETs and liver metastasis is a common outcome.

While the disclosed modulators may be advantageously used to treat neuroendocrine tumors they may also be used to treat, prevent or diagnose pseudo neuroendocrine tumors (pNETs) that genotypically or phenotypically mimic, resemble or exhibit common traits with canonical neuroendocrine tumors. Pseudo neuroendocrine tumors or tumors with neuroendocrine features are tumors that arise from cells of the diffuse neuroendocrine system or from cells in which a neuroendocrine differentiation cascade has been aberrantly reactivated during the oncogenic process. Such pNETs commonly share certain phenotypic or biochemical characteristics with traditionally defined neuroendocrine tumors, including the ability to produce subsets of biologically active amines, neurotransmitters, and peptide hormones. Histologically, such tumors (NETs and pNETs) share a common appearance often showing densely connected small cells with minimal cytoplasm of bland cytopathology and round to oval stippled nuclei. For the purposes of the instant invention commonly expressed histological markers or genetic markers that may be used to define neuroendocrine and pseudo neuroendocrine tumors include, but are not limited to, chromogranin A, CD56, synaptophysin, PGP9.5, ASCL1 and neuron-specific enolase (NSE).

Accordingly the modulators of the instant invention may beneficially be used to treat both pseudo neuroendocrine tumors and canonical neuroendocrine tumors. In this regard the modulators may be used as described herein to treat neuroendocrine tumors (both NET and pNET) arising in the kidney, genitourinary tract (bladder, prostate, ovary, cervix, and endometrium), gastrointestinal tract (colon, stomach), thyroid (medullary thyroid cancer), and lung (small cell lung carcinoma and large cell neuroendocrine carcinoma). Moreover, the modulators of the instant invention may be used to treat tumors expressing one or more markers selected from the group consisting of NSE, CD56, synaptophysin, chromogranin A, ASCL1 and PGP9.5 (UCHL1). That is, the present invention may be used to treat a subject suffering from a tumor that is $NSE^+$ or $CD56^+$ or $PGP9.5^+$ or $ASCL1^+$ or $SYP^+$ or $CHGA^+$ or some combination thereof.

With regard to hematologic malignancies it will be further be appreciated that the compounds and methods of the present invention may be particularly effective in treating a variety of B-cell lymphomas, including low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al., "Lymphomas", IN CANCER: PRINCIPLES & PRACTICE OF ONCOLOGY, Vol. 2: 2131-2145 (DeVita et al., eds., 5.sup.th ed. 1997). It should be clear to those of skill in the art that these lymphomas will often have different names due to changing systems of classification, and that patients having lymphomas classified under different names may also benefit from the combined therapeutic regimens of the present invention.

The present invention also provides for a, preventative or prophylactic treatment of subjects who present with benign or precancerous tumors. Beyond being a DLL3 associated disorder it is not believed that any particular type of tumor or proliferative disorder should be excluded from treatment using the present invention. However, the type of tumor cells may be relevant to the use of the invention in combination with secondary therapeutic agents, particularly chemotherapeutic agents and targeted anti-cancer agents.

XII. Articles of Manufacture

Pharmaceutical packs and kits comprising one or more containers, comprising one or more doses of a DLL3 modulator are also provided. In certain embodiments, a unit dosage is provided wherein the unit dosage contains a predetermined amount of a composition comprising, for example, an anti-DLL3 antibody, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water. In certain preferred embodiments, the composition comprises one or more substances that inhibit protein aggregation, including, but not limited to, sucrose and arginine. Any label on, or associated with, the container(s) indicates that the enclosed composition is used for diagnosing or treating the disease condition of choice.

The present invention also provides kits for producing single-dose or multi-dose administration units of a DLL3 modulator and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed modulators in a conjugated or unconjugated form. In other preferred embodiments the container(s) comprise a sterile access port (for example the container may be an intravenous solution bag or a vial having a stopper pierceable by a hypodermic injection needle). Such kits will generally contain in a suitable container a pharmaceutically acceptable formulation of the DLL3 modulator and, optionally, one or more anti-cancer agents in the same or different containers. The kits may also contain other pharmaceutically acceptable formulations, either for diagnosis or combined therapy. For example, in addition to the DLL3 modulator of the invention such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents. Such kits may also provide appropriate reagents to conjugate the DLL3 modulator with an anti-cancer agent or diagnostic agent (e.g., see U.S. Pat. No. 7,422,739 which is incorporated herein by reference in its entirety).

More specifically the kits may have a single container that contains the DLL3 modulator, with or without additional components, or they may have distinct containers for each desired agent. Where combined therapeutics are provided for conjugation, a single solution may be pre-mixed, either in a molar equivalent combination, or with one component in excess of the other. Alternatively, the DLL3 modulator and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody and any optional components to an animal or patient, e.g., one or more needles or syringes, or even an eye dropper, pipette, or other such like apparatus, from which the formulation may be injected or introduced into the animal or applied to a diseased area of the body. The kits of the present invention will also typically include a means for containing the vials, or such like, and other component in close confinement for commercial sale, such as, e.g., injection or blow-molded plastic containers into which the desired vials and other apparatus are placed and retained. Any label or package insert indicates that the DLL3 modulator composition is used for treating cancer, for example small cell lung cancer.

In other preferred embodiments the modulators of the instant invention may be used in conjunction with, or comprise, diagnostic or therapeutic devices useful in the diagnosis or treatment of proliferative disorders. For example, in on preferred embodiment the compounds and compositions of the instant invention may be combined with certain diagnostic devices or instruments that may be used to detect, monitor, quantify or profile cells or marker compounds involved in the etiology or manifestation of proliferative disorders. For selected embodiments the marker compounds may comprise NSE, CD56, synaptophysin, chromogranin A, and PGP9.5.

In particularly preferred embodiments the devices may be used to detect, monitor and/or quantify circulating tumor cells either in vivo or in vitro (see, for example, WO 2012/0128801 which is incorporated herein by reference). In still other preferred embodiments, and as discussed above, the circulating tumor cells may comprise cancer stem cells.

XIII. Research Reagents

Other preferred embodiments of the invention also exploit the properties of the disclosed modulators as an instrument useful for identifying, monitoring, isolating, sectioning or enriching populations or subpopulations of tumor initiating cells through methods such as flow cytometry, fluorescent activated cell sorting (FACS), magnetic activated cell sorting (MACS) or laser mediated sectioning. Those skilled in the art will appreciate that the modulators may be used in several compatible techniques for the characterization and manipulation of TIC including cancer stem cells (e.g., see U.S. Ser. Nos. 12/686,359, 12/669,136 and 12/757,649 each of which is incorporated herein by reference in its entirety).

XIV. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Generally, nomenclature used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Abbas et al., Cellular and Molecular Immunology, $6^{th}$ ed., W.B. Saunders Company (2010); Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art. Moreover, any section headings used herein are for organizational purposes only and are not to be construed as limiting the subject matter described.

XV. DLL3 References

All references or documents disclosed or cited within this specification, including those set forth immediately below are, without limitation, incorporated herein by reference in their entirety.

Apelqvist A et al. (1999). Notch signalling controls pancreatic cell differentiation. Nature. 400:877-81. PMID: 10476967.

Bigas A and Espinosa L (2012). Hematopoietic stem cells: to be or Notch to be. Blood. 2012 PMID: 22308291.

Cabrera C V (1990). Lateral inhibition and cell fate during neurogenesis in *Drosophila*: the interactions between scute, Notch and Delta. Development. 110:733-42. PMID: 1709404.

Chapman G et al. (2011). Notch inhibition by the ligand DELTA-LIKE 3 defines the mechanism of abnormal vertebral segmentation in spondylocostal dysostosis. Hum Mol Genet. 20:905-16. PMID: 21147753.

Chen H et al. (1997). Conservation of the *Drosophila* lateral inhibition pathway in human lung cancer: a hairy-related protein (HES-1) directly represses achaete-scute homolog-1 expression. Proc Natl Acad Sci USA. 94:5355-60. PMID: 9144241.

Cook M et al., (2010). Notch in the development of thyroid C-cells and the treatment of medullary thyroid cancer. Am J Transl Res. 2:119-25. PMID: 20182588.

de la Pompa J L et al (1997). Conservation of the Notch signaling pathway in mammalian neurogenesis. Development. 124:1139-48. PMID: 9102301.

D'Souza B et al. (2010). Canonical and non-canonical Notch ligands. Curr Top Dev Biol. 92:73-129. PMID: 20816393.

Dunwoodie S L (2009). The role of Notch in patterning the human vertebral column. Curr Opin Genet Dev. 19:329-37. PMID:19608404.

Dutta S et al., (2008). Notch signaling regulates endocrine cell specification in the zebrafish anterior pituitary. Dev Biol. 319:248-57. PubMed PMID: 18534570.

Fre S et al. (2005). Notch signals control the fate of immature progenitor cells in the intestine. Nature. 435:964-8. PMID: 15959516.

Fre S et al. (2009). Notch and Wnt signals cooperatively control cell proliferation and tumorigenesis in the intestine. Proc Natl Acad Sci USA. 106:6309-14. PMID: 19251639.

Galluzzo P, and Bocchetta M (2011). Notch signaling in lung cancer. Expert Rev Anticancer Ther. 11:533-40. PMID: 21504320.

Geffers I et al. (2007). Divergent functions and distinct localization of the Notch ligands DLL1 and DLL3 in vivo. J Cell Biol. 178:465-76. PMID: 17664336.

Glittenberg M, et al., (2006). Role of conserved intracellular motifs in Serrate signalling, cis-inhibition and endocytosis. EMBO J. 25:4697-706. PMID: 17006545.

Goldbeter A, and Pourquié O (2008). Modeling the segmentation clock as a network of coupled oscillations in the Notch, Wnt and FGF signaling pathways. J Theor Biol. 252:574-85.PMID: 18308339.

Habener J F et al. (2005). Minireview: transcriptional regulation in pancreatic development. Endocrinology. 146:1025-34. PMID: 15604203.

Harris P J et al. (2012). Targeting embryonic signaling pathways in cancer therapy. Expert Opin Ther Targets. PMID: 22239436.

Henke R M et al. (2009). Ascll and Neurog2 form novel complexes and regulate Delta-like3 (DLL3) expression in the neural tube. Dev Biol. 328:529-40. PMID:19389376.

Hoyne G F, et al. (2011). A cell autonomous role for the Notch ligand Delta-like 3 in a3 'I'-cell development. Immunol Cell Biol. 89:696-705. PMID: 21151194.

Huber K et al., (2002). Development of chromaffin cells depends on MASH1 function. Development. 129:4729-38. PMID: 12361965.

Ito T et al. (2000). Basic helix-loop-helix transcription factors regulate the neuroendocrine differentiation of fetal mouse pulmonary epithelium. Development. 127:3913-21. PMID: 10952889.

Jensen J et al. (2000). Control of endodermal endocrine development by Hes-1. Nat Genet. 24:36-44. PMID: 10615124.

Kageyama R, et al. (2007). Oscillator mechanism of Notch pathway in the segmentation clock. Dev Dyn. 236:1403-9. PMID:17366573.

Kameda Y et al. (2007). Mashl regulates the development of C cells in mouse thyroid glands. Dev Dyn. 236:262-70. PMID: 17103415.

Klein T, et al. (1997). An intrinsic dominant negative activity of serrate that is modulated during wing development in *Drosophila*. Dev Biol. 189:123-34. PMID: 9281342.

Klimstra D S, et al. (2010). The pathologic classification of neuroendocrine tumors: a review of nomenclature, grading, and staging systems. Pancreas. 39:707-12. PMID: 20664470.

Klöppel G. (2011). Classification and pathology of gastroenteropancreatic neuroendocrine neoplasms. Endocr Relat Cancer. 18 Suppl 1:S1-16. PMID: 22005112.

Koch U and Radtke F (2010). Notch signaling in solid tumors. Curr Top Dev Biol. 92:411-55. PMID: 20816403.

Kusumi K et al. (1998). The mouse pudgy mutation disrupts Delta homologue DLL3 and initiation of early somite boundaries. Nat Genet. 19:274-8. PMID: 9662403.

Ladi E et al. (2005). The divergent DSL ligand DLL3 does not activate Notch signaling but cell autonomously attenuates signaling induced by other DSL ligands. J Cell Biol. 170:983-92. PMID:16144902.

Liu J et al. (2010). Notch signaling in the regulation of stem cell self-renewal and differentiation. Curr Top Dev Biol. 92:367-409. PMID: 20816402.

Nagase H et al. (2011). γ-Secretase-regulated signaling pathways, such as notch signaling, mediate the differentiation of hematopoictic stem cells, development of the immune system, and peripheral immune responses. Curr Stem Cell Res Ther. 6:131-41. PMID: 21190540.

Raetzman L T et al. (2004). Developmental regulation of Notch signaling genes in the embryonic pituitary: Prop1 deficiency affects Notch2 expression. Dev Biol. 265:329-40. PMID: 14732396.

Rebay I, et al., (1991). Specific EGF repeats of Notch mediate interactions with Delta and Serrate: implications for Notch as a multifunctional receptor. Cell. 67:687-99. PMID: 1657403.

Sakamoto K et al. (2002). Intracellular cell-autonomous association of Notch and its ligands: a novel mechanism of Notch signal modification. Dev Biol. 241:313-26. PMID: 11784114.

Schonhoff S E et al. (2004). Minireview: Development and differentiation of gut endocrine cells. Endocrinology. 145:2639-44. PMID: 15044355.

Shimizu K et al. (1999). Mouse jagged physically interacts with notch2 and other notch receptors. Assessment by quantitative methods. J Biol Chem. 274:32961-9. PMID: 10551863.

Shinkai Y et al. (2004). New mutant mouse with skeletal deformities caused by mutation in delta like 3 (DLL3) gene. Exp Anim. 53:129-36. PMID: 15153675.

Schonhoff S E et al. (2004). Minireview: Development and differentiation of gut endocrine cells. Endocrinology. 145: 2639-44. PMID: 15044355.

Sprinzak D et al. (2010). Cis-interactions between Notch and Delta generate mutually exclusive signalling states. Nature. 465:86-90. PMID: 20418862.

Sriuranpong V et al. (2002). Notch signaling induces rapid degradation of achacte-scute homolog 1. Mol Cell Biol. 22:3129-39. PMID: 11940670.

Sternberg P W (1988). Lateral inhibition during vulval induction in *Caenorhabditis elegans*. *Nature*. 335:551-4. PMID: 3419532.

Wharton K A, et al., (1985). Nucleotide sequence from the neurogenic locus notch implies a gene product that shares homology with proteins containing EGF-like repeats. Cell. 43:567-81. PMID: 3935325.

Yao J C et al. (2008). One hundred years after "carcinoid": epidemiology of and prognostic factors for neuroendocrine tumors in 35,825 cases in the United States. J Clin Oncol. 26:3063-72. PMID: 18565894.

Zarebczan B, Chen H (2010). Signaling mechanisms in neuroendocrine tumors as targets for therapy. Endocrinol Metab Clin North Am. 39:801-10. PMID: 21095546.

XVI. Selected Embodiments of the Invention

In addition to the disclosure and Examples herein, the present invention is directed to selected embodiments specifically set forth immediately below.

Putative Claims:

1. An isolated DLL3 modulator.
2. The isolated DLL3 modulator of claim 1, wherein the DLL3 modulator comprises a DLL3 antagonist.
3. The isolated DLL3 modulator of claim 1, wherein the DLL3 modulator comprises an antibody or immunoreactive fragment thereof.
4. The isolated DLL3 modulator of claim 3 wherein the antibody or immunoreactive fragment thereof comprises a monoclonal antibody.
5. The isolated DLL3 modulator of claim 4 wherein the monoclonal antibody is selected from the group consisting of chimeric antibodies, humanized antibodies and human antibodies.
6. The isolated DLL3 modulator of claim 4 wherein said monoclonal antibody comprises a neutralizing antibody.
7. The isolated DLL3 modulator of claim 4 wherein said monoclonal antibody comprises a depleting antibody.
8. The isolated DLL3 modulator of claim 4 wherein said monoclonal antibody comprises an internalizing antibody.
9. The isolated DLL3 modulator of claim 8 wherein said monoclonal antibody further comprises a cytotoxic agent.
10. The isolated DLL3 modulator of claim 4 wherein said monoclonal antibody comprises a light chain variable region having three complementarity determining regions and a heavy chain variable region having three complementarity determining regions wherein the heavy and light chain complementarity determining regions comprise at least one complementarity determining region set forth in FIG. 11A and FIG. 11B.
11. The isolated DLL3 modulator of claim 4 wherein said monoclonal antibody comprises a light chain variable region and a heavy chain variable region wherein said light chain variable region comprises an amino acid sequence having at least 60% identity to an amino acid sequence selected from the group consisting of amino acid sequences as set forth in SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162 SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 198, SEQ ID NO: 200 and SEQ ID NO: 202 and wherein said heavy chain variable region comprises an amino acid sequence having at least 60% identity to an amino acid sequence selected from the group consisting of amino acid sequences as set forth in SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201 and SEQ ID NO: 203.

12. An isolated DLL3 modulator comprising a CDR from any one of the heavy or light chain variable regions set forth in of claim 11.

13. An isolated DLL3 modulator comprising a competing antibody wherein said competing antibody inhibits the binding of an isolated DLL3 modulator of claim 10 or 11 to DLL3 by at least about 40%.

14. A nucleic acid encoding an amino acid heavy chain variable region or an amino acid light chain variable region of claim 11.

15. A vector comprising the nucleic acid of claim 14.

16. The isolated DLL3 modulator of claim 1 comprising an amino acid sequence as set forth in SEQ ID NO: 3 or a fragment thereof.

17. The isolated DLL3 modulator of claim 16 wherein the DLL3 modulator further comprises at least a portion of an immunoglobulin constant region.

18. The isolated DLL3 modulator of claim 1 wherein said modulator reduces the frequency of tumor initiating cells upon administration to a subject in need thereof.

19. The isolated DLL3 modulator of claim 18 wherein the reduction in frequency is determined using flow cytometric analysis of tumor cell surface markers known to enrich for tumor initiating cells.

20. The isolated DLL3 modulator of claim 18 wherein the reduction in frequency is determined using immunohistochemical detection of tumor cell surface markers known to enrich for tumor initiating cells.

21. The isolated DLL3 modulator of claim 18 wherein said tumor initiating cells comprise tumor perpetuating cells.

22. The isolated DLL3 modulator of claim 1 further comprising a cytotoxic agent.

23. A pharmaceutical composition comprising the isolated DLL3 modulator of claim 1.

24. The pharmaceutical composition of claim 23 wherein said isolated DLL3 modulator comprises a monoclonal antibody.

25. The pharmaceutical composition of claim 24 wherein said monoclonal antibody comprises a humanized antibody.

26. The pharmaceutical composition of claim 25 wherein said humanized antibody comprises a cytotoxic agent.

27. The pharmaceutical composition of claim 26 wherein said cytotoxic agent comprises a pyrrolobenzodiazepine.

28. A method of treating a DLL3 associated disorder comprising administering a therapeutically effective amount of a DLL3 modulator to a subject in need thereof.

29. The method of claim 28 wherein said DLL3 modulator comprises a DLL3 antagonist.

30. The method of claim 28 wherein said DLL3 modulator comprises an antibody or immunoreactive fragment thereof.

31. The method of claim 30 wherein the antibody or immunoreactive fragment thereof comprises a monoclonal antibody.

32. The method of claim 31 wherein the monoclonal antibody is selected from the group consisting of chimeric antibodies, humanized antibodies and human antibodies.

33. The method of claim 32 wherein said monoclonal antibody comprises a light chain variable region and a heavy chain variable region wherein said light chain variable region comprises an amino acid sequence having at least 60% identity to an amino acid sequence selected from the group consisting of amino acid sequences as set forth in SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162 SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 198, SEQ ID NO: 200 and SEQ ID NO: 202 and wherein said heavy chain variable region comprises an amino acid sequence having at least 60% identity to an amino acid sequence selected from the group consisting of amino acid sequences as set forth in SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161. SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201 and SEQ ID NO: 203.

34. The method of claim 33 wherein said monoclonal antibody is a humanized antibody.

35. The method of claim 31 wherein said monoclonal antibody comprises a neutralizing antibody.
36. The method of claim 31 wherein said monoclonal antibody comprises an internalizing antibody.
37. The method of claim 36 wherein said internalizing antibody comprises a cytotoxic agent.
38. The method of claim 37 wherein said cytotoxic agent comprises a pyrrolobenzodiazepine.
39. The method of claim 38 wherein said DLL3 associated disorder comprises a neoplastic disorder.
40. The method of claim 39 wherein said neoplastic disorder comprises a tumor exhibiting neuroendocrine features.
41. The method of claim 40 wherein said tumor exhibiting neuroendocrine features comprises a neuroendocrine tumor.
42. The method of claim 39 wherein said neoplastic disorder comprises a hematologic malignancy.
43. The method of claim 42 wherein said hematologic malignancy comprises leukemia or lymphoma.
44. The method of claim 39 wherein the subject suffering said neoplastic disorder exhibits tumors comprising tumor initiating cells.
45. The method of claim 44 further comprising the step of reducing the frequency of tumor initiating cells in said subject.
46. The method of claim 45 wherein the reduction in frequency is determined using flow cytometric analysis of tumor cell surface markers known to enrich for tumor initiating cells or immunohistochemical detection of tumor cell surface markers known to enrich for tumor initiating cells.
47. The method of claim 45 wherein the reduction in frequency is determined using in vitro or in vivo limiting dilution analysis.
48. The method of claim 47 wherein the reduction in frequency is determined using in vivo limiting dilution analysis comprising transplant of live human tumor cells into immunocompromised mice.
49. The method of claim 48 wherein the reduction of frequency determined using in vivo limiting dilution analysis comprises quantification of tumor initiating cell frequency using Poisson distribution statistics.
50. The method of claim 47 wherein the reduction of frequency is determined using in vitro limiting dilution analysis comprising limiting dilution deposition of live human tumor cells into in vitro colony supporting conditions.
51. The method of claim 50 wherein the reduction of frequency determined using in vitro limiting dilution analysis comprises quantification of tumor initiating cell frequency using Poisson distribution statistics.
52. The method of claim 28 further comprising the step of administering an anti-cancer agent.
53. The method of claim 28 wherein said DLL3 modulator comprises one or more CDRs from any one of SEQ ID NOS: 20 to 203.
54. The method of claim 28 wherein said DLL3 modulator comprises a pan-DLL modulator.
55. A method of reducing the frequency of tumor initiating cells in a subject in need thereof comprising the step of administering a DLL3 modulator to said subject.
56. The method of claim 55 wherein the tumor initiating cells comprise tumor perpetuating cells.
57. The method of claim 56 wherein said tumor perpetuating cells are $CD324^+$ or $CD46^+$ cells.
58. The method of claim 55 wherein said DLL3 modulator comprises an antibody.
59. The method of claim 58 wherein said antibody comprises a monoclonal antibody.
60. The method of claim 59 wherein said monoclonal antibody further comprises a cytotoxic agent.
61. The method of claim 55 wherein the subject is suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer and breast cancer.
62. The method of claim 55 wherein the frequency of tumor initiating cells is reduced by at least 10%.
63. The method of claim 55 wherein the reduction in frequency is determined using flow cytometric analysis of tumor cell surface markers known to enrich for tumor initiating cells or immunohistochemical detection of tumor cell surface markers known to enrich for tumor initiating cells.
64. A method of treating a subject suffering from a hematologic malignancy comprising the step of administering a DLL3 modulator to said subject.
65. The method of claim 64 wherein said DLL3 modulator comprises a monoclonal antibody.
66. A method of sensitizing a tumor in a subject for treatment with an anti-cancer agent comprising the step of administering a DLL3 modulator to said subject.
67. The method of claim 66 wherein said DLL3 modulator comprises an antibody.
68. The method of claim 66 wherein said tumor is a solid tumor.
69. The method of claim 66 wherein said anti-cancer agent comprises a chemotherapeutic agent.
70. The method of claim 66 wherein said anti-cancer agent comprises an immunotherapeutic agent.
71. A method of diagnosing a proliferative disorder in a subject in need thereof comprising the steps of:
   a. obtaining a tissue sample from said subject;
   b. contacting the tissue sample with at least one DLL3 modulator; and
   c. detecting or quantifying the DLL3 modulator associated with the sample.
72. The method of claim 71 wherein the DLL3 modulator comprises a monoclonal antibody.
73. The method of claim 72 wherein the antibody is operably associated with a reporter.
74. An article of manufacture useful for diagnosing or treating DLL3 associated disorders comprising a receptacle comprising a DLL3 modulator and instructional materials for using said DLL3 modulator to treat or diagnose the DLL3 associated disorder.
75. The article of manufacture of claim 74 wherein said DLL3 modulator is a monoclonal antibody.
76. The article of manufacture of claim 74 wherein the receptacle comprises a readable plate.
77. A method of treating a subject suffering from neoplastic disorder comprising the step of administering a therapeutically effective amount of at least one internalizing DLL3 modulator.
78. The method of claim 77 wherein said DLL3 modulator comprises an antibody.
79. The method of claim 78 wherein said antibody comprises a monoclonal antibody.
80. The method of claim 79 wherein the monoclonal antibody further comprises a cytotoxic agent.
81. The method of claim 80 further comprising the step of administering an anti-cancer agent.

82. A method of treating a subject suffering from neoplastic disorder comprising the step of administering a therapeutically effective amount of at least one neutralizing DLL3 modulator.

83. The method of claim 82 wherein said DLL3 modulator comprises an antibody.

84. The method of claim 83 wherein said antibody comprises a monoclonal antibody.

85. The method of claim 84 wherein said monoclonal antibody comprises a humanized antibody.

86. The method of claim 85 wherein said humanized antibody further comprises a cytotoxic agent.

87. The method of claim 82 wherein the neoplastic disorder comprises a tumor exhibiting neuroendocrine features.

88. A method of identifying, isolating, sectioning or enriching a population of tumor initiating cells comprising the step of contacting said tumor initiating cells with a DILL3 modulator.

89. The method of claim 88 wherein said DLL3 modulator comprises an antibody.

90. A DLL3 modulator comprising a humanized antibody wherein said humanized antibody comprises a light chain variable region and a heavy chain variable region wherein said light chain variable region comprises an amino acid sequence having at least 60% identity to an amino acid sequence selected from the group consisting of amino acid sequences as set forth in SEQ ID NO: 204, SEQ ID NO: 206, SEQ ID NO: 208, SEQ ID NO: 210 and SEQ ID NO: 212 and wherein said heavy chain variable region comprises an amino acid sequence having at least 60% identity to an amino acid sequence selected from the group consisting of amino acid sequences as set forth in SEQ ID NO: 205, SEQ ID NO: 207, SEQ ID NO: 209, SEQ ID NO: 211 and SEQ ID NO: 213.

91. A method inhibiting or preventing metastasis in a subject in need thereof comprising the step of administering a pharmaceutically effective amount of a DLL3 modulator.

92. The method of claim 91 wherein the subject undergoes a debulking procedure before or after the administration of the DLL3 modulator.

93. The method of claim 92 wherein said debulking procedure comprises the administration of at least one anticancer agent.

94. A method of performing maintenance therapy on a subject in need thereof comprising the step of administering a pharmaceutically effective amount of a DLL3 modulator.

95. The method of claim 94 wherein said subject was treated for a neoplastic disorder prior to the administration of the DLL3 modulator.

96. A method of depleting tumor initiating cells in a subject suffering from a proliferative disorder comprising the step of administering a DLL3 modulator.

97. A method of diagnosing, detecting or monitoring a DLL3 associated disorder in vivo in a subject in need thereof comprising the step of administering a DLL3 modulator.

98. A method of diagnosing, detecting or monitoring a DLL3 associated disorder in a subject in need thereof comprising the step contacting circulating tumor cells with a DLL3 modulator.

99. The method of claim 98 wherein said contacting step occurs in vivo.

100. The method of claim 98 wherein said contacting step occurs in vitro.

101. A method of treating a tumor exhibiting neuroendocrine features in a patient in need thereof comprising the step of administering a therapeutically effective amount of a DLL3 modulator.

102. The method of claim 101 wherein said tumor exhibiting neuroendocrine features is a neuroendocrine tumor.

103. A DLL3 modulator derived from an antibody selected from the group consisting of SC16.3, SC16.4, SC16.5, SC16.7, SC16.8, SC16.10, SC16.11, SC16.13, SC16.15, SC16.18, SC16.19, SC16.20, SC16.21, SC16.22, SC16.23, SC16.25, SC16.26, SC16.29, SC16.30, SC16.31, SC16.34, SC16.35, SC16.36, SC16.38, SC16.39, SC16.41, SC16.42, SC16.45, SC16.47, SC16.49, SC16.50, SC16.52, SC16.55, SC16.56, SC16.57, SC16.58, SC16.61, SC16.62, SC16.63, SC16.65, SC16.67, SC16.68, SC16.72, SC16.73, SC16.78, SC16.79, SC16.80, SC16.81, SC16.84, SC16.88, SC16.101, SC16.103, SC16.104, SC16.105, SC16.106, SC16.107, SC16.108, SC16.109, SC16.110, SC16.111, SC16.113, SC16.114, SC16.115, SC16.116, SC16.117, SC16.118, SC16.120, SC16.121, SC16.122, SC16.123, SC16.124, SC16.125, SC16.126, SC16.129, SC16.130, SC16.131, SC16.132, SC16.133, SC16.134, SC16.135, SC16.136, SC16.137, SC16.138, SC16.139, SC16.140, SC16.141, SC16.142, SC16.143, SC16.144, SC16.147, SC16.148, SC16.149 and SC16.150.

104. An isolated DLL3 modulator that binds to an epitope associated with the EGF1 domain of DLL3.

105. The DLL3 modulator of claim 104 wherein said DLL3 modulator comprises an antibody or immunoreactive fragment thereof.

106. The DLL3 modulator of claim 105 wherein said antibody or immunoreactive fragment thereof comprises a monoclonal antibody.

107. The DLL3 modulator of claim 106 wherein said DLL3 modulator comprises an ADC.

108. The DLL3 modulator of claim 107 wherein said ADC comprises a pyrrolobenzodiazepine.

109. The DLL3 modulator of claim 108 further comprising a linker.

110. An isolated DLL3 modulator that binds to an epitope associated with the EGF2 domain of DLL3.

111. The DLL3 modulator of claim 110 wherein said DLL3 modulator comprises an antibody or immunoreactive fragment thereof.

112. The DLL3 modulator of claim 111 wherein said antibody or immunoreactive fragment thereof comprises a monoclonal antibody.

113. The DLL3 modulator of claim 112 wherein said DLL3 modulator comprises an ADC.

114. The DLL3 modulator of claim 113 wherein said ADC comprises a pyrrolobenzodiazepine.

115. The DLL3 modulator of claim 114 further comprising a linker.

116. An isolated DLL3 modulator that binds to an epitope associated with the EGF3 domain of DLL3.

117. The DLL3 modulator of claim 116 wherein said DLL3 modulator comprises an antibody or immunoreactive fragment thereof.

118. The DLL3 modulator of claim 117 wherein said antibody or immunoreactive fragment thereof comprises a monoclonal antibody.

119. The DLL3 modulator of claim 118 wherein said DLL3 modulator comprises an ADC.

120. The DLL3 modulator of claim 119 wherein said ADC comprises a pyrrolobenzodiazepine.

121. The DLL3 modulator of claim 120 further comprising a linker.

122. An isolated DLL3 modulator that binds to an epitope associated with the EGF4 domain of DLL3.

123. The DLL3 modulator of claim 122 wherein said DLL3 modulator comprises an antibody or immunoreactive fragment thereof.

124. The DLL3 modulator of claim 123 wherein said antibody or immunoreactive fragment thereof comprises a monoclonal antibody.

125. The DLL3 modulator of claim 124 wherein said DLL3 modulator comprises an ADC.

126. The DLL3 modulator of claim 125 wherein said ADC comprises a pyrrolobenzodiazepine.

127. The DLL3 modulator of claim 126 further comprising a linker.

128. An isolated DLL3 modulator that binds to an epitope associated with the EGF5 domain of DLL3.

129. The DLL3 modulator of claim 128 wherein said DLL3 modulator comprises an antibody or immunoreactive fragment thereof.

130. The DLL3 modulator of claim 129 wherein said antibody or immunoreactive fragment thereof comprises a monoclonal antibody.

131. The DLL3 modulator of claim 130 wherein said DLL3 modulator comprises an ADC.

132. The DLL3 modulator of claim 131 wherein said ADC comprises a pyrrolobenzodiazepine.

133. The DLL3 modulator of claim 132 further comprising a linker.

134. An isolated DLL3 modulator that binds to an epitope associated with the EGF6 domain of DLL3.

135. The DLL3 modulator of claim 134 wherein said DLL3 modulator comprises an antibody or immunoreactive fragment thereof.

136. The DLL3 modulator of claim 135 wherein said antibody or immunoreactive fragment thereof comprises a monoclonal antibody.

137. The DLL3 modulator of claim 136 wherein said DLL3 modulator comprises an ADC.

138. The DLL3 modulator of claim 137 wherein said ADC comprises a pyrrolobenzodiazepine.

139. The DLL3 modulator of claim 138 further comprising a linker.

140. An isolated DLL3 modulator that binds to an epitope associated with the DSL domain of DLL3.

141. The DLL3 modulator of claim 140 wherein said DLL3 modulator comprises an antibody or immunoreactive fragment thereof.

142. The DLL3 modulator of claim 141 wherein said antibody or immunoreactive fragment thereof comprises a monoclonal antibody.

143. The DLL3 modulator of claim 142 wherein said DLL3 modulator comprises an ADC.

144. The DLL3 modulator of claim 143 wherein said ADC comprises a pyrrolobenzodiazepine.

145. The DLL3 modulator of claim 144 further comprising a linker.

146. An isolated DLL3 modulator that binds to an epitope associated with the N-terminal domain of DLL3.

147. The DLL3 modulator of claim 146 wherein said DLL3 modulator comprises an antibody or immunoreactive fragment thereof.

148. The DLL3 modulator of claim 147 wherein said antibody or immunoreactive fragment thereof comprises a monoclonal antibody.

149. The DLL3 modulator of claim 148 wherein said DLL3 modulator comprises an ADC.

150. The DLL3 modulator of claim 149 wherein said ADC comprises a pyrrolobenzodiazepine.

151. The DLL3 modulator of claim 150 further comprising a linker.

152. An isolated DLL3 modulator residing in a bin selected from the group consisting of bin A, bin B, bin C, bin D, bin E, bin F, bin G, bin H and bin I.

153. An isolated DLL3 modulator residing in a bin defined by a reference antibody selected from the group consisting of SC16.3, SC16.4, SC16.5, SC16.7, SC16.8, SC16.10, SC16.11, SC16.13, SC16.15, SC16.18, SC16.19, SC16.20, SC16.21, SC16.22, SC16.23, SC16.25, SC16.26, SC16.29, SC16.30, SC16.31, SC16.34, SC16.35, SC16.36, SC16.38, SC16.39, SC16.41, SC16.42, SC16.45, SC16.47, SC16.49, SC16.50, SC16.52, SC16.55, SC16.56, SC16.57, SC16.58, SC16.61, SC16.62, SC16.63, SC16.65, SC16.67, SC16.68, SC16.72, SC16.73, SC16.78, SC16.79, SC16.80, SC16.81, SC16.84, SC16.88, SC16.101, SC16.103, SC16.104, SC16.105, SC16.106, SC16.107, SC16.108, SC16.109, SC16.110, SC16.111, SC16.113, SC16.114, SC16.115, SC16.116, SC16.117, SC16.118, SC16.120, SC16.121, SC16.122, SC16.123, SC16.124, SC16.125, SC16.126, SC16.129, SC16.130, SC16.131, SC16.132, SC16.133, SC16.134, SC16.135, SC16.136, SC16.137, SC16.138, SC16.139, SC16.140, SC16.141, SC16.142, SC16.143, SC16.144, SC16.147, SC16.148, SC16.149 and SC16.150.

154. An antibody drug conjugate of the formula:

$$M\text{-}[L\text{-}D]n$$

or a pharmaceutically acceptable salt thereof wherein
a) M comprises a DLL3 modulator;
b) L comprises an optional linker;
c) D is a anti-proliferative agent; and
d) n is an integer from about 1 to about 20.

155. The antibody drug conjugate of claim 154 wherein said DLL3 modulator comprises an antibody or immunoreactive fragment thereof.

156. The antibody drug conjugate of claim 155 wherein said antibody comprises a monoclonal antibody.

157. The antibody drug conjugate of claim 156 wherein said antibody is derived from an antibody selected from the group consisting of SC16.3, SC16.4, SC16.5, SC16.7, SC16.8, SC16.10, SC16.11, SC16.13, SC16.15, SC16.18, SC16.19, SC16.20, SC16.21, SC16.22, SC16.23, SC16.25, SC16.26, SC16.29, SC16.30, SC16.31, SC16.34, SC16.35, SC16.36, SC16.38, SC16.39, SC16.41, SC16.42, SC16.45, SC16.47, SC16.49, SC16.50, SC16.52, SC16.55, SC16.56, SC16.57, SC16.58, SC16.61, SC16.62, SC16.63, SC16.65, SC16.67, SC16.68, SC16.72, SC16.73, SC16.78, SC16.79, SC16.80, SC16.81, SC16.84, SC16.88, SC16.101, SC16.103, SC16.104, SC16.105, SC16.106, SC16.107, SC16.108, SC16.109, SC16.110, SC16.111, SC16.113, SC16.114, SC16.115, SC16.116, SC16.117, SC16.118, SC16.120, SC16.121, SC16.122, SC16.123, SC16.124, SC16.125, SC16.126, SC16.129, SC16.130, SC16.131, SC16.132, SC16.133, SC16.134, SC16.135, SC16.136, SC16.137, SC16.138, SC16.139, SC16.140, SC16.141, SC16.142, SC16.143, SC16.144, SC16.147, SC16.148, SC16.149 and SC16.150.

158. The antibody drug conjugate of claim 157 wherein said antibody is humanized.

159. The antibody drug conjugate of claim 154 wherein the linker comprises a cleavable linker.
160. The antibody drug conjugate of claim 159 wherein said cleavable linker comprises a peptidyl linker.
161. The antibody drug conjugate of claim 154 wherein said anti-proliferative agent comprises a cytotoxic agent.
162. The antibody drug conjugate of claim 161 wherein said cytotoxic agent comprises a pyrrolobenzodiazepine.
163. The antibody drug conjugate of claim 162 wherein said pyrrolobenzodiazepine comprises a pyrrolobenzodiazepine dimer.
164. A DLL3 modulator comprising a CDR from any one of SEQ ID NOS: 20-203.
165. The DLL3 modulator of claim 164 wherein said modulator comprises a plurality of CDRs from any one of SEQ ID NOS: 20-203.
166. A DLL3 antibody modulator that competes for binding to a DLL3 protein with a reference antibody selected from the group consisting of SC16.3, SC16.4, SC16.5, SC16.7, SC16.8, SC16.10, SC16.11, SC16.13, SC16.15, SC16.18, SC16.19, SC16.20, SC16.21, SC16.22, SC16.23, SC16.25, SC16.26, SC16.29, SC16.30, SC16.31, SC16.34, SC16.35, SC16.36, SC16.38, SC16.39, SC16.41, SC16.42, SC16.45, SC16.47, SC16.49, SC16.50, SC16.52, SC16.55, SC16.56, SC16.57, SC16.58, SC16.61, SC16.62, SC16.63, SC16.65, SC16.67, SC16.68, SC16.72, SC16.73, SC16.78, SC16.79, SC16.80, SC16.81, SC16.84, SC16.88, SC16.101, SC16.103, SC16.104, SC16.105, SC16.106, SC16.107, SC16.108, SC16.109, SC16.110, SC16.111, SC16.113, SC16.114, SC16.115, SC16.116, SC16.117, SC16.118, SC16.120, SC16.121, SC16.122, SC16.123, SC16.124, SC16.125, SC16.126, SC16.129, SC16.130, SC16.131, SC16.132, SC16.133, SC16.134, SC16.135, SC16.136, SC16.137, SC16.138, SC16.139, SC16.140, SC16.141, SC16.142, SC16.143, SC16.144, SC16.147, SC16.148, SC16.149 and SC16.150 wherein binding of the DLL3 antibody modulator to the DLL3 protein is inhibited by at least 30%.
167. A DLL3 modulator that binds to a DLL3 protein epitope comprising amino acids Q93, P94, G95, A96 and P97 (SEQ ID NO: 9).
168. A DLL3 modulator that binds to a DLL3 protein epitope comprising amino acids G203, R205 and P206 (SEQ ID NO: 10).

EXAMPLES

The present invention, thus generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

Example 1

Analysis of Marker Expression in Selected Tumors with Neuroendocrine Features

Neuroendocrine tumors (NETs) arising from the dispersed endocrine system are rare, with an incidence of 2-5 per 100,000 people, but highly aggressive. Neuroendocrine tumors occur in the adrenal gland, kidney, genitourinary tract (bladder, prostate, ovary, cervix, and endometrium), pancreas, gastrointestinal tract (stomach and colon), thyroid (medullary thyroid cancer), and lung (small cell lung carcinoma, large cell neuroendocrine carcinoma, and carcinoid). These tumors may secrete several hormones including serotonin and/or chromogranin A that can cause debilitating symptoms known as carcinoid syndrome. These tumors can be denoted by positive immunohistochemical markers such as neuron-specific enolase (NSE, also known as gamma enolase, gene symbol=ENO2), CD56/NCAM1, and synaptophysin. Traditional chemotherapies have not been successful in treating NETs, and mortality due to metastatic spread is a common outcome. Unfortunately, in most cases surgery is the only potential curative treatment, provided it takes place following early detection and prior to tumor metastasis. In this context work was undertaken to identify novel therapeutic targets associated with tumors comprising neuroendocrine features.

To identify and characterize such tumors as they exist in cancer patients a large non-traditional xenograft (NTX) tumor bank was developed and maintained using art-recognized techniques. The NTX tumor bank, comprising a substantial number of discrete tumor cell lines, was propagated in immunocompromised mice through multiple passages of heterogeneous tumor cells originally obtained from numerous cancer patients afflicted by a variety of solid tumor malignancies. (Note that in some of the Examples and FIGS. herein the passage number of the tested sample is indicated by p0-p# appended to the sample designation where p0 is indicative of an unpassaged sample obtained directly from a patient tumor and p# is indicative of the number of times the tumor has been passaged through a mouse prior to testing.) The continued availability of a large number of discrete early passage NTX tumor cell lines having well defined lineages greatly facilitate the identification and characterization of cells purified from the cell lines. In such work the use of minimally passaged NTX cell lines simplifies in vive experimentation and provides readily verifiable results. Moreover, early passage NTX tumors respond to therapeutic agents such as irinotecan (i.e. Camptosar®) and Cisplatin/Etoposide regimens, which provides clinically relevant insights into underlying mechanisms driving tumor growth, resistance to current therapies and tumor recurrence.

As the NTX tumor cell lines were established, their phenotype was characterized in various ways to examine global gene expression. To identify which NTX lines in the bank might be NETs, gene expression profiles were generated by whole transcriptome sequencing and/or microarray analysis. Specifically, the data was examined to identify tumors expressing high levels of specific genes known to be elevated in NETs or used as histochemical markers of neuroendocrine differentiation (e.g., ASCL1, NCAM1, CHGA) as well as tumors with changes in NOTCH pathway genes indicative of suppression of NOTCH signaling (e.g., reduced levels of NOTCH receptors, and changes to ligands and effector molecules).

More particularly, upon establishing various NTX tumor cell lines as is commonly done for human tumors in severely immune compromised mice, the tumors were resected after reaching 800-2,000 mm³ and the cells were dissociated and dispersed into suspension using art-recognized enzymatic digestion techniques (see, for example, U.S.P.N. 2007/0292414 which is incorporated herein). The dissociated cell preparations from these NTX lines were then depleted of murine cells, and human tumor cell subpopulations were then further isolated by fluorescence activated cell sorting and lysed in R$^L$Tplus RNA lysis buffer (Qiagen). These lysates were then stored at −80° C. until used. Upon thawing, total RNA was extracted using a RNeasy isolation kit (Qiagen) following the vendor's instructions and quantified on a Nanodrop spectrophotometer (Thermo Scientific) and a Bioanalyzer 2100 (Agilent Technologies) again using the manufacturer's protocols and recommended instrument settings. The resulting total RNA preparations were suitable for genetic sequencing and gene expression analysis.

Whole transcriptome sequencing using an Applied Biosystems (ABI) SOLiD (Sequencing by Oligo Ligation/Detection) 4.5 or SOLiD 5500xl next generation sequencing system (Life Technologies) was performed on RNA samples from NTX lines. cDNA was generated from total RNA samples using either a modified whole transcriptome (WT) protocol from ABI designed for low input total RNA or Ovation RNA-Seq System V2™ (NuGEN Technologies Inc.). The modified low input WT protocol uses 1.0 ng of total RNA to amplify mRNA at the 3' end which leads to a heavy 3' bias of mapped gene expression, while NuGen's system allows for a more consistent amplification throughout the transcript, and includes amplification of both mRNA and non-polyadenylated transcript cDNA using random hexamers. The cDNA library was fragmented, and barcodes adapters were added to allow pooling of fragment libraries from different samples.

ABI's SOLiD 4.5 and SOLiD 5500xl next generation sequencing platforms enables parallel sequencing of transcriptomes from multiple NTX lines and sorted populations. A cDNA library is constructed from each RNA sample, which is fragmented and barcoded. Barcodes on each fragment library allow multiple samples to be pooled at equal concentrations and run together while ensuring sample specificity. The samples are taken through emulsion PCR using ABI's SOLiD™ EZ Bead™ robotics system, which ensures sample consistency. Paired-end sequencing generates a 50 base read in the 5' to 3' direction and a 25 base read in the 3' to 5' direction for each clonally amplified fragment on a single bead that exists in the pool. In the case of the 5500xl platform, for every set of 8 samples pooled in the method mentioned above, beads are evenly deposited into 6 single channel lanes on a single chip. This will, on average, generate more than 50 million 50 base reads and 50 million 25 base reads for each of the 8 samples and generates a very accurate representation of mRNA transcript level in the tumor cells. Data generated by the SOLiD platform mapped to 34,609 genes as annotated by RefSeq version 47 using NCBI version hg19.2 of the published human genome and provided verifiable measurements of RNA levels in most samples.

The SOLiD platform is able to capture not only expression, but SNPs, known and unknown alternative splicing events, small non-coding RNAs, and potentially new exon discoveries based solely on read coverage (reads mapped uniquely to previously un-annotated genomic locations). Thus, use of this next generation sequencing platform paired with proprietary data analysis and visualization software thus allowed for discovery of differential transcript expression as well as differences and/or preferences for specific splice variants of expressed mRNA transcripts. Sequencing data from the SOLiD platform is nominally represented as a transcript expression value using the metrics RPM (reads per million) and RPKM (read per kilobase per million), enabling basic differential expression analysis as is standard practice.

Whole transcriptome sequencing of four small cell lung cancer (SCLC) tumors (LU73, LU64, LU86 and LU95), one ovarian tumor (OV26) and a large cell neuroendocrine carcinoma (LCNEC; LU37) resulted in the determination of gene expression patterns commonly found in NETs (FIG. 4A). More specifically, these tumors had high expression of several NET markers (ASCL1, NCAM1, CHGA) as well as reduced levels of Notch receptors and effector molecules (e.g., HES1, HEY1) and elevated markers of Notch suppression (e.g., DLL3 and HES6). In contrast, 4 normal lung samples, 3 lung adenocarcinoma tumors (LU137, LU146 and LU153), and 3 squamous cell lung carcinomas (LU49, LU70 and LU76) all have expression of various Notch receptors and effector molecules, and do not show elevated expression of Notch suppressors such as HES6 and DLL3.

Figure 4B:
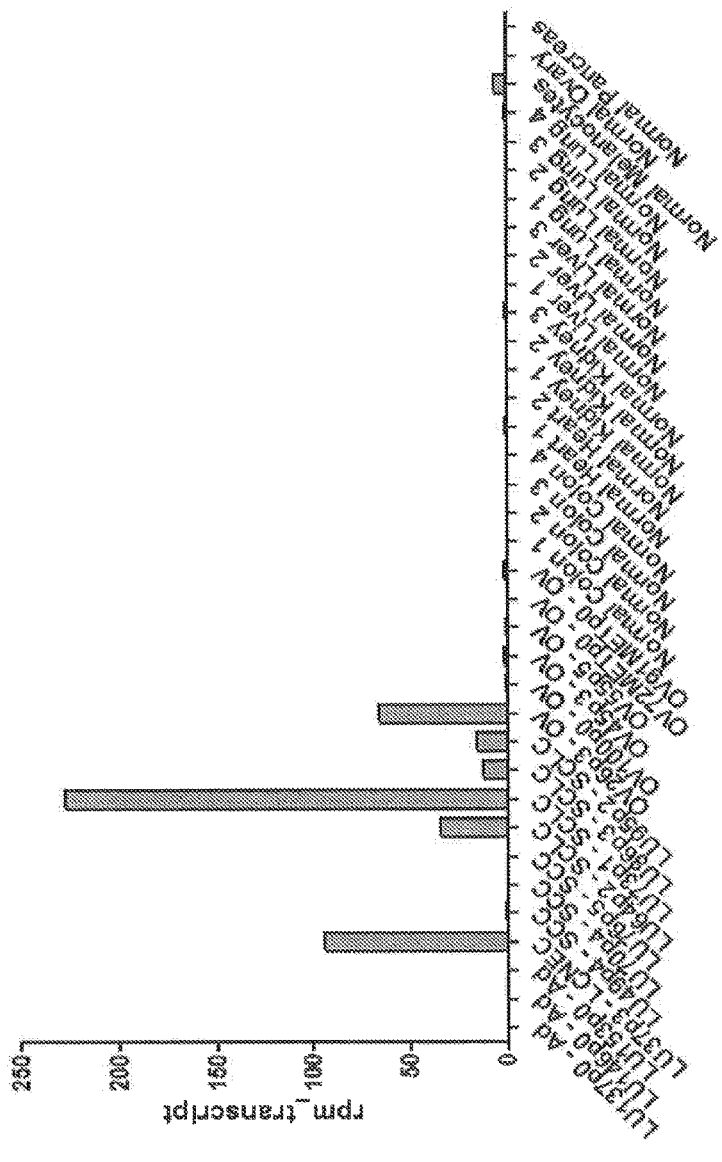

After identifying which NTX in the tumor bank are NETs, each was analyzed using whole transcriptome sequencing data to find potential therapeutic targets upregulated in NETs when compared to non-NETs (including LU_SCC, LU_Ad, and normal lung). High expression of DLL3 was found in NET NTX tumors including SCLC, LCNEC, and OV26, compared to low to non-existent expression in normal lung, normal ovary, other OV NTX, LU_Ad and LU_SCC NTX lines (FIG. 4B). High expression of DLL3 in NETs relative to a variety of normal tissue types was of great interest, as DLL3 is a known suppressor of Notch signaling. Given this, and in view of the generated data, DLL3 was selected for further analysis as a potential immunotherapeutic target.

With the discovery that DLL3 may prove to be a viable target for modulation and treatment of certain proliferative disorders, work was undertaken to determine the expression pattern and levels of DLL3 variants. As discussed above, there are two known splice variants of DLL3 encoding proteins which differ only in that isoform 1 has an extended intracellular C-terminus (FIG. 1E). More specifically isoform 2 is a 587 amino acid protein (FIG. 1D; SEQ ID NO: 4) encoded by mRNA variant 2 (FIG. 1B; SEQ ID NO: 2), which contains exons 8a and 8c while isoform 1 is a 618 amino acid protein (FIG. 1C; SEQ ID NO: 3) encoded by mRNA variant 1 (FIG. 1A; SEQ ID NO: 1), which contains exon 8b. A schematic diagram illustrating the identical extracellular domain (ECD) of isoform 1 and isoform 2 in presented in FIG. 1F.

Again, using the whole transcriptome data obtained as described above, selected NET tumors were examined to determine the expression patterns of the aforementioned exons which, by extension, provides the expression ratio of the two isoforms. As shown in FIG. 5 it was found that while the particular expression ratio between the two isoforms may vary somewhat, isoform 1 expression was predominant in each tumor. In this respect it is important to note that, as described above, the cumulative DLL3 expression (both isoforms) in each of the tested tumors was elevated with regard to normal tissues. Accordingly, while isoform ratios may be indicative of certain tumor types and relevant to genotypic modulator selection it is not as critical with regard to phenotypic modulator strategies. That is, because the ECD region of both DLL3 isoforms are identical, it is expected that a phenotypic modulator of the instant invention directed to the ECD region (e.g., an anti-DLL3 antibody) would react with either isoform. Thus it is the absolute expression levels of the DLL3 ECD (regardless of isoform) that is dispositive as to the effectiveness of such strategies.

Example 2

Microarray and RT-PCR Analysis of Gene Expression in Selected NTX Tumors with Neuroendocrine Features In an effort to identify additional NETs in the aforementioned NTX bank beyond those for which SOLiD whole transcriptome data existed, a larger set of NTX lines was examined using microarray analysis. Specifically, 2-6 µg of total RNA samples derived from whole tumors in 46 NTX lines or from 2 normal tissues were analyzed using a OneArray® microarray platform (Phalanx Biotech Group), which contains 29,187 probes designed against 19,380 genes in the human genome. More specifically, RNA samples were obtained (as described in Example 1) from forty-six patient derived whole NTX tumors comprising colorectal (CR), melanoma (SK), kidney (KD), lung (LU), ovarian (OV), endometrial (EM), breast (BR), liver (LIV), or pancreatic (PA) cancers. Normal colorectal (NormCR) and normal pancreas (NormPA) tissues were used as controls. Still more specifically, lung tumors were further sub-classified as small cell lung cancers (SCLC), squamous cell cancers (SCC), or large cell neuroendocrine carcinoma (LCNEC). RNA samples were run in triplicate using the manufacturer's protocols and the resulting data was analyzed using standard industry practices for normalizing and transforming the measured intensity values obtained for the subject gene in each sample. An unbiased Pearson Spearman hierarchical clustering algorithm in the R/BioConductor suite of packages called hclust.2 was used to create a standard microarray dendrogram for these 48 samples. As known in the art R/BioConductor is an open-source, statistical programming language widely used in academia, finance and the pharmaceutical industry for data analysis. Generally the tumors were arranged and clustered based on gene expression patterns, expression intensity, etc.

Figure 6A:
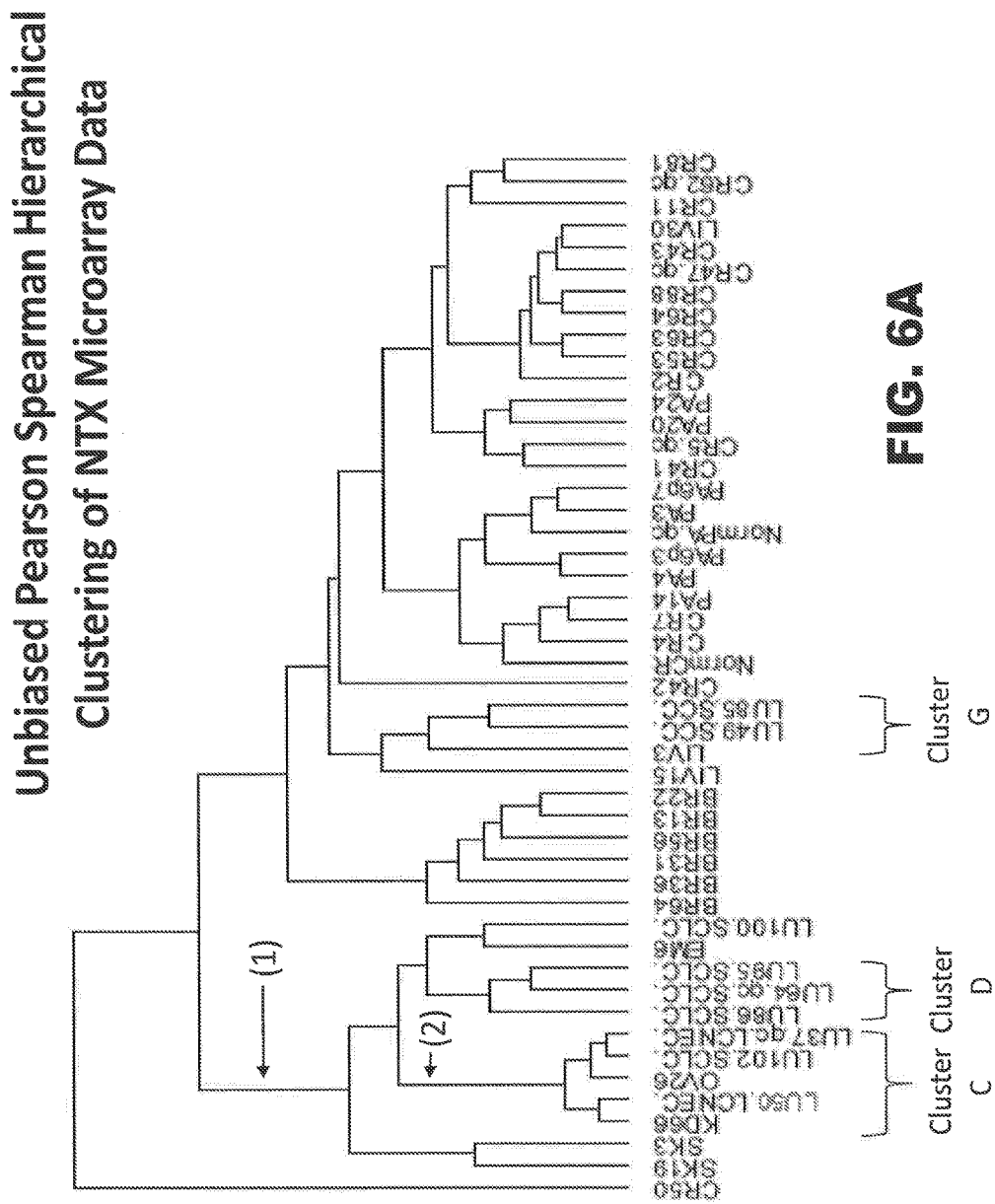

As shown in FIG. 6A, the dendrogram derived from the 48 samples and across all 19380 genes, clustered NTX lines together based upon their tumor type or tissue of origin. Several tumors typically associated with neuroendocrine phenotypes clustered together on the branch denoted by (1); these included skin cancers, numerous lung cancers and other NETs. Interestingly, a sub-branch, denoted by (2), showed that two large cell lung cancers with neuroendocrine features (LU50.LCNEC and LU37.LCNEC) and a small cell lung cancer (LU102.SCLC) clustered with an ovarian (OV26) and a kidney (KD66) tumor (cluster C) suggesting these later tumors also possessed neuroendocrine phenotypes. Moreover, FIG. 6A shows cluster D which consists of 3 additional SCLC tumors, and to its right is a small cluster containing an additional SCLC NTX (LU100) and a neuroendocrine endometrial tumor (EM6), all expected to possess some neuroendocrine features as is generally understood from the literature and pathology experience in the clinic. The fact that cluster G, comprised of squamous cell carcinomas of the lung, can be found on a completely different branch of the dendrogram of FIG. 6A indicates that the clustering is not driven exclusively by the organ of origin for the tumor.

Closer inspection of a collection of gene markers associated with NETs (FIG. 6B) shows that they are strongly expressed in tumors comprising clusters C and D, while they are minimally expressed in tumors in Cluster G (squamous cell carcinoma of the lung), suggesting clusters C and D represent NETs or tumors with a neuroendocrine phenotype. More specifically, cluster C NETs highly express ASCL1, CALCA, CHGA, SST and NKX2-1, while cluster D NETs highly express CHGA, ENO2, and NCAM1, and it is the expression of these neuroendocrine phenotype genes that is in part responsible for the clustering of these tumors. An interesting feature is the strong expression of KIT in cluster D, a gene occasionally reported to be associated with neuroendocrine tumors, but clearly linked to oncogenesis in other contexts. This is in contrast to the SCC tumors in cluster G which lack strong expression any of these genes (FIG. 6B).

With regard to Notch signaling, tumors in cluster C show a phenotype consistent with a reduction in Notch signaling: a lack of expression of any Notch receptor, a relative lack of JAG1 and HES1 expression, and strong levels of ASCL1 expression (FIG. 6C). Interestingly, cluster D shows high expression of HES6, a transcription factor that can support ASCL1 activity by antagonizing HES1 activity through heterodimer formation. Most importantly, these microarray data show high levels of DLL3 transcription in tumors in clusters C and D (relative to cluster G), suggesting that in these tumor types, DLL3 provides an attractive therapeutic target for treatment of NETs.

In view of the aforementioned results, mRNA expression of HES6 was examined from various NTX lines and normal tissues using an Applied Biosystems 7900HT Machine (Life Technologies) to perform Taqman real-time quantitative RT-PCR (qRT-PCR) in accordance with the manufacturer's protocols. RNA was isolated as described above and checked to ensure quality was suitable for gene expression analysis. RNA from normal tissues was purchased (Agilent Technologies and Life Technologies). 200 ng of RNA was used for cDNA synthesis using the cDNA archive kit (Life Technologies). cDNA was used for qRT-PCR analysis on Taqman Low Density Arrays (TLDA; Life Technologies) which contained the HES6 Taqman assay to measure mRNA levels of HES6.

Figure 6D:
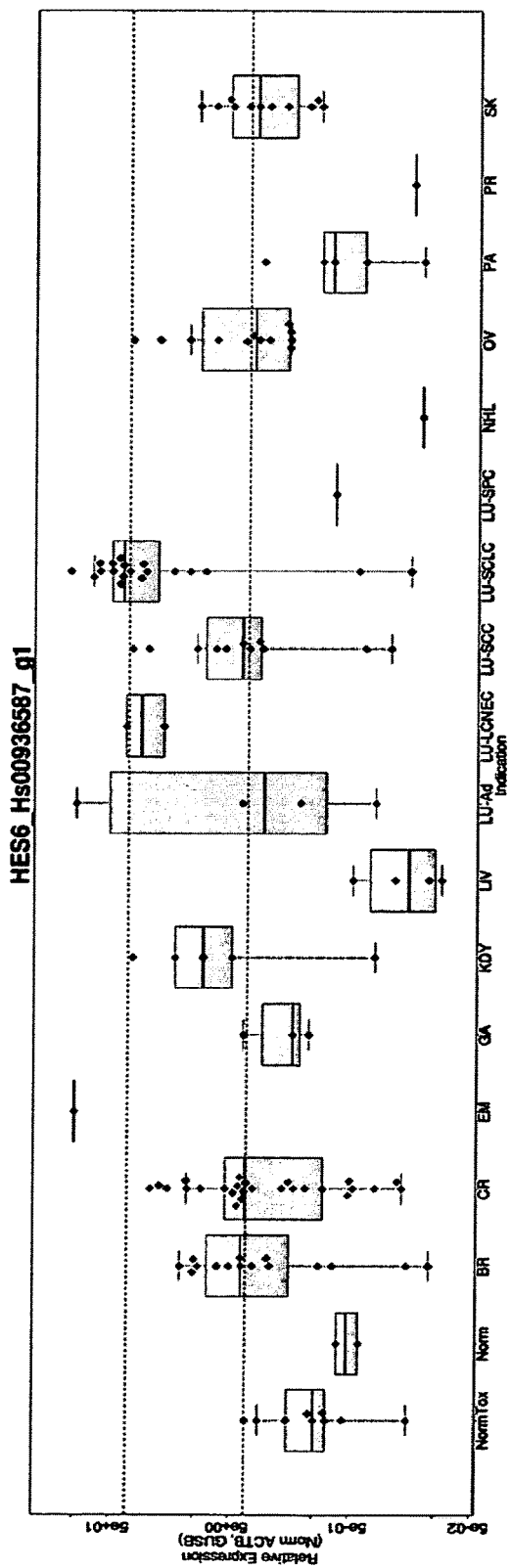

HES6 mRNA levels are shown for each NTX line or normal tissue sample (single dot on graph) after normalization to endogenous controls. Normalized values are plotted relative to the average expression in the normal tissues of toxicity concern (NormTox). This technique allowed for the rapid identification and characterization of a variety of tumors having neuroendocrine features from the NTX tumor bank through measurement of HES6 and other relevant markers. FIG. 6D illustrates general overexpression of HES6 in the sampled tumors with neuroendocrine features (e.g., LU-SCLC, LU-LCNEC) compared to normal tissues, breast, colon, liver and other selected tumors. Significantly these microarray and qPCR data show that at least some endometrial, kidney and ovarian tumors may exhibit neuroendocrine tumor features (FIGS. 6A and 6D).

Example 3

RT-PCR Analysis of DLL3 in Tumors with Neuroendocrine Features

Figure 7:
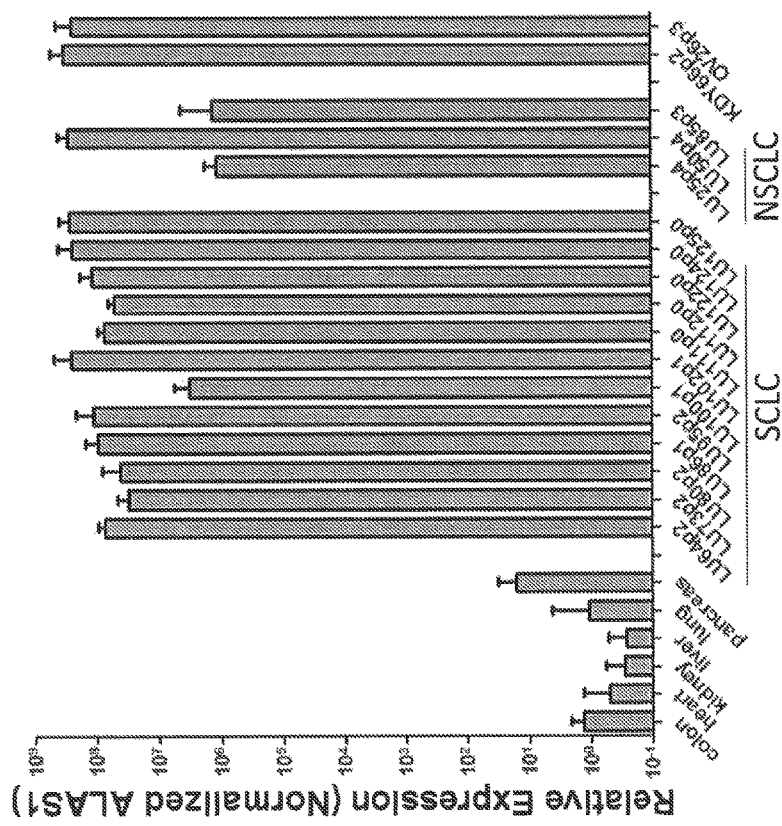
FIG. 7 is a graphical representation showing relative expression levels of DLL3 transcripts as measured by qRT-PCR in a variety of RNA samples isolated from normal tissues, primary, unpassaged patient tumor specimens (denoted with "p0"), or bulk NTX tumors derived from lung, kidney and ovarian neoplasia wherein specific NTX lung tumors are grouped by small cell lung cancer (SCLC) and non-small cell lung cancer (NSCLC) (denoted with p1, p2, p3 or p4 to reflect the number of passages through mice), wherein the tumor type is denoted using the abbreviations set forth above.

To confirm the generated SOLiD and microarray data and extend the analysis to additional NTX samples, DLL3 mRNA expression was analyzed by qRT-PCR using RNA samples from various NTX lines, primary biopsies and normal tissues. The analysis was again performed using an Applied Biosystems 7900HT Machine (Life Technologies) substantially as described immediately above but optimized for DLL3 detection. DLL3 expression is shown relative to the average expression in normal tissues and normalized to expression of the endogenous control gene ALAS 1. As seen in FIG. 7, qRT-PCR interrogation of gene expression showed that DLL3 mRNA is elevated more than 10,000,000-fold in NET populations versus normal tissues. In this Example the sampled tumors include additional SCLC NTX lines beyond those tested previously as well as a number of RNA samples derived from primary biopsies (p0). Taken together these data demonstrate that DLL3 gene expression is dramatically upregulated in tumors exhibiting neuroendocrine features and, given that the same pattern is seen in primary biopsy samples, that the observed upregulation is not an artifact of growing human tumors in mice.

In addition, three subtypes of NSCLC as defined by clinical pathology are also represented in FIG. 7: LU25 is a spindle cell lung carcinoma, LU50 is a large cell neuroendocrine carcinoma (LCNEC), and LU85 is a squamous cell carcinoma (SCC). The highest DLL3 expression was seen in the LCNEC tumor LU50, though elevated levels were also noted in the SCC and spindle cell tumors. KDY66 and OV26, a kidney and ovarian tumor, respectively, clustered on the microarray with SCLC and LCNEC tumors (FIG. 6A), suggesting they comprise tumors exhibiting neuroendocrine features (i.e., NETs or pNETs). Such a conclusion is corroborated by the high mRNA levels of DLL3 seen in both tumor samples (FIG. 7). While all of the tumors display a striking upregulation of DLL3 mRNA relative to normal tissues (FIG. 7), comparison of tumors found both on FIGS. 6A and 7 shows that subtle differences in measured DLL3 mRNA expression in FIG. 7 correspond to differential clustering in FIG. 6A; e.g., cluster C contains KD66, LU50, OV26 and LU102, which are at the high end of DLL3 expression as shown on FIG. 7, whereas LU85 and LU100, each of which cluster away from clusters C and D in FIG. 6A, are among the lower end of DLL3 expression for the tumor samples measured. Small cell lung cancer tumors in cluster D in FIG. 6A (e.g., LU86, LU64, and LU95) show intermediate levels of DLL3 mRNA expression and may very well be susceptible to treatment with the modulators of the instant invention.

Example 4

Expression of DLL3 mRNA and Protein in Various Tumor Specimens

To extend the analysis of DLL3 expression to a wider array of tumor specimens, Taqman qRT-PCR was performed substantially as described in the previous Examples on a TissueScan™ qPCR (Origene Technologies) 384-well array. This array enables comparison of gene expression across 18 different solid tumor types, with multiple patient derived samples for each tumor type and from normal adjacent tissue.

In this regard, FIGS. 8A and 8B show the relative and absolute gene expression levels, respectively, of DLL3 in whole tumor specimens (grey dots) or normal adjacent tissue (NAT; white dots) from patients with one of eighteen different solid tumor types. Data is normalized in FIG. 8A against mean gene expression in NAT for each tumor type analyzed. Specimens in which DLL3 was not detected were assigned a Ct value of 50, which represents the last cycle of amplification in the experimental protocol. Each dot represents a single tissue specimen, with the geometric mean value represented as a black line. Using this Origene TissueScan Array, overexpression of DLL3 was seen in a subset of adrenal, breast, cervical, endometrial, lung, ovarian, pancreatic, thyroid and bladder cancer, many of which may represent NETs or tumors with poorly differentiated neuroendocrine phenotypes. A subset of lung tumors showed the greatest overexpression of DLL3. The highest expression was seen in 2 LCNEC tumors on the array. As shown by the absolute gene expression in FIG. 8B, normal testis is the only normal tissue with high expression of DLL3. This suggests that DLL3 expression in NETs and other tumorigenic cells might play a role in tumorigenesis and/or tumor progression in a wide variety of tumors.

Given the elevated DLL3 transcript levels associated with various tumors, work was undertaken to demonstrate a corresponding increase in the expression of DLL3 protein in NETs relative to other tumors. To this end a DLL3 sandwich ELISA was developed using the MSD Discovery Platform (Meso Scale Discovery, LLC) to detect and quantify DLL3 expression in selected NTX tumor samples. Briefly, NTX tumor samples were lysed and total protein concentration, as well as DLL3 protein concentration, were measured in the lysates using an electrochemiluminescence detection based sandwich ELISA format. More specifically, DLL3 concentrations from the samples were interpolated from electrochemoiluminescent values using a standard curve generated from purified recombinant protein and are expressed in FIG. 8C as nanograms of DLL3 per milligram of total protein.

More specifically NTX tumors were excised from mice and flash frozen on dry ice/ethanol. Protein Extraction Buffer (Biochain Institute, Inc.) was added to the thawed tumor pieces and tumors were pulverized using a Tissue Lyser system (Qiagen). Lysates were cleared by centrifugation (20,000 g, 20 minutes, 4° C.) and protein was quantified using bicinchoninic acid (BCA). Protein lysates were stored at −80 C until assayed.

MSD standard plates (Meso Scale Discovery, LLC) were coated overnight at 4° C. with 30 µl of SC16.34 antibody (obtained as set forth in Example 7 below) at 2 µg/ml in PBS. Plates were washed in PBST and blocked in 150 ul MSD 3% Blocker A solution for 1 hour. Plates were again washed in PBST. 25 µl of the SC16.4 antibody (obtained as set forth in Example 7 below) conjugated to the MSD sulfo-tag and was added to the washed plates at 0.5 µg/ml in MSD 1% Blocker A. 25 µl of 10× diluted lysate in MSD 1% Blocker A or serially diluted recombinant DLL3 standard in MSD 1% Blocker A containing 10% Protein Extraction Buffer was also added to the wells and incubated for 2 hours. Plates were washed in PBST. MSD Read Buffer T with surfactant was diluted to IX in water and 150 µl was added to each well. Plates were read on a MSD Sector Imager 2400 using an integrated software analysis program to derive DLL3 concentrations in NTX samples via interpolation. Values were then divided by total protein concentration to yield nanograms of DLL3 per milligram of total lysate protein. The resulting concentrations are set forth in FIG. 8C wherein each spot represents concentrations derived from a single NTX tumor line. While each spot is derived from a single NTX line, in most cases multiple biological samples were tested from the same NTX line and values were averaged to provide the data point.

Figure 8C:
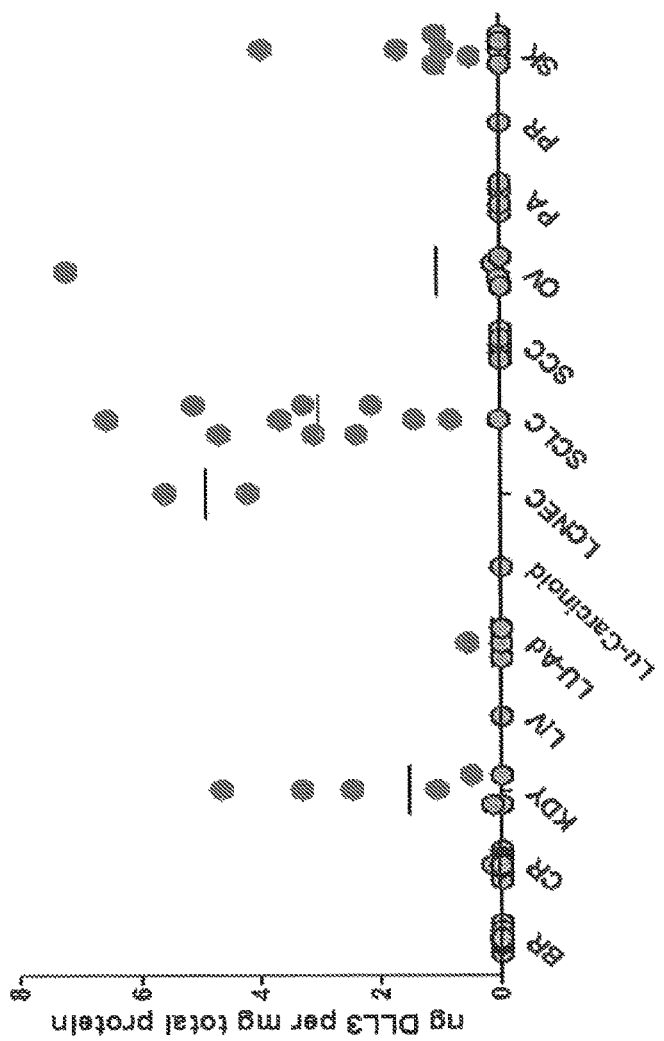

In any event FIG. 8C shows that the highest expression of DLL3 was found in SCLC, LCNEC, as well as other neuroendocrine tumors including selected kidney samples and a single ovarian tumor. FIG. 8C also demonstrates that certain melanoma NTX lines exhibited elevated DLL3 protein expression which is particularly interesting in that these NTX lines also clustered near NET NTX lines in the microarray analysis conducted in Example 4 (FIG. 6A).

These data, combined with the transcription data for DLL3 expression set forth above strongly reinforces the proposition that DLL3 determinants provide attractive targets for therapeutic intervention.

Example 5

Expression of NOTCH Receptors and Delta-Like Ligands on the Cell Surface of Selected NTX Tumor Lines To further extend the observations from Examples 1 and 2 above, cells isolated from several NTX tumors found in Clusters C and D (KDY66, OV26, LU64; FIG. 6A) as well as a SCLC tumor determined to have high expression of DLL3 by SOLiD sequencing or qRT-PCR (LU73, FIGS. 4 and 7) were analyzed using flow cytometry for determination of the levels of protein expression for various Notch receptors and other DLL family members. Generally flow cytometry-based protein expression data was generated using a FACSCanto II (BD Biosciences) as per the manufacturer's instructions. Data in FIG. 9 shows individual tumor cells displayed as histogram plots, wherein the background staining of isotype control antibodies is shown in the gray, filled histograms and expression of the protein of interest, as determined using commercially available antibodies is displayed by the bold, black line.

Figure 9:
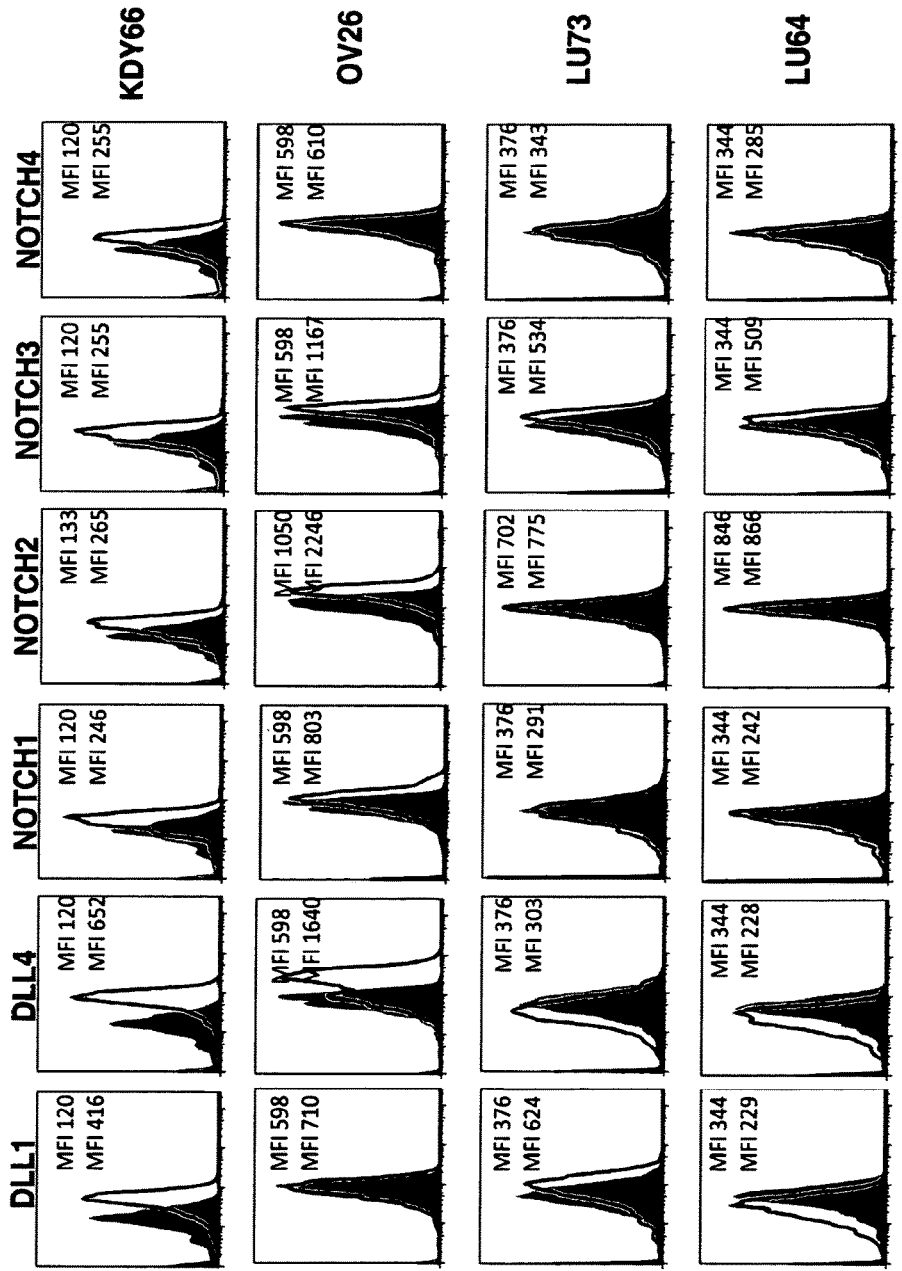
FIG. 9 provides graphical representations of flow cytometry-based determination of surface protein expression of various Notch receptors and ligands (e.g., DLL1, DLL4) in individual human tumor cell populations derived from kidney, ovarian and small cell lung NTX tumors, displayed as histogram plots (black line) referenced to fluorescence minus one (FMO) isotype-control stained population (solid gray) with indicated mean fluorescence intensities (MFI)

As can be seen graphically in FIG. 9, little to no expression of any of the Notch receptors (e.g., NOTCH1-4) was observed in any of these tumors, as determined relative to fluorescence minus one (FMO) isotype-control stained cells. This is indicated graphically by the histograms, as well as numerically in the reported mean fluorescence intensities (MFI) for each measurement. Similarly, the two lung cancer derived NTX cells showed no expression of either DLL1 or DLL4. Slight expression of DLL4 alone (OV26) or DLL1 and DLL4 (KDY66) could be observed for two of the tumors. In general, these observations confirm the results obtained and presented in Examples 1 and 2 above, that these tumor types show little to no expression of Notch signaling pathway components, consistent with loss of Notch signaling in NETs or poorly differentiated tumors with neuroendocrine phenotypes.

Example 6

Generation of Anti-DLL3 Modulators

DLL3 modulators in the form of murine antibodies were produced in accordance with the teachings herein through inoculation with recombinant human DLL3-Fc or with human DLL3-His (each comprising the mature ECD of DLL3 set forth in FIG. 1C; SEQ ID NO: 3) in two separate immunization campaigns. In this regard three strains of mice (Balb/c, CD-1 and FVB) were inoculated with human recombinant DLL3 to provide hybridomas secreting high affinity, murine monoclonal antibody modulators.

The hDLL3-Fc fusion construct was obtained from Adipogen International (Catalog No. AG-40A-0113) where it had been purified from the supernatant of DLL3-Fc overexpressing HEK 293 cells as described in the manufacturer's product data sheet. Recombinant hDLL3-His protein was purified from the supernatants of CHOK1 cells engineered to overexpress hDLL3-His. 10 μg of hDLL3-Fc or hDLL3-His immunogen was emulsified with an equal volume of TITERMAX® Gold (CytRx Corporation) or alum adjuvant and used for the immunization of each mouse. The resulting emulsions were then injected into three female mice (1 each: Balb/c, CD-1 and FVB) via the footpad route.

Solid-phase ELISA assays were used to screen mouse sera for mouse IgG antibodies specific for human DLL3. A positive signal above background was indicative of antibodies specific for DLL3. Briefly, 96 well plates (VWR International, Cat. #610744) were coated with recombinant DLL3-His at 0.5 μg/ml in ELISA coating buffer overnight. After washing with PBS containing 0.02% (v/v) Tween 20, the wells were blocked with 3% (w/v) BSA in PBS, 200 μL/well for 1 hour at room temperature (RT). Mouse serum was titrated (1:100, 1:200, 1:400, and 1:800) and added to the DLL3 coated plates at 50 UL/well and incubated at RT for 1 hour. The plates are washed and then incubated with 50 μL/well HRP-labeled goat anti-mouse IgG diluted 1:10,000 in 3% BSA-PBS or 2% FCS in PBS for 1 hour at RT. Again the plates were washed and 40 μL/well of a TMB substrate solution (Thermo Scientific 34028) was added for 15 minutes at RT. After developing, an equal volume of 2N $H_2SO_4$ was added to stop substrate development and the plates were analyzed by spectrophotometer at OD 450.

Sera-positive immunized mice were sacrificed and draining lymph nodes (popliteal and inguinal, and medial iliac if enlarged) were dissected out and used as a source for antibody producing cells. A single cell suspension of B cells ($228.9 \times 10^6$ cells) was fused with non-secreting P3x63Ag8.653 myeloma cells (ATCC #CRL-1580) at a ratio of 1:1 by electrofusion. Electrofusion was performed using the BTX Hybrimmune™ System, (BTX Harvard Apparatus) as per the manufacturer's directions. After the fusion procedure the cells were resuspended in hybridoma selection medium supplemented with Azaserine (Sigma #A9666), high glucose DMEM medium with sodium pyruvate (Cellgro cat#15-017-CM) containing 15% Fetal Clone I serum (Hyclone), 10% BM Condimed (Roche Applied Sciences), 4 mM L-glutamine, 100 IU Penicillin-Streptomycin and 50 μM 2-mercaptoethanol and then plated in three T225 flasks in 90 mL selection medium per flask. The flasks were then placed in a humidified 37° C. incubator containing 5% $CO_2$ and 95% air for 6-7 days.

After six to seven days of growth the library consisting of the cells grown in bulk in the T225s was plated at 1 cell per well in Falcon 96 well U-bottom plates using the Aria I cell sorter. The selected hybridomas were then grown in 200 μL of culture medium containing 15% Fetal Clone I serum (Hyclone), 10% BM-Condimed (Roche Applied Sciences), 1 mM sodium pyruvate, 4 mM L-glutamine, 100 IU Penicillin-Streptamycin, 50 μM 2-mercaptoethanol, and 100 μM hypoxanthine. Any remaining unused hybridoma library cells were frozen for future library testing. After ten to eleven days of growth supernatants from each well of the plated cells were assayed for antibodies reactive for DLL3 by ELISA and FACS assays.

For screening by ELISA 96 well plates were coated with denatured human DLL3 or cell lysates of 293 cells overexpressing human DLL3 (obtained as discussed below), in sodium carbonate buffer overnight at 4° C. The plates were washed and blocked with 3% BSA in PBS/Tween for one hour at 37° C. and used immediately or kept at 4° C. Undiluted hybridoma supernatants were incubated on the plates for one hour at RT. The plates were washed and probed with HRP labeled goat anti-mouse IgG diluted 1:10,000 in 3% BSA-PBS for one hour at RT. The plates were then incubated with substrate solution as described above and read at OD 450. Wells containing immunoglobulin that preferentially bound human DLL3, as determined by a signal above background, were transferred and expanded.

Figure 10C:
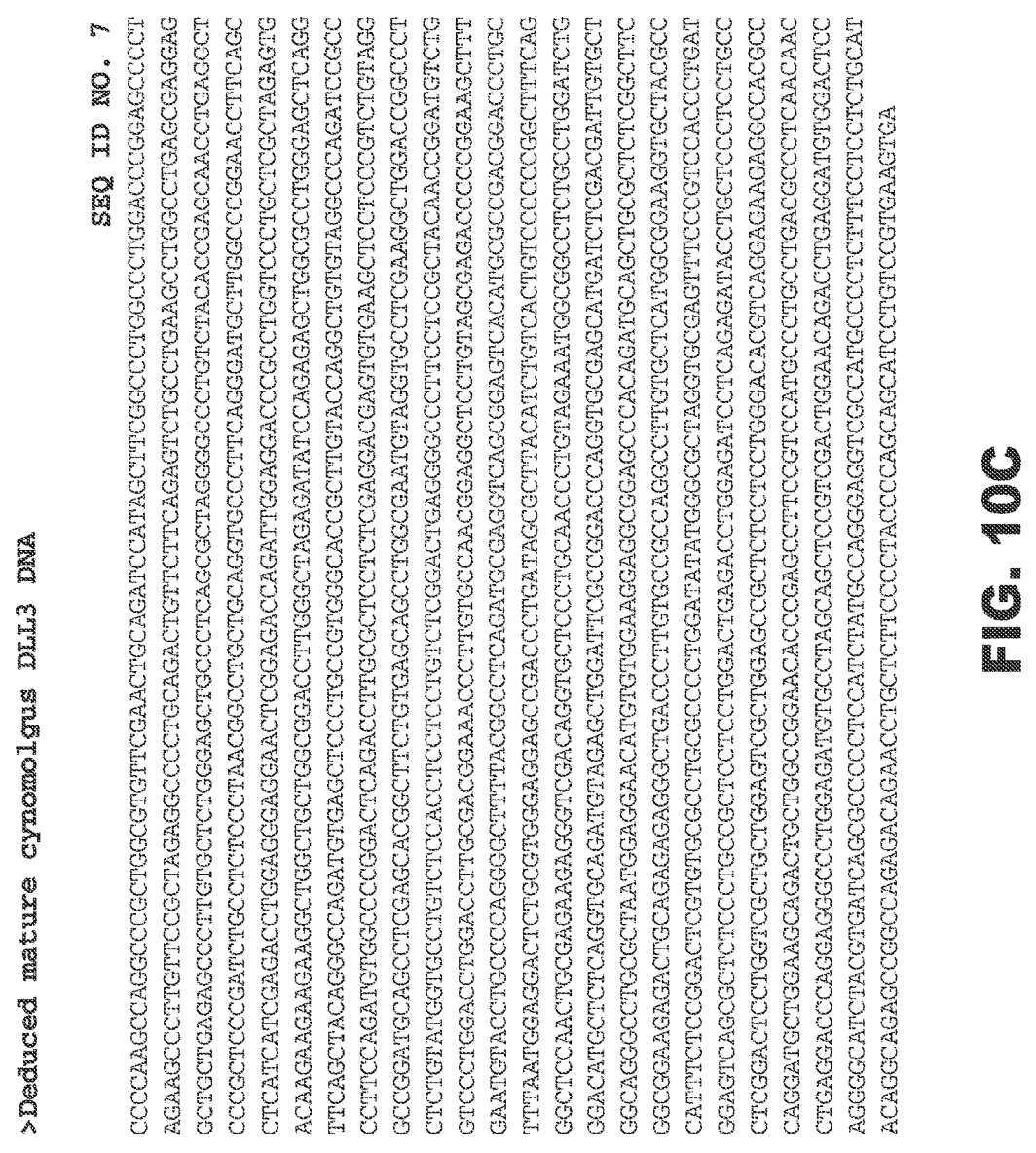

Growth positive hybridoma wells secreting murine immunoglobulin were also screened for human DLL3 specificity and cynomolgus, rat and murine DLL3 cross reactivity using a flow cytometry based assay with 293 cells engineered to over-express either human DLL3 (h293-hDLL3), cynomolgus DLL3 (h293-cDLL3), rat (h293-rDLL3) or murine DLL3 (h293-mDLL3) proteins. h293-hDLL3 cells were made by transduction of 293T cells using a lentivirus made from a commercial bicistronic lentiviral vector (Open Biosystems) that expressed both hDLL3 and a GFP marker. h293-mDLL3 cells were made by transduction of 293T cells using a bicistronic lentiviral vector expressing both mDLL3 and a RFP marker, constructed as follows. A DNA fragment (FIG. 10A; SEQ ID NO: 5) encoding the mature murine DLL3 protein (FIG. 10B; SEQ ID NO: 6) was obtained by PCR amplification from a commercial murine DLL3 construct (Origene) and subcloned downstream of an IgG K signal peptide sequence previously engineered upstream of the multiple cloning site of pCDH-EF1-MCS-IRES-RFP (System Biosciences) using standard molecular cloning techniques. Similarly, h293-rDLL3 cells were made by transduction of 293T cells using a bicistronic lentiviral vector expressing both rat DLL3 and a GFP marker, constructed by cloning a synthetic DNA fragment (GeneWiz) comprising a codon-optimized sequence encoding the mature rat DLL3 protein (accession NP_446118.1, residues 25-589) downstream of an IgK signal peptide sequence previously engineered upstream of the multiple cloning site of pCDH-EF1-MCS-IRES-GFP (System Biosciences) using standard molecular cloning techniques. Finally, cynomolgus (e.g., *Macaca fascicularis*) DLL3 (cDLL3) sequence was deduced using the human DLL3 sequence to BLAST against the publically available *Macaca fascicularis* whole-genome shotgun contigs, and assembling the exon sequences of the Cynomolgus gene assuming maintenance of exonic structure in the gene across species. PCR amplification and direct sequencing of the individual exons 2-7 from Cynomolgus genomic DNA (Zyagen) was used to confirm that the deduced sequence was correct across the ECD region of the protein. The cDLL3 DNA sequence (FIG. 10C; SEQ ID NO: 7), encoding the cDLL3 protein (FIG. 10D; SEQ ID NO: 8), was manufactured synthetically (GeneWiz) and subcloned downstream of an IgG K signal peptide sequence previously engineered upstream of the multiple cloning site of pCDH-EF1-MCS-IRES-GFP (System Biosciences) using standard molecular cloning techniques. Transduction of 293T cells with this vector yielded the h293-cDLL3 cells.

For the flow cytometry assays, $50 \times 10^4$ h293 cells transduced respectively with human, cynomolgus, rat or murine DLL3 were incubated for 30 minutes with 25-100 µL hybridoma supernatant. Cells were washed with PBS, 2% FCS, twice and then incubated with 50 µL of a goat-anti-mouse IgG Fc fragment specific secondary conjugated to DyLight 649 diluted 1:200 in PBS/2% FCS. After 15 minutes of incubation, cells were washed twice with PBS/2% FCS and re-suspended in PBS/2% FCS with DAPI and analyzed by flow cytometry using a FACSCanto II as per the manufacturer's instructions. Wells containing immunoglobulin that preferentially bound the DLL3+ GF+ cells were transferred and expanded. The resulting hDLL3 specific clonal hybridomas were cryopreserved in CS-10 freezing medium (Biolife Solutions) and stored in liquid nitrogen. Antibodies that bound h293-hDLL3, h293-cDLL3, h293-rDLL3 and/or h293-mDLL3 cells were noted as cross-reactive (see FIG. 12). Based on this assay all the selected modulators that were cross reactive with the murine antigen were also cross reactive with the rat antigen.

ELISA and flow cytometry analysis confirmed that purified antibody from most or all of these hybridomas bound DLL3 in a concentration-dependent manner. One fusion of each immunization campaign was performed and seeded in 64 plates (6144 wells at approximately 60-70% cloning efficiency). The hDLL3-Fc immunization campaign and screening yielded approximately 90 murine antibodies specific for human DLL3, several of which were cross reactive with murine DLL3. The hDLL3-His immunization campaign yielded 50 additional murine antibodies specific for human DLL3, a number of which cross reacted with murine DLL3.

Example 7

Sequencing of Murine DLL3 Modulators

Based on the foregoing, a number of exemplary distinct monoclonal antibodies that bind immobilized human DLL3 or h293-hDLL3 cells with apparently high affinity were selected for sequencing and further analysis. As shown in a tabular fashion in FIGS. 11A and 11B, sequence analysis of the light chain variable regions (FIG. 11A) and heavy chain variable regions (FIG. 11B) from selected monoclonal antibodies generated in Example 6 confirmed that many had novel complementarity determining regions and often displayed novel VDJ arrangements. Note that the complementarity determining regions set forth in FIGS. 11A and 11B are defined as per Chothia et al., supra.

As a first step in sequencing exemplary modulators, the selected hybridoma cells were lysed in Trizol® reagent (Trizol Plus RNA Purification System, Life Technologies) to prepare the RNA. In this regard between $10^4$ and $10^5$ cells were resuspended in 1 mL Trizol and shaken vigorously after addition of 200 µL of chloroform. Samples were then centrifuged at 4° C. for 10 minutes and the aqueous phase was transferred to a fresh microfuge tube where an equal volume of isopropanol was added. The tubes were again shaken vigorously and allowed to incubate at RT for 10 minutes before being centrifuged at 4° C. for 10 minutes. The resulting RNA pellets were washed once with 1 mL of 70% ethanol and dried briefly at RT before being resuspended in 40 µL of DEPC-treated water. The quality of the RNA preparations was determined by fractionating 3 µL in a 1% agarose gel before being stored at −80° C. until used.

The variable region of the Ig heavy chain of each hybridoma was amplified using a 5' primer mix comprising thirty-two mouse specific leader sequence primers, designed to target the complete mouse $V_H$ repertoire, in combination with a 3' mouse Cγ primer specific for all mouse Ig isotypes. A 400 bp PCR fragment of the $V_H$ was sequenced from both ends using the same PCR primers. Similarly a mix of thirty-two 5' Vκ leader sequence primers designed to amplify each of the Vκ mouse families combined with a single reverse primer specific to the mouse kappa constant region were used to amplify and sequence the kappa light chain. The $V_H$ and $V_L$ transcripts were amplified from 100 ng total RNA using reverse transcriptase polymerase chain reaction (RT-PCR).

A total of eight RT-PCR reactions were run for each hybridoma: four for the Vκ light chain and four for the V gamma heavy chain (γ1). The One Step RT-PCR kit was used for amplification (Qiagen). This kit provides a blend of Sensiscript and Omniscript Reverse Transcriptases, HotStar-Taq DNA Polymerase, dNTP mix, buffer and Q-Solution, a novel additive that enables efficient amplification of "difficult" (e.g., GC-rich) templates. Reaction mixtures were prepared that included 3 µL of RNA, 0.5 of 100 µM of either heavy chain or kappa light chain primers (custom synthesized by IDT), 5 µL of 5×RT-PCR buffer, 1 µL dNTPs, 1 µL of enzyme mix containing reverse transcriptase and DNA polymerase, and 0.4 µL of ribonuclease inhibitor RNasin (1 unit). The reaction mixture contains all of the reagents required for both reverse transcription and PCR. The thermal cycler program was set for an RT step 50° C. for 30 minutes, 95° C. for 15 minutes, followed by 30 cycles of PCR (95° C. for 30 seconds, 48° C. for 30 seconds, 72° C. for one minute). There was then a final incubation at 72° C. for 10 minutes.

To prepare the PCR products for direct DNA sequencing, they were purified using the QIAquick™ PCR Purification Kit (Qiagen) according to the manufacturer's protocol. The DNA was eluted from the spin column using 50 μL of sterile water and then sequenced directly from both strands. The extracted PCR products were directly sequenced using specific V region primers. Nucleotide sequences were analyzed using IMGT to identify germline V, D and J gene members with the highest sequence homology. The derived sequences were compared to known germline DNA sequences of the Ig V- and J-regions using V-BASE2 (Retter et al., supra) and by alignment of $V_H$ and $V_L$ genes to the mouse germline database to provide the annotated sequences set forth in FIGS. 11A and 11B.

More specifically, FIG. 11A depicts the contiguous amino acid sequences of ninety-two novel murine light chain variable regions from anti-DLL3 antibodies (SEQ ID NOS: 20-202, even numbers) and five humanized light chain variable regions (SEQ ID NOS: 204-212, even numbers) derived from representative murine light chains. Similarly, FIG. 11B depicts the contiguous amino acid sequences of ninety-two novel murine heavy chain variable regions (SEQ ID NOS: 21-203, odd numbers) from the same anti-DLL3 antibodies and five humanized heavy chain variable regions (SEQ ID NOS: 205-213, odd numbers) from the same murine antibodies providing the humanized light chains. Thus, taken together FIGS. 11A and 11B provide the annotated sequences of ninety-two operable murine anti-DLL3 antibodies (termed SC16.3, SC16.4, SC16.5, SC16.7, SC16.8, SC16.10, SC16.11, SC16.13, SC16.15, SC16.18, SC16.19, SC16.20, SC16.21, SC16.22, SC16.23, SC16.25, SC16.26, SC16.29, SC16.30, SC16.31, SC16.34, SC16.35, SC16.36, SC16.38, SC16.41, SC16.42, SC16.45, SC16.47, SC16.49, SC16.50, SC16.52, SC16.55, SC16.56, SC16.57, SC16.58, SC16.61, SC16.62, SC16.63, SC16.65, SC16.67, SC16.68, SC16.72, SC16.73, SC16.78, SC16.79, SC16.80, SC16.81, SC16.84, SC16.88, SC16.101, SC16.103, SC16.104, SC16.105, SC16.106, SC16.107, SC16.108, SC16.109, SC16.110, SC16.111, SC16.113, SC16.114, SC16.115, SC16.116, SC16.117, SC16.118, SC16.120, SC16.121, SC16.122, SC16.123, SC16.124, SC16.125, SC16.126, SC16.129, SC16.130, SC16.131, SC16.132, SC16.133, SC16.134, SC16.135, SC16.136, SC16.137, SC16.138, SC16.139, SC16.140, SC16.141, SC16.142, SC16.143, SC16.144, SC16.147, SC16.148, SC16.149 and SC16.150) and five humanized antibodies (termed hSC16.13, hSC16.15, hSC16.25, hSC16.34 and hSC16.56). Note that these same designations may refer to the clone that produces the subject antibody and, as such, the use of any particular designation should be interpreted in the context of the surrounding disclosure.

For the purposes of the instant application the SEQ ID NOS of each particular antibody are sequential. Thus mAb SC16.3 comprises SEQ ID NOS: 20 and 21 for the light and heavy chain variable regions respectively. In this regard SC16.4 comprises SEQ ID NOS: 22 and 23, SC16.5 comprises SEQ ID NOS: 24 and 25, and so on. Moreover, corresponding nucleic acid sequences for each antibody amino acid sequence in FIGS. 11A and 11B are appended to the instant application in the sequence listing filed herewith. In the subject sequence listing the included nucleic acid sequences comprise SEQ ID NOS that are two hundred greater than the corresponding amino acid sequence (light or heavy chain). Thus, nucleic acid sequences encoding the light and heavy chain variable region amino acid sequences of mAb SC16.3 (i.e., SEQ ID NOS: 20 and 21) comprise SEQ ID NOS: 220 and 221 in the sequence listing. In this regard nucleic acid sequences encoding all of the disclosed light and heavy chain variable region amino acid sequences, including those encoding the humanized constructs, are numbered similarly and comprise SEQ ID NOS: 220-413.

Example 8

Humanization of DLL3 Modulators

As alluded to above, five of the murine antibodies from Example 7 were humanized using complementarity determining region (CDR) grafting. Human frameworks for heavy and light chains were selected based on sequence and structure similarity with respect to functional human germline genes. In this regard structural similarity was evaluated by comparing the mouse canonical CDR structure to human candidates with the same canonical structures as described in Chothia et al. (supra).

More particularly murine antibodies SC16.13, SC16.15, SC16.25, SC16.34 and SC16.56 were humanized using a computer-aided CDR-grafting method (Abysis Database, UCL Business Plc.) and standard molecular engineering techniques to provide hSC16.13, hSC16.15, hSC16.25, hSC16.34 and hSC16.56 modulators. The human framework regions of the variable regions were selected based on their highest sequence homology to the subject mouse framework sequence and its canonical structure. For the purposes of the humanization analysis the assignment of amino acids to each of the CDR domains is in accordance with Kabat et al. numbering (supra).

Molecular engineering procedures were conducted using art-recognized techniques. To that end total mRNA was extracted from the hybridomas and amplified as set forth in Example 7 immediately above.

From the nucleotide sequence information, data regarding V, D and J gene segments of the heavy and light chains of subject murine antibodies were obtained. Based on the sequence data new primer sets specific to the leader sequence of the Ig $V_H$ and $V_κ$ light chain of the antibodies were designed for cloning of the recombinant monoclonal antibody. Subsequently the V-(D)-J sequences were aligned with mouse Ig germ line sequences. The resulting genetic arrangements for each of the five humanized constructs are shown in Table 1 immediately below.

TABLE 1

| mAb | human VH | human DH | human JH | FW changes | human VK | human JK | FW changes |
|---|---|---|---|---|---|---|---|
| hSC16.13 | IGHV2-5 | IGHD1-1 | JH6 | None | IGKV-O2 | JK1 | None |
| hSC16.15 | VH1-46 | IGHD-2 | JH4 | None | IGKV-L4 | JK4 | 87F |
| hSC16.25 | IGHV2-5 | IGHD3-16 | JH6 | None | IGVK-A10 | JK2 | None |
| hSC16.24 | IGHV1-3 | IGHD3-22 | JH4 | None | IGVK-A20 | JK1 | 87F |
| hSC16.56 | IGHV1-18 | IGHD2-21 | JH4 | None | IGKV-L2 | JK2 | None |

The sequences depicted in TABLE 1 correspond to the annotated heavy and light chain sequences set forth in FIGS. 11A and 11B for the subject clones. More specifically, the entries in Table 1 above correspond to the contiguous variable region sequences set forth SEQ ID NOS: 204 and 205 (hSC16.13), SEQ ID NOS: 206 and 207 (hSC16.15), SEQ ID NOS: 208 and 209 (hSC16.25), SEQ ID NOS: 210 and 211 (hSC16.34) and SEQ ID NOS: 212 and 213 (hSC16.56). Furthermore, TABLE 1 shows that very few framework changes were necessary to maintain the favorable properties of the binding modulators. In this respect there were no framework changes or back mutations made in the heavy chain variable regions and only two framework modifications were undertaken in the light chain variable regions (i.e., 87 F in hSC16.15 and hSC16.34).

Following humanization of all selected antibodies by CDR grafting, the resulting light and heavy chain variable region amino acid sequences were analyzed to determine their homology with regard to the murine donor and human acceptor light and heavy chain variable regions. The results, shown in Table 2 immediately below, reveal that the humanized constructs consistently exhibited a higher homology with respect to the human acceptor sequences than with the murine donor sequences. More particularly, the murine heavy and light chain variable regions show a similar overall percentage homology to a closest match of human germline genes (85%-93%) compared with the homology of the humanized antibodies and the donor hybridoma protein sequences (74%-83%).

TABLE 2

| mAb | Homology to Human (CDR acceptor) | Homology to Murine Parent (CDR donor) |
| --- | --- | --- |
| hSC16.13 HC | 93% | 81% |
| hSC16.13 LC | 87% | 77% |
| hSC16.15 HC | 85% | 83% |
| hSC16.15 LC | 85% | 83% |
| hSC16.25 HC | 91% | 83% |
| hSC16.25 LC | 85% | 79% |
| hSC16.34 HC | 87% | 79% |
| hSC16.34 LC | 85% | 81% |
| hSC16.56 HC | 87% | 74% |
| hSC16.56 LC | 87% | 76% |

Upon testing, and as will be discussed in more detail below, each of the humanized constructs exhibited favorable binding characteristics roughly comparable to those shown by the murine parent antibodies.

Whether humanized or murine, once the nucleic acid sequences of the variable regions are determined the antibodies of the instant invention may be expressed and isolated using art-recognized techniques. To that end synthetic DNA fragments of the chosen heavy chain (humanized or murine) variable region were cloned into a human IgG1 expression vector. Similarly the variable region light chain DNA fragment (again humanized or murine) was cloned into a human light chain expression vector. The selected antibody was then expressed by co-transfection of the derived heavy and the light chain nucleic acid constructs into CHO cells.

More particularly, one compatible method of antibody production comprised directional cloning of murine or humanized variable region genes (amplified using PCR) into selected human immunoglobulin expression vectors. All primers used in Ig gene-specific PCRs included restriction sites which allowed direct cloning into expression vectors containing human IgG1 heavy chain and light chain constant regions. In brief, PCR products were purified with Qiaquick PCR purification kit (Qiagen) followed by digestion with AgeI and XhoI (for the heavy chain) and XmaI and DraIII (for the light chain), respectively. Digested PCR products were purified prior to ligation into expression vectors. Ligation reactions were performed in a total volume of 10 μL with 200 U T4-DNA Ligase (New England Biolabs), 7.5 μL of digested and purified gene-specific PCR product and 25 ng linearized vector DNA. Competent E. coli DH10B bacteria (Life Technologies) were transformed via heat shock at 42° C. with 3 μL ligation product and plated onto ampicillin plates (100 μg/mL). The AgeI-EcoRI fragment of the $V_H$ region was than inserted into the same sites of pEE6.4HuIgG1 expression vector while the synthetic XmaI-DraIII VK insert was cloned into the XmaI-DraIII sites of the respective pEE12.4Hu-Kappa expression vector.

Cells producing the selected antibody were generated by transfection of HEK 293 cells with the appropriate plasmids using 293fectin. In this respect plasmid DNA was purified with QIAprep Spin columns (Qiagen). Human embryonic kidney (HEK) 293T (ATCC No CRL-11268) cells were cultured in 150 mm plates (Falcon, Becton Dickinson) under standard conditions in Dulbecco's Modified Eagle's Medium (DMEM) supplemented with 10% heat inactivated FCS, 100 μg/mL streptomycin, 100 U/mL penicillin G (all from Life Technologies).

For transient transfections cells were grown to 80% confluency. Equal amounts of IgH and corresponding IgL chain vector DNA (12.5 μg of each) was added to 1.5 mL Opti-MEM mixed with 50 μL HEK 293 transfection reagent in 1.5 mL opti-MEM. The mix was incubated for 30 min at room temperature and distributed evenly to the culture plate. Supernatants were harvested three days after transfection, replaced by 20 mL of fresh DMEM supplemented with 10% FBS and harvested again at day 6 after transfection. Culture supernatants were cleared of cell debris by centrifugation at 800×g for 10 min and stored at 4° C. Recombinant chimeric and humanized antibodies were purified with Protein G beads (GE Healthcare) and stored under appropriate conditions.

Example 9

Characteristics of DLL3 Modulators

Various methods were used to analyze the binding and immunochemical characteristics of selected DLL3 modulators generated as set forth above. Specifically, a number of the antibody modulators were characterized as to affinity, kinetics, binning, binding location and cross reactivity with regard to human, cynomolgus, rat and mouse antigen recognition (i.e., using the cells and constructs from Example 6) by art-recognized methods including flow cytometry. Affinities and kinetic constants $k_{on}$ and $k_{off}$ of the selected modulators were measured using bio-layer interferometry analysis on a ForteBio RED (ForteBio, Inc.) or surface plasmon resonance using a Biacore 2000 each according to the manufacturer's instructions.

The characterization results are set forth in tabular form in FIG. 12 where it may be seen that the selected modulators generally exhibited relatively high affinities in the nanomolar range and, in many cases, were cross-reactive. FIG. 12 further lists the empirically determined modulator bin as well as the DLL3 domain bound by the subject modulator as determined using yeast mediated antigen fragment expression such as described in more detail in Example 10 immediately below. Additionally, FIG. 12 further includes the ability of the modulators to mediate cytotoxic induced cell killing of an NTX kidney tumor line (% Live Cells) determined as set forth in Example 12 below. Taken together, these data demonstrate the varied binding properties of the disclosed modulators as well as their potential for use in a pharmaceutical setting.

As to antibody binning, a ForteBio RED was used per manufacturer's instructions to identify competing antibodies that bound to the same or different bins. Briefly, a reference antibody (Ab1) was captured onto an anti-mouse capture chip, a high concentration of non-binding antibody was then used to block the chip and a baseline was collected. Monomeric, recombinant human DLL3-Flag (Adipogen International) was then captured by the specific antibody (Ab1) and the tip was dipped into a well with either the same antibody (Ab1) as a control or into a well with a different test antibody (Ab2). If additional binding was observed with a new antibody, then Ab1 and Ab2 were determined to be in a different bin. If no further binding occurred, as determined by comparing binding levels with the control Ab1, then Ab2 was determined to be in the same bin. As known in the art this process can be expanded to screen large libraries of unique antibodies using a full row of antibodies representing unique bins in a 96-well plate. In the instant case this binning process showed the screened antibodies bound to at least nine different bins (designated as Bins A through I in FIG. 12) on the DLL3 protein. Based on the apparent size of the DLL3 antigen (where the ECD is approximately 56 kD) and the resolution of the binning methodology employed, it is believed that the nine identified bins represent the majority of the bins present on the DLL3 extracellular antigen.

In addition to evaluating the exemplary modulators as set forth above, flow cytometry was performed in order to confirm that selected SC16 antibody modulators can immunospecifically associate with human DLL3 and to determine whether the same modulators cross-react with cynomolgus, rat and/or murine DLL3. More particularly the exemplary murine modulators were analyzed by flow cytometry using a FACSCanto II and 293 cells overexpressing murine, rat, cynomolgus or human DLL3 (i.e., h293-hDLL3, h293-cDLL3, h293-rDLL3 and h293-mDLL3 expressing GFP) substantially as described in Example 6 above. In some cases, exemplary murine modulators were analyzed by flow cytometry using a FACSCanto II and yeast cells displaying cynomologus DLL3 using the methods described by Cochran et al. (J Immunol Methods. 287 (1-2):147-158 (2004).

Based on flow cytometry all of the selected antibody modulators were found to bind to human DLL3 overexpressed on 293 cells (data not shown) while a number of the tested antibodies were found to cross-react with cynomolgus and/or murine DLL3 (all antibodies reacting with mouse also reacted with rat). In this regard, and as listed in FIG. 12, it was found that eight out of the thirteen modulators that immunospecifically react with human DLL3 also react with murine (or rat) DLL3. Specifically mAbs SC16.4, SC16.8, SC16.15, SC16.34, SC16.39, SC16.46, SC16.51 and SC16.56 were found to cross-react with murine DLL3 to a greater or lesser extent while mAbs SC16.7, SC16.10, SC16.13, SC16.25 and SC16.65 did not appreciably associate with murine DLL3. Such results are not unexpected given that murine DLL3 is approximately 83% homologous with isoform 2 of human DLL3 (see FIG. 2B). It will be appreciated that this cross-reactivity may be advantageously exploited in the context of the instant invention through the use of animal models in drug discovery and development.

Besides the aforementioned assays, humanized constructs hSC16.13, hSC16.15, hSC16.25, hSC16.34 and hSC16.56 from Example 8 were analyzed to determine if the CDR grafting process had appreciably altered their binding characteristics. In this respect the humanized constructs (CDR grafted) were compared with "traditional" chimeric antibodies comprising the murine parent (or donor) heavy and light chain variable domains and a human constant region substantially equivalent to that used in the humanized constructs. With these constructs surface plasmon resonance (SPR) was conducted using a Biacore 2000 (GE Healthcare) to identify any subtle changes in rate constants brought about by the humanization process.

Exemplary results for one of the tested modulators (SC16.15) and a tabular summary of the results for each of the humanized and chimeric constructs are shown in FIGS. 13A-13C. Based on a concentration series of 25 and 12.5 nM of human DLL3 antigen (generating the curves from top to bottom in the FIGS. 13A and 13B for SC16.15) and using a 1:1 Langmuir binding model, the $K_D$ of the SC16.15 antibody binding to human DLL3 antigen was estimated to be 0.2 nM. Similar experiments were then run with the other humanized constructs and chimeric constructs (data not shown) to provide the affinity values set forth in FIG. 13C. Such results indicated that the humanization process had not materially impacted the affinity of the modulators.

Example 10

Domain and Epitope Mapping of DLL3 Modulators

In order to characterize and position the epitopes that the disclosed DLL3 antibody modulators associate with or bind to, domain-level epitope mapping was performed using a modification of the protocol described by Cochran et al., 2004 (supra). Briefly, individual domains of DLL3 comprising specific amino acid sequences were expressed on the surface of yeast, and binding by each DLL3 antibody was determined through flow cytometry.

More specifically, yeast display plasmid constructs were created for the expression of the following constructs: DLL3 extracellular domain (amino acids 27-466); DLL1-DLL3 chimera, which consists of the N-terminal region and DSL domain of DLL1 (amino acids 22-225) fused to EGF-like domains 1 through 6 of DLL3 (amino acids 220-466); DLL3-DLL1 chimera, which consists of the N-terminal region and DSL domain of DLL3 (amino acids 27-214) fused to EGF-like domains 1 through 8 of DLL1 (amino acids 222-518); EGF-like domain #1 (amino acids 215-249); EGF-like domain #2 (amino acids 274-310); EGF-like domains #1 and #2 (amino acids 215-310); EGF-like domain #3 (amino acids 312-351); EGF-like domain #4 (amino acids 353-389); EGF-like domain #5 (amino acids 391-427); and EGF-like domain #6 (amino acids 429-465). (For domain information see generally UniProtKB/Swiss-Prot database entry Q9NYJ7 which is incorporated herein by reference. Note that the amino acid numbering is by reference to an unprocessed DLL3 protein with a leader sequence such as set forth in SEQ ID NO. 3.) For analysis of the N-terminal region or the EGF domains as a whole, chimeras with the family member DLL1 (DLL1-DLL3 and DLL3-DLL1) were used as opposed to fragments to minimize potential problems with protein folding. Domain-mapped antibodies had previously been shown not to cross react with DLL1 indicating that any binding to these constructs was occurring through association with the DLL3 portion of the construct. These plasmids were transformed into yeast, which were then grown and induced as described in Cochran et al.

To test for binding to a particular construct, 200,000 induced yeast cells expressing the desired construct were washed twice in PBS+1 mg/mL BSA (PBSA), and incubated in 50 µL of PBSA with biotinylated anti-HA clone 3F10 (Roche Diagnostics) at 0.1 µg/mL and either 50 nM purified antibody or 1:2 dilution of unpurified supernatant from hybridomas cultured for 7 days. Cells were incubated for 90 minutes on ice, followed by 2 washes in PBSA. Cells were then incubated in 50 µL PBSA with the appropriate secondary antibodies: for murine antibodies, Alexa 488 conjugated streptavidin, and Alexa 647 conjugated goat anti mouse (both Life Technologies) were added at 1 µg/mL each, and for humanized or chimeric antibodies, Alexa 647 conjugated streptavidin (Life Technologies) and R-phycoerythrin conjugated goat anti human (Jackson Immunoresearch) were added at 1 µg/mL each. After a twenty minute incubation on ice, cells were washed twice with PBSA and analyzed on a FACS Canto II. Antibodies that bound to DLL3-DLL1 chimera were designated as binding to the N-terminal region+DSL. Antibodies that bound specifically to an epitope present on a particular EGF-like domain were designated as binding to its respective domain (FIG. 14A).

In order to classify an epitope as conformational (e.g., discontinuous) or linear, yeast displaying the DLL3 extracellular domain was heat treated for 30 minutes at 80° C., then washed twice in ice-cold PBSA. Yeast displaying denatured antigen (denatured yeast) were then subjected to the same staining protocol and flow cytometry analysis as described above. Antibodies that bound to both the denatured and native yeast were classified as binding to a linear epitope, whereas antibodies that bound native yeast but not denatured yeast were classified as conformationally specific.

Figure 14A:
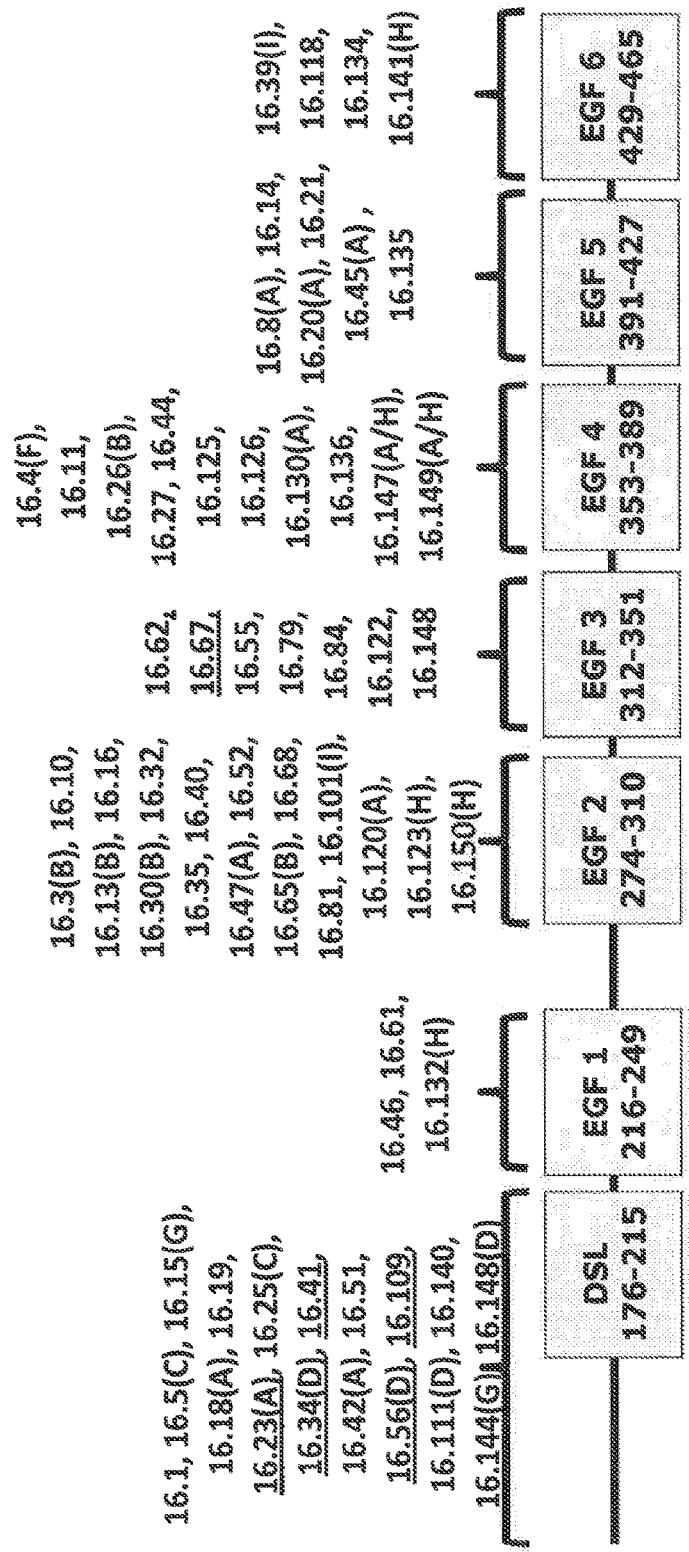
FIGS. 14A and 14B depict, in schematic and graphical form respectively, the results of domain level mapping analysis of exemplary DLL3 modulators isolated, cloned and engineered as described in the Examples herein (FIG. 14A) and a correlation between the binding domain of selected modulators and the ability to kill DLL3 expressing KDY66 NTX cells in vitro (FIG. 14B)

A schematic summary of the domain-level epitope mapping data of the antibodies tested is presented in FIG. 14A, with antibodies binding a linear epitope underlined and, where determined, the corresponding bin noted in parenthesis. A review of FIG. 14A shows that the majority of modulators tended to map to epitopes found either in the N-terminal/DSL region of DLL3 or to the second EGF-like domain. As previously alluded to, FIG. 12 presents similar data regarding bin determination and domain mapping for a number of selected modulators in a tabular form.

Figure 14B:
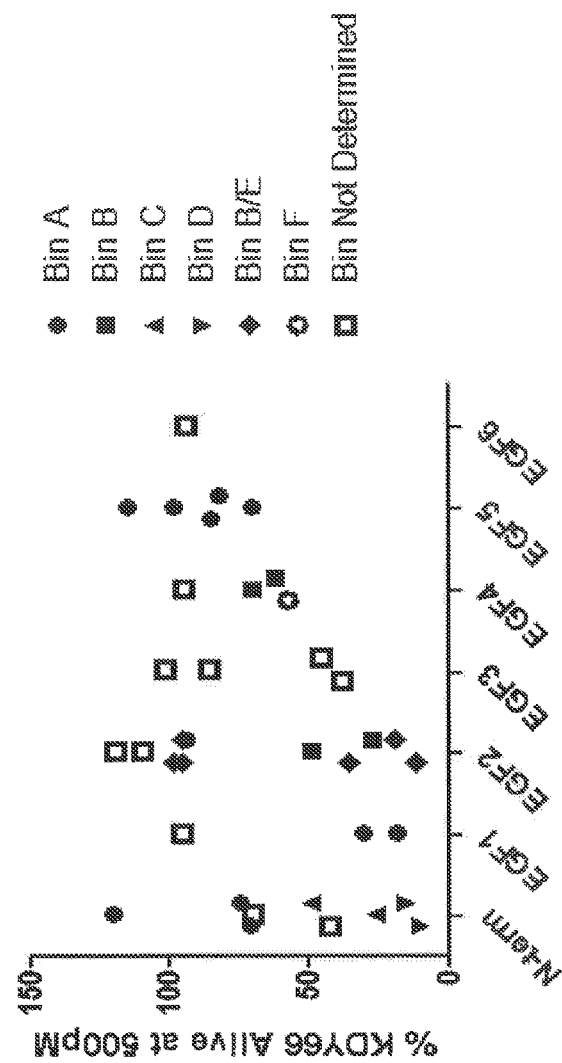

To document the ability of the disclosed modulators to effectively eliminate tumorigenic cells despite binding to different DLL3 regions, killing data was correlated with domain binding. More particularly, FIG. 14B shows modulator mediated in vitro killing of the KDY66 PDX line (derived as set forth in Example 12 below) plotted against the binding domain of the selected modulator. These data show that domain specific modulator killing is somewhat variable as measured using this in vitro killing assay. However, for modulators that are effective, an interesting trend appears where maximum killing in each domain increases as the epitope moves towards the N-terminus in the primary sequence. In particular, maximum killing efficiency improves from EGF6 to EGF2, and plateaus across the N-terminal domain, EGF1, and EGF2. Additionally, out of the antibodies tested in this assay, the highest percentage of efficacious antibodies bind at the N-terminal domain. This suggests that modulators that associate or bind with the DSL domain or N-terminal region of DLL3 may prove to be particularly effective as drugs or as targeting moieties for cytotoxic agents.

Fine epitope mapping was further performed on selected antibodies using one of two methods. The first method employed the Ph.D.-12 phage display peptide library kit (New England Biolabs E8110S) which was used in accordance with the manufacturer's instructions. Briefly, the antibody for epitope mapping was coated overnight at 50 µg/mL in 3 mL 0.1 M sodium bicarbonate solution, pH 8, onto a Nunc MaxiSorp tube (Nunc). The tube was blocked with 3% BSA solution in bicarbonate solution. Then, $10^{11}$ input phage in PBS+0.1% Tween-20 was allowed to bind, followed by ten consecutive washes at 0.1% Tween-20 to wash away non-binding phage. Remaining phage were eluted with 1 mL 0.2 M glycine for 10 minutes at room temperature with gentle agitation, followed by neutralization with 150 µL 1M Tris-HCl pH 9. Eluted phage were amplified and panned again with $10^{11}$ input phage, using 0.5% Tween-20 during the wash steps to increase selection stringency. DNA from 24 plaques of the eluted phage from the second round was isolated using the Qiaprep M13 Spin kit (Qiagen) and sequenced. Binding of clonal phage was confirmed using an ELISA assay, where the mapped antibody or a control antibody is coated onto an ELISA plate, blocked, and exposed to each phage clone. Phage binding was detected using horseradish peroxidase conjugated anti-M13 antibody (GE Healthcare), and the 1-Step Turbo TMB ELISA solution (Pierce). Phage peptide sequences from specifically binding phage were aligned using Vector NTI (Life Technologies) against the antigen ECD peptide sequence to determine the epitope of binding.

Alternatively, a yeast display method (Chao et al., Nat Protoc. 1(2): 755-768, 2007) was used to epitope map select antibodies. Briefly, libraries of DLL3 ECD mutants were generated with error prone PCR using nucleotide analogues 8-oxo-2'deoxyguanosine-5'-triphosphate and 2'-deoxy-p-nucleoside-5'triphosphate (both from TriLink Bio) for a target mutagenesis rate of one amino acid mutation per clone. These were transformed into a yeast display format. Using the technique described above for domain-level mapping, the library was stained for HA and antibody binding at 50 nM. Using a FACS Aria (BD), clones that exhibited a loss of binding compared to wild type DLL3 ECD were sorted. These clones were re-grown, and subjected to another round of FACS sorting for loss of binding to the target antibody. Using the Zymoprep Yeast Plasmid Miniprep kit (Zymo Research), individual ECD clones were isolated and sequenced. Where necessary, mutations were reformatted as single-mutant ECD clones using the Quikchange site directed mutagenesis kit (Agilent).

Individual ECD clones were next screened to determine whether loss of binding was due to a mutation in the epitope, or a mutation that caused misfolding. Mutations that involved cysteine, proline, and stop codons were automatically discarded due to the high likelihood of a misfolding mutation. Remaining ECD clones were then screened for binding to a non-competing, conformationally specific antibody. ECD clones that lost binding to non-competing, conformationally specific antibodies were concluded to contain misfolding mutations, whereas ECD clones that retained equivalent binding as wild type DLL3 ECD were concluded to be properly folded. Mutations in the ECD clones in the latter group were concluded to be in the epitope. The results are listed in TABLE 3 immediately below.

TABLE 3

| Antibody Clone | Epitope | SEQ ID NO: |
|---|---|---|
| SC16.23 | Q93, P94, G95, A96, P97 | 9 |
| SC16.34 | G203, R205, P206 | 10 |
| SC16.56 | G203, R205, P206 | 10 |

More particularly, a summary of selected antibodies with their derived epitopes comprising amino acid residues that are involved in antibody binding are listed in TABLE 3. In this respect antibodies SC16.34 and SC16.56 apparently interact with common amino acid residues which is consistent with the binning information and domain mapping results shown in FIG. 14A. Moreover, SC16.23 was found to interact with a distinct contiguous epitope and was found not to bin with SC16.34 or SC16.56. Note that for the purposes of the appended sequence listing SEQ ID NO: 10 will comprise a placeholder amino acid at position 204.

Example 11

Flow Cytometry Based Detection of DLL3 on the Surface of Cells and Immunohistochemical Staining of DLL3 in Tumors To confirm the immunospecific nature of the disclosed modulators, exemplary SC16 antibody modulators were tested using flow cytometry to determine their ability to selectively recognize engineered 293 cell lines expressing DLL3 protein on their surface. In this regard cells expressing DLL3 were produced as set forth substantially in Example 6, exposed to selected modulators and examined by flow cytometry as described herein. Isotype-stained and fluorescence minus one (FMO) controls were employed to confirm staining specificity. As demonstrated by the representative data shown in FIG. 15 for the SC16.56 modulator, some of the SC16 antibodies (e.g., SC16.56) gave strong staining of 293-hDLL3 cells (FIG. 15B) and 293-mDLL3 cells (FIG. 15C), but not of non-DLL3 expressing parental 293 cells (FIG. 15A). These data demonstrate, via flow cytometry, that the disclosed modulators immunospecifically recognize human DLL3, and in the instance of SC16.56, murine DLL3 as well.

To confirm these findings and demonstrate that DLL3 expression could be detected on human tumor cells, DLL3 protein expression on the surface of selected NTX tumors was assessed by flow cytometry using several exemplary SC16 antibodies. In this regard data for one of these antibodies, SC16.56, and three particular tumors, OV26, KDY66, and LU37, are set forth in FIG. 16. More specifically, NTX tumors were harvested, dissociated, and co-stained with commercially available anti-mouse CD45, anti-mouse H-2Kd, anti-human EpCAM and the above-described anti-human/mouse DLL3 (SC16.56) antibodies. Similar to the 293-staining experiments described above, isotype-stained and fluorescence minus one (FMO) controls were employed to confirm lack of non-specific staining. As seen in FIG. 16, anti-DLL3 staining was higher in a fraction of the human NTX tumor cells, as indicated by the fluorescent profile shift to the right, and by changes in the mean fluorescence intensity (MFI) values, for the ovarian OV26 NTX (FIG. 16A), kidney KDY66 NTX (FIG. 16B), and lung LU37 NTX (FIG. 16C) tumor cell lines. SCLC NTX tumors were also stained in an identical manner and similarly demonstrated positive expression of DLL3 (data not shown). These data suggest that DLL3 protein is expressed on the surface of various NTX tumors and therefore amenable to modulation using anti-DLL3 antibody type modulators.

To further corroborate the presence of DLL3 protein and localize it in the tumor architecture, immunohistochemistry (IHC) was performed on human patient tumor-derived NTX tumors, normal human tissues and primary SCLC tumors. More specifically IHC was performed on formalin fixed paraffin embedded (FFPE) tissue sections, using an indirect detection method, including a murine monoclonal primary antibody against DLL3 (SC16.65), mouse specific biotin conjugated secondary antibodies, avidin/biotin complex coupled with horse-radish peroxidase, tyramide signal amplification and DAB detection (Nakene P K 1968; 16:557-60). When staining human patient tumor derived NTX tumors, a mouse IgG blocking step was used to reduce background due to non-specific binding. SC16.65 was first validated and confirmed to be appropriate for IHC by showing specific staining in 293 cells overexpressing DLL3, but not non-DLL3 expressing parental 293 cells, and that staining was diminished in cells treated with DLL3-targeted hairpins designed and validated to knockdown expression of DLL3 RNA and protein (see Example 14 below, data not shown). IHC on a panel of xenograft NTX tumors showed that DLL3 is localized both on the membrane and in the cytoplasm of many of SCLC NTX and NET tumors that previously tested positive for DLL3 mRNA (FIG. 16D). Staining intensity was scored from no staining (−) to high expression (+++) with the percent of positive cells also noted. Staining of normal human tissues showed no detectable expression of DLL3 (FIG. 16E). Significantly, staining of primary SCLC tumor samples confirmed that 36/43 tumors were positive for DLL3 (FIG. 16F). Chromagranin A (CHGA) staining was also performed to confirm that tumors were indeed SCLC tumors. Most tumors that lacked DLL3 also lacked CHGA staining, indicating these sections might not contain tumor tissue or that the tissue was compromised during processing. Two tumors that tested positive for DLL3 but were negative for CHGA, were both later stage (IIIa) SCLC tumors. This data suggests that DLL3 provides an effective therapeutic target as it is not generally expressed in normal human tissues, but is present in the majority of SCLC tumors.

Example 12

DLL3 Modulators Facilitate Delivery of Cytotoxic Agents

To determine whether DLL3 antibody modulators of the instant invention are able to mediate the delivery of a cytotoxic agent to live cells, an in vitro cell killing assay was performed using randomly selected DLL3 antibody modulators.

Figure 17A:
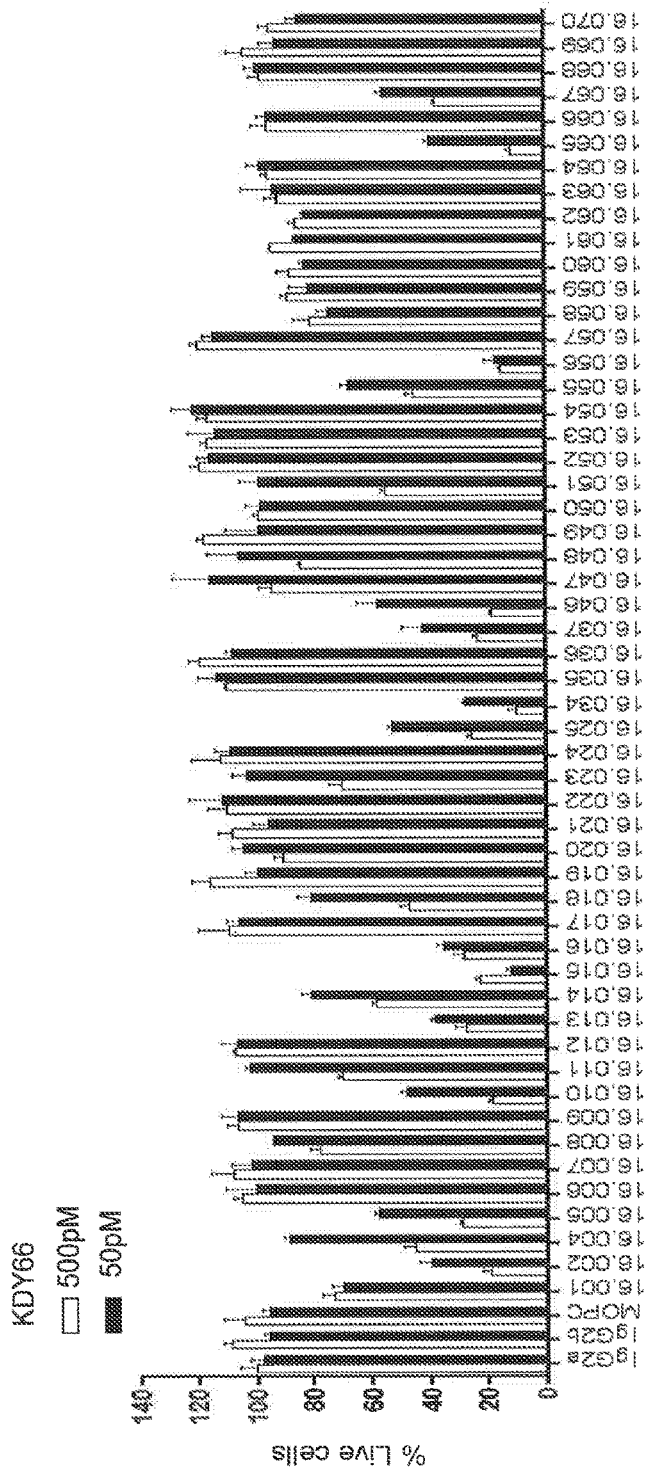
FIGS. 17A-17C illustrate the ability of the disclosed modulators to effectively direct cytotoxic payloads to cells expressing DLL3 wherein FIG. 17A documents the ability of exemplary modulators to kill KDY66 NTX tumors or 293 cells overexpressing hDLL3, and FIGS. 17B and 17C demonstrate the ability of disclosed modulators to deliver cytotoxic payloads to OV26 (FIG. 17B) and LU37 (FIG. 17C) where the downward sloping curve is indicative of cell killing through internalized cytotoxin.
Figure 17A:
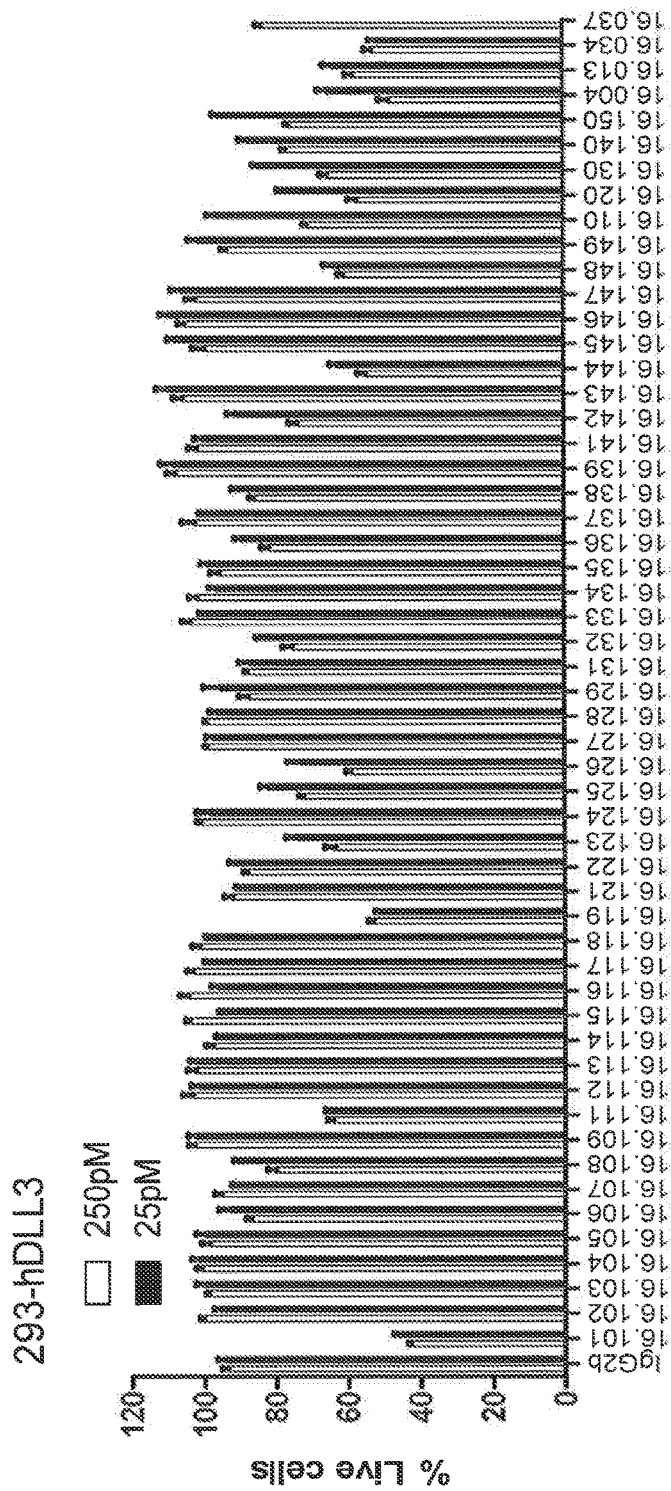

Specifically 2,500 cells/well of human KDY66, a NET NTX expressing endogenous DLL3, were dissociated into a single cell suspension and plated on BD Primaria™ plates (BD Biosciences) in growth factor supplemented serum free media as is known in the art, one day before the addition of antibodies and toxin. Various concentrations of purified DLL3 modulators, such as those described in Examples 6 and 7, and a fixed concentration of 4 nM anti-Mouse IgG Fab fragment covalently linked to saporin toxin (Advanced Targeting Systems, #IT-48) were added to the cultures for seven days. For killing on 293-hDLL3, 500 cells/well were plated in a single cell suspension and plated on BD tissue culture plates in DMEM with 10% FBS one day before addition of antibodies and toxin. Two concentrations of various DLL3 modulators and a fixed concentration of 2 nM anti-Mouse IgG Fab fragment covalently linked to saporin were added to the cultures for three days. The ability of the saporin complexes to internalize and kill cells was determined by enumerating viable cell numbers using Cell Titer Glo® (Promega) as per manufacturer's instructions. Raw luminescence counts using cultures containing cells with the saporin Fab fragment were set as 100% reference values and all other counts calculated accordingly (referred to as "Normalized RLU"). Using this assay it was demonstrated that a subset of DLL3 antibodies tested at 500 and 50 pM killed KDY66 cells, as well as a subset of antibodies tested at 250 and 25 pM on 293-hDLL3 overexpressing cells (FIG. 17A). Isotype controls did not affect cell counts as shown by the IgG2a, IgG2b, and MOPC bars at the left of the graph (FIG. 17A).

Figure 17B:
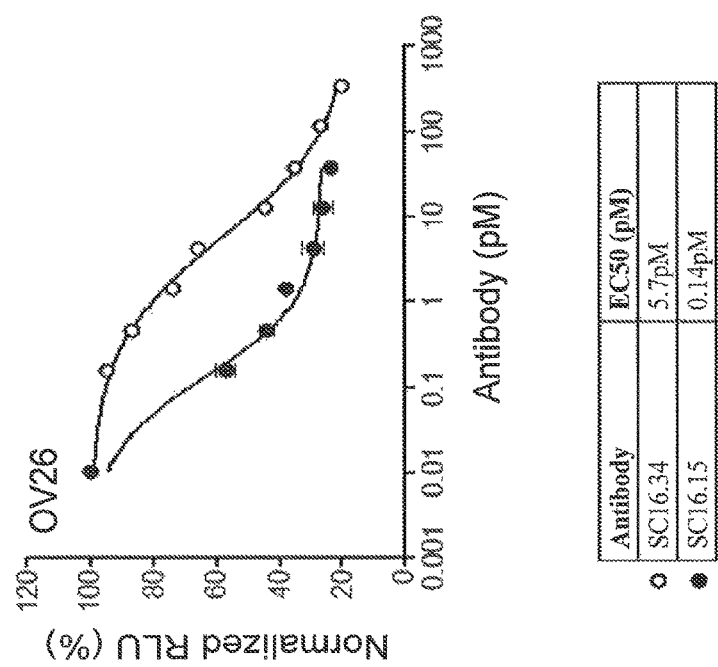

A subset of DLL3 modulators showing efficient killing in the first assay described above were tested in dilution to determine EC50 values for activity. Two such representative antibodies, SC16.34 and SC16.15, are shown in FIG. 17B, in which it was determined that SC16.15 showed efficient killing of OV26, an ovarian NET NTX tumor, with a subpicomolar EC50 (e.g., 0.14 pM) relative to the killing profile shown by SC16.34 (e.g., 5.7 pM). As saporin kills cells only upon uptake into the cytoplasm where it inactivates ribosomes, this assay also demonstrates that internalization may occur upon binding of the DLL3-specific antibody to the cell surface, without the need for additional crosslinking or dimerization.

Figure 17C:
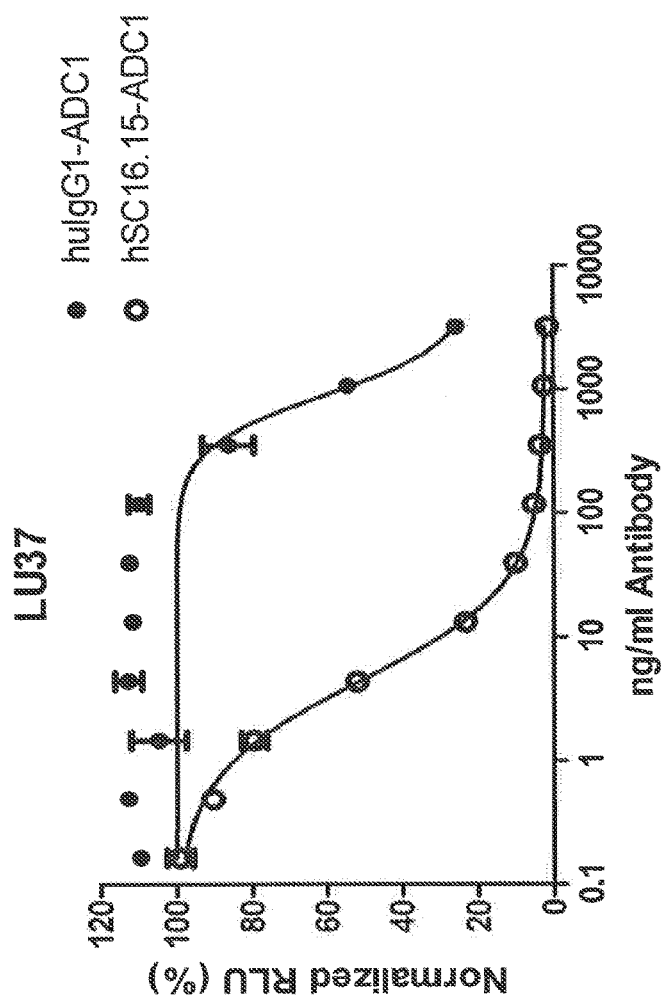

Lastly, LU37 was treated with humanized SC16.15 conjugated to ADC1 or with a humanized IgG1 control ADC1 (conjugated as per Example 13 immediately below). Specifically, 2,500 LU37 NTX cells were plated in each well on BD Primaria™ plates (BD Biosciences) in growth factor supplemented serum free media as is known in the art one day before the addition of the conjugated antibodies. Various concentrations of huIgG1-ADC1 or hSC16.15-ADC were added to the cultures for seven days, and the ability of the cytotoxic agents to kill was determined by enumerating cell numbers (as detailed above). Using this assay it was demonstrated that hSC16.15-ADC1 efficiently killed LU37. In contrast to >1,000 ng/ml of control ADC needed to kill 50% of LU37, <10 ng/ml of hSC16.15-ADC1 killed 50% of LU37 (FIG. 17C).

Example 13

Preparation of DLL3 Antibody-Drug Conjugates

Based on the foregoing results with saporin and to further demonstrate the versatility of the instant invention, anti-DLL3 antibody drug conjugates (DLL3-ADCs) were prepared using covalently linked cytotoxic agents. More specifically, DLL3-ADCs were prepared comprising a linker as described herein, or in the references immediately below, and selected pyrrolobenzodiazepine (PBD) dimers that were covalently attached to the disclosed modulators (see, e.g., U.S.P.Ns. 2011/0256157 and 2012/0078028 and U.S. Pat. No. 6,214,345 each of which is incorporated herein by reference in its entirety).

PBD drug-linker combinations were synthesized and purified using art-recognized techniques in view of the cited references. While various PBD dimers and linkers were employed to fabricate the selected drug-linker combinations, each linker unit comprised a terminal maleimido moiety with a free sulfhydryl. Using these linkers, conjugations were prepared via partial reduction of the mAb with tris (2-carboxyethyl)-phosphine (TCEP) followed by reaction of reduced Cys residues with the maleimido-linker payload.

More particularly, the selected DLL3 antibody modulator was reduced with 1.3 mol TCEP per mol mAb for 2 hr at 37° C. in 25 mM Tris HCl pH 7.5 and 5 mM EDTA buffer. The reaction was allowed to cool to 15° C. and the linker payload in DMSO was added at a ratio of 2.7 mol/mol mAb followed by an additional amount of DMSO to a final concentration of 6% (v/v). The reaction was allowed to proceed for 1 hour. The unreacted drug-linker was capped by addition of an excess of N-acetyl cysteine. The DLL3-ADC (or SC16-ADC) was then purified by ion exchange column using an AKTA Explorer FPLC system (G.E. Healthcare) to remove aggregated high molecular weight antibody, co-solvent and small molecules. The eluted ADC was then buffer-exchanged by tangential flow filtration (TFF) into formulation buffer followed by concentration adjustment and addition of a detergent. The final ADC was analyzed for protein concentration (by measuring UV), aggregation (SEC), drug to antibody ratio (DAR) by reverse phase (RP) HPLC, presence of unconjugated antibody by hydrophobic interaction chromatography (HIC) HPLC, non-proteinaceous materials by RP HPLC and in vitro cytotoxicity using a DLL3 expressing cell line.

Using the aforementioned procedure, or substantially similar methodology, a number of ADCs (i.e., M-[L-D]n) comprising various DLL3 modulators and PBD dimers were generated and tested in a variety of in vivo and in vitro models. For the purposes of these Examples and the instant disclosures, such ADCs may generally be termed DLL3-ADCs or SC16-ADCs. Discrete ADCs will be named according to the antibody (e.g., SC16.13) and the specific linker-cytotoxic agent designation ADC1, ADC2, etc. Thus, exemplary modulators compatible with the instant invention may comprise SC16.13-ADC1 or SC16.67-ADC2 where ADC1 and ADC2 represent individual PBD dimer cytotoxic agents (and optionally a linker).

Example 14

Specificity of Anti-DLL3 Antibody-Drug Conjugate Mediated Toxicity

To demonstrate that toxicity from anti-DLL3 antibody-drug conjugates is specific to cells expressing endogenous DLL3, experiments were conducted to show that tumor cells known to have endogenous DLL3 expression are no longer killed by SC16-ADC in vitro when DLL3 expression is suppressed by knocking down expression of DLL3 mRNA and protein using a short-hairpin RNA (shRNA).

KDY66 is a patient-derived xenograft from a papillary renal cell carcinoma that exhibits neuroendocrine features and expresses DLL3 mRNA and protein (e.g., see FIG. 7 and FIG. 16B). Expression of DLL3 was reduced in KDY66 cells by transduction with GIPZ Lentiviral Human DLL3-targeted shRNA (Thermo Fisher Scientific Inc.) containing an anti-DLL3 shRNA. More specifically the lentiviral vector was generated through transfection of 293T cells with a bicistronic lentiviral plasmid expressing anti-DLL3 shRNA (DLL3HP2) or a control non-silencing shRNA (DLL3NSHP) in the presence of viral packaging plasmids. Resulting lentiviral particles contained in the supernatant were concentrated and harvested by ultracentrifugation. These particles were then used to transduce the KDY66 cell cultures and introduce the shRNA (i.e., DLL3HP2 or NSHP) wherein the anti-DLL3 shRNA binds endogenous DLL3 mRNA and targets it for destruction thereby preventing translation into DLL3 protein. Both vector constructs contained an independent GFP expression module for verification of successful transduction and selection of transduced cells.

Following transduction, expression of DLL3 was evaluated by flow cytometry. Briefly, a sample of disassociated, single cell suspension of DLL3HP2-transduced cells were labeled with a DLL3 modulator (SC16.34) conjugated to Alexa Fluor 647 (Life Technologies) and analyzed on a FACS Canto II flow cytometer under standard conditions. To demonstrate a reduction of DLL3 protein expression on the surface of the DLL3HP2 transduced cells, fluorescence intensity was compared with a similarly prepared sample of KDY66 DLL3NSHP cells stained with a non-reactive control antibody (647-IgG1) and KDY66 DLL3NSHP cells stained with 647-DLL3. DLL3NSHP.KDY66 cells were found to exhibit DLL3 protein expression substantially equivalent to naïve KDY66 cells (data not shown). As seen in FIG. 18A, DLL3 protein surface expression was reduced in cells transduced with DLL3HP2 compared with naïve cells stained with the same AlexaFluor-647 labeled antibody.

In order to examine the consequences of DLL3 expression on the growth of tumors DLL3HP2 transduced cells (DLL3) and naïve KDY66 cells (DLL3$^+$) were transplanted into immunodeficient mice. From the sample prepared as described above, live human GFP$^+$ cells were sorted to collect cells that contain the anti-DLL3 shRNA. Five-mouse cohorts were injected (140 cells/mouse) with either DLL3HP2 or naïve KDY66 cells and tumor growth was monitored weekly. From each cohort, two of five recipients grew tumors. Tumor formation in the two DLL3HP2.KDY66 recipients lagged roughly 22 days behind tumor formation in the two naïve KDY66 recipients (FIG. 18B). This observed delay in growth suggests that DLL3 expression may be connected to increased or accelerated tumor formation since knockdown of DLL3 impacted tumor growth.

As they reached the appropriate volume for randomization (~160 mm$^3$), the DLL3HP2 KDY66 tumors and naïve KDY66 tumors were harvested from recipient mice and dispersed into suspensions of single cells. Continued reduction of DLL3 expression (i.e., that DLL3 expression was not induced during in vivo growth) in DLL3HP2 cells was confirmed on suspensions of single tumor cells by flow cytometry as described above. In this respect FIG. 18C shows that DLL3HP2 transduced cells grown in vitro show reduced expression of DLL3 protein when compared to naïve cells grown in similar conditions.

Using standard biochemical techniques naïve KDY66 cells or DLL3HP2 KDY66 cells were plated into 96 well plates and grown in serum-free media. A dilution series of either humanized hSC16.56-ADC1 (SC16-ADC1) or humanized anti-hapten IgG-ADC1 (as a control) antibody-drug conjugates produced as set forth above were added to cells in triplicate. After 7 days of exposure to antibody-drug conjugate, the quantity of live cells was measured with a luminescence-based detection of ATP in the cell lysates of each well (Cell Titer Glo, Promega) substantially as set forth in Example 12.

Figures 18D, 18E:
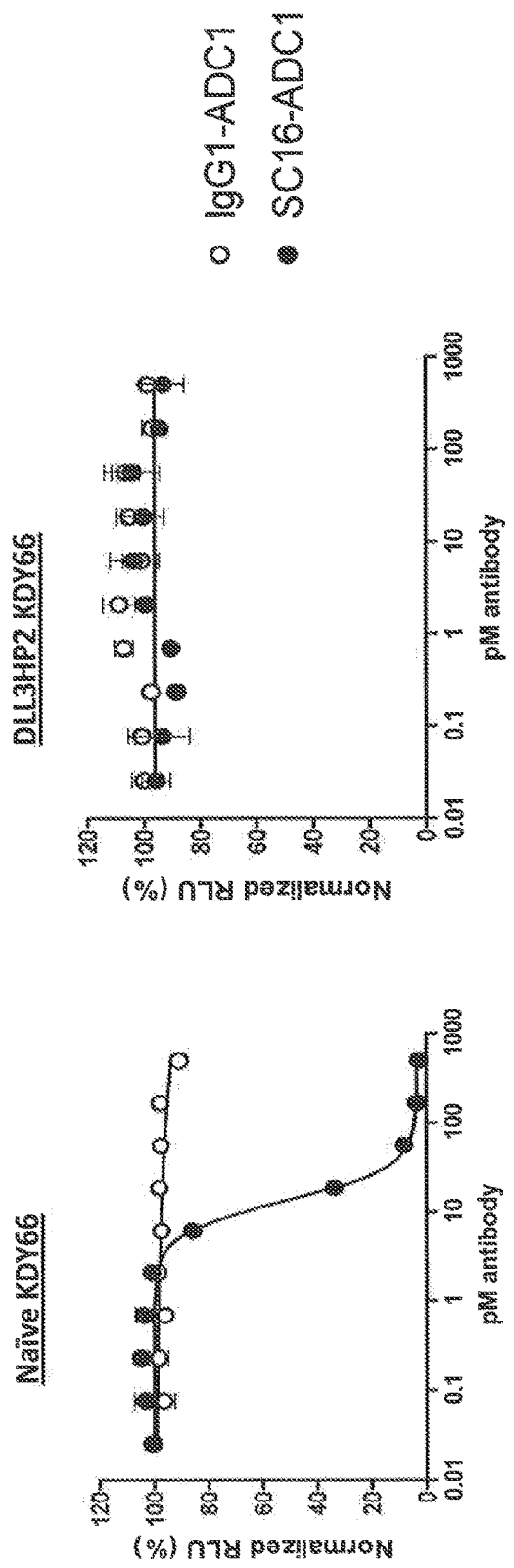

While 50% of naïve KDY66 cells were killed by a relatively low dose of 13.27 pM SC16-ADC, no dose of SC16-ADC1 was able to kill even 20% of DLL3HP2.KDY66 cells (FIGS. 18D and 18E). Of note, loss of endogenous DLL3 protein expression resulted in a complete loss of in vitro killing by SC16-ADC1. This demonstrates that hSC16-ADC1 cytotoxicity is specifically targeted to DLL3-expressing cells with little, if any, non-specific toxicity.

Example 15

Conjugated DLL3 Modulators Suppress Tumor Growth

Based on the aforementioned results work was undertaken to demonstrate that conjugated DLL3 modulators of the instant invention shrink and suppress growth of DLL3 expressing human tumors in vivo. In this regard a number of selected murine antibody modulators were covalently associated with a PBD cytotoxic agent and the resulting ADCs were tested to demonstrate their ability to suppress human NTX tumor growth in immunodeficient mice.

To this end patient-derived NTX tumors were grown subcutaneously in the flanks of female NOD/SCID recipient mice using art-recognized techniques. Tumor volumes and mouse weights were monitored twice weekly. When tumor volumes reached 150-250 mm$^3$, mice were randomly assigned to treatment groups and injected with indicated doses of SC16-ADC2 or an anti-hapten control IgG1-ADC2 (each produced substantially as described in Example 13 above using the PBD dimer ADC2) via intraperitoneal injection. Mice were given three equal injections, spaced evenly across seven days. Following treatment, tumor volumes and mouse weights were monitored until tumors exceeded 800 mm$^3$ or mice became sick. For all tests, treated mice exhibited no adverse health effects beyond those typically seen in immunodeficient tumor-bearing NOD/SCID mice.

Figure 19A:
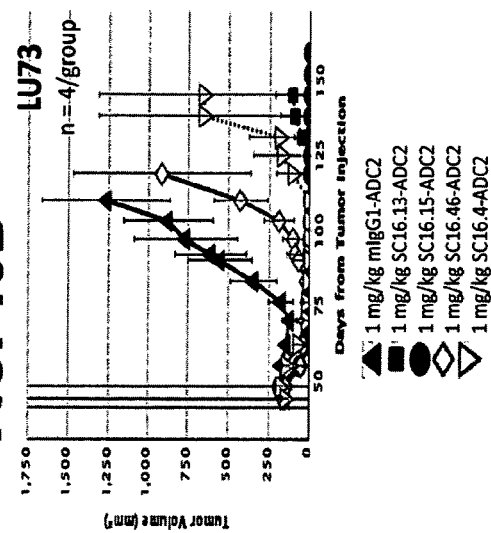
FIGS. 19A-19C show the ability of selected conjugated embodiments of the present invention to kill and/or suppress growth of exemplary lung tumorigenic cells in vivo.
Figure 19B:
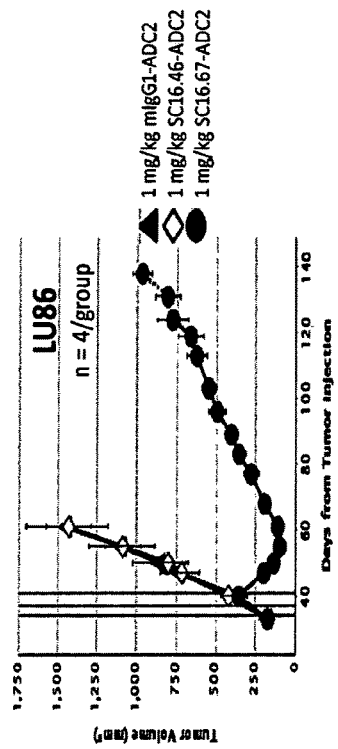
Figure 19C:
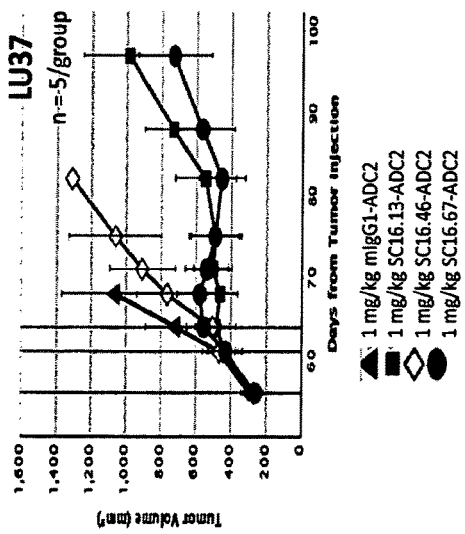
Figures 20A, 20B:
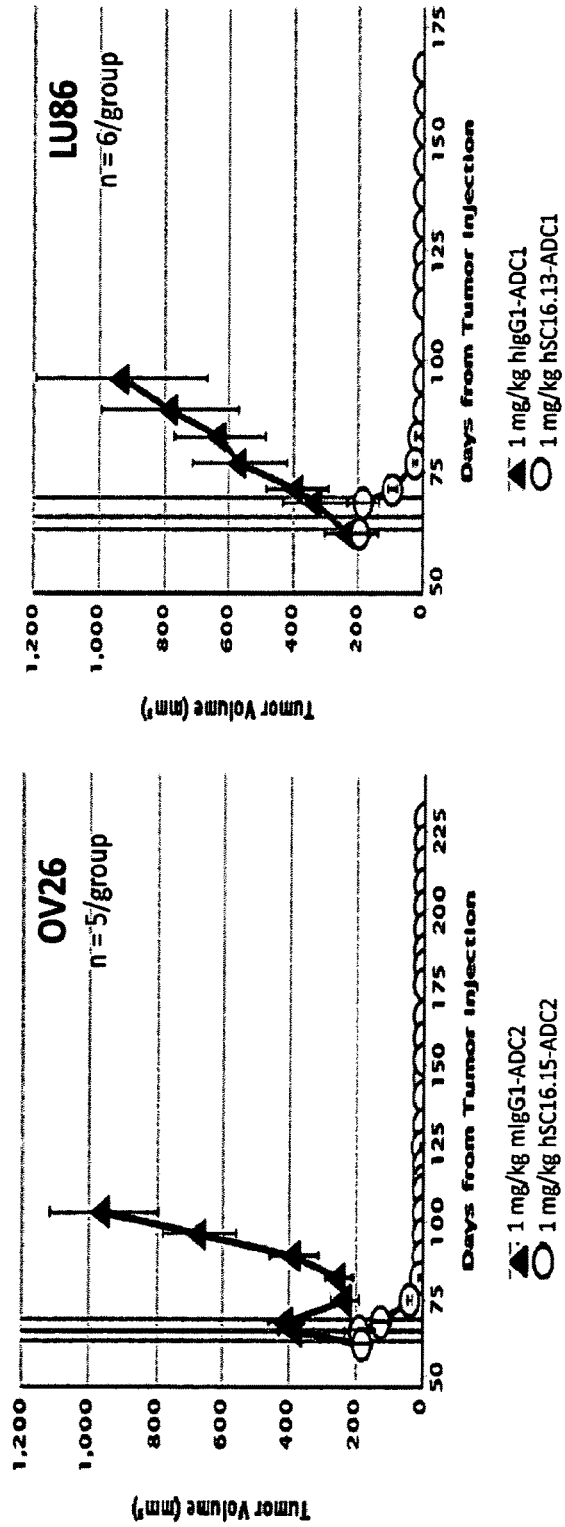

FIG. 19 shows the impact of the disclosed ADCs on tumor growth in mice bearing different lung tumors exhibiting neuroendocrine features (two small cell lung cancer and one large cell lung cancer with neuroendocrine features). In this respect treatment of LU37, a large cell neuroendocrine lung carcinoma, with three exemplary modulators (SC16.13, SC16.46 and SC16.67) conjugated to ADC2 resulted in tumor growth suppression lasting as long as 20 days in the case of SC16.13-ADC2 and SC16.67-ADC2 (FIG. 19A); conversely, though SC16.46 moderately reduced tumor growth it exhibited less activity than the other tested modulators. Similarly, treatment of LU73, a small cell lung carcinoma, with four exemplary modulators (SC16.4, SC16.13, SC16.15 and SC16.46) produced durable remissions lasting, in some cases, beyond 120 days post-treatment (FIG. 19B). However, as with the antibodies tested against LU37, the antibodies tested against LU73 varied somewhat in the duration of tumor repression. Finally, treatment of LU86, another small cell lung carcinoma, with two conjugated modulators (SC16.46-ADC2 and SC16.67-ADC2) produced tumor shrinkage with a time to progression of 40 days in one case (SC16.67-ADC2; FIG. 19C). Note that in FIG. 19C two of the curves substantially overlap (mIgG1-ADC2 and SC16.46-ADC2) and are difficult to distinguish.

The surprising ability of a variety of conjugated modulators to dramatically retard or suppress tumor growth in vivo for extended periods further validates the use of the DLL3 as a therapeutic target for the treatment of proliferative disorders.

Example 16

Humanized DLL3-ADC Modulators Suppress Tumor Growth

Given the impressive results provided by DLL3-ADC2, additional experiments were performed to demonstrate the efficacy of exemplary humanized ADC modulators in treating various types of tumors (including ovarian, lung and kidney cancer) in vivo. Specifically, selected humanized anti-DLL3 antibodies (hSC16.13, hSC16.15, hSC16.34 and hSC16.56 produced as set forth in Example 8 above) were conjugated (via a linker unit) to two discrete PBD cytotoxic agents (ADC1 and ADC2) as described above and, with controls, administered to NTX tumor implanted immunodeficient mice as set forth in the previous Example. In each study, tumor volumes and mouse weights of the control animals were monitored until tumors exceeded 800 mm$^3$ or mice became sick. The results of these experiments are presented in FIGS. 20A to 20F.

A review of FIGS. 20A-20F show that tumor volume reduction and durable remission was achieved in various tumor types, some exhibiting neuroendocrine features, following treatment with 1 mg/kg hSC16-ADC. For example, treatment regimens, where administration is delineated by the vertical lines in the subject FIGS., produced complete and durable eliminations of tumor mass in ovarian carcinoma with neuroendocrine features (OV26, hSC16.15-ADC2, FIG. 20A), a papillary renal cell carcinoma with neuroendocrine features (KDY66, hSC16.34-ADC1, FIG. 20E) and three small cell lung carcinomas (LU86, hSC16.13-ADC1, FIG. 20B), (LU64, hSC16.13-ADC1, FIG. 20C; LU64, hSC16.13-ADC2+hSC16.13-ADC1, FIG. 20D). Absence of tumor recurrence was observed for more than 100 days in all these cases, and in some cases beyond 225 days post-treatment where mice were followed for an extended period of time. Additionally, treatment with the disclosed modulators produced tumor volume reduction and growth suppression in a clear cell renal cell carcinoma xenograft that exhibits high levels of DLL3 using a lower dose of 0.5 mg/kg (KDY27, hSC16.56-ADC1, FIG. 20F).

Finally, it should be noted that certain recurrent tumors remained sensitive to hSC16-ADC toxicity. Eighty days after initial treatment with SC16.13-ADC2, recurrence was observed in LU64 (FIG. 20D). Treatment of recurrent tumors with hSC16.13-ADC1 resulted in elimination of observable tumor mass that persisted more than 100 days after the second treatment.

Again these results demonstrate the surprising versatility and applicability of the modulators of the instant invention in treating a variety of proliferative disorders.

Example 17

Reduction of Cancer Stem Cell Frequency by DLL3 Antibody-Drug Conjugates

As shown in the previous Examples the disclosed modulators are extremely effective in suppressing tumor growth, particularly in ADC form. Moreover, as demonstrated above, DLL3 expression is associated with cancer stem cells that are generally known to be both drug resistant and fuel tumor recurrence and metastasis. Accordingly, to demonstrate that treatment with DLL3-ADCs reduces the recurrence potential of NTX lines, in vivo limiting dilution assays (LDA) were performed to determine the frequency of tumor-initiating cells (TIC) in small cell lung cancer tumors following treatment with hSC16.13-ADC1 (labeled SC16-ADC in FIG. 21).

Figures 21A, 21B, 21C:
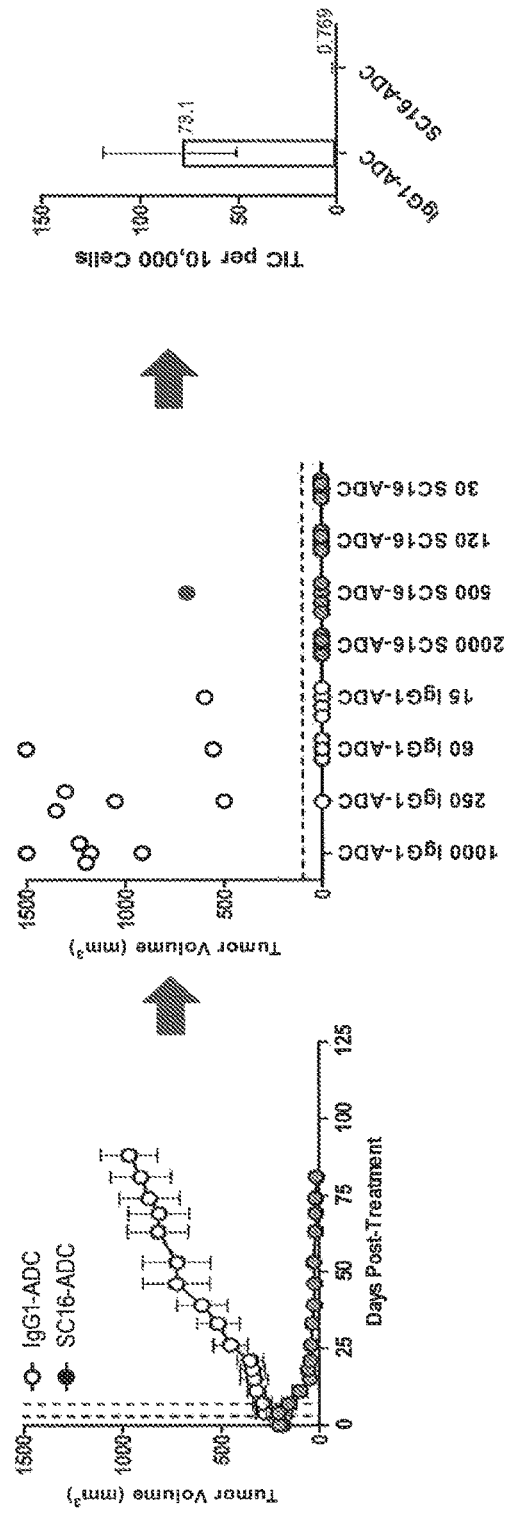
FIGS. 21A-21F demonstrate that conjugated modulators of the instant invention reduce the frequency of cancer stem cells as determined by a limiting dilution assay (LDA) for two exemplary small cell lung tumors, LU95 (FIGS. 21A-21C) and LU64 (FIGS. 21D-21F) where
Figures 21D, 21E, 21F:
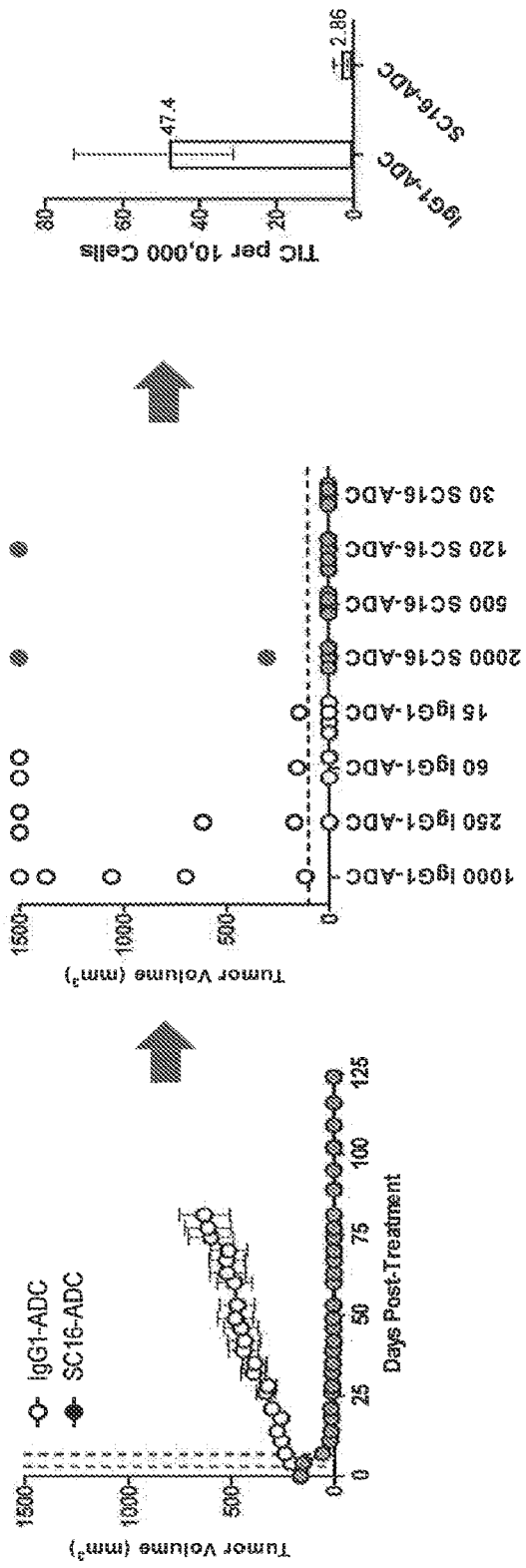

Patient-derived small cell lung cancer xenograft tumors (LU95 and LU64) were grown subcutaneously in immunodeficient host mice. When tumor volumes averaged 150 mm$^3$-250 mm$^3$, the mice were randomly segregated into two groups of seven mice. Via intraperitoneal injection, mice were injected on days 0, 4 and 7 (FIGS. 21A and 21D, dashed vertical lines), with either human IgG1-ADC1 (1 mg/kg; n=7 mice) as a negative control or hSC16.13-ADC (1 mg/kg; n=7 mice). On day 8, two representative mice from each group were euthanized and their tumors were harvested and dispersed to single-cell suspensions. As shown in FIGS. 21A and 21D while tumors treated with hIgG1-ADC (IgG1-ADC) continued to grow in the five remaining mice, volumes of tumors treated with hSC16.13-ADC1 (SC16-ADC) were reduced to zero or nearly zero in the five remaining mice.

Using standard flow cytometry techniques and a labeled anti-DLL3 antibody, the two harvested tumors from each of the two treatment groups were confirmed to have similarly positive DLL3 expression. The tumors cells from each respective treatment group were then pooled and live human cells were isolated by FACS using a FACSAria III (Becton Dickenson) in accordance with the manufacturer's instructions and art-recognized techniques. Briefly, the cells were labeled with FITC conjugated anti-murine H2Kd and anti-murine CD45 antibodies (both BioLegend, Inc.) and then resuspended in 1 µg/ml DAPI. The resulting suspension was then sorted under standard conditions with DAPI$^-$, mH2Kd$^-$ and mCD45$^-$ human cells being collected and the murine cells being discarded.

Cohorts of five recipient mice were then transplanted with either 2000, 500, 120 or 30 sorted live human cells from tumors treated with hSC16.13-ADC1. For comparison, cohorts of five recipient mice were transplanted with either 1000, 250, 60 or 15 sorted live human cells from tumors treated with the control IgG1-ADC1. Tumors in recipient mice were measured weekly, and individual mice were euthanized before tumors reached 1500 mm$^3$. After the onset of tumor growth, the study was ended after four consecutive weeks without a new tumor appearing in any additional mouse. At that time, recipient mice were scored as positive or negative for tumor growth, with positive growth having volumes exceeding 100 mm$^3$.

Across all injected cells doses, recipients of LU95 cells treated with hSC16.13-ADC1 produced only one tumor, compared to twelve in recipients of LU95 cells treated with IgG1-ADC1 (FIG. 21B). Similarly, recipients of LU64 cells treated with SC16.13-ADC1 produced three tumors, compared to 13 tumors in recipients of LU64 cells treated with IgG-ADC1 (FIG. 21E).

Using Poisson distribution statistics (L-Calc software, Stemcell Technologies), injected cell doses of recipients with and without tumors at 18 weeks post-transplant were used to calculate the frequencies of tumor-initiating cells in each population. The number of TIC per 10,000 live human cells in LU95 was reduced more than 100-fold, from 78.1 in tumors treated with IgG1-ADC to 0.769 in tumors treated with hSC16.13-ADC1 (FIG. 21C, from 1:128 cells in the control treated to 1:12,998 in the modulator treated). In LU64, the number of TIC was reduced 16.6-fold, from 47.4 TIC to 2.86 TIC per 10,000 live human cells in tumors treated with IgG1-ADC1 or hSC16.13-ADC1, respectively (FIG. 21F, from 1:211 cells in the control treated to 1:3,500 cells in the modulator treated). This substantial reduction in TIC (e.g., cancer stem cell) frequency demonstrates that, in addition to reducing tumor volumes as previously demonstrated, the modulators of the instant invention are significantly and specifically reducing cancer stem cell populations and, by extension, the recurrence, metastatic and re-growth potential of the tumors. This reduction in recurrence and re-growth potential are strongly evidenced by the significant tumor-free survival observed in the forgoing Examples.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PBD, and translations from annotated coding regions in GenBank and RefSeq cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention claimed is:

1. A method of treating cancer in a subject, the method comprising administering to the subject a therapeutically effective amount of an antibody drug conjugate (ADC), or a pharmaceutically acceptable salt thereof, wherein the antibody drug conjugate (ADC) comprises the formula M-[L-D]n, wherein:

M comprises a humanized anti-DLL3 antibody comprising a light chain variable region set forth as SEQ ID NO: 212 and a heavy chain variable region set forth as SEQ ID NO: 213;

L comprises a linker;

D comprises a pyrrolobenzodiazepine (PBD) comprising the formula AC:

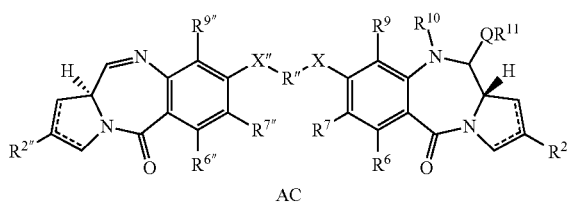

AC wherein:

the dotted lines indicate the optional presence of a double bond, and wherein only one of the dotted lines in a given ring can be a double bond;

$R^2$ is selected from H, OH, =O, =$CH_2$, CN, R, OR, =CH—$R^D$, =$C(R^D)_2$, O $SO_2$ R, $CO_2R$, COR, and halo, where $R^D$ is selected from R, $CO_2R$, COR, CHO, $CO_2H$, and halo;

$R^6$ and $R^9$ are each independently selected from H, R, OH, OR, SH, SR, $NH_2$, NHR, NRR', $NO_2$, $Me_3Sn$ and halo;

$R^7$ is selected from H, R, OH, OR, SH, SR, $NH_2$, NHR, NRR', $NO_2$, $Me_3Sn$ and halo;

$R^{10}$ is the linker connected to the anti-DLL3 antibody;

Q is selected from O, S and NH;

$R^{11}$ is either H, or R or, where Q is O, $SO_3M$, where M is a metal cation;

R and R' are each independently selected from optionally substituted $C_{1-12}$ alkyl, $C_{3-20}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;

X is selected from O, S, and N(H);

$R^{2''}$, $R^{6''}$, $R^{7''}$, $R^{9''}$, and X" are as defined according to $R^2$, $R^6$, $R^7$, $R^9$, and X, respectively; and R" is a $C_{3-12}$ alkylene group, which comprises a chain optionally interrupted by one or more heteroatoms, one or more rings, or both one or more heteroatoms and one or more rings, wherein the optional one or more rings are optionally substituted; and n is an integer from 1 to 20.

2. The method of claim 1, wherein the cancer is lung cancer.

3. The method of claim 2, wherein the lung cancer is small cell lung cancer.

4. The method of claim 1, wherein the cancer comprises a neuroendocrine tumor.

5. The method of claim 1, wherein the cancer is large cell neuroendocrine carcinoma.

6. The method of claim 1, wherein the cancer is thyroid cancer.

7. The method of claim 1, wherein the cancer is prostate cancer.

8. The method of claim 1, wherein the subject has relapsed from chemotherapy.

9. The method of claim 1, wherein the linker comprises a cleavable linker.

10. The method of claim 1, wherein:

$R^2$ is R, wherein R is a $C_{5-20}$ aryl group;

$R^6$ and $R^9$ are H;

$R^7$ is OR, and wherein R is a $C_1$ alkyl;

Q is O, and wherein $R^{11}$ is H; and/or

X and X" are O.

11. A method of treating a tumor comprising neuroendocrine features in a subject, wherein the tumor is characterized by elevated expression of ASCL1, the method comprising administering to the subject a therapeutically effective amount of an antibody drug conjugate (ADC), or a pharmaceutically acceptable salt thereof, wherein the antibody drug conjugate (ADC) comprises the formula M-[L-D]n, wherein:

M comprises a humanized anti-DLL3 antibody comprising a light chain variable region set forth as SEQ ID NO: 212 and a heavy chain variable region set forth as SEQ ID NO: 213;

L comprises a linker;

D comprises a pyrrolobenzodiazepine (PBD) comprising the formula AC:

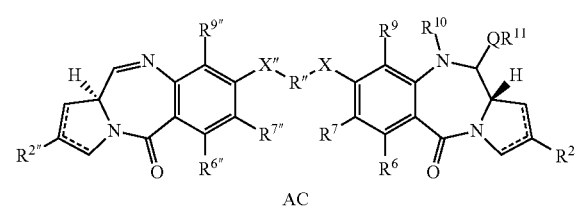

AC wherein:

the dotted lines indicate the optional presence of a double bond, and wherein only one of the dotted lines in a given ring can be a double bond;

$R^2$ is selected from H, OH, =O, =$CH_2$, CN, R, OR, =CH—$R^D$, =$C(R^D)_2$, O $SO_2$ R, $CO_2R$, COR, and halo, where $R^D$ is selected from R, $CO_2R$, COR, CHO, $CO_2H$, and halo;

$R^6$ and $R^9$ are each independently selected from H, R, OH, OR, SH, SR, $NH_2$, NHR, NRR', $NO_2$, $Me_3Sn$ and halo;

$R^7$ is selected from H, R, OH, OR, SH, SR, $NH_2$, NHR, NRR', $NO_2$, $Me_3Sn$ and halo;

$R^{10}$ is the linker connected to the anti-DLL3 antibody;

Q is selected from O, S and NH;

$R^{11}$ is either H, or R or, where Q is O, $SO_3M$, where M is a metal cation;

R and R' are each independently selected from optionally substituted $C_{1-12}$ alkyl, $C_{3-20}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;

X is selected from O, S, and N(H);

$R^{2''}$, $R^{6''}$, $R^{7''}$, $R^{9''}$, and X" are as defined according to $R^2$, $R^6$, $R^7$, $R^9$, and X, respectively; and R" is a $C_{3-12}$ alkylene group, which comprises a chain optionally interrupted by one or more heteroatoms, one or more rings, or both one or more heteroatoms and one or more rings, wherein the optional one or more rings are optionally substituted; and n is an integer from 1 to 20.

12. The method of claim 11, wherein the tumor shows suppressed Notch signaling.

13. The method of claim 11, wherein the tumor shows elevated levels of DLL3 and/or HES6 as compared to normal tissue or non-tumorigenic cells.

14. The method of claim 11, wherein the tumor is characterized by a poorly differentiated neuroendocrine phenotype.

15. The method of claim 11, wherein the tumor occurs in lung, genitourinary tract, gastrointestinal tract, thyroid, or kidney.

16. The method of claim 15, wherein the tumor comprises small cell lung cancer.

17. The method of claim 15, wherein the tumor is a large cell neuroendocrine carcinoma.

18. The method of claim 15, wherein the tumor comprises ovarian cancer.

19. The method of claim 15, wherein the tumor comprises prostate cancer.

20. The method of claim 15, wherein the tumor comprises medullary thyroid cancer.

21. The method of claim 15, wherein the tumor comprises renal cancer.

22. The method of claim 11, wherein the linker comprises a cleavable linker.

23. The method of claim 11, wherein:
$R^2$ is R, wherein R is a $C_{5-20}$ aryl group;
$R^6$ and $R^9$ are H;
$R^7$ is OR, and wherein R is a $C_1$ alkyl;
Q is O, and wherein $R^{11}$ is H; and/or
X and X" are O.

24. A method of treating a recurrent tumor in a subject, the method comprising administering to the subject a therapeutically effective amount of an antibody drug conjugate (ADC), or a pharmaceutically acceptable salt thereof, wherein the antibody drug conjugate (ADC) comprises the formula M-[L-D]n, wherein:

M comprises a humanized anti-DLL3 antibody comprising a light chain variable region set forth as SEQ ID NO: 212 and a heavy chain variable region set forth as SEQ ID NO: 213;

L comprises a linker;

D comprises a pyrrolobenzodiazepine (PBD) comprising the formula AC:

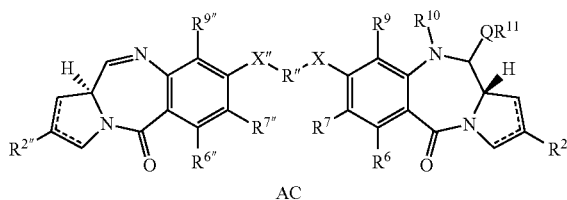

AC wherein:

the dotted lines indicate the optional presence of a double bond, and wherein only one of the dotted lines in a given ring can be a double bond;

$R^2$ is selected from H, OH, =O, =$CH_2$, CN, R, OR, =CH—$R^D$, =C($R^D$)$_2$, O SO$_2$ R, CO$_2$R, COR, and halo, where $R^D$ is selected from R, CO$_2$R, COR, CHO, CO$_2$H, and halo;

$R^6$ and $R^9$ are each independently selected from H, R, OH, OR, SH, SR, NH$_2$, NHR, NRR', NO$_2$, Me$_3$Sn and halo;

$R^7$ is selected from H, R, OH, OR, SH, SR, NH$_2$, NHR, NRR', NO$_2$, Me$_3$Sn and halo;

$R^{10}$ is the linker connected to the anti-DLL3 antibody;

Q is selected from O, S and NH;

$R^{11}$ is either H, or R or, where Q is O, SO$_3$M, where M is a metal cation;

R and R' are each independently selected from optionally substituted $C_{1-12}$ alkyl, $C_{3-20}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;

X is selected from O, S, and N(H);

$R^{2"}$, $R^{6"}$, $R^{7"}$, $R^{9"}$, and X" are as defined according to $R^2$, $R^6$, $R^7$, $R^9$, and X, respectively; and R" is a $C_{3-12}$ alkylene group, which comprises a chain optionally interrupted by one or more heteroatoms, one or more rings, or both one or more heteroatoms and one or more rings, wherein the optional one or more rings are optionally substituted; and n is an integer from 1 to 20.

25. The method of claim 24, wherein the recurrent tumor comprises lung cancer.

26. The method of claim 25, wherein the recurrent tumor comprises small cell lung cancer.

27. The method of claim 26, wherein the lung cancer is refractory, relapsed or resistant to a platinum based agent and/or a taxane.

28. The method of claim 26, wherein the subject has previously undergone a debulking procedure.

29. The method of claim 24, wherein the linker comprises a cleavable linker.

30. The method of claim 24, wherein:
$R^2$ is R, wherein R is a $C_{5-20}$ aryl group;
$R^6$ and $R^9$ are H;
$R^7$ is OR, and wherein R is a $C_1$ alkyl;
Q is O, and wherein $R^{11}$ is H; and/or
X and X" are O.

* * * * *